US009567587B2

(12) United States Patent
Freier et al.

(10) Patent No.: US 9,567,587 B2
(45) Date of Patent: Feb. 14, 2017

(54) ANTISENSE MODULATION OF GCCR EXPRESSION

(71) Applicant: Ionis Pharmaceuticals, Inc., Carlsbad, CA (US)

(72) Inventors: Susan M. Freier, San Diego, CA (US); Sanjay Bhanot, Carlsbad, CA (US)

(73) Assignee: Ionis Pharmaceuticals, Inc., Carlsbad, CA (US)

( * ) Notice: Subject to any disclaimer, the term of this patent is extended or adjusted under 35 U.S.C. 154(b) by 0 days.

(21) Appl. No.: 14/523,751

(22) Filed: Oct. 24, 2014

(65) Prior Publication Data

US 2015/0141493 A1 May 21, 2015

Related U.S. Application Data

(63) Continuation of application No. 13/660,885, filed on Oct. 25, 2012, now Pat. No. 8,901,098.

(60) Provisional application No. 61/551,378, filed on Oct. 25, 2011.

(51) Int. Cl.

| | |
|---|---|
| ***C07H 21/02*** | (2006.01) |
| ***C07H 21/04*** | (2006.01) |
| ***A61K 31/70*** | (2006.01) |
| ***C12N 15/113*** | (2010.01) |
| ***A61K 31/7088*** | (2006.01) |
| ***A61K 45/06*** | (2006.01) |
| ***A61K 31/7115*** | (2006.01) |
| ***A61K 31/712*** | (2006.01) |
| ***A61K 31/7125*** | (2006.01) |
| *C12N 5/00* | (2006.01) |

(52) U.S. Cl.

CPC ....... *C12N 15/1138* (2013.01); *A61K 31/7088* (2013.01); *A61K 31/712* (2013.01); *A61K 31/7115* (2013.01); *A61K 31/7125* (2013.01); *A61K 45/06* (2013.01); *C07H 21/04* (2013.01); *C12N 2310/11* (2013.01); *C12N 2310/315* (2013.01); *C12N 2310/321* (2013.01); *C12N 2310/322* (2013.01); *C12N 2310/3231* (2013.01); *C12N 2310/3341* (2013.01); *C12N 2310/341* (2013.01); *C12N 2310/346* (2013.01); *C12N 2310/3525* (2013.01)

(58) Field of Classification Search

None

See application file for complete search history.

(56) References Cited

U.S. PATENT DOCUMENTS

| | | | |
|---|---|---|---|
| 5,801,154 | A | 9/1998 | Baracchini et al. |
| 5,872,242 | A | 2/1999 | Monia et al. |
| 5,877,309 | A | 3/1999 | McKay et al. |
| 5,985,558 | A | 11/1999 | Dean et al. |
| 6,133,246 | A | 10/2000 | McKay et al. |
| 6,248,724 | B1 | 6/2001 | Moore et al. |
| 6,582,908 | B2 | 6/2003 | Fodor et al. |
| 6,649,341 | B1 | 11/2003 | Vedeckis et al. |
| 6,656,700 | B2 | 12/2003 | Gu et al. |
| 6,821,724 | B1 | 11/2004 | Mittman et al. |
| 7,122,527 | B2 | 10/2006 | Yoon et al. |
| 7,919,472 | B2 | 4/2011 | Monia et al. |
| 8,372,967 | B2 | 2/2013 | Bhanot et al. |
| 2001/0016575 | A1 | 8/2001 | Miraglia et al. |
| 2001/0053519 | A1 | 12/2001 | Fodor et al. |
| 2003/0022848 | A1 | 1/2003 | Baker et al. |
| 2003/0092616 | A1 | 5/2003 | Matsuda et al. |
| 2003/0166591 | A1 | 9/2003 | Gleave et al. |
| 2003/0180739 | A1 | 9/2003 | Primiano et al. |
| 2003/0190659 | A1 | 10/2003 | Lacasse et al. |
| 2003/0203862 | A1 | 10/2003 | Miraglia et al. |
| 2003/0228597 | A1 | 12/2003 | Cowsert et al. |
| 2004/0018176 | A1 | 1/2004 | Tolentino et al. |
| 2004/0081986 | A1 | 4/2004 | Matsuda et al. |
| 2004/0082534 | A1 | 4/2004 | Gleave et al. |
| 2005/0014257 | A1 | 1/2005 | Crooke et al. |
| 2005/0043524 | A1 | 2/2005 | Bhanot et al. |
| 2005/0053981 | A1 | 3/2005 | Swayze et al. |
| 2005/0074801 | A1 | 4/2005 | Monia et al. |
| 2005/0142581 | A1 | 6/2005 | Griffey et al. |
| 2005/0164271 | A1 | 7/2005 | Bhanot et al. |
| 2005/0203042 | A1 | 9/2005 | Frieden et al. |
| 2006/0025373 | A1 | 2/2006 | Bhanot et al. |
| 2006/0063730 | A1 | 3/2006 | Monia et al. |
| 2006/0160760 | A1 | 7/2006 | Bhanot et al. |
| 2007/0031844 | A1 | 2/2007 | Khvorova et al. |
| 2007/0066557 | A1 | 3/2007 | Monia et al. |
| 2009/0062131 | A1 | 3/2009 | Mounts |

(Continued)

FOREIGN PATENT DOCUMENTS

| | | |
|---|---|---|
| CA | 2588023 | 8/2006 |
| JP | 2003265184 | 9/2003 |

(Continued)

OTHER PUBLICATIONS

Flanagan et al., "The development of C-5 propyne oligonucleotides as inhibitors of gene function" in Applied Antisense Oligonucleotide Technology, 1998, Stein & Krieg ed., Chapter 9, pp. 175-191.

Altmann et al., "Novel Chemistry" Applied Antisense Oligonucleotide Technology (1998) Stein & Kreig (eds.) Wiley-Liss, Inc., pp. 73-107.

Bamberger et al., "Glucocorticoid receptor beta, a potential endogenous inhibitor of glucocorticoid action in humans" J. Clin. Invest. (1995) 95(6):2435-2441.

Braasch et al., "RNA interference in mammalian cells by chemically-modified RNA" Biochemistry (2003) 42:7967-7975.

Branch et al., "A good antisense molecule is hard to find," TIBS (1998) 23:45-50.

(Continued)

*Primary Examiner* — Sean McGarry

(74) *Attorney, Agent, or Firm* — Ionis Pharmaceuticals, Inc. Patent Dept.

(57) ABSTRACT

Provided herein are methods, compounds, and compositions for reducing expression of GCCR mRNA and protein in an animal. Such methods, compounds, and compositions are useful to treat, prevent, delay, or ameliorate metabolic disease, for example, diabetes, or a symptom thereof.

24 Claims, No Drawings

(56) References Cited

U.S. PATENT DOCUMENTS

| | | | |
|---|---|---|---|
| 2009/0306357 A1 | 12/2009 | Bhanot et al. |
| 2010/0222412 A1 | 9/2010 | Monia et al. |
| 2013/0143943 A1 | 6/2013 | Bhanot et al. |

FOREIGN PATENT DOCUMENTS

| | | |
|---|---|---|
| WO | WO 88/00975 | 2/1988 |
| WO | WO 00/49937 | 8/2000 |
| WO | WO 00/58337 | 10/2000 |
| WO | WO 01/42307 | 6/2001 |
| WO | WO 01/77344 | 10/2001 |
| WO | WO 02/096943 | 12/2002 |
| WO | WO 03/008583 | 1/2003 |
| WO | WO 03/062453 | 7/2003 |
| WO | WO 03/070887 | 8/2003 |
| WO | WO 03/070888 | 8/2003 |
| WO | WO 03/085110 | 10/2003 |
| WO | WO 03/099215 | 12/2003 |
| WO | WO 2004/034969 | 4/2004 |
| WO | WO 2004/048606 | 6/2004 |
| WO | WO 2004/094636 | 11/2004 |
| WO | WO 2005/005599 | 1/2005 |
| WO | WO 2005/019418 | 3/2005 |
| WO | WO 2005/023986 | 3/2005 |
| WO | WO 2005/023995 | 3/2005 |
| WO | WO 2005/042030 | 5/2005 |
| WO | WO 2005/071080 | 8/2005 |
| WO | WO 2006/034348 | 3/2006 |
| WO | WO 2006/086739 | 8/2006 |
| WO | WO 2007/035759 | 3/2007 |

OTHER PUBLICATIONS

Bray et al., "Variations of the human glucocorticoid receptor gene (NR3C1): pathological and in vitro mutations and polymorphisms" Hum. Mutat. (2003) 21(6):557-568.

Breslin et al., "Multiple promoters exist in the human GR gene, one of which is activated by glucocorticoids" Mol. Endocrinol. (2001) 15(8):1381-1395.

Brubaker et al., "Structure-function of the glucagon receptor family of G protein-coupled receptors: the glucagon, GIP, GLP-1, and GLP-2 receptors" Recept. Channels (2002) 8(3-4):179-188.

Cadepond et al., "Heta shock protein 90 as a critical factor in maintaining glucocorticosteroid receptor in a nonfunctional state" J. Biol. Chem. (1991) 266(9):5834-5841.

Chakravarti et al., "Role of CBP/P300 in nuclear receptor signalling" Nature (1996) 383(6595): 99-103.

Chen et al., "Multiple glucocorticoid receptor transcripts in membrane glucocorticoid receptor-enriched S-49 mouse lymphoma cells" Journal of Cellular Biochemistry (1999) 74:418-429.

Chin "On the Preparation and Utilization of Isolated and Purified Oligonucleotides" Document purportedly located on a CD-ROM and contributed to the public collection of the Katherine R. Everett Law Library of the University of North Carolina on Mar. 14, 2002.

Chrousos, "The hypothalamic-pituitary-adrenal axis and immune-mediated inflammation" N. Engl. J. Med. (1995) 332(20):1351-1362.

Crooke et al., "Basic Principles of Antisense Therapeutics" Antisense Research and Application (1998) Chapter 1:1-50.

Dean et al., "Antisense oligonucleotide-based therapeutics for cancer" Oncogene (2003) 22:9087-9096.

Deroo et al., "Glucocorticoid receptor-mediated chromatin remodeling in vivo" Oncogene (2001) 20(24):3039-3046.

Elbashir et al., "Analysis of gene function in somatic mammalian cells using interfering RNAs" Methods (2002) 26:199-213.

Encio et al., "The genomic structure of the human glucocorticoid receptor" J. Biol. Chem. (1991) 266(11):7182-8188.

Engelmann et al., "Downregulation of brain mineralocorticoid and glucocorticoid receptor by antisense oligodeoxynucleotide treatment fails to alter spatial navigation in rats" Eur. J. Pharmacol. (1998) 361(1):17-26.

Expert Panel on Detection, Evaluation, and Treatment of High Blood Cholesterol in Adults, "Executive Summary of the Third Report of the National Cholesterol Education Program (NCEP) Expert Panel on Detection, Evaluation, and Treatment of High Blood Cholesterol in Adults (Adult Treatment Panel III)" JAMA (2001) 285(19):2486-2497.

Freier & Watt, "Basic Principles of Antisense Drug Discovery" in Antisense Drug Technology: Principles, Strategies, and Applications, 2nd edition, Crooke ed., 2008, Chapter 5, pp. 117-141.

Freier, "Methods of Selecting Sites in RNA for Antisense Targeting" in Antisense Drug Technology: Principles, Strategies, and Applications, Crooke ed., 2001, Chapter 5, pp. 107-117.

Friedman et al., "Phosphoenolpyruvate carboxykinase (GTP) gene transcription and gyperglycemia are regulated by glucocorticoids in genetically obese db/db transgenic mice" J. Biol. Chem. (1997) 272(50):31475-31481.

Fryer et al., "Chromatin remodelling by the glucocorticoid receptor requires the BRG1 complex" Nature (1998) 393(6680):88-91.

Gautschi et al., "Activity of a Novel bcl-2/bcl-xL-Bispecific Antisense Oligonucleotide Against Tumors of Diverse Histologic Origins" J. Natl. Cancer Inst. (2001) 93:463-471.

Geary et al., "Pharmacokinetics of phosphorothioate antisense oligodeoxynucleotides" Curr. Opin. Investig. Drugs (2001) 2(4):562-573.

Gehring et al., "Assignment of the human gene for the glucocorticoid receptor to chromosome 5" PNAS (1985) 82(11):3751-3755.

Gettys et al., "RU-486 (Mifepristone) ameliorates diabetes but does not correct deficient beta-adrenergic signalling in adipocytes from mature C57BL/6J-ob/ob mice" Int. J. Obes. Relat. Metab. Disord. (1997) 21(10):865-873.

Giguere et al., "Functional domains of the human glucocorticoid receptor" Cell (1986) 46(5):645-652.

Godfray et al., "The Potential of Antisense as a CNS Therapeutic" Expert Opin. Ther. Targets (2003) 7(3):363-376.

Grunweller et al., "Comparison of different antisense strategies in mammalian cells using locked nucleic acids, 2'-O-methyl RNA, phosphorothioates and small interfering RNA" Nucleic Acids Research (2003) 31:3185-3193.

Hansen et al., "Glucagon receptor mRNA distribution in rat tissues" Peptides (1995) 16:1163-1166.

Heiske et al., "Differential effects of antidepressants on glucocorticoid receptors in human primary blood cells and human monocytic U-937 cells" Neuropsychopharmacology (2003) 28:807-817.

Hittelman et al., "Differential regulation of glucocorticoid receptor transcriptional activation via AF-1-associated proteins" Embo J. (1999) 18(19):5380-5388.

Hollenberg et al., "Primary structure and expression of a functional human glucocorticoid receptor cDNA" Nature (1985) 318(6047):635-641.

Honda et al., "Expression of glucocorticoid receptor beta in lymphocytes of patients with glucocorticoid-resistant ulcerative colitis" Gastroenterology (2000) 118(5):859-866.

Jiang et al., "Glucagon and regulation of glucose metabolism" Am. J. Physiol. Endocrinol. Metab. (2003) 284:E671-E678.

Karin, "New twists in gene regulation by glucocorticoid receptor is DNA binding dispensable?" Cell (1998) 93(4):487-490.

Kenyon et al., "Glucocorticoid receptor polymorphism in genetic hypertension" Journal of Molecular Endocrinology (1998) 21:41-50.

Khvorova et al., "Functional siRNAs and miRNAs Exhibit Strand Bias" Cell (2003) 115:209-216.

Konishi et al., "Inhibition of HBV replciation by siRNA in a stable HBV-producing cell line" Hepatology (2003) 38:842-850.

Korte et al., "Antisense to the glucocorticoid receptor in hippocampal dentate gyrus reduces immobility in forced swim test" Eur. J. Pharmacol. (1996) 301(1-3):19-25.

Kumar et al., "High-Throughput Selection of Effective RNAi Probes for Gene Silencing" Genome Research (2003) 13:2333-2340.

(56) References Cited

OTHER PUBLICATIONS

Lee et al., "Mammalian APH-1 interacts with presenilin and nicastrin and is required for intramembrane proteolysis of amyloid-beta precursor protein and Notch" The Journal of Biological Chemistry (2002) 277:45013-45019.
Leung et al., "Association of glucocorticoid insensitivity with increased expression of glucocorticoid receptor beta" J. Exp. Med. (1997) 186(9):1567-1574.
Link, "Pharmacological regulation of hepatic glucose production" Curr. Opin. Investig. Drugs (2003) 4(4):421-429.
Martinez et al., "Single-stranded antisense siRNAs guide target RNA cleavage in RNAi" Cell (2002) 110:563-574.
Matveeva et al., "Thermodynamic criteria for high hit rate antisense oligonucleotide design" Nucleic Acids Research (2003) 31:4989-4994.
Miyagishi et al., "Comparison of the suppressive effects of antisense oligonucleotides and siRNAs directed against the same targets in mammalian cells" Antisense and Nucleic Acid Drug Development (2003) 13:1-7.
New England Biolabs 1998/99 Catalog (cover pages and pp. 121 and 284).
Nie et al., "A specificity and targeting subunit of a human SWI/SNF family-related chromatin-remodeling complex" Mol. Cell. Biol. (2000) 20(23):8879-8888.
Oakley et al., "The human glucocorticoid receptor beta isoform. Expression, biochemical properties, and putative function" J. Biol. Chem. (1996) 271(16):9550-9559.
Opherk et al., "Inactivation of the Glucocorticoid Receptor in Hepatocytes Leads to Fasting Hypoglycemia and Ameliorates Hyperglycemia in Streptozotocin-Induced Diabetes Mellitus" Mol. Endocrinol. (2004) 18:1346-1353.
Orti et al., "Agonist-dependent phosphorylation and nuclear dephosphorylation of glucocorticoid receptors in intact cells" J. Biol. Chem. (1989) 264 (17):9728-9731.
Peng et al., "Silencing expression of the catalytic subunit of DNA-dependent protein kinase by small interfering RNA sensitizes human cells for radiation-induced chromosome damage, cell killing, and mutation" Cancer Research (2002) 62:6400-6404.
Pepin et al., "Decreased glucocorticoid receptor activity following glucocorticoid receptor antisense RNA gene fragment transfection" Mol. Cell. Biol. (1991) 11(3):1647-1653.
Pepin et al., "Impaired type II glucocorticoid-receptor function in mice bearing antisense RNA transgene" Nature (1992) 355(6362):725-528.
Picard et al., "Two signals mediate hormone-dependent nuclear localization of glucocorticoid receptor" Embo J. (1987) 6(11):3333-3340.
Pujols et al., "Expression of glucocorticoid receptor alpha- and beta-isoforms in human cells and tissues" Am. J. Physiol. Cell. Physiol. (2002) 283(4):C1324-1331.
Quesada et al., "Physiology of the pancreatic α-cell and glucagon secretion: role in glucose homeostasis and diabetes" J. Endocrinol. (2008) 199:5-19.
Randall et al., "Clearance of replicating hepatitis C virus replicon RNAs in cell culture by small interfering RNAs" PNAS (2003) 100:235-240.
Ray et al., "Physical association and functional antagonism between p65 subunit of transcription factor NF-kappa B and the glucocorticoid receptor" PNAS (1994) 91(2):752-756.
Reichardt et al., "DNA binding of the glucocorticoid receptor is not essential for survival" Cell (1998) 93(4):531-541.
Reynolds et al., "Rational siRNA design for RNA interference" Nature Biotechnology (2004) 22(3):326-330.
Richards et al., "Energy balance and lipid metabolism in transgenic mice bearing an antisense GCR gene construct" Am. J. Physiol. (1993) 265(1 pt 2):R146-R150.
Rosmond, "The glucocorticoid receptor gene and its association to metabolic syndrome" Obes. Res. (2002) 10(10):1078-1086.
Saetrom et al., "A comparison of siRNA efficacy predictors" Biochemical and Biophysical Research Communications (2004) 321:247-253.
Saetrom, "Predicting the efficacy of short oligonucleotides in antisense and RNAi experiments with boosted genetic programming" Bioinformatics (2004) 20(17):3055-3063.
Sanghvi et al., "Heterocyclic Base Modifications in Nucleic Acids and Their Applications in Antisense Oligonucleotides" Antisense Research and Applications (1993) pp. 273-288.
Schaaf et al., "Molecular mechanisms of glucocorticoid action and resistance" J. Steroid Biochem. Mol. Biol. (2003) 83(1-5):37-48.
Schwarz et al., "Asymmetry in the Assembly of the RNAi Enzyme Complex" Cell (2003) 115:199-208.
Scott, "Diagnosis, prevention, and intervention for the metabolic syndrome" Am. J. Cardiol. (2003) 92(1):35-42.
Steckler et al., "Conditioned Activity to Amphetamine in Transgenic Mice Expressing an Antisense RNA Against the Glucocorticoid Receptor" Behavioral Neuroscience (2001) 115(1):207-219.
Tilesi et al., "Design and validation of siRNAs and shRNAs" Current Opinion in Molecular Therapeutics (2009) 11(2):156-164.
Vickers et al., "Efficient Reduction of Target RNAs by Small Interfering RNA and Rnase H-dependent Antisense Agents" J. Biological Chem. (2003) 278(9):7108-7118.
Watts et al., "Reduction of Hepatic and Adipose Tissue Glucocorticoid Receptor Expression with Antisense Oligonucleotides Improves Hyperglycemia and Hyperlipidemia in Diabetic Rodents without Causing Systemic Glucocorticoid Antagonism" Diabetes (2005) 54:1846-1853.
Weinberger, "Identification of human glucocorticoid receptor complementary DNA clones by epitope selection" Science (1985) 228(4700):740-742.
Woolf et al., "Specificity of antisense oligonucleotides in vivo" PNAS (1992) 89:7305-7309.
Wrange et al., "The purified activated glucocorticoid receptor is a homodimer" J. Biol. Chem. (1989) 264(9):5253-5259.
Yiu et al., "Filtering of Ineffective siRNAs and Improved siRNA Design Tool" Bioinformatics (2005) 21(2):144-151.
European Search Report for application EP 11152132.4 dated Aug. 1, 2011.
International Search Report for application PCT/US12/61984 dated Mar. 18, 2013.
International Search Report for application PCT/US2006/036527 dated Jan. 10, 2007.
Database EMBL [online] "Method for estimating binding between a low-molecular-weight compound and a protein"; database accession No. EMBL: DD435349, Jul. 3, 2007.
Liang et al., "Antisense oligonucleotides targeted against glucocorticoid receptor reduce hepatic glucose production and emliorate hyperglycemia in diabetic mice" Metabolism, Clinical & Experimental (2005) 54(7): 848-855.

SEQUENCE LISTING

```
<160> NUMBER OF SEQ ID NOS: 69

<210> SEQ ID NO 1
<211> LENGTH: 162001
<212> TYPE: DNA
<213> ORGANISM: Homo sapiens

<400> SEQUENCE: 1

aggctgttgc gtatgtgagt ctggagttcg gaagagacat ccaagttgct gacataaatt     60

tcggtcttca gtgtagaaat ttgatttaaa gccattgggt taaacaaacc aaccaaggta    120

agagtatttg caggtaagag aagagaccca aggacttagc cctaaggcac tccagcatta    180

tgatgtaggg gagatgagga accagcaaag gaggctgaat ggaaacagag aaggaatggc    240

gagttctgtg caagagacag gaagaaagag aatgcaaaat ggtcaaacaa taaataatta    300

agttgaatta gatggtaaag aaataaatgc aaggaaatgc aaggccatag tcactgggca    360

gacagagtaa aagaacatga tgaatcaggt gagattaatc acccctcctg gaactatcag    420

aaaaagatac tcactgacag tgaggcagtc atgttagtcc ccaagttgat gactaatgga    480

aactaaggtc acagtgcaca ttaatttctt ttgaagcaaa ggataaaaac aaacaaaata    540

taaaagatta agatgtaaac gttagtgtac actaattcag agaagaatta aatgattttt    600

aaaacttcaa gaaggaggac agcattctaa atgcattgtt ctaaaacgat agtaagatgg    660

gataaatagt cacactaggg tgatgatttt ggatgtgtta aatttgtcac tttgagacca    720

gatatgctcc atttcacttc atgccagctt ttaagaacat atatcataga aaaagagaaa    780

agaaacagtt gaatcaaagt gaagagaaat attgtgaagc aaataaatcc agggaaaaat    840

taataaaacc ctattcccac cctaaaaaaa agaaactaaa agaagtgcaa atataaagtt    900

caataggagt cattagagat tgtaaattgg gctctgagct tcctaccaac aaaagcacaa    960

aggaaaatat gatcactggt attaaaaaaa aacacctatg gtttccaaaa gattaaaaca   1020

aaccagcagt tttatagaag ctaacactaa aatctaaagg aactacgttc tatggagcca   1080

cttaatatgg ataaacactt tgacaatatt ctttcaacaa ctacagtaac aagtttctta   1140

gagtccattt ctttttacat ccataatgaa ttgtaaatct tttctacttc ttaagtaaaa   1200

catcaccact taattctggt aacttttcca tattaacttt ttagaacaat tgcaaacgta   1260

ccataaatga ttgttgtcac agtggtaact atttgaccct gactgttatt ttgtatatag   1320

cagcttttaa aataaaaagg caacaagttt ctaggcgtaa tttccacaga tcttttatgt   1380
```

```
aaaacaatga catcctttgc aacttctgcc atttaatcta tctcaagcaa gctctctgga   1440
aacaaatcta tttgaaagat tctattgtaa ttagaaatca gggtaactga atgcactaga   1500
tgaaaacctt ctgactgggg ccaatgaagt caataaagtc aaaactgctg tgaatgctca   1560
actgtctgca gatcagatgt cttgggatgg aatccgttct cgaggccacc atcattaata   1620
tcaatttggc catgtaatac aagcctcact tgttccactg ttacaaatgt gcttaaaact   1680
gagctcattt acaatccaaa tacatatgta ggatggtaac caaggcatca cactaattta   1740
ggtattatgt tttaggggga acaaaaggta tgttaatatt ttattcatct ccaaattaac   1800
tataaattgt gcattcttgc atagatcctc cttgggaatg agaaattagg aaaatccagt   1860
tgttaaaatg aatgcctaaa atcaaaataa aatttgtttt tctggcacct gcttgatgac   1920
acagactaat aaccaatgac aaaattgccc ttgaacccaa gttttcattt cctcctattg   1980
tgtggtcagg ttatgtaagg gtttgctttc accccattca aaaggtacct cttcctcttc   2040
tcttgctccc tctcgccctc attcttgtgc ctatgcagac atttgagtag aggcgaatca   2100
ctttcacttc tgctggggaa attgcaacac gcttctttaa atggcagaga gaaggagaaa   2160
acttagatct tctgatacca aatcactgga ccttagaagg tcagaaatct ttcaagccct   2220
gcaggaccgt aaaatgcgca tgtgtccaac ggaagcactg ggcatgagt ggggaaggaa   2280
tagaaacaga aagagggtaa gagaagaaaa aagggaaagt ggtgaaggca gggaggaaaa   2340
ttgcttagtg tgaatatgca cgcattcatt tagttttcaa atccttgttg agcatgataa   2400
aattcccagc atcagacctc acatgttggt ttccattagg atctgcctgg gggaatatct   2460
gctgaatcag tggctctgag ctgaactagg aaattcacca taattaggag agtcactgta   2520
tttctctcca aaaaaaaaaa agttataccc gagagacagg atcttctgat ctgaaatttt   2580
cttcacttct gaaattctct ggtttgtgct catcgttggt agctatttgt tcatcaagag   2640
ttgtgtagct ggcttcttct gaaaaaagga atctgcgtca tatctaagtc agatttcatt   2700
ctggtgctct cagagcagtt agcccaggaa aggggccagc ttctgtgacg actgctgcag   2760
aggcaggtgc agtttgtgtg ccacagatat taactttgat aagcacttaa tgagtgcctt   2820
ctctgtgcga gaatggggag gaacaaaatg cagctcctac cctcctcggg ctttagttgt   2880
accttaataa caggaatttt catctgcctg gctcctttcc tcaaagaaca aagaagactt   2940
tgcttcatta aagtgtctga gaaggaaggt aggttatatt tttattccca ttctatagct   3000
gggtaaagtg agttctaaca aagttacttg ttaaaggtca ctcagaggtc agagcatcag   3060
aaaaaaagac aatcacaagg ctgatgttgt gtgctggata gtttaaactg aacaggaaga   3120
aaacattttt gtgggcttta tctaaaaaga aatagtttgc tctgagtttc tcagtttcat   3180
ttattcagca agtatgtgcc aagtgctatt gtaggcaatg aagatacagc agggaacaaa   3240
acaaaactga catggagctt ccaactagaa aggagaacga gacaacgcgt tttaaaatat   3300
atataatgtg ttaggtaaaa agtgctataa ggagagctaa aacacaatga gaggctagaa   3360
gagtgatagt ggcggagggg cttctctgag gagatgacat ttgatcaggg gtctgaataa   3420
agtaaagagg ccagttatgt gaatatctgg aagactcaag gggcagggcg gaaatagcca   3480
gtagaaaggc cctgaggtag gaaggtgtgt ggcaagtttg aggaaaagga aagacagtct   3540
gactggagca aagagaactg gagctgaggc catcaaggca gccaggagcc aggtgcagac   3600
tgggctttga ctctgcctgc agggaggaac tgctgaaggt tccaagcaaa ggaccgccct   3660
gacctgcctt aggtttgaac aggatccctc tggctggtgt gtgaagaatt aactgtagat   3720
```

-continued

```
gggcaagtgt ggaaggaagg agagcagtca ggaagctgcc ataaccatct acatgagaga   3780
ggtaaggcct cagatggagg ggagcagtgg aatggtggaa agtgtttatt ttgaatgtta   3840
agcctgcagg agttgctgga ggattggaca tgggggatga gaaaaagaga gaggcttaca   3900
gatcaggtaa tttagctgat cttaagcccc ttacagctta atattattcc aaggtgccaa   3960
taacagccaa ggtaaacaac cttgtcttgg acattctgcc tttatttgcc cacacaagat   4020
gaaattaaat atatatatat atatataatt taaataaata aattatatat atatataatt   4080
taaataaata aattatatat atatatattt agtgctgttt ccatcagcta ctagctgaga   4140
cacttgggca aatgagggtg atctccagtc ctcagtatcc ttgctgttaa tgagagatgg   4200
tcatttcttc tctgcctagc tcaaaagaat atgttaaata aaactctgtg aactttaggc   4260
agcacaggct tagggcttct tagtaacatc atcagcacca tcagagttaa cttcatgagt   4320
cagttgagtt gcctttgggg tatatcatta acagattcca ggaagctccc ctgcccaaaa   4380
gcctcccacc aatggcctgc cttgttgaaa gaattacaca attagcccaa ttcctttcca   4440
ttaaggcatt gtggactcca aacatcctcc tttaaaatgg aaactaaatc gagctactgt   4500
cagtcatttg tccttttagg tgacgttata tatcagatca cttttctgcc attagagcta   4560
gttgaagttt gaatagggaa aaggaacgaa tgaacgtggg gcagagaacg caatagtcgg   4620
tgggttactc agtaggctgt ggacagatgg agaggatccc ggtgggagga gcctctaaag   4680
ataaactttc tatgggaaaa tgttgacaga tttacctgag tcatggtttt tcttacacct   4740
cataaaaatg aaggcttcca agggcagctc cttgaaatag ctgtaacaag tagccacaga   4800
agttgagttg cttaaagaaa aacattgaat tcatggggaa ccgtacgctt taatagcccc   4860
tttggcttac tttgtttaaa caaactcatc ccgagcatct cacacttcac caattttgag   4920
tgtccctgct ttacctcagc cttttaaaga gtgtctttcc cctaaatatt tctggaaatg   4980
cctaagggtg ctgacgtgca gccagaaata gttcacttct gtccccacta tggcaggaat   5040
ccatggacca aggctctgat gtttccacaa agatgcccct caggactaga aatctgtccc   5100
catccccgtt gccaccacag tcaccatcac ctggaaatcc tgcaggacca atgtttgtga   5160
atttggaata tatgctagat gccttactac cttgttatga ccttatttct ttatagcact   5220
tttaacctag cgcattacat attttaaatg tataattcag cgatccagat cactggtcca   5280
gtgtcacctc ccactcagca aagtgagatg aacacacttg gtgctacatt cagctaggct   5340
ggcactgtag atgcacccag tcccaggtat tctagtggct catgacaggg cttcctcact   5400
ggagacatgc tgagccaagc aaggcagttt ttaccaccaa ccctgatagt cgtacacata   5460
ttctgctcct ccacccccac caaggttgaa actccgctcc tgtcagcttt gcagctacca   5520
ccaccccctc agggagagtc atctctgttc ccaaacccat ataaatgtca ttcaaagcca   5580
gaggatgtaa ttgctgtagt aattgttata gtccactcat ccaggggccc cactgcaaag   5640
ctgattaaac catagtgtta ctacctttta cagagttatt attcttccaa atcaacccac   5700
tgcacctttc tccaaggcta caaaagtgcc cctagggtgg ctgtgtacag gcaagttttg   5760
atgtcagctg ggaaactacc tataaccccc actctctgct aacaccaact tttctttttc   5820
tattttattt tattttattt tactttaagt tctgggatac atgtgcagaa cgtgccggtt   5880
tgttacacag gtatgcatgt gccatggtgg cttgctgcac ctatcaaccc accacctagg   5940
ttttaagcct cgcatgcatt aggtatttgt cctgatgctc tccctcccct taccccccac   6000
cccctgacag gcccgggtat gtgatgttcc cctccctgtg tccacatgtt ctcattgttc   6060
aactcccact tatgagtgag aacatgcata acaccaattt ttcttattgg aattgtagtg   6120
```

```
ccagtttagt tcttcagtgg aagcacttgt tcttctctat aatctgttct ccatctggga   6180
acaccctact ttctcagaca taggtttgca gtgcattggt gggcaggatt tcagtccttt   6240
ctctgaaagt tcctaagccc tattgaaaaa tgaatgcact ggggaagggt gtggcccatc   6300
tctctcccca gaagctcctg agccacattt cttacccagt cccggaaccc tggtatccta   6360
aaccatgtct gaacctgtac ccctgtggcc ccagaaaggg accaaacagt acatcccatg   6420
aaaccacaaa gagatcataa ccttctcctc tctcctccca catctctaca taaacaacat   6480
ttatatagat gactgaattc aagatacgtt tatttggtac tgatggtcaa ctggaagttc   6540
ctaagcagaa ttacttataa tgtgggactg tgtttttagt ggttgcagtg aaggctcaac   6600
accoctaaac acggtgggaa cttgctgagg aggcaggctg tgaagggcag ggtattagca   6660
tctttcctta aaataacatg tgtcttagtg tgctcaggat gctacagtaa aaataccata   6720
gatttggtgg cttaaacaac aaacatttat ttctcacagt ctggaggctg tgaagtccaa   6780
gatcaaggca ctgacagatc cagtgtctgg taaaggcctg catcctagtt catagcccgc   6840
tgtcttctca ctgtcctcaa gaggctgaaa gggtgagaga gctcttccga gactctttca   6900
taagggcact aatcccattc atagggctcc accttcatga cctaattact tacaaaggcc   6960
ctacctccta ataccatcat attgggggtt aggatttcaa cgtatgaatt ttggggagac   7020
acaaacattc agtctatata acaacacgta ccgtgaaact ttcctactca taaaagtaat   7080
atatcttcac tggagaaagt aaaaaagtac agaaaaatat gtagaagaaa atctaccatc   7140
atctcacatc cagagatatc catggtaaat attttaatac aattcctgtg aagttattca   7200
gtacacatta atagagtttg aaaacataat ctaatataaa agcatgaaat tcataaagat   7260
attttaaaat aaagttaata tgtatgtgtg tatatgtatt tttatatata cacaaacata   7320
tatgcttatt atttttattg tgagcattcc cccatattat tagaaaacca tgattttttg   7380
ttctttttct ttttctttc ttttcttttt tttttttgga gatggagtct cactctctca   7440
cccaggctgg agtgcagtgg tgcaatcttg gcttactgca acctccacct cccaggctca   7500
agcaattctc ctgcctcagc ctcccgagta acagggatta caggcccctg ccaccatgcc   7560
catctaattt ttttgtattt ttagtagaga tggggtttca ccatgttggc caggctggtc   7620
ttgaactcct gacctcaggt gatctgccca cctcggcctc ccaaagtgct ggaattacag   7680
gcataagcca ccgcaccaga ccaaaaacca tgatttttga tggcatcatc ttatggatgc   7740
aatataatta atttaaccat tcttctacta gttaatatta aggtcatttc caacttttat   7800
tgttgttaca ttgcctctca ttttctttat aaatatttgg ctctttttat tttggatatg   7860
ttgtagctaa aatgccatcc agatagttta ttctgattta gtgcccacca ggttctaggt   7920
gcatgactgc catagcagag atagttgcat acagttcaag tttagatttt gtttgtgagc   7980
gggagaatcc aaagaccaag ttcctaatat tcttttgcct gaaaaatggc tacataacct   8040
tgccaaatct cttaacattt tcatgccttt gtttctaata tggaaaatga agatactcac   8100
caatttgtaa ctgtaaacta ctacacaaga atgaggtatt catttaacca tatggtgaga   8160
ttttgtagtt aaaattaatt aattgtgctc agtggtcaga ctactggctt taaatcctgg   8220
atccattatt cattacttcc tattgtgtaa cctgggcaag ttacttaact tctcttctcc   8280
ttagtttcct catctataaa atgaataaca gaagcactta ccataagtga ggatgagata   8340
agatggtggt atatgtgagt ggtacacatc tgttactatt attatcattg ttatttatta   8400
ttaagcagtg aatttagact caatgtgaaa tggtttagaa gtcatcagct tcccgtttca   8460
```

-continued

```
tgttcttaaa gcactggtga taagagtatg cctgtatcat gcagttataa ctttaatcaa   8520
aatatgaaag taactttaat caaaatgcca agtcaaatta gcaaagtcag cccttttcaa   8580
aatgtgtgcc ctaaagtaat aaggtctgca gggtgtgccc cagggacctt tggtggggag   8640
tgggtggtag tcagaatggc gaaaacagtg gggattttta gggcccccac tcacattgct   8700
ttgcttttat agcaaaaatt gttggctgat gaacaaaatc atttcctttt cttggactca   8760
cagctagacc taacttccca agtcctgtac agttaaatgt taccatacaa ttacagtgga   8820
gccatatgtg tctgtctcaa ccacccaagc ctgccattgc agtgtgaaag cagccatagg   8880
caatacttaa acaaagggat gtgctgtgtt ccaataaaat gttaccaaac tttcctatag   8940
tttgccagcc cctgaactag agcatggtaa ggcaagagag aattgtagaa cgtggttgga   9000
aaggcagaag gagtcaggga ggaaagacct tgtggaactc tagcacaaag tttggatttt   9060
atcctaaaag cagaagggaa gcctttgaag ggttttagaa aagggtatga cctgaattac   9120
agaagctcag tcctcagcag atcagtattt caacattcac tcaccatgtg aaccattgat   9180
cccattttgt tacttcctct gtagaatctc ctcttaagga aattgaaagc aagctcctga   9240
atgagatggc attttcaggg aaagaccagg aggcagaccc caaggggctt cacaagatgg   9300
catttttgtg gccttggtgg atttgccatg accttggctt ggcaggatca gaaacctgaa   9360
tctattcgcc tgtaagtcct cttttcttgt aagtcctata agacttacac taagttcagg   9420
tgattaacat attaagtcaa aaagcccatt ttagtaattt ttaatgaaaa acataattgc   9480
cacatgtgag aagcccattc tattttcata gacatactta tattagaata acaatgacca   9540
taatggttag catttattaa caataacatt gtgccaggca cagtgtcaag cattttccat   9600
gatgacctca caagtctatc ggtaggaatt gtggttaaaa ccctcttata gataaagtca   9660
gaggttctaa acttataaga tcacaatgct agtgagtggt agagatgaga tttgaaccca   9720
cacagtgtaa accagagtgt ggatacctag ccactacaac atagtgtctc ataggagaca   9780
tgttcagaag gttgctagtg gacattgaat ccatggggga aaagaaggca gaaaaatctg   9840
attttaatgt tatcaggtta atggggcctg atgcagccat cttgcagaag aacggtattg   9900
ctagcaggtc ctccatgttt gtttacaaca ctggctacgg ccttcccact aggatgggaa   9960
ttcccaaatc ctataatttc ctagatggtg ctggaagagg cactgctgag gtttgttttg  10020
ccaactatct ttcccctctt cttcttgcct tatttgtcat tctatccatt aaggtgactt  10080
ttcatccatt ttatatgaat ttcataatta acctctcagg gtaattcccc cagcccaccc  10140
tactatcagg gcagtcccca atatgactaa tcattcccac atactaagac cacagactgc  10200
ttcagaatct gtatttatat tttcactatt aaaaaactat gctatcgttt cctgaaatct  10260
ctatgaaaaa aaaatactaa gctatatctg gagtgaaatg gtcagtaaga acacagtttg  10320
tcacacaaaa taatgaaaat gctatttctt acttatagtg cagactgggg ttcttcctct  10380
agaattagaa atattaggct tgctaagatg tgatggggag ttcattgggg ctagtgtttt  10440
agcttttgaa ctcttcaaaa ggaacagaaa tgaagaaaaa gacctgcttt aataaacaag  10500
gttaagtctg tatgatttat ggacttatga gcaaatctga catccactca catgggtggt  10560
cctcccaagg gataaacttc gtaaaagcac atttaagaaa aagggagcag atactgttgg  10620
tgccctcttc accaggagac acactgaaag gctgcagtag cacatcagag cctcacaggt  10680
cagcatcagc caaacagctg ttctgtgcat cacaagaatt cgtacatatt tcaaaatgac  10740
taatttgtac ctatgagaca ggatttgacc cactaatttt tgtaccgtaa cgttttaata  10800
aaaattgttt tttcaaagcg aagctttgct gagcagatga attatcatgt gggagtttaa  10860
```

```
aaattagtca aaggagtctt gacaactaag tcctttaagc ttggccttcc cttggcctct  10920
gcctactcct gatcataatc tgaataaact ttaacttttc gactagaatg caaaacacgt  10980
gtttttgtaa aacgaatatt aatggcataa ctcgtgcttt attattttag ctgatttgta  11040
tcaatgtatc aacattccaa agaaaatagg gagcatatgt tggttaataa tttttgttat  11100
gactattgac atgtaattca catgacataa actttaccat tttaaaaagt acaattcagt  11160
gagtttgagt atgttcttaa ttttgtacaa ccatccccgc tatcaaattt caaagcatat  11220
ccatcacacc aacaataaac tctggttcta ttagtagtca ctcccaattc ccttttccct  11280
agccccctgg cgaccactaa ttaattattt ctctgtctct atggatttgc ctaccatgaa  11340
cattgcatat aaatggaatc acacaatatg tagtcttttg tgtctggcac cttccactca  11400
acatactgta ttaaaggttt ctccatgtta tagcatgcat cgatccacac ttcatttcct  11460
gttatggctg aataacattt tgtcctctga atctaccata tttgtttatc cactcatgag  11520
ctgatcactt aggctgttgc cacttattag ctattatgaa taatgttgtt atgaacgttc  11580
atgtacaagt ttttgggcag acatgttatt tctcctgggt aaattcctag gagttgaatt  11640
gctgggtcat atagtaactc tatgtttacc tttttgagaa aactgccaat atgttttcca  11700
cagtgtctga accattttat aatttcgctg gcaatgtatg agagttccac tttctccaca  11760
tcttcaccaa catttatttt cctttttta aaaaacaatt attgctgtcc tagtgggtat  11820
gaagtgatat ctcctgtatt ttcaatttgc atttctgtaa tgaataatga tattgtgcat  11880
cttttatgtg cttattggct agttgcacat cttctttaga gaactatcag gtcatttgcc  11940
ttttttgaa atgttggttg tctttttatt gttgaaatat aaaagttctt tatatattct  12000
agatctagac ctttactgga tatatgactt gcaaattcta ccatttctgt acgttgtcta  12060
caatttcaac cattctgtgg gttgtctttt tattttcttc acaacgtctt ttgaagcaga  12120
atagtttttc attgtgatga agtccagttt gactattttt ttcttgtgct tttggtattg  12180
taactaacaa accattgact aatccgagat tctgatgtac atacatgctt tcttctaagt  12240
tttataattt tagcttttac atttaagttt ttaatccatt ttgagttaat tttttaaata  12300
ttcttttgca tgtagctatc cagttgtccc aatgctattt gttgaatagg tgattctttc  12360
ctcattgaat ggtcttggta ttcttgtaaa aaatcagttg actgtaggca tatgggtttc  12420
tggactctca attctacccg actgatctga atgcctatcc tcatgccagt actacactgt  12480
cttgattact gcagctttgt agtatgtaag tagtagtacg ttttgtgagt cctcgaactt  12540
tgcctttttt tatagattgt tttgctattt tgagttaagt atttttttaa aacatcaagt  12600
taaaaatgaa gctgccactc tctaaaggag gacaatttca gaaaggcact gagacctgtg  12660
cttggtatgt agtaggtgct tttgaaaatg tttgttgcat ggaatggatt gatttcatct  12720
ctattctaac actcaatgcc atgttcattt ccccttttgga gcctttcatc tctcccttct  12780
cttttctaag aaaatcagta actctctcat tcatacattg tacacataca tatctttatt  12840
tgtttatgtg tctattttcc actaattaga ctataatgcc atataaggct agaattacat  12900
ctaattcatt gctgggtccc aaagccatgc ttaagaccat aagtatatag gggtttttt  12960
tcttttaaaa agtttttatt tttaattatt atggatacat aagagttaca gatatgtaaa  13020
gggtacatgt gacattttga tacaagcata caccatataa tgatcaaatc agggtaactg  13080
ggatatccgt cacctcaagc atttgtaatg tatttgtgtt agaagcattg caattccact  13140
cttagttatt ttgaaatata caataaattt ttgttaactg tagtcaccct gttgtctact  13200
```

-continued

```
gaacactaga tcttattcct catatctgac tgcattttcg tatccattaa acacccctct  13260
tttttatttt ttattttatt tattattatt atactataag ttttagggta catgtgcaca  13320
atgtgcaggt tagttacata tgtatacatg tgccatggtg gtgcgctgca cccattaact  13380
cgtcatctag cattaggtat atctcccaat gctatccctc ccccctcccc acaccccaca  13440
acagtcccca gagtgtgatg ttccccttcc tgtgtccatg tgttctcatt gttcaattcc  13500
cacctacgag tgagaatatg cggttaaaca ccccctcttt atcccccctc cccactaccc  13560
ttcccagacc ctagtaacca tcattctatt ctttctctct ctgagttccc acatatgagc  13620
aagaaatgtg atatttgtct ttctgtgcct ggcttatttc tcttgcataa tgtcctccag  13680
ttccatccat gttgatgaaa gagacataat ttcattcttt tttatggctg aataacattt  13740
cattgtgtat atgtacaaca ttttctttat tcatctgttg gtggacactt aggttgattc  13800
cataccttgg ctattgtgaa tagtgctgcg gtaaacatgg gagtgcagat atctcttcga  13860
tatactgatt ttctttcttt tgggtatatg tccagcagtg ggattgctgg gtaatatggt  13920
agctctattt tgttgttgtt gttgttttta ggaaccttca tactgttctc catagtggct  13980
gtactaattt acgttcccac caacagtgta tgagggttcc cctttctcca cacttttgag  14040
agcatccgta attccctgtc tttttgatag aagcaatttt cactgggatg agatgatatc  14100
tcattgtagt ttagacttat atttctctga tgattaagga tgttgagtat ttttggccat  14160
tcgtatgtca tctattcaga tcttttgacc atttttaaat caaattattt tttcctattg  14220
agttgtttac acaacttata tattctgttt attaatccct tatcagatag gtagcttcca  14280
gatattttat tccattctgt gagttgtctc ttcactttgt tgatggtttc ctttgctgtg  14340
cagaagcctt ttagcttgag gtgatctcat ttgtccactt ttgcactggt tgactgtgct  14400
tttgatgtct tattcaaaaa atatttggcc agaccaatgt catctcttgc catatacaaa  14460
aatcaaatca aattggatta aaaacctaaa tcgaaggcct gcaagtatga aaccactaga  14520
ataaaacaat atatatgtgt tggagggaga gaagaaagta atgaagaaag aaaggccagg  14580
tgagaaagta agagagaagg gaaaatgaac aagaaagaca aaagtcattc caggcactgt  14640
tttaaggggc atctcattta ttcttacaac cttatgagat aagcactctt actttcagtt  14700
tgttcaggat gctataacag aatcccatag actgcgtggg ttataaacaa tagaaattta  14760
tttctcttag ttctagtgac tgggaagtcc atgatcaagg cactgacaga actgttatct  14820
ggtgaggacc tgcttcctgg tttacaaatg gacagccatc ttctcttctt gctttgtcct  14880
cacatggtgg gaaggggtaa agaagctccc tgaggcctct tttatatggg cactaatccc  14940
attcatgagg gctctgccct catgaccaaa tcacctccca aaggttccac ctcctaatgc  15000
catcaccatg ggggttaggat ttcaacagga atttggaaag gacacagaca ttcagaacat  15060
agcaccccca ttttacagat aagaacagtg agaaacagag agttaaataa ttttctcaag  15120
gtcatacaac gaacccgtag cctaggcagc ctggctcttt ggtcatgttc ttaaatacta  15180
tgccatactg tctctcaaat aaacactaaa atcaagatac ttgggatgat cgttgggagg  15240
cagagcccag atatctatac tttaaacaaa ttcccaaatg atctgatggg caactcagat  15300
gaaaatcaat gcttcaagaa atagccaaat aaaactctat ggaaggtaaa gatggggaga  15360
gcttggtgag atgtcatact tgggaggaaa agccagggaa agtaagagaa aactgggtat  15420
tagtaaagat catggagaag ggaaaacaca agatattgct aggctaaaaa agaggcagac  15480
ctgatgaagc agtgaacacc acttcagcca ctccctacct tggccccagc tggccctggc  15540
tgtgactgtg ttccatactc tgcaatgaca tgtaacttcc accacgtcca tatcatacct  15600
```

```
aaagcctact tcagtgtgtc cacaaaagca agtaagaata aaaagtaaga gaaacaactc  15660
acatttattt gctgcttatt atgtgccagg ctatgtcctt ttttttttga gatagagtct  15720
cactctgtca cccaggctgg agtgcagtgg tgtgagcttg gctcactgca acttctgcct  15780
cctggggtca agtgattctc ctgcctcagc ctcccaagtg gctgaaatta caggcacgtt  15840
tagtagagat ggggttttgc tatgttggcc aggctgatct tcaattccag acctcaagtg  15900
atgtgcccac ctcagcctca caaagtgctg ggattacagg tgtgagcctc cacacccatg  15960
tgccaggcta tgttttaagt gctctaccca tgagaactca cttagtcctc ataacaatcc  16020
tgtgaggtag gtactattgt ttccccccat tttacaggga aggactctga agcacacaga  16080
ggttaaggag tttatcaagg tcactgtagc taacaagcag cagaaccaga ttcaaacccg  16140
gagcccacac tcttaatcac tatgttgctt ctagaagaaa gaaaataagg gatgaaggat  16200
agtaaaaaca tgcaagccct tctgagcccc ctgttgttgg ccccactttg gcaggagtgt  16260
taggaagact atgggaactc aaaggtgaca cttagcactc tcctccagag gctacaggag  16320
ccatcattgg tagctagcca tttgtatccc ccgtgatggt ggagaaaagc ccacactgtt  16380
gcaagtttcc agaatttttct ctgctctgga aaagactccc aaactagggt taatcaagta  16440
tctttttgg tgaatttcat taaaattacc acataaaaaa agaagaattt gtcctgaatt  16500
atacatatag gagaaaaatg ataaaataaa ataatttcca ttatctttgt agcaaaaaaa  16560
gttggaatga ttccaccagg ttctctgaag gactttgttt tcaaaggaga tgttaaaatg  16620
tgtaaaatat ccaaaggata cacttttgca gctgaattta ggatcttaag aaacatggtt  16680
ttaccgtgtt tcccaatgat tgttgaaaag aagcagtgac tgggttacat ctagggcagg  16740
gtttctcagc ctcggcacta ttgacatttt gggccgggta attctttgtt gtggggggct  16800
gtgctatgca ttgcaggatg tttagcagga tccctggctt ctacccacta gatgccaata  16860
agattctccc tttccatctg tgacaaccaa aaatgtctcc aggaatttcc aaatatcccc  16920
tagggccaaa atcacccagt tgaaaactag tgttctaggg aaaaccatta taattaatag  16980
catgtctatg atctcccctg ttgcgggaag tcagggaccc caaacggagg gaccagctga  17040
agccatggca gaagaacgtg gattgtgaag atttcatgga catttattag ttccccaaat  17100
taatacttct ataatttcct atgcctgtct tcactgcaat ctctaaacac aaattgtgaa  17160
gatttcatgg acacttatca cttccccaat caataccctt gtgatttcct atacctgtct  17220
ttactttaat ctcttaatcc tgtcatctcc taaactgagg aggatgtatg ttgcctcagg  17280
accctgtgat aattgtgtta actgcacaaa ttgtagagca tgtgtgtttg aacaatatga  17340
aatctgggca ccttgaaaaa agaacaggat aacagcaatt gttcaggtaa taagagagat  17400
aaccttaaac tctgaccgcc ggtgagccag ggggaacaga gccatatttc tcttctttca  17460
aaagcaaatg ggagaaatat tgctgaattc tttttctcag caaggaacat ccctgagaaa  17520
gagaatatgc ccctgagggt gggtctctga aatggccccc ttgggtgtgg ctgtcttcta  17580
tggttgaaac tgtagggatg aaataaaccc cagtctccca tagcgctccc aggcttatta  17640
ggaagaggaa attcctgcct aatatatttt ggtcagacca gttgctctca aaccctgtct  17700
cctgataaga tgttatcaaa gacaatggtg cccaaaactt tgttagcaat tttaatttcg  17760
cccccgtcct gtggtcctgt gatttcgccc tgcctccatt tgccttgtga tattctatta  17820
ccttgtgaag cgcgtgatct ctgtgaccca cacctattcg tacattccct cccctttttga  17880
aagtccctaa taaaaacttg ctggttttgc ggcttgtggg gcatcacgga acctaccaac  17940
```

```
atgtgatgtc tcccccagac gcccagcttt aaaatttctc tcttttgaac tctgtccctt  18000
tatttctcaa actggctgac gcttagggaa aatagaaaag aacctatgtg actatcgggg  18060
caggttcccc gatactcccc aaagtattgc atggaatgcc acatttcttt tatcatagtg  18120
cttcaaataa gtatttcagt gtgttactga aaatatttat aaacaaaata tatttgatag  18180
cagggtatga atatgcccgt gtccttggaa gagaaagagg ggacaagaga acaggtataa  18240
cagcatgttg ttggtgaaaa taaattggta gtaatataga ttgaatatcc cttatccaaa  18300
atgcttccga caggaagggt tttggatttc agatattttc agattttgaa atatttgcag  18360
aatacataca ggtagagcat ccctaatcca aaaatccaaa atctgaaatg ttccaatgag  18420
catttccttt gagcatcatg atagcactca aaaagctttg gattttggag catttccgat  18480
ttcagaattt gggattaggg atatttgacc tatagtaatg ccaaatactg cactaaaatt  18540
agcaaatgta atctcattga attgtgacaa cagccttaag aggaaacccg atcattatgc  18600
ctacttagta gatgaggaaa cagaggtaac taggtcaagg tcacacaact tggagtgtca  18660
gagtctggat tctttctagt tctgccctcg tccaagccag ttctgttaac actattcttc  18720
ctttcagcat aatctgtgtc atcactggag cttatgtcta cctgcctgcc acccagcacc  18780
aactgtttac cctttaagtc tcattctgcc tcctccagga gccttccctg acccctgcct  18840
tcaccttctg acctgtgccc cttcacaccc tgtgccctct taactgggaa agccctgagg  18900
gcaggggcca taccttattt acctctatct ccagctcact gcacagaggc attcagcaga  18960
tgaccagtaa atatgggctg tctagtaaaa actttgcagt tagagataat gaaagaaaca  19020
taattacttc tgtgtgggtt gagaaagaag ggaagggaaa gtccagatac ttaagcagaa  19080
aaaggcaaac agtccaaaag gggaaaagta acttgcccaa atcatgcagt tgagggcagg  19140
aagaaagggg gacaaagcca aaaccaaaac ccagtccctt gtcccagccc agtgctttgt  19200
ctgctacgtt acacaaactg tgattgtgaa attaaagggt ttttgatggc actgatataa  19260
gtaaataaat ggctttatga gttaacacat gacaagcaat aaactcataa aaggtaaata  19320
ttgacaactg aagattatat atcactatgt ttagtgtgtg gagaacccaa ctaggaatta  19380
ggaaagcttg cacattcagt ctggtttctt ggcaaatcaa tgagacttca aacaaatcat  19440
tttatttctc tgtgcttctg tttcttttgg ctgtagtatt ttgctggtta aagagcacgt  19500
gatcaatgtc tatgctttta aatgtctgtc tttatttgag catgctcagc tggatgtgga  19560
aaacctatgg ttctcttggg tttcataagg atcaaatccc acagtgatat gtaaacttgt  19620
gtggtttata gaattatagg acctcaaagc tgggagaggc ctgataaatc atatagtgaa  19680
aatttccagc cagtgcctgg atttctttta cagaatcttt cttttattgg acaggtgctc  19740
ccttcacaat ccatgatgta aggagaaaag gggcttcgtt tgaaggaagt tagtgtattg  19800
tgtatgggcg tgtacttttct gcttggggtg tgcctacagg gctatctcac tttctgaaag  19860
cgtaataata agttacttta ccatgcatta attaaatgtc agagaccatg ctaaatgctt  19920
tacagagaat atctttttta atctgtataa gaacctcctg aggcagataa tattattaac  19980
cttacttttc agataaggaa actaacattc agaaaagtta agtaacttgc taaagacatg  20040
tgtctactag gaggtagagt ctcaagtcta tttcaagctc ctaataagta aataaatgtc  20100
tattgaatcc aactaatgac atcccactcc atattcccct gccactgatg agagagagaa  20160
gtataaagtt tatgtaaata agacagaagc aatgttttat ataagcattg tggatttaat  20220
tccactaagg gattgatttt tcatcttaat ggaacttttt cttcagctat caagtttcag  20280
tttcaagatc gcaaatgcta agaagatatt aaaatatttt aatacataat tccactagat  20340
```

```
catatttata ggtactgtta atatattacc aaatctacta taaacaaaac aataaaacaa  20400
aaggctggat caatatggaa agtagagtaa taatttaggc cctaaagaaa aactacgtaa  20460
gacatttctt agaggattac caggtttctc tctctctctc tttttaaaca cagcctaaaa  20520
tagaaaagca atttatgtat taataaaaaa aatagaaacc tgaggcagat gtaaccagaa  20580
taggtgaatt aactgaagac tgatattctt atttatgttt gtgtatttta aataaagaag  20640
gagtttgacc atctcatcta gttaatcatt aaaaggaaac tcgagccaaa cttgtgaagc  20700
aggtaaagtt tatttttaga cattcaactg gcttctcttt tgggctcccc ttttcttttg  20760
gggtcatcct ccatgtctgg taaccttaac ctccctgtct cttccagaag gagcaacacc  20820
cccatgtttt agacctttac ttctgatgtc aggacccttt ctgatgcaag tgttagctaa  20880
ctccagctgg ctgaagagga aggaggagga agagaaggag ggggaataat gtattgaagt  20940
gtgtaatagt caagtctagg agcagccctc accttaggat ctagacattc atattatata  21000
attgggaatc tatttccaga tctctttgct tttttttttt gcaaacctca atccaatgga  21060
gtctctaagt ggtagaccac agctgctcca agcttgcatc gtatcagctt agctattcct  21120
gttgagaaac aagacaagtt tccaagtagt cccagaaagc caagaattaa ggtgtatctg  21180
tccctgtcat gtgcctatct ctgatattac cagacctggc ccatgcagag ttacagatgg  21240
gttaatacca ccataagcgc atggaccaaa gttagggaaa ggatagtttt ccaaaggaaa  21300
tgttaggtcc tagtatcata tgtggagagg ggatacttgg caagtaaaac agtacctatc  21360
taccatgtgg ccacaacagg gcagatcagg gtccctggta ggatggaggc agccatcaag  21420
cattatggta tccctgaata atcccttccc agttcatatg taaaccaatc ctcttaaatt  21480
gttaatgcat ttaacataag gatggattca gcaaaactgt atcaatagca aaacatgagg  21540
ggtctccagc tagtagcctg tcctgcatag ccatccatga ctactgctct aattgatttt  21600
ttctagaatg tctaaaggaa gatgaaagta gaaaatgagc tgtagtggac aagcattttt  21660
aaaatgagcc caataatgta gcacttttgg gtgcttgata attgttgcaa atcacatttg  21720
cctgagaaat ttcaattcta taataattgt acaatagcag aaagatctag atacaaaaat  21780
attcattgca gcatggcttg caatagtgaa aaattgaaaa caatttacat atacttcaat  21840
aaggaaaggt taaaacaatg gtatactatg ctactattac ctgaaaatat tgaaaagatg  21900
aaaagatgtc caataacatt tgatgaataa aggttgaaaa atacatgtag taaaatctca  21960
tttttgtttt taaaaaacat atatgcatgc atgcatccat gtatagacaa aaaggatttg  22020
aaaatataca ataaattata gttaatcaca tttaccttat ggtactgcag aacatcagaa  22080
ctcattcctc ttatctagct gtaattttgt aatcgttaac taatctctcc ccatcctccc  22140
cttccccctg cccttcccag cctctgatag tcacaattct actttctatt tcacataata  22200
aaagttttta aagaggggaa taatggggtg ggggatctgg aatatacata aaaactcaaa  22260
aataattaca aatttgttgc catcaaaata taaaaagaaa aaaatagtta catctgcaaa  22320
atgggattgt gtgaggaagt ttttaccttt atacatttct accttctgta tgtttggatt  22380
tttacaataa gtatgtgtta ttttctagca tcttttgaag tttttttctt aaaggcataa  22440
gtaatatcta aagttatttt tcatccttct aatgccgtct acacaaagat aacgattttt  22500
cttggatggc cccaatctct cttctgtaag atctttcccc atttgtcata tccataactc  22560
ataacctcct cacccttcac tgctctccat ttctctata aagtgagccc agtcagtact  22620
tgtaggcttg ttaagcatta cttctaataa gaaagactaa cttgtaaagc aaatgtggaa  22680
```

```
atgtactaat atagcatcaa gcacaaaata gccattcaat aaccgaacta tttaattcct  22740
tttttttcac acttcatcct ttccctaatt ccagaaagaa cttgaactgg gtcataacaa  22800
agacaaattt agacagacag ataaagatat ctcataggta gaaataaaac tgagtgatta  22860
taaactaatc acaggaggct ctgttagtct gatgaacaga aacacacgtg ataaaatcac  22920
agagaggtaa aatagaaaat gaaaatcagg atcaagaaaa gggaaataaa aatatgctgg  22980
acatcattca ataactattt gctgatggta attataggga tggaaaaccc atcaggccta  23040
tggagctaaa attaatcagc aagtattcac agagtgccta ctgcttctat tactggttct  23100
ggcttcctgc ctgcccagtg cagaggcttg agacatttgc gtgacattca gcttgtcaag  23160
acagaaggag caaaataagc agacagaggc tcactgcagc cgcctatacc catcatattg  23220
ttggaatcat attcaagtga gacaaactcc ttcagtggaa gacgataaaa ctagcttaaa  23280
agttgtaaac atcacttcat cacccaaaaa aggcccaatt aagtggagat actatttctg  23340
caaagcaatc atcaattcat ttgtgtaaca tttgaaattt caaagtacaa acccacattc  23400
tattaaaggc aggaagtgaa accaataaaa cttgtaacaa ctatacttaa ttttcagggt  23460
tctttccatt gctgacaaac attttaagtc atgtctattc tcttaaaatg taaaatatga  23520
tgtttatgtc actgttaata ttttgataaa aagctattgt catggacatc tgggtttttt  23580
tctgcatgcc cagaaatccc ttttctccta tttaaattta aaatctccaa ttatttggag  23640
aagcacctcc tcttctctct ctttcatttg taccccattc ttaggtgtca gtggtgggca  23700
cttgagctag gctttgccca tcatagtaca cattcctgac atcccttggt catagttatt  23760
ggtccaggga taagcatttg aaccaactag accagtgaaa cccctcccag gaacaactac  23820
taaaattatg ggaaaagaac tctttccact gaagttacta acctggcagg atgtgttaaa  23880
tccaggtgcc acaggccacc aggtggagag gtggagataa tctttccaga aaacaaaaca  23940
aaacaaaaca ggaaaatgaa gctaagggat aaaatttaag ccctttggac ttcatttgag  24000
cccctgaatc cagtcatgcc tcctgaaatt aaacttcccc tggacttttc agtgaatcaa  24060
aaaactctgt ttttaacagt ggggtttctt ataaatgcac caaaaaatga cctaatgaat  24120
gttgtctaca agcttccatt agaagtatta tcttcaagag aaaaaaaaaa caaataactt  24180
gaagaaaacc cttcataatt caagtcagtc ctgctaacct ctaggaaacc ctccgtgacc  24240
accatctcca tatccacacc cattttccta accttaaaca ccagatgact tcttgaagct  24300
tatgaagtgc cctatgcatc taacacattt ctgtaagtct gcattgttct ataatgactt  24360
gtaaccgtat ctgtctccat ttcctccaga gaagagattg ttatcatttt gatatccctg  24420
cagccttata ctggggccta acatataata gttgctattt tgttgaagga attgtatttt  24480
gttgaaggaa ttctcttttg ttgaaggaat gaatggagag aatattaatt aagaaagtct  24540
cttctattaa taaacattcc ctgattgatt gaaaccatgc ctaaaatagc taatcatcag  24600
aagaccaaag taaacaacat atccaaactg aatcctcaaa gtgttagtca ttggtagctg  24660
tatagctgag aatctttcct tcttctggtc attagggttg aaagggtggg tgaatgtgga  24720
gacatgattc tttcttttgc aaaacattta ctattttta aactccataa aatgtaataa  24780
cttctcttga aaaatgttaa aacccaaaca aaaaaacctg taatgtggaa tatagattgt  24840
aggttataat ggaggaagca gggaaagtgg ggaaaactgt ggttgccaga agttttctga  24900
taactaatag gcaagacaat agggtggctt ttggtagggt ccttctttat ggcatagcaa  24960
agaaaaatag gaatgaagaa gtgagaagca tgaaagggga cagcaatata tgtgtaacac  25020
agggtgattc agtgtgagag ttttataatt aaaattgcca aatgtgagaa aaaaaaatct  25080
```

```
actataaatt gggataggct caaggcatgg agatgaacaa ataacccctc catgtgggca  25140
aaaatcaatg aaattactag atgagtagct tagtatgtga gttccagttg caacatgtta  25200
ctggtatttg gggcttcccc tccccctcc ccccctgcac tttgaggcaa ttcgacattt  25260
gactaacaat ccagcctaac tttctccatc tgatataaag atatttacct tgaaatccta  25320
gaactgccaa catctcctac ttcctactac aaccctccct gactcctttt ctctggcaca  25380
gctttctatg cactcacccc attcaactaa gcctgcttac tcttcaccag aaggtcttct  25440
cttagcataa aaagttcctg gaagtccatc tctttcatag agctgctgga tgactgcttt  25500
gcttaccttt ggccttcaaa atacctctcc tgtccaacca tagctcccca gctcccctgc  25560
cattgcaacc aatacaaact tcgtcatctt tccttgggcc aatgtgcctg tctcctcact  25620
gctctccctg ctttctccct tagcccctac aactcatact ccacatcgca agcagaacga  25680
gcttttcaaa tagtaaatta gattatgtcc attagtgtgt tagtaaatgt ttaacagctc  25740
ctgaggggaa cagagtatct atgtgtttta taatttttac atatatgtat cacataattt  25800
acaaaaagca agaaaaaata taacactctt aatagtaaat tctatatggc catgtgattt  25860
tcacagaacc atttcagtga tttttgcaga atatttgtgt ccatagccaa cctacagcta  25920
aaattcaaac acgtttggca aaatcagacc acaaataaat atctgattaa tatccaatca  25980
gcaaagaagt cattcatggt actgaagtcc caacatgaat gttggttgat atttttacat  26040
taatgagcga gataaaagtg aagcaacaaa aatggatgtt ggaactaaac tcgttcatta  26100
atgacagaag tgacttcttt tgctgataat agctttcaag tactagaaaa atatttcctc  26160
aagtttttgt gttcacaaac taaggcactt ttaagttcaa tcttcattat taaaatttct  26220
tctactctgt cagtctagac aatcaacaaa acaaatcaag ctctggtttg tcatgtttcc  26280
caatttctat agtataggta ctccaccatg gttgatttca aactaccaaa ataacatttc  26340
tgaatgcagc gttaggaagg gatacgctgc atcataccat cgtatggtat gttcttatac  26400
agaacagaca gaaataactt taagaacata gataatagta aaatggagta aaataattag  26460
gcagtaaagt cttcagcatt tatttttgtt gttaaaatat ttgattgtga gtttataaat  26520
aatttggttt ttaataatga ctgtgattaa caaccaactt acaaaatctc tgaaaattta  26580
acagtcagtg cttgcaagct ggtacaattg tttccggtgc actactgaat tatcactccc  26640
ctgcctaaaa ttccagactg cccattgcac tgattccctg ggaaataagt gaaaagagac  26700
aatgataatt ttcatttttg ttgtggtgaa gtgatagtgc aaaaattcca taagctcctc  26760
taagttttcc aaataaagct tagtgtttaa aaacgtttga acacatgatc ccatgtaagg  26820
cctacattac ttcctgtgtg ataggtgggg tagatatcat tatccttcct ttacagattg  26880
aaaaacaagg ctgagaaaaa tcaaatgcct accccaggct cattcaagta agtaaatggc  26940
agaatagggt ctaaaaacca ggtcttgtat tgaaaattca acaagaggat agagaaaatt  27000
taattgacaa atactgatct caaaacaatt ttttttcaa tggtgacaaa tgtcctttgt  27060
agcactttgg agtttgatat gaagtatctt cttatcttgt taagggatcc ctataccaag  27120
aatgttttca tctcaacccc actatttcta agttagctta aaaacaaaac aaaaccctgt  27180
gtgctctaat aagaagatat aagaaccaaa atggaaatgc aggttctcaa atgagctgaa  27240
agattccaca tagcagcggg gcagattgaa acactcttta ccaaaggaac atgggagaga  27300
aaaggagatt aaatcaagaa aggaagaaag ctaatgacat atgaggagcc acaaatgcca  27360
caaatgaaaa aacaaagtac gtaatacttg ttgcaattat tcagtgtgct tgctctaatg  27420
```

```
cctccaaaca ttaaaaacat tgagttcctg cttatggcaa catttatctc atttatctgc  27480
tgatagctgc ctcatccttg aatcaggtat tgcttaaact aagttctgcc agcataaaga  27540
ataaagtcaa ccaggacacc cattgggcat ttcacgcata tgagcacaaa ttgtgatatt  27600
ttaggttgct tatgatgaaa tcattgaaag catcatgaaa gacagcaaaa cagcaggaaa  27660
gctagtaata atttagcatt tcccagtcca ggcgggaatg ttaattctaa ttacaacgag  27720
gaataccaaa gtggagttca ttatgattaa gaacttgctg tactagtgtg aattgtttat  27780
aataggcatg tctggcataa aatacaaata ttgaagcaga cagagatggc tcattcaaag  27840
ctcagctggg ttcccttgaa cctcttacct tataaagtta aataggaata gaagtatttt  27900
ccaaagtcaa gatattattt taaagagaca aataatagct atgatagctg caggaataat  27960
tttttaaagt aagttctaac caccaataaa agctgtttgt gtgggcttaa catgttcaaa  28020
atacacaata cacatgtaca caatacacgt atacatggtt cccatttata tttaacatca  28080
cacatttaaa gtgagagagt acagaaaaaa agaataaatg gaaactgaag ccatgacaaa  28140
gaatcacgga ctataggaaa ataagtcaca aagaagtatg cttatgtaag aggaaatata  28200
tgtgataaac aacaggagac atgggaatga atgtggtgtc ttatgtcctt tctttaacag  28260
aatcgtgtaa cagacactac tcaatatcga tctcaactga tccagttctc cagtctccct  28320
ggaaaacaat ggattgatgc ccagggtgcg ctgaacactg gaaccatggt cacttctgca  28380
cttcacacga ttctgctccc accagttgag ctaccaacag ttcctggtgc ttttgcttcc  28440
caaacatgtt tatgccattt gttgcttatt actgtactta cttaatttga ttaaatatta  28500
agtaaaatga tgaaatgagt gtaaaaaatt gttctataaa atctaaatgg aaagatgccc  28560
tatagccttc cttgacttac agttgcgtca agtaaggtgg atgtaagaca attttaaaag  28620
actggtgtgg gggcaggagt gaggaatcat aaaaatttag aaatctgcac gaaaattatt  28680
ctaaaagtac acattgaaca tccctaactt gaaaatctga attttgaagt gctccaaaat  28740
ccaaaacttt ttgagcattg ttatgatacc acaaatgaaa aatcctacat ggaagtactt  28800
accacaaact ttgcttcatg ccccaaatta ttttaaatat tgtataaaat tatcttcagg  28860
ctataaggtg tatatgaaac aaaaaatgaa tttcctattt agacttgggt cccatggccg  28920
agatatctca ttataatgca aatattccaa aatcagaaaa aaaaaaatcc aaaatctaaa  28980
acactttcag tattaagcat ttcaggtcat ggatactgaa tgtgtatctt taatttcttg  29040
ttctactttg tttaaaaaaa agggggaaaa tagtaattct acagatgaat aataattgct  29100
aatgatgagc aaatacttcc tatgacccag gaattcgtct aagcacttca catatatcaa  29160
actggtttaa tctttataaa tcagtactat tattatcccc attttacaga tgatggaaaa  29220
aggcacagag agttagcctg cccaaggtta cattcctttt agtggtggag actgtatttg  29280
gcctttatag tctggctttt aactgctaca ctatatcaat gcattacagg tatagtttat  29340
acacacacta aagaagacat ggaactccag tcagtgggct cataaaagct ttagaccttc  29400
atcaaaagat tagaaaataa atgttcaatc acaggtttta ggtttcaaaa gtttcaaaag  29460
tttaaagttt gcaagttatc tttcttaaaa ttatttcctt cttttaacta atttttaaat  29520
taaactccag ttcaatcaca tccactagaa ggcttcactt tctacaaagg ggtaggtaaa  29580
ggtgatgatc ttaaatacca tactgggagt tgggatctgt gtagcactag aatcaagagt  29640
tattgtatat acttgagaag gagcacagcc tgatttagtt gatgttttgg aggggtaatc  29700
tggcagtaca gcttggatta ttttagtggg aatggagatg acaaaacatg aagagaatgg  29760
gagaactcac ttgggtaata tatcagtttc tgaaatcaat gtatcaagtg gtttggttat  29820
```

```
tagtcaggct taaggtttta ttggccttag gacatagtct ctaagaccat atattatctt  29880
cattcattca tttaaccaac acccactgag caccaactat gcactagtga tacaggggtg  29940
aacaaacaga cacagtccct gcctttgcag aacttatgtt ctggtgggtg atacagagaa  30000
ataacaaatg agggcacaaa taatgaacta tcattgtaat gtgctaacaa agtatgcaga  30060
atactataag aacatacaat caagaatcta atctagttta ttttaaaaaa aagtgggggg  30120
agcactcaga tgtttaaaca caaaacaata aaaatgagga tcttgagggt tatctgtaca  30180
ctttttatta acccatttgg ccacaacaat aacccagtaa aagtgatttt acatctagtt  30240
aactagttga ctcaatgtta ttataaccct gtaatgtatt tgttgggtgc ctgctatgta  30300
gtgggctgtg ttccaggagt gggacataaa gctatgacaa gatagatcag gtccttgcct  30360
tgactgagtc tgaatacatc accttcattt ccacctctgc ttctaagaca atcaaatacc  30420
ttcccactca gatagggatt catcctattt cttgtagtaa ttataagttc ccagggttac  30480
agattagtaa atgccatacc taaagactta ggatactgtg cataaaacac tttcaatagt  30540
gtctgtcaga cagcagatgc gcaataaatg ttgactttcg ttagaattgt gttattatta  30600
taatgctaaa tctcacgtcc tttctggcac actggagttc atctcttcaa ttaaattccg  30660
taagcacata ttgtaagtag tctatcagaa ttgatatact acttcatgtt aatgattgag  30720
atcagtgagg aaaaccactt taatattgtc taattcctct cttaatgcat aggagccatg  30780
tgaacttaga caagcatcaa cctctgtaag cctgttgtcc tcatattgaa aaatcgaata  30840
acaataccta tctcatttaa ttgttgtcag caaaagtggg cagcagaaga gtggggatca  30900
ataaatgtta gccacaaatc ataactattt gtattactct gaaaaagagg ggttaactta  30960
tagttcatgc atgcttccaa atgaatgtga aagactaaag aatgagaatt tttttgctat  31020
caaattaaaa aattaacagg cacatttaga ttgctgaaga gagaaattag gataagtttt  31080
ttttttttt tgctcaatta aaaacgtttt caatggcata tttaaaacta cgtattcttc  31140
cccattaaga tctgcagaga aaaaaaaatg aagggagaat aattgggaac tcttgtgaaa  31200
tcataaatta tttaagcaga gtacctacca ctaaggattt gagcatgtat gagcgatgag  31260
gtggattctt agagcagaga ttcagcagtg agacaggcta atggcatggg gagatgtgtt  31320
ctattagaca actgtattgt ccccttaatt atatacatat atatgtatat aatatatatg  31380
tgtatacata tgtatacata catgtatata taaatagaat tcttaatcat tttaagcagt  31440
gtacaaggat aattattagc atgggctatt taactcactt ttaaaacgtg taaaacatta  31500
ttgtagggtt gggtcttgat ttgtttccca tgaaactgtt ggtagtttag gggccaaatt  31560
aacgaaagac atctcattct agtgcttgag gctcagaaat tggaaaaacg ggcaactagg  31620
tcaagcagtg ttctcatagc ctcacagatg agcatccaaa gcaagggcct ccttctagtt  31680
gacttgtgcc aagggacagg agaagcggag tctgccttct gggtccagaa gggggttttg  31740
ttaacatgga gttgctcagc gcccttcata aaaattcttc tggctgaggg ttctacgttg  31800
gcatacggtt ggttccctct tcttttccga ggtggcgagt atctcttcct ttgccaagat  31860
ggcggctcca gaatcctctg gaggcggccc ccgtagatcg tctccggaca agaggcttgc  31920
tgaaagccta cttctttcct ttcacatcag acaatgcaca gggaaccgtt taccccttgag  31980
aaccaaggaa ggacggctta ggctacccgc gatcgcgaac ctttgccaag atggtggccg  32040
cggggacggg ctggcgacac tgtaccctac caagatggcg gcgggcggct tccgggacgc  32100
gcttccccaa tcgtcttcaa gatgtcagag caggggggagc cgccgtcagt ctgagcgcgg  32160
```

```
cgggaggtga gagagtggct gtggccgagc gcccgagcag gattaggtgg agctgcggca  32220
gcccccgccc gtgtcaggag ctggcaagcg atgtcacctg tgggggcgca aaagttacct  32280
ccccaaaccc taaacccaca cagcacaacc tttcccagag tcacaaaaat cataatctgt  32340
gccgcacaag gtaggaggct cggtcccggc atcgtccaag ccttcccgac gcggcgagct  32400
ggggaaggga gctggggcgg gggcttcccg cacgggcacc cctcgcccca cggccctctc  32460
ctttctcagg acggaccacg agttcccttc cccttggact gagggggaag ctcctaacag  32520
gaacatctgt agggagttga acgctggcat tttaaagctg cctgtatttt gttttatttg  32580
taggggcagg ggtcctatga acgtgatagg gtgagcaacg cacagagtcg agggcagcaa  32640
atgtcaagat tcgggggtgg ggcctgcacc gggaacttgg acgcgggccc tggccggggt  32700
ggaagaagag gtcaggagtt tcggaagggg ggctatattt cgccagcaac ttactatttc  32760
gcctgcaact tgcttttaag cctgccgccc cctgctttcc ttaatcataa taataaaaaa  32820
aaagtgcaaa gaaatccagc tcgctggagg ttttgcattt ggcgtgcaac ttccttcgag  32880
tgtgagcaca ttgggcggga ggggtggggg ttgaacttgg caggcggcgc ctccttctgc  32940
cgccgccgcc gcctcgcaga ctcggggaag agggtggggg acggtcgggg cgcgggggag  33000
ggtgggttct gctttgcaac ttctctccca gtgcgagagc gcggcggcgg cagctgaaga  33060
cccggccgcc cagatgatgc ggtggtgggg gacctgccgg cacgcgactc cccccgggcc  33120
caaagtacgt atgcgccgac ccccgctatc ccgtcccttc cctgaagcct ccccagaggg  33180
cgtgtcaggc cgcccggccc cgagcgcggc cgagacgctg cggcaccgtt tccgtgcaac  33240
cccgtagccc ctttcgaagt gacacacttc acgcaactcg gcccggcggc ggcggcgcgg  33300
gccactcacg cagctcagcc gcgggaggcg ccccggctct tgtggcccgc ccgctgtcac  33360
ccgcaggggc actggcggcg cttgccgcca aggggcagag cgagctcccg agtgggtctg  33420
gagccgcgga gctgggcggg ggcgggaagg aggtagcgag aaaagaaact ggagaaactc  33480
ggtggccctc ttaacgccgc cccagagaga ccaggtcggc ccccgccgct gccgccgcca  33540
cccttttttcc tggggagttg gggcggggg gcgaagcgcg gcgcaccggg cggggcggcc  33600
acgccagggg acgcgggcgt gcaggcgccg tcggggccgg ggtggcgggg cccgcgcgga  33660
gggcgtgggg gcagggaccg cgggcgcccc tgcagttgcc aagcgtcacc aacaggttgc  33720
atcgttcccc gcggccgccg cgcggcccct cgggcgggga gcggccgggg gtggagtggg  33780
agcgcgtgtg tgcgagtgtg tgcgcgccgt ggcgccgcct ccacccgctc cccgctcggt  33840
cccgctcgct cgcccaggcc gggctgccct ttcgcgtgtc cgcgctctct tccctccgcc  33900
gccgcctcct ccattttgcg agctcgtgtc tgtgacggga gcccgagtca ccgcctgccc  33960
gtcggggacg gattctgtgg gtggaaggag acgccgcagc cggagcggcc gaagcagctg  34020
ggaccgggac ggggcacgcg cgcccggaac ctcgacccgc ggagcccggc gcggggcgga  34080
gggctggctt gtcagctggg caatgggaga ctttcttaaa taggggctct ccccccaccc  34140
atggagaaag gggcggctgt ttacttcctt tttttagaaa aaaaaaatat atttccctcc  34200
tgctccttct gcgttcacaa gctaagttgt ttatctcggc tgcggcggga actgcggacg  34260
gtggcgggcg agcggctcct ctgccagagg taagaagcga ggcgggaggg ggccggggcg  34320
cgctcgctcc cccgaggtgc cgctgggacc ggagacaact cgggggccgc cgcgggagcc  34380
tacaaacttt tattagcctc ggggagtggg ggtggggggc tggcaagggc cgggcgacgg  34440
tgacgaaagg gcagcgcgcg ggtgacagcg ctggcctctt cctctccctc cgcaggcgtc  34500
ccctggccgg gccgaggggg aggaacctga cctcggacgg cgagcggagc cctgtcgaac  34560
```

```
tgccgggggc ttcgagcctc tcattcctcg cgggaatcct ggcctctttt ctccccctag  34620
tgtcccctt  ccctccaagg gggtcgcccg acacccgttt tcgtggtgaa cgctaagccg  34680
cgtctgaatt ttactcgccc gaatatttgc acgccacccc ggcgcgcccg agcgcgagcc  34740
cgggctccgg ggaggccccg gcggcgcctg gcttgaggag ggcgtgcggg gcgcgtgagg  34800
gtgcacacgc ggggggctga cagcccgcaa cttggagact gcggccgggg ccggcgttat  34860
ctgttagaag tgggcgtgtc ggagagagaa ctcaacaggt ctggacgtac ttctctttta  34920
acctcgcact tttttctctt ctccaccccc gccccgcaag ggcttgctct ttagcgtttg  34980
ttgttaattc gcgcctgagg tttctaagtg gcccctttta gaaaaagacc ccctgtaacc  35040
gtaatggttt tgtgctgcga tttttacaag tgctagtttg acgtttgggg ttgcagactt  35100
gataattgca accttgtaat accacttaag accctctggc atggttcatt agggccaatt  35160
aatgtggctg ggttatttgc aacttaaact gggggataat gtcgcttgag ggagcgtttt  35220
cgttttagga aatattgttt tggtttcggg tttgaaggca gctgtcaaaa aagcggcatg  35280
gaaattcatt gggctccatt cgatacctcg tgtttagaga tcgttatcgc ctcagataaa  35340
cggggcagag aggtggggag ataagcagtt taccctcaag atttgtagtg gcaagtccac  35400
acccctctct ctaccttcat attcactttt cagtgagggc cagtgacatt tatgctgcct  35460
aacgtcatcg cataggaaaa gttacctttt attggacggg atttgactat agtgtcccaa  35520
atgcgcttct ccgtcttagc ccatctctta aaacaccctg attaacgata tactaacagt  35580
cttactctct tgagaatagg ctgagaattg ggataggtga aggtttggat aggtgaaggc  35640
agagaaaatt attttgaaca ttttactgga tacagttgta cctgaattta tatgaatgtg  35700
attttacggt tctgtgtttt tccatttttc agtacttcga tatttgtttg gaaaggaaag  35760
aacttagaga tgtaatagca tttcatattg aggatctcaa gcaatgtaaa caaatgtagc  35820
ttaatctaga tgtttttgtg agttatgata agggtcagct atatttaagt tatgtaagct  35880
aacaacgtag tgagaaacta ctacaccttc tcttctgctc tttaaaatct aaattttagt  35940
tggcctatat aaagtgtatc tcatttcata tatccaaaat ttggaggtag gcacatccag  36000
tcagaagtat gggttaaaaa gccttttccc agcctgtcgg aagataagca gatcagcatt  36060
gtttattttt caaagaaaac gtgcatggtt caccagttgg ttgtactcaa aggtttggat  36120
gtgtgactag ctggtaggag ggaaatttgg aagtaattag ggattgagaa ttctagcata  36180
gtatttatca aatgttatat gtattggttc tcagaaaagc aaacagccgt gattgaaaag  36240
aggtaggaat tttaatgatc acacttcctt tttttgaaat taaatacttt gacatcaact  36300
tgaaccttca gaataatcag atgtaatgaa ttataatgtc tgtgattaac aaagctacac  36360
gttcagtgag cggcaggatg aatagccaag cttagttcga tacacttttg ccctcagctg  36420
tgcaaatgga ttgcattgta cttttaaatg tggcatgctg aatgggagca ggggacatgg  36480
ctttttattc tggaagatag aaactactct tctggtaaca aagaatttga ttcggagtta  36540
actaaaaggt tcatttaaca agctgcctct tactaatcgg atcaggaaga taatgtgact  36600
ttagagctta tgatgttttc cccccgtttt tgttttttgt tttgtagttg atattcactg  36660
atggactcca aagaatcatt aactcctggt agagaagaaa accccagcag tgtgcttgct  36720
caggagaggg gagatgtgat ggacttctat aaaaccctaa gaggaggagc tactgtgaag  36780
gtttctgcgt cttcaccctc actggctgtc gcttctcaat cagactccaa gcagcgaaga  36840
cttttggttg attttccaaa aggctcagta agcaatgcgc agcagccaga tctgtccaaa  36900
```

```
gcagtttcac tctcaatggg actgtatatg ggagagacag aaacaaaagt gatgggaaat  36960
gacctgggat tcccacagca gggccaaatc agcctttcct cgggggaaac agacttaaag  37020
cttttggaag aaagcattgc aaacctcaat aggtcgacca gtgttccaga gaaccccaag  37080
agttcagcat ccactgctgt gtctgctgcc cccacagaga aggagtttcc aaaaactcac  37140
tctgatgtat cttcagaaca gcaacatttg aagggccaga ctggcaccaa cggtggcaat  37200
gtgaaattgt ataccacaga ccaaagcacc tttgacattt tgcaggattt ggagttttct  37260
tctgggtccc caggtaaaga gacgaatgag agtccttgga gatcagacct gttgatagat  37320
gaaaactgtt tgctttctcc tctggcggga gaagacgatt cattcctttt ggaaggaaac  37380
tcgaatgagg actgcaagcc tctcatttta ccggacacta aacccaaaat taaggataat  37440
ggagatctgg ttttgtcaag ccccagtaat gtaacactgc cccaagtgaa aacagaaaaa  37500
gaagatttca tcgaactctg cacccctggg gtaattaagc aagagaaact gggcacagtt  37560
tactgtcagg caagctttcc tggagcaaat ataattggta ataaaatgtc tgccatttct  37620
gttcatggtg tgagtacctc tggaggacag atgtaccact atgacatgaa tacagcatcc  37680
ctttctcaac agcaggatca gaagcctatt tttaatgtca ttccaccaat tcccgttggt  37740
tccgaaaatt ggaataggtg ccaaggatct ggagatgaca acttgacttc tctggggact  37800
ctgaacttcc ctggtcgaac agttttttct aatggctatt caaggtaaga tcagtgtttt  37860
tctgtttctt aagaatggta catttaaggt agattaatag atgtaaatct tcattgattt  37920
atatgtgttc tctaaagatt catgtgcttt tttatatgaa taagtttaag tggccttttg  37980
aaagtaggaa aggtagacaa cctaagtgac atctgtacgt aaccatttca ggtttttccc  38040
ttaaatagtg gttttcagta tcccattggc caacggtgag gattttattt aacattttta  38100
aaataatgtt gctcattaac agatatctta acgaaaaatt atataaattc aggagagtat  38160
aatgtctcat aatatcatat tgtgttgtgc atggtcattc agctgtttta gaatatgttc  38220
ttatattaca ataaatgata cccttactta catagtcaaa agttgtgctg ccttatttgt  38280
aaattcgtta agtgttagct tgagattaaa gagttaaaag cagaagtact aacaaagagc  38340
cctattcttc aaactgaatc ttctgttaaa gaatttgagt tttgaagttg ctaaagcaat  38400
gcagtgaaca gtgtaccaga ccatagtatt agacacaggt cttgctcaca gggttcttgc  38460
cataaagtag acaagttatg tctgctgatc aatctcttta agagaggaat tggtgtcaac  38520
atggtgcaaa acaaaatttt acgttcaaat gttcctgcaa gttctcaagt agataactga  38580
tggccaaaat tgttaagctt caattttcag ctttcgtttg atttttctct ttttttact  38640
cagtcgttta taagcatact gatatttttg tctgacccaa aaaggtcaga aaatggaatt  38700
atcagaaaaa agttctaaat gtagatatac gtgttggtag gggtgaattt ctctaccccg  38760
taacctcatc cccaattcag ataaatgcta ggttttatat ccattttagt tgtgaaggaa  38820
aatataaaaa tgtggattgt agtgacacaa gattgattaa tcagcgggtt tttttaaaag  38880
aagacatggt agacagtgat ttatttgtat gtaactattg aagttttttc ttaaatgtta  38940
gtgatattca tcgttcccat taactagtta ttcagatttt tgaaaatcct ttttctgtga  39000
aagctatcct aacctggagg atgtctcttt tctttcctct gtacttaaga agcttttctt  39060
gttagggaaa taatttagaa ttagatttag gctatgttct gttcttctaa aaggcttagt  39120
tgtcaaaaaa aaaaaaaaaa aaaccaaaaa accttggttc ttacatgtct taatgtgaac  39180
tacctcctaa tctattgttt aaataattat cctttattta gaagaacact acttcaacct  39240
gagttgaagg tttaaaatct tttcagtaag gagatttgag atctttatta ttgcataagc  39300
```

```
tgttgtgttt taaatgctaa aagacatgct gtgttttaaa attttcaatt gcaaattttt  39360
ggcaatagaa ttcgcatact tggttttctt aaaagagtta agtacggttg atttgactaa  39420
gctatctgta ggaaactctt aaattgattt ataaaacatg taattataca aagaaaaata  39480
aaacatctta ggaaactctt ggggattatt aatggatttt gccctgataa tcatcatggc  39540
atggttttca ttttccttac tataaagaaa aggcaaggga caaaacttat tttccatttg  39600
ctatgaactt ttaaacccta taaaatctgg gatatagagt ataagtagat gaacatagtt  39660
actcttaaat cactaaaggt gattttaatg ctttaacttt tatagtactt catgacataa  39720
agtatcttta cgtattttta atttgggtcc cataacctta tggaggtagt aggcaaggca  39780
atgatgatgc ggctctttag aagttcttta atatcaaatg aaattattat ttttatgcca  39840
atctgtgatt gggaaatata atcagtagtc tgtgtcctaa caagaaggta taatacttta  39900
tacagggtat tttgttaata tttgaagatt ttataccta tggcattaac ttagcactgg  39960
gaactatgat tacccaaaac aaagcttcat ccaaataaat tgaaacagtg tttcttttaa  40020
accatcattg aattagtcta ttgtttccaa acaacagccc tgatatagct aaaattagtt  40080
gctttctctt ctctatatgt tacatgactg tagccaaaca tttgctatga ccagtgaccc  40140
tgagtgatca gcaaataatc aacacattga gaccacaact tgaatactga ccttctgact  40200
ttacgaagaa aaatattaaa tgccactaat aacttgaatt ccttttaaat taaaaaaagt  40260
tataaattgc aatttgactt tttaaaatgc cacctaaaat tgtttttatc agaatactta  40320
aaaaaaaatc ctcactttat tctctggggg tgggaagagg caattccttc cttccaccac  40380
aacattgaat tatcacataa aattgtaaaa ttatgaatat tatgattgag cttagtaaag  40440
cattttctaa gttcatttat agtaaaacaa gagaaacctt attctcaaaa tctattcttt  40500
aagtaaaaca aactagtcat tctaacttaa tatgctttta aaaatactga agttcagtac  40560
atttagcata aacttattga cgaaggcaca tttctgcatt atttgatttt cagccttgtt  40620
tcatttaagc attaatgaca gaggtagaga acagaaatgg ttttaggtgg tattagagct  40680
tttattggga ttatgttgaa attttagtgt taaaaaattg ttcgtatcct gaagggaggg  40740
attattggag agaatgaatg atgtaggatg aacttgtaaa ttcagttttc ggcagagtct  40800
aaaattaagt gatgattggc acttaatgaa gctactaaaa tttatgtaga ttttaatgtc  40860
tcattagtaa tcgcatctgt atctggtttt ataaaagtaa tgaaattgaa gacctgtaca  40920
aatacagaat gaatgaagca aattctgcta acatcatgtt gaatgttttc tcagaaaaag  40980
aggaaatacg aagagaagag atttgttttg actgtgattt accctcaccc ccatggatac  41040
tttctttact tcctaccttt tttctttttc ttttccttct aaagattctg gcaatgggtg  41100
tttcagtgtt ttttaagctt aatatttctg gtactcattt atgtaaagtg atttctgaat  41160
gttaaaggag atttcttttt aaatatattt tcacttattt ttagctttat gatgagaatc  41220
ttatttttta aatctgtaac ttgttatggc tacatgatta gtaaaaaaag tttttaaaac  41280
acactgtgta ttcaggtgtg tcattttagt gtgaaatgac taatgcagaa atatgtgact  41340
agcatgtggt cagattttat tgaaattact tacgatgttt ctatggctag tccccttgta  41400
tttttataat tggtaacata attcatatgt tattttggtc ttgtctattt gtgttacatg  41460
tattttagtc tgaccacttt tgctacttat ttaatgttta tacattttat gaaagactta  41520
ttctgaaata taccttgcat aaatgtaggt taaatgcaaa ttgtattaat agtgaaatgg  41580
atatgtgggt agagatcact ttaggggcct tttgagattt agtgaaggaa agattggatc  41640
```

```
aaaagggttt actttaatgt gactgcctaa tgtgaaagtc ggaacatctg cattaattgg  41700
ttagttacat aaatcttagt ctactctggc ctgcaggtga ctgaaacagc ccaggaaatc  41760
ttaatttaca ttaagcttag acaaggtctg aggcttaggc ttagttctta aagcacattc  41820
ttttttactt taatgattat tcctaatttt aatgagcagt gggttctcat tgtgtactag  41880
tacttaggtg ggcaaattaa ataagcaaaa taggtttgtg ctgaatagca tttacccttc  41940
tgaggacatc ctggtaatat tttcatcaag agtaattgtg taatgcaata tttacaggta  42000
tttgccagat taatgggcac ttgttttcat atttctgagt catggaaaat atacattgat  42060
gattcctgtt gcataaagag ttttcaagaa aattttgttg aattaagcta taactacaaa  42120
aaaaaatcca ttacatattg acctttagaa aggattttta aaagcccatg ctgtccttat  42180
ttctgcagct tcagagagcc gactgctctt attttcttct ggcatattct attaatactt  42240
gggttttgta tttttcaagt aaataaaata ttcctattga gaatttcaat tttaaaaaag  42300
aaaaggtcta ctaagtgttc ctttccctgt tgaattatgt gtgatcattt ctatgctaaa  42360
ctagattagg gtgtgacttg tgatggtgat ttttgttcat tttacatatt aagaaagaaa  42420
tagaatttta ttgcagttca aaattatttg tagacagtgg ttttaacccc cagacaccta  42480
attgtgacag gttgctttcc ttagtgctca atactgttgt aaatgtctct aaatacagaa  42540
tttccagtgg agttcatgaa ttaattgggg gtggagggtg aagagggagg agcaacagag  42600
atgtgggatg ctatagataa gtttaggaat atccagatca gttctgaaaa ctaacagttt  42660
ggatcaactg tcatgaatta gaggtttaag aaaagaaaaa tttaggacta taggtacaag  42720
ggaatgcatc aatcagaatt acaatttaat ttcttttatt tcaggtagaa atctaaaact  42780
gaccatggct atataatact aatttttgag ttatgttgtt tcttactatg ctttattatc  42840
aaaaaaggat aaaatgcaca ttttacttga agattatttt agctaagatt aagttcatat  42900
ttttctcatt tttatttaag ctgctgttta ataaatgaaa atctaatgac ttgaatgtag  42960
tcgacctaat gtcttaatgt tgatataatc atttcatata tcatagtgcc cttttacagc  43020
cattgtcaac tgactggaga gcaacccttt tctttggtaa tatatttcta tgggttatgt  43080
atttttctgc tggaatattg agaaaattaa tttttcataa tatgcagaat aaattatggg  43140
gttctgcaag tgctagacag tcacttaaac catttatatt gcaatacatt ccttaaattc  43200
agtattttga atgaaagtgt gttatccccg aattttatca cttgtccaat ttaaatatta  43260
attacatccc aatagagctg catgcttaaa catgcttttt cagagtaacc caagtattaa  43320
tttcgagtgc ttttaaatat tttttctttt tagcaagttt caacaacatt aatcctgtct  43380
ataatgcagc aagttcagtg aaagtacctg ttgttttata attttttttt cattctcact  43440
gtagggcacc aaaaatatat ataaggggaa aaaagtttta atgatatgat tagttgtaaa  43500
tgtttacgca ttatcttacc ttgaattttt atttttgtaa ctaataattt gagagttcaa  43560
taagtatgca gtgtttaaga catagtttgt tgcaaaaagt gttaacttac tatttctttt  43620
tacaataaaa ttagccttta ttctagttga tttcataact gtccataata tttagctgtg  43680
gctattatga aagtatattt gatagccaaa ttttgaaagc tattatgaaa tgatacaatt  43740
cactacatga tttattattt catgctggtt ggggcagtgc tgtgacttat gaccttatga  43800
ttgtcacatg ctgaacacta aagctctacc agtttgttat ggacactgtt ttactttatg  43860
ttatcgtttt aatgttttct tttataatta ttgaggataa gagcttcctt aattttaaga  43920
ctatttaaat tgcagatttt gctttttat tttttaacc atcccttcca aagaatttga  43980
tttagatatt cagtagtaga aacagaagaa aaatactcaa ctaaaagtcc aaagacctag  44040
```

```
tttctaatgc taagggagac agtccatggc ctccaactag gtactttgga gtcaaaaata  44100
ctttctttac aactgtgttt gaattgtttt caaaacacct gtgtgtgtgt ttctaaaatt  44160
ccacaatcct tttaacccgt caatttgatg agggaagtaa ttagggtagg gaatggtata  44220
acaaagttgg ttctttgaca ttttctttat agattatcga atgtaagaca aatagatgtg  44280
aatgcagatt tggtgttttt ataagataag gatttaaaat aatgtagttg gtgatatata  44340
aaaataaact attgctgctg ttagcacccg agaggtgggg ctcttgggtt ctcagagctt  44400
gttttctatg ttcgttacag ttattttaga ttagaactta aaagaacttg agagtttccc  44460
taattctacc ccctaatttt ttcgaatgag aaattgagat ccatagaaag tgttgaggta  44520
aagatcacaa aacacttaat gagcggtgtt gccagtttga atatctcaat tcttagttat  44580
ctaagttccc tggtaggctt ctttaattat ctgggtctct tctagacatc tggaacaaat  44640
agttgattga cataatacag actagccaca tattttataa gagttacttt tgactcattt  44700
agatttttaa aatatacagt gtctgtattc ttctctattc attttgttaa ttttttttta  44760
cctaataatg attaagcacc aattatgtga cagcactatg ctaagcactt tgcatgcatt  44820
catctcattt aaatctcaac tctgtgaaag tttttattct agttactgta ttaagtctca  44880
attctgtcaa tatccatgaa gcacagaagg cagctgttat ttaccttaat tttacagatg  44940
tgaaaactaa aggcatttaa agagaaaaag aaaaaaaaaa ccaggaaacc ttaacactta  45000
tctgaaggga aatatttaat attgggtatg ttagttcctc atgtatcttt aataattttt  45060
gtcaacagcg aatctttaaa taaaatataa aggatcaggc ctctgctctc ctgcatatat  45120
ttgtaaagtc acttactgct ttttgtcaca gtttcaattt ctgtaaaata gtgagagggt  45180
ttttacctga caggatttgt gcatgtacgt ttactttgaa aattaaaaag cattaggcca  45240
ggcgcggtgg ctcacgcctg taatcccagc actttgggag gccgaggcgg gcagatcatg  45300
aggtcaggag attgagacca tcctggctaa cacggtgaaa ccctgtctct actaaaaata  45360
cagaaaatta gccgggcatg gtggctggtg cctgtagtcc cagctactcg ggagcctgag  45420
gcaggagaat ggtgtgaacc tgggaggcgg agcttgcagt gagccgaggt tgcaccactg  45480
cactccagcc tgggcgacag agcgagtctc cgtctcaaaa aaaagaaaaa aaaaagaaaa  45540
gaaaattaaa aagcattata aaaatgcaag gtggaatttt taaagctctg ccaagtccac  45600
ttagcttaaa ccagcatgac tctcattggc taagtacgtt atgacatctg tgactgtggt  45660
gtaggtattg cctataatca agaatctttt agggtctgct atgtgcaatc cctgaagggt  45720
catggatcgc agtttcataa agactgctgt attttaaagc cttcaaatgc caacgtagta  45780
tcttcacaat gatttttttt ttcagtttta ttatttttg aaagcgcctt cgacaaagtt  45840
ttcagtggat tttgttgagg gatattaagt atgccatcta cataatagcc atagtgataa  45900
ctccaaccac attgttatat ttttattaat aaatgctaga gtattctctt tctggtattt  45960
cctattctga tatttttata taatcaagta tgcaaagatt ctttgtcatt ggaaacctta  46020
atttgcctga aaatgggaat gaaattttca ggtttaaaat ttttttacat ttattacatt  46080
tattgaagct gtctgaaaaa gctcttgagt atattgaata ccaaaattta tcctaactgc  46140
ataaagttgg gaggattgtg aaacttgact gcactgactt gttttcttta ttgatcaaat  46200
ggttgaaaaa aacttcagtt aaacaaattt gatctattaa accaaagtta taaaagcaga  46260
ggaaagcata gaattattaa acggcagttt aaattggtaa acataccgat gtagaaccta  46320
agtttgtagg cagctttctt agatggaaac ttaaaaaaat tttaatcaga acattatgtg  46380
```

```
aaatttgtca tctggaattc agctgggttt attaaggaca aagtgtatgg ctataaaata  46440
gattgagttt ttttttaaa acagaaaacc caaaataaat gttctaagtt tccaccttag  46500
gaggctatgt atattgctcc tctttgaaac tgccttcaga accaccttgt aagccataaa  46560
agaaaatcgg actcattgca ctatagtaac acctaactgt tcttgctcaa agaaaatgta  46620
tttatccctt agctttattt gtgtgactcc aaatcatatg agtattgcca gatatttaga  46680
aatttaatcc tctctcgaat gataacattt attttctttg agggttttta aaagagccca  46740
catagatatt tctacagaaa atgtttaatt ctgttttgaa tatgcctgga ataagtgaat  46800
agcttcccag ggtgactatt ctgaaatggg tgatgcttag tggttaagtt ctgatttgtg  46860
ttttcttgaa gttattaagg aactttatga taacagttta tatattccct cttcttggca  46920
tagtaatgaa gtaatagaga ctattcacct ctaagcctga ttttttaaat aagtgtttat  46980
tttatgttta agtaaggtag gtctgctttt ggcttggact tgaatttggc aatagcagat  47040
ataaagtaaa cataatgtga attcctacaa cagtctccca aacagtttaa tttctcattc  47100
atacacattt cccttagtgt atcagggaat taagtatctg attatcagta tagcaagaac  47160
aactcaagta tactgaagtt atttatactc ataaaatagt ttgagttata gctacaatat  47220
aaaattaata tatttttgac ttttattcct cacaacctga aaaaaacctc tgcgattact  47280
gatagtactt ttaaaaacta aatgaatttt gttactacta tttgctaaat ttagtcatgt  47340
ttactgttca aaaaatgcta ggttaaaatg gatcctaatc tttgaaatga tgaagacatg  47400
tgtagtggtg tcaaaaatag gatattcatt ttgtaactat tctgttagtg ccgaagttct  47460
tagaatttct ttgtgacaac agcctgctta agaactttag attttttaga attgtactaa  47520
aagcaaactg ttttcttgga tatttgttct ttctccccaa aagatgattt ataagttttc  47580
agagctaaga aatgggaagg aagagccatc ctagcatggc aggtaatgtt ttactgctaa  47640
caggttttct ctgcactgct ttatttgcct tgaacctctt actttgttct gtcagctggg  47700
aggctggtag attttctatt aggtagcaaa tgcttctcat cactaaacac atatcatggg  47760
ctggtgttag tgcagtctgt ggatgggcac tacattttta atcaagaaat gtttttaaag  47820
gaaagacaaa ttggtgaagt aatttctaat tcagtatttt agggatgagt gaccttttaa  47880
ttgataatga tatttaacag agctgtacag tgctttgggg gtcccacaga catgtttaaa  47940
caagaaaaca gtaaataagg aagccagaag gaaaagttat aaaactatta agaaagaaaa  48000
tgaaaattct aaacttcaat tctggtgcct ggctaaattt gatttttgta tgcctcagtg  48060
tttctctatg gacactggga aatcaataag caacctagct acgttattat gttcgtaagt  48120
ggaagaacta aagaactaca aagacatgtt ctaggccaag aattctggtg gtaggtagag  48180
tgggaggtta actagatgat ctccaaggtc cttctaattg cacttggcag cagcaagcat  48240
ttatcaagct agacactggg catatggaga tgaagaagat gaatatcccc agcagcatgg  48300
agagcactct gatgatagtc atccctgcct ccccctccct cagtttgctt tttgaaatgt  48360
gagcttgaaa gatctcaaac tccttcctgg gaagacataa ctgaaacttc atggaggaaa  48420
gtgcatgaat gaatgggaaa caagatttga ttcaactatt tggaataaga aaaggggcaa  48480
caaggagtct gaaacaaatg aaagaaaaga tggaaagaat tagttgacta gatgaggact  48540
gagtacatag gaatgagcca acaggagact tcagcaacta atggatgaaa gtattatgtg  48600
catgcatgtt gtcatcaaat atcacatgat acaagacaag gagaaaacat gactttcacc  48660
ataacctcag tttgtgtacc ctagttgcaa gatatttttt tcttctagtc acttaagaat  48720
atccttattg tctaggagaa ataatcctct ttctgggctc cccagtgtat aagcccaaat  48780
```

```
ctgaggaaaa tttacctgaa atgttctttc cccagatacc cacatggttt actctctcat  48840
ttaaatgtca gctctgtaaa agagatctct gactgctcta tctgaaatag tagaatcttt  48900
cacagtcttt ccttcttctt gacatcatct atttgtgtct tatctgctca cctgctacaa  48960
tgtaagctcc atgagagcag tgatactgtc tgccttgctt actcctgtat gccagcgtct  49020
agaatagtgt ctagcacata gtaagacctc tacaaataca tgttgaatac ctaaataaac  49080
aaaatttaac atataaacca aaaagatata taggaatgga ttatatttct aatctttctc  49140
gagtgaggaa aatgtcagca gatagtgaat atcactgaga gagagatgat agcccaggtt  49200
atcttcccca gatagaaata agccttaaga ctgacaggtg tatatgaata cagagagtat  49260
acataaagaa gatgtatttt caattgacag tctctaaatt tgctttaaga cttcgaaatg  49320
gattgctttt cataatttct tagaataact ctggtctgtt taccattgaa aaattagagt  49380
agccaatgtt tgtaaatgaa gggttagagg gtttttttcct ttggtggttt gttaaaagct  49440
tgctcaaggc agtaacatag taaattgtca atataggaac ttttgtagca gaagctttat  49500
gcttttcact tttataagaa ttgagattat ttaagcagat gagtctaatg tatatgtttg  49560
tactgactta cctagaaggt caggcaagaa atcggtttcc tcatttttca gataagtgtg  49620
tgtgtaatca ctgagtacct taagagagga ggggtgtttt atttttgcct gaattttcaa  49680
aatatctttc ttcagcttat ttatatttta gatttgactt attctgtcta tagtatataa  49740
cagtcaggag gttggtagga taagttcatc tcttctacta agagttatag gagagttcaa  49800
cctaatatgg caatgacagt cgcagaaaag agaaaatgca agttaagtag gtgttagcca  49860
tagcaagaaa atcagatgag gtcatttaag aatgaactgc tctaatgttc aggaaaaaag  49920
aggggaggga caaggacagg gctctagaag gcaaccaaag agagcagcca caaaataaat  49980
gaatagctga agaattagga gacaacaatc ttaaaatgtg gcagggagag ggtagttgtc  50040
acattaacta gcatagaaga gacagaatag aataacataa atatatgagt gattattgtt  50100
cttgaaacca gtctttaaaa catgggaaca ttcccaaaaa tcaaagccag ataaattagg  50160
gaaatcttaa atggcacaat ataactagtg atttcgttta taattttttt aaaaaggaga  50220
cttaaatttg aaatttagat gtaattaaag cagataataa gaaacatact tctgagacca  50280
caaagaccct gagattcagt taagagtaag gtagaaaggc tggaagccag aagggaatta  50340
agtttctgtt ccctgagaag ccaacacaac aggaaaaaac tggccacacc ctagttcaaa  50400
ctcttattac tcttatcaat agtctcctaa ttgtttctct agttttctcc tctcccttct  50460
taattcattc tgcagtctac tgccagatta atcttcctag aacaccactt tcagtattat  50520
tcccctgatc aaaaaatgtc tgtggttttg ttgctcatag catagtggtt ctccttcttt  50580
gtaccacagc ccatatgcac gatgatagat ggtgggtagc cacatgaact ctccataacc  50640
tttggaggat ttgggttata cacagtctgt tatccaagaa agcatatctg agtgtaagtg  50700
agcattatag ggatagtctt ataattgact ccttttaaaa tttgttcttc tttttgcaaa  50760
tgccccttca gaatttacag aaatagtgtg ttcattccat cagtaaaatt ataccccaaa  50820
atgttaataa gcttatttcc atcacgtctc ctttcctatt tctttctttc ctctttcttc  50880
ctgcacatct ccccttatcc tccacatttc tctgtaatta cataagcata aacagacaca  50940
tatgagattt tctgggttgc ttgcctttaa ataaaagaat gggattatct tataccccctt  51000
tgtctgcagc ttgcttttct cacctaacaa gtacaccctg aacatccttc caggttaaca  51060
gatgcggatc ccattctttt aaatagacaa tattctattc atgtggtttc gtgattttttg  51120
```

ccactacaag caagtttcta ataaacaccc ttttctatgt accctttaca aatagcaact 51180
ttttttctaa atataaatgc tatggtttgg ctctgtatcc ccacccaaat ctcatcttga 51240
attataatcc tcacatatca ggggaggggc ctggtgaaag gtgattgaat cctggaggca 51300
gacttctcct ctgctgttct catgatagtg agttctcatg agatctggtt gcttgaaaat 51360
gtatggcact tccctcttca ctcactgtct ctcctgctct gccatgtgaa aacatggttt 51420
ctttgccttc cactgtgagt gtaagtttcc tgaggcctcc cagtaatgct tcctgttaag 51480
cctgtggaac tatgagtcag ttgaacctct ttctctttgta agttacccag tctcagttag 51540
ttctttatag cactgtgaaa atggactagt acagaaactt ggtaccagga cagtggggca 51600
ttgctataaa gatacatgaa aatgcggaag caactttgta actggataat gggcagaggt 51660
tgcaacagtt tggaggactc agaagaagac aggaagatga gggaatgttt ggaacttcct 51720
agagacatgt tgaatggttt tgaccaaaat gctgatagtt atatggacaa taaagtccag 51780
gctgaggtgg tctcaggtgg agatgaggca cttattggga actggagcaa agttcacttt 51840
tgctttgctt tagcaaatag actgacagca ttttgcccct gccctagaga tctgtggatc 51900
tttgaacttg agagagatga tttagagttc gtggcagaag aaatttctaa gtagcaaagc 51960
attcaatatg tggcctggct gctcctaaca acatacagtc atatgtgttc acaaagagat 52020
ggtctgaagt tggaacttag gtttaaaaga gaagcagagc ataaaagttt ggaaaatttg 52080
cagcctgacc ttgtggtaga aaagaaaaac ctattttctg gggagcaatt caagtgagct 52140
gcagaaatat gcatagatga agagtagcct aatgttaata gccagtagaa tagggaaaat 52200
gtttccaggg catgtcagag accttcatgg cagcccttcc tatcacaggc ctggaggtct 52260
aggaggaaaa aatggtttcg tgggccaggc ccagggttgc gctgctctct gcagcctcag 52320
gacatggtgc cctgcatccc agctgctcta gctccagctg tggctaaaag gggccaggag 52380
ataatcttgg gctgttgctt cagagggggt aagcctcaaa ccttggcagc cttcatgtgg 52440
tgttgggcct atgggtgtgc agaaggcaag agttgaggct tgaaagcctc tgccttgatt 52500
tcaggatgta tggaaatgcc tggatgtcca tgcattctgc aggggcagag ccctcatgga 52560
gatcctctgc tagggcagtg cagaggagat acatggggtt agagccccca cacagagacc 52620
ccactggggc actgcctagt ggagccgtga gaagagggat accatcctcc agactccaga 52680
gtggtagatc cactgacagc tttcaccatg tgcctggaaa agctgtaggc actcaatgct 52740
agcctgtgaa agcagctgca gggtctgtac ccagcagagc caccagggca gagctgtcca 52800
aggccttggg agctcacccc ttgtgtcagc gtggcttgga catgagacgt ggagtcaaag 52860
gagatcattt tggattttta agatttaatg actgtcctgc aggtttttgg acatgcatgg 52920
ggcctgtagc ctctttgtct taaccaattt ctctagtttg gaatggggga atttacccaa 52980
tgcctgtatc ccaatttttt cttggaagta actagttttt gattttacag tctcataagc 53040
agagtggact tgccttgacc caagaagact ttgtacttgg acttttgagt taatgctgga 53100
aggagttaag acttccgggg actattgaga atgcaagatt gtgttttgaa atgtaagaac 53160
atgagattta ggaggggccg ggggcagaat aatatggctt ggctgtgtgt ccccacccaa 53220
atctcaatca cttgtaatcc ccacatgtca ggggaggggc ctagtgggag gtgactgaat 53280
cacaagggtg gacttccctc ttgttgttct catgatcgtg agttctcatg agacctggtt 53340
gtttgaaagt gtgtggcact tccccccttct ctctctgtct cctcctctgc catgtgaaca 53400
tgtgcttgct tctccttcaa cttccaccag gattctaagt ttcctgaggc ctctcagtca 53460
tgcttccttt gaagcctgtg gaactgtaag tcaattaagt ctctgttctt cataaattat 53520

```
ccagacacag gtagttcttt attgcagtgt gaaaacggaa taatacaata gatttcccca  53580
aagttgggtt cctgagtcag ggtatgtgt atttaaaatt ttaacagata tttccaaatt  53640
actttttttcg aggattatgg caagtcacag ttccccctgg cagtgtttat acttttcttt  53700
ataataaaaa tacataaatc attattacta acaaattcct tgccatgagt cctaaattga  53760
taacaacata ccagtgtgcc atataacata gctgaggact gttgcagtct agaattcagg  53820
ctccttctct ctgcttttaa caatatgtgt aatgttcaag accaatttag tgccacttat  53880
tttgtatgct ttcctttatg tagtccaggc catagccccc cacctcatct gatggtatcc  53940
tctggcagcc acagaccaca cagttctttc tacctaaatt agtcattagc acatagtagg  54000
tacccagtaa atgtttgttg aattaatact gtttatatat ttctaattta tctccaagta  54060
aatccagtct ccttaaggac aaggaacgtt ttcactataa cacctagcac ttaaggtact  54120
caatttaggt agggctgttt gaacaaagaa ccacagagga agcaaatagc atggccttgc  54180
ctttaataca tatattttac tttctcttag ggaaaactgg aactgtaaga atctagtaac  54240
aataataaga acagcacttt tattgagcag ttactatatg tgaggcacag ttcaaactgc  54300
agaggataca acagtggaca aagctttagt tgtttctgcc tttctgaagc ttatggttta  54360
tgggtgttac attcaagaca tttgtaggac acattctaaa atgccatcca atttcaggct  54420
ctttccagca gaaactgtgg aatatttttc cgttcattca gcatttactt agtgcctgct  54480
ctgccaggaa ttgaagagaa agcccaaaga caggcagacc ttacctgaga ggtagtgaac  54540
tgaccaggat gactgtgggc agtagacttg tttcccaaac tagcctcacc atttctgtat  54600
ttgcatatac gaggaaagga ttagatatag ggattcatgt cagcatacac cccagggaca  54660
tttgttttta gtgaaaggtg ccagtcttca tccctgtacc cagtacacaa accacgaaga  54720
agtatgctcc cgtcattgtc aaagaatcat agaattccaa atggagctag ttttgatatc  54780
cagatctcac ttcatatgag gaaactaggt ccagtattgt gagtaagaat taggactctt  54840
cagattccct gggtatgaat ctgactaaca actgtgtgaa cttgaccaaa ttcataaccc  54900
tgtaaactct gtttcctcac ttttaaaatg ggcacaacaa agtgatgcat gtaaactgca  54960
tagcacagtg tctggcactt aaaaagcact cctgaagtta tttttagtga tgtgttttaa  55020
gattagacaa ctccttaatg ccaaaggttt ttacttgaga actctgtctg ttgtgccata  55080
ctacacgctg ttcataagat aagccttttt cattaattga tctcaaactg gcttcattat  55140
gatcttaact ttatttcagt tttattttta aaatttattt ttaattttta tgggtatata  55200
gtaggcatat atatttatgg ggtacaggtc atgttttaat gcaagcatgc aattgtgggg  55260
gtgatatata attgactggg gtgagatatc tcattgtagt tttgatttgc atttctctga  55320
tgattaagga tgttgaacat ttcttcatac acctgttggc catttgtatg tcttttgaga  55380
aatgtctatt cagatctttt gtccattttt taagttggat tgtttgattt tttcctgttg  55440
tctgaactct ttatatattc tagttattaa tcccttctca gatgggtagc ttgcaaatat  55500
tttcttccat tttgtgggtt gcttctttgt tgtttccgtt gctgtgcaga agttttttag  55560
cttgatgtga tcccatttgt ccatttttgc attggttgcc tgtgcatttg aggtattact  55620
aaagaaatct ttgcccatac cagtgtcctg gagagcttcc caaatgtttt cttttagtat  55680
cctagtttca ggtcttagat ttagggcttt agtccatttt tatttgattt ttatatgtgg  55740
tgagagatag ggtctagtt tcattctgcc tatggatatc cagttttccc agcaccattt  55800
attgaagaga ctgtcctttc cctagtgtat gttcttggca cctttgctga aaatgagttc  55860
```

```
actgtaggtg tatgaatttg tttctgggtt ctctaggtct gtgtatctgt ttttatgcta  55920
gaactatgtt gtttgggtta ttatagtttt gtagcataat ttgaagtcag ataatgtaat  55980
tcctccagtt ttattttttt tgttcaggat ggctttggct attccggggc ttttgtggtt  56040
ccatataaat cctatgattt tttttttcta tttctgtgaa gaatgtcatt gatatttatt  56100
aataaagatt gcattgaatc tgtagattgc tttgggtagt atggacattt taacaatatt  56160
gattcttcca atccatgagc atggactatc tttctttttt tgtgtgtcct cttcaatatt  56220
tttcctcagt gttttattgt tttcattgta gagctctttc acttctttcg ttgagtttat  56280
tcctaggtgt tttattttat ctgtagctat tgtaaatgag attactttct gatttctttt  56340
ttagattgtc ctctgttggc atctagaaat gccacagatt tttgtatgtt gattttgtat  56400
cctgtaactg tactgaattt atctgttcta atattttttt ggtggagtct ttaggctttt  56460
ccaataagat catacagtct gcaaacaaga ataatttgac ttcttccatt ccattttgga  56520
ttccctttat atctttctct tgtctgatta ctctaggtag gtcttccagt acttccagtt  56580
gaataacagt gggcactctt gtcttgttgt agatcttaga agaaaggctt tcagtttttc  56640
cccattcagt atgatactag ctgtcagttt gttgcagatg gcataacttt caaactaatt  56700
gattatagtt aggaagtgga tactttaact tgtggtacca ttatcagatt tatatttcgg  56760
ccataagctt gaagaggagc tgaaaaatgc atatgtgatg catatgcttc ctatttggct  56820
ctcttctccc accccccctgc cctataatcc acacaagttc ctctctcagt cactcatcaa  56880
ctacttgaac ctctgaggaa cttggggtta aggtaaatta gaataaaact gtctgaagaa  56940
gagcaagcct ttcatgtctt gagaaattct tggggtttta gaaataactt cattgctttt  57000
tttctccagt tactttggct tcttcttaaa gagaatacta acactttgaa cgtcataata  57060
ctaaggttct gcctcttcaa ataaagactt taaaaaaaaa tggtttttgt atgattcagt  57120
gtgaattaaa tcccacagtg taaaggactt tactttctta atgtagattt tcaaatacac  57180
aattactgat gtttataagt agatttatta caccaaagca cctagcaaat tcttgaatgg  57240
atcaggtctt atttttcagt cttactttgc aaatttaagt caaataatta aggatttgtt  57300
aaatatttgt cttaatatca agcttttgca tatcggggcc ctcttttata agctttataa  57360
gcaatctttt gttttctctg cttgctcaaa gtagctatgt ttgttgtatc tgttagtatt  57420
tgctctataa caaacatact gggtgccttc ccacttagat ttggcaatta tcactcctgt  57480
aaatgagata ttacataaga taggaaaaag aacagtatct ttccaagaag aatagtatcc  57540
ttccatatta acagtttaga gctgactgct tttaaaattt agtggcttta aaataacaac  57600
catttattat tcttcatgag tctacaaatg aggtgggcag ttctgctgat ctggccaagc  57660
tgaacttatc tcagctgggc acattcagcg tatctgctgt cagttggctg gttggctgta  57720
gcaatgaatg gtgaaagtag gctgccctta actttttcac acagtagcat tagagttaca  57780
aaagaaccag cagaaccatg caaaactctt taagacctag gcttggaaca actatatttc  57840
taccacattc tattggtcaa agcaaatcac ggggctagtc tagattcaag tgggtggagg  57900
agctgcaatt acactgcaaa ggagtgtgac tgtagggaga ggtgtttttt tatttttatt  57960
tttttgcgat ttgtcacagt agttgtagga atcaggtgta tttaaaattc tgatccttct  58020
gtgatatccg aattgttcat gaaccttgcc tctggtggaa aggcagaatc attgtgacag  58080
aaggataaaa tcttggaatt tagagactaa caaaggttca gattccagct ccatcactta  58140
tttctgcaat cctgcagaag ttaatcttcc tgataggcat tcagtaatga ttgattcacc  58200
tgaacctcag attctttatg tattttaaag aaagggctag gtaaatgcaa agcacttatg  58260
```

```
taactgcttt tattattgca aacctggctc ccacactcca ttcaaggtgt aagactcagt  58320
gtcttccttg aattaaaaag gaagagaaag tgtgttaggg aaaggaagag aaatatttga  58380
ctaattgtgg ccccaataaa gtgaccactc actgggggta ttttcctgta agaaaagaat  58440
ggttgaggct cagagttaag agatacaaat ccaaaagtct ccttggggta ggattccctg  58500
tgattcatgg gttgagaggt gtaacattag acacagtccc agtctagatt ttttttttaa  58560
agaattgtag tccatcctat acacactggg tgccttaata ctatatgtgg caattatcac  58620
tcctataaat caggttttac ataagatagg aaaaagaaca gtatcattcc acattaacaa  58680
ttgaaagatg actgctttta aaaaattaaa agggccatat agaaataaaa tcacataaat  58740
ttcttgtgtt aaacatagtt gtcatattgg atgaggacta aacacctaaa ttcatccaac  58800
tagtagtaat agaaaagatg aaacacacac acagtaaaac tagattaatt taatttatac  58860
aaagggccag atatctcaga attcagacag tcagagatgt tgactagagt taatgcctct  58920
tttaggagag gtaccaggta agtgttctca aagaactgga aactgagacc accacctctg  58980
gcattatcta tttgtgaaca caagcaagtc tgaatttttc cgcaccatag ctacctttca  59040
tgtaagcttc ttttcttaga agaaaagaag gtaacatttg ggtgtaattt tttattaagg  59100
gtgaaattta gtgtagagag taaaggcatt tggcatagaa gcccttagtt ttttttgttt  59160
ttaagttgaa ctgccagcct ttatggattg cagtcttcgc tgttttgatt gacatttccc  59220
aattcatttt gtattattta ttttttttaag agacagggtc tcactctgtt acccaggctg  59280
gagtgcaatg gggcaaactt ggatcactgc agccttgaac tcctgggctc aagcaatcct  59340
cccacctcag cctcccaagt agcttggact ataggtgtgc accaccatcc ttggctaatt  59400
ttttaaatct tttgtagaga cagggtagtg ctctgttgcc caggctggtc tcacattcct  59460
ggcctcagtt gatgctctgg tctcagcctt ccaaaatgct gggattacaa gtgtgagcca  59520
ctgcacctgg cccccaattt catcctttac aaagactact ttcaaccata aatcaacgga  59580
aacttcagct ccctcagaca tatttgggat ccaaggatat tttcccaaat gattaatgct  59640
aatttcatat caatacattt ttgcaaaacc tacaaaaatg gactagtaaa gaaagactct  59700
taatttggga aagacagtta cttggagaga agagaaactt aagaggcagg tcgagttcag  59760
tgttcagaaa tgagaggatc ataaagagat agccataaaa atgtttctcc ctatattgcc  59820
tgctgatagg gtgtatcagt gaaggtctta ctaaggacct tgtacctttt cagcgctgca  59880
ctgcgtgctc atagggagga aagataaatc atgtgttttt tctgacctca aaggagcctg  59940
tatctggcta gagagacatg atgcagacac atgaaataat taagaaacaa ttaactgtag  60000
caggtgctga agaatatacc aggaggtcag agaatggtag agctagtgtg ggcgaaggta  60060
tagcccagag catcatcaga tgattcttcc ttatgcaaat tcacatctcc tctgggtcaa  60120
gtatcatcct ggcatgcagc agctccatag gtaatgccct aaggctagcc tgaggcaagt  60180
tgcaaaagcc atcatattga gtcatggcct ttttttgtgt gggggggaggg gaatggcatc  60240
cccttcctgt ctgccaaatc aaggaataca gtgccctcct aaacctgctt tgttttagtg  60300
gattgttaaa aagaagtgaa tgaatttatg cttcattagg gaaaggttac agtggaatac  60360
tgaggagtaa ggggtatttc tatttaacaa atgacataac ttgaaggaat gaaatcataa  60420
ggatggaatt tcaggcatta ataaaaagct gatgagagat actttgagac aaaagagcct  60480
tcccagtgta accgagatca cagcacctac ttcacataca caggaaacca gtcctatctg  60540
tctctcccat agagcagtag ctgccttgtt tttcctccct cctccatcat tcattctaaa  60600
```

```
tctccagtcc tccaccgcac cttatccaaa ccctgatacc cttaagtcac agatggtgaa  60660
tcagtcaaaa gtagtattaa aaactagtgg tacacagcta cacctggaat gcagtaagaa  60720
aaatacggat ttctgtacat catcttccct ccctgctctt acccccattt aagagttaca  60780
gggtcagaac ccaagagtct gagtttttga aagtccctaa aaattttgga tgatcaccta  60840
catttagaac cactgcacta agaaggacaa caaatatgcc aataaattct gttgccaagg  60900
aggtgattat gcaagctgga accctgataa catgaggaga atcccacaat agccaaatag  60960
tccatgtact agttacatta taataaagcc aaaagcagca ggcctacctg actttctcct  61020
gaggtctatc atgagcttag agagaaggaa cgtggacata tagaggtagc tctagatgga  61080
gaagggcact aggtgtcatg gaaagaatca tgtgcaagaa gtaaagaggt gctctgaatg  61140
tcctagccct gcttaggtgt ctgtgtcctc acatgagaat ttatccacag ttctttcccg  61200
ctgtaacaat ctttggttcc aactgcattt gtgagacagc aaaaagctat ggtccagtct  61260
ccttccattg tatcatctca tcaatgtatt tctcccacta cccttgtgtg aaatacaaac  61320
tttttggct tattgtgatt atgcaaggtg tatgccaact ttttttttt ctccacatct  61380
ttcagctttc tgatgggtaa aaattttcct tattttgctt tagaaaaatt ctcattggca  61440
tagatctaat ttcagggagc ctcccttgaa agctaaataa cattgagaat tcatgaaaat  61500
ataatgtaga gcattatgcc tgttagcata ttagtttaaa tagaagtggt tcatgaaaat  61560
ttttgaaatg ccagaccctg tcctgtgttt tgtattctcc caaatactca tccagatact  61620
gttcagaatg taacatgatt attttgaaat aaagattttc ccctagtttt taaaaaagtt  61680
actttataca ttaaccctta tgttcctctt tgatcaattt ttccagtagt gtaaacagtc  61740
ttcagggaag tagatttctt acagaaattg tcaagtggct ctctgctgtt agcatggtta  61800
ctaatctttt ggttactttt catatttttt atactttctg gaagtggaca acttacttgt  61860
aaataaaagt gcataatttg tattaaaaat ttttagtaac aatctaattt gtaaaataga  61920
tgtgagcagc atgaatgtgt gtgatatgcg tacatacgaa ttatgtctct taaaaatgta  61980
tcacagacat ctttccgtgt ccaaacaaat ctacctcatt ctttctaata gccatatggg  62040
tataccataa tatatttaac taggccccta ttaaaagaat tttgactctt ttgtagctac  62100
tatagtgttg cagtgtgtat ctgtgtatgt atctttgtgt gtgtatcttt gtacgagtgt  62160
acatatattt tccccttggc tatttcagat tttttttag gtttaaatct taggaaaggt  62220
tttgaaattg tcttaagtat tttcagaagc attaaatcat ggttttttta catttttctt  62280
ttagaagttt tatgtcatct ctatgagtag ctttcagtaa tttgttctgc ataaaattcc  62340
cgaaaacttc catttaaaaa taggtggcat gactagactt tctcagccga aagagtgagg  62400
tcccaggaag gattttggag aagctgtgtt caaatatagc tgctgacctg atgtctgcct  62460
agagtctggc aaggtgatgt gttgaatcta gtgtctgcct gcatgccagc atccctttac  62520
tgatgagatt tgtggttttc atcacttcat ggtaatcatc ccaagttata agatggagtc  62580
tctagaaaat cagtagagta tgaaggccca agtaaaatac atgtgagtgc atgtatgtgt  62640
gcatacaaat tacttctctt aaaaacgtat cctgggcatt taaagaatga ggacctccga  62700
aggattttgt ggaagctgtg ttcaagtaca gctgctgagc gtatgtcagc ctggagcctg  62760
gcaaggtgaa gtgttgaatc tagtgtcttt ttgactcact gtttttttg actcactgtg  62820
ctttgaagcc cttgtcattt gggctcataa aatagatttc tgtatactgt ctctcctccc  62880
tgccctcgcc cccatttaaa agtatagtgg cagaacccaa gaatcagagt tactaaaaac  62940
tctctagaaa atttggatga tcacccacct gatcatgtct tttttactca ctatgttttt  63000
```

```
ttttttttg agacagagtc tcgctctgtc gcccaggctg gagtgcagtg gcatgatctt  63060
ggctcactgc aagctccgcc tccctggttc acgccattct cctgcctcag cctcccatgt  63120
agctgggact acagggcctg ccaccgcgcc cggctaattt tttgtatttt tagtagagtc  63180
ggggtttcac tgtgttagcc aggatggtcc cgatctcctg acctcgtgat ccacccgcct  63240
cggcctccca aagtgctggg attacaggcg tgagccacca cacccggccc tttactcact  63300
atgtttttaa gcccttgttt tcatttgctc cactgtaaaa cattccccaa gccaatctgg  63360
agctgaggca aatttttaac aatttaaaat ctggggaata taaatattgg ataatgatca  63420
tcctgaaaaa acaatgaagg tagtagcata atactttata tatcaataaa atggcaaaat  63480
aagacagttg ttgaaggaca gaaagagtaa ctgaagttag gagcttatct taacacattt  63540
tttgtgtcat accataggca tcatattttt taaatttttt ttatttcata cacataggaa  63600
aatatatgtg tgtaagaaat aataaacacc tctttgtacc taccacccaa cttaaggaac  63660
agctcattgc tattcccttt ggtgctcgct ggatgccctt tcccagtcac atccccctcc  63720
cttcccatct gcaggactat actagtaaat tttgtatttt ttgcattatt ttgctttgtt  63780
ttatgatttt actacctatc tacatatccc taaataatac attatttagt ttcatatgtt  63840
ttaactttat gttgtggaat cacattaaat gtagtctttt ttttttatat tatactttaa  63900
gttctagggt acatgtgcac aacgtgcagg tttgttacgt aggtatacat gcgccatgtt  63960
ggtttgctgc acccatcaac tcgtcattta cactgggtat ttctcctaat gctatccctc  64020
ccctagcccc ccaccccccg ataaatgtag tctttataac ttgttttttt aactcaacat  64080
tgtttgtaag attcatccat gtaagctgaa gctttttttat agagatcttt gttaagcctt  64140
ttaatgaata cagtacatac atttctctgt tcccctgtta gtggacactt ggattgtttc  64200
cagagttttg ctgttttgaa caacgctgct gtgaaaatgt ctcctgaaac acatttataa  64260
gagttttttt ttccccaagg gaattatacc tagaaattga ataactagat cacaaggcat  64320
acacatctac aacttctgct aggtaatgcc aaattgtttc caaggagcgt tagaagtgtt  64380
ctcatcaact tttactagtg ctagtctttt acatttgtgg cagtatggtg ggtgtgaaat  64440
atttatgttt agtttttctt ggtgccattt aataattttt ataaaaaata tttagaagtc  64500
aaggcagttt tttgttttttg tttttatttt ttgcttgttt tgttttaatg cagacattga  64560
gattacgact tggaataaac attggttgca aagttcctaa aaggaaaact ttttttggta  64620
ttctggagct tttctggtac tgaataaaat aagtatgtta aattatgcat gtgtagttta  64680
gaagtcagag caataattgt gattgttgaa cagaatggca gtaaaaagtt tctaaacgat  64740
tgtactgtac aagggacact tgttgtgggt cagttttagc ctccccaact tttatgttaa  64800
aagttgcaac aaggtttaag ggcttatgtt tgataggcca gatggtgacc agctgtgata  64860
aaacacaggg aacccttgca aaggatttca aaatttatgc agtagtccgc cttatctgca  64920
gttttgcttt ccaaggtttc agttacccgc agtcaactgt gttctgaaaa tattaagtga  64980
aaaattacag aaataaagaa tcgaagagtt ttaaatttta tgcttcccac ccatcccacc  65040
tgggatgtga atcattcctt tgttcagcat ctccatgctg taggtgctgc ctgcccctta  65100
gtcacttggt agccatccag gttatcagat tgactcttct agtattacaa cacttggctt  65160
caagtaatcc ttattttact tcatagtggc cccaaagtgc aggagtggtg atcctggcaa  65220
ttcagatatg tcaaagagaa gctgtaaatt gcttccctta agtgaaagat gaaaattcta  65280
gacttatata taaagaaaag aaatcatatg ctgagactgc taagatctat gataagaatg  65340
```

```
aatcttttat acatgaaatt gtgaagaatg aaaaagaaat gcgtgctggt tttgctgtca  65400
tatctcagac tgcaaaagtt tgcagccaat gtgtatgata agtgcttagt taaaaggaaa  65460
aaggcattta aggtaagtat atatagtgtt tggtactacc tgtgatttca ggcatccatt  65520
gggggtctcc tgagtataag gggagactac tcttttagtg ttaaatgaac actaaggaac  65580
agagatgggg aagaggttgg agaagattag ttcagcagtt tgagtatagg taaacagttg  65640
tttgagaaag aagaaaaatg tgattagtat tttaccttag caatagtggc atagataatg  65700
ataaattata gtcacacaga actcttagta tttacagaac gttcacattt gtgatcccat  65760
ttaacaataa ctctgaaaga aaggtatcat ctaccactgc tttattgata aagatataaa  65820
aggtaagaga gatgaaacat attggccaat gatacccatc tggtaagaga cagggatggg  65880
gtgggacccc aaggctcttc tcgccaagcc cacggttttt ttgctttata ctttttttgcc  65940
tcctgatcac catggctgca gtttctactg tggacaatgt ctgtcagcaa gcattgatcc  66000
cctgccttca gcactcttac gtcttagcaa ggactggaaa gaaaaagcca ggagtttaca  66060
gtctgctgga gcaacagaaa agaatgatat gaaatatgaa gagaccaaaa tgatttataa  66120
taaggtgcta gactatgtag taaaaatctg ctttagctgt aagtcaaaag caagagcagt  66180
cttttcagaa tggaatagaa atgttggaat taaaggaatt ttcaaagttg tgaatttttt  66240
tcaagataaa catgttttat tttggtaatt atggtattac taatttgata accttcaggg  66300
agccacctaa tattatagaa gatgtacata taatgacaaa agcaaacatt ttatttttaa  66360
ggaccacaat ctaatctaaa acaaaatttc cccttttttct ggtctttggt taattaagga  66420
cttatttaaa tatcaaagaa agacacatag aaaacattta gtatatttct atacttttat  66480
taatgtcctc cataccttac acagatactt gacttggcta tggtctagat aatccatgaa  66540
aatttaaagg acagatttta acaactttat gctaaattga tagatctcta ggatcagatt  66600
gccatcactc tcagatgcga agcttccaac cacttatagg ttcctgatat cttgctttta  66660
tacagaccta atttctcttc ctttaaactt tcttttcctc agttgctatt tgattgaaat  66720
attgagtcat taaaaatttc caagtgggaa tttttgtgtt tcttcatcta tcatgaagct  66780
gctcaaataa gtaggtgttt gaataggagt agaaacagta ataggctgaa gccagaccaa  66840
tacagcttca gctaaatgcc gaccttgcta aagtctggga ggaccggtgt ggtattctac  66900
aatgtacaag tctgtagccg gtgcccttaa tatgttggct tcatgtctca tgactctctt  66960
ctgtaaatat gcagtttaaa aaatacaagt tattctgctg tagaagatac atttgcaaaa  67020
ttgatgtatc ccctctaagt aaagttggct aaacaataag gacatattta taattaatga  67080
atttgagaag aatgctgacg atatgcatta ttctttgaag ttaacatttt tcaggtccta  67140
aataaacaaa aagtaggtta cttctgtctg gagtgtatgc aaggggtacc atcttgtcct  67200
tggttcctgg ctgctattcc aaggtgctat aaagtcagct aaagagagca atcataatac  67260
attgatagca tccctcaatg tgtttctgag ctacttgaga atcttatttt tgaataggta  67320
gcaggaaacc atctttgcag ggcagcatgg gcaaagggat tggagggact attattataa  67380
agatccactg aactgcttca gtatcataat atcttaaact aaaggactgg aaagagccag  67440
attccaattt aatctgctct tctatgaatt cttagctggg ttcatttaaa aagaaaaaac  67500
ttgaagattg caagattttg aagacatctt aaaataggtg aactccaagg tgcactttaa  67560
acttgagact gataactgaa tactccttca ccttttgatc tgatattgtc aaaatgaatg  67620
aggacttagt gctctagtaa gtttggaaca gaatgatatt aatttatttt ctcatgattg  67680
attctttttt gctttttaat agattaaact tcaccgtaga acagtttctc aacctctgga  67740
```

```
ctattgacat ttttgattgg ataattcttt gctgtcaggg ctgttctgtg tgttgcagga  67800
tagttagcaa catccctgac aatcacaaat gttactttct gtctctatgg atttgcctat  67860
tctggacatt tcgtataaat agaatcatat atatgtggct tcttgtacct ggcttatttc  67920
acttaacatg ttttcaaggt tcatccatat tgtagcatgt aacagcactt cattttcttt  67980
ttatggctga gtaatattct gttatgtgga tatactacca tattttgtct atccactcct  68040
tagctgatgg tcttttaggt tgtgtccatt ctttggctat tataaataat gctgttaaga  68100
acattcatat acaagtttct gtgtagacat atatctttat ttctcttgtg tggataccta  68160
ggagtagaat tactggatca tatgataact ctatgtgtta ccttttgagg aactgccaaa  68220
catttttcta cagtggctgt atcattttac actcccatca gcaatgtata agaattccaa  68280
tttctctgtc cttgcctata tttattaact gtcttttctt attagccaac tgctgtggtt  68340
cgaatgtttg tcccctccaa aactcatgtt ggaacataat ccccaatgtg gcagtattga  68400
gatgtgaggc ctttaagaag tgcttgggtc atcagaggtc tgccctcatg aataggctaa  68460
tccattcatg agttaatgta ctaatgggtt atcactggat tgggactagt ggctttataa  68520
gaagaggaag agaactaatc tagtaagctc agccttctca ctatgtgatt gctgccctgt  68580
gtcaccttgg gactctgcag agagtcctcc agcagcaaga agttcttcat cagctgtggc  68640
cccttgacct tggacttccc agcctccaga aatgtaagaa atccatttct ttttttaat  68700
aaattacaca gtctcacgta ttcagttata ccaacagaac acagactaag acaccatcct  68760
attgggtatg ggtatctcat tgtgtttttt atttgtgtct cccaaatgac taacgatgtt  68820
gaacatcttt tcatctgctt tttggacatt tgtgtatttt ctttgaagaa atgtctttaa  68880
cattctttgc ccattttaaa attaggttgt ctttttattg ttgagttgtc ggtgtgtgtg  68940
tgtgtgtgtg tgtgtgtgtg tgtgtatcta gaatatatgt gtatgtatat atgcagatat  69000
attctaaaca ctagaccctt atgaaatata taatttgagg acaatttctc ccatttaaaa  69060
ggccatcttt tcacttcttg atagtgtcat ttgactcaca agtttttaat ttttatgaag  69120
tccaatttat tttttaattc tttgtttttg gcactgtatc tttaaaaagt tgcctgatct  69180
aaggtcaaac tgattttcac ctatgttttc atctaagaat tatagtttta gctcttacat  69240
ttaggccttt gatccatttt gaattaattt gtgtatatgg tgtgaagtag ggctctaact  69300
tattcttttg tgtaatgata cctagttgtc ccagcaccat ttgttgaaaa gattattctt  69360
tccccattga atggtcttga taccttgttg aaatcaactg accataaata tataggctta  69420
ttcctggact cacaattcta tgagtctgta tgtctaatct tatgccagta ccacactgtt  69480
ttgattatta catctttgta caaagttttg aaattgggaa atgtgagtct tccaactttg  69540
ttctttttta agattacttt gcctatattc cgtgttcgtt gcaaactcat atgaatttta  69600
aatcaactct ccatttctgg aagaaaaaaa gaggcaattg aagttcagat agggattgca  69660
ttgaacctgt agatcagttt ggggaatatt gccatcataa caattagtag gtcttccaac  69720
ccatgaatac aagacttctt tccatttctg tagatattta gtttctttca ttaatatttt  69780
gtagttttca atataaaagt cttgtacttc gattaaattt attcttgaat attttgggtt  69840
ttgatgcttt tatgaatttg ttttcttaat ttcactttaa gattgttcat tgctactgat  69900
tagtaatgca actgattttt gtgtgttgat ttttgtatcc tgcaacctag ctgaaatcat  69960
tgattagcat aatagagtat ttaatagatt taggatttct atatataaga tcatgtcatc  70020
tgcaattaga gataatttta cttcttccct ttcaatctgg acattttta cttcttttc   70080
```

```
ttgcctagtt gccctagcta gaacctccag tgcagtgttg aatagcagtg gtgagaatga  70140
gcatctttgt gttggtcttc atcttgtggg gaaacctttc agtttaagtg tgttgttgtg  70200
gggttttcat agttgtcctt tatcagattg agaatgttcc tttctgttcc tagtttgttg  70260
agtgttttct ttttgattgt tttaatcagg aaagggcatt agattttgtc aaatgctttt  70320
tctgcagcta ttgagatttt tgtgtgtttt tctggtcttt tatggtttat cacattaatt  70380
gattttcata tgtcaaacaa accctgtgtt cttgggtttc atctcacttg gttatggttt  70440
ataatccttt ttatatactt gtagattcag tttgccagta ttttgttgag gatgcttgca  70500
tttatattta taagggatat tggtctgttg tagctgacca gtaagtatag taagctgtat  70560
agtttactaa gtgttccctc tgttttgggg gagactttga gaagaaggat tgttggtaat  70620
tgttctttaa acatttggta aaattcacta gtgaagccat ctggggtctt ctttggaagt  70680
tttttgatta ctaacttaat gtctttactt gtttgttata agtccattca gatttttttc  70740
tccttgagtc atttttgaca gttggttgag gaatttgttc atttcatgta gttatctaat  70800
tggttagtgt ataattattc atagtattcc tttataatct tatttttttg ctgtaaggtc  70860
agtcataatg ttcactcttt catttcggat tctggtaatt taagagtctt ctctcctttt  70920
ttttcttggt cagtctagct aaagtaaagt tttgtccgtt ttcaggggaa cagctttttt  70980
tttttttttg aggcagaatt tccatcttgt cacccagtct agagtgcagt ggtgcaatct  71040
cggctcattg cagcctccgc ttcccgggtt caagagattc tcctgcctca gcttgccaag  71100
tagctgggat tacaagcgcc caccaccacg cctggctaat tttttatatt tttagtagag  71160
acggggtttc accatgttgg gcaggctggt ctcgaactcc tgacctcagg tgatctgcct  71220
gccttggcct cccaaagtgc tgggattaca ggtgtgagct accgtgccca acccagcttt  71280
ggttattttt gttgacctac tctattgttt ttctcttctc tatttcactt atttctacac  71340
tggtctttat tattttcttc cttatgcttg ctttggactt agttcttctt tttctagtct  71400
cttaaggtgg ataattaagt tcctgatttg aattcttact tctttgtaag gtggtcatgt  71460
actgctatga atttccttct cagaaatgta tatgctttca ctgcatccct taagatttgg  71520
tatgttgtat ttttgtttc atttgtctca aggtatagtc ttctgatttc cattgtgatt  71580
tcttccccct ctaacccgtt tattatttag gaacttgttg atttccacat acctgtgaac  71640
tttccagatt tccttctttg ttaattctca gtgtcattcc attctggtcc gagaacatac  71700
tttgtatgat ttctatcttt taaaatttat ttggcttgtc ttatgaccta atacattgtc  71760
tatcctggag gatgtttcat gtacacttga gaagaatgtg tattctgctt ttgttgggta  71820
gagtgtttga caggtgtgtt ggtacatagt tctgttcaaa tctgtttcct tgcagatttc  71880
tatctagttg ttctgtctat tggaagtagg atattgaaat ctccaactaa tattgctgaa  71940
ttgtttattg ttttcttcag ttctgtcact ttttgcttta tatattttga aattctattg  72000
ttaggtacaa gtaagtttat gattattata tcttcttgat agattgattc ttttatcatt  72060
atacagtgcc ctataagaac aatttttatc ttaagtctat ttgtctatat tagtatagcc  72120
acttcagctt tcttttgttt actgtttgca tggaatattt tcttctttta ctttctattt  72180
gtgttcttga gtctaaggtg aatctctgta gatagcaatt ggatctgcca atctttgctt  72240
tttatttggg gagtttaaac cattgacatt taatgtaatt attgatgagg aagattactt  72300
ctgatatttt gccatttgtt tcctttattt tgtgtctctt gttcttaaat tcttccatta  72360
ctaccttctt tcttttgtat tacatatttt ctagtgtaac gattttaatt tctttgtcat  72420
ttcttttgtt gtatgttttt agttattttc ttagtggttg ccacggagat tttattgtca  72480
```

```
ttttaacagc ctaggttggg cacagtggct catgcctgta atcccagcac tttgggagac  72540
tgaggcagga ggatagcttg agtccaggag ttcaagacca gcctgggcaa cttactgaga  72600
tactgtctct acaaaaaaat acaaaaatta gccaggcatg gtggtgtgtg cctgtagtcc  72660
cagatgcttg agaggctgag ttgggaggat agcttgagcc caggaggttg aggctgcagt  72720
gaactttgat cacaccactg cactccagcc tgggtaccag ggcaaaacta gcccaaagaa  72780
atgaaggaaa aaaaaaatct aatttagatt aatatcaact caacttcaac agtgtataaa  72840
aactttgcct ctgtatacct cttctgcttc cactctgtgc tgttattgtc atagattttc  72900
atctttctac actgtgtgtt tatcaatgta gatttaaaaa tattgcttag tagttgtctt  72960
tagaatccga tacggagaaa aggagatata aacaaaagat gcatttttac tgtcttgtat  73020
gtttacttat gtaattccct ttcctgatgt tgtatttcta aaggcaaagt agggttattg  73080
tgagtgtcct tttgtttcaa cctgaaagac tccttttagc atgtgttgga gatatgctaa  73140
tgatggactc tcacagtttt tgttatctgg gaatgtgtta atttatcctt catttttgaa  73200
ggatagtgtt ggcaggatac agaattcttg gttgacatgt aattctttca gcattatgaa  73260
tatgtcatcg tactgtcttc tgacctccat ggtttctgat aaggaatcaa ctgttaatct  73320
tattgaggat cacttgtttg taatgacttg cttgtcgtgc tgctttcaag attcattctt  73380
tgcctttagc ttttggtagt ttgattgtga tgcatttagg tgtgtacttt attagtctgt  73440
tctacttgga gtttgttgag ctttgtagat gtatttcatc agatgtgtca agttcttttg  73500
ccactatttt ttttttaaat aatctttttg cccctttccg ctccttctgt cactctgatt  73560
atttgtgtgt tgctttgttt ggtggtgtcc cagaagtctc tgagactctg tccagttttt  73620
tcctccccat tctttttttct ttcacttcct cagactggat gatctcaatt tgacctatct  73680
tcgagttcat ggattttctc ttctccaagt gacatctgtg agatgaattt ttttctagag  73740
aatttttcat ttcagttatt ctacttcaaa atttctcttt ggttcagttt tatcattgct  73800
atctttatat tattctcagt ttaatgagat actgttttat actttccttt agttctttag  73860
acatagttta tgtcactgaa tatatttaaa atagctgatt ttaagtcttt tttttttttat  73920
tttttggag atggagtctc gctctgtcac ccaggctgga gtgcagtggc acgatctcag  73980
ctcactgcaa gctccacctc ctgggttcac gcaatgattt taagtctttg tctatgaagt  74040
ctagtatctg ggcttcctca ggcatagttt ctgttttctt tctttctttt cctgtgtact  74100
tcgtttcttt gtataccttg taattgttgt tgttaactgg acattttgaa tattatagtg  74160
taacaactct ggcagtcaga ctgtctcccc tccccagtat ttgttgttgg tgagtattgt  74220
agatgtttgt ttagtgactt ttcatggcta attctgtaaa ttttatattc tttgaagatt  74280
gtgggcaccc tgaagtctct gtttgttagt ttagtggtca cctaataatt aacagagatt  74340
tcattaaatg cctagaagca aaatatcttc cagtctttgc ccatggcctc tgtgtatgca  74400
ttagggcagg ccttgaactc ttacccaggg agtttacaac cctgccttag cctttactac  74460
cagcttctgc agagcattaa ggtcaacagg tggtgagagt ttggagccta ctccatcttt  74520
cctgagcata tacacagccc tactcatgca tgtggccctc tagatttcca ggagtatgtt  74580
ggaccctttc aaagccctta cagactcccc agcttttcct ctcaatcttt agactagtgt  74640
gttgttttct tcaacagtta tctgtcaggc agcagcaaat taagagatta gcataaatgt  74700
tttcaactcc tccacccgtc atgtgcccca gggaagcact aagccagttc taagttaggc  74760
aaaataaaga caatcctttt gaggtggtct tccatggagt caccagacag gtaaaccaaa  74820
```

```
taattaatta caagtctttg gctggataca gtggctcaca cctgtaatcc cggcactttg  74880
ggaggctgag gcaggtggat cacaaggtca ggagattgag accatcctgg ctaacacggt  74940
gaaaccctgt ctctactaaa aatacgaaa aaataggtgg ctgtggtggc gggcgcctgt  75000
agtcccagct actcgggagg ctgaggcagg agaatggaat gaacccagga ggtggagctt  75060
gccgtgagcc gagatcacac tactgcactc cagcctgggt gacagagcaa gactccgtct  75120
caacaaaaaa aaaaaaaaac aagtcttcat gaaagaggtc cattctgctg tctttcatac  75180
caggaatgtg gaatgtggac tgttattttc atggctactg ctaagctagg aatcaaggga  75240
tagatgggga ctgggtaaaa caccacagag tttgctgttc ttaccaagaa taagctgggg  75300
aagagggttg tttttgtttt tcagtaaaaa ttccctgggc tgcttcaagc cgttgattaa  75360
ttttcaggtt ccgaaaaagt tcagtttgac agtttttgcc ctttttattt gcttttatgg  75420
atatgtagaa cttgagttct tttttccacc agttttgctg acattgtttt aaaagcactt  75480
tttgtaaaac ccaaatgttg tctctctcaa ggctagccaa taattaaaaa tactgttact  75540
cccctttgat tttggaaatg aattcgtatt gaccaaaatt caatactaga ggtctttcaa  75600
gctgttttac catttatcta aactttagaa tctaatgatt cctgtacatt gtctagcata  75660
ctggtggtcc tcaattgtca taagttcaac tttggaacaa atgaactttt tgtgtgcaag  75720
tttccaattg tttggaaatt acattgatgc cccctccatc aaactgttat tcgtgggaca  75780
tctaggaatt tcttacagca gctgacaaat atttcaagtc agtgcctggt agtactgtcc  75840
accaggcaac agcttcagta gtagagcgat ctttatctat aaggcagtgt ttgagcaatt  75900
gtttattagt gttttcctaa ctactcagaa gaactatcag gggttataga ggtagctcag  75960
agagttgggt gcaagtagag aaatccaccc ggcttgcatt acacatctta tttctagaga  76020
agctttcctt tgaagaagga gttctaaggt ttaaaaaatt accttgaatg ccacttatat  76080
tgcattttaa ttttatttta gagaaatcaa tggaaagtag aaaaattaag gcactgatac  76140
tagtgttaag aatgttggtt aaagcttctg gcaattaatt ttttatttcc ttttttaatt  76200
ttattaaaat ttaacaattt tcagtttatg ctgtaatcca gaccaaggtt tcaatctaat  76260
gaagttaatg ccagtgttgc tgctacctat tttgtcttta gtcattcagc catgcttcct  76320
acttatactg aataagctag cttaatctaa caatcaaaaa agaaagctgt tgcctaagtt  76380
aagaaaaaca gtttgaactg ttttcaaact aaatacccag tagactctct agttgttgac  76440
aggagaatgc ttaattcaga attgtcctgc agtagatcat tttatctcat tcctgttctt  76500
ctataggata gcttatttgt ttgaaattgt atttaatatg ttgtgatttt tgtgtgcttg  76560
tttctatttt tcactggata gactcaagat aaaacctggt accctgcagt gtagctatca  76620
gtttatagca gaggaaattt acattagaac ttggctgtgt atttacatgt atctaacttg  76680
gaggtcactc tgcttactgt tgatatatca gtcatattag atgagtccct aatgagatac  76740
cagaaacccc ggaaacatca ttaggtggaa cagtgtcctt aatgctttat taagtgttat  76800
aggtaagaca aagcctagta ctatttgtgg catcaaggtt aggtgtttaa agacctgtat  76860
tcttctattg tcatgttgaa attgttccct tgatgtagca atagaaaatt ttagattagg  76920
cttaagttaa tcagcaaaca aagataaaag tctgatacta tcctaaatat tttgtgtttc  76980
taaataattt aacagtgatc caattagcta ctcctgtaga aatgtaattg ataaactttt  77040
cactctcttt taaattgcca tcttgaattt tacctgtttt ttaaagctgt ctcaagtcct  77100
ctctaaaaaa aggcagtcat ttataaattt agaaaagctt gatagcacag aaagtcacag  77160
aaaaatgtaa acatagttta aaactgaatt gtatacaagc cactagaagt acttttatta  77220
```

```
agtttacaaa tattagtaga gtggaactca tgcatttaat atgtttgaaa cttttgatca  77280
aatactgtgc tatgaaaaac attttagata attattcttt aatcatgtgt gtgtaaaatg  77340
tggctttttt tgacaaccaa gtagcttttc tgtgtgccaa actgtgactt taaaatttta  77400
aagtactcaa cagagtaaac aaaccacaaa taccacttaa actgtacaca tttgcacatg  77460
catttcctat aaatagtaca tgggtttcaa gtcttcactt ttgaaattca gaaatgggtt  77520
ttttctcctt ccagtagaaa taaaaacttg atttatttta tttatttatt tattttattt  77580
ttgagacgga gtctcgttct gtggcccagg ctatggtgca ggagggtgat ctcagctcac  77640
tgcaacctct gcctcctggg ttcaagtgat tctcctgcct cagcctgccg agtagctggg  77700
attacaggtg cctgccacca tgcccagcta atttttgtat ttttagtaga gatggggttt  77760
ctccatgttg ggcaggctgg tctcgaactc ctggcctcag gtgatctgtc tgtctcagcc  77820
ttccaaagtg ctggggatta caggtgtgag ccaccgcatc cagctaaaaa cttgattttt  77880
aaaaatccaa atcgaagaca gaattgtgta ttttagtaca tttattagca gccttgacgc  77940
tataccatat ggctgtttat catttaaaca gcttgtaaaa gcaaacactt caggattcat  78000
gagtggcaga aggactgagt actttgggaa ataagagaga acttttgttg aggatggttg  78060
aggaagagtc caagacaata ataggcagaa taagcaaaaa tctagagact cattgtaggc  78120
actcaagtat gtatttgtta gaatgaatgg ctgaacttgg tatattgagg aacactgaga  78180
aagccatact gactggaaga tagttcctac aagaaactgg tgagacatat gttacagtct  78240
agattttggt gagccttgtt aaagtttggg ctttattttt atacggggag aaagtttcac  78300
aggggtttgg aaatgaggct tggagctgtt aatggggaca cagtgaggtt ttagggtagt  78360
ggctttcaaa ctgtttaaat ccaaactttg atgataaccc tgacataact attgtttata  78420
acttccattt cagttgtatt ggttttatca aaacatcttc attgatctta ctgattgctt  78480
cctatgcaga ttaatattat aaatttgaat gtacaaagga agctttagca gtaaaatagc  78540
aacttttatc tgtcttacgt attggaggtt ctgcataaga tttaattttt tttttttttg  78600
aaatggagtt ttgctcttgt tcacggggct ggagtgcaat ggtgtgatct cggctcacca  78660
caacctctgc ctcccgggtt taagtgattc tcctggctca gcctcccaag tagctgggat  78720
tacaggcatg tgccaccatg cccggctaat tttgaatttt agtagagacg gggtttctcc  78780
atgttggtca ggctggtctc gaactcctga cctcaggtga tccgcctgcc tcagcctccc  78840
aaagtgctgg gattacaggc gtgagccacc gcgcccggcc aagatttaat tttttaaaag  78900
aaaatatttt gctaagggtt tggaaactct tgttttagca agaatggatt aagactgatt  78960
aaaactaaag gcaaagagga ggctcttatg tttggaattc tttgctaata tttacacaat  79020
ataattctct ccacaaatat ttaatggtac cagatattag atggttataa tggcaaaagt  79080
gttcaaagga tgctatcata ttcatgattc atgatcaaaa tgaacattat aaggctatcc  79140
ctcttcagaa ttaaatacgt tactcctgtg gaaaacttgc ttttaatgta gaagttgtcc  79200
cagagccttt cttcctttct catgtcctct tatgtccact gctgagctaa catgggtctc  79260
actgaatgat taagaaaaaa catcttaggt ggggagttct gtatatagta aatgtttaat  79320
ttattggggt ggtgaacggg aagtgctgct ggcaagagag gatgggaaga gaaatctacc  79380
caaatcctta cccgctttac agaacataaa cttcctattc agtagtacac aataacttaa  79440
cgatcaaggc atcttaactt ttctgttttc agatgaaaga actatcgttt ggcttgatca  79500
agtatttagt atttattcgt tcactcaagt gcttacgttt ttttgttatc tcagggtttt  79560
```

```
acgttagtta ttaaccaaaa gaactagttt tagttctgga agtctaaaat atataagaga  79620
aggtgaggag taataagaga agatgaaggg agactttcgg aatggcctat gaacttctag  79680
taactatacc accttaaaat agacaaatta caatgcagtt atgaagatat gtatttttca  79740
gtgaagacaa ctaaaatgtt tgcacagaat tttctttttt attgagtgtt agaaattcta  79800
ttttggagat actaccttgc acaacataaa aagaaaaagt gagtgtggaa tctaggaatc  79860
tacgtggctc taggaaattt tttaagtgtg gaaactgaag gagagcaaga gaaagggagc  79920
atggcattcc cctgtttgta gttcatgagg tgggtttaaa ttgccttttg ccaatgcagc  79980
tgcacactga ggattacaga attcttttta aatgtttgta gaattatttt tcacttatta  80040
ggtaaaacgt gtattttttg attttctcca atttcagctt tctcatgttg ctatgctcaa  80100
ttttgtatac catatatagt tttgttaaat tgacaaagtg gtgtttttttg ttcttctttt  80160
tcccattggt taaaatttaa agagaaagtg gaagctagaa atttatctaa aaaatgtaac  80220
tttccctgta attattaaag tatcaatcta aatttgaatt ttctttgtgc ataatctttt  80280
ttcaagctat ttaccatgtt gacaaacttg ctttcctgtg gcaaatacac tagcaatacg  80340
ttataaatat gtaactttca acctatttac agttgatgct tttttagccc tttggattta  80400
aaatacaagc actgaagagg tgaggaagta ccactgctgc ctcagcatta tttcgaaatt  80460
ctgtttataa actatacaat ttccaaggtc atgaatccag cacctttcca ggtactaact  80520
attgggacaa agatagaatt tgattttatt tatttaccta ttgactgaag tctaacttaa  80580
atcttgcacc tagtaagatc ttagaaataa cgtgtgtact ctgacctgta aactaatcct  80640
agtattctgt gtgtatattc tttctcattt gggctcttaa aaggaaaagt aacgtacatc  80700
tgatgatcat tagcactgag ctttttcagc aaaaagtata tgtttataaa gaagtatagg  80760
ataatttagt aatttaataa tgtgacaaca tttgcgtgtg tttttttttt tgagaaatac  80820
aaattgtgag aaacagaaaa gtaaaagaag cagcagcaga aatatcacta taggatcaaa  80880
agattgcagg aaccaaaact ccaaaattat tgggcataat gtactaaaaa cagggcagtg  80940
gaggaaaggg acagtccaga ctagctctga gggtccaaag aaagtattaa atattgttac  81000
tggagtgatt tgctctgcta tttgggcttg ggaattaagt gaaattgttg atatactaga  81060
cagatacttc ccacccattt ttctcttgat aatcagggtt catttttttct attttctatt  81120
tctctggatg ctccatttct taatattaat attaatatta agctctcagt ctttatgcta  81180
aaaattggtt atttaaaaca atttaaatca acttcagtct aattggctta agttcaaatc  81240
cattttaaga tcgatattgt gtcctttaaa aattttattt aaaagatatt taaactgatg  81300
agaggatact acccattcca ctgataaact attactgtaa gtttgtctat tgagggctag  81360
ttatttggtt taaaaatgct gagattatgg aaagtggatt ggaatatttt ggagcaatat  81420
taaaaacagt atctgtaaca atttaataaa cttataaatt cctctttctc tgttgatcta  81480
tcttgaaaag acactctatg tctctaggca ttccttctct gtggtgtgat tggtagacag  81540
ggagtaaaca acttactgta aatgggcacc atgccagttg gcttcaggca gcatcaagct  81600
tgtgactcac agtcagggtt aggaaaatgc cttttaactt gtttgtctct gcctctttta  81660
aacattaaag gcacaactgt actaattatt aagtatttca taaggtcttt tagggcttat  81720
aagatctttt aggaatggcc tggaagttat tagtactgtt tcattgaatc tgaatacctt  81780
taacatgata atgagaagtt tttaaagggt ggttttatag ttaaacggaa tttctcaaat  81840
tggcttgctc cttatgttga tttatttagg atcacatttg ggagtttctc tgccctactt  81900
tcaatgtatt taatttactg accatcacta tttgggggga aaatgttata tgatatttag  81960
```

```
aaaccaagag ttttggagtt tttcccccat tagatgtatt tatttattta tttattattt  82020
tttaaagaca gggtcttgct ctgtcaccca ggctggagca cagtggcatg atcctagctc  82080
actgtattct tgaactcctg ggctcagact gtcctcccac ctcagcccaa gtggctaagt  82140
atcaagtaag aatcacctgg caaattccaa ggctgtatac cagatttcct aaattagaat  82200
tttggggttg ggtatctgaa ttttagtaaa gccctccaaa tgtttctggt attgcttcta  82260
agaacaattg ataacataat agctgtggcc attatagggg tattctgtca tatttagata  82320
taagcatacc ttgttttatt gtacttccca aatattgcgt gtttattttg ttttgtttca  82380
cttacaaatt gaaggtttgt ggcaacccta tattaagcga gtctgtcagt gccatttttc  82440
caacagcttg tgctcatttt gtgtctctgt gtcacatttt ggtaattctc tcaatatatc  82500
aaactttttc atcattttttg tatctgttac gaccagtgat cagtgatctt tgatttttttc  82560
ttttttttt ttttttgag acggactttt gctctgtcac ccaggctgga gtgcagtggt  82620
tcaatcttgg ctcacagcaa cctctgcctc ccaggttcaa gcaatcctcc tgcctcagcc  82680
tccccagtag ccgggcctac aggcgtgtgc caccacgcct ggctaatttt tgtattttta  82740
gtagagatgg ggattcccca tgttggccag gctggtctcg aactcctgac ctcaggtgat  82800
ccgctcacct tggcctccca aagtgctggg attaccgtgc cagcctgatg ttactatttt  82860
aattgttttc aggcaccata aacctcacct gtataaggca ccgtacttaa ttgataaata  82920
ttgcgcatga tctgactgct cttccaactg gccattccct gtctgtctcc ctcttcctgg  82980
gactctcaaa tccctgagag acaataatat taaaattaag ctaattaata accctacagt  83040
ggcctctaag tgttgaagtg aaagagttgc atgtctctca ctttaaataa aaagctagaa  83100
gtggctaaac ttagtgagga aggcacatca aaagccaaga caggccaaaa gcaaggactc  83160
ttgtactaaa cagctaaatt gtgaatgcaa aggaaaagct cttgaaggaa ataactagtg  83220
ctactccagc aaacatgtga atgatcagaa agtgaaacag ccttcttgct gatacgaaga  83280
aagttttagt ggtctggaca gaagatcaaa ccattcacaa cattccttta agccaaagct  83340
taactctctt caattctatg aaggctgtga gaggtgagaa agctgcagaa gaaaaattgg  83400
aagctagcag aggtcggttg atgaggttta gggaaagaag ccagcgctgt aacataaaag  83460
tgtaaggtga agcagcaagt gctgatacag aaactgcagc aagttatgta gaagatctag  83520
ctaagattac taaataatag attttccatg tagatgaaaa agccttttgt tggaagaaga  83580
tgccatctag gactttcata gctagaaagg agtcaatgtc tggcttcaga ggacaggctg  83640
acattcttgt taggggctaa tgtagttggt gactttaagt tgaagccagg tctcatttac  83700
cactccaaaa atccgaagac ccttaagact tatgcttaat ctactctgct tgtactctag  83760
aaatgaaaca acaaagcctg gatgacagca catctgttta tagtatgctt cactgaatat  83820
tttaaggcca ctgtaaagac ctgttcaact gctcagaaaa aaatgattac tttcaaaata  83880
ttgctgttca ttgacagtgc acctgggctc acccaagagc tctaatggaa ttgtacaaca  83940
agatggatgt tgttctcatg cctgccaaca catcatccat ttgtagccca tgaatcaggg  84000
agtgatttca agtttcaaat cagtacattt tgtaaggcta tagctgctat agacagtgat  84060
tgctctggtg gacctgggca aagtaaatca aaaaccttct gaaaaggatt ggccattcta  84120
gatgctatta agaatttgtg attcgcagga ggaggtcaaa ggatcaacat tagtagcagt  84180
ttgaaagaag ttgattccaa cagttataga tgaatttgag gggttcaaca cttcagttta  84240
ggaagtcact gcagatgtgg tagaaacagc aagagaacta gaattagaag tggagcccga  84300
```

```
aaatgtgacg gaattgctgc aatctcatga gaaaacgtga atggatgagg agttgcttct  84360
tatggacaaa tgagcaaata aattttttc ttgagatgga atctactcct ggtgaagatt  84420
ctgtgaacct tgttgaaata acaacaaagg atttagagta ttacataaac ttaattggta  84480
aagcagcagc atggtttgag tggattcatt ccagttttga aagagtttct actgtgggta  84540
aaatgctatc aaacagcatc tcgtgctaca aagaaatctt ttatgaaaag aaaagtgaaa  84600
cttcattgtt gtctacttta agaaattgcc acagccaccc caccttcagc aaccacctct  84660
ctgatcagtc agcaggcatc aacactgaag caagaccctc cacaaggaaa aagattacaa  84720
ctcactgaaa gttcaaatga ttgttagcat ttttaagcaa tattttaaga ttaaggtaaa  84780
tacattttta aagacacaat gctattgcac acttaataga ctacagtata gtataaatat  84840
aacttttata tgtagtggga aaccaaaaaa ttcgtctgac ttgctttgtt gcaatattca  84900
ctttattgtg gtctagaacc gaacctgaaa tatctcagag gtatgcctgt attaatatta  84960
ttttgcaagt aaaaaaccca gcatataaaa aaaacgtaga atatgttgag agttcagtaa  85020
tatggatgaa aatgttttc tctaactgaa gaacatgata aattataatt agggaaggat  85080
ataaaccaag aaaatatgtc tgagatagcc aattcttgca gttcataata tgaaaactca  85140
ttataccaat ctcagtaaga atacttttaa tagctgttat ttctttggga tatagaattt  85200
ataaagtaca cagtaatctt cttatgatca atcctaggat cactttacaa ccacttaccc  85260
catattacaa tgtagtacca agacaagcag accaaattat agaaggacaa agtttttgct  85320
aagcatattt tgtcatcagc ataccgcatt gtgtgtgcat gcatgtgtgt gtttgtgcat  85380
gtgtgtgatt gtataaaata ttagaaagcc accccagaaa agttaaatga ctaggaatgt  85440
tgtgaaggga ttaagctacc cctaaaatta tataacaaaa ctctcttcat ctattattag  85500
gtcatcttta gaacatcttc tcttaaattt gttataggtc tctctcatct gtttggatta  85560
aaattggtct gaaagcctaa aatggctttt tacctatata attatttccc aactagcttg  85620
tagtataggt gcaaagctat cacacttgct aggttagtga agtatgtaaa aactaccatc  85680
tttcaattag gaaccatcgg atagcttcta caggattgct ggggagaacc tttataaaga  85740
aagttatatc tttataaatt ttttgtcatt ttacttagct gagaatataa aataagttag  85800
ctaataatag agtagaaatg ttttctgtaa cagattaata ttgatcaaat gtgttattaa  85860
atgctaaaac accatttttt ttctctgtaa gccatgtgtt tcatgccaca acacaaaagg  85920
gacaattgtc tgtgttttat gacagttctg ttctgtcaga tgctgtttgt tcattttggt  85980
gaataaatga agagagccct ggacacatct tttttcctc aacaaaagag gaaaattatt  86040
cttgtctgta tgtctataat cctgactctt tgaatggctt taattttttt aaagtcagca  86100
ttttttata aagataggtg tttggaatgt gggcgatatg gctggacagt tagattggga  86160
ccaaataatg gaaggctttg aacatcatgc taagaggttt gggttttact ctgaaggcag  86220
tagagaacca ttatgttttt aagccaggat tgacttgttc taagctgtac cttagaaata  86280
ttactctggc agttgtacat aggatgagct gtatgttgct ttgttttgtt tggggagaca  86340
gttctcgaag agagactaca tacgaaggca gttatatgag tcattactaa aggtctggca  86400
agaagtagta aaagcattaa ctggagtggt agcagtaggg aaggaaataa aaggatagat  86460
gtgggagtca tttggaaagt atgaggcaat tcattgacct tacagaatca ctggttttct  86520
gcttccactc cattcacatt gacctttcca aggttatcag tgacctgctt gtccttaaat  86580
tcagtgggca ctttccagta acctactgtt ggcaccagcc ctgtgctaga caccaggatc  86640
ctgtttgtaa aggcatctgc cagtggtttc tgtgacacaa ttctgtttct agttttcctc  86700
```

```
cttctacttc tctagcctct tggcaagttc ttctttcaga gtttctcaga gctttgtgct  86760
aggccctctt ctcattttct ccttctctaa gtgatcccat ccttttctgt tgcttcagtt  86820
accatttgtc cttatgcaaa ggacagccat atctactgta tctccagctc agatgtatct  86880
ctttgcctcc tgacccatat ttccaactat ctaactgggt atcttttctt ggatgagtta  86940
taggtctctc aaacacaaca tgtccagaat aattcattga cttattctaa ggcctgcttc  87000
ctctttctcc tgtagtccct atctcaggaa atatatggtg ctatcaaccc caaagcagaa  87060
atctggacat aatccctaac taccctttc ccctctctgt gcacataatt tcagtcatta  87120
ggcctcatag attggactaa ataaatacct cgcaaaccct tctacttata ttcttaactg  87180
ctcctacctt aagccaggct accataattt tgtagctgga tgactgcatc atcatcttga  87240
ctggctccct tgtcatcttc aatctatatt ctatactgca gctagagctt tcaaacataa  87300
acatgtgatc agattagtcc cctctttaga acaccctagg gttctcactg tcctgagtac  87360
agtctaaggg tttaccatgg cttacagggt cttttatgat ttggtgagct ttttattgta  87420
taacctttct aaactgcctt tacttccctc tttcttggct ctgtgtcttt gcataatgct  87480
gttccctata cttcacctca cgtctaacct tcatctcctt ttcacttctc ctcttcctcc  87540
aaaatccagc tgaatatcac attgtcatgc aggcccattc ttgatctccc acgtttgggt  87600
tagatatccc tcttcagtac catcaccgca ccaggtgtgt ccccctatcct agcatttgcc  87660
tcattgtatt acaactactg tgtactcgtc tctacagctc ctgctagtct aaaagttttg  87720
ggagagcaaa ggttcatgtt tgtgtttttc actgtggtat accccagtgc ctagtatatg  87780
ataagctctc aaaatatttg ttagatgtat gaagaaatga gaaagagaac aggaagaggg  87840
taagtttcaa gactaggaaa caaggctatg aaagctgcag gaaagcagca ggttaaaacc  87900
tagaagaaga gtttgtttta ggaaatactg tgttttaaac cactataact gaagcaaaaa  87960
cccaaggcct gggtgtggat agagtccact atctgataac agtggatact gatgcatggc  88020
agagttggag aggaagagag ccagattcca aaacagaagg ggtaaagtct tctaagaaga  88080
tagattatag taagaaggat taggggatag aaatatgagc ctgttccact catagatctc  88140
aaacatgaaa tgatgagtca tcatgaagag agtaggcaat tgtccagtga agaaggggat  88200
gctaaccctt cttaaccttg aatctctcag gtagaagcag ttagagaagg aacagccatc  88260
atcagatagt gttgtaagga aaatgatatc cttggggaaa cctgcatttt ggtaaagcaa  88320
agcaactaag aaagaatata ctaccactgt ttaacaatcg ccacaaaaag acagtaggat  88380
catctttgac ccccctcatc ctttctcagg aacttggagg actaagaaga gagaaatctg  88440
tagaagaggc ttctctctct gatcctccct ccacttcagt tttaccacat gtaatgcaac  88500
aataattaag aatttgtgta aaatttcacc aggttggcat gcatggagag aaaaattatt  88560
cagatgtttt cctttgtcaa taatacaagg agcatttgta gggaaaaata tttacaaata  88620
cagtaagacc tattctcttt ctatatttat gggaaaattt taagttgtgc ccttgtttca  88680
tgtgtgtttc tatttaaaga taccatactt aatatatatt gttgattcat taacattgaa  88740
ctcatggcta acagcactat aaatcatgtc tgatcaaaac ttatgataca tgtactttct  88800
tcgtaaggta catcatagtc ttctcgtaca tgggaactct aggtagtact tcaggactat  88860
gcatagaggc cattttaaac agcaaaattc ccaacaaaaa gcacaaaact caaaaaatgt  88920
gccactaaat ttaccatgaa aaggacactt gtttacagtt tgagagctaa aacaagaagg  88980
tggcgtgtca cttcgtttga cttcagctgg gaacatgcat atcagtcgac tcaaattttt  89040
```

```
tgctattctg tgcttatcca cgaatcgata ggaaagcaag tgtggatttg ggggttacaa  89100
ataaaatgta gcaaatgtgt aaacttgcag atgtggaatc tacaagtagt tagaatcaac  89160
tatgttagtc tgatcattaa atcagttttt taaagtacta ttgtaacacc ttataacctg  89220
ccccattcac tgagtgttgt agtttatagt ttcattgggc attttcagta gttttatctg  89280
aagtcacatt tcaaattttg taattgaagc tccaaagtat gctaccggaa acacgagctg  89340
atgctgtgag acaaaatcaa caggtaatcc accatcacaa ctgtgggcta gaatgctcaa  89400
gaaaccttgg aggcccagag agctgagatg aatactgaag aatcataggc aggtttactc  89460
tgtcaagctg cctgtatttt gagggtgtag tcctcaaacc aaaaagacac caaatgaaca  89520
aactcagatg gcctcactgg ggaacagaga ttgaaagctg acactggaat gtgtacttaa  89580
aaaaatgaga gcccgttttg gaaaggcaga ctgggcacag aatgtggaga gctatatttg  89640
ctaactgaag aaatttagac tttatcctct acaaaacaaa gctattggtt tttgaaggtt  89700
gcataaaagc tgcattttag cagcatatat tttggtagag ctgttacctg cctgaaaaca  89760
tcaatgtcat ttcacacaaa tgatacttat cccttggtgt ttgatctaaa tttctacaat  89820
gagaatgtga ttttatagtc tttactgggg aaggaagtag gtttttcagg ccgaaattct  89880
tgtgtagcaa aaattaacac ttaagttagc ccttggcaat ctccagttct ataatggtaa  89940
aatggatttc ccagaaagtc actctctatc cctttgaata gacattagaa ataacatgta  90000
ctttaagtgg gatttacaga ggaagggggc ctttaattct ttactagtgt gatgccctgt  90060
aaaaaaataa ctaacattag agttgaggcc tagaaatagc agcactgggt taaagtctgt  90120
tttcaagtgc aagtttttct ttttattcgt gtgtgtgtgt gtctgtgtgt gtttcacata  90180
gaaggaggaa atgccaattt cagttcttac aaatattaat gactgcaact tataaaaatg  90240
ttacagacta tattcttccc ttttgtaaca gatgagaaga ttttgaaatt tagtctctac  90300
tttttagttt ggtaagacaa tttgaataaa ctgcaataat tgcaaaagaa ttctgaatat  90360
ttgaacattt gacattttct atgtcaaata tacatttctt gtactatata aacattctag  90420
aaaagagaga caggcaggga ggaaagtgct cattaaaaag agcttcaccc tctctgaaaa  90480
gggatttcct ttacagtgct gtgtactaaa gcctgtgttg taaatcagaa agcactgagc  90540
acacatgttg ctgctttggt agcatcagaa gtcgattttc attagcctta taccattcac  90600
tatttctgcc aagcaatctt aaattataaa agaatcttat ttgattttgt gattctcttg  90660
ttttctgctc ataaagaaaa tatcctaaat tgaacaatgg catgctacgt ttttagtttt  90720
taagacagct aatgtgtaaa aagacattta aagtatagtt gtgttaagtt tttgaagttt  90780
acagttgttt caattttgct gctatacttt gttaacatat tttaggaata tttcatttta  90840
gtcacaacta ggatataaac attattttgg tggcgatctc cttgtaatca cgacgtcaac  90900
caaatttggg aaattttgat ttgttagatt tataaatttt acagtaacac aaaagtctaa  90960
tttcctatat attttcaagg cccctatacc tttgtcaaaa taaagtatca atgaaaaatg  91020
aaaaaatcat aaactatgtt caggccaaac tgatactgac tttgttaaaa ggctagatag  91080
aaatctgttt tcctcttctg ttacatctcc tcttctggag accactctgt gtggactgaa  91140
ggtttgagat cctaggacct aggctagaac agattaggag attgtgctgt atgttaagtg  91200
gcagatacca tggaattcta agcctgttac gaaggaggag aagaagaggc acaatgaccc  91260
tgacacagcc cctgggttga ccacagcaga tatctcactt gagcaagtag atatcatctc  91320
aattgcttgc tgattatctc taacttgtca gtaacttact ttgataacct agatttagga  91380
gtctgacagc atgcagtgta tgcctcataa taatctgctg tttatgaaag tcataacatt  91440
```

```
gtatgtttag cataatggtg aagagcctgc catctggaat ggtctactta tttgggatcc  91500
acatacagta agctctcact taacatcatc agtaggttct tggaaactgt gaccttaagc  91560
aaaacaacct ctaatgaaac caattttacc acaggctaat tgatataaac aagagttaag  91620
ttcctgtggc atatttctgg tcacaaaaac atcactaaac ttctaaataa agacccaaaa  91680
cacttataat attaaccact gaaataaatg tgagctatat atatacattt aagaataata  91740
aaaacaaaaa ataattattt acccaatttt tggtgaacca gtgagtgata gtgatcatag  91800
tgatggtgga tgaaatcaag gaataaatat ttgcaaagtg aaaattgtaa gaagcacccc  91860
ctgtcaccac atagctcaga aataataatt agggcaggct tgctgagcat ttttaaactg  91920
cactgtttat tgtcatgcat ttgaatgatt atcgcagact ttatgaattt tcattttata  91980
ttaatttgta ggccaggcac agtggctcac gtctgtaatc ccggcacttt gggaggccaa  92040
ggcaggcggg tcactggagg tcaggagttc aacaccagcc tgaccaacat ggggaatccc  92100
catctctact aaaaatacaa aaattagcca ggtgtggtgg tacacacctg taatcccagc  92160
tatttgggag gctgaggcag gagaattgct tgaacctggg aggtggaggt tgcagtaagc  92220
cgagattgtg cccctgcact ccggcctggt gacagagcta gactctgtct caaaaaacaa  92280
taataataat ttgtattcat tcattttcca atgtgttcat tccagttcag ggtccagggg  92340
gcctgcagct tatactcata gctcagagca actgacccta tagacaggac gccaccccat  92400
tgtagggtgc actcaaatgc acactcacac tcaaactggg acccttcaga catgccagtt  92460
accgtatcac acacagcttc gggatgtggg aggaaagcga agtatctgga gaaaaactac  92520
acagacatgg gaagaacgag ccaactctac acagacagtg gccctggaca gagctgggca  92580
ggcatcagtt ttttttcttt tttttgtggg gggtgagggt ggggcatgga gtctcactct  92640
gtcacccagg ctggattgca gtgcagtggt gtgatctcag ctcactacaa cctccacctc  92700
ccgggttcaa gagtttctcc tgcctcagcc tcccaagtag ctgggattac aggcgcccgc  92760
caccacacct ggctaatttt tgtattttta gtagagacaa ggtttcacca tgttggccaa  92820
gctggtctgg aactcctgac ctcaggtgat ccacccgcct tggcctccca aagtgatggg  92880
attacaggcg tgagctaccg cgcccagtca gcatcatttt tttttctca tcaacgttaa  92940
aacaatgttg aacaaaacat tattcaaaga cctgccgtat ggctattttc tagttgtgtg  93000
actttctttg ggaaagttag caacccttc tgagcttaaa tgtcctcatt cataaaatgg  93060
ggctagtaat aatgcataag gtttttgtaa gaattagaat taataaagta cttagaccat  93120
aataactaat tagtattagt tgttgtcttt gctattattt tgatgtggtg gttgtttggt  93180
ttcacctgtg tactatcagg acatgctgaa ataaaattta agaattggct ttataatatt  93240
agaaaagcaa actttgtac gatatgggta tgaaaaattg ttgggagtct actttttctc  93300
tcttacctaa tttgtcttag tctttttaaa gcttagattt tccaaatgag ccatagcaaa  93360
atataatgtt taaaaatgtt taaattctaa gcactatgtc atagttaaat aacttaaagg  93420
tgctacatct tatacagtcc aaaaggaaca taattagtaa aattctacaa tttagaaaaa  93480
aaaatagctg acagtgactg atttataaaa gtaaaatatc ttttgttaat actaatattc  93540
tttttataaa ttaattgatg acaaaaaatt gagtgaatga gatttgcagt tcatttatct  93600
atgatgctgg tttatttaat ctctataatt tgctgtattt gaaagagcat agtgatagag  93660
gtcatgataa aatctaggcc cagtgccaca actaaatccc tgtaggaact ctcaaggttt  93720
tgatttcatc tctgaatggg aataacacct tccaagaata ttatgaagat taaaaagtta  93780
```

```
cgtatcataa atacacacag agtaacaata ctgggaatat tgcaacttgt aagaaagagg  93840
aagcatatgg catattctga tggttaggga tatggactct gtagctggga tgcctgaaag  93900
agaactctga ctccactaat ggctagttat atgaaattgt gcagataatt taacttctct  93960
gagtttgcat ttttctttgt ctatataatg gggataataa tagtacctac ctcacacata  94020
gtgttaattt ctattagtgg ttctcattaa gatagtattg ttgttcatcc ctggttgtta  94080
gccatcatgt atctgagtta gagagtcatt gattttagaa agtcccgagg agactatcag  94140
gtcaagcaac ctgcctcctg ctagacaatt agctttatcc atgagttacc aaagagggag  94200
ccgaaaccca gggaagctga aagagctgtt gattgtcacc ctgtgagttg gtgatagaaa  94260
gatatctgga atcccagtag ttgcccattt cctagttctg ggctctgcat tgcactagaa  94320
tactgtgcca ttctaaatat gaaaaggcag tatgaccatt gtgcttgtca ctttccattc  94380
cctagatgct atcttatatt tgtccttatg aaatttaacc tgtgactttc agatcactta  94440
gaaccttggt tggacagtgt tttctagtgt tatttagtat atttttttgt catcttctgt  94500
tgtctttggg ttcccctaaa agagctatac tctgggtgcc aggaaacttc acacatgact  94560
gtcttctctt cctcgacttc cctctctact tacctttcca gctcgtagca aatcagaaga  94620
cttctctgac acctctctat gtctaaaggt cctttgatat tctcacatgg cggcatgaat  94680
cacagtgtat tttaactggc cttttccttg tatgtctcct acaatgagct gttgaagctt  94740
catgaaaaca caatctgttt tactcagggc agttataatt ccaattacaa agcacatttc  94800
ctggctcctg gctaggaact cgatcatttt tcgatgcttc cttgctcagg actttctgat  94860
tccttcttaa aacattttgg ggcatctcct tctcctggtt tttggaaaca tattctcata  94920
ctgctatgaa ggtttttact gacatttcca acttctctta aattgattca gcaaatgttt  94980
ttccataata aatgtcattg atatgtcatc aatatggaga gcaacaacag aatgcattga  95040
gtaaactcct cccctggagg tctgagaatc tagattccag ttctcacaga gccaccacct  95100
tggtgacctt ggacagtaga ccttctaagc ctcagtttcc ttatccctta agtggggata  95160
ttaatagaac ccattctcag agatgttgcc aagattaaaa taaccaagat aattcctgta  95220
gatgatttgg catagtgcct gccacgtact aagcaagagt tagcctccgt cattatagta  95280
tgatcataaa aaatgaacag actaaacgaa gtaaccagaa ggaaagaaat tttaattctt  95340
aaaatgtaat agtttcttgg tttttttttt tctgtgaaac acctgcatgg cacctttttg  95400
ttattcatac tgttttgact gtggctgtcg tagattcttg ttgaaagtct gagagactga  95460
gacttgtcat tttgaacatg gcatcagtgg aacagcttat gattcaataa ttgcatcatc  95520
ctggacaagc accagtagaa gtgagtcagg acatgtgata aaaagacatt cattttgccc  95580
ctcctccctc tctgtatttt ctttgctata aaattattga tgttaagccc atagtactaa  95640
tatttcagtt caattcataa taaaatttga gggcatttga atatattatc tgttgtaaat  95700
tataatttta tatttgacca cagagtattt gaagtgggtc ttttctttcc ccaaaattct  95760
attttaataa ctaaaaaata ttcttaggag aagtattatt taagaacagg tttatattaa  95820
ataacatcat ttcactttca actttctggt ggtcaaaaaa tatgctaata ctaattagga  95880
tatgatacac atgttctgtt agaacagttt tggcagttag aagacttctc ttcttgtgtt  95940
tgaaagggat gttacttggg gtagttatga gccatgtatc cagatgtcct gaaaggacca  96000
gtggtagatg tatttctatt tttgtctttt cttttttctt tctggcattc tagttgctga  96060
gtgactgact tttgttttca gctcttctca caatcaccat tgttctaata actttgctta  96120
aatagaatgt ctccttttgc tataagccat ggggccattt accgttaatt ttttaaagta  96180
```

```
ctgaaatgag aacctcataa attaaagaac actcctgatt ctgagttagc agatcctact  96240
aagcctttg cagatggaaa tttcctttaa attggtttgt tttcctttaa cattccatta  96300
tcctattgtt cattctttgg agctgtgatt tgtttaatat atttcaggct tcttaataaa  96360
tcaagtcatg taagttatta tttggatcat ttcgaaacta caacagctta tcaaacctct  96420
gaaagaagaa ttttgtgttt gcccacagac tgaagaactg attcagtttt attggctgag  96480
ctaccttcat tattcatatt taattcctgg tactgagggt gggaggaggg agaggagcag  96540
aaaagataca actattgggt actgggccta atatctgggt gatgaaataa tatgtacaac  96600
aagcccccgt gacatgtgtt tacctattta acgaaccctc acatgtatcc ccaagcctaa  96660
aagtttaaaa atatatattt ggtaaatcaa ttgatgtgtt ttaaaaaata tcgccttttg  96720
gccgggtgtg gtggcccatg tctgtaaccc cagcactttg ggaggccaag ccgggcggat  96780
cacgaggtca ggagttcaag accagcctgg ccaacatggt gaaaccctgt ctctactaaa  96840
aatacaaaaa atagctgggc gtggtggcgc gcacctgtaa tcccagctac tcgggaggct  96900
gaggcagggg aatctcttca acccaggagg cggaggttgc agtgagccaa gattgtgcca  96960
ttggactcca gcctgggcga cagagcgaga ctctgtctca aaaaaaaaaa aaaaaaaaaa  97020
aaatcatctt taaagagata actaaccctt ccccagaagg cagggccaaa gtctaaggtt  97080
cttccaggtc ctttgtattc cctataaatt ttagagtcag cctgtcaatt tctatacaca  97140
cacaaaaaaa gcctgctggg attatgattg gtattgcatt gaaattaaat caatttgggt  97200
ataagagact tcaatttggg gattgagtct atattgagtc ttccaatcca ggaacactgt  97260
atatctctcc atttagtcag atatttagtt tatttcaaca atattttcag atctttagtt  97320
cctttcagca atattttctc atttttcctg taaagctctt gcacatcttt tgtcccatat  97380
ctattgtgta tatgtgtttt gctagttatt aaattatatt aatataaatt ttattttcca  97440
attgtttgtc gcatatatag aatgttttaa aaatattgtg tcctgtgacc atgctaaatt  97500
aactaattct agtcattatg tcttcattat ctttctcttg aattttcatt gtcttcccct  97560
tctgggactc cattcatatg taaggccatt tgatactgtc tctcaggtcc atgaagttct  97620
gttaattttt cttcattctt ctttttctct gtgttcttca actgaatgaa tgccattaat  97680
aatttggtat gtaatggctc acttaaactt ccttttgttt ttaagatatt tctactctca  97740
gctgtgtctg gaatccttta gtccggagcc ccaccaaccc tcagcctaga aggaaggagg  97800
agaaggatag ggtgaaagga aggggagagc ttctagcttc aggacagaga tcagaacaaa  97860
caacagagca gtcatcttgg ataaggaaac ttccctcaaa cctattactt atatcctcag  97920
aaataagaaa aataatgcat ttatcaaatt aaaggatttt gaaaaaggga acattcagag  97980
aataaaacta aactcttgaa agttaaaagg atgataacat aaatgaaaag ctcagttgaa  98040
ggattgaaag ataaaagtaa gaaaatatcc cagaaataag agcaaaaaga cagcaatgta  98100
aaatagggga gaagataaga gaattagaga accagcttag gagttctaga aagagaaaat  98160
gtagacaaca aaaggtaaga aatcatcaaa gactggagta ggggaggtca tgctatctgt  98220
ttctttttct attttttatt ttgagttaca ttttttttta ctgtgaaaca agcatatgta  98280
catgagaatg aacaaaacaa atatgcagtc atgtattgct taacaacaga gataggttct  98340
gagaaatgca tcattaggcg atgtcatcat tgtgcagaca tcatagagtg aacttacaca  98400
aatctgaatg gtatgtccta cagtacacct ggaccatatg gtatagctgt tgcttccagg  98460
ccacaaactt acagcatgtt actgtactga acactgcagg cacctctaat acatcggtaa  98520
```

```
gtatttatgt atctaaacat agaaaaggta caataaaaat acaatataaa agaggaaaaa  98580
aatagtacac ctgtataggt gcttactgtg aatagggctt ccaggattgg aagttgctgt  98640
gagtcattga gtagtgagtg aatgtgaagg cctaggacat ttattatatg aagtctactg  98700
tagtgtaaac tctgtagact taggctacac taaatttata gaaaaatttt cttcaataat  98760
aaattaacct tagcctactg taactttttt actttgtaaa cttttaattt ttttaacatt  98820
ttgactcctt tttagtaaca cttagcttaa aacacacaca ttgtacagct gtaaagaaaa  98880
ttttatgtcc ttcttctgta agcttttttc catttttaag atgtttttat ttttaaaact  98940
gttactaaaa actaatacac aaacacacac attaacctag gcctatacaa agtcagtgtc  99000
atcagtgttc aaccttcaca tgttatccca ctggaaggcc ttcaggggca ataacaaaca  99060
cagagctgtc gttttctgtg ataacagtgc ctttttctga tatacctact gaaagacctg  99120
gctgagagtg tttgacagtt aacaaaaaaa aaaaaggaca agaagtacac tctaaaataa  99180
tgaaaaaagt ataatacagt aaatacataa accaccaaca tagtcattta ttatcattat  99240
cgagtattat gtactgtaca cagttgtatt tgctgtactt ttctataact ggtagcacgg  99300
taggtttgtt tataccagca tcaccacaaa cataagcatg gtgttgtatt acaatgcaca  99360
gctgcagcta agtgatagga ctttttcagc tccattataa ttttatggga ccatcactat  99420
aaatgctgtc catcattgac tgaaatttat gtcgtgcatg accatacata caatttaatg  99480
aaaaataata ataataaagc tagcagtgtg taattaccaa ccagggcaag aaatagaata  99540
ttgccaatac cttggaggcc tccagtatga ccatataagt ttacaaatcc tattttgttc  99600
ctcctcccca gaggtaacca ctgccctgac aaatgtgatc gttgttttct tgtttttctt  99660
actacctata taaacatcct taaacaatat aactcagttt gtatattttg aattccatgt  99720
taatagaata tcatatgtat atgaatttta tgtgaataga atattatata tgtcattttg  99780
catcttgctt ttttcattca acattgtagg attcattcat gttgtagtgt acagctgtcg  99840
tttattcatt gctgtataga attatatcct cagagataag atatatggat gtttataaat  99900
cattccacta ttatgaacat ttgactagtt tgtagttttt atttaaccaa aaaaatgctg  99960
ctgccaacat tcttacacat tttactgtat atgcacatta atttatttac aagtataaat 100020
ttctttttga atacatatct attgatggag ttgctacatc ataggacatt cttgtctttg 100080
actttactgg ataataccaa actgtcttcc aaaatgatta catccttaaa ctcaggacac 100140
atcttattgt caaatgttta atttttgtca gtctgatggg tatgtaagtt attttattgt 100200
cgttttaatt tgcatttccc tgattactaa ttaagctgag taacttttca tatgtttatt 100260
ggccatttgg agttcctgta ttgtaaagta taagtttttt tgtccatttt tctagttttc 100320
tgtcctttta gttgaaatcc aaatttgcct aaatctgtta ttctctgagc acaagtaact 100380
tgggatgctt tcctttagat ttagcctaat tctttatcat tttgtcagct tgatggtgct 100440
tttaaggaga tatatatgtg tgtgtgcgca cacatgtgcg tgtgtgtata tatatatatg 100500
tatatgtatg tatgtatttt ttgagacagg gtctcactct gtcacccagg ctggagtgca 100560
gcggcacagt cttggctcac tgcagcctcc acctcctggg ttcaagcttt tccctgtctc 100620
agcaacccga gtagctagga ttacaggtat gccaccatac ccgctaattt ttgtatttaa 100680
tagaaacagg gtttcgccat gttgacaggc tggacttgaa ctcctcactt gaactcctca 100740
cgtcaagtga tctgcctgct ttagcctccc aaagtgctgg gattacaggc atgagctacc 100800
gcgcctggcc tggatatttt ttaaaaatat tttttatcta gcactttggt ttttggcagg 100860
caggttggca ctcatagtct gacctaccat ttctataaaa agaaacctgt aaatgttctt 100920
```

aaacagactt tgaaccagtc ttcctgattt tgaacccccta cctttacccc cagtttttga 100980
gcctttcaga attttttttc ataataatta ggttgcttct tagctttccc cactggtgac 101040
ttaacagatc ttaggaagcc aacaatcctt gtccatctgc tttctgtctt gtgaactgtt 101100
gctggtattg tctcttctct ttattcttag aggtgtatgc ttttaaaaac atatactggg 101160
tttgagaggg agctgaaata aaagcatgtg ttaaatatac catctttaac cagaactaca 101220
tttgactggt cattttattt tcaagctcac atacacttca aacagagata tggctaaagg 101280
aattatcatg tgaacaacag ccagggctct gaacatcaca gattatatca tcatacttga 101340
aatatttgaa attttgattc aaaatgagag ctttatagct atgtcctcaa tggactaagt 101400
gtttaagtac ttaacatcca aaacattctt actaatcaag agaagacaaa caccccaaca 101460
gagaaatagg caaattttat caatagccag ttcaccagat ttgttttctg ttagaagcga 101520
atatggggaa atacatgtgt ccatgttttg cctacttttc ctggagcagg taaggagagg 101580
cagtttaagg atccatgtga taaaccctaa agttgtccat cggctttcca gtcccttcta 101640
ggaatttaac ttagggaaat aatcagacat ttgcaaaggt gtgtacagtg gtatttataa 101700
tagtgaaaaa ccaaagaatg accaataacg ggagaatgga agttacagcc aaatacttta 101760
caactactaa agaatcatgt aaaatatcta ttgacatagg agttttatca aaatgtgaag 101820
tatacagatg aatagtacca cacataaaaa gcaaggtgca aattagccat ttatattgtt 101880
atccccaaaa taaatagatg cagttttttt aaaagatgca ggctatatat ggaagtgttt 101940
gctggttttc tgtcaaaaga atggcgactt tattttctaa tttaaacttt ttgctgtttt 102000
ctaaattgtc taaatagtta tagtttttat aatgtaaaag tatcttccaa tttagcttca 102060
tttgacaaat taccttttca ttctatctag ctatgtaatt ctaaatgaat ttacagcagt 102120
aatcttagag cagatgaatt tacaacaata atcttagagt agactacgga ttagatgtaa 102180
aaacatgagt tgggctttat ggttacagag agttttcctc agtgtgggga tcatagctgt 102240
attgagttta ttcagttttc ctttcccaca tgaatgaaaa atggggccag cctacaactg 102300
gaagggcctc ggcatgtacc actgtactgt gtatgatgtg atttcttgat gctagtaggg 102360
agagaatcaa attgcctcct attcaaacca agacccacaa atagcgtcaa ccagtcattt 102420
cagctactcc ctgcagtgtc aagaaggtgt gaacccctca tgttctctat tgcataccct 102480
tgtctaattc agtgtttctt cttcttttca ggttttggct ttatgctaca tttcagaaat 102540
cataataacc ttttctggta ttattttatt ctttttcgca ctgtgagaaa aattaaactt 102600
tcaagtggat gcttcttata aactatttat accctttttgc tccctttttgg gaggcaggga 102660 cagggacaga gttcctcctc aggctaacta agaaaactta ctgcttccaa tgtaatttaa 102720
aagatctccc tctttctatt gctctctgta ctcttaattc tttttttttt ttttcacagc 102780
agagacaagt gaacatttat ttttatgcct ttcttcctat gtgtatttca agtctttatc 102840
aaaacaaggc cccaggactc tccagattca attatgtcct tgggcttggt cgactgctgt 102900
aggagtctca gggagccttc tacaaatgct agagtgactc atttaccaac attaaaccct 102960
aggatacatg caacaaagca ggactccttc ctccatggaa tgtgccgatt tcagatgaca 103020
cagcacccaa tgtagaaaac gctggaattt ttccttggaa ctagactgtg atgagaggtg 103080
cttgacatga acataagcta ctgtcttttc ttttttttttg agacagagtt tcgcttgttg 103140
cccaggctgg agtgcaatgg cgtgatctca gctcactgca acttccacct cccaggttca 103200
agcgattctc ctgcctcagc ctcctgagta gctgggatta caggcacgtg ccaccatgcc 103260

```
cggctaattt ttgtattttt agtagagatg gcatttctcc atgttggtca ggctggtctc 103320
gaactcccaa cctcaggtga tctgcctgcc tcagcctccc aaagtgttgg gattacaggc 103380
atgagccacc acgaccggcc agctactgtc ttttctttga cccttccttt ccagtttttg 103440
aagataaagc aggaaataat cttctctgaa gatacttgat aaaaattccc aaaacaacaa 103500
aacgcatgct tccacttcac tgataaaaaa tttaccgcag tttgtcacct aagagtatga 103560
caacagcaat aaaaagtaat ttcaaaaagt taagatttct tcagcaaaat agatgattca 103620
catcttcaag tcctttttga aatcagttat taatattatt ctttccccat ttccatctga 103680
atgactgcag caatagtttt ttgtttgttt gtttgtttgt ttgtttgttt tttgagatgg 103740
agtctcgctc tgtcgcccag ctggagtgca ctggcgcaat cttggctcac tgcagtctct 103800
gcctcctggg ttcaagcgat ttcctgcctt tagcctctcg agtagctggg actacaggca 103860
cgtgccacca cacccagctc atttttgtat ttttagtaga gacagggttt caccatgttg 103920
gccaggatgg tctcaatctc ctgacctcat ggtctgcccg ccttggcctc ccaaagtgct 103980
gggattacag gcgtgagcca ccgcgcccgg ccagcaatac agtttttagt tactcgacat 104040
ctttaagcct ataactctta ggctatgcat agccccatgt cctaatcagg cattcactga 104100
tcccagcagg tctccatcta tttgtaccag cctcctcttt cctcccaatc tcaaggttac 104160
tcttaaatac tagtaaatgc aaaaagaact tgtaaagtgg caaggcatgg cctatcaaaa 104220
gtcagcccaa gggcagtttt cagccctgcc tcacctgggt ctagttcagc tgacggatga 104280
gctgattgat gcgttcaccc cgatagccag gtgtgcccat ctccttgagg aagcccactc 104340
tatttttggt agcatgatgg gccactgaga ggtggaaagg gcgcaagaac catgagatct 104400
cctggaaatg cttccctggg aaggcaattt catgaatgag gtcttccaag caaatgaagc 104460
caaacttccc caggtgctcc tcaatcactg tgttgtctgt cagagggatg gtcttattct 104520
tgaccttggc ttgtccacgt ttcaaaatga gttctcggac agacttcaga tttggaaatc 104580
cccaggtcac ataaggttcc actatatgca gcatttttag attctagggg gtaactttta 104640
caaagatacc actaaaaatt ttctttaggc gaagtcttgc agtggttctc tgcacccgta 104700
aactcacgcc atcaatcctt tcgatgcgta caacaaaggc caaggaatgt ttatctggca 104760
attccaaggc atgaggtttc acttctagtc gtctgagacg caccttgtca cgtttctgcc 104820
gccaggaatc atgtaggaat gattccagtc gcttaaacct gagccctttt cctttcttct 104880
gtcttgctac tgccatcttt ctagtggtgc agctactcaa ttcttttttt aattataatt 104940
tttattttaa gttccagggt acatgtgcag gatgtgcagg ttacataggt aaacatgtgg 105000
ccatggtggt ttgctgtacc tatcaactca tcaggtatta agcccggcat gcgttagcta 105060
tttttcctaa tgctgtcccg cccccccacc caacgggccc cagttacact cttaatcctt 105120
atagctcaga tgttatgatc cacagtgtgg ttcttacaga aagttatgga ttaaaaaaaa 105180
aaaaaaacac tcaaagtgcc cgaactttct taaaataatc ctggtacagc taaactcatg 105240
cactgactgt ccacctaata tttaacagtc tgtgttgtga tatattgttt taatgttctg 105300
aatgcttgtc agctttcagt attgaagatg tgaatcattt atcagcaatg acacatttag 105360
tctaaggttg tcagctattt atgctacaaa ttaatgactt gtccttaaaa tatcaatttt 105420
gtgattcatg ttttggcagg tggttagatg ttttgtgttc taattttaaa ctatggataa 105480
aggttttgtc ataatcattg ttttattggt tccttttctc ccctgcccac tccccaaaaa 105540
accctgcaat tctttttttgt taaactttta ttttaggttc agaggtacat gtgcaggttt 105600
gttatatagg caaattttgt gccacagggg tttgctgtac agattatttc atcacccagg 105660
```

```
aaataaacac agtacttgat ggataggttt ttagtcttca ttctcttccc accctcaagt 105720
aggccccagt gtctgtcctt cccttctttg tgtccctgtg tactcaatgt ttagttccta 105780
gttataactg agaagaacat gtggtatttg gttttctatt cctgtgttag tttgcttagg 105840
ataatggctg ccagctccat ccatgttgcc gcaaaggaca tgatttcatt ctttttatcg 105900
ctgtgtagaa ttccatggtg tatatgtacc acattttctt tatgcagtct tctgttgatg 105960
ggcttttagg ttgattctat gtctttgcta ttgtgagtag tactgcagtg aacatacaca 106020
tgcatgcgtc tttatggtag aatcatttat attcctctgg gtatataccc agtgatggga 106080
ttgctgggtc gaatggtagt tctgttttaa gttctttgag aaatcatcaa actgctttcc 106140
acaatggctg gattaattta cacttccacc aggagtgtat aagcatttcc ctttctctgc 106200
aacctcacca ggatctatta ttttctgact ttttaataat agctgttctg actggtgtga 106260
gatggtatcc cagcaccatt tattgaatag ggagtccttt ccccattact tgtttttgtt 106320
gactttgttg aagattggat ggttttaagt gtgtggtctt atttctgggc tctattctgt 106380
tgcattggtc tatgtgtctg ttttgtacca ataccatgct gttttggtta ctttagcctt 106440
gtagtagttt gaagtcgggt aatacggtgc ctccagcttt gttcttttgg cttaggattg 106500
ctttggctat ttgtgccctt ttttgattct atatgaattt taaaatagtt tttttctaat 106560
tctgtgatga atgtcattgg tattttgaga gcaatagcac tgaacccgct aattgctttg 106620
ggcagtatgg cgattttaac aatatcgatt ctttctatcc cctgcaattc tttgttgttg 106680
tatttaacta tttttacttg tgaagttttt tcagggatga ttttgttgaa agtgacaact 106740
ctaaaaatta tgttggtaat taaaatttta agtaatgact tttattttca gagattccac 106800
ttctcttaga ctttggagct gttaacagca gtgtccaatc tgcagtggta ctcagcagtt 106860
tctgtttcct gcatgcagaa ctgcttatat gaaaacacag ttttaaaaat gctttcttat 106920
ggctgacatt cacattctta ttccttttga ttcttttcaa gagggatttg gtttgttaaa 106980
attaattttt gcaatacttt tatgaagata caaactctga caaagctttt aaaacaagtt 107040
tgagagaata cagtattgat ttcacttgta aatctgacga ttattttaga aaaaaggaaa 107100
atattattta ctattatttt gcttataaat gtttatcaat tttaaagctt ccacattgca 107160
catctcccac tacaacagta gctaccattt attctttctc aaaaaaagtg ctaagtgtgc 107220
ccttgaaatt tttacattgt gcagaatatc cctaaaattt taaaacaaaa attacatcat 107280
cacttgcttt aaatgtttct tctttattta acatacagtt tctaaaatgt tagcaaatag 107340
cattttagaa gagacacgtt acttttctaa tgaatgttct aaaatgaacc acagtaacct 107400
atacttactt agactgtgaa aaacaaaact tatattctat tgttaaattt tcaaaagtga 107460
aactacacga tagtttactt ggcacatcac tctgttattg tgaattgaca aatgtatatg 107520
tagacaaata tgtgaaaatc agagtacata tacattatat gcagcaccac aatacatttt 107580
ttagtatgtt ttgactgata tttaattata taatttacca agaggatctc accagaatgt 107640
agaaaagtat tgaattttag aacaattcac atatttaaaa aaaatgtagt cagccctttt 107700
atctgtatct ggagaatgca gggtaaagga ataatacatg agtattggta tttaaaaaaa 107760
ggtgttaatt tcttacctat gatacctgtt actttgggta tcatttaacc tttatttctg 107820
tgaaatagag gagttctaac atcctctaat tattataata ttgttctaat ttaatctatc 107880
ttaatctgtg atacagtttg aaaaccaagc ttttactatt ggcatgtgca aaaaaataaa 107940
gcagcagtag acttggaatc ttgaatgcaa atttagattt tgcctcttaa taaatgtata 108000
```

atatagtgtt ctgggaccaa ttctctaaca tttctgagtc ctagtttctg catctgtcaa 108060
atgggattag agatacctac tttcaggatg tgatatggtt tggctctgtg tccccaccca 108120
aatcttatct tgaattgtaa tccccatata ttgagggagg gacctggtgt gaggtgtttg 108180
gatcatggaa gtgatttcct ccatgctgtt ctcgtgatag tgtgggagat cgcaaaacat 108240
ctgatggttt aaatatggca gtttcccctg tgctttctct ctctcctgcc accatgtaag 108300
actttccttg cttcctcttt gccttctgcc atgattgtat gtttcttgag gcctccccag 108360
ctatgcagaa ctatgagtaa attaaacctc ccttataaat tacccagtct cagatattct 108420
ttatagtagt gtaaaaactg actaatacag agaattggta ctggcagggt tgggtactgc 108480
tataaagata atctgaaaat gcggaagtga ctttggaact gggtaacagg cagtggttag 108540
aacagtttgg agggctcaga agaaaactgg aagatatagg aaagtttgga acgtcctaga 108600
gacttgtttt gaatactttt gaccaaaatg ctgatagtga cgtggacaat gaagtccagg 108660
ctgaaatggt cccagagatg aggaacttat tgggaactgg agcaaaggtt atttttgcta 108720
tgctttagca aaaagactgg cagcatttta cccctgccct agagaactga tgaactttga 108780
gatgatttag ggtatttggc agaagaaaat ttctaagcag caaagcatcc tagtggtgac 108840
ttggctgatt ctgaaagcgt tcagtcatgt gcattcacga agatatggtc tgaaattgga 108900
acttaggttt agaagtgaag cagaacataa aggtttggaa aatttgcagc ctgaccatgt 108960
agtagaaaag aaaaccccat tttctgggga ggaattcaag ccagctgcag aaatctgaat 109020
aagtaacaag gagtaataag taataataag taaaaagtaa taagtaataa gtaacaagga 109080
gccaaatgtt aataaccaag acaatggaga aaatgtctcc agggcatggc agagatcttc 109140
ggggcagccc ctcccatcac aggcctgaga actaggaggg aaaaatggtt tcctgctcag 109200
ggccttgctg ctctgtacag cctcacgaca tggtgccctg catccctgat gctccagctc 109260
cagctgtggc tgtaaggggc caagttacag ctcgcaccat tgcttcagag ggtgcaagcc 109320
ccaagctttg gcagctttca cgtggtgttg ggcctgcagg tgcgcagaag acaagagttg 109380
aggtttggga acctgtgcct atatttaaga ggatgtatag aaacgcctgg atgtccaggc 109440
agaagtctgc catggaggca gagccttcat ggagaacctc tgctagggca atgcggaagg 109500
gaaatatggg gttggatccc tcatacagag tccccactgg ggcactacct agtggagctg 109560
tgagaagagg gcctctgtcc tccaggcccc agaaaggtag attcaccgac agtttgcagt 109620
atacgtctgg aaaagccaca gaatgccagc ctgtgaaagc cacaggggta ccctgctgag 109680
ccacaggggc ggagctgccc aagggtatga aagcccaccc cttacttcag tgtgccctga 109740
atgtgagaca tggagtcaaa ggagattttg gagcttttag atttaagggc tgcccagctg 109800
ggtttcagat ttcatggggc ctgtggccct tggtttgacc agtttctccc atttggaaca 109860
ggaacattta cccaatgcct gttccctcat tgtatcttgg aagtaactaa cttgcttttg 109920
attttatagg ctcatacgtg gaagggactt gccatgtctc agatgagact ttggtcttgg 109980
acttttgagt taatgctgta ataagacttt gggggactgt tgtgaaggca taattggttt 110040
taaaatgtaa aaagacatgg gatttgagag ggagcaagtg caaaataata tggtttggct 110100
ctgtgtcccc acccaaatct aatcttgaat tgtaacccgc atgttttggg ggagggacct 110160
ggtgggaggc agttggatca tggggggttt ttttccatgc tgttcttgtg atagggagtt 110220
ctcaggagag ttgatggttt aaatgtggca gtttcccttg tgctctttct ctctcctgct 110280
gccaggtgag acgtgtcttg cttcccctgc cccttccacc atgatcataa gtttcctgag 110340
gcctccccag ccatgcagaa ctgtgagtca attaaacctc ctttccgtat aaattaccca 110400

```
gtctcagata gtatctttat agcagtgtca gaatggacta atacaggata gtaatgaaga 110460
ttacagaata tgtagatgaa gaagtgctaa gtaaatagca gctattatta tgtagtcaaa 110520
ttgaatgtat acattgtggt acttcagtgt cctttaaatt gaataactag aaatttgttg 110580
gctttctcaa tctgctcaca tcagatgaca tgttaattta tgcctatact tttttctagt 110640
taatagatat aaatctattc actcaacttc tattgacaga actggtagtg tggcaagaca 110700
tctcatttct agttaaggct gtataatatt aagttcattt tacttaaatt aactatggtt 110760
tgggaaatgc ttttcatgtc atcatgtatg cccaatttga tactttagtg ggacagtata 110820
tttcagaaaa aaacaaatgc ttccccaaaa attccagggt tgaatacatt agtcagacat 110880
ataacaatgt acttcagagt tcctctaagg gcaaaaatcg tggtatgaat atacaaaaca 110940
ctcctattta tacttttgta tttttgaaat gtagtcttca tgttaattta gcatttcaat 111000
gaccagcatg acattatctt aataatttgg aatgccaata tgttcattta agacttaata 111060
tagtaagtat ctaaagaaaa aaatggaagt gactgaatgc ttttgtatct cttaattata 111120
atttgtgctc cattgtgata tgaaggatag aaggggcagg atagatagaa aacagaaatt 111180
aactttgatg tttaacctta ccttaagact gtctgttaag tgacccacat aatcttaaaa 111240
aactctgtca agcttaatgg atgctactct gcaggcccct gccaggcaac agtcacaagg 111300
ttatgaggtg catagatttt ggaattaggc agagctgaat tcagatccag gtgttgcctt 111360
ataatgcgac tttgggcaaa taaaaggccc aatttttgta ttcttatctg taaaatggac 111420
tcagtaaaaa ttatttgaga taatttattt gtgtactgta cctaggcatg cagcttgaca 111480
cacagaatta caagtcagta gtttccagta tgattattat tgtgaaagag atattttgtt 111540
tcacctactg aaaacttttt tcagtcttaa attttttatc taactggctg tattgcagat 111600
gtctgctata taacttttat ataattttaa aaactatttc tttcctcctt gatcttctag 111660
gggtaaggtt accaatgttt tcattattta ctaaatatag cagcccccac cccttattca 111720
tggaggatag gttccaaaac ccctagtgta tgcttgaaac cacagaccac agataatccc 111780
aaatcctata tgtatattgt ttttcctata catacatacc tatggttaat gtttaaccta 111840
ctaattagga agagtaaaag agtaatagta actaataata aaataaaaca attgtaacaa 111900
tattccagca tcactattct tgtgctttag ggccaccatt aagtaaaata agggttactt 111960
gaacacaagc actgtgatac tgtggcagtc caactggtaa cagagatagt gatgcggttt 112020
ggctgtgtcc tcaccagaat ctcaacgtga attgtatctc ccagaattcc tatgtgttgt 112080
gggagggacc caggggggagc taattgaatc acagggtctg gtctttccct tgctattctc 112140
gtgatagtta ataagtctca catgatctga tgggtttatc aggggtttcc ccttttgcct 112200
cttcctcatt tttcttttgc caccaccatg taagaagtac cttttgcctc ccgccatgat 112260
tctgaggcct ccccagccct gtggaactct aagtccaatt aaacctcttt ttgttcccag 112320
ttttgggtgt gtctttatca caagcatgaa aatggactaa tacagtaaat tggtaccagt 112380
agagtgggtg ttgctgaaaa gatacccaaa aatgtggaag cgactttgga actttggagg 112440
actcagaaga agacgggaaa atgtgggaaa gttaggaacc tcctagagac atgttgaatg 112500
gctttgacca acatgctgat agtgatatga acaataagat ccaggctgag gtggtctcag 112560
atggatatta ggaacttttt gggaactgga gcaaaggtta ctatgttatg ttttagcaaa 112620
aagactggca gcattttgcc tctgccctag agatttgtgg aactttgaac ttgagagaga 112680
tgatttaggg tatctggtgg aagaaatttc taagcagcaa agcactcaaa aggtgacttc 112740
```

ggtgctgtta aaagcattct gttttaaaag ggaaacagca taaaacttca gaaaatttgc 112800
agcctgacaa tgcagttgaa aagagaaacc catttttga gaagaaatta aagctggctg 112860
cagatatttg cataagtagc aaggagccta atgttaatcc ccaagaccat ggggaaaatg 112920
tctccatggc catgtcagag accttcacag cagcccttcc catcacaggc ccagagaccc 112980
aggaggaaaa agtggtttcg tgggccaggc ccacggtcct catgctatgt gtaggctagg 113040
gactttgtgc cctgtgtccc agctgctcca gctgtggctg aaaggagcca atatagagct 113100
caggctgtga cttcagaggg tggaggcccc aagccttggc agcttccaca tggtgctgag 113160
cctgtgggta cacagaagtc aagaattgag gtttgggaac ctctgcctag attttagaag 113220
acgtatggaa acacctagat gcccaggcag aagtattact gcagggcagg gctgtcatgg 113280
agaacctttg ctagggcagt gcagaaggga aatgtgggat tggagccctc acacagaatc 113340
cctactgggg cactgcccag tggagctgtg ggaagagagc cgtcatcctc cagaccccag 113400
aatggtagat ccaccaacaa cttgcaccat gtacctggaa aagccacaga cactcaatgc 113460
cagcctgtga aagcagccgg gaggtaggct gcaaagtcac aggggcggag ctgcccaaga 113520
ccatgggaat ccatcttttg catcagcatg acctggatat gagacctgga gtcaaaggag 113580
atcattttgg ggctttaaaa tttgactaac tcactggatt tcagacttgc atgggccccg 113640
taacccccttt gttttggcca atttctccca tttggaacag ctgtatttaa cctgtgacac 113700
ccccctaccc cctgcccccc atccctccgg cccttgtatc tggaagtaac tagcttgctt 113760
ttgattttat aggctcatag gcagaagaga cttactagcc ttgtctcaga tgagactttg 113820
gactgtggac ttctgggtta atactgaaat aagctaagac tttgggggac tattgggaag 113880
gcatgattgg ttttgaaatg tgaggacatg agatttggag gggccagggg tggaatgata 113940
tggtttggct gtgtccccac cctaatctca acttgaattg tatgtcccag aattcccatg 114000
tgttgtggga gggacccggg ggtgggggtg cagtaattga atcatggggg ctggtctttc 114060
ctgtgctatt ctcatgatag tgaataagac tgacgagatc tcatgggttt atcaggggtt 114120
tccaaaactt ttgcctcttc ctcattttc tcttgccacc accatgtaag aagtaccttt 114180
cacctcctgc catgattctg aggcttcccc agccatgtgg aactgtaagt ccaattaaac 114240
ctctttttct tcccagtttt aggtatatct ttatcagcag tgtgaaaaca actaatacag 114300
atggctagta agggactaac cggcagggag cgtctccagt gtggatatgc tggacaaagg 114360
gatgattcac gttccagggc ataagatttc attactcaga attgcacaga atttaaaact 114420
tattaattat ttctggaatt ttccacttaa tgttttcaaa ctgtggttga ctgcaggtac 114480
ctgaaactgt caaaagtgaa accacagata agtggggagt cctgtaccta agattattcc 114540
tttaaattgt ttcagtggat atgtagggac ctgagtgtga agtgagagca gcagcatcaa 114600
aacctgaggg aaatccagat agcaaaagaa acttgtctag tatactggca tgacagagaa 114660
accaaaaagt tctcaagtta atgtgagaat ctaagaatta aagaattaag cctttgcctt 114720
tgagggaagg aaaggggtaa tgtggcttta aatcaggttg agattggttc tgagggttcc 114780
ttttccttcc tttatattga tatgaatata gacacaactg ttctgcattt ccatttgttt 114840
ttataaatgt ctttttagga tttaggaact gctaattatg caatatgaga tatctgttag 114900
tttgaggaac atttgaaaat ttggtcaaat gacacagatc gtcacacagt tttaagacaa 114960
atgtttttac ctatttgacc tagtctggca atccctattt gggcaaaaat cttcatttgc 115020
aggtcatgat tggaggcagg cacagaaaaa aaattgccac ctttttttgca ttatgtcatc 115080
aagacatcaa acttcagcct acaaagtaga aagtgttatt tctcaagttg aaggcctgga 115140

```
tatacctcag cttctcagtt ctgacacttt atcatagtgg aaaatgaaga agattgctta 115200
agaacactga tgttggtgtc agaaagacct gggtttgaac cctgacttta ctagttactt 115260
agatcacttt aggcaactca acttttctaa atcttgtttc ttcatctgta aatgctgaaa 115320
atagtaccca cctcttaggt ctgtggagag gattaaatga gataatctat acaaagaaag 115380
agcttgcata atagtgccaa gtaatggtga ggttatacct gtattctgat tataatctca 115440
taaatattta ccatgttagc tgtctcagag ttcttttgca aaacagataa agatagaaag 115500
tataaataag aaaaataagt gaacatatac tgaactttgt acaagatgct ggcgatatgg 115560
agagacccaa gacatgggcc ctacctaaaa gagattattg atagaaacag gatacatata 115620
catcaaaagg taacatagga tcatctgtgc aaagtgctat atggcagtgt tttaggaagt 115680
ctagaagctg tcatggatca ggaataccat ggtggacact tcaggcaggg aaaacagatc 115740
ttagcaaaag ctactcctat cataggtact tgataaatat ttgtagaatc caggatccct 115800
gtagtgataa agaaactaca tggattatgt aggggagtga taagacatat gactggaaaa 115860
ataaaaagac caaattatgg accatactga gcttgtacta taaacagtgg aggagccctt 115920
cagattttta atcatgttga gaaaagagtt ttagcagtgt gtgggggata gaatggaaag 115980
agaagccagt gccagaagga ctacttagta tcaaccattg cagtggttaa agcaagaggt 116040
gagagaaggc atgcattaga atggcagcgg tcagagtgga tgggaaggaa taggtcctga 116100
catagtgtta cagggagtaa taaataggat gtggaagatg ggttagaatt ggcaaaatct 116160
ctgcatgtaa gtctgggtta ctaaatatag tgagagaaat tcaaatctct ctttaagaat 116220
cgaataaaat atttagaaat aagttactgt tgtatttgag gtgaacacaa atggcatttc 116280
aaagatgctc gagatacctt gttggaaaaa gtcaataact gcactattgt ctccaacatg 116340
ttcttgcctt ctctgaagac atcatgttcc taattctgaa ttatgaacca tctattatcc 116400
ttgtatgctc ttatgtgtga ggaaccataa ggtgggaaca aaatccggtc ttcattctag 116460
aaataactat gcgatcaaaa agtttttagt ctttcttctt accatactgg ttcttggtat 116520
tctgtttacc attcaatgta ctattattgc ttctgcttaa aactcgcatc ccctaatgca 116580
agcctgagca aacagaactg ataacacaca gcctgagaag ggagtgcttg gggtctcaag 116640
acttattctg tttttctcca tctttgacac ttggtttgaa gagcaaagaa ggatacagct 116700
gttaggaagt aagttaccca aacacagtga ccaaactgga ttaattcttc caatgagaaa 116760
gaaatacatt atttctgtga gacagattag actttaagta gcatagataa catgattata 116820
ttctctctac aaataaatac acaggaccta agaaaccctt tacagatcca agtgttttcc 116880
tctccacttt tccatcccca aacccatctt gcaagatatg gccagcttat ttggagttaa 116940
ttaaatcaag accttcgttt tacagacagg gaaaccaagc ccagagacac tgagtagtag 117000
gccactggtg tcttagaggt ctgaaaaatc ctttactgaa cattctcttg atctattaat 117060
gtataggttt tgttgctgta accctctccc caagaggagt gaatataaat gatgcagagt 117120
ttggatgaac tatcttaata agaacctaaa gttgaaacca atgcaaacct ctctcaataa 117180
atgcaaagca aagagaataa tcagtctttc tttggcttgt taaataagat aaaatgtgtt 117240
ctgctaaaac catttaacag aaatattgtg aaaggtttcc cctaaagcat ttttctattt 117300
gatttgaaaa ctattccata gcttattatc aaacaaatca gtaattcttt agctaatgca 117360
gagataaatg ggcagtcaga aaatataatc acctggtgtg tgcagctgag tatttacatt 117420
tttcctaatg aacaaagata agaaaagtgc aggtgacttt aatgtgtaaa aactaccttt 117480
```

```
tagtgctagc gctagaggga aaaagaaatt actggctcaa gccaatcctg tacttgataa 117540
ctaagccgta tagtccatgg cttggcttca gttctgtttt gaatctcttt ttggacttgt 117600
cttgaatgga ctgtttaggg ctgcttcagt agtgcagttg ttgcattttt aagcatagtt 117660
taggttttaa aatgtttctg gtcccttttt ttttttcttt tccactttat gttgcttaaa 117720
gctttatggc caggttttct catcctcagc attattgaca tttgaagctg gatacttctt 117780
tgtggtgggg gctgtcctgt gccttgtagg ctggttagca gcatccctcg cctcttctca 117840
cttagatgcc aatagcattt ccccaaccgt gataaccaaa agtgttttca gacactgcca 117900
aatgtctcct agagagcaaa attgctctct gttgagaact actgtgttac ggtgtttgga 117960
caaaaactga caagccaatg ggaatattct attggtagtt gtaaaaaatt aatccagtta 118020
tagcagctgt atttctggaa tttttttcca tattaacact tgctttctga ggtgataata 118080
tctttgtttt ttttctccca aatagatttc ttgcattaca ctgaaaaatt gctgattaat 118140
tcacttaaat tgaagactaa gccaatcatg tcatttgggt aatagtttac caactctgcc 118200
cctttctctg tcagggaagc ctctaattta gtaagcgata ctgtatcctt ttgtcaggta 118260
cattaccatt cctattagca atagggcaat tgagattgag aaagattaaa aggtcaccaa 118320
gctattacat tgtagaatta ggttatgaat tgtagcctat ctggtttaga atctttacct 118380
tactagtctc cataacaaca attcttccag tgtggtccat ggggccctgg gagtctcccc 118440
ttaaagggca gactattttc acagtaacac gtactttatt tgccatttca ttatgtcagc 118500
atttgcaata atggtacaaa agcaaagatg agtaaaactg ttggcatctt agtatacagt 118560
agttactgta ttcactgtca tgcacttaaa atctttgaag aagcaaaaaa attattaatt 118620
acattaaatt tcaaccctta aatacatgtg gtctttctca tgtcagtgtg acaaaatgag 118680
aaggtgcata atccacttat atcgcatata gcatttgata gttgtctcaa agaaaagtgt 118740
ataagattaa actgtgagtt aacctacttt ttttcatgga gtaccatgag agataaactc 118800
tggttttcag ccttgggtat ttggcgatgt tttcccaaaa atgactgaag taaacttagc 118860
actttaagga aaacaactta aagtatttgt tgccaattga taaaatatag gtttcaagca 118920
aaaatcagaa tttttgaaga cttgtatctg ccactgtgag cttgacaaat gtgactcttt 118980
tatattacat aatgaactat gtcaacattt gaaagatctg cataactcag tgaaccagta 119040
ttttccagat gactaatgca tgataataca aaatcatgca tgggtaaaag atacattcaa 119100
agtgcaagat agactgacat atttcaatgt aacaatcaaa agttcattga taacagtttt 119160
ggattccaca ttgcaatact aaaaccttta aaaaacgaaa ttgtccaatt ttggtgtagt 119220
aatcagaaaa ggcaatctat aattacctga acttaagttt ctggaggacc attaaccttc 119280
tacaggctca tggggaagac tgtagcactt ctctttccct aagatcctcc agaaaggaag 119340
aaggtaatcc ttgggggtag ggtagagacc tattgtgtga tgatcaccaa gtatgtaaca 119400
atgctttata taactctaat atatataatc cacacaaacc ccctaaaatg gcactaataa 119460
gggaatggac tcaaagaagt taagtcagct agccactgtc acagctatta gagcactgga 119520
actaggattt gaacccagat ttgtctgtat gtaaagctga ttctcttcgt aatagtactg 119580
agacacaaga ggcggctaca aaatattctg gtactccatc ctagaccaga gtttcaaggt 119640
tcgttatcat ttgtagcatg atactggatc ctcacagtgc ttgcctttca ttcaggtgcc 119700
aggaaacgtc tgcctgaatg aatgggtgta atttacctgc acattttaca tgcttctcta 119760
ggtgtgtgat taactcataa tccatccatg actttcaccc ataatcctcc ttgtagcaat 119820
tgctttgctt gcaacaaaac taagtagaca tatctagctt tatgcatggt tttctctctc 119880
```

```
tgaactctaa cataaactca gcctcaggaa ttattcggtt tctactacat ttgccattct 119940
gattgggaac caccagcatt caggtattca cctggaacaa ggcattttgt tccaagggtt 120000
cctcacttaa aagcaagcac cctagcaata gttcataatg gaacttctta acattctcag 120060
aatgtttggc acagctgtga gtgaacacac attgagcaat caataactat tacagataat 120120
gatgccctta agaccaggat attttagctt tcccattcaa agggggtgaa atatgcactc 120180
ttactatggt atacttttgg ttccttctgc catgtatcct taataaaaga tgtcaattcc 120240
atatggtttt ctcttgagtt ctaaccattt tgttgtaccc tagccctttt aacaatatca 120300
aacttgcaac tgaataccat ttagcattca tccatttttt ccaatggtgt tcattatagg 120360
ctatcttact cctcctattt gtatgacaaa aattggcttt tttcaccgat gtctatggta 120420
catctggcag ctttccatgt actcagttct tatctgatgt agcccagaac gactgcctga 120480
agggatgcca aaagcctgat tgaggttcca aattttcagc tactgtacta tcaatccatt 120540
tgttcatttt tactttccct tgtcatctgt agcttacagt tgagtggcct gaacatgttt 120600
tgcatacatt gtaatatcta agaatttggg aatacggtcc taggatttag acttaatact 120660
accttccatt tatataatac ttactcataa aatcttcagt gttcctgaaa aagaaaaagg 120720
aacatgtatt gagtgcctgc tagaagcagg aacttgtagt agattttcta tgtgttacct 120780
tattttcaca acacacacac aggtgatatc cttcccagtt tactgatgag gaaactcagg 120840
ggtcaaagta gtagatacct acccaaggta acagaagctg tgaagtggta cagctgggat 120900
ctaaaatatg tcagcttcac cgtagatagg ctccctgatg aaccacctgc cacggcccgt 120960
atgaccgcat ccaggggtga tgatgtcatt ttcacagggt tattgagagc taaaactacg 121020
aagtactaca aactattatt taaaatataa atacatacta tatatgcata tgtgtgtata 121080
tataattaat ggggtaaaca ttacagaata ctgtcctaac ctttaaacaa tgcactcgtt 121140
ttctgtaaac taatatacaa acaactgttt ggtccctaaa aatagatgtc aggtgacaga 121200
gactggctga gcaagaatag gagtatcttc agaatagaag ccagaggagt ttttgcttcc 121260
ccaacacatt gtcgcaccat tcactgttcc aggaccttcc tacttctctg gaaaactctg 121320
gcccaaagca gctcctctac attagtcaca agtttccatt aatcaggggt ggcctgtgcc 121380
ggacctacag cagagtcatt tcaggttatt ctgttacagg ctttcgacgt gtagtcagtc 121440
cactcgccca aatctagcag ggaatgaatg ccttgtaata cggaagcatc tacaaattct 121500
tcttaacagt gttcagagaa caatgtgaaa ccctggggcc ttttcccaga attagggtgg 121560
tgggaatgct gtcctattga ctaagcctgt taggtaagca ggcagttggc aagattcagg 121620
aagcttcatt tgaagataga atttagggcg atcgtttgga tttactggct taattactta 121680
aggtaacatt tataaaagaa attgtcattc cattattatt accttttaac ttttattcct 121740
aaacggaaca ttagcaacaa actacattac ttgataaatg taatttctaa ccagattgat 121800
aactagaaaa aaattttaag ttactttgct ctgtgaatta gtttaaacat atttgtaatt 121860
gagacttact actgttattg gctgaaataa ataaaagcaa gagataataa agaataacag 121920
agacaacgaa cacccaattt aagtttattt ctaagttcca tcttttttag agaaaaggca 121980
aattaagaaa agtttagaga gaggtactag tatatttatg aacttgtata gatgataagc 122040
aaaacggact ttaatatgta gaattccaga atcaacaggt tgccagcatc catgtttttg 122100
aagatttgct taagaacaca accaaaaatg gaatgggcag tctctaatta caagcagaag 122160
gctacaaaat cattttagct gcataataca gttttggttc taaagtcagc acgtaagagg 122220
```

aaaattcctt aggaaaatac aacattgaaa accattgtgt catgtaatat gaaatgcaat 122280
aattaatttt tcctccagta atagaaagat cactgtttca ttggtttata aaaatatatc 122340
tttatcatta aatgtggcaa aatgttaaga cttggtgaat attggtgaaa agtatatatc 122400
cattgtacaa ttctttccaa ttttttttga gattgaaaat ttttaaaaca acaaattatc 122460
ttttaaacag ctaataatca ctagacctgc actctttgtg gtgagactat gaaaaatgtt 122520
agagacctag taagagaagc agattcacat ttctgtcttc ttcttcaagc caaacagtca 122580
tagagtggag tgggcagaat ggaactcact tttgaaagcc tagtgctttg tccaatctta 122640
ctgcaagcca gacaggaagg ttatagaaaa tgtttctgga tcagtcttct ctgagtcata 122700
tgaaattgtg gtttcagcca agatgacatt aggaattaga gacatgggac aaaaacttta 122760
agattgtaaa aaaattttga ctctagtagg aaacatgggt agaattgtaa tgacacttga 122820
ttgaatttta aaagatgcct gtataagatc ttaaaattag gaaaaaaatt atggcctaag 122880
caattaaagg cataggaggc atctttttgg gatgatggaa atatcctctc tcctgattgt 122940
gatagtagtt acatgaatat tcatttaaca aaaaccataa attatagact tagaaaacag 123000
taaatgttac tgtatgtgac accttaataa acgtgattat aaaaataaat cctaagcatc 123060
taaaaaaaaa aaaaaaaaga agaagaagtg aaccagaacc acaccattct attttggaga 123120
cacttcaaaa gaaatgacct cattcttaat tttgtttaaa gaagaatata acatgatttg 123180
aatatattta gctaggatat tttagtgcct gctagcactt gaagccagag ttcactgtga 123240
gcattctgac tatgaagtga gaagctaaga gaactgtatt ttgatattcc tttgacagtt 123300
aaatcataac actgttcttc cccttcttta gccccagcat gagaccagat gtaagctctc 123360
ctccatccag ctcctcaaca gcaacaacag gaccacctcc caaactctgc ctggtgtgct 123420
ctgatgaagc ttcaggatgt cattatggag tcttaacttg tggaagctgt aaagttttct 123480
tcaaaagagc agtggaaggt agtgtgtgtt ttgaagagtt tatttttcct ctacttggtt 123540
ttcatttctc agggtggatt ttgaaatttc cattatatgc aaagcccatg aaaggctaaa 123600
tatcagttaa gaggggagag gagggtggct cctaggtcct ctaatgggca ggaaagtatt 123660
taaaacaaca atacaaaaag atctagaata aaatagaaaa gtacaagttg atgtctggga 123720
gtttggtcag ggagcataag gtaacactat aagaaagtgc tatcatatga aatgatggtg 123780
ttaagtttgg gcataacata atgttcattg tattagaaac atgggcttta acttccataa 123840
gctaataggt ttcaaagtca ccaactttac tggcctggca aaaatgagtc acagtgagaa 123900
ctgtgacagg aaaaaaaaaa gatattcatt tcatttctta ttcatttttt ttttctatta 123960
agccagggca ctgtgctaag tggtataaat accaataaga cctgatcctt accctctggg 124020
aagtcacact ccactgaagt gaaagatgag ttaacaatga caaggtacag agattataat 124080
atagatgagg gagagagaaa ctcggcctga ggaggtcagg aaaggtattt tagagaaact 124140
gatttcacta tataaatgtt gtattaacac aaatcttact ttgttatgga ttcagactgc 124200
tgacagggca acagcattat ctccctaaag aatgagaaat tcattccata gcaaatttat 124260
tagaagagag tctaaaatgt cctaatacta ccagtgactc ctctaggaaa aaaattgtca 124320
tataatttag ttatttctaa agcagtttga aagtagcttg gcctaaagct ctgattatat 124380
taatttttta aagaaacaat tattcattca ctgtatgagg attattatta tttgtctcat 124440
gttgtgtttg catatccatg agagttagat gagtcatttt cttttgtttt actttttaat 124500
acattagcaa attataaaat tactcatatt acaccacaaa gattacaagg atggcagctt 124560
tggccagtgt agtagtccca cctattgatt agagtcaaaa gtaaagccca gccctgcttt 124620
gtgcattgct cctaataaag tggatgttac ttaacacata cgcagaagac agaagcgtct 124680
tcgtgtcctc actttactcc tcactttctt aactgcttaa gtatttccac gatataaatg 124740
cagtgataat aataatacgg acagtccctg acttaacgat ttttcaactt ttatgatggt 124800
gggaaagtga tacgcattca gtatggctcc tcgacttaca atggggttgc ctccagataa 124860
acccattgtg aattgaaaat atcttacact tagcactcca ttcttaatac ctgctagaat 124920
tatagattat ccctcaaaat tggcatagta taatatgggt atcagcaagt tgttgcactt 124980
tattcagagc tttacactag gcaggggtgg gctttacttt tgactctaat caataggtgg 125040
gactactaca ctagccaaag ctggcatcct tgtggtctct gtggagtaac gtgagtagca 125100
ttataattta catcccccat aacaaatgat ccaagagagt atgtgatcaa tgcagcagaa 125160
ctattgtctt ttattatctg atttcacatg taacatgcca tcacttctgc catattttat 125220
tggccacaca gaccaatctt ggtaaaggac ggaaagggac tgcacaagac catgcattca 125280
aggaggcaga gatcactggg ggccatcttg ggaggctggc taccacaccc accataaata 125340
gaaaaccaga attatttgcc aaaaatagac tttaaccaca aaaatgaata ccatataaac 125400
aaaacaaagt cacaaaattt cagctgactt gaagactcat ctttctatta gttagaaagg 125460
gaatttacca agtagtagaa gacacaggaa ctccaaaata agatatctca ttgtcttatc 125520
agaagggttg acaggaaaat gggctgggca ctgtggctca aggaaaatgg gctgtgcact 125580
gtggctcaca cctattatcc cagcaatttg ggaggccaag atgggaggat tgcttgaggc 125640
ctggagtttg agaccagcct gagcaacata acgagacccc gtctctacag gaaaaaaaaa 125700
aaaaaaaaaa acgttatcca ggcatcgcac ctgtagtctc agctactcag gaagctaaag 125760
caggagattc aggctgcaaa gagctatgac acaccactgt actccagcct aggcaacgta 125820
gcaagaactt gtctaaaaat aaataaataa atgagtcaag gaatgaatga atggattgac 125880
aggaaatgac tattagttgt acgtggccat gtgttatgaa atagtgaata ctagttaaaa 125940
ctcctcattt tatagataag gaacagatag atagacttgt ccaacttcat gctaataacc 126000
acaaagggct atttttaact tatgaaggta cattgcctct gatcctatag ctcagagtct 126060
tagctgtgca caagacatac ctgggataaa gaaatcaaga ttggcgtaat gtgcacatcc 126120
tgacatttca gttggatata aacaaaactt tggaattttt catttttagc agtgggtgat 126180
tttttttctt tttttcttcc agtaactgta ggacagtgat ttagagattc cttatagggt 126240
ataacttttt tgtattataa ccacttcatc aatagatgta tctgttgatc gtacttttga 126300
tttatagggg atagaattgg gttagtgctt ccattttctg tccaagtaaa gaagctagga 126360
tatttataga gtacaaaaag aaattgaaac agctggtaca gatatttggc attggagagc 126420
agctctgaac aaaggtgaat tatagtctag tggtcaattt tgtggcctat tctttacaaa 126480
gaattgaacc tgatacagtt aaccatctac cccaaactat tatttgttta aaacacaatc 126540
tattggctgg gcgtggtggc tcatgcctgt aatcccagca catcgggagg ccgaggcggg 126600
tggatcacga ggtcctgaga tcgagacaat cctagccaac atggtgaaac cctgtctcta 126660
ctaaaaatat aaaaattagc caggcgtggt ggcgtgcacc tgtaatccca gctactcggg 126720
agtctgagcc aggagaattg cttgaacctg ggaggcagag gttgcagtga ggtcatgcca 126780
ctacactact acactcccag cctgggcgac agagcgagac tccatctcaa aaaaataaaa 126840
ataaaaaaac ataatctatc aaactgtgta aaacacagtt tatcaaaaaa gtagttaccc 126900
ttggtgggta ctggctggaa ttgggcagaa agggggcctg ttggggtact gttctgtttc 126960
ttgatctgag agctgattac ataaaggttc ttggtttgta aaaatttatt aaatggttca 127020
ctgatttgtg tacttttttt atatgtgaat actgcaataa ggttttttat tgcactgttt 127080
tcagtttgtt gaacagaaaa agggagactc tttttgttgt ttttgacctc tcgacctcat 127140
aatggcaatg taggcaagaa cattccctca aggcaatacc tgtgggtgtc ttggttatat 127200
tccaccggaa acaaagacag aggctgtcct tataaaatat gtttgaagac ctgtgaaact 127260
ttaatagtgc cttttattcc atataggaca gcacaattac ctatgtgctg gaaggaatga 127320
ttgcatcatc gataaaattc gaagaaaaaa ctgcccagca tgccgctatc gaaaatgtct 127380
tcaggctgga atgaacctgg aaggtaatat aaatatctga aagcaattgt ttgtctctgt 127440
agcttataaa aatttatcat tttacttttg aagatacacg taagcagatg taattaatgt 127500
agtcagttca gtatatatat gcttgactag cataatgtta ctgcccaata aaaatgggaa 127560
atttttttca tgaatatgtc atattgtttg tttatccacc agttcttctt acacacactg 127620
aattcagtac agccagacta tatacaaaga aaggaaatta tgtaataatg aaacttacac 127680
aacatgcagc aactttatta ttcttactcc tttttttcagc ctcaaaacta ttccctaggg 127740
ttggaaatgt ttctgtatca gacatattta catgtccatt tttctgtttg ccttttaaaa 127800
gcatacettt tacttggaga tctgtgtttt attacagatc ttcaagcggg gggtggtggg 127860
aaaaaaaaaa cctcaaggaa gaactggatg ggttttgttt tggttttcaa gtaaagaaga 127920
aacctgggcc gggtgcagtg gctcacgcct gtaatccccg aagtttgtga gaatccttct 127980
gtctagtttt tatgtgaaga tattaccttt tccaccgtag gcctcaaagc gctccaaata 128040
tccacttgca gattctataa aatgagtgtt tgaaaaactg ctcaatcaaa agaaacgttc 128100
aactccatga cctgaatgca cacaacagtg agaagtttct gagaaagttt cttggtctcc 128160
ccgcactttg ggagaccaag gcaggcggat cacgaggtca agagatcaag atcatcctgg 128220
ctaacatggt gaaaccctgt ctctgctaaa aacacaaaaa ttagcggagc gtggtggtgt 128280
cacctgtagt cccagctact caggaggctg aggcaggaga atcacttgaa cccgggaggc 128340
agaggttgca gtgagccgag atcacaccac tgtactccag cttggcgaca gagcaagact 128400
ccgtcttgga aaaaaaaaaa aaaaaagaaa cctgaaacta gttataagtt agagtttcat 128460
atccctgttt atataacaag ttgtataatt aacactgatc tcagcattaa aaaattttcc 128520
tctgaaaaaa gtttggaatt ctgctgtggt tgaaattgca agttctgtga aggtagtggt 128580
gatctcataa cacatatgct tagtatttat tgtgaaatta gcacttttat tcaacaaata 128640
tgcaccaaca aggcagtcac taggtataaa atgaataaaa tagtgcctgt attcaagtag 128700
tttatctgct agttaggttg cagagtcagt cacaaaatag catggcacac catagagggc 128760
atagggccac aggaacaaga ggaaggtcac ctaattctgt cttggaagtc aaggaagaag 128820
taacattgaa ttttaaatct ataagctgag taggaattag atagatgaaa aataagggca 128880
gagacatgat cagatttgta ttttacaaag actaatctta catggagaga ccaattaagt 128940
gaatatggca gtcctccaga taagagatgg cagtactgag agagaatgga aaccatgtgg 129000
ttccttttat gattatgatg attattatta ttttagagac agagtctaac tcttgtcacc 129060
caggctggag tgcagtgaca tgaacatggc tcactgcagc cttgaactcc tagactcaag 129120
ccatcttccc acccagtagg gctacggatg tacactacca tgcccagctg attttttttt 129180
aatttttgtt ttaatttttt gtagagacaa aggggtcttg ctatgttccc aggctggtgt 129240
ctaactcctg gccttaagtg atcctcccaa cgtggcctcc caaagtgctg gtattacagg 129300
tgtgagccac tgcaactgac ctatgtggtt cttttgatag gagagactaa ttgttggtgc 129360
tatctagcac acactgtgtg tagacatctt gttaaataga aaatagattt atgggtatga 129420
ctatgaagag tctaattccc caaaccacac acacaactct atctacgttt gaccaggcta 129480
tttaaactta actgcagagt gtcagcatgt taaacattga tttacataaa atgatagctg 129540
cccactttct tgtaaatgtt ataaaaactg tagagattaa ctaaaaaatg cacacagaag 129600
tttgctttca gttccacaag ggtagtttat ttttgttata aaaacagtat tccccacttt 129660
cttagatacc agatctctgc ccagatttta cccagtttca tcttgctgct ctctaatctc 129720
ctatgtatgt aatatacttt gaccatttaa atatgtatta agacacttga gtttttagtg 129780
ccctttggtt tattttctcc ggtcccaatt atctctaatc ttcatttttt catttttacct 129840
attttatatt tcgaaatagg ttttgaatga agctcaaagg acaaacccaa ataaaattct 129900
gtcgtatctc taatatattg tggttgctta cccagtaaca tttttaggtg cttttctgaa 129960
tacatataaa gtttaagatc tttggagttt taagtatata atgtttttct gggcaatttc 130020
tccctatcca aactatgagg gccttctttc atcaaaagaa aaaagatata tcaactacaa 130080
agtaatgatt ttgatggact aggctacgaa atctgtccat tttttcctcc ttcttacagt 130140
ttaatagcaa ttgcagtgcc ctttgccctt actgtactag aagacgaccc caggcagtga 130200
ctgacatctg atttttctat taattatacc atcactgcca tttccagttg aatcttttgt 130260
tggacatcag aaatttttct tacatgaata aaatttaagc atacggttgg gcgcggtggc 130320
tcatgcctgt aatcccagca ctttgggagg cctaggcagg tggatcacga ggtcaggaga 130380
tcgagactat cctggctaac acggtgaaac cccgtctcta ctaaaaatac aaaaaattag 130440
ccaggcgtgg tggcgggcgc ctgtagtccc agctactcgg gaggctgagg caggagaatg 130500
gcatcagccc aggagttgga gcttgcagtg agccaagatc gcgccactgc actccagcct 130560
gggcgacaga gcgagactcc gtctcaaaaa aaaaaaaaaa aaaaaaaaaa aaaaaaaaaa 130620
aaaaatttaa gcatacaatt taggctgcag tttctcaaaa tattgtatta aaaataacca 130680
attatatgct tttatagtca gtataacgta tccagttagt gtagaaattg gcatttgttg 130740
aaaactacta catgttagtc tttgatatac attcttctac tttttggacc ctgattatta 130800
aaaacacctt tgaatagggc catgatttac tttatatcca tttttatact acatagtgga 130860
agaaaattct gatttgttat ttcctactat gatatgtacc gtgtggcaca tatcatataa 130920
atgatccaat tctacttgta gatgaattga aagaaaggct taaaaaagtt cttagggttt 130980
gtgtgtgtgg tttcactgta aaactatcat ttttgtattg aactaacctc agtatacata 131040
aaatctttat ttggcctggt atgtacgtat gccaggaatc tttggcagac cctaacactt 131100
acaatacaga tgagccatgt gtttcacact ttttttttaa caaccttcag aaatattctc 131160
ttgttcatca gagtgcttcc cctaagccaa gcagtttcga tgatagcccc agaataactt 131220
tgcccaagtc tctccataaa tgtaacttag gactccaagt ggtgtatttt tatactcttg 131280
ccccatacca agtaaatctc aagatttatt ttaagggagt ggccttcact gcttaaaggg 131340
cctagcattt aagaacagat aagattttta atggtgatcc taaatgtttt tttttaaaaa 131400
acttgcttgt ttttctcttg aaactaaatg tttttattca cttcatttta agatatattg 131460
taatcaatcc aaagtatggc tttattttta gtataaacag tcaaatgaag cttagtcttg 131520
tggcattgtc agatttataa ccaaatatta ctgaaactaa tttttttaag ttcaaaaacc 131580
caatctagta gtttctctct tattttcaac ttttatttta gattctaggg gtacatgtac 131640
aggtttgtta ctaagataca ttgtgtgatg ccggtgtttg gagtatgatt gaacctttca 131700

```
tctaggaagt aagcacagta cctaacaggt gctttttaac ctgtgcctcc cttcctctat 131760
ccccccctctt gtatttccca gtgtctgttc ccatctttat gtctatgtgt actcaatgtt 131820
tagctcccat ttataaatga gaacatggta tttgtttttc tgcattagtt catgtaggat 131880
actggccgcc tgctacatcc atgttgctgc aaaggacgtg atttcattct ttttgtggcc 131940
acatagtatt ccatggcata taaataccac attttcttta tccagtccac tgttgatggg 132000
cacctgggtt ggttccatgt ctttgctatt gcaaaccatg ctgcagtgaa catatgggta 132060
catgtgtctt tttgatagaa tgatttattt ttctttgggt atattcccag caataggatt 132120
gctaggttga atggtagtta aactcttaat tctttgaaga atctccaaac ttctttccac 132180
agtggtgtca ttgtggtttt gacttgcatt tctctgatga ttaacaatca gcatttttcc 132240
atatgtttgt tggccacacg tatgtctttt tttgagaagt gtctgttcat gtcctttgcc 132300
catttttaat ggggttgttt ttgcttgtta atttaagttc catataaact ctggatatta 132360
gggctttgtc agatgcatag tttgcaaata ttttctccca ttctgtagat tgtgatagtt 132420
tctcttgatt tgcagaaact ctttagttag gtcccattgt caatttttgt ttttgttgca 132480
gtttcttttg gggattagtc ataaattctt tcccaaggcc aatgtcgaga aggttatttc 132540
ctaggttttc ttctaggatt ttcatagttt gaggtcttac atttacatct ttaatccacc 132600
ttactaattt ttatatggca gtaggtaggg gtccagtttc attcttctgc acatggatag 132660
ccagttatcc cagcaccatt aatggaatag ggagtctttt ccctatggct tatttttatc 132720
aactttgtgt agattacatg gctgtaggtg tgtgtcttta tttctggact ctattctgta 132780
ccattgtgtg tggttttttt ttaccagtac catgctgttt cggttactat agcctgtagt 132840
atagtttgat ttggggtaat gtgatgttgc caactttgtt ctttttgctt aggattgctt 132900
tggctatttg gggcattttt tggttccata ggaattttag aatgcttttt gctaattctg 132960
tgaaaaatga cattgtagtt tgataggaat agtgttgaat ctataaattg ctttgggtag 133020
tatgaccatt ttaactatac tgattctacc agtccatgag catggaatgt tattccattt 133080
gtttgtgtca tctttgattt ctttcagcag tgttttgtag ttctccttgt aaaaatttta 133140
aactaactta gatgcattcc taggtatttt actctttttg tgactgttac aaatgggatt 133200
gcattcttga tttggctctc agcttgaaca ttactggtgt atagaaatgc tactgatttt 133260
tgtacattga ttttaaatcc tgaaccttta ccaaagttgt ttatcagctc caggagcctt 133320
ttgacagagt cttcagggtt ttctaggtat agaatcataa gtgaaaagag atcgtttgat 133380
tatttatttt cctatttgga agccttttat ctctttctct tacctgattg ttctgactag 133440
gatttccagt actatgttaa attggaatgg tgacattggg catccttgtc ttattgcatt 133500
aaggggaatg cttccagctt ttgcccattt ggtatgatgt tggctgttgg tttgtcatac 133560
agggctcttt attactttga ggtatgttcc ttcaatacct agtttggtga aggtttttat 133620
catgaagaga tgctggattt tatcgcaact ttttctgcat ctattgagat gatcattatt 133680
ttttttgtta tgtggtgaat cacatttatt gatttgcata tgttgaacga gccttgcatc 133740
ccagaaataa agcctacttg attgtggtga attaactttt tgatgtgcag ctggattcag 133800
tttgctagtg ttttgttgaa gatttttgta tctgtgttca tcagggatat tggcctgtag 133860
ttttgttgtt gttgttgttt ctctaccagg ttttggtatt agaatgatgt ttcccttgta 133920
gaataagtta gggatgaggc cctctttcta gattgctttt ttagaatagt tttagtagga 133980
ttagtaccag ctcttctttg tacatctggt agaatttggc tgtgaatcca tctggtcaag 134040
ggcttttttt aattggtagg ttttttatta ttgattcaat ttcagaactc gttattggtc 134100
```

tgttcagaat ttcagtttct tcctggttca atctaggcag gttgtgtgtt tccatttcca 134160
catacatact tactccaaat aatggcttta tatatacggg ggtcagctga aaacaaaaat 134220
gatactttca tagtaaactc cacccgcccc cccacccaca tacacacaca cataaaccct 134280
agatttttta aagcctttgt tccaatttat ccatttcctc tagattgtct actttgtgtg 134340
catagaggtg cttgtaatag tgtgaagatc tttttcactt ctgtggaatc tcttgtaatg 134400
tcatctttta catttttat tgtgcttatt tgggtcttca ctcttttttt ctttgttaat 134460
cttgctagtg gtctatcaat cttgtttatc ctttcaagta accaactttt ataaactagg 134520
ttttaagcta attaagattt ctctactttc attaagaagg aagtagtgtt accacagact 134580
catgaacact tctgtggagc tcctgtattg actgctaatc aactatatgc tccaatgggt 134640
caggaattta tataaagttg tattaactaa gttgctttaa aatagtgatt gcttaactaa 134700
atgattcagt tcagttaact ccttcctgaa gatattttga aaaattaatt agtattattt 134760
cttgctctag tcagtacagc acagttgggt tcaattgtac tttctgagct gtattgaaaa 134820
acatcagttt tctcatttag aactatatat aagtagtgag aaattaatta caaactgagt 134880
catagaaaat gttttttttt aatcctccag cttgttactc tttcttcctt gttctaatgt 134940
ggagtaaaga aatatgcatt ccaaaccatt taaagttatg actaattgag gctgtcaaag 135000
tactgtttca gtgtattgat ttggcacatg tgtgttctct tttacattgt caacaaaagt 135060
acattttatg attttggatc aagatttcac tgagatactt ctggttgttt aaagagtttc 135120
tttatgtatt ggtgtctttc ctttttaaaa ttttatcact cctctattaa gttgtgatat 135180
ccaaatttaa aatattctaa aaacatgttc tcctgcaagt tgaggtaatg atagttgtta 135240
tgtggtactt actataatat atgccaggaa ctgttctaag cattttacat atttaattct 135300
cacaacaacc ctatgaggta gggactaata ttgtcctcat tttacagaag gggaaatgaa 135360
gagtcaggga gtaacttgca cagatatcca gctacaacat ggcagaacca ggacttaaat 135420
ccaaatatgc tgatttcagg tttctgccct ttagtcctat atcatactgt gcctccaaga 135480
gagcatggta aactaattag catggttcta tcatgattct gtttctattt tgaactatta 135540
ataaaaattt ttgcaattct cagttacccc atttagtata gaacacaata agaatggaac 135600
cattctattc taacattgta cattgagata tcgttcccac caccatatct gtcctccata 135660
gactatatgg tgtgtcattt taaggacaga ggatctaaaa atgattttta aaggtgattt 135720
acatttactc ttccctttgc aaaatggttt gcatccctaa taatttagac aagtacattt 135780
cttcgtgata taaattacat ttcttgcctt tccctggaat tctgagtact ttccctctga 135840
gagaacaatg taattcttat ttatttagtc actaaaataa cttcaggagt atgaataagt 135900
ctactaaaaa gtctacagga tccatgttgt agtttgagta gatggttcca taccaagtca 135960
aggtaaaaga taatttatat ataatatgaa aatggctgct ttaggtttat agagtaatca 136020
atataaatct tccttataaa agggaaattt cccacttata atttatgtaa tgtaaagttt 136080
ttcatttcat cttcccaaat gtttttagtc ccacgcagta tttatgttag tacctatgta 136140
aaggtgaaaa gtgaattttt tctactggta gaactaatac tatttttagc atgtaatctg 136200
ctgtcatctt cctatcttta taagtggctt tgaacaagtg taaatagtgt aattctcttc 136260
attatatata ctaccatgat ttagattaat cttaaaccac agtttgtaat ccgttactcc 136320
aagcttagat tttttttca gtttatagta agagtaattt gccttatata accaatgaaa 136380
ttgttgcatt tagagtgaaa gtgagataaa aaaataattt atagaagaat ttacaaaagt 136440

```
tatttactca gattgtttta acataccgtt ataatacttt gtataaggaa taactctaat 136500
gaagtttctg gcctatttgt aggcaaaatt aattgggaat aggttcctct ggatcttttg 136560
ctttcagaaa aaaaaaagtt ttttctcctt ttccatgtca ctttatcata attgctaaat 136620
aaaatatttc tcccatctta atagttttag aaagtaaaaa tacttcttga ataaactgtg 136680
tagcgcagac cttcccatta cagttcattt ctatgtattt gtttaaatac ccacagctcg 136740
aaaaacaaag aaaaaaataa aaggaattca gcaggccact acaggagtct cacaagaaac 136800
ctctgaaaat cctggtaaca aaacaatagt tcctgcaacg ttaccacaac tcacccctac 136860
cctggtgtca ctgttggagg ttattgaacc tgaagtgtta tatgcaggat atgatagctc 136920
tgttccagac tcaacttgga ggatcatgac tacgctcaac atgttaggag ggcggcaagt 136980
gattgcagca gtgaaatggg caaaggcaat accaggtaag atgcaaaaca taaaagagca 137040
actatataaa cctttgtgtt ttcttcagca aaaacacttt ggcttttata tcatcgtgag 137100
cccatggctt atcttgtttc tcttagttct ggggactatg aaggggagag tcaggtgaat 137160
acaggtgata gggagtttat aataaaacat ttacattact ccctgctttt caaatcatta 137220
tgcacaggat ggtaatttca cataggatga tgtaatatca gaattcaagt tacaagactc 137280
actcaaaact ccttttacac tgaagtttgg ggaaagaaaa tgtttttagt taattccatt 137340
tgttttcctt cattgtgcca cttttaaaaa tcaggttgtt tgtaagattg gtaaacatca 137400
agtatgttga ttgtcaaaat ttgtactaaa gtagaatgat tttaaccctt cactaaatga 137460
aatgctacac attgaatgta attttaaaga taattttaaa taaaagttac cctattggaa 137520
tttggtgtgg aatggcagag gtcaatgtta gtgtcagctc tgactttaaa gacagggaat 137580
tgacaagcct gtgttcacgc aaatagttag ggagagagca agaaagtaac ctgacctcct 137640
gtcatccttg ttttattaag ggggaaagag gtgtgaatag cagggcaaat gttttgctta 137700
actcattgat taatacctca agccaagatt cttttctgtt ttttaaaatc aatacataat 137760
agttgtacat atttactgta catatttata tttagggggt acatgtaata atttaataaa 137820
agcatacaac gtgtaaggat caaatcagag taactgggat atccatcacc tcaaacattt 137880
gtttggggaa cattccaaat cttctctttt agctattttg aaatataaag taaattattg 137940
ttaactatag tcatcctgtt gtgctactga acactaaaac ttatttcttc taactgtatt 138000
tttgcacccg tcaaccattc ccgcttcatc cccatcacca ctatctttcc cggtcactgg 138060
taaccgccaa gccaagaatt ttggctattt tactatttag ttcatgttta cttaagcaga 138120
cagaggtgac aaaactggct tttttttttt tttttacat taaaagctat taaaaagcac 138180
ctagggggct gggtgcgatg gctcacgcct gtaatcccag cactttggga agcccaggtg 138240
ggtggatcag ttgaggtcag gagttcgaga ccagcctggc cagcatagca aaaccccatc 138300
tctactaaaa ttacaaaaat tagccgggca tggtggtatg aatctgtatt cctagctact 138360
tgggaggctg gcactgagaa tcacttgaac ccgggaggcg gaggttgcag tgagccgaga 138420
tggcaccatt gcactccagc ctgggtgaca gagcaagact ttgtctcaat taaaaaaaaa 138480
aaaaaaaaaa aaaacacaag agggtttgtg agtcttaaag tgtcagatga cagaagaaaa 138540
ctgtgtctac ctagtattta atttccattt tctgttaggg gtgcccttgt tttgacaggg 138600
ctaattgatc tcattgctcc ttggcaattc ccacagagat gatcttctga agagtgttgc 138660
ctcatacctt tatttctctt aattcaggtt tcaggaactt acacctggat gaccaaatga 138720
ccctactgca gtactcctgg atgtttctta tggcatttgc tctggggtgg agatcatata 138780
gacaatcaag tgcaaacctg ctgtgttttg ctcctgatct gattattaat gagtaagttg 138840
```

```
tatgtgtgtc attttccctg tattcatagg gtatctttaa ccagctgatg ttttcctgat 138900
tgactgctat tgtgataatt caggactgaa acaatcctac taggtatcta ggatctaggc 138960
aaactggaaa tagagttatg agtgcttggg gcaggacaag tgtaatgtaa agcaaatgta 139020
catgtggcat tattactgtc ccaggacatg tttgaggata tttaacagca tatctgaggt 139080
tagtaaagtc tgtcgcaagc aacaaggaat cttactgtga tatcatttac ataaccctat 139140
tccagaaaga aaaaggagca tggtaaaact catgtggatt cagtggggac aattgtagat 139200
gaggatatct aggctgatgg ggtgggacat atggacccag acacaagagg tatctctttg 139260
catggcaagg ctcacccagt gtctgtggtt taagaatatg ggaacaaatt tgttttgttt 139320
aactgagaga agaccaagcc tttaagattt tataaatcag ctattctctt atcctctaag 139380
cttattcctg tgtctgcgaa atacttcagg tgtccatttc cccttacctc attgcagttg 139440
tttcctcact cgttttctcc ctccagtgta acgttcatca tgttggctaa tgtttgcttc 139500
ctcaagcaca gtctgactgc atcacatatc tccccagtac acagattgtc ttcagtatct 139560
tcccactgac cctccagtac atattctgca tgatttcaga ctttccagaa tctgacctca 139620
cttcctctcc cattgttttc cttcacacac tcttcattcc catccatcct ttccagcata 139680
ctcttagact cttggtgttc acatcaccag atacacagca gagaagtcac atcctagtta 139740
ctctcacttt ctaccttgta ttactacttt tcgtacccct agcttattgc tattagtaca 139800
atgtaaacag ggagttcaca cacacatacc cctggtctaa gaagaataaa aaatgaagga 139860
gatttctgtt tgtatagaaa acagaagtca ccttgacttt tattgccaaa aagaggactg 139920
ttcaaactac tgcatcacaa tgtaacaaga ttaggtagtt ggatccaatt ttaaattaac 139980
tggtaaatat atttagtttc tggggaaact gaagacatta ttactcatca taatcctacc 140040
atgctgttta aaaaatacca tgttggcagt atttgttttt tagtcacttt ctaatatgta 140100
atttgaaggc atttaagtgg aattaaaagc ataaacagat ttgtatgaaa caccaactta 140160
tcctggttta taaaactaac ctaatttagg gtttttatta ttagggcatt cagatttagc 140220
tttaagcagt cacagcaaaa tctaatcatg ccacatacat tccttacata aagtgggatt 140280
tataattttt tttcctcaac agatttacat tagtttcatt ttcattaagg gatatgtact 140340
tcctattctt gtgttctcat gctgctgcct aaaagatggg cagtcctcca cctttttctt 140400
ttcttttttt ttttttttt ttttgagacg agtcttactc tgtcacccag gctcaagtgc 140460
agtggtgtga tcttggctca tggcaacctc tgcctccagg gttcaagtga ttctctgcct 140520
cagcctcccg aatagctggg attacaggcg cactccacca cacttggcta attttttgta 140580
tttttagtag agacggggtt ttgccatatt ggccaggctg gtcttgaact cctgacctca 140640
agtgatccac ccactttggc ctcccaaagt gctgggatta caggtgtgag ccaccgcacc 140700
cagccctcca cccttttttc ttagcccact atgtttccat actgctctgg tgtctgtgac 140760
aggcagatat tgcatatcag aaagtatgca ttcaagttct gaccctctat agagctgtca 140820
aacagtctct catggttgcc cttaggtcag aacgttgtgg gggaaaaaaa aattgttgtt 140880
gtttttacag ccaacaagaa tgagttttta cttattctac tacactataa ctttgttgaa 140940
attttcagtt atatgagtat aaccatgtac aagaaactaa aggaaaaaaa ggtgcctccc 141000
agaaaaggag tgctttacct actattaagg actagggagg tgcctcttcg gtaagagcag 141060
attttaaatt tgaagagcct ctgatcactt tggcagcata taagtcatgt ctaatttatt 141120
ttatataaag gaataaacca catattcagt agagaaaaat aataaccttt ctgttgttaa 141180
```

gtccaagacg actttctgtc agaaacttaa aaaaaaaaaa aaatcttgaa gcattttaaa 141240
agctgtgaac tgggcccagt ttcaggctct tagtgtcatt tcacaagtca ggaaacttta 141300
gagacctatt tgaaaatcat aggtatgtaa tgacttcaga atcataagca agaattggtt 141360
tagtaccttt agtttaaaga atattaaggc atatgcctgt cagaggcaga ttttgagcat 141420
cagaagtcta gaatcaagtt ctaggtctcg ccctctgcat aactgtgaac agtgtcacac 141480
atttttgtct ttaggatgga ctgctgtgaa aaaatttacc tttaaaaatc aagtgtgtag 141540
gacctaaaac tgtcgtctaa ttgaccgtat tcaaatgata aaccttgatt taaatgagca 141600
actagtaata agttctataa gaattctaac actttaatta aataataaaa taatacatgg 141660
catgcatgat agaaaataat atctccactg ttacattaga ttattcatta gtctatttaa 141720
acagccaaga tgcaggaagt ttaaggaaag ttctccaaaa ttctgatttt atagggaatt 141780
agcaataata ttattgcagt agttgttttt ctttatgagt tcatagtttt gcaaaacaaa 141840
acaaaaatgt gctttttggg gggaagtagc agtatttcta actaataccc tgctatttat 141900
ctttcacagg cagagaatga ctctaccctg catgtacgac caatgtaaac acatgctgta 141960
tgtttcctct gagttacaca ggcttcaggt atcttatgaa gagtatctct gtatgaaaac 142020
cttactgctt ctctcttcag gttggtagaa cacctttttca ccttatgtca aaagcatgaa 142080
atatgaaggc ctagaaacaa aggttaattt atatacatag tactaataat tataccaagt 142140
ctactattat ttcctactag tcagatgatt tttatgaatg taaaatatta gaaaggcaca 142200
gtaagtgaca ccaagattaa taagacaaat aggtatggca gaaacagaga ggtatatgag 142260
ctgcataggg atctctgttg ataagaatct gtgtagactt ttttctcctt ccttcctttg 142320
atctttgatc atgggaagac atggaaaaag aaagctaact acagtgattt tgtccactac 142380
actgttattt ggttaaaaat tttagtttcc taatgagtat tagcatgtat gagaaattat 142440
gggagaaaaa ggcgcatcct agaaaaggtg tgcttaatta ctattgggga ttggttaaca 142500
tagcatggga gctggattgt cagagattca ttatctagaa aatggcaaca agagtttata 142560
aaacgaactt ctgtgagatt actttttagc tagcaaagac aaagatgtcc ttcagtaggt 142620
gaagtgataa actatgatac atccagatga tggaatacta ttgaggacta aaaagaaata 142680
agctgtcaag ccatgaaaac acatggaggg acgttaaatg catattacta agtgaaaaaa 142740
gctaatctga aagggctaca tactgtgtga ttctaactat ataacattcc ataaaaggca 142800
aaactgtgaa gacagcaaaa aaaaatcagc ggttgccagg gtttagaagg aagggaggga 142860
taaatgtgca gagcacagag gatttttagg gcagtgaaaa tacttcgtat gatactacaa 142920
tggtggaaac atgtcattat acatttatcc aaacccaaag aatgtccacc accaagagtg 142980
aaccctcaac tatggacttt gggtgatgat gtgtgggaca ggaggtatat gaaaaatctc 143040
tgtaccttcc tcccaatttt gctgtgaact taaaactgct ctaaaaaaag tctttttttaa 143100 aaaaagctct atgaactagt tggtattata aaccttaggc catttcaagt aaaaattaca 143160
tatcaatgtt tattaaatac tgagttaata gctgaatacc tctttcatat acaaataagt 143220
acatttgcaa ttttttaaaa agtcttaatt ccattagtaa ctgtggtttc atagttgcca 143280
aataactgta agctatggat gttgcacaag actgtgattt tatttaatca tttcatatct 143340
atttaaacat ttccaaagcg cacattcatc ttaatgtttt cacactattt ttgctcaaca 143400
aaaagttatt ttatgttaat ggatataaga agtattaata atatttcagt caaggcaaga 143460
gaacccgata aagatcattg ctagagacgt ttaatgttac ctgtagcggt acacttgtta 143520
aagaagtgat taagcagtta cataaaattc tgatcatagc tttgattgat accatgaagg 143580
tataattcag tgcctggata ctaacaactt tacttgttta aaaaaaaaaa aaaaagaatg 143640
gtttcaattg tatacatccc agactaattg agctatatga ttttttcat tgtaaataat 143700 atcacgagtt cttcttgtta aaaaataata gaatcataag gatggaaata tataccttaa 143760
gatatagact tctactatga tagactactg gaataggtat ataacctccc accaaaaatg 143820
ctagactaaa aaaattaaga actaagtgaa ggcaggaacc tacagagata agtggaactc 143880
aagccaactt gctctttgac ggcatttgta gaacctggta aattagtaag tttagtaagt 143940
tggggttttt ttaagtttat aatctttttt aaaatgattt caataggttt ttggggaaca 144000
ggtagtggta ggttacatga ataagttctt tagtggtgat ttctgggatt ttggtgcacc 144060
catcacccga gcagtgtaca ctgtacccaa tgtgtagtct ttcatccctc atcccctccc 144120
caaccctagt ccacaaagtc cataatatca ttctcatgcc tttgcatctt catagtttag 144180
ctcccactta gaagtgagaa catgcaatat ttggtttccc attcctgggt tacttcactt 144240
acaataatgg tttccagttc catccaggtt gctgcaaatg ccattatttt gttccttttt 144300
gtggctgagt agtattccat ggtatatata taccacattt tctttatcca ctcgttgatt 144360
gatgggcatt tggactggtt ctgtatattt agtaagttta aaaacaaggg atggaaatat 144420
aaatgcagtt gaaaaggcag tggatggatc taaaagcaga agaatacaat tgtttttaat 144480
gattgtgtat atgtttgtgt atataaacca caagggaaat ctgtaggtac tgaaaatcac 144540
aacaggaaaa tggcaacaaa gctatagaaa ctggaaaagc aatgactttt cttagatccc 144600
tcagagaatg gaggtcatag gacaaaccac cacttcaaaa tctagaagaa tagacaaata 144660
cagagaaaca gccaagatca gcttactggg aaaagatgcc actgaagcca ggaagactat 144720
ggcaatttgg gaaaagatgc cactgaagcc aggaagacta tggcaatttt gatgaattgc 144780
tggaggctga gtgaggacta gcttcagagt taaaaactcc cagggaccca gtcttagtgg 144840
gggtttcctg caatttcttg ggtttacccc acaaaatttc taacttccag aaactccaca 144900
aggttcttat ggtgaagatg caagaaaaat tccctccttt ttctggtagg agtagaggga 144960
aggtaaaatt tggaaatacg tagcagagtg ttcacaacaa aaggcctgcc ctgtaaggaa 145020
aactaattca acaggccctt atgtgacctg ggggaaaggc aaatagagga ttctagccct 145080
tccttagcct tcttgtctca tttctgaaag tcacagccca gggattcaga cccactaaaa 145140
aaaactgaga tttaatcata aagattaaaa aacaattccc ctccccctcc ccaacacctt 145200
accaccatat aaacagggct ccaggataaa ataacagtgg attacaactg agagagctgc 145260
aagacacaag ctgtttaagg agctcttagg aaacccaaaa acaacagaag aaaaagtaaa 145320
taaaaacaag gaaactagag gaaactgaag cctccagtac ctacaattat ggcaaacatt 145380
aaatacagcc cagctcctag ccagattagc atgaaacctc acactaaaag tctaattact 145440
tcagttttga tatatcaatc atgtccagct ttcagcaaaa aaactacaag gcatgctaaa 145500
aggcaagaaa aacccacggt ctgaagagac aaaacaagca tcagaagcag tcctcagata 145560
tgacacaaat atttcaatta tcagataggg aatttacaat acctatgatt agtaggttaa 145620
aggctccaat ggaaaaaagt agacaacatg caagaagtga tgtacgcaga gagatggaaa 145680
ctctaaaaat aaatgctaag gaatgctgta aggaaatgca gaatgatgtt gatgggctca 145740
tcagtagact gagcacagcc aagcaaagag tcagtgagct tgaagataga taggtcaaag 145800
gaaattcccc caaactcaaa tgcaatataa acatagtaga cattaatcca gctgtatcag 145860
taattacttt aaatttgaat gctctaagta caccaatcag ctattttttt aactaggagg 145920
tgaaaataaa gtttgccacc agatgctcac taaaaaatta ttagaggata tatcccagcc 145980
aggcgtggtg gctcacaccg gtaatcccaa cactttggga ggctgaggca ggcagatcac 146040
agagtcaaga gatcaagacc atcctggctt acgtggtaaa accccatctc tactagaaat 146100
acaaaactta gctgggggtg gtggtgcgcg cctgtagtcc cagctactca ggaggctgag 146160
gcaggagaat cacttgaacc tgggacgtag aggttgcaga gagccaagat agcaccactg 146220
cactccagcc tagtgacaga gggagactcc atcttagaaa aaaaataata aaagtaatcc 146280
catctttaag aaggactgaa gaataacaaa agtggtaaat aatatagata catttaaact 146340
gacatttact atgtatataa aataacaaca gtaacaattt ccttgagggc taaaaagtag 146400
aactaaagta agtttcaagg atgacaacta gaaatagggt atgcagggta tgcaaagtac 146460
caaaccattg gggaagagaa atacctaaga aaaacaatcc aaaagaatga aagacatgag 146520
aggagggaga aaaaaatgca taaacaaggg catgataaca ggaagtaaca gataaggtac 146580
attagtacag ctaaattcaa acacatcagt agtttagttt cattaaatat agagatgggg 146640
ccaggtgtag tggctcacac ctataatccc agcactttgg gaggctgtgg gcagatcact 146700
tgaggtcagg agttcgagac cagcctgacc aacatggcga aaccccgact ctactaaaac 146760
tataaaaagc cgggtgtggt ggtgcatgcc tgttatccta gctactcggg aggctgaggc 146820
acaagaatca tttgaacctg ggagatggag gttgcagtga gccaagatcg tgccactctt 146880
ctccaaactg ggtgacagag ggacactgtc tcaaaaataa aataaatgta gagatggact 146940
gaatgctcca agctaatctg acaggatttt agaaataatc caaatttatg ctatttaaaa 147000
aaagctatat ctgaataaag atattgaaag gctgaagtaa aaggatctac tttgcatagt 147060
ataacccaag acatggccaa ctttttctgt aaagggccag atggtaaatg ttgttagctt 147120
tgcacagtct ctgtcacagc tactaaactc tgcccttgtg gcaggaacat agtcattgac 147180
ggtactcaaa tagaacaggc atggctgtgt tccaataaaa ctttatttac aaatacaggc 147240
tgcaagtagg atttggccca taggccaaag tttgctggcc cctatattga ccaaaacaaa 147300
accgaaggag ctacattatt accaagcaaa atagatgtta aggcaaaata ctccttaaag 147360
catttgttca ggaaaaataa ttgtaaatat atagtttcaa attacataat acaaaaattc 147420
atagaacaag aatacttaga taaatctagt aaaaataatg agattttact atacctttct 147480
tacaaattaa gcagacaaaa aaataaggat atggatgtac atttcatctc tcttgggtca 147540
atactgaggt gtgagatcac tgggacatag gttgagtgtg tgtttaaatt tatttttaaa 147600
attgccaaac ttttccgcaa ttgttaacat ttaccagaaa tgtatgagac ttcttaagat 147660
ccattctata tcctcctcag tacttggtac tgtcagcctc tttcatcgta ggtatactga 147720
tgattaaaaa tattaagcat cttttcatgg gcttattggc cacctatatt tcttatttgg 147780
tattgtgcct cttttaatct tttgcccatt ttttaactgg gttttaagaa ttgttcaaat 147840
attctcaatg tggccctttg ttaaatatat gttttgcatg ttttctttaa gtggattaca 147900
tttacagttt tcttaaaaaa atgtagagat gagcaaaagt gtataatttt gaagaaagct 147960
tcgtgtcttt gtttactaag aaagttttgc ttaatccagg gttaaaaaga ttttctacta 148020
tttgttttct tatagaaatt ctgtagtttc agctcacatg cttaagtata tgatgcaagg 148080
taagggacaa ggttcatttt cttccccaaa atccatatct ggttgctcca gaacttgact 148140
ctcttttccc tattgagtta cttggcaatt ttgtagaaaa tcagttgttt gtatatgtgt 148200
gggtctactt tcagactctt tttcttaccc aacgatctgt atttcttacc caatgatctg 148260
tatgcctata ttcatattga taacaccctg tcttgattac tgttgcatta cagtaaatct 148320

```
tgaaatttgg taatatgaat tctccaaatc tgttgttctt ttccaaactg ttgttttgga 148380
tattctagtt tccttgcatt tccacttcct tttttttttt ttttttgag atggagtctc 148440
actattgttg cccaggctgg agtgcagtgg catgatcttg gctcatcgca gcctcagcct 148500
ccccagcagt gggattgcag gcacccacca tcatgcttgg ctaatttttg tatttttagt 148560
agagacgggg tttcgccatg ttggccaggc tggtctcaaa ccctgacctc aggtgatcca 148620
cccacctcgg cctcccaaag tgctgggatt acaggcatga gccactgtgc ctggtcttcc 148680
acgtattttt taattagctt gacaatctct accaaaaagt cttttggggc tgggtgtggt 148740
agttcatgcc tgtaattcca ccactttgag aggccaaggc aggcagatcg cttaagccca 148800
ggagtttgag accagcctgg gcaaaatgtc gaaaccctgt cactacacaa aatagaaaaa 148860
attagccagg catggtagct tgtgcctgta gtcccagcta cccaggaggc tgaggaggga 148920
ggtcaaggct gcagtgagcc atgatcatgc cagtgcactc tagcctgggc aacagagtga 148980
gactctgtct caaaaacaca gtctgataga atttttatta ggatagcctt gaatctatag 149040
atccatttga aaataattaa catcttaaat ttccaatttc tggccgggcg ctatggctca 149100
cgcctgtaat tccagcacgt tgggaggccg aggtgggcag atcatcaagt caggagttcg 149160
agaccagcct gaccaacatg gtgaaaccct gtctctacta aaaatacaaa aaaattagcc 149220
aggcgtggtg gcacatgcct gtagtcccag ctactcagga ggctgaggca ggagaatcgc 149280
ttgaatctgg gaggcagagg ttgcagtaag ccgagattgt gccactgtac tccagcctgg 149340
gcaacagagt gaggctccgt ctccaaaaaa aaaaaaaaaa attccagttg ttgagaaaga 149400
ataggaattc cagctttgga ggagtgggga gaccatcaaa tcctctttcc aaaaatacta 149460
ctaaaatact actgagcaga gtatagttcc acaaatagtc ttctgtaaag agactcacag 149520
tacatatttg tctttgtagg ccatatagtc cctgttgcaa tttctcaatt ctacagctat 149580
aacaggaaag cagctatata cagtatgtga atgcttgtgt tctaatacaa atttatttgc 149640
aaaatcagga aaatggcttg aaatggttta agatctagtt ttctgactag atcatggtat 149700
ataatctttt ccatatatat tttgaatttg gtttgctaat attttgctga tcatttttat 149760
atctctcttt atgaaggatg ctgatctaca actttctttt cttgtgatat ctttttctgg 149820
ctttgctacc agggtagtac tagcctctta aaatgagttg agaagtattt tctgttttct 149880
taaagagttt atagagtatt gatcttattt attctttaaa tatttgatac atgttaccag 149940
tgaagccatc tgggtctgtg ttttctttca gggaagattt ttaattattt gcttatttgt 150000
tatatagatc tattcagaat ttatattttt ccttgacata gttttgtaat ttgtgtgttt 150060
ctatgaaatg agccattttg tctgagttgt ctaacttggg cataaagttg tttgtaatcc 150120
tttaagtttt gtaggatcca tagaggtgtc ccctccatta tagattttca taatttgtgc 150180
ctgatcatct tttttcatg gtcagtctag ttaaaaattt atcaattttg ttggtcttta 150240
caaagaacca atttttagtt tcattgaaat ttttagtttc attgattttc tctttttgtt 150300
tcctatgtca ttgattatta tttcttcttt tctgcttgct tttcatttaa tttgttcctc 150360
tttttctagt ttaaggtaga agcttccatt gttagttgaa gaccttattt tcttatatag 150420
atgtttaaag ctatacattt tttgtatatt ttcattcatt tcattttcta atgtccttca 150480
tgattttttt cattgaccca tgtgtattgc ttaattttta tatatttggg gatttttccat 150540
atctcttcct attcatttct aatttaattc cactgaggta ggaggtacat tgaaggactc 150600
taatattgaa tgactccaat aagtcttctg agactttttt aggcacttgc atatggtcta 150660
```

-continued

```
tcctgagtgt tccatgagtg cttgaaaaaa aacttactgt gctcttgtta agtagagttt 150720
tatgaacgtc agttaggtca agttgattga tagactaatt caagttttct gtatctttgc 150780
tgattttctg tctagttgtt ctagatccta caactttgtc tacatccttg ccagagcttg 150840
gtatggtttt tttattatcg ctatcctaga gagtatgtag ttgacccttg tgacttgcca 150900
tgcatttaat gactgcccat gttcatagca gcattattca taatagcaaa aaaaactttt 150960
atcatatgct tttgtgcctc aagatcatat atttttcgtt tttagtcact aatatggtat 151020
aatggtataa tatactgttt aatttctgag taattgacta gcctttcatt ccggggataa 151080
atcctatttg gttatgatat agtatccttt ttacatatag ctgaattcat tgtactaaaa 151140
ttttggtatt tttgcatcta aatccatgag ggatatattc tatagctttg gtgttatgat 151200
aatatggtat tatttctttc ttaaacgttt ggtaaaactc agcagtgaag ctgtcttggt 151260
ttgtttggag cctttttgt agaaaggttt tcaagtacaa gttcatcaaa tgtttactga 151320
taatatgttt attcttgagt gagctttgtt ggtttacatc tttgaaggaa tttaactgtt 151380
tccttcaaat gttgaattta ttggtataaa gttaagttat tcataatatt cccataaatat 151440
ccttctaatg gctccagtat ctctagtgtt attccctttc attcccgaca ttggtattta 151500
atatattctt gcttttttt ttttttttta atcagtctgg ctaaaagttt ttcagtttta 151560
ccaatgtttt catagaacca gcttggtctt gattttgttg ttgtttatgc atgttcttag 151620
ttattcgttt ctactcttta tcctttccat ttttcttgtg tttagggtag aagcatatat 151680
aattaattga gacctttctt ttctaatcaa agcttttaat gctgtaaatt ttctaagcac 151740
tgtcttcatt gcatcccaca cattttgata tgctgtgttt tcagtactag agatttttaa 151800
ttttatgata ccttatttaa tcatgatgcc ttatttaatc tatagcttat taaatgtcaa 151860
attctaaaca tttgggtttt tctccagata tgtttgttac tgacttctat tttaatctca 151920
tttttgtcag acagcattca ttgtatgact taatcctcct aaatgtattc agacttgttt 151980
tatgttctag attaatgttc tgtgtatact tgaaaagaat gcaagttctt gggtagactg 152040
tttcagaaat gtcagtcaaa tttaagtctt gtttattctt attgattctg agacaaaggt 152100
gtttataatg ttagatttgt ctgctatatc tctgacattg ccaaatatcc ccttggaggc 152160
aaaatctccc cctccctttt gagaaccact gatctatgta gcctttttc tgggactaat 152220
ttagccttgc ttctgagatg tggcccctag gtctctactg aatgcccggc atatttaatt 152280
agatctttct ttcctctatg gcctcaaggg atttcaccct aagtatgcac aaatttttat 152340
tcagccgaag actgtacaga tttctggagg cctttctttg tgtacctcct tcgtttccag 152400
tagtctgacc cataaattgt acagatttct ggaggccttt ctttgtgtac ctccttcgtt 152460
tccagtagtc tgacccataa attgtacaga tttctggagg cctttctttg tgtacctcct 152520
tcgtttccag tagtctgacc cataaattaa agctgcttta gcctccccaa acttcaatct 152580
ctttctcctc aacccagcaa gattgctaga ccctgggttc cctttccctt cactgcagta 152640
tgataattac tttcaagcac aaaggtttag aattaagatt tcttactcct gggctaggta 152700
tggcttaccg tatttgtttc tcttttccta gggatcataa tcatgtattg cttgttgtcc 152760
agttttccag taggagggga attccaggct gtacttactt cctgcagcca aaagaggaag 152820
taatgttagt gatttcaata ttaaaacatt aaaaaaaaat ttaagatgga tgaaattctt 152880
ttatatgcat attgaattgg gcttcaccat agttattttt agaattagga ctaaccggca 152940
gggaaaaaaa ctatacggca gggaaaaaaa ctataagcca tcgctgtttt acaattttgc 153000
aataattaga ttttctgtag tatagtaatg tgtaaaatta acccattgtt aatatagaat 153060
```

```
gccgttatca ctcctgatta agcggtcttc attttcatgt taatactgat gtcttgtaat 153120
gctttatgga atcaaacatt ttcatacata ttcattagtc taattctaat cataatccaa 153180
tgaaaaagag caggaaagat gctcaaggag gttatattca agtccacatg gcaagtaaga 153240
aataagacta ctcggctggg catggtgact tactgcctga aatcccagca ctttgggagg 153300
ccaaggtgag cggaattgct tgaacctggg aggcggaagt ggcagtgagc tgagatcatg 153360
ccaatgcact ccagcctagg caacacagca agactctgtc tcgggaaaaa aataataata 153420
ataagacttc tagaagctcc taaatccata gcttttcctc tataccagca tcttctaaaa 153480
atgtcagcag cagtgaagtt tcagtttggg aaataatgca tttcccctct ctggagagtg 153540
cacagttata tctccaagaa gtactgaaat tcagaagtct gcctaatatg tattaaacat 153600
ttagcttttc tcaaactttg accaccaaat cctttgtctc gctctaacta tagttaacac 153660
agaatcagtg ttcccaggag cacactgtga aaaatgtagc actctacaaa agtcctaatc 153720
tccacaggat taagtgaaac catgattaac cctctgttcc ttgtccttat tagtaccatt 153780
ttctgaagag taatgtatcc ccccaaaact tttatactag tttcactaac cagaatccat 153840
gtacataagg aaggacagat atttgctccc tactaagaca tatctattag ctacattaaa 153900
aaaagtattg catgccgatt ttaaagttat aattaactgg tgatatcaca gatattccaa 153960
gatataattg ctggaataaa cactgttgtt gaagccttct atctatctca gtactagaat 154020
taaactcaag tgcagaatgg cagacaaagt taactaaaaa tcactgtatt atttcatttg 154080
gtcctccaaa tagctttgtg agctaaggag gagaaggtgt atcatcacca cttccatttt 154140
atagatgaga aatcaagtga tttactcaag gttaagtcct ccaattcttt gttatcctgc 154200
attttctctt ggctgtagtt taattaataa tcctaagaaa atgcttatat tttagagtgc 154260
agtaagagta cataaacaat gttaaatgcc catcttgcat gtataaaaag ttatagcaag 154320
aaatctggct gggaatggtg gctcacacct gtaatcctgg cactttggga ggccgaggca 154380
ggaggattgc ttgagcccag gagtttaaga ccagcctggg caacataggg agatcctgtc 154440
tctacaaaaa aatttagcca gacacagtgg cttgtgtcct agctactcag gaggctgagg 154500
tgggaggatc acttgagcca aggaggtcaa ggctccagtg agctatgatt atgccactca 154560
gacatggtgg cttgtgccta cagtcctagc tactcaggag gctgaggtgg gaggatcact 154620
tgagccaagg aggtcaaggc tccagtgagc tatgattatg ccactgcact ccagcctgga 154680
tgacacagtg agaccctatc tatctcaaaa aaaaaaaaaa aagaaaagaa aagaaaaaga 154740
aaatccttta actgacttca tcttaacctt ttagttccta aggacggtct gaagagccaa 154800
gagctatttg atgaaattag aatgacctac atcaaagagc taggaaaagc cattgtcaag 154860
agggaaggaa actccagcca gaactggcag cggttttatc aactgacaaa actcttggat 154920
tctatgcatg aagtaagtgt caaacataaa gccaaatata agagttttct gggacaaagt 154980
atgttttgat tagtgaatat aattatatac cagcagcgcc cccacccccg cccccagttt 155040
gtggatgttg gtgatagctt gagttcaact tatgaacttc agttttgtag acatttttcc 155100
taaggccaat tatgaaatat cctttcacct agtcatgtgt atataaaatc accatgttat 155160
tacagaattt agtaatactg tttttaaaaa gtatgattaa tccattaaat tagaataatg 155220
cacccttcat atattatggt actacagtga ttcatgaaat aattctatat aattctacat 155280
acaatcaaag aaatataaaa tgtgttttgt acggaagtgc ttatttttca tctggggaat 155340
tccagtgaga ttggtatatt ctaggccaga taattttttc aaaatagagg acaacaaaca 155400
```

```
tgagatgttc ccactgacca atttggaagc ctgatcatta ccatatcttc tcttgcaggt 155460
ggttgaaaat ctccttaact attgcttcca aacatttttg gataagacca tgagtattga 155520
attccccgag atgttagctg aaatcatcac caatcagata ccaaaatatt caaatggaaa 155580
tatcaaaaaa cttctgtttc atcaaaagtg actgccttaa taagaatggt tgccttaaag 155640
aaagtcgaat taatagcttt tattgtataa actatcagtt tgtcctgtag aggttttgtt 155700
gttttatttt ttattgtttt catctgttgt tttgttttaa atacgcacta catgtggttt 155760
atagagggcc aagacttggc aacagaagca gttgagtcgt catcactttt cagtgatggg 155820
agagtagatg gtgaaattta ttagttaata tatcccagaa attagaaacc ttaatatgtg 155880
gacgtaatct ccacagtcaa agaaggatgg cacctaaacc accagtgccc aaagtctgtg 155940
tgatgaactt tctcttcata cttttttca cagttggctg gatgaaattt tctagacttt 156000
ctgttggtgt atcccccccc tgtatagtta ggatagcatt tttgatttat gcatggaaac 156060
ctgaaaaaaa gtttacaagt gtatatcaga aaagggaagt tgtgcctttt atagctatta 156120
ctgtctggtt ttaacaattt cctttatatt tagtgaacta cgcttgctca tttttcttta 156180
cataattttt tattcaagtt attgtacagc tgtttaagat gggcagctag ttcgtagctt 156240
tcccaaataa actctaaaca ttaatcaatc atctgtgtga aaatgggttg gtgcttctaa 156300
cctgatggca cttagctatc agaagaccac aaaaattgac tcaaatctcc agtattcttg 156360
tcaaaaaaaa aaaaaaaaaa gctcatattt tgtatatatc tgcttcagtg gagaattata 156420
taggttgtgc aaattaacag tcctaactgg tatagagcac ctagtccagt gacctgctgg 156480
gtaaactgtg gatgatggtt gcaaaagact aatttaaaaa ataactacca agaggccctg 156540
tctgtaccta acgccctatt tttgcaatgg ctatatggca agaaagctgg taaactattt 156600
gtctttcagg accttttgaa gtagtttgta taacttctta aaagttgtga ttccagataa 156660
ccagctgtaa cacagctgag agacttttaa tcagacaaag taattcctct cactaaactt 156720
tacccaaaaa ctaaatctct aatatggcaa aaatggctag acacccattt tcacattccc 156780
atctgtcacc aattggttaa tctttcctga tggtacagga aagctcagct actgattttt 156840
gtgatttaga actgtatgtc agacatccat gtttgtaaaa ctacacatcc ctaatgtgtg 156900
ccatagagtt taacacaagt cctgtgaatt tcttcactgt tgaaaattat tttaaacaaa 156960
atagaagctg tagtagccct ttctgtgtgc accttaccaa ctttctgtaa actcaaaact 157020
taacatattt actaagccac aagaaatttg atttctattc aaggtggcca aattatttgt 157080
gtaatagaaa actgaaaatc taatattaaa aatatggaac ttctaatata tttttatatt 157140
tagttatagt ttcagatata tatcatattg gtattcacta atctgggaag ggaagggcta 157200
ctgcagcttt acatgcaatt tattaaaatg attgtaaaat agcttgtata gtgtaaaata 157260
agaatgattt ttagatgaga ttgttttatc atgacatgtt atatattttt tgtaggggtc 157320
aaagaaatgc tgatggataa cctatatgat ttatagtttg tacatgcatt catacaggca 157380
gcgatggtct cagaaaccaa acagtttgct ctaggggaag agggagatgg agactggtcc 157440
tgtgtgcagt gaaggttgct gaggctctga cccagtgaga ttacagagga agttatcctc 157500
tgcctcccat tctgaccacc cttctcattc caacagtgag tctgtcagcg caggtttagt 157560
ttactcaatc tccccttgca ctaaagtatg taaagtatgt aaacaggaga caggaaggtg 157620
gtgcttacat ccttaaaggc accatctaat agcgggttac tttcacatac agccctcccc 157680
cagcagttga atgacaacag aagcttcaga agtttggcaa tagtttgcat agaggtacca 157740
gcaatatgta aatagtgcag aatctcatag gttgccaata atacactaat tcctttctat 157800
```

cctacaacaa gagtttattt ccaaataaaa tgaggacatg tttttgtttt ctttgaatgc 157860
tttttgaatg ttatttgtta ttttcagtat tttggagaaa ttatttaata aaaaaacaat 157920
catttgcttt ttgaatgctc tctaaaaggg aatgtaatat tttaagatgg tgtgtaaccc 157980
ggctggataa atttttggtg cctaagaaaa ctgcttgaat attcttatca atgacagtgt 158040
taagtttcaa aaagagcttc taaaacgtag attatcattc ctttatagaa tgttatgtgg 158100
ttaaaaccag aaagcacatc tcacacatta atctgatttt catcccaaca atcttggcgc 158160
tcaaaaaata gaactcaatg agaaaaagaa gattatgtgc acttcgttgt caataataag 158220
tcaactgatg ctcatcgaca actataggag gcttttcatt aaatgggaaa agaagctgtg 158280
ccctttttagg atacgtgggg gaaaagaaag tcatcttaat tatgtttaat tgtggattta 158340
agtgctatat ggtggtgctg tttgaaagca gatttatttc ctatgtatgt gttatctggc 158400
catcccaacc caaactgttg aagtttgtag taacttcagt gagagttggt tactcacaac 158460
aaatcctgaa aagtattttt agtgtttgta ggtattctgt gggatactat acaagcagaa 158520
ctgaggcact taggacataa cacttttggg gtatatatat ccaaatgcct aaaactatgg 158580
gaggaaacct tggccacccc aaaaggaaaa ctaacatgat ttgtgtctat gaagtgctgg 158640
ataattagca tgggatgagc tctgggcatg ccatgaagga aagccacgct cccttcagaa 158700
ttcagaggca gggagcaatt ccagtttcac ctaagtctca taattttagt tcccttttaa 158760
aaaccctgaa aactacatca ccatggaatg aaaaatattg ttatacaata cattgatctg 158820
tcaaacttcc agaaccatgg tagccttcag tgagatttcc atcttggctg gtcactccct 158880
gactgtagct gtaggtgaat gtgtttttgt gtgtgtgtgt ctggttttag tgtcagaagg 158940
gaaataaaag tgtaaggagg acactttaaa ccctttgggt ggagtttcgt aatttcccag 159000
actattttca agcaacctgg tccacccagg attagtgacc aggttttcag gaaaggattt 159060
gcttctctct agaaaatgtc tgaaaggatt ttattttctg atgaaaggct gtatgaaaat 159120
accctcctca aataacttgc ttaactacat atagattcaa gtgtgtcaat attctatttt 159180
gtatattaaa tgctatataa tggggacaaa tctatattat actgtgtatg gcattattaa 159240
gaagcttttt cattattttt tatcacagta attttaaaat gtgtaaaaat taaaaccagt 159300
gactcctgtt taaaaataaa agttgtagtt ttttattcat gctgaataat aatctgtagt 159360
taaaaaaaaa gtgtcttttt acctacgcag tgaaatgtca gactgtaaaa ccttgtgtgg 159420
aaatgtttaa cttttatttt ttcatttaaa tttgctgttc tggtattacc aaaccacaca 159480
tttgtaccga attggcagta aaatgttagcc atttacagca atgccaaata tggagaaaca 159540
tcataataaa aaaatctgct ttttcattat gtgactccaa catgcttttg tagaacttgt 159600
acagttccga ttgtccaatc tgatttttgt ttactgaaag tagagttacc cctgcttcag 159660
gaaccttaag ataatatggt gggcatttaa atgtcagtgt ggcaatgttc gcctgctaat 159720
atggcataga ttcaaaataa gcttaaccct ggtgccaaag acctgaagat tatcccatcc 159780
atgcctcaaa tggttgtgtg ccaattactg caaagggtac taagggaagg agaaattcac 159840
tcctgaggct gcttcaaatg tatgtcttta tcacaaaaga tgacatttta tgtaagctaa 159900
tgttatctag tcaaaattct tagcttattt taaaatcaac tcttcaagaa aaggaataaa 159960
catttaatat aaatatcata gcagtattgc acatagaata gaaaggtcgg gcagggtagt 160020
ggaagtcagc tattctatac aatccattcg gtattttcca aaacatttga tgttcaggcc 160080
atatccagga actggatgac ctaacaaact tctctgagta cctttttttc cacaagagat 160140

```
ctccatcact aagaaaaaaa gcattgtgat ttaaaagcca aatttgcctt atccatcatc 160200
atgtgcacca agtatttgct acctgcctac tatataatat tgaagataca atgtgaataa 160260
gaaaaatact attgctaccc tcaatcagag tatgtgattg gaaaagtgta taacaaacct 160320
ttcccagtgt cttcaggtat aatgcagaga taccagatac ggcatcaatg tgtatacaca 160380
ttatggctgt accattcact ttaagtagta accttacatt tctgtagaac accttcacat 160440
acatttttaa caagcctcac tgaatgaatt aatgacatga aaataatgag gcagattatt 160500
ctcgtttcca ttttataagg aagtaaactc tgtaagaaag taaacaggct cagaatttaa 160560
gcactgattc atagccccta gctcccatgt tattgaaatt tgaatggaaa gcctctaatg 160620
aggccattca tctatcagat gtcaaagagc atgtctctgg cctatgagcc tctcagggaa 160680
ctggttatgt ttttctgttt taaattaaac taatgcttta ctgagcactt actatgtgcc 160740
acgcacaatg ataattcaat atattatttc atttaatcat agtacccctc taaagtacta 160800
ctgtaaagca gtgctattat cctcattgca tttatatcag gaaactgtgg cttaaagaat 160860
tgagtaactt gcctacagtc acaaagctag ctccagaatc catagtttta aaaaccacta 160920
ttgagaaatt actaatatga gctaactagg gcgaatgaac ccatattgat cattatgtgt 160980
ctggcctttt gacatgtcct catttaatct aatccctttt gctaccgtat caattttgac 161040
ttagaaattt aacaatgata cattagtccc cgcttatcta cggaggatat gttccaagac 161100
tcccaatgga tgcctgaaac atagatagta ctgaactgca tgttttttcc tatattacat 161160
acctatgata aagttaattt acaaattaga tgcagcaaga gattaacaat aactcaatta 161220
caacaatata ctgtaataaa agttatgtga atgtgagctc tcaaaaaatc gtactatact 161280
gagggtaact gagaccacgg aaagtgaaac cgcagataag gcgggcacta ttgtatttcc 161340
ttctcttaaa aacgtgtcct gtaccctggg gtggttgatg gtggaaaata ctagttgccc 161400
acagattaca gaatgccctt tggtttgtct aatatacaac agggagcctg tctcactaat 161460
gcccacagaa aaatcaaaca tttcttcaag tgatatggag catatagggt acagtcaaac 161520
caaggaagaa agttgtttat aaatgagaac tatagtgcaa gttaaaattt gctcctagtt 161580
ttgcaggtaa agagccagac tttgggtgta gaaaaaaagt tgaaaatact gaggctttta 161640
cataaggtga tttttttttt tttttttttt ttttagaatt tcaactaatc tcttttaact 161700
taagtcgttc ttaacagtat tggtaacttc atagcacttt ctttctggtg aaataacccc 161760
atcctccctc ttatttaggc ttcctgtttc ctagttaaaa tggggcagta ctttgttagg 161820
gaagtatttt tacttcactt ggttacaaac atgtaagtct cagaacaaaa gagtttgtgc 161880
agaccatatc agacactcaa aagactttct tcactctacc cacttgagta agagacaatt 161940
tatattctgt tcaccttatg taccctcacc aaaaatattc aatagggtaa taatgtgtat 162000
a                                                                 162001
```

```
<210> SEQ ID NO 2
<211> LENGTH: 157001
<212> TYPE: DNA
<213> ORGANISM: Macaca mulatta
<220> FEATURE:
<221> NAME/KEY: misc_feature
<222> LOCATION: (18521)..(20122)
<223> OTHER INFORMATION: n is a, c, g, or t
<220> FEATURE:
<221> NAME/KEY: misc_feature
<222> LOCATION: (28894)..(28913)
<223> OTHER INFORMATION: n is a, c, g, or t
<220> FEATURE:
<221> NAME/KEY: misc_feature
```

<222> LOCATION: (30263)..(30282)
<223> OTHER INFORMATION: n is a, c, g, or t
<220> FEATURE:
<221> NAME/KEY: misc_feature
<222> LOCATION: (39920)..(39939)
<223> OTHER INFORMATION: n is a, c, g, or t
<220> FEATURE:
<221> NAME/KEY: misc_feature
<222> LOCATION: (73181)..(73341)
<223> OTHER INFORMATION: n is a, c, g, or t
<220> FEATURE:
<221> NAME/KEY: misc_feature
<222> LOCATION: (85318)..(85587)
<223> OTHER INFORMATION: n is a, c, g, or t
<220> FEATURE:
<221> NAME/KEY: misc_feature
<222> LOCATION: (132898)..(132958)
<223> OTHER INFORMATION: n is a, c, g, or t
<220> FEATURE:
<221> NAME/KEY: misc_feature
<222> LOCATION: (137376)..(137450)
<223> OTHER INFORMATION: n is a, c, g, or t

<400> SEQUENCE: 2
gagagaatgt aaaatggtca aataataaat aattaagttg aattagatgg taaagaaata 60
aatgcaaggc catagtcact gggcagacag agtgaaagaa catgatgaat cagatgagat 120
taatcacccc tcctggaact atcacaaaaa gatactcact gacagtgagg cagtcgtgtt 180
agtccccaag atgatgacta atagaaacta aggtcacggt gcacattaat ttcttctgaa 240
gcaaaggata aaaacaaaca aaatataaaa gattaagatg taaacctaag tacagcatac 300
actaattcag agaagaatta aatgatttta aaacttcaag aaggatgata gcattctaaa 360
tgcattgttc taaaataata gtaagatggg ataaacagtt gcactaaggt gatgattttg 420
gatgtgttaa gtttatcacg ttgagaccag atatactcca cttcccttca tgccagcttt 480
taagaacata tatcatagaa aaagagaaaa gaaacagttg aatctaagtg aagagaaata 540
ttgtgaagca ataaatccag ggaaaaatta ataaaaccct acttccaccc taaaagaaag 600
aaattaaaag aaatgcaaat ataaagttca ataggagtca ctagagattg taatttgggc 660
tctgagcttc ctaccaacaa aagcacaaag gaaaataaga tcactgctat attaaaaaca 720
aaaacaaaaa acctatagtt tccaaaagat taagattaaa acaaaccagc agttttgtag 780
cagctaacac taaaatctaa aggaactacc ttctatggag ccacttaata tgcataaaga 840
ccttgacaat attctttcaa caactacagt aacacgtttc ttagagttca tttcttttta 900
catccttaat gaattgtaaa tctttaagta aaacatcacc acttaattct ggtaactttt 960
ccatattaac tttttagaac aattgcaaat gtaccataat gattgttgcc acagtggtaa 1020
ctatttgaca tgactgttat tttgtatata gcaactttta aaataaaaag gcaacaagtt 1080
tctaggcgta atttccacag atattttatg taaaacaatg acatcctttg caacttctgc 1140
cgcttaatct gtctcaagta agctctctgg aaacaaatct atttgaaaga ttctattgta 1200
attagaaatc agggtaactg aatgcactag atgaaaacct tctgactgga gccaatgaag 1260
tcaatgaagt caaaactgct atgaatgctc aactgtctgc agatcagatg tcttgggatg 1320
gaatccgttc ttgaggccac catcatcaat atcaatttgg ccatgtaatg caactctcac 1380
ttgttccact gttacaaatg tgcttaaaac tgagctcatt tacaatccaa atacatgtgt 1440
aggatggtaa ccaaggcatc acacgaattt aggtattatg ttttagggga aacaaaaggt 1500
atgttaatat tttattcatt tccaaattaa ctataaattg tgcattcttg tatagatcct 1560
cgttgggaat gagaaattag gaaaatccag ttcttaaaat gaatgtctaa aatcaaaata 1620

```
aaatttgttt ttctggcacc tgcttgatga cacagactta taaccaatga caaaattgcc   1680

cttgaaccca agttttcatt tcctcctctt gtgtggtcag gttatgtaag ggtttgcttt   1740

caccccattc aaaagatacc tcttcctctt cttttgctcc ctcttgccct cattcttgtg   1800

cctgtgcaga catttgagta gaggcgaatc actttcactt ctgctgggga aattgcaaca   1860

cgcttcttta aatggcagag agaaggagaa aacttagatc ttctgatacc aaatcactga   1920

accttggaag gtcagaaatc tttcaagccc tgcaggaccg taaaatgccc atgtccaaca   1980

gaagcactgg ggcatgagtg gggaaggaat agaaacagag tcagaaaggg gataagagaa   2040

gaataaaagg gaaagtggtg aaggcaggga ggcaaattgc ttagtgtgaa tatgcacgcg   2100

ttcatttagt tttcaaatcc ttgttgagca tgataaagtt cccagcatca atcctcacgt   2160

gttggtttcc gttaggatct gcctggggga atatctgctg aatcagtggc tctgagctga   2220

accaggaaat tcaccatgat taggagagta gctgtgttag tcagggtctc tccaaaaaaa   2280

agttataccc aagagacagg atcttctcat ccaaaatttt cttcacttct gaaattctct   2340

ggtttgtgct catcattggc agctatttgt tcatcaagag ttgtgtagtt ggcttcttct   2400

ggaaaaagga atctgcgtca tatctaagtc agatttcatt ctggtgctct cagagcagtt   2460

agcccaggaa gggggccggc ttctgtggct actggtgcag aggcagatgc agtttgtgtc   2520

ccacagatat taacttcaat aagcacttaa tgagggcctt ccctgtgcga gaatggggag   2580

gaacaaaatg cagctcctgc cctcctgggg ctttagttgt accttagtaa gaggaatttt   2640

catctgcctg gctcctttcc tcaaagaaca aagaagactt tgcttcatta aagtgtctga   2700

gaaggaaggt aggttatatt tttattccca ttctatagct gggtaaagtg agttctaaca   2760

aagttacttg ataaaggtta ctcagaggtc ggagcaccag agaaaaagac aatcacaaga   2820

ctgatgttgt gtgctggaaa gtttaaactg aacaggaaga aaacattttt gtgggcttta   2880

tctaaaaaga aataggttgt tctgagtttc tcagtttcat ttattcagca agtatgtgcc   2940

aagtgctgtt gtaggccatg aagatacagc agggaacaaa acaaaactga catggagctt   3000

ccgtctagag aggagagcga gacaacgcgt tttaaaatat atataatgtg ttaggtaaaa   3060

agtgctataa ggagagctaa aacacaatga ggggctagag tgatagtggt ggggggtggt   3120

gcttctctag gaggtgacat ttgaccaggg gtctgaataa actaaagagg ccagtgatgt   3180

gaatatctgg aagactcaag gggggggggg aaatagccag tagaaaggcc ctgaggtaag   3240

aaggtgcgtg gcaagtttga ggaacaggaa agacagtccg acgggagcaa agagaaccgg   3300

agctgaggcc atcagggcag ccaggggcca ggtgcagact gggctttgac tctacgtgca   3360

gagaggagct gctgaggatt ccaagcaaag gactgccctg acctgcctta ggttttaaca   3420

ggatccctct gattggtgta tgaagaatta actgtagaca ggcaagtgtg gaagaaggga   3480

gagcagtcag gaagctgcca caacatgaga gaggtgaggc ctcggagtgg agcagtggag   3540

atggtgaaaa gtgtttattt tgaatgtgaa gcttgcagga tttgctggag gattggatat   3600

gggggatgag aaaaagagag aggcttacag atcaggtaat ttagctgatc cttaagcccc   3660

ttacagctta atattattcc aaggtgctaa taacagccaa ggttaacaac cccgtcttgg   3720

accctctgcc tttatttgcc tgcacaagcg caggttccat cagctgctag cggagacact   3780

tgggcaaatg agtggttatc tctagtcctc agtatccctg ctgttaatga gggatgatca   3840

tttcttctct gcctagctca aaagaatatg ttaaataaaa ctctgtgaac tttaggcagc   3900

acaggctgag ggcttcttag taacatcatc agcaccatca gagttaactt tatgagtcag   3960

ctgagttgcc tttgggtata tcattaacag attccaggaa gctcccctgc ccaaaagcct   4020
```

```
cccaccaatg gtctgccttg ttgaaagaat ttcacaatta gcccaattcc tttccattaa   4080
ggcactgtgg actccaaaca tcctccttta aaatggaaac taaatcgagc tactgtcagt   4140
catttgtcct tttaggtgac gttatatatc agatcacttt tctgccatta gagatagttg   4200
aagtttgaat aggaaaaagg aaagaatgaa catggggcag agaatgcaat agtcggtggg   4260
ttactcagta ggctgtggac agatggagag gatcctggcg ggaggaacct ctaaagataa   4320
actttctatg ggaaaatgtt gacagattta cctgagtcat ggtttttctt acacctcata   4380
aaagcgaagt cttccaaggg cagctccttg aaatagttat aacaagtagc cacagaagtt   4440
gagttgctta aagaaaaaca ttgaattcat ggggaaccgt acgctttaat agcccctttg   4500
gcttactttg tttaaacaaa ctcatcccga gcatctcaca cttcaccaat tgtgagtgtc   4560
cctgctttac ttcagccttt taaagagtgc ctttccccta aatatttctg gaaatgccta   4620
agggtgctga cgtgcagcca gaaataattc agttgtgtcc ccactatggc aagaatccat   4680
ggacccaggc tctgatgttt ctgtaaagat gcccctcagg actagaaatc tgtccccatc   4740
cctgttgcca ccacagtcat caccacctgg aaatcctgca ggaccgacgt ttgtgaattt   4800
ggaatatctg ctagatgcct tactaccttg ttatgacctt atttctttat aacacttttt   4860
acctagtgcc ttacatattt taaatgtata atttggtgat tcagatcact ggtccagtgt   4920
cacctcccgc tcagcaaagt gagatgaaca cacttggtgc tacgttcagc taggctggca   4980
ctgcagatgc acccagtacc agctattcta gtggctcagg acagggcttc cttgctggag   5040
atatgctgag ccaagcaagg cagttttggt ccccaatcct gatagttgta cacatattct   5100
gctcctccac ccccaccaag gttgaaactc tgctcctgtc agctttgcag ctaccaacac   5160
cccctcaggg agagtcatct ctgttcccaa acccatataa atgtcattca aagccagagg   5220
atgtaattgc tgtagtaatt gttatagtct gctcatccag gggccccact gcaaagctgt   5280
ttaaacccca aagtgttact accttttaca gagttattat tcttccaaat cacacccaca   5340
gcacctttct ccaaggctgc aaaagtgccg ctagggtggc tgggtacagg caagttttga   5400
tttcagttgg gaaactacct gtaaccccca ctctctgcta acaccaactt ttcttttatt   5460
aattaaaata aattaattat tttattttat tttattttac tttaagttct gggatacatg   5520
tgcagaatgt gtcagtttgt tacataggtt tgcatgcgcg atggtggttt gctgcaccta   5580
tcaacccatc acctacgttt tattttgttt tgttttttag ttatacttta tgttctagcg   5640
tacatgtgca caacgtgcag gtttgttaca tatgtataat gtgccatatt ggtgtgctgc   5700
acccattaac ttgtcattta cattaggtat atctcctaat tatatccctc ccctctcccc   5760
accccacgac aggccctggt gtgtgatgtt ccccttcctg tatccaagtg ttctcattgt   5820
tcagttctca cctatgagtg agaacatgag gcatcatcta ggttttaagc cctgcatgca   5880
ttaggtattt gtcctgatgc tctccctccc cttgcccccc aacccctgac aggcctaggt   5940
gtgtgatgtt cccctccctg tgtcaacgtg ttctcattgt tcaactccca cttatgagtg   6000
agaacatgca taacaccaac ttttcttatt ggaattgtag tgccagttta gttcttcaga   6060
ggaggcactt gttcttctct ataatctgtt ctccatttgc aaacacccta ctttctcaga   6120
cataggtttg cagtgcattg gtgggcagga tttcagtctt ttctctgaaa gttcctaatc   6180
cctgttgaaa aatgaatgca ctggggaagg gtgtggctca tctctgctcc ccagaagctc   6240
ctgagccaca tttcttaccc agtcctggaa ccctggtgtc ctaaaccatg tctgaacctg   6300
taccctcttg gccccagaaa gggaccaaac agtacatccc atgaaaccat aaagagatca   6360
```

```
taaccttctc ctctctcctc cagcatctct acataaacaa catttatata gatgactgaa   6420
ttcaagatat gtttatttgg tactggttaa ctggaagttg ctaagtagaa ttacttataa   6480
agtggggatg tgtttttagt gattgcagag aaggctcaac acccctaaac atggtgggaa   6540
ctttctgggg aggcaggctg tgaaggacag ggtgttagca tctttcctta aaataacatg   6600
tgtcttagtg tgttcatgct gctacagtaa aaataccata gatttggtga cttaaacaac   6660
aaccatttat ttctcacagt tctggaggct gggaagtcca agatcaagac actgatagat   6720
tcagtgtctg gtaaagacct gcatcctagt tcatagccag ttgtcttctc actgtgtcct   6780
cacaaggctg aaggggtgag agagctcttc cgtgactctt ttataagggc actaatcccc   6840
ttcgtggggc tccaccttca tgacctaatt acttacaaag gccctacctc ctaacatgat   6900
catattgggg gttaggattt cagcatatga attttgggga gacacaaaca ttcagtctat   6960
ataacaacac gtactgtgaa actttcctac tcataaaagt aatatatctt cactggagaa   7020
agtaaaaaag tacagaaaaa tatgtagaag aaaatctacc atcatctcac atccagagat   7080
atccatggta aatattttaa tacatttcct gtgaagttat tcagtaaact aacagagttt   7140
agaaaacata atctaatata aaagcatgaa attcctaaag atatatttaa aataaagtta   7200
atatgtatgt gtgtatatgt gtttatatat atacaaatat atatgcttat tattttattg   7260
tgagcattac cccatattat tagaaaacca tgattttttt ttcctttttt ttttttttt   7320
ttgagatgga gtctcactct ctcacccagg ttggagtgca gtggtgcaac cttggcttac   7380
tgcaacctct gcctcccagg ctcaagcaat tcacctgcct cagcctcctg agtaactggg   7440
attacaggta cccacctgta attttttttg tatttttagt agagaagggg tttcaccatg   7500
ttggccaagc tggtctcaaa ctcctggcct caggtgatct tcccaccttg gcctcccaaa   7560
atgctgggat tacaggcacc actgcaccag acaaaaaccc atgatttttg atggcaacat   7620
ttcatcttat ggatgcaata taattaattt aaacgttcta ctactagtta atattaaggt   7680
cgtttccaat ttttattact gttacattgc ctctcatttt tttataaata tttggctctt   7740
tttattttgg atatatgtag ctaaaatgcc atccagatag tttattctga tttagtgccc   7800
actgggttct aggtgcacga ctgccatagc agagagaatt gcatacagtt caagtttaca   7860
ttttgttttg agcgggagaa actgaagacc aagttcctaa tattctttgg cctgaaaaat   7920
ggctacataa ccttgccaaa tctcttaaca ttttcatgcc ttagtttcta atatggaaaa   7980
tgaggatcct caccaatttg taattgtaaa ttattacaca agaatgaggt attcatttaa   8040
ccatatgatg agattgtgta gctaaagtta attaattggt gctcagtggt cagactactg   8100
gctttaaatc ctggatccat tattcattac ttcctattgt gtaacctggg caagttactt   8160
aacatctctt ctccttagtt tcctcatcta aaaaatgaat aacaaaagca cttaccgtaa   8220
gtgaggatga gataagatgg tgctatatgt gagtagtaca catctgttac tattattatc   8280
attgttactt attattaagc agtgaattta gattcaatgt gaaatggttt agaagtcatc   8340
agcttcccat tgtgtgtcct taaagcactg gtgatatgag tatgtctcta tcacgcagtt   8400
ataactttaa tcaaaatatg aaagtaattt taatcaaaat gccaagtcaa attagtaaag   8460
tcagcctctt caaaacgtgt gccccaaagt aataaggtct gcagggtatg cctcagggac   8520
atttggtggg gagtgggtgg tagtcagaat ggtgaaaaca gtgggaactt ttagggtccc   8580
cactcacatt gctttgcttt tatggcaaat attgttagct gatgaacaaa atcatttcct   8640
tttcttggac tcacagctag acctaacttc ccaagtcctg tacagttaaa tgttaccata   8700
caattacaat ggggccatat ggtgtctttc ccaaccaccc aagcctgcca ttgcagtgtg   8760
```

```
aaagcagcca taggcaatac ttaaacaaag ggattcgttg tgttccaata aaatgttacc   8820
aaactttcct agtttgccaa cccctgaact agagcatggt gaggcaagag agaattgcag   8880
aacgtggctg gaaaggcaga aggagtcagg gaggaaagac cttgtggaac tctagcacag   8940
agtttggatt ttatcctaaa agcagaaagg aagcctttga caggttttag aaaagggtat   9000
gacctgaaat atagaagctc agtcttcagc agatcagtat ttcagctttc actcaccata   9060
tgaaccattg atcccatttt gttacttctt ccatagaatc tcctcttaag gaaatttaaa   9120
gcaagcttct gactgagatg gcattttcag ggaaagacca ggaggcagac cccaaggggc   9180
ttcacaagat ggcatttttg tggccttggt ggatttgcca tgaccgtggc ttggcaggat   9240
cagaaacctg aatctgtcag cccaccttcc gtcttttccg tctttacact ttatagtgta   9300
tacagtgtaa agacgtctta cactttatag aattacacta agtaattctt tataggaaat   9360
tacactaagt gtaggtgatt aacgtattaa gaattacact aagaattaca ctaagtttag   9420
gtgattaatg tattaagtca aaatgcccaa tttagtaatt tttaatgaaa aacataattg   9480
ccacatgtga gaagcccatt ctattttcat agacatacta atattagaat aacaatgacc   9540
ataatggtta gcatttatta acaataacat cgtgccaggc acggtgtcaa gcattttcca   9600
tgatgacctc acaagtctat cggtaggaat tgtggttaaa accctcttat agataaagtc   9660
agaggtttta aacttgtaag atcacaatgc tagtgaatgg tagagatgag agttgaaccc   9720
acataatgta aactagagtg tggataccta accactaaga cagtgtctca tagaagacgt   9780
gttcagaggt tgccagtgaa cattgaatcc atgggggaaa ggaaggcagg caaatctgct   9840
tttaatgtta tcaggttaat gtggcctgat gcagccatct tgcagaagaa cggtattgct   9900
agcaggtcct ccatgtttgc ttataacact ggctatggcc ttcccactag gataggaatt   9960
cccaaatcct ataatttcct agatggtgct ggaaaaggca ttgctgaggt ttgttttgcc  10020
aactagcttt cccctcttct tcttgcctta tttgtcattc tgtccgttaa gatgactttt  10080
catccatttt acatgaattt cataattaac ctctgagggt aattccccca gtccacccta  10140
ctatcagggc agtccccaat atgactaatc attcccaaat actaagacca cagactgctt  10200
cagaatcttt atttatatct ttactattaa aaaacgatgc tatcatttcc tgaaatctca  10260
aaaaaaaaaa aatactaagc tatatctgga gtgaaatggt cggtaagaac acagtttgtc  10320
acacaaaata atgaaaatgc taacttctta cttatagtgc agaccagggt ccttcctcta  10380
gaattagaaa tattaggctt tccttagatg tgatggggag ttcattgggg ctagtatttc  10440
agcttttgaa ctcttcaaaa ggaacagaaa tgaaaaaaaa agacctgctt taataacaag  10500
attaagtcta tatgatttat ggacttatga tatgagcgaa tctgacatcc actcacatgg  10560
gtggtcctcc caagggataa acttcgtaaa aacacattta aggaaaaggg agcagatact  10620
gttggtggac tcttcaccag gaaacacact gaaggttgca gtagcacatc agagcctcac  10680
aggtcggcat cagtcaaaca gctgttccat gcaccaaaag aattcgtaca tatttcaaaa  10740
tgactaattt gtacctatga gacaggattt gacccactaa ttattgtacc gtaacgtttt  10800
aataaaaatt gttttttcaa agtgatgctt tgatgagcag atgaattatc atgtgggcgt  10860
ttaaaaatta gtcaaaggag tcttgacaac taagtccttt aaacgtggcc ttcccttggc  10920
ctctgcctac tcctgatcat aatctgaata aactttaact tttcgactag aatgtaaaac  10980
atgtgttttt ataaaacaaa tattaatggc ataactcttg tgctttatta ttttagctga  11040
tttgtatcaa tgtatcaaca ttctaaagaa aataggaagc atatgttggt taataatttt  11100
```

```
tattactatt gacatgtaat tcacatgaca taaacttaac catttttaaa agtacaaatc  11160
aatgagtttg agtatgttct taattttgta caaccatccc cgctatcaaa tttcaaagca  11220
tatccatgac accaacaata aactctggtt ctattagtag tcactcgcaa ttcccttctc  11280
cctagccccc tggcgaccac taattaatta cccttctgtc tctatggatt tgcctaccgt  11340
gaacattcca tataaatgga atcacacaat aggcagtctt ttctgtctgg caccttccac  11400
ttaacataat gtattaaaag tttctccatg ttgtagcatg cctcaatcca cacttcgttt  11460
cttgttatgg ctgaataaca ttttgtccta tgaatctacc acatttgttt atccactcat  11520
gagctgatca tttaggctgt tgccatttat tagctattat gaataatgtt gttatgaatg  11580
ttcatgtaaa agctttagga tagacatgtt atttctccta ggtaaagtcc taggagttga  11640
attgctgggt catatagtaa ttctatgttt acctttttga gaaaactgcc aatatgtttt  11700
ccacagtgtc tgaaccattt tataatctcg ctggcaatgt atgagagttc cactttgtcc  11760
acatcttcac caacatttat tttccttttt taaaaaaata attattgctg tcctagtggg  11820
tattaagtga tatctcctgt attttcaatt tgcatttcta taatgaataa tgccattgtg  11880
catcttttat gtgcttattg gctacttgta catcttcttt agagaactat caggtaatgt  11940
agcttttttt gaaatattgg ttgtcttttt attgttgaaa tataaaagtt ctttatagat  12000
tctagatcta gacctttatt ggatatatga cttgcaaatt tctgtgtgtt gtctaccatt  12060
tctaccattc tgtgtgttgt ctttttattt tctttataat gtcttttgaa gcagaataat  12120
ttttcatttt gatgaagtcc agtttgacta tttttcttg tgcttttggt atcataacta  12180
acaaaccatt gactaatccg agattctgat gtatgtacat gctaagtttt acaattttag  12240
cttttacatt taagttttta atccattttg agttaatttt tttaaacatt cttttgcatg  12300
tagttatcca gttgtcccag cgccatttgt tgaaaaggtg attctctcct cgttgaatag  12360
tcttggtatt cttgtaaaaa atcagttgac tataggcata tgggtttctg gactctcaat  12420
tctaccccac tgattgaaat gcctatcctt atgccggtac tacactgtct tgattactgt  12480
agctttgtag tatgtaagta gtagtagatt ttgtgagtcc tcgaactttg ccttttttaa  12540
tagattgttt tgctattttg agtgaagtat tttttttaaa tatcaagtta aaaatgaagc  12600
tgccattctc taaaggaggg cgatttcaga aaggcaccga gatctgtgct tggtatgtag  12660
taggtgcttt tgaaaatgtt tgttgcatgg aatgaattga tttcatctct attctaaccc  12720
tcaatgccat gttaatttcc cctttggagt ctttcatctc tcccttctct tttctaagaa  12780
aatcagtaac tctgtcattc atatattgta cacacatgta tctttatttg tttatgtgtc  12840
tgttttccac taattagact ataatgccat ataagactag aattacatct aattcattgc  12900
tgggtcccaa agccatgtct taagaccata aatgcatagg gttttttttct tttcaaaaat  12960
ttttattttt aattattatg gatacataag agttatagat acttacaggg tacatgtgat  13020
attttgatat aagcatacat catataatga tcaaatcagg gtaactggga tatccaccac  13080
ctcaaacatt tgtcatgtat ttgtgttaga aacattgcaa ttccactctt agttattttg  13140
aaatatacga taaattattg ttaactatag tcaccttgtt gtgctactga acactagatc  13200
ttattcctca tatctaactg catttttgta tccattaaac atcccctctt tatctcccct  13260
ccccactacc cttcccagac cctggtaacc atcattctat tatttctctc tctgaatttc  13320
cacatatgag caagaaatgt ggtatttgtc tttctgtgcc tggcttattt ctcttgacat  13380
aatgtcctcc agttccatcc atattgatga aagaggcaga ctttcattct tttttatggc  13440
tgaataacat ttcattgtgt atatgcacaa catttttcttt attcatctgt tggtagacac  13500
```

```
ttaggttgat tccatatctt ggctattatg aatagtgctg cagtaaacat gggagtgcag  13560
atatctcttt gatatactga ttttctttct tttggatata tatccagcag tgggattgct  13620
agataatacg gtagctctat tttgttgttg ttgttgttgt tgtttgggtt tttttttttt  13680
ttttttttaaa gaagcttcat actgttctcc atagtagctg cactaattta cattcccacc  13740
aacagtgtat gagggttccc ctttctccac atttttgaga gcatccataa ttccctgtct  13800
ttttgataaa agcgattttc accaggatga gatggtatct cactgtggtt tagacctata  13860
cttctctgat gattaaggat gttgagtatt tttggccatt tgtatgtcat ttattcagat  13920
cttttgacaa tttttaaatc aaattatttt ttcctattga gttgtttaag ccccttatat  13980
attctgttta ttaatccctt atcagatagg tagcttccag atattttatt ccattctgtg  14040
agttgtgtct tcactttatt gatgacttcc tttgctgtgc agaagccttt tagcttgagg  14100
tgatctcatt tgtccatttt tgcatggttg actgtgcttt tgatgtctta ctcaaaaaat  14160
ctggctgtga ctgcgttcca tactctgcaa tgacatgtaa cttccagcaa gtccatatta  14220
tacctaaagc ctacttcagc gtgtccataa aagcaagtaa gaataaaaag taagagcaac  14280
aactcatatt tatttatttg ctgcttatta tgtgccaggc tgtatccttt tttttttttt  14340
tttttagata gagtctcact ctgtcaccca ggctggagtg cagtggtgca aggttggctc  14400
actgcaactt cccctcctgg ggtcaagtga ttatcctgcc tcagcctccc tggctgaaat  14460
tacaggcacg tgccaccacc cctggctaat ttttttgtat ttttagtaga gatggggttt  14520
tgctatgttg gccaggctgg tctccaactc cagacctcaa gtgatccacc cacctcagcc  14580
tcccaaagtg ctgggattgc aggtgtgagc caccatgccc atgtgccagg ctatgttcta  14640
agtgctctac ccatgagaac tcacttagtc cttgtaacag tcctgtgagg taggtactat  14700
tgtttctccc cattttacag ggaaggaatc tgaggcacac agaggttaag gagtttagca  14760
aggtcactgt agctaacaag tggcagaacc agattcaaac ccagagccca cactcttaat  14820
cactatgttg cttctagaag aaagaaaata atggatgaag gatagtaaaa acatgcaagc  14880
ccttctgagc cccctgttgt tggccccact tcagcagcag tgttagcaag actatgggaa  14940
ctcaaaggtg acacttagcg ctctcctcca gaggctgcag gagccaccat tggatagcta  15000
gccatttgta tccctgtgat ggcggagaca agctcacact gttgcaggtt tctctactct  15060
ggaaaagact cccaaactag ggttaatcaa gtctcttttt tggtgaattt cattaaaatt  15120
accacataaa aaaagagttt gtcctgaatt atacatatag gagaaaaatg ataaaataaa  15180
ataatttcca ttatctttgt agcaaaaaaa agtttgaatg attctaccag gttctctgaa  15240
ggactttgtt ttcaaaggag atgttaaaat gtgtaaaata tccaaaggat acacttttgc  15300
agctgaattt aggatcttaa gaaacatcgt tttactatgt ttcccaatga ctgttgaaaa  15360
gaagcagtga ctgggttaca tctagggcag ggtttctcag cctcggcact attgacattt  15420
tgggctgagt aattctttgt tgtagggggc tgtgctatgc aatgcaggat ggttagcagg  15480
atccctggcc tctacccact agatgccaat aagattctcc ctttccatct atgacaacca  15540
aaaatgtctc caggaatttc caaatattcc ctaaggccaa aatcacccag ttaaaaacta  15600
gtggtctagg gaagaccatt ataattaata gcatgtctat gatctcccca aggtattgca  15660
tggaatgcca cttttctttt atcatagtac ttcaaatact tgtgtgttac tgaaaacatt  15720
tataaacaaa atatatttga tagcaggata taaatatgcc tgtgtccttg gaagagaaag  15780
aggggacaag agaacaggta tgacagcatg ttgttggtga aaataaattg gtaatataga  15840
```

```
ttgaatatcc cttatctgaa atgctttgga caggaagagt ttcagatttc agatattttc  15900
agattttgaa atatttgcag aaatacatac aggtagagca tccgtaatcc aaaaatccaa  15960
aatctgaaat gctccaatga gcatttcctt tgagcatcat gatagctctc aaaaagtttt  16020
ggattttgga gcatttccga tttcagaatt tgggattagg gatatttgat ctacagtaat  16080
gccaaatact gcactaaaat tagcaaacgt aatctcattg aattgtcaaa acagccttaa  16140
gaggaaaccc gatcattatg cctacttagt agatgaggaa acagaggtaa ctaggtcaag  16200
gtcacacaac ttggagtatc agtctggatt ctttctagtt ctgccctcgt ccaagctagt  16260
tctgttaaca ctattcttcc tttcagcata atctttgtca tcactggagc ttatatctac  16320
ctgcctgcca cccagcacca accgttcacc ctttaagtct catcctgcct cctccaggag  16380
ccttccctca cccctgcctt caccttctga cctgtgctcc cttcacaccc tgtgccctct  16440
taactgggaa agccctgagg gcagggacca taccttattt acctctatct ccagcttcct  16500
gcacagaggc attcagcaga tgaccagtaa atatgggctg tctaataaaa aaactttgca  16560
gctagagata atgaaagaca caattacttc tgtgtgggtt gaggaagaag ggaagggaaa  16620
gtccagatac ctaagcagag aaaggcaaac agtccaaaag gggaaaagta acttacccaa  16680
atcatgcagt tgagggcagg aatggggaca aagccaaaac caaaacccag cccctcgtgc  16740
ccagcccagt gctttgtctg ctatgttata ctaactgtga tcatgaaatt aaagggtttt  16800
tgatggcact gatacaagta aataaatggc tttatgagtt aacacatgac aagcaataaa  16860
ctcataaaac gtaaatattg acatctgagg attatatatc actatgttta gtgtgtggag  16920
aacccaacta ggaattagga aagcttgcac gttcagttta gtttcttggc aaatcaatga  16980
gacttcaaac aaatcatttc atttctctgt gcttttgttt cttttggctg tagtattttg  17040
ctggttaaag agcacgtgat caatgtctgt gcttttaaat gtctgtctgt atttgagcat  17100
gctcagctgg atgtggaaaa tctatggttc tcttgggttt cataaggatc aaatcccaca  17160
gtgatatgta aacttgtgtg gtttatagaa ttataggacc tcaaagccgg gagagtcctg  17220
ataaatcata tagtgaaaat ttccagccag tgcctggatt tattttacag aatctttctt  17280
ttattggaca ggtgctcact tcacaatcca tgatgtaagg agaaaagggg cttagtttga  17340
aggaagttag catagtgtgt gtgcgtgtcc tttctgcttg gggtatgcct acagggctat  17400
ctcactttct gaaagtgtaa taataacaaa attactttac cgtgcattaa ttaaatgtca  17460
gagaccatgc taaatgcttt acagagagta tcttatttaa tctgtataag aacctcatga  17520
ggcaggtaat attattaagc ttacttttca gataaggaaa ctaacattca gaaaagttaa  17580
gtaacttgct aaagacatgt gtctactagg aggtagagtc tcaagtctat ttcaagctcc  17640
agattgagct ggagctatta ataagtaaat aaatgtctat tgaatccaac taatgacatc  17700
ccactccata ttcccctgcc actgatgaga gagagaagta taaagtttat gtaaataaga  17760
cagaagcaat gttttataag cgttgtggat ttaattccac taagggattg atttttcatc  17820
ttaatggagc tttttcttca gctatcaagt ttcagtttta aggcaaacgc taagaagata  17880
ttaaaatatt ttaatacata attccactag atcatattta caggtactgt taatatatta  17940
ccaagtctac tataaataaa atgataaaac aaaaggctgg atcaatatgg aaagtaggcc  18000
ctaaagaaaa actacataag acatttctct tagaagatta ccaggttttt ctctctctct  18060
ctctctctct ttttaaacac agcctaaaat agaaaagcaa tgaatgtatt aataaaaaaa  18120
atgaaaacct gaggcagatg taaccagaat aggtgaatta actgaagatt gatattctta  18180
tttatgtttg tgtattttaa ataaagaagg agtttgacca tctcatctag ttaatcatta  18240
```

```
aaaggaaact cgagccaaac ttgtgaagca ggtaaagttt atttttagac attcaactgg  18300
cttctctttt gggctcccct tttcttttgg ggtcatcctc caggtctggt aaccttaacc  18360
tcccgctctc ttccagaagg agcaacaccc ccatgtttta gacgtttact tctgaggtca  18420
ggatcctttc tgatgcaagt gtgagctaac tccagctggc tgaagaggaa ggaggaggaa  18480
gagaaggagg gggaataatg tattgaagtg tgtaatagtc nnnnnnnnnn nnnnnnnnnn  18540
nnnnnnnnnn nnnnnnnnnn nnnnnnnnnn nnnnnnnnnn nnnnnnnnnn nnnnnnnnnn  18600
nnnnnnnnnn nnnnnnnnnn nnnnnnnnnn nnnnnnnnnn nnnnnnnnnn nnnnnnnnnn  18660
nnnnnnnnnn nnnnnnnnnn nnnnnnnnnn nnnnnnnnnn nnnnnnnnnn nnnnnnnnnn  18720
nnnnnnnnnn nnnnnnnnnn nnnnnnnnnn nnnnnnnnnn nnnnnnnnnn nnnnnnnnnn  18780
nnnnnnnnnn nnnnnnnnnn nnnnnnnnnn nnnnnnnnnn nnnnnnnnnn nnnnnnnnnn  18840
nnnnnnnnnn nnnnnnnnnn nnnnnnnnnn nnnnnnnnnn nnnnnnnnnn nnnnnnnnnn  18900
nnnnnnnnnn nnnnnnnnnn nnnnnnnnnn nnnnnnnnnn nnnnnnnnnn nnnnnnnnnn  18960
nnnnnnnnnn nnnnnnnnnn nnnnnnnnnn nnnnnnnnnn nnnnnnnnnn nnnnnnnnnn  19020
nnnnnnnnnn nnnnnnnnnn nnnnnnnnnn nnnnnnnnnn nnnnnnnnnn nnnnnnnnnn  19080
nnnnnnnnnn nnnnnnnnnn nnnnnnnnnn nnnnnnnnnn nnnnnnnnnn nnnnnnnnnn  19140
nnnnnnnnnn nnnnnnnnnn nnnnnnnnnn nnnnnnnnnn nnnnnnnnnn nnnnnnnnnn  19200
nnnnnnnnnn nnnnnnnnnn nnnnnnnnnn nnnnnnnnnn nnnnnnnnnn nnnnnnnnnn  19260
nnnnnnnnnn nnnnnnnnnn nnnnnnnnnn nnnnnnnnnn nnnnnnnnnn nnnnnnnnnn  19320
nnnnnnnnnn nnnnnnnnnn nnnnnnnnnn nnnnnnnnnn nnnnnnnnnn nnnnnnnnnn  19380
nnnnnnnnnn nnnnnnnnnn nnnnnnnnnn nnnnnnnnnn nnnnnnnnnn nnnnnnnnnn  19440
nnnnnnnnnn nnnnnnnnnn nnnnnnnnnn nnnnnnnnnn nnnnnnnnnn nnnnnnnnnn  19500
nnnnnnnnnn nnnnnnnnnn nnnnnnnnnn nnnnnnnnnn nnnnnnnnnn nnnnnnnnnn  19560
nnnnnnnnnn nnnnnnnnnn nnnnnnnnnn nnnnnnnnnn nnnnnnnnnn nnnnnnnnnn  19620
nnnnnnnnnn nnnnnnnnnn nnnnnnnnnn nnnnnnnnnn nnnnnnnnnn nnnnnnnnnn  19680
nnnnnnnnnn nnnnnnnnnn nnnnnnnnnn nnnnnnnnnn nnnnnnnnnn nnnnnnnnnn  19740
nnnnnnnnnn nnnnnnnnnn nnnnnnnnnn nnnnnnnnnn nnnnnnnnnn nnnnnnnnnn  19800
nnnnnnnnnn nnnnnnnnnn nnnnnnnnnn nnnnnnnnnn nnnnnnnnnn nnnnnnnnnn  19860
nnnnnnnnnn nnnnnnnnnn nnnnnnnnnn nnnnnnnnnn nnnnnnnnnn nnnnnnnnnn  19920
nnnnnnnnnn nnnnnnnnnn nnnnnnnnnn nnnnnnnnnn nnnnnnnnnn nnnnnnnnnn  19980
nnnnnnnnnn nnnnnnnnnn nnnnnnnnnn nnnnnnnnnn nnnnnnnnnn nnnnnnnnnn  20040
nnnnnnnnnn nnnnnnnnnn nnnnnnnnnn nnnnnnnnnn nnnnnnnnnn nnnnnnnnnn  20100
nnnnnnnnnn nnnnnnnnnn nntttttccc ctcttcaaaa acttttatta tgtgaaatag  20160
aaagtagaat tgtgactatc agaggctggg aagggcagag ggaaagggat gggagagatt  20220
agttaacaat tacaaaatta cagctagata agaggaatga gttctgatgt tctgcagtac  20280
cttaaggtaa atgtgattaa ctataattta ttgtatattt tcaaacgctt tttgtctacg  20340
caaggatgca agaatgcata tatgtttttt aaaaacaaaa atgagatttt actacatgtt  20400
tttttcaacc tttattcatc aaatgttatt ggacatcttt ttatcttttc aatattttca  20460
ggtaatagta gcatagtata ccgttgtttt aaccttttcc ttattgaagt atatttaaat  20520
tgttttcaat ttttcactat tgcaagacat gccgcaatga atattcttga ccctccccaa  20580
```

```
caccatctcc atatccacac ccacttccct gatcttaaac accagatgac ttcttgaagc  20640
ttatatagtg ccttatgcat ctatcacatt tctgtaagtc tgcattgttc tataatgact  20700
tgtaatcgta tctatctcca tttcctccag agaagagatt tgatcatttt tatatccctg  20760
tagccttata ctggggccta acatataata gttgctattt tgttgaagga attctctttt  20820
gttgaaggaa ttctcttttg ttgaaggaat gaatgaatag gagagaatat taattaagaa  20880
agtctcttct attaataaac attccccgat tgattgaaac catgcataaa atagctaatt  20940
atcagaagac caaggtaaac aacatctcca aactgaatcc tcaaagtgtt agtcattgga  21000
agctgcatag ctgagaattc ttcttctggt cattagggtt gaaagggtgg gtgaatgtgg  21060
agacatgatt ctttcttttc caaaacattt actatttttt aagctccata aaatgtaata  21120
acttctcttg aaaaatgtta aaacccaaac aaaaaaacctg taatgtggaa tacagattgt  21180
atgttataat ggaggaagca gggaaagtgg gaaaaccgtg gttgccagaa gtttgctgac  21240
aactaatagg caagacaata gggtggcttt ctgtagggtc cttctttatg gcatagcaaa  21300
gaaaaaccag gaatgaagta gtgagaagca tgaaaggggg cagcaatata tgtgtaacac  21360
agggtgattc agtgtgagag ttttataatt aaaatcgcca aatgcgagaa aaaaatctac  21420
tataaattgg aataggctca aggcatggag atgaacaaat aaccccctcca tgtgggcaaa  21480
aatcaatgaa attcctagat gagtagctta gtatgtgagt tccagctgca acatgttatt  21540
ggtatttgca gcttcctctc cccacctgca ctttgaggca attcgacatt taaataacaa  21600
tccagcctaa ctttctccat ctgctataaa gatatttacc tttatctatc ctagaactgc  21660
caacatgtcc tacttcctac tacatccctc cctgactcct tttctctggt gcagctttct  21720
atgcactcaa ctgagcctgc ttaagtccat ctcttccata gagctgctgg atgactgctt  21780
tgcttacctt tggcctccaa aatacctctc ctgtccaacc atagctcccc agcttccccg  21840
ccattgcaac caatacaaac tttgtcatct ttccttggac caatgtgcgt gtctcctcac  21900
tgctctccct gctttctccc ttagccccta caactcatac tccatatcgc aagcagaatg  21960
agcttttcaa atagtaaatt agattatgtc cattagtgtg ttagtaaatg tttaacagct  22020
gtctgagggg aacagagtat ctatgtattt attataattt ttacatatat atatatatat  22080
cacataattt acaaaaagaa aagatataac acttttaaat agtgaattct atatggccac  22140
atgattttca caaaaccgtt tcagtgattt tggcagaata cttgtgtcca tagctaacct  22200
acagctgaaa ttcaatgatg tttggcaaaa tcagaccaca aataaatatc tgattaatat  22260
tcaatcagca aagaagtcat tcatggtacc gaagtcccaa catgaatgtt ggttgatatt  22320
tttacattaa tgagtgagat aaaagtgaag caacaaaaat ggatgttgga actaaactca  22380
ttcattaatg acaggagcga cttcttttgc tgataatagt tttcaagtac tggaaaaata  22440
tttcctcaag tttttgtgtt caagaactaa ggcactttta agttcaatct tcattattaa  22500
aagttcttct attgtgtcag tctagacaat caacaaatta agctctggtt tgtcatgttt  22560
cccaatttct atagtatagg tactccacca tggttgattt caaactacca aaataacatt  22620
tctgaatgca gcattaggaa gggatacact gcatcatacc attgtacggt atgttcctat  22680
acggaacaga tataaataac tttaagagca cagataatag taaaacggag taaaataatt  22740
aggcagtgaa gttttcagca tttatttttg ttaaaatatt tgattttaag tttataaata  22800
atttggtttt taatgactgt gattaacaac cgacttacaa aatctctgaa aatttaacag  22860
tgcttgcaag ctggtacaac tggttccggt gcacttccga attatcactc ccctgcctaa  22920
aattccagac tgcccattgc actgattacc tgggaaataa gtgaaaatag gcaatgataa  22980
```

```
ttttcatttt tgttgtggtg aagtgataat gcaaaaattc tataagcccc tctaagtttt  23040
ccaaataaag cttagtgttt aaaaactttt gaacacatga tcccatgtga ggcctacatt  23100
atttcctgtg agataggtgg agtagatatc attatccttc ctttacagat tgaaaaatga  23160
ggctgagaaa aattaaatgc ctaccccagg ttcattcaag taagtaaatg acagaatagg  23220
gtctaaaaac caggtattgt attgaaaatt caacaagagg atagagaaaa tttaattaac  23280
aaatactctc tcaaaacaat ttttttcaa tggtaacaaa catcctttgt agcactttgg  23340
agttggatat gaagtatctt cttatcttgt taagggatcc ctataccaag aatgttttca  23400
tcttaacccc actatttcta agttagctta aaacaaaaca aaacaaaaca aaacacaaac  23460
aaaaccaaaa ccttgtgctc taataaataa gaagatataa gaaccaaaat ggaaatgtag  23520
gttctcaaat gagctgaaag attccacata gcagtggggc agattgaaac actctttacc  23580
aaaggaacat gggacagaaa aggagattaa atcagaaaag gaagaaagct aatgacatat  23640
ggggagccac aaatgccaca aatgaaaaac aaagtacgta atacttgtcg caattattca  23700
gtgtgcttgc tctagtgcct ccaaacatta aaaatattga gttcctgctt atggcaacat  23760
ttatctcatt tatctgctga tgtctgcctc atccttgaat caggtattgc ttaaactaag  23820
ttctgccagc ataaagaata aagtcaacca ggacacccat agggcatttc atgcatatga  23880
gcacaaattg tgatatttta ggctggttat gatgaaatca ttgaaagcat catggaaaac  23940
atcaaaacag cagggaagct agtaacaatt tagcatttcc cagtccaggc gggaatgtta  24000
attctaatta caaaaaggaa taccaaagtg gagttgatta tgattaagaa cttgctgtac  24060
tagtgtgaat tgtttataat aggcatgtct ggcataaaat acaaatattg aagcagacag  24120
agatgggtca ttcaaagctc agctgggttc ccttgaacct cttaccttat aaagttaaat  24180
aggaatagaa gtattttcca aagtcaagat attattttaa agagacaaat aatagctatg  24240
atagctgcag gaataatttt ttaaagtaag ttctaaccac caataaaagc tgtttgggct  24300
taaaattaac atgttcaaaa ttattaatac atatacacaa tacatgtata catgattcca  24360
atttatattt aacatcaaac atttaaagtg ggagagtaca gaaaaaaaga ataaatggaa  24420
accgaagcca tgacaaagaa tcacggacta taggaaaata agtcacaagg aagtatgctt  24480
atgtaagagg aaatatatgt gataaacaac aggagacgtg ggaatgaatg tggtgtgtta  24540
tgtcctttct ttaacagaat cttgtaacag acactactca atacattgat ctcaactgat  24600
ccagttctcc ggtctccctg gaaaacaatg gattgacgcc caggttgcac tgaacaccag  24660
aaccatggtc atttctgcac ttcacacgat tctgctccca tcagttgagc taccaacagt  24720
tcctggtgct tttgcttccc aaacatgttt atgccatttg ttgcttatta ctgtacctac  24780
ttaatttgat taaacattaa gtaaaatgat gaaatatgag tataaaaaat tgttctataa  24840
aatctaaatg gaaagatgcc ataaagcctt ccttgactta caattgctgt caagcaaggt  24900
ggatgtaaga caattttaaa agattggggt gggggcagga acaaggaagc ataaaaattt  24960
agaaatctgc actaaaatta ttctaaaagt acgtgttgaa catccgtaac ttgacaatct  25020
gaattttgaa gtgctccaaa atccgaaact ttttgagcat tgttatgata ccacaaatga  25080
aaaatcccac gtggaagtac ttaccacaaa ctttgcttca tgccccaaat tattttaaat  25140
attgtacaaa attatcttca ggctataagg tgtatatgaa acaaaaatga atttcctgtt  25200
tagacgtggg tcccaccgct gagatttctc attataatgc aaatattcca aaatcagaaa  25260
aaaaaaaaaa atccaaaatc taaaacactt tcagtattaa gcatttcagg tcatagatac  25320
```

-continued

```
tgaatgtgta tctttaattt cttgctccac tttgttaaaa aatggggaaa atagtaattc  25380
tacagatgaa taataattgc taatgatgag taaatacttc ctatgaccca ggaattagtc  25440
taagcacttc acatatatca aacttgttta atctttataa attagtacta ttattatcct  25500
cattttacag atgatggaaa aaagcacaga gagttagcct gcccgaggtt acattccttt  25560
tagtggtgga gactgtattt ggcctttata gtctgtcttt taactgctac gctacatcag  25620
tgcattacag gtatagttta tacacacact aaagaagaca tggaactcca gtcagtgggc  25680
tcataaaagc tttagacctt catcaaaaga ttagaaaata aatgttcaat cataggtttt  25740
aggtttcaaa agtttaaagt ttgcaagtta tctttcttga aactatttcc ttaattttta  25800
aattaaactc cagttcaatc acatccgcta gaaggcttca ctttctacaa aaggggcagg  25860
taaaggtgat gatcttaaat accataccgg gagttgggat ctgtgtagca ctagaatcaa  25920
gagttattgt atatacttga gaaggagcac ggcatgattt agttgatgtt ttggaggggt  25980
aatctgagag tacagcttgg attatttttg agggaatgga gatgataaaa catgaagaga  26040
atgggagaac tcattgggta atatgtcagt ttctgagatc aatgtatcag gtggtttggt  26100
tattagtcag gcttaaggtt ttgttggcct taggacatac tctctaagac catatagtat  26160
tcattcattt aaccaacacc cactgagcac caactatgca ctagtgataa aggggtgaac  26220
aaacagacac agtcccttcc tttgcagagc ttttattctg gtgggtgaca cagagaaata  26280
acaaatggag gcacaaataa tgaactatca ttgtaatgtg ctaacaaagt atgcagaata  26340
ctataagaaa atacaatcac gaatctaatc tggtttactt tttaaaaaat ggggggagca  26400
ctcggatgtt taaacacaag acaataaaaa tgaggatctt gagtattatc catacactat  26460
ttataaccca tttggccacg acaataaccc agtaaaagtg attttacatc tagctaacta  26520
gttgagtcga tgtgattata acactgtaat gtatttactg ggtgcctact atgtagtggg  26580
ctctgttcca ggagtgggac ataaagctat gacaagacag atcaggtcct tgccttgatg  26640
gagtttgaat acattacctt catttccacc tctgcttcta agacaatcaa atacattccc  26700
actcagacag ggattcatcc tatttcttgt agtaattata agttcccaga gttacagatt  26760
agtaaatgcc atacctaaag acttaggata ttgtgcgtaa aacactttca atagtgcctg  26820
tcagacagca gatgcgcaat aaatgttgac ttttgttaga atcgtgttat tattataatg  26880
ctaaatctca tgtcctttct ggtacactgg agttcatctc ttgaattaaa ttccataagc  26940
acttattgta agcctatcac agaattgata tactactcca tgttaatgat tgagctcagt  27000
gaggaaaacc actttaatat tgtctaattc ctctcttaat gcatagaagc cgtgtgaact  27060
tagacaagca tcaacctctg taagcctgtt gtcctcatat tgaaaaatcg aataacaata  27120
cctatctcgt tcaatggttg tcagcaaaag tgggcagcag aagagtgggg atcaataaat  27180
gttagccaca aatcataact atttgtatta ctctgaaaaa gaggggttaa cttacagttt  27240
atgcatgctt ccaaatgaat gcggaagact aaagaatgag aatttttttg ctattaaaaa  27300
attaacaggc acatttagat cactgaagag agaaattagg aaaagtttat tttttttgct  27360
caattaaaag tgttttcaat ggcatattta aaactatgtg agtattcttc cctgttaaga  27420
tctgcagaga aaaaaaatgg agggagaata attgggaact cttgtgaaat cataaattat  27480
ttaagcagag tacctaccac taaggatttg agcatgtatg agtgacaagg tggattctta  27540
gaccagagat tcagcagtga gacaggctta tggcatgggt agatgtgttc cattagacaa  27600
ctgtattttc cccttaatta tatacatata tatgtatata catatgtata cgtatatgta  27660
tatataaata gaattcttat tttaagcaca tgtacaagga taattattag cacgggctat  27720
```

```
ttaactcact tttaaaacgt gtaaaacatt attgtagggt cgggtcttga tttgtttccc  27780
atgacactgt tggtagctta ggggccaaat taaagaaaga catctcattc tagtgcttga  27840
ggctcagaaa ctggaaaaag gggtaactag gtcaagtagc gctctcagag cctcacagaa  27900
gagcatccga agcaagggcc tccttctagt tgacttgtgc caaggggaaa gagaagcgga  27960
atctgccttc tgagtccaga aaggggtttt gttaacatgg agttgctcag cgcccttcat  28020
aaaaattctt ctggctgagg gttctacgct ggcataaggt tggttccctc ttcttttccg  28080
aggtggcgag tatctcttcc tttgccaaga tggcggttcc agaatcctct ggaggcggcc  28140
tccgtagatc gtctccggac aagaggcttg ctgaaagcct atttctttcc tttcacacta  28200
gaaaacgcac agggaaccgt ttacccttca gaaccgagga agaacggctt aggctacccg  28260
cgatcgccaa cctttgccaa gatggtggcc gcggggtcgg gctgacgtca ctgtacccta  28320
ccaagatggc ggcgggcggc ttccgggacg cgcttcccca atcgtctcca agatgtcaga  28380
acagaggcgg ctgccgtcag tctgagcgcg gcgggaggac agagagtggc tgtggccgag  28440
cgcccgagca ggactaggtg gagctgcggc agccccgcc cctgtcagga gctggcaagc  28500
gatgtcacct gtgggggcgc aaaagttacc tccccaaacc ctaaagccac acagcacaac  28560
ctttccccga gtcacaaaaa taatctgccg cacaagatac gaggctcggt gcaggcatcg  28620
cccaagcctt cccgacgcag cgagctaggg aagggagctg gggcgggggc ttccctcgcc  28680
ccacggccct ctcctctctc aggacgggcc acgtgtttcc ttcccctcgg actgaggggg  28740
aaagctcgta acaggaacag ctgtagggag ttgaacgctg gcattttaaa gctgtccgta  28800
ttttgtttta tttgtagggg ctggggtccc atgaacgtga tagggtgagc aacgcataga  28860
gtcgagggca gcaaatgtca aaatttgggg gtgnnnnnnn nnnnnnnnnn nnntgccgcc  28920
ccctgctttc tttaatcata ataataaaaa tgcaaagaaa tccagctcgc tggaggtttt  28980
gcgtttggcg tgcaacttcc ttcgagtgtg agcgcaatgg gcgggagggg tgggggttga  29040
acttggcagg cggcgcctcc ttctgctgcc gccgcctcgc agactcgggg aagagggtgg  29100
gggacggtcg gggcgcgggg gagggtgggt tctgctttgc aacttctctc ccagtgcgag  29160
cgcgcggcgg cggcagctga agacccggcc gcccagacga tgcggtggtg ggggacctgc  29220
cggcacgcga ctgcccccgg gcccaaagta cgtatgcacc gacccccgct ctccagtccc  29280
ctccctgaag cctcctcaga gggcgtgtct ggccgcccgg ccccgagcgc ggtggagacg  29340
ctgcggcacc gtttccgtgc aaccccgtag tccctaccga agtgacacac ttcacgcaac  29400
tcggcccggg gacggcggcg cgggccactc gcgcagcgct gccgcgggcg gcgccccggc  29460
tcctctggcc cgcccgctgt cacccgcagg ggcactggcg gcgcttgccg cggaggggca  29520
gagcgagctc ccgagtgggt ccggagccgc ggagctgggc gggggcggga aggaggtagt  29580
gagaagagaa actggagaaa ctcggtggcc ctcctaacgc cgccccagat agaccaggtc  29640
ggcccccgcc gccgccgccc tgtctttttc ctggggagtt gggggcgggg gacgaagcgc  29700
ggcgcgctcg gctgggctgc cacgccgtgg gccgcgggcg tgcaggcgcc gtcggggccg  29760
gggtggcggg gcccgcgcgt agggcgtggg ggcagggacc gcgggcgccc ctgcagttgc  29820
caagcgtcgc caacaggttg catcgttccc cgcggccgcc gcgcggcccc tcgggcgggg  29880
agcggccggg ggtggagtgg gagcgcgtgt gtgcgagtgt gtgcgcgccg tggcgccgcc  29940
tccacccgct ccccgctcgg tcccgctcgc tcgcccaggc cgggcggccc cttcgcgtgt  30000
ccgcgctccc ttccctctgc cgccgcctcc tccattttgc gagctcgtgt ctgtgacggg  30060
```

```
agcccgagtc accgccggcc cgtcggggac ggattcagtg ggtggaaaga gacgccgcag  30120
ccggagcggc cgaagcagct gggcgccggg acggggcacg cgcgcccgga agcccggacc  30180
cgcggagcct ggcgcggggc ggagggctgt cttgtcagct gggcgatggg agactttctt  30240
aaataggggc tctcccccca ccnnnnnnnn nnnnnnnnnn nnctgcgttc acacgctaag  30300
ttgtttatct ctgctgcggc aggagctgcg gaccgtggcg ggcgagcggc tcctctgtca  30360
gaggtaagaa gcgaggcggg gagggggccg gggcgcgctc actccgacga ggtgccggtg  30420
ggaccggaga cgactcgggg gccgccgcgg gagcctacaa acttttatta gcctcgggga  30480
gtgggggtgg ggggctggcg agggccgggc gacggtgacg aaagggcagt gcgcgggtga  30540
cagcgctggc ttcttcctct ccctccgccg gcgtcccctg gccgggcaga gggggaggaa  30600
cctgagctcg gacggcgagc ggagccttgt cgaactgccg gggtttcga gcctcttatt  30660
ccccgacggg aacactggcc tcttttctcc ccccgaatgt cccctttccc tccaaggggc  30720
cgcccaacac ccgttttcgt ggtgaacgct aagccgcgtc tgaattctac tcgctcgaat  30780
atttgcactc caccccggcg cgcccgagcg cgagcccggg ctctggggag gccccgtcgc  30840
gcctggcttg gggagggcgt gcagggcgcg tgagagtaca cacgcggggg gctgacagct  30900
tgctacttgg agactccggc aggggctagc gttatctggt ggaagtgggc gtgtcggaga  30960
gagaactcaa caggtctgga catatttctc ttttaacctc gcactttttt tctcccccac  31020
cccccgcccc cgccccgcaa gggcttgctc tttagcgttt gttgtcaatt cgcgcctgag  31080
gtttctaagt ggcccctttt agaaaaagac tccctgtaac cgtaatagtt ttgtgttgcg  31140
attttcgaca agtgctagtg tgacgtttgg ggttgcagac ttgataattg caaccttgta  31200
ataccactta agaccctctg gcatggttca ttagggccga ttaatgtggc tgggttattt  31260
gcaacttaaa ctgggggata atgtcgcttg agggagcgtt ttcgttttag gaagtattgt  31320
tttggtttcg ggtttgaagg cagctgtcag aaaacggtat ggaaattcat tgggctccat  31380
ttgatacctc gtgtttagag atcgttatca cctcagataa acagggcaga gagtggggag  31440
ataagcagtt taccctcaag atttgtagtg gcaagtccac acccctctct ttaccttcat  31500
attcactttt cagtgagggc cagtgacatt tatgttgcct aacgtcatcg tataggaaaa  31560
gtttcctttt attgggcagg atttgactat actgtcccaa atgtgcttct cagtcttagt  31620
ccatctctta aaacaccctg attaacgata gcctaacagt cttattctct tgagaatagg  31680
ctgagaattg ggataggtga aggtttgata ggtgaaggca gagaaaatta ttttgaacat  31740
tttactggat accgttgtac ctgaatttat atgaatgtga ttttacgatt ctgtgttttt  31800
tcatttttcg gtacttcgat atttgtttgg aaaggaaaga acttggagat gtaatagcat  31860
ttcatattga ggatctcaag caatgtaaac aagtgtagct tgatctacat ggttttgtga  31920
gttatgataa gggtcagcta tatttaagtt atttaagcta acaatgtagt gagaagctac  31980
tacacattgt cttctgctct ttaaaatcta aattttagtt gacctatata atgtgtatct  32040
tatttcatat atccaaaatt tggaggtagg cacatccagt cagaagtatg ggttaaaaag  32100
ccttttccca gcctgtcgga agataagcag atcagcatcg tttatttttc aaagaaaatg  32160
tgcatggttc accagttggt tgtacttaaa ggtttggatg tgtgagtagc tggtaggagg  32220
gaaatttgga agtaattagg gattgaggaa ttctagcaca gtatttatca aatgttatat  32280
gtattgattc tcagaaaagc aaacagcctt gattgaaaag aggtaggaat tttaatgatc  32340
acacttcctt tttttgaaat taaatacttt gacatcaact tgaaccttta gaataatcag  32400
atgtaatgaa ttataatgtt tgtgattaac aaagctacac gttcagtgag tggcaggatg  32460
```

```
aatagccaag cttagttcta tacaattttg ccctcagctg tgcaaatgga ctgcattgta  32520
cttttaaatg tggcacgctg aatgggagca ggagacatgg ctttttattc tgaaagatag  32580
aaattactct tttggtaaca aagaatttga ttcggagtta actaaaaggt tcatttaaca  32640
agctgtctct tactaatcag atcagggaga taatgtgact ttagaattta tgatgttttc  32700
ccccgttttt gtttttgtt  ttgtagttga tattcactga tggactccaa agaatcatta  32760
actcccagta gagaagaaaa ccccagcagt gtgcttgctc aggagagggg aaatgtgatg  32820
gacttctata aaaccctaag gggaggagct actgtgaagg tttctgcatc ttcaccctca  32880
ctggctgtcg cttctcagtc agactccaag cagcgaagac ttttggttga ttttccaaaa  32940
ggctcagtaa gcaatgcgca gcagccagat ctctccaaag cagtttcact ctcaatggga  33000
ctgtatatgg gagagacaga aacaaaagtg atgggaaatg acctgggatt cccacagcag  33060
ggccaaatca gcctttcctc gggggaaaca gacttaaagc ttttggaaga aagcattgca  33120
aacctcaata ggtcgaccag tgttccagag aaccccaaga gttcagcatc cactgctgtg  33180
tctgctgccc ccacaaagaa ggagtttcca aaaactcact ctgatggatc ttcagaacag  33240
caaaatttga agggccatac tggcaccaac ggcggcaatg tgaaattgta taccgcagac  33300
caaagcacct ttgacatttt gcaggatttg gagttttctt ctgggtcccc aggtaaagag  33360
acgaatgaga gtccttggag atcagacctg ttgatagatg aaaactgttt gctttctcct  33420
ctggcgggag aagacgattc attccttttg gaaggaaatt cgaatgagga ctgtaagcct  33480
ctcattttac cggacactaa acccaaaatt aaggataatg gagatctggt tttgtcaagc  33540
cccaataatg caacactgcc ccaagtgaaa acagaaaaag aagatttcat cgaactctgc  33600
acccctgggg taattaagca agagaaactg ggcacagttt actgtcaggc aagctttcct  33660
ggagcaaata taattggtaa taaaatgtct gccatttctg ttcatggtgt gagtacctct  33720
ggaggacaga tgtaccacta tgacatgaat acagcatccc tttctcaaca gcaggatcag  33780
aagcctattt ttaatgtcat tccaccaatt cccgttggtt ctgaaaattg gaataggtgc  33840
caaggttctg gagacgacaa cttgacttcc ttggggactc tgaacttccc tggtcgaaca  33900
gtttttctca atggctattc aaggtaagat cagtgttttt ctgtttctta agaatggtac  33960
atttaagata gattaataga tgtaaatctt cattggtttg tatgtgttct ctgaagattc  34020
atgtgctttt ttatatgaat aagctcaagt ggccttttga aagtagaaag ggtagacaac  34080
ctaagtaaca tctgtacgtc accatttcag ttttttcct  taaatagtgg tattcagtat  34140
cccattggcc aatggtgagg attttattta acatttaaaa aataatattg ctcattaaca  34200
gataaggaaa aattatatac attcaggaga gtataatgtc tcaataccat attttgttgt  34260
gcatgttcat tcagctgttt tagaatatgt tcttatatta caataaatga tacccttact  34320
tacatagtca aaagttgtgc tgccttattt gtaaatttgt taagtgttag cttgagatta  34380
acgggttaaa agcagaagta ccaacaagta gtagaagtac cctgttcttc aaactgaatc  34440
ttctgttaaa ggatttgagt tttgaaattg ctaaagcaat gcagtgaaca gtgtaccaga  34500
ccatagtatt agacacaggt cttgctcaca gggttcttgc cctaaagtag acaagttatg  34560
tctgccgatc aatctcttta atagaggaat tggtgccaac atggtgcaaa acaaaatttt  34620
actttcaaat gttcctgttc tcaagtagat aactgatggc caaaattgtt aagcttcaat  34680
tttcagctat catttgattt ttctcttttt tttttatact cacttataag catactgata  34740
ttctgtctga cccaaaaagg tcagaaaatg gaattatcag aaaaaagttc taaatgtaga  34800
```

```
catatgtgtt ggtagaggtt aatttctcta ccctgtaacc tcattcccaa ttcagataaa  34860

tgctaggttt tatatccatt ttaggtgtga cggaaaatat aaaaatgtgg attgtagtga  34920

cccaagattg attaatcagc aggttttttt taaaaagaag acatagcaga cagaatgatt  34980

tatttgtatg taaccattga agtttttttct gaaatgttaa tgatattcat cattcccatt  35040

aacttgttat tcagattttt gaaagtactt tttctatgaa agctatccct aaccctgagg  35100

acgtctcttt ctttcctctt cacgtaggaa gttcttgtta gggaaataat ttaggcttag  35160

atttagggta tgttctgttc ttctaaaagg cttagttgtc aaaaaaaaaa caaaacaaaa  35220

caaaacacaa aaaacaaaaa caaaaaaccc ttggttctta cggttaatgc gaactacttc  35280

ctaatctatt gtttaaataa ttatctttta tttagaagaa cactacttca acctgagttg  35340

aaggtttaaa atgtttttag taaggagatt taagatgttt cttactgcat aagctgttgt  35400

gttttaaatg ctaaaagaca tgctgtgttt taaaattttc aattgcaaat ttttggcaat  35460

agaattcaca tacttggttt tcttaaaaga gttaagtatg gttgatttga ctaagctatc  35520

tgtaggaaac tcttaaattg acttataaaa cgtaattata caaagaaaaa taaaacatct  35580

taggaaactc ttggggatta gtaatggatt ttgtcctgat aatcatcatg catggttttc  35640

atttttccta ctataaagaa aaggcatggg acaaaactta ctttccattt gctatgaact  35700

tttaaaccct ataaaatctg ggatatagag tataagtagg tgaacatagt tactcttaaa  35760

tcactgaagg tgattttaat gctttaactt ttatagtact ttatgacata aagcatcttc  35820

atgtattttt aatttgggcc ccataacctt atggaggtag taggcaaggc aatgatgatg  35880

ctgctcttta gaagttcttt aatatcgaaa gaaatgatta tttttatgcc agtctgtgat  35940

tgggaaatat aatcagtagt ctatgtccta ataagaaggt ataatacttt atacagggta  36000

ttttgttaat atttgaagat tttgtacctt acggcattaa cttagcactg ggaactatga  36060

ttacccaaaa caaagcttca tccaaataaa ttgaaacagt gtttctttta aaccatcatt  36120

gaattagtct attgtttcca aacaacagcc ctgatatagc taaaattagt tgctttctct  36180

tctctatatg ttacatgact ctagccaaac atttgctatg accagtggcc ctgagtggtc  36240

agcagataat caacacattg agaccacaac ttgattgaat actgaccttc tgactttaca  36300

tagaaaaata ttaaatgcca ctaataactt gaattccttt taaattaaaa aaaattataa  36360

attgcaattt gactttttaa aatgccacct aaaatttttt ttatcagaat gcttcaaaaa  36420

aaaaaaaaat cctcacttta ttctctgggg gtgggaagag gcaattcctt ccttccacca  36480

caacattgaa ttatcacata aaattgtaaa attatgaata ttatgattga gtttagtaaa  36540

gcattttctt tttaagttca tttatagtaa aacaagagaa accttattga ttctcaaaat  36600

ctattcttta agtaaaacaa actagccatt ctaacttaat gtgcttttaa aaatactgaa  36660

attcagtacg tttagcataa acttactgac gaaggcacat ttctgcatta tttgattttt  36720

cagccttgtt tcatttaagc attaatggca gaggtagaga aaagaaatgg ttttaggtgg  36780

tattagagtt tttattggga ttatgttgaa attttagtgt taaaaaattg ttcatatcct  36840

gaacggaggg attattggag agaatgaatg atgttggatg aacttgtaaa ttcagtcttc  36900

ggcagagtct agggctctga tgattggcac ttaatgaaac tactaaaatt tatgtagatt  36960

ttaatgtctc agtcgcatct gtatctaatt tcataaaagt aatgaaattg aagacctata  37020

cagatacaga atgagtgaag caaattctgc taacatcatg ttgaatgctt tctcagaaaa  37080

agaggaaata taaagagaag agatttgagt atgatttacc ccctccccca tggatacttt  37140

ctttacttcc tacctttttt ctttttcttt tccttctaaa gattctggca gtgggtgttt  37200
```

cagtgttttt taagcttaat atttctggta ttcatttatc tgaagtgatt tctgaatgtt 37260
aaaggagatt tccttttaaa tatttatttt tagctttatg atgagaatct tatttttttaa 37320
atctataact tgttatgact atatgattag taaaagaaaa gcttttaaaa cacactgtgt 37380
attcaggtgt gtcattttag tgtggaatga ctaatacaga aatatgtgac tagcatgtgg 37440
tcagatttta ttgaaaatac ttgtgatgtt tctatggctg ttccccttat atttttataa 37500
ttggtaacat aattcatatg ctattttggt tttgtctatt tgtgttacat atattttagt 37560
ctgatcactt ttgctgttta tttaatgttt attcatttta tgaaagaatt attctgaaat 37620
ataccttgcg taaatgtagg ttaaatgcaa attgtattaa cagtgaaatg aatatgtggg 37680
tagaggtcac tttaggggcc ttttgagatt tagtgaagga aagattgtat cgaaagggtt 37740
tacttcagtg tgactgccta atgtgaaagt cagaacatct gcattaattg gttagttaca 37800
taaatcttag tccactctgg cctacaggtg attgaaacag accaggaaat cttaatttac 37860
attaagttta gactaggtct gaggcatagt tcttaaagca cattcttttt tactttaatg 37920
attataccta attttaatta gcagtgagtt ctcattatgt gctactactt atgggggcaa 37980
attaaataag caaaataggt ttgtgctgaa tcgcatttac ccttctgagg acatcctggt 38040
aatattttca tcaagagtaa ttgtgtaatg cagtatttac aggtatttgc cagattaatg 38100
ggcacttgtt ttcatatttc tgagtcatga aaaatacaca ttggtgattc ctattgcata 38160
aagagtttc aagaaatatt tagttgcatt aagctataac tacaaaaaaa atcaattact 38220
tattgacctt tacagagaat ttttaaaagc ccatgctctc cttatttctg cagcttcagg 38280
gagccaactg ctcttacttt cttctggcat attctattaa tacttgggtt ttgtattttt 38340
caaataaata aaatattcct attgagaatt gaaaaagaaa agatctacta agcgttccct 38400
tcccctttgg attatgtgtg atcgtttctg tgctaaacta gattagggtg tgacttgtga 38460
tggtgatttt tgttcatttt acatattaag aaagaaatag aattttatcg cagttcaaaa 38520
ttagttgtag acagtggttt taacccccaa acacctaatt ttgacaggtt gctttcttta 38580
ttcctcagta ccgttgtaaa tgtctctaaa tacagaattt ccagtggagt tcataaatta 38640
attggtagtg gaaggtgaag agggaggagc aacagagatg tgcagtgcta tgaataagtt 38700
taggaatatc aagatcaatt ctgaaagcta acagtttgga tcaactgtca tgaattagag 38760
gtttaaggag agaaaaattt agggctatat ttaggcacaa ggaaatgcat taatcaggat 38820
tacaatttag cttcttttat ttgaggtaga aatctaaaac taatcatggc tatataatac 38880
taattgttga gttatgttgt ttcttactat gctttattac caaaaaagga taaaatgcac 38940
attttacttt cttttagatt attttaggta agattaagtt catatttgtc ccatctttat 39000
ttaagctgct gtttaataaa tgaaaatcta atgacttgaa tgtagtcaac ctgatgtctt 39060
aatattgata taatcatttc atatttcata gtgccctttt acagccattg tcaactgact 39120
ggagagcaac ctttttcttt ggtaatatat ttctatggat tatgtatttt ttctgctgga 39180
atattgagaa aattaatttt tcataatata tatgtagaat aaattatggg gttctgcaag 39240
tgctagacag tcacttaaac tatattgcaa tacattcctt aaattcaata ttttgaatga 39300
aaatgtgtta tcccctaatt ttatccctgg gctaatttaa atattaattg catcccaata 39360
gagctgcatg cttaaacata ctttttcaga gtaacccaag tattaattct gagtgcttca 39420
aaatattttt tagcaagttt caacaagatt aatagtgttt ataatgcagc aagttcagtg 39480
aaagtacctg ttgttttaga atttttttc attcacacta tagggcacca aaaatatata 39540

```
taaggggaaa aaaggtttaa tgatatgatt agttgtaaat gtttacacat tatcttacct  39600
tgaattttta tttttgtaaa aaaataattt gagagttcag taagtatgca gtgtttaaga  39660
tacacagttt gttgcaaaaa gtgtgaactt actatttctt tttacagtaa aattagcctt  39720
tattctagtt gatttcataa ttgtccataa tatttagccg tggctattat gaaagtatat  39780
ttgatagcca aattttgaaa gctattgtga aatgatacaa ttcagtacat gatttattat  39840
ttcatgttgt ttggggcaat gctgtgactt acgaccttat gattgtcacg tgctgaacac  39900
taaagctcta ccagtttgtn nnnnnnnnnn nnnnnnnnnt ttgtaattac tgaggataag  39960
agcttcctta attttaagac tatttaaatt tcagattttc ctttttttatt ttttttaacc  40020
cttaagtccc ttccaaagaa tttgatttag ttatttagta gtagaaacag aagaaaaata  40080
ctcaactaaa agtccaaaga cctagtttct aatgctaagg gagacagtct gtggcctcaa  40140
actaggtact ttggagtcaa aaatacttta tttatgacta tgaattgttt tcaaaacacg  40200
tgtgtgtgtt tctaaaattc caaaatcctt tcaacgcatc aatttgatga gggaagtaat  40260
tagggtgggg aatggtataa caaagttagt tctttgacat tttctttata gattatcaag  40320
tgtaagacaa atagatgtga atacagattt ggggttttta taagataagg atttaaaata  40380
acgtagttgg tgatacataa aaagtaaact attgctgttg ttagcacccg agaggtgggg  40440
ctcttgggtt ctcagagctt gttttctatc ttaggtacag ttattttaga ttagaactta  40500
aaagaacttg agagctcccc taatcttacc ccctaatttt ttcgaatgag aaattgagat  40560
ccataggaag tgttgaggta aagatcacag aacacttaat tagcggtgtt gccagtttga  40620
atatctcaat tcttagttat ctaagttccc tggtaggctt ctttaattat ctgggtctct  40680
tctagacatt tgaaacaaat agtcgattga cataatacag actagccaca tactttataa  40740
gagatacttt tgactcattt agatttttaa aatatacagt gtctatattc ttccctatac  40800
attttgttaa cctatttttc cctaataatg attaagcacc aattatgtga cagcactatg  40860
ctaagcactt tgcatgcatt catttcattt aaatctcaac tctgtgaaaa gtttttattc  40920
tagttaccgt attaagtctt gattctgtca atatccatgt agcacagaag gcagcagtta  40980
tttaccttaa ttttacaaat gtgaaaacta gaggcatttt aagagaaaaa gagaaaagaa  41040
tagccaggca aatcttaata cttatctgaa gggaaatatt taatattggg tatgttagtt  41100
cctcatgtat ctttaataat ttttgtcaac agcaaatctt taaataaaat ataagggatc  41160
aggcctttac tctcttgcat atatttgtaa agtcacttac tgctttttgt cacagtttca  41220
gtttctgtaa aatacggcgt ttttacctga caggatttgt gcatgtatgt ttactttgaa  41280
aattagaaag cattataaaa atgcaaggtg gaatttttaa agctctgcca aattcactta  41340
gcttaaacca gtatgacgct cattggctaa agtgcattat gacatctgtg actgtggtgt  41400
aggtatttcc tataattaag actcttttag ggtctgctac atgcaatccc ggaaaggtca  41460
tgaattgcag tttcgtgaag actactgcat tttacagcct tcaaatgcca aggtagtatc  41520
tttacaatga ttttttttt cagttttatt tttttgaaag tgccttcaat gaagttttca  41580
gtggattttg ttgagggata tgaagtatgc catctaaata atagccatag tgataactcc  41640
acccacattg ttatattttt attaataaat gctagagtat tctctttctg gtatttcctg  41700
ttctgatgtt tttgtgtaat caagtatgca aagattcttt gtcattagaa accttaattt  41760
gcctgaaaat gggaatgaag taaggattaa attttttta catttattac atttattgaa  41820
gctgtctgaa aaagctcttg agtatgttga ataccaaaat ttatcctaac tacataaatt  41880
tgggaggatt gtgaaacttg actgcactta cttttttct ttattgatca agtggttgaa  41940
```

```
aaaaacttga gttaaacaaa tttgatgtat taaaccgaag ttataaaagc agaggcaagc  42000
atagaattat taaacggcag tttaaattgg taaacatacc gatgtagaac ctaagtttgt  42060
aggcagcttt cttagatgga aacttaaaaa aaaatttaat tagaacatta tgtgaaattt  42120
gtcatctgga attcagctgg gtttattaag gataaagtgt atgactataa agtagatttt  42180
ttttttaaac agaaaaccca aaataaatgt tctaaatttc caccttggga ggctatgtat  42240
attgctcctc tttgaaactg ccttcagaac caccttgtaa gccataaaag aaaattggac  42300
tcattgcatt atagtaacac ctaactgttc ttgctcaaag aaaatgtatt tattcctaag  42360
ccttatttgt gtgacttcaa atcatttgag tatttccaga tatttagaaa tttactcctt  42420
tcttgaatga catttatttt ctttgagggt atttaaaaaa gcccacatag ataattctac  42480
agaaaatgtt taattctgtt ttgaatatgc ctggaataag tgaatagctt gccagggtga  42540
ctattctgaa atggatgatg cttgttggtt aagttctgat ttgtgttttc tttattaagg  42600
aactttatgc taacagttta tatattcccc cttcttggca tagtaaagaa gtaatagaga  42660
ctactcacct ctaagcctga tttttaaaat gagcatttat tttatgttta agtaaggtag  42720
gtctgctttt gacttggact taaagggaac ttggcaatag cagatataat gtaaatataa  42780
tgtgaattcc tacaacagtc tcccaaacag tttaatttcc cattcataca catttccctt  42840
agtgtatcaa ggaattaagt atctgattat cagtatagca agagcaactc aagtatacta  42900
aaattattta tgcttataaa atagtttgag ttataactac aatataaaat tcatatattt  42960
atgactttta ttcctcacaa cctgaaaaaa acctctgcga ttactgatag tacttttaaa  43020
aactaaatga attttgttac tactattttc taaatttagt catgtttact gttcaaaaaa  43080
tgctagacta aaatggatcc taatctttga aatgatgaag acacgtgtag tggtgtcaaa  43140
aataggatat tcattttgta accattctgt tagtgctgaa gttcttagaa tttctttgtg  43200
acaacagcct acttaagaac tttaaatttt ttaggattgt actaaaagca aactgttttc  43260
ttggatattt gttctttctc cccaaaagat gatttataag ttttcagagc taagaaatgg  43320
ggatgaagag ccattctagc atagcaggta atgttttact gctaacagat ttttctctac  43380
actgctttat tagccttgaa cctcctagtt tgttctgtca gctgggaggc tggtagattt  43440
tctattaggt agcaaatgct tctcatcact aaacacatat catgggctgg tattagtgca  43500
gtctgtagat gggcactgca cttttaatca agaaatgttt ttgaaggaaa gaaaaatagg  43560
tgaagtaatt tctaactcag tattttaggg atgagtgacc ttttaattgg taatgacatt  43620
taacagagct gtacagtgtt ttgggggtcc cacagacata tttaaacaag aaaatagtaa  43680
ataaggaagc cagaaggaaa agttataaaa ctattaagaa aaaaatgaaa attctaaact  43740
tcaattctgg tgcctggcta aatttgattt ttgtatgcct cagtgtttct ctatggacac  43800
tgggaaatca ataagcagcc tagctacgtt attatgttcg taagtggaag aactaaagaa  43860
ctacaaagac atgttctagg ccaagaattc ttgagataga tagagtggga ggttaactag  43920
atgatctcca aggtccttct aattgcgctt ggcagcagca agcatttatc aagctagaca  43980
ctgggcatat ggagatgagg aatatgaaaa tccccagcag catggagagc actctgatga  44040
tactcatccc tgcctactcc tccctcaatt tgctttttga aatgtgagct tgaaggatct  44100
caagctcctt cctgggaaga cataactgaa atttcatgga ggaactgcat ggatgaatgg  44160
gaaacaagat tttattcaac tatttggaat aagaaaaggg gcaacaagga gtatgaaaca  44220
aagaaaagat ggaaagaatt agttgactag atgaggactg agtagatagg aatgagccaa  44280
```

```
caggagactt cagcaactaa tggctgaaag tattatgtgg atgcatattg tcatcaaata  44340
ctacatgata caagacaagg agaatacatg actttcacca taacctcagt ttgtgtaccc  44400
taggtacaag gtattttttt cttctagtca cttaagaata tccttaccct ctaggagaaa  44460
taatcctctt tctgggctcc ccagtgtata agctcaaatc tgaggaagtt ttaactgaaa  44520
tgttctttct ccaggtaccc acatagttta ctctctcact taaatgtcag ctctgtaaaa  44580
gagatctctg actgctctct cggaaatagt agcatctttc acatagtctt tccatcttct  44640
taacatcatc tgtctaattg tgtcttatct gctcacctgc tacaatgtaa gctccgtgag  44700
atcagtgata ctgtctgcct tacttacttc tgtatgccac catctagaat agtgtctagc  44760
ctatagtaag acctctacaa atacatgttg aatacctaaa taaacaaaat ttgacatata  44820
caccaaaaag atgtatagga atggattata tttctaatct ttcccgagta agaaaaatgt  44880
cagcagatac tgaatatcac tgagagagat gatagcccag gttatcttcc ccagatagaa  44940
ataagcctta agactgacag gtgtatatga atacagagag aagtgtacat aaagatgtat  45000
tttcaattgt tgtcagtctc taaatttgct ttaagacttt gaaatggatt gcttttcata  45060
atttcttgga ataactctgg tctgtttacc attgaaaaat tagactagcc aatgtttgta  45120
aatgaaggat tagagggtgt tttcatttgg ttggttggta aaagcttgct caacgcagta  45180
acttatagta aattgtcagt ataggaactt ttgtagcaga agctttatgc ttttcacttt  45240
tataagaatt gagattgttt aagcagatga gtctaatgta tgtttgtact gacttaccta  45300
gaaggtcagg caagaaatcg gtttcctcat ttttcaaata agtgtgtgtg taatcactaa  45360
gagaggaggg gtgtcttatt tttgcctgaa ttttcaaagt atcttttttc agcttattta  45420
tgttttagat ttcacttatt ccatctatag tatataacag tcaaagggtt ggtaggataa  45480
gttcatctct tccactaaga gttatgggag agttcaacct aatatggcaa tgacagtcag  45540
aaaagagaaa atgcatggta agtaggtgtt agctatagca agaaaatcag atgaggtcat  45600
ttaagaatga actgctctaa tgttgaggaa aaaagagggg agggacaagg acagggctct  45660
ggaaggcaac cgaagagaac agccacaaaa aataatgaat agctgaagaa tgaggagaca  45720
acaatcttaa aatgtggcag ggagagggta gttgtcgtat caactagcat agaagagacg  45780
gaatagaata acataaatat atgagtgatt attgttgttg aaaccaatcc ttcaaacgtg  45840
aacattctca aaaatcaaag ctagataaat tagggaaatc ttaaatggca caatattact  45900
agtaattcgt ttatattttt ttaaaaaagg aaccttaaat ttgaaattta gatgtaatta  45960
aagcagataa taagaaacat acttctgaga cacaaagacc ctgagatttg gttaagagta  46020
aggtacaaag gctggaagcc agaagggaat taagtttctg ttccctgaga agtcaacaca  46080
acaggaaaaa actggccaca ccctaattca aactcttacc actcttacca gtagtctcct  46140
aattctctag ttttcccctc tcccttctta attcattctg cagtctactg ccagattaat  46200
cttcctagaa caccactttc agtgttattc ccctgatcaa aaagtgtctg tggttttgtt  46260
gctcatagca tagtggttct ccatctttgt accacaaccc atatgccagc tgatagatgg  46320
tgggtagcca caggaattgt ccataacctt tggaggattt ggcttataca tagtctttta  46380
tccaagaaag catatctgag tgtaagtgag cattataggg atagtctttg aatcgactct  46440
ttttaaaatt tattcttctt tttgcaaatg ccccttcaga atttacagaa ataatgtgtt  46500
cattccatct gtaaaatacc ccaaaatgtt aataaactta tttccgtcac ctctcctttc  46560
ctatttcttc ctgcacatct ccccttattc tccacatttc cttgtaatta tataagcata  46620
aacagagaca tatatgatat tttctgggtt gcttgccttt aaataaaata atgggattat  46680
```

```
cttataccct tttgtctgca gcttgctttt ctcacctaac aagcacacct tggacatcct  46740
tccaggtcaa cagacgcgga tcccattctt ttaaatagtt atacgatatt ctattcaggt  46800
ggtgtcataa tttttgccac tacaaacaag tttctaataa acaccctttt ctatgtatcc  46860
tttacaaata gcaacttttt tcctaagcat agatgatata gtttggctct gtgtccccac  46920
ccaaatctca tctcaaattg taatccccac atatcagggg aggggcctga tgaaaggtga  46980
ttgaatcatg gaggcagact tctcctttgc tcttctcatg atagtgagtt ctcatgagat  47040
ctggttgctt gaaaatgtgt ggcacttccc tcttcactca ctgtctctcc tgccctgcca  47100
tgtggaaaca tgctttcttt gccttccact gtgggtgtaa gtttcctgag gcctcacagt  47160
catgcttcct gttaatcctg tggaactatg agtcagttga acctcttttc tttataagtt  47220
accagtctca ggtagttctt tatagcactg tgaaaatgga ttagtacaga aaattggtac  47280
caggacagtg ggggcattgc tgtcaagata cctgaaaatg tggaagtgac tttgtaactg  47340
ggtaatgggc agaggttgca atggtttgga ggactcagaa gaagacagga agatgaggga  47400
aagtttggaa cttcctagag acatgttgaa tggttttgac caaaatggtg atcatcatat  47460
ggacaataaa gtccaggcta aggtgatttc aggtggagat gaggcactta ttgggaactg  47520
gagcaaaggt cacttttgct ttgctttggc aaatagactg acagcatttt gcccctgccc  47580
tagagatctg tggaactttg aacttgagag agatgattta gagtatctgg cagaagaaat  47640
ttctaagtag caaagctttc aagatattgc ctggctgctc ctaacaacat acagtcatat  47700
gtgttcacaa agagatggtc tgaagttgga acttacgttt aaaagggaag cagagcataa  47760
agatttggaa aatttgcagc ctgaccttgt ggtaggaaag aaaagcctat tttctgggga  47820
gcaattcaag ccagctgcag aaatatgcat aggtaaatgt taatagccag tacaataggg  47880
aaaatgtctc cagggcatgt cagacacctt cgtggcagcc cttcccatca caggtctgga  47940
ggtgttggag gaaaaaaatg gtttcgtggg ccaggcccag ggttgcactg ctctctgcag  48000
cctcaggaca tggtgacctg catcccagct gctccagctc cagctgtggc taaaaggagc  48060
caggagatat cttgggctgt tgattcagag ggggtaagcc tcaagtcttg gcagccttct  48120
tgtggtgttg ggcttgtggg tgtgcagaag gcaagagttg aggcttgaaa gcctctgcct  48180
agatttcagg atgtgtggaa atgcctggat gtccaggaag aagtctgctg caggggcaga  48240
gccctcatgg agctcctctg ctagggcagt gcagaggaga tatatggggt tagagccccc  48300
acatagagac cccactgggg cactgcctag tggagctgtg agaagaggga taccattctc  48360
cagactccag aatggtagat ccactgacag ctttcaccat gtgcctggaa aagctgcagg  48420
cactcgatgc tagcctgtga aagcagtcgc aggggcttga acccagcaga gccactgggg  48480
tggagctgtc caaggccttg ggagcccacc ccttgtgtca gtgtggcttg gatgtgagat  48540
gtggagtcaa aggagatcat ttcggatttt taagatttaa tgactactac aaaaacctac  48600
tcaggttttt ggacatgcat ggagcctgta gcctctttgt tttaaccaat ttctctcatt  48660
tggaatgggg gcatttaccc aatgcctgta ccccagtttt tttcttggaa gtaactagtt  48720
ttttatttta cagtctcata agcagaatgg acttgccttg acccagtgag actttgtact  48780
tggacttttg agttaatgct ggaaggagtt aagactttgg gggactattg ggaatgcaag  48840
attgtgtttt gaaatgtgag aacatgagat ttaggagggg ccagaggcag aataatatgg  48900
cgtggctctg tgtctccacc caaatctcaa tcacttgtaa tccccacata ttgagggagg  48960
ggcctagtgt gaggtgattg aatcacaagg gtagacttcc tcttgttctc atgatagtga  49020
```

```
gttctcatga gatctggttg tttgaaagtg tgtggcactt ccccttctc tctctgtctc  49080
ctgctctgcc atgtaaacat gtgcttgctt ctccttcacc ttccaccatg attctaagtt  49140
tcctgaggcc tctcagtcat gcttcctgtg atgcctgtgg aactgtaagt cacttaaacc  49200
tctgttcttc ataaattatc cagacacagg tagttcttta ttgcagtgtg aaaatggact  49260
catacaatag atttccccaa agttgggttc ctgaatcagg ggtatgtgta tttaaaattt  49320
taacagatat ttccaaatta ttttttcaa ggattatagc aagtcacagt tcccccggca  49380
gtgtttacac ttttctttac aataaaaata tataaatcat tattactaac aaattccttg  49440
ccatgagttc taaaattgat cacaacatat cagtgtgcca tataacatag ctaaagactg  49500
ttgcagtctg gaattcaagc tccttctctg tgcttttagc aatatgtaat gttcaaaacc  49560
aatttaatgc tacttactct gtatgctttc ctttatggag tccaggccat agccccccctc  49620
cctcatctga tagtatcctc tggcagccac agaccacaca gttctttcta cctaaatttg  49680
ccattagcac atagtaggta cccaataaat gtttgttgaa ttaataatgt ttatatattt  49740
ctaatttatc tccaagtaaa tccagtctcc ttaaggacaa ggaatgtttt cactatacca  49800
cctagcagtt aaggtactca atttaggtag ggctgtttga acaaagaacc acagaggaag  49860
caaatagcat ggccttgcct ttaatacata tattttactt ctcttaggga aaactggaat  49920
ggtaagaatc tagtaacaat attaagaaca gcacttttat tgagcagtta ctatatgtga  49980
gacacagttc aaactgcaga ggatacaaca gtgaacaagg ctgaagttgt ttctgccttt  50040
ctggagctta tggtttaaag gtgttacatt caagacattt gtaggacaca ttttaaaaat  50100
gccatccaat ttcaggctct ttccagcaga aactgtggaa tatttttcca ttcattcagc  50160
atttacttag tgcctactct gccaggaatt gaagagaaag cccaaagaca ggcagacctt  50220
acctgagagg tagtgaactg accaggatga ctgtgggcag tagacttgtt tcccaagcta  50280
gcctcaccat ttctgtattt gcatatacaa ggaaaggatt agatataggg attagtgtca  50340
gcatataccc cagggacatt tgtttttagt gaaaggtgct agtcttcatc cctgtaccca  50400
gtacacaaac cactaaggag catgctcctg tcattgtcaa agaatcgtag aattccaaat  50460
ggagctagtt ttggtatcca gatctcactt catgtgagga aactaagatc caatattgtg  50520
ggtaagaatt aggactcttc agattccctg ggtatgaatc tgactaacaa ctgtgtgaac  50580
ttgaccaaat tcataaccct ataaactgtt tcctcacttt taaaatgggc gttacaaaat  50640
taggtaaact gcatagcaca gtgtctggca cttaaaaagc actcctgaag tttttagtga  50700
tgtggtttca gattaggcaa ctccttaatg ccaaaggttt ttacttgaga actctattgt  50760
gccaaaccac accctattca taagcctttt tcattaattg atctcaaact ggcttcatta  50820
tgatcataac tttatttcag tttattttta aaatttattt ttaattttta tgggtatata  50880
gttaggcata tacatttatg gggtacaggg catgttttga tgcaggcatg ctttgtgggg  50940
gtgagatata attgactggg gtgagatatg ccattgtagt tttgatttgc atttctctga  51000
tgattaagga tgttgaacat ttcttcatat acctgttggc catttgtatg tcttttgaga  51060
aatgtttatt cagatctttt gtccattttt ttagttggat tatttgatgt tttcctatta  51120
agttgtctga actctttata tattctggtt atcattccct tctcagatgg gtagcttgca  51180
aatattttct tccattttgt gggttgtctc tttgttgatt gtttcctttg ctgtgcagaa  51240
gctttttaac ttgatgtgat cccatttgtc catttttgca ttggttgtct gtgcatttga  51300
ggtattactc aagaaatctt ctcccatacc aatgtcctgg agagcttccc cagtgttttc  51360
ttttagtttc ctagtttcag gtcttagatt taaggcttta atccattttg atttgatttt  51420
```

```
tatatgtggt gagagatagg ggtctagttt cattttgcct atggatatcc agttttccca  51480
gcaccattta ttgaagagac tgtcctttcc ctagtgtatg ttcttggcac ctttgctgaa  51540
aatgagttca ctgtaggtgt atgaatttgt ttctgggttc tctagtctgt tctattggtc  51600
tatgtatctg tttttatgct agtactatgc tgttttggtt attccagttt tgtagtataa  51660
tttgaagtca gataatgtaa ttcctccagt tttatttttt tttactcagg atggctttgg  51720
ctattctggg gcttttgtgg ttccatataa attctagaac ttttttttcta cttctgtgaa  51780
gaatgtcatt gatatttatt ggtaaagatt gcattgaatc tgtagattgc tttgagtagt  51840
atggacattt taacaatatt gattcttcca atccatgagc gtggaatatc tttctatttt  51900
tttgtgtcct cttcaatatc tttcagtttt cattgtagag atctttcact tctttggttg  51960
agtttattcc taggtgtttt attttatctg tagctgttgt aaataagatt actttcttgc  52020
tttttagat tgttctctgt tggcatctag aaatgccatt gattttttgt atgttgattt  52080
tgtgttctgc aactgtactg aatctgtttt aatagttttt tggtggagtc tttacatttt  52140
tctaataaga tcatacagtc tgcaaacaag gataatttga ctttttccat tccagtttgg  52200
attccctttt tatctttctc ttgtctgatt actctgggta ggtcttccag tactatgttg  52260
agtaacagtc ggcacccttg tcttgttgta gatcttagaa gaaaggcttt cagttttttc  52320
ccattgagta tgatactagc tgtcagtctg ttacatatgg cgtaactttc aaactaattg  52380
attatagtta ggaagtgaag acttaaactt gtggtaccat tatcagattt atatttcagc  52440
cgtaagcttg aagaggaact gaaaaatgca tatgtgatgc atgtgcttcc tatctggctc  52500
tcttccccga ccctcctgcc ctgtaatcta cacaagttcc tctctcagtc actcatcaac  52560
tacttgaacc tctgaggaac ttggggttaa ggtaaattag aataaaactg tctgaagaag  52620
agcaagcctt tcatgtcttg agaagttctt ggggttttag aaagaacatc attgcttctg  52680
ttctccaatt actttgactt cttcttaaaa agaatactaa cgttctgaaa gtcataatac  52740
caaggttcta cctcttcaaa taaggacttt taaaaagttg gtttttgtat gattcagtgt  52800
gaattaaatc ccacaatgaa aaggatttta ctttcttaat gtagattttc aaatacataa  52860
ttactgatgt ttataagtag atttattata cacaccgaag caccttgcaa attctcgaat  52920
ggatcaggtc ttatttttca gccttacttt gaaactttaa gtgaaataat taaggattta  52980
ttaaacattt ctcttaatat caaggttttc catgttgggg ccctctttta taagcaatct  53040
tttgttttct ctgcttgctc aaagtagcta tgtttgttgt atctgttagt atttgctcta  53100
taacaaacac actgggtgcc ttcacactta gatttggcaa ttatcactcc tgtaaatgag  53160
atattacata agataggaaa aagaacagta tcattccgta ttaacaattt agagctgact  53220
gcttttaaaa tttagtgtct ttaaaataac catttatttt tcctcatgag tctataaatc  53280
aggtgggcag ttctgctgat ctggccaagc tcaacttatc tcagctgggc acattcagtg  53340
tatctgctat cagctggctg gctggctggc tgtagcaatg aatggtgaca gcaggctgcc  53400
cttaactttt tcacacagta gcatcagagt tacaaaagaa ccagcagaac cgtgcagaac  53460
tcttgaagac ctaggcttgg aacaactata tttctaccac attctattgg tgaaagcaaa  53520
tcacagggct agtctagatt caagtgggtg aaggagctgt aaattacact gcaaaggagt  53580
gtgactgtag ggagaggggt gtgtgtgtgt ggttttttttg tttgtttgtt ttgttttgtt  53640
ttgttttgtt gttttgcaat ttgtcacagt ggttgtagga atcaggcgta tttaaaattc  53700
tgatccttct gtgatatcga attgttcatg aaccttgcct gtggtggaaa gacagaacca  53760
```

```
ttgtgacaga aggataaaaa cttgtaattt agagactaac aaaggttcag attccagttc  53820
catcacttat ttctgcaatc ccgcagaagt taatcttcct gataggcact cagtaatgat  53880
tgattcacct gaacctcaga ttctttatgt attttaaaga aagggctagg taaatacaaa  53940
gcacttatgt aactgctttt attattgcaa acctggctcc cacactccat tcaaggtgta  54000
agactcagta tcttccttga attaaaaagg aagagaaagt gtgttaggga agggaagaga  54060
aatattttac taattgtggc ctcagaataa agtgaccact cactgggggt attttcctgt  54120
aagaaaagaa tggttgaggc tcagagttaa gagatgcaaa ttcaaaagtc tccttggggt  54180
aggattctct gtgattcatt tggtgagagg tgtaacatta gacacagtcc cagtgtaggt  54240
ttcttttttt aaagaattat ggtccatccc atacacactg ggtgccttaa tacaagattg  54300
ggcaattatc actcctttaa atcaggtttt acataagata ggaagaagaa cagtatcatt  54360
ccacattaac aattgaaagc tgactgcttt taaaaaagta aaagggccat atagaaataa  54420
aatcacatga atttcttgtg ttaaacatag ttgtcatatt cggtgaggac taaacaccta  54480
aattcatccc actagtagta atagaaaaga tgaaacatac acacacagta caactagatt  54540
aacttataca aagggccaga tatctcagaa ttcagacagt cagaaatgtt gactagagtt  54600
aatgcctctt ttaggagagg taccaggtaa gtgttctcaa agaactggaa acggagacta  54660
ccacctctgg cgttatctat ttgtgaacac aagcaagtct gtgaattttt ctgcactata  54720
gctacctttc atgtttaata attatacatt cttctaagaa aagaaggtaa catttgggtg  54780
taatttttta ttaaggataa aatttagtgt agacaataaa ggcattcggc atagaagccc  54840
ttactttttt tttgttttta agttaaactg ccagccaacc tttatggatt gcagtctttg  54900
ctttttttaat tgacatttcc caatttcatt cattttgtat ttttttttta agagacaggt  54960
tctcactctg tcaccaggct ggagtgcagt ggggcaaaca tggatcactg cagtcttgaa  55020
ctcctgggct caagccatcc tcccacctca gcctcccaag tagcttggac tacaggtgtg  55080
caccgccatc ctttgacttt tgtagagatg gggtagtggt ctgttaccca ggctggtctc  55140
acattcctgg cctcaggtga tgctctggtc tcagccttcc aaaatgctgg gattacaagt  55200
gtgagccact gcacctggcc cccaatttca aagactactt tcaaccataa atcaacggaa  55260
actccctcag acatatttgg gatccaagga tattttccca aatgattaat gctaattcat  55320
gtcaatacat ttttgcaaaa cctacaaaaa tggactacca aagaaagatt cttaatttgg  55380
gaaagacagt tacttggaaa gaagagaaac ttgagaggca agtcgagttg agtgttcaga  55440
aatgggagga ttataaagag atagccataa aaatgtttct ccctgtatta cctgctgata  55500
ggatgtatca atgaaggtct tactaaggac cttgtatctt ttcagtgctg cactacgtgc  55560
tcatagggag gaaagataaa tcatgtgttt ttcctgacct caaaggagcc tgtatctggc  55620
tagagagaca tgatgcagac acatgaaata attaagaaac aattaactgt agcaggtgct  55680
gaagaatata ccaggaggtc agagaatggt aaagtgagtg tgggctaaag aatagcccag  55740
agcatcgtca gatggttctt ccttatgcaa attcacattt cctctaggtc aagtatcatc  55800
ctggcaccag cagattcata ggtaatgccc taaggctagc ccaaggcaag ttgcaaaagc  55860
catcatattg agtcatggcc tttttttggc ggggggggatg gcaccccctt cttctctgcc  55920
aaatcaagga gtacagtgcc ctcctaaacc tgctttgttt tagtggattg ttaaaaagaa  55980
gtgaatgaat ttatgcttcg ttagggacag gttacagtgg aatcctgaga agtaaggggt  56040
atttctattt aacaaatgac ataacttgaa ggaatgaaat cataaggatg gactttcagg  56100
cattaataaa aagctgatga gcgatacttt gagacaaaag aggctcccca gtgtaactga  56160
```

```
gatcacagca cctacttcac acacacggga aaccagtcct atctgtctct cccatagagc  56220
agtggctgcc ttgtttttcc tccctccccc tatcgttcat tctaaatctc cagtcctcca  56280
ctgcacctta tccaagccct gatattctta agtcacagat ggtgaatcaa tcaaaattag  56340
cgttaagaac tagtggtaca taactacatc tggaacgcag taagaaaaat atggatttct  56400
gtatgctgtc ttcgctcccc actcttaccc ccatttaaga gttacaggat cagaacccaa  56460
gaatctgaga tttttaaaa gtccctaaaa attttggatg atcacccaca tttagaacta  56520
ctgctctaag aaggacaata aatatgccaa taaattctgt tgctaaggaa gtgattatgt  56580
gagttggaac cctgataaca tgaggagaat cccacaatag ccaaatagtc catgccctag  56640
ttacatcata ataaagccaa aagcagcagg cctacctgac tttctccaga ggtctgtcat  56700
gagcctagag agaaggaaca tggacatata gaggtagctc tagatggaga agggcactag  56760
gtgtcatgga aagaatcatg tgcaagaagt aaagaggtgc tctgaatgtc ctagccctgc  56820
ttagttgtct gtgttctcac ttgagaattt atccacaatt ctttcccatt ctaacaatct  56880
ttggttccag ctgcatttgt gagacagcaa aaagttatgg tccagcctcc ttccactgca  56940
tcatctcatc catttatttc tcctactacc cttgtgtgtc aaacactttt ttgttgatag  57000
tttctcccac tactccggtg tgtcaaacac tacccttgtg tgtcagaaac ttttttgact  57060
tcctgtgatt atccaaggtg tatgccaact ttttttttc tccacatctt tcagctttct  57120
gatgggtaaa aaatttcctt actttgcttt agaataattc tcattggcat aaatctaatt  57180
tcagggagcc tcccttgaaa gctaaatgac attgataatt tatgaaaata taacatagag  57240
cattatgctt attagcatgt tagtttaaat agaagtggtt cgtgaaaatt tttgaaatgc  57300
caaaccctgt ccagtgtttt gtattctccc aaatactcat ccagatacta ttcagaatgt  57360
aacatgattg ttttgaaaca ggattttccc ctagttttta aaaaaggcac tttatacatt  57420
aacccttatg ttcctctttg atcaattttt ccagtagttt aaacagttct cagggaagta  57480
gatttcttac agaaattgtc aagtggctct gtgctgttag catgggtact aatcttttgg  57540
ttacttttca tattttttat aatttctgga agttgacaac ttacttctaa ataaaagtac  57600
ataatttata ttaaaaattt tgaataacaa tctaatttgt aaaatatatg tgagcagcgt  57660
gtatgtgtgt gatgtgtgca catacaaatt atgtctctta aaaatgtatc atggacatct  57720
ttccatgtcc aaacaaatct acctcatttt ttctaatagc catataggta taccataata  57780
tatttaacga ggcccctatt aaaagaattt tgactctttt gtagctatta tagtgttaca  57840
gtgttgatct gtgtatgtat ctttgtatat gtgtatgtgt attttccccc tggctgtttc  57900
agatttttct ttagttttaa attttagaaa ggaaaggttt tgaaattgtc ttaagtgttt  57960
tcagaagcat taaatcatag ctttttttaca tttttctttt aaaagtttta tgtcatctct  58020
atgactaact ttcagtaatt tgttctgcat aaaattcccg aaatcttcca tttaaaaata  58080
ggtggcatga ctagacttcc tcagctgaaa gactgaggtc ccgggaagga ttttggagaa  58140
gctgtgttca aatatagctg ttgaactgat gtccgcctgg agtctggcaa ggtgatttgt  58200
tgaatctagt gtctgcctgc atgccagcat ccctttactg agatttgtag ttttcatcac  58260
ttcatggtaa tcatcccaag ttataagatg gagtctctag aaaatcagta gaatatgaag  58320
gcccaagtca cttgggaaag agaaacagca aactatagat accaaataaa acaggacctg  58380
ctaatttttt ttcttatttt tttctttttt ttaagacagg gtcccactct ttctcccagg  58440
ctagaatgca gtggctcagt catggctcac tgcagcctct acccccaggc tcaagcagtc  58500
```

```
ctcctgcgcc agcctactga gtaactggga ctatgggcat gtgccaccac acctggctaa  58560
ttaaaaaacc attttttttt ttttaatgtg tggagatggg attccactat gtggctcagg  58620
ctggtctcaa actcctgggt tcaagcagtc cttcctcctc agcctcccaa agtgcttgga  58680
ttacaggtgt gagccactgc gcctggctgt tgcttacttt tgatactttt tatactttct  58740
ggaggtttat aatttacttg taaataaaat tgcataatct cttattttca aaaaatttga  58800
gtaatatagt gatttgtaaa atacatgtga gtgcatgcat gtgtgtgtgc atacaaatta  58860
tgtctcttaa aaatatatca tgggcattta aagagtgagc acctccgaag gattttgtgg  58920
aagctgtgtt caaatatagc tgctgacctg atgtcagcct ggagcctggc aaggtgaagt  58980
gttgaatcta gtatcttttt gactcatttt ttttcttttt tttttttttg actcactgtg  59040
ttttgaagcc ctgtcatttg ggcttaaaaa atagatttct gtacactgtc tctcctcctt  59100
gccctcgccc ccatttaaaa gttatagggg cagaacccaa gaatcagagt tactaaaaac  59160
tctctagaaa atttagatga tcacccacct gatcatgtct tttttactca ctatgtttat  59220
aaggccttct tttcatttgc tccactgtaa aacattcccc aagccagtct gaggctgagg  59280
caaattttta acaatttaaa atctggggaa attaatgtaa atgttgaata atgatcatcc  59340
tgaaaaaaca atgaaggtag tagcataata ctttatatat caataaaatg gcaaaataag  59400
acagttgtag aagttgaagg acagaaaaga gtaactgaag ttgagagctt atcttaacac  59460
atttttttgt ataataccat aggcaccata tatttttaaa tttatttatt tcatacacat  59520
aggaaactat atgtatgtgt gtaaaaaata acacctcttt gtacctacca cccaatttaa  59580
ggaacagctc attgctatta cctttggtgc tcgctggatg ccccttccca gtcacatccc  59640
cctcccttcc cacctgcagg actataatag taaatgtcat attttttgca ttattttgct  59700
ttgttttatg attttactac ctatctacat atccctaaat aatacattat ttagttttat  59760
atgtgttaac tttatgtttt ggaatcacat gtagtcttta tttatttttt attatacttt  59820
taagttctag ggtacatgtg tgcaacatac aggtttgtta cataggtata catgtgctgt  59880
gttggtttgc tgcacccatc aactcgtcat ttacattagg tatttctcct aatgctatcc  59940
ctcccccagt cccccaccca ccaataaatg tagtctttat aacttttttt aactcaacat  60000
tgtaagatta attcgtgtaa actgaagctt ttttatagat atctttgtta agccttttaa  60060
tgaatacagt acatacctct ctctctagtc ccatcagtgg acacttggat tgcttccaga  60120
gttttgctgt tttgaacagt gctgctgtga aaatgtctcc tgaaacacat ttataagagt  60180
tttttttcccc aagggaatta tacctagaag tggaataacc agatcataag gcatacacat  60240
ctacagcttc tactaggtaa tgccaaattg tttccaagca gcgttataag tgttctcatc  60300
aacttttttct agtgctagtc ttttacattt gtgccagttt ggtaggtgtg aaatatttac  60360
atttagtttt tcttggtgcc atttaatagt tttttcaaaa aaatatttag aagtcaaggc  60420
agttttttgt ttttgttttt attttttgct tgttctgttt taatgcagac attgagatta  60480
ggacttggaa taaacattgg ttgcaaagtt cctaaaagga aaactttttt ttggtattct  60540
ggagcttttc tggtactgaa taaaccaagt atgttaaatt atacatgtgt agtttagaag  60600
tcagagcagt aattgtgatt gttgaaccga atggcagtaa aaagtttctg aacagttgta  60660
ctgtacaagg gacacctgtt gtgggtcagt tttagcctcc ccaactttta tgttaaaagt  60720
tgcaacaaag tttaagggct tatgttcgat aaactggatg gcgaccagct gtggtaaaac  60780
acagggaacc cttgcgaaga atttcaaaat ttacgcagta gtcctcctta tctgcagttt  60840
tgctttgcaa ggtttcagtt atctgcagtc agctgtgttc tgaaaatatt aagtgaaaaa  60900
```

```
ttatataaat aaagaatcga tgagttttaa attttacgct gtcccaccca tcccacctgg  60960
gatgtgaatc gttcctttgt tcagcgtctc catgctgtag gtgctgcctg ccccttagtc  61020
acttagtagc catccaggtt atcagattga ctcttctagt gttacaacac ttgggttcaa  61080
gtaagcctta ctttacttca tagtggcccc aaagagcagg agcggtgatc ctggcaattc  61140
agatatgccg aagagaagct gtaaatagct tcccttaagt aaaaaatgaa aagtctagac  61200
ttacatataa agaaaagaaa tcatatgctg agactgctaa gatctatgat aagaatgaat  61260
cttttataca tgaaattgtg aagaatgaag aataaatgca tgctggtttt gctgtcatat  61320
ctaaaactgc aaaagttgca gccaatgtgc ataagtgctt agttaaaagg aaaaaggcat  61380
ttaaggtaag tatatgtagt gtttggtact acctgtgatt tcaggcatcc actgggggtc  61440
tcctgaatat agggggagac tgctctttta gtgttaaatg aacactaagg aacagaggtt  61500
gggaagaagt tggaaaagat tagttcaaca gtttgagtgt aggtaaacaa ttatttgaga  61560
aagaagaaaa atgtgattag tattttacct tagcagtagt ggcatagata ataagttata  61620
gtcacacaga actcttagca tttacagaat gttcacattt gtgatcccat ttaacaataa  61680
ctctgaaaga aaggtatcat ctaccactgc tttattgata aagagataaa aggtaagaga  61740
gatgaaacat gttggccaat gatacccatc tggtaagaga cagtgatggg gtgtgacccc  61800
agggctcttc tcgccaagca cagggttctt ttgctttata cttttctgcc tcctgatcac  61860
catggctgca gtttctactg tggacaatgt caacaagcat tgatcctctg ccttcagcac  61920
tcttatgtct tagtaaggat tggaaagaaa aagccagatt cctgcccagg agtttacagt  61980
ctgcaggagc aacagaaaag actgatatga aatatgaaga gaccaaaatg atttataata  62040
aggtgctaga ctatgtagta aaaatctgct ttagctgtaa gtcaaaagca agagcagtct  62100
tttcagaatg gaatagaaat gttggaatta aaggaatttt caaagttctg aattttttttc  62160
caagataaac acgttttatt ttggtaatta tggtattact aatttgataa ccttcaggga  62220
gccacctaat attatagaag atatacatat aatgacaaaa gcaaacattt tatttttaag  62280
gaccacaatc taatctaaaa caaaatttcc ccctttttctg gtctttggtt aattaaggac  62340
ttagttaaat atcaaagaaa gacacatgga aaacatttag tatatttcta tacttttgtt  62400
aatatccttc atgccttgca caggtacttg ctatggtcta gataatccat gaaaatttaa  62460
aggacagatt ttaacaactt tatcttgaat tgatagatct ctaggatcag attgccttca  62520
ctctcagatg caaagcttcc aaccacttat aggttcctga tatcttgctt ttatacagac  62580
ctaatttctc tttctttaaa gtttgttttc ctcagttgct attttttttg aaataatgag  62640
tcagtaaaaa tttccaagtg ggaatttttg tgtttctgca tctatcatga aggtgctcaa  62700
ataagtaggt gtttgaatag gagtagaaac agtaataggc tgaagcaaga ccaatacagc  62760
ttcagctaaa tgccaacctt gctaaaggct ggggggacca gtgtggtatt ctacaatata  62820
caagtctgta gccagtgtcc ttaatatgtt ggcttcacgt ctcctgattc ccttctgtaa  62880
atatgcagtt taagaaattc aagttattct gctctagaag aaacatttgc aaaattaatg  62940
tatcccctca ttttaagtaa agttggctaa accataaaga catatttata attagtgaat  63000
ttgagaagaa tgataatatg cattattctt tgaagttaat atttttcagg tcctaaataa  63060
acaaaaagta ggtttcttct gtctggagtg tatgcaaggg ggtaccatct tgtccttgct  63120
tcctggatgc tattccaagg tgctataaag tcagctgaag agaacaatca taatacattg  63180
atagcatccc tcaaagtgtt tctgagctac ttgggaatct tatttgtgaa taggtagcag  63240
```

-continued

```
aaaaccatct ttgcggggca gcatgggcag aaggattgga gggactgtta ctataaagat  63300
ccactgaact gttcaatatc ttaaagaact ggaaagagcc agattccagt ttaatctgct  63360
cttctataaa tttttagctt ggttcattta aaacaaaaaa aaaaaacttg aagattgcca  63420
gattttgaag acatcttaaa ataggtgaac tccaaggtgc actttaaact tgaaactggt  63480
aactgaatac tccttcacct tttgatctga tcgtgtcaaa atgaatgagc aattagtgct  63540
ctagtaagtt tggaacagaa tgatattaat gtattttctc atgattgatt attttttgct  63600
ttttaataga ttaaacttca ccgtagaata gaatttctca atctcaggac tattgacatt  63660
ttttgactgg atgattcttt gccgtcgggg ctgttctgtg tgttgcagga tggttagcaa  63720
catccctgac acagatctta ctttctgtct ctatggattt gcctattctg gacatttcat  63780
ataaatagaa tcatatatat gtggcttctt gtacctggct tatttcactt aatatgtttt  63840
caaggttcat ccatattgta gcatgtaaca gcacttcatt ttctttttgt ggctaaataa  63900
tactctgtta tgtggatata ctatcatatt tttttatcca ctctttagct gatggacttt  63960
taggttgtgt ccactctttg gctattataa ataaataatg ctgttatgaa tattcatata  64020
caagtttctg tgtagacata tatctttatt tctcttgtgt agataactag gagtagaatt  64080
actggatcat atgataactc tatgtgttac cttttgagga actgccaaac atttttccac  64140
agtggctgta tcattttacg ctcccaccag caatgtagag aattctaatt tctctgtcct  64200
tgcctatatt tgttactgtc ttagccaact gctgtggttc gaatatttgt cccctccaaa  64260
actcatgttg gaacataatc cccaatgtgg cggtattgag atgtgaggcc tttaagaagt  64320
gcttgggtca tcagagctct gccctcatga atgggctaat ccattcatga attaatggac  64380
tagtgggttt tcactggatt gggactagtg gctttataag aagaggaaga gaactaatct  64440
agtaagctca gccttctcac tatgtgattg ctgccctgtg tcaccttggg actctgcaga  64500
gagtccccag cagcaagaag ttcttcatca gctgtggccc cttgatcttg gacttcccag  64560
cctccagaaa tgtaagaaat ccatttttaa aaaaaataaa ttacacagtc tcatgtattc  64620
agttatacca acagaaaaca gactaagact ccatcctatt tggtatgggt atcccattgt  64680
gttttttttat ttgtatctcc caaatgacta acgatgttga acatcttttc atgtgctttt  64740
tggtcatttg tgtattttct ttgaagaaat gtctattaac attctttgcc cattttaaaa  64800
ctaggttgtc tttttattgc tgagttgttg gtgagagaga gagagagaga gagagagaga  64860
gtgtgtgtat gtgtatgtat ctagaatgta tgtgtatgta tatatgtaga tatattctag  64920
atactagacc gttatgaaat atctaatttg tggacaattt ctaccattta gaaggccatc  64980
ttttccctta ttgatagtgt catttgactc acaagtttta atttttatga agccagtgta  65040
ttttttaatt catgtttttg gcattgtatc tttaaaaagt tgcctgatct aaggtcacac  65100
tgattttcac ctatgttttc atctaagact tatagtttta gctcttacat ttagaccttt  65160
gatccgtttt gaattaattt gtgtatatag tgtgaagtag ggctctaact tattcttttg  65220
tgtaatgata cctagttgtc ccagcaccat ttgttgaaaa gattattctt tccccattga  65280
atagtcttga taccttgttg aaatcaactg accataaata tatggactca ttgctggact  65340
cacaattcta tgagtctgta tgtctagtct tacgccagta ccacactgtt ttgattatta  65400
catctttgta cagagttttg aaattgggaa atgtgattct tccaacttta ttctttttaa  65460
gattactttg cctgtattcc atgttcattg caaattcata tgaattttaa atcaactctc  65520
catttctgga agaaaaaaaa aggccattga agttcagata gggattgcat tgaacctgta  65580
gataagtttg ggcaatattg ccatcataac aattagtagg tcttccaacc cataagtaca  65640
```

agacttctct ccatttctgt agatatttaa tttcttttat tcatactttg tagttttcaa 65700
tatacaagtc ttgtacttct ttgattaaat ttattcctaa atattttgtt tttgatgctt 65760
ttatgaattt gttttcttaa ttttatttta aggttgttca ttactactga ttagtaatgc 65820
aactgatttt tgtgtgttga tttttgtatc ctgcaacctt gctgaaatca ttgattagca 65880
taatacagtt tttaatagat ttaggatttc tgtatcatgt catatgtctc tgcaactaga 65940
aatagtttta cttcttccct ttcaatctgg acacttttta cttctttttc ttgcctagtt 66000
gccctagcta gaacctccat tgctgtgttg aatagcagtg gtgagaatgg gcatttttgt 66060
gttggtcttc atcttggggg aaaacctttc agtttaaatg tgttgtgtgg tgttcatagt 66120
tgtcctttat cagattgaga atgttccctt ctgttcctag tttgtggagt gttttctttt 66180
tgtttgtttt aatcaggaaa aggtgttaga ttttgtcaaa tgctttttct gcagctgttg 66240
agatttttgt gtttttttaa tggtctttta ttcttatggt ttatcacatt aattgatttt 66300
catatgttaa acaaaccgtg ttcctgggtt tcatctcaat tggttatggt ttataatcct 66360
ttttatatac ttgtagattc agtttgccag tattttgttg aggatgcttg catttatatt 66420
tataagggat attggtctgt tatagctgac cagtaagtat agtaaactgt atagcttact 66480
aagtgttccc tctgtttttg gggggagttt gagaagaaag attgttggta attgttcttt 66540
aaacatttgg taaaattcac tagtgaagcc atctgggatc ttctttggaa gatttttgat 66600
tactatctta atgtctttac ttgtttgtta taagtctatt cagatttttt tctccttgag 66660
tcagttttga cagttggttt aggcatttgt tcatttcaca tagttatcta attggttagc 66720
atgtaattat tcatagtatt cctttataat cttttttttt ttttttctg taaggtcagt 66780 cgtaatgttc actctttcat ttctgattct agtaatttaa gagtcttttt ttttttcttg 66840
gtcagtctag ctaaagtttt gtccattttc agtgaaacag ctcattttat tttattttat 66900
tttattttat tttagacagt ttccattttt tctcccctaa agtgcagtgg tgcaatctcg 66960
gctcactgca gcctccgcct cccgggttca agtgattttc ctgcctcagc ctcccgagta 67020
gctgggatta caggagcctg ccaccatgcc tggctaattt tttgtatttt tagtagagac 67080
agggtttcgc catgttgggc aagctggtct caaactcctg acctcaggtg atccatctgc 67140
cttgacttcc caaagtgctg gaattacagg tgtgagctac cctgcccagc ccagcttttt 67200
ttttttgttt ttgttgtttt ttttttcttt tttttaacct actcttgttt ttctgttctc 67260
tatttcactt atttctacac tggtcttaat aattttcttc cttgtgcttg ctttggactt 67320
agttcttctt tttctagtct cttaaggtgg ataattcagt tcctgatttg aattcttact 67380
tctttgtaag gcggtcattt actgctatga atttccttct cagaaaagta tatgctttca 67440
ctgcatccca taagatttgg tatgttgtat ttttgtttcc atttgtctca aggtatattc 67500
ttctgatttc ccttgtgatt ttttttcctg tctaacccat ttattattta ggaacttgtt 67560
gatttccaca tatctgtgaa ctttccagat ttccttcttt gtaattctca gtgtcattct 67620
attgtggtca gagaatatac tttgtatgat ttctgtcttt taaaatttat ttggcttgtt 67680
ttatgacctc atatattgtc tgtcctggag gatgtttcat gtacacttga gaagaatata 67740
tattctgctt ttgtcgggta gagtgtttga caggtgtgtt ggtataagtt gtgttcaaat 67800
ctgtttcctt cagattttct gtctagttgt tctatctgtt gaaagtggga tattgaaatc 67860
tacaactaat attgctgaat tgtttatttt tctcttcaat tctgtcactt tttactttat 67920
gtattttgaa atgctattag gtgcaagtaa gtttataatt attatatctt cttgatagat 67980

```
tgattctttt atcattatac agtgccctat aagcacaatt tttatcttaa gtctatttgt  68040
ctaatattag tatagccact tcattttttt tttgtttact gtttgcatgg aacgtttttt  68100
gcttttactt tctgtttgtg ttcttgagtc taaggtgagt ctctgtagat agcaattgga  68160
tctgccaatc tttgcttttt atttggggag tttaagccat tgacacttaa tataattatt  68220
gatgaggaag attatttctg acattttgcg atttgtttcc tttattttgt gtctcttgtt  68280
cttaaattct tccattacta ccttctttct tttgttctat atattttcta gtgtaacaat  68340
tttaatttct tggtcctttc ttttgttgtg tatttttagt tattagtgct tgccatggag  68400
attttattgg cattttaaca gtctaggttg gacacagtgg cttatgcctg taatcccagc  68460
actttgggag actgaggcag gagggtcgct tgagtccagg agttcaagac cagcctgggc  68520
aacttagtga gatactgtct ctacaaaaaa aatacaaaaa ttagccaggc atggtggtgt  68580
gtgcctgtag tcccagatgc tttgagaggc tgaggtggga ggatagcttg agcccaggag  68640
gttgaggctg cagtgaactt tgatcacacc gctgtactcc cccctgggca ccagggcaaa  68700
actagctcaa agaaatgaag gaaaaaaaaa tctaatttag attaatacca actcaacttg  68760
aacagtgtat aaaaactttg cctctgtata cctcttctgc ttcaactctg tgctgttatt  68820
gtcatagatt ttcatctttc tacactgtgt gtttatcaat atagatttaa aatcattgct  68880
caatagttgt ctttagagtc tgacaactgg acttcataga caaagactta aaatcagtag  68940
agaaaaggag atacaaacaa aagatgcatt tttattgtct tgtatgttta cttatgtaat  69000
tccctttcct ggtgttacat ttctaaaggt gaagtcgagt tattctgagt gtccttttgt  69060
ttcaacctga aagacttctt ttagcatgta ttggagatat gctaatggtg gactctcaca  69120
gtttttgtta tctgggaata tgttaattta tccttcattt ttgaaggatg gtgttgccag  69180
gatgcagcat tcttggttga catgtaattc tttcagcatt atgaatatgt catcctactg  69240
tcttctgacc tccatggttt ctgataagga atcagctgtt aatcttattg agaatcactt  69300
gtttttgctt gtcgtgctac tttcaagatt cactctttgc ctttagcttt tgatagtttg  69360
attgtgatgt atttaggtgt gtactttatt ggtctgttct acttggagtt tgttgagctt  69420
tgtagatgta tttcatcaga tttggcaagt tcttttgcca ctattttttt tttaataatc  69480
tttttgcccc tttccactcc ttctgtcact ctgattattt gtatgttgct ttgtttgatg  69540
gtgtacgaga agtctctgag acgctgtcca gttttttttc ccattctttt ttctttcact  69600
tcctcagact ggatggtctc agttgatctc tttgagttca tggattttct cttctccagc  69660
tgacatctgt gaggtgaatt tttttctaga gaatttttca tttcagttat tctacttcaa  69720
aatttctatt tggttcaatt ttatcattgc tatctatatt attctcactc taatgagata  69780
ctgttttaca cttcccttta gctctttaga catagtttat gtcactgaat atatttaaaa  69840
tagctgattt taagtctttg tctatgaagt ccagtatctg ggcttcctca ggcatagttt  69900
ctgttgattt ctttctcttc ctgtatactt tgtttctttg tataccttgt aatttttatt  69960
gttcactgga cattttgaat attatagtgt gatagctctg gcagtcagac tctctcccct  70020
ctccagtatt tgttgttggt gagtattgta gatgtttgtt tagtgacttt tcacggctaa  70080
ttctataaat gttatattct ttgaagattg tgggcacccc aaagtctctg ttttgttagt  70140
ttagtggtca cctgataatt aacagagatt tccttaagtg cctagaagca aaatatcttc  70200
cagtctttgc ccatggcctc tgtgtatgca ttaggacagg ccttgaactc ttacccagga  70260
agattacaac cctgccttag cctttactac cagcttctgc agaacatcaa ggtcaacagg  70320
tggtgagagt ttggagccta ctccctcttt cctgagcata tacacagccc tgcttatgca  70380
```

```
tgtggccctc tagatttcca ggaatatgct ggaccctttc aaagccctta tagaatcccc  70440
agcttttcct cccaaccttt agactagtct attgttttct tcaacagtta cctgccaggc  70500
agcagcaaac taagatatta acataaatgt tttcaacttc tccacccgca atgtgcccca  70560
gtgaagcact aagccagttc taagttaagc aaaataaaga caatcctttt gaggtgttct  70620
tccatggagt caccagacag gtaaaccaaa taattaatta caagtctttg gctgggcgtg  70680
gtgactcatg cctgtaatcc cagcactttg ggaggccaag gtgggcggat catgaaggcg  70740
ggtggatcat gaagtcagga gatggagacc atcctggcta atgtggtaaa accctgtctc  70800
tactaaaaat acaaaaaaat agcctggcat ggtggcaggc acctgtagtc ccagctactc  70860
aggaggctga ggcaggagaa tggtgtgaac ctgggaggtg gagcttgctg tgagccaaga  70920
tggtgccact gcactccagc ctgggtgaca gagtgagact tcgtctcaaa aaaaaaaaaa  70980
aaattacatg tctttgtgaa agaggcccat tctgctgtct ttcataccag gaatatggaa  71040
tgtggactgt tattttcatg gctactgcta agctggggat caggggatag atgggactgg  71100
gtaaaacacc acagagtttg ctgttcttac caagaattag ctggggaaga gggttgtttt  71160
ttttttgttt ttcaataaaa attccctggg ctgcttcaag cctttgatta attttcaggt  71220
tctgaaaagg ttcagtttga cagtttttgc cctttttatt tgcttttatg gatgtgttga  71280
acttggagtt ctttattcca ccagttttgc tgacattaat tgttttaaaa gcactttttg  71340
taaaacccaa gtgttgtctc tctcaaggct tgccaataat taaaaatact cttactcccc  71400
tttgattatg gaaatgaatt cctattgacc aaaattcaat actagaggtc tttcaagctg  71460
ttttaccatt tatctaaact ttagaatcta atgattcctg tacattgtct gacatgctgg  71520
tggtcctcga ttgtcgtaag ttcaactttg gaacaaatga actttttgtg tgcaagttgc  71580
cgattgttta gaagttacaa attgatgctc cctccgttga actgttactc gtgggacatc  71640
taggaatttc ttatagcagc tgacaaatat ttcaagtcac tgcctggtag tactgtctgc  71700
caggcaacag cttcagtagt agagccatct ttatctatac ggcagtgttt gagcaattgt  71760
ttactggtgt tttcctaact actcagaaga actatcaggg attatagagg tagctcagag  71820
agttgggtgc aagtagagaa atctacccag cttatatcac acatcttatt tctagagaag  71880
ccttcctttg aagaaagagt gctaaggttt aaaaaattac cttgaatgcc acttatattg  71940
cattttaatt ttattttaga gaaattaatg gaaagtagaa aaattaaggt actgataact  72000
agtgttcaga atgttggtta aagcgtctgg caattaattt tttatttcct ttttgaattt  72060
tattaaaatt taacaatttt cagtttatgc tgtaatccag accaaggttt cagtctgatg  72120
aagttaatgc cagtattgct gctacctatt ttgtctttag tcattcatcc atgcttccta  72180
cctatactga ataagctagc ttaatcttaa cattcaaaaa agaaagctgt tgcctaagtt  72240
aagaaaaaca gttctgaact gttttcaaac taaataccca gtagactctc tagttgctga  72300
caggagaatg cttaattcag aattgtcctg cagtaggatc attttatctc attcctgttc  72360
tttcttctat aggatagctt atttgttttc aattgcattt aatatgttgc gattttttgt  72420
gtgtgttttg ttcgtttctg tttttcaatg gatagactca agataaaacc tggtacccta  72480
ctgtagtagc tatcagttta tagcagaggg aatttacatt agaacttagc tgtatatgta  72540
cgtgtatcta gcttggagat cactctgctt actgtttatc agtcatatta gatgagtccc  72600
taatgagata ccagaaaccc cagaaacatc attaggtgga atagtgtctt taatgcttca  72660
ttaagtgtta taggtaagac aaagcctagt accatttgtg gcatcaaggt taggtgttta  72720
```

```
aagacctgta ttcttctgtc ttcagattga aatcgttctg tttttgtagc aatagaaaat  72780
tttagactaa gcttaatcag caaacaaaga taaaagtctg atactttcct gaatattttg  72840
tgtttctgaa taatttaaca atgatccagt tagctactcc tatagaaatg taatggataa  72900
acttttcatt ctcttttaaa ttgccatctt gaatttaacc tattttttaa agctatctca  72960
agtcctctct aaaaaaaggc agtcatcatt tataaattaa aaaaaaaaag cttgacagca  73020
cacaaagtca cagagaaaaa tgtaaacata ttttaaaatt gaattgtata caagccacta  73080
gaaatacttt tgctaagttt acaaatatta gtagagtgga actcatgcat ttagtatgtt  73140
tgaaaatttt gatcaaatac tgtgctatga aaaacatttt nnnnnnnnnn nnnnnnnnnn  73200
nnnnnnnnnn nnnnnnnnnn nnnnnnnnnn nnnnnnnnnn nnnnnnnnnn nnnnnnnnnn  73260
nnnnnnnnnn nnnnnnnnnn nnnnnnnnnn nnnnnnnnnn nnnnnnnnnn nnnnnnnnnn  73320
nnnnnnnnnn nnnnnnnnnn ntaatttatt tttattttg agacggagtc tctgtggccc  73380
aggctatagt gtaggagggt gatcttggct caccgcaacc tctgcttcct gggttcaagt  73440
gattctcctg cctcagcctg ccgagtagct gggattacag gtgcctgcca ccatgcccag  73500
ctaattttg tatttttagt agaaacgagg tttctccatg ttggccggac tggtctcgaa  73560
ctcctgacct caggtgatat gcctgtctca gcctcccaga gtgctgggga ttacaggcgt  73620
aagccaccac gcccaactaa aaacttgatt ttttaaaaatc caaatcaaag aattgtgtat  73680
tttaatacat ttattggcag ccttgatgct ataccatatg gctctttatc atttaaacag  73740
cttgtaaagg caaacacttc aggattcatg agtgacagaa ggattgagta ctttgggaga  73800
taagagagaa cttttgttga ggatggttga ggaagagtcc aagacaataa caggcagaat  73860
aagcaaaaat ctagagaccc actgtaggca ctcaagtata tgtttgttag aatgaatggc  73920
tgaacttggt gtattaagta acactgagaa aaccatactg actggaagat agttcctaca  73980
agaaactggt gagacgtatg ttacagtcca gattgtggtg agccttgtta aagtttggat  74040
tttattttta taaggctctc cttataaaag gtttcatagg gggttggaaa tgaggcttag  74100
ggctgttaat ggggacaaag tgaggtttta gggtagtggt tttcaaactg tttaaatcca  74160
aactttgatg ataaccctga cataacgatt gtttataact tccacttcag ttttactggt  74220
tttgtcaaaa catcttcatt gatcttactg attgcttcct atgcagatta atattataaa  74280
tttgaatgta caaaggaagc tttagcagta aaatagcaac ttttatctgt cttatgtatt  74340
ggaggtgctg cataatattt aatttttttt tttttttttt tttttttga gacagagtat  74400
ctctcttgtt ccccgggctg gagtgcaatg gtgtgatgtc ggcactctgc aacctttgcc  74460
tcccgtgttt aagcgattct cctggctcag cctcccaagt agctgggatt acaggcacat  74520
gccaccacgc ccagctaatt ttgtgttttt agtagagaca gggtttctcc atgttgatca  74580
ggctggtctt gaactcctga cctcaggtga tctgcctgcc tcagcctgtt aaagtgctgg  74640
gattacaggc atgagctacc acgcctggcc aagatttaat tttttaaaag aaaatatttt  74700
gctaagggtt tcgaaactct tattttagca agaatggatt aagacaaatt aaaactaaag  74760
gcaaagagga ggctcttgtg tttggaattc tttgctaata tttacacaat ataattcttt  74820
ccacaaatat ttaatgatac cagatattag atggttataa tggcaaaagt gttcaaagga  74880
tgctatcata ttcatgattc atgaccaaaa tgaacattat aaggctatcc ctcttcagaa  74940
ttaaatacgt tacttctgtg gaaaacttgc ttttaatgta gaagttgtcc cagagacttt  75000
cttcctttct catgtcctct tatgtccact gctgagctaa catggctcac tgaatgacac  75060
agaaaaaaca tctttggtgg ggagttctct atatagtaaa tgtttcattt attgaggtgg  75120
```

```
tgaacgggaa gtgctgctgg caagagagga tgggaagaga aatctaccca aatccttacc  75180
cgctttacgg aacataaact ttgtgttcag tagtatacaa taacttaacg atcaagacat  75240
cttaacttgt ctgttttcag acgaaagaac tatcatttgg cttgatcagg tatttagtat  75300
ttattcgttc aagcaagtgc ttaagttttt tgttatctca gggttttacg ttagctatta  75360
accaaaagaa ctaattttag ttctggaagt ctaaaaggaa gtaagagaag gtgaggagta  75420
ataagagaag atgaagggag actttgggaa tggtctatga acttctagta actgtaccac  75480
cttaaaatag acaaattaca atgcaattat gaagatatgt atttttcagt gatgacaact  75540
aaaatgtttg cacagaattt tctttttat tgagtgttag aaattctact ttggagatac  75600
taccttgcac aacaaaaaaa taaaaagtga gtgtggaatc tcatcttgtg gctctaggaa  75660
attttttaag tgtggaaact gaaggagaag aggagaaagg gagcatggca ttcccctgtt  75720
tgtagttcac gaggtgggtt taaattgcct tttgccagtg cagctgcacg ctgaggatta  75780
tagaattatt tttaaatgtt tgtagaatta tttttcactt attagataag atgtatatct  75840
tttgattttc tccaatttca gctttcttat gctgtgatgc tcaagacaat tttgtatacc  75900
atatgtagtt ttgttaaatt aacaaagtgg tgttttttgt ttttcttttt cccattggtt  75960
aaaatgtaaa gagaaagtgg aagttagaaa tgtatccaaa aatgtaactt tccctataat  76020
tattaaaata gcaatctaaa tttgaatttt ctttgtgcat aatctttttt caagctattt  76080
gccatgttaa caaacttgct ttcctgtagc aaatatacta gcagtacatt ataaatatgt  76140
aactttcaac ctatttaatg aacagttgat gctttttag ccctttggat ttaaaataga  76200
agcactgaag aggtgatgag ccactgctgc ctcagcatta tttcaaaatc ctgtttataa  76260
actctacaat ttccaaggtc atgaatgtag cacctttcca ggtactaact attgggacaa  76320
agatagaatt tgattttatg tatttaccta ttgactgaag tctaacttaa atcttacacc  76380
tagtgagatc ttagaaataa catatgtact ctgacctgta actaatccta gtattctgtg  76440
tgtatattct ttctcctttg ggctcctaaa aggaaaatta acgtacatct gatgatcatt  76500
agcactaacc tttttcagca aaacgtaaat gtttagaaag aagtatacga taatttagta  76560
atttaataat gtgacaacat ttgtgtgtga tttttttttt tttttgagaa tacaaattgt  76620
gagaaacaaa agtaaaagca gcagcagaag aaatatcatt ataggatcaa aagattgtag  76680
gaaccaaaac ttcaaaatta ttgggcataa tgtactaaaa acagggcagt ggaggaaggg  76740
gacagtccag acaagctctg agggtccaaa caaagtatta aaatccacaa tcctatattg  76800
ttattgaagt gatttgctct gctatttggg cttgggaatt aagtgaaatt gttgatatac  76860
tagacagata cttcctatcc atttttctct tgataatcag ggttcatttt ttctatttcc  76920
tatttctttg gatattccat ttcttaacaa tctcagtcct tatgctaaga attggttatt  76980
taaaacaatg taaatcaacc tcagtctaat tggtttaagt tcaaatccat tttaagatcg  77040
atactgcgtc ctttaaaaat tttatttaaa agatacttaa actgatgaga ggatactacc  77100
cattccactg ataaagtgtt acgtaagttt atctattgag ggctagttat ttggtttaaa  77160
aatgctgaga ttatggaaag tggattggaa tattttggag caatattaaa aacaatatct  77220
gtaataattt aataaactta taaatccctc tttctctgtt gatctatctt gaaaagactc  77280
tcttctgtct ctaggcattc cttctctgcg gtgtgattgg tagacaggga gtaaacaact  77340
tactgtaaat gggcaccatg ccagttggct tcagacaaca tcaagcttgt gacttgcagt  77400
cagggttagg aaaatgcctt ttaacttgtt catctctgcc tcttttaaac attaaaaaaa  77460
```

ggcacaactc tactaattat taagtatttc ataggtcttt tagggcttat aagatctttt 77520
aggaatggcc tggaagttat tagtactgtt tcattgaatc tgaatacctc taacatgata 77580
atgagaagtt tttaaagggt ggctgtatag ttaaacggaa tttctcagat tgacttcctc 77640
cttatgttga tttatttggg atcatatttg ggagtttctc tgccctactt tcaatgtatt 77700
taatttactg accatcacta tttgggggga aaaagttata tgatatttaa aaaccaagag 77760
ttttacagtt attccccctt ttagatttat ttatttattt attttttaaa gacagggtct 77820
tgctctgtca cccaggctgg agcagagtgg catgatccta gctcactgca gccttgaact 77880
cctgggctca ggctatccta ccacctcagc ccaagtagct aagtgtcaag taagaatcac 77940
ctgggaaatt ccaaggctgt ataccagatt tcctaaatta gatttttggg gttgggtatc 78000
tgaattttgg taaagccctc cacgtgtttc tggaattgct tctaagaaca attgataaca 78060
taatagctgt ggccactata ggggtagtct gtcatattta gatataggca taccttgttt 78120
tattgcactt tacaaatatt gcgtgtttat ttggttttgt ttcacttaca aattgaaggt 78180
ttgtggcaac cctatattaa gcgagtcagt cagtgccatt tttctaacag cttgtgctca 78240
ttttgtgtgt ctgtatcaca ttttggtaat tctctcagta tttcagactt tcttatcatt 78300
attgtatctg ttatgaccag tgatcagtga gctttgattt tttttttttg agatggactt 78360
ttgctctgtc acccaggctg gagtgcagtg gtgcaatctc ggctctcagc aacctctgcc 78420
tcccaggttc aagcaatcct cctgcctcag cctccccagt agctggaact acagacgtgt 78480
gcaccacacc tggctaattt ttgtattttt agtagagacg gggactcccc atgttggcta 78540
ggctggtctc gaactcctga cctcaggtga tccgctcacc tcggcctccc aaagtgctgg 78600
gattaccgtg ccggcctgat gttactattt taattgtttt caggcaccat aaaccttgcc 78660
tacataagat accatactta attgataaat attgcacatg ttctgactgc tctaccaact 78720
ggccattccc tgtctctctc cctcttcttg ggactgtcaa atccctgaga cacaataata 78780
ttaaaattaa gctaattaat aaccctacag tggcctctaa atgttgaagt gaaagagtcg 78840
catgtctctc actttaaata aaaagctaga agtggttaag cgtagtgagg aaggcacatc 78900
aaaagccaag acaggccaaa agcaaggact cttgtactaa acagttagct aaattgtgaa 78960
cgcaaaggaa aagctcttga aggaaataac tagtgctact ccagcaaaca tgtgaatgat 79020
cagaaagtga agcagcttac ttgctgatac aaaggaagtt ttagtggtct ggacagaaga 79080
tcaaaccagt cacaacattt ctttaagcca aaggctaact ttcttcaatt ctgtgaaggc 79140
tgtgagaggt gagaaagctg cagaagaaaa actggaaact agcagaggtc ggttgatgag 79200
gtttaggaaa agaagccatc tctgtaacat aaaagtgcaa ggtgaagcag caagtgctga 79260
tatagaaact gcagcaagtt acctagaaga tctagctaag attgctaaac aaaagatttt 79320
ccatgtagat gaaaaagcct tttgttggaa gaagatgcca tctaggactt ttcacagcta 79380
gagaggagtc aatgtctggc ttcaaaggac aggctgacac tcttgttagg ggataatgta 79440
gctggtgact ttaagttgaa gccagggctc atttaccact ccaaaaatcc aaagaccctt 79500
aagaattatg cttaatcttc tctgcttgta ctctagaaat gaaacaacaa agcctggatg 79560
acagcacatc tgtttatagt atgcttcact gaatatttta aggccactgt aaagacctgt 79620
tcaactgttc agaaaaaaaa tgattacttt caaaatatta ctgtccattg acaatgcacc 79680
tgggctcacc caagagctct aacggaattg tacaacaagt tggatgttgt tctcatgcct 79740
gccaacacat catccgtttg tagcccacga atcaaggagt aatgtcaagt ttcaaatcag 79800
tacattttgt aaggctgtac ctgctataga cagcgattcc tctggtggac ctgggcaaag 79860

```
taagtcaaaa accttctgaa aaggattggc cgttctagat gctattaaga atttgtgatt  79920
cacaggagga ggtcaaagga tcaacattaa tagcagtttg aaggaagttg attccaacat  79980
ttatagatga atttgagggg ctcagcactt cagtttagga agtcactgca gatgtggtag  80040
aaacagcaag agaactagaa ttagaagtgg agcctgaaaa tgtgatggaa ttcctgcaat  80100
ctcatgagaa aatgtgaatg gatgaggagt ttcttcttat ggatggatga gcaaataaat  80160
ttgtttcttg agatggaatc tactcatggt gaagattctg tgaaccttgt tgaaataaca  80220
aaggatttag agtattacat aaacttaatt ggtaaagcag cagcatggtt tgagtggatt  80280
gattccaatt ttgaaagaat ttgtactgtg ggtaaaatgc cattgaatag cgtctcatgc  80340
tacaaagaaa tcttttatga aaagaaaagt gaaactccat tgttgcctac tttaagaaat  80400
tgccacagcc cccccacctt cagcatccac ctctctgatc agtcggcagg catcaacacc  80460
gaagcaagac cctccaccag gaaaaagata acaactcact gaaagttcag atgattgtta  80520
gcatttgtaa gcaatatttt aagattaagg taaatacatg tttaaagaca taatgctatt  80580
gcacacttaa tagactacag tatagtataa atataacttt tatgtgtagt gagaaaccaa  80640
aaaattcatg tgatttgctt tgttgccata ttcactttat tgcagtggtc tagaaccgaa  80700
cctgaaatat ctcagaggta tgcctgtatt aatattattt tgcaagtaaa aaacccagca  80760
tataaaaaaa cgtagaatat gttgagattt cagtaatatg aatgaaaatg tttttctgta  80820
actgaagaac atgataaatt gtaattaggg aagaatgtaa accaagaaaa gatgtccgag  80880
atagccagtt cttgtagttc ataatataaa atttcattat cccaatctca gtaagaatac  80940
ttttaatagc tgttatttat ttgggatata gaatttataa agtacacagt catcttctta  81000
tgatcaattc taggatcaca ttataaccgt ttacccagta ttacagtgta gtaccaagac  81060
aaggagacca aattatagaa ggacaaagat ttgctaagca tattttgtca tcagcatacc  81120
acattgcatg tgcatgcatg tgtgtgtttg tgcatgtgtg tgattgtata aaatattaga  81180
aatccacccc ccaaaagtta aatgactagg aatgttgtga agggattaag ctacccctga  81240
aattacataa caaaactctt ttcatctatt aggtcatctt tcgaacatct tctcttaaat  81300
ttgttataga tctgtctcat ctgtttggat taaaattggt ctgaaagcct aaaatagctt  81360
tttacctata taattatttc ccaactagct tgtagtatag gtataaagct atcacacttg  81420
ctattttagt gaagtatgta aaaactacca tctttcaatt aggaaccatt ggatagcttc  81480
tacaggattg ctggggggaa ccttcataaa gaaagttata tctttttttaa tttttgtca  81540
ttttacttag ctgagaatat aaaataagtc tgctaataat agagtagaaa tgtttctgt  81600
aacagattaa tattgatcaa atgtgttatt aaatgctaaa acaccatttt ttttcctctg  81660
taagccatgt gtttcatgcc acaacacaac agggacaatt gtctgtgttt tatgacagtt  81720
ttgttctgtc agatgttgtt tgttcatttt ggtgaacaaa tgaagagagc cctggacaca  81780
tctttttttc cttaacaaaa gacgaaaatt attcttatct gtatgtctat aatcctgact  81840
ctttgaatgg ctttaatttt ttttaaatca gcatttttta taaagatagg tgtttggaat  81900
gtgggcgata tggctggaca cttagattgg gaccaaataa tagaaggttt tgaacatctt  81960
gctgagaggt ttgggtttta ctctgaaggc agtagagaac cattatgttt ttaagccagg  82020
attgacttgt tctaagctgt accttagaaa tattactctg gcagttgtac atgggatgag  82080
ctgtacgttg ctctgtttta tttggggaga cagttctcta ggagagacta cataggaagg  82140
cagttatatg agtcattaac aaaggtctgg caaaaagtag taaaagcatt aactggagtg  82200
```

```
attagcagtg gggaaggaaa taaaaggata gatgtgggag tcatttggaa agtatgaggc  82260
aattcattga ccttacagaa tcactggttt tctgcttcca ctccattgac ctttccaagg  82320
ttatcagtga cctgcttgtc cttaaattca gtggacactt tccagtaacc tactgttggc  82380
accagccctg tgctagacac caggatcctg tttgtaaagg catctgccag tggtttctgt  82440
gacacaattg tttctagttt tcctcctact tctctagcct cttcgcaagt tcttctttca  82500
gtttctcaga gctttgtgct aggcgctctt cttattttct ccttctccaa gtgatctcat  82560
ctttttctgt tgcatcaatt accatttgtc cttatacaaa ggacagccat atctactgta  82620
tctccagctt agatctctct ctttgcttcc tgacccatat ttccaactat ctaactgggt  82680
atcttttctt ggatgagtta ccgttctctc aaacacaaca tgtccaaaat aattcattga  82740
cttattctaa ggcttgcttc ctctttctcc tgtagtccct gtctcaggaa atatatggtg  82800
ctatcaatcc caaagcagaa atctggacat aatccctaac taccctttc ccctctctct  82860
gcatataatt tcagtcatta ggcctcatag atttgactaa ataaatacct tgcaaacccc  82920
tctacttata ttcttaactg ctcctacctt aagccaggct gccataattt tgtagctgaa  82980
taactgcatc atcatcttga ctggctccct tgtcatcttc aatctatatt ctggattgca  83040
gctagagctt tcaaacataa atatgtgata agatcagtcc tgtgtttaga ataccctagg  83100
gttctcactg ttctcagtac agtctaaggg tttaccatgg attacagggt cttttatgat  83160
ttggtgagct ttttattgta taatctttct aaactgcctt tacttccctc tttcttggct  83220
ctctttgcat aatgctgttc cctgtacttc acctcatgtc taaccttcat ctccctttca  83280
cttctcttcc tccaaaattc ctctgaatat cacattgtca tgcaggccca ttgttgatct  83340
cccacgtctg ggttagatat ccctcctcag taccatcacc gcaccagacg tgtcccccat  83400
cctagcattt gcctcagtgt attgcaacta ctgtgtactt gtgtctgtga ctcttgctag  83460
tctaaaagtt ttgggagagc aaaggttcat gtttgtgttt ttcactgtgg tataccccag  83520
tgccagtata tgataagctc tcaaaatatt tgttagatgt atgaagaact gaaaaagaga  83580
acaggaagag gtaagtttca agactaggaa acaaggctat gaaagttgca ggaaagcagc  83640
aggttacaac ctagaagagg agtttgtttt aggaaatact gtgttttaga ccactataac  83700
tgaagcaaaa aaccaaggcc tgggtgtgga tagtccacta tctggtaaca gtggatactg  83760
atgggtggca aagttggaga ggaagagagc cagattccaa aacagaaggg gtaaagtctt  83820
ctaaaaagat agattatagt aagaaggatt aggggatgga aatatgagcc tgttccactc  83880
atagacctta aacatgagat aatgagccat catgaagaga gtaggcagtt gtccagtgaa  83940
gaaggggatg ctaacccttc ttaagcttga acctttaggt agaagcagtt agagaaggaa  84000
cagccatcat cagatagtgt tgtaaggaaa atggtatcct tggggaaacc tgtgttttgg  84060
taaagcaaag caactaagaa agaatatact accgttgttt aacaatcacc acaaaaagac  84120
agtaggatca tctttgaccc ccctcatcct ttttcaggga cttgaaggac taagaagaga  84180
gaaatctgta gaagagggtt ctctctctga tcctccctcc acttcagttt taccacacat  84240
aatgcaacaa taattaagaa tttgtataaa atgtcaccag gttggcatgc acggagagaa  84300
aattattcag gtgttttcct ttgtcaataa tacaaggagc atttgtgggg ggaaatattt  84360
acaaatatag taagacccat tctctttcta tatttatgtg aaaattttaa gttgtgccct  84420
tgttttatgt gtttctactt aaagatacca tacttaatat atattgttga ttcattaaca  84480
tcgaactcat ggctaatagc accataaatc atgcctgatc aaagcttatg gtactcgtac  84540
tttctctgta aggtacatta tagtcttctc atacatggga actctaggta gtactatgca  84600
```

```
tggaggccat tttaaacagc aaaattcccg agaaaaagca caaaactcaa aaaaatgtgc  84660
cagtaaattt accatgaaaa ggacacttgt ttacagtttg agagcttaaa gcaagaaagt  84720
ggagtgtcag ttcgtttgac ttcacctggg aacatgcata tcagttgact caaacttttt  84780
gctattctgt gtttatccac gaattgacag gaaagcaagt atggatttgg gggttacaaa  84840
taaaatttag caaacacata aacttgcaga tgtggaatct acaagtaatt agaatcaact  84900
atattagttt gatcattaaa tcagtttttt aaagtactat tataacacct tctaacctgc  84960
cccattcact gagtgttgta gtttatagtt tcattgggca ttttcagtag ttttatctga  85020
agtcactttt gaaattttgt acttgaagct ccaaagtatg ctaccggaaa cacgagttga  85080
tgctgtgaaa caaaatcaac aggtaatcca ccatcacagt tgtgggctag aatgcttaag  85140
aaaccttgga gacccagaga tctgagatga atactgaaga attataggca ggtttactca  85200
gtcaagctgc ctgtattttg agggtgtagt cctcagacca aaaagacacc aatgaacaaa  85260
ctcagatggc ctcactgggg aacagagatt gaaagctgac actggaatgt gtacttannn  85320
nnnnnnnnnn nnnnnnnnnn nnnnnnnnnn nnnnnnnnnn nnnnnnnnnn nnnnnnnnnn  85380
nnnnnnnnnn nnnnnnnnnn nnnnnnnnnn nnnnnnnnnn nnnnnnnnnn nnnnnnnnnn  85440
nnnnnnnnnn nnnnnnnnnn nnnnnnnnnn nnnnnnnnnn nnnnnnnnnn nnnnnnnnnn  85500
nnnnnnnnnn nnnnnnnnnn nnnnnnnnnn nnnnnnnnnn nnnnnnnnnn nnnnnnnnnn  85560
nnnnnnnnnn nnnnnnnnnn nnnnnnnatg aaattctttg tgtagcaaaa attaacactt  85620
aagttagccc ttggcaagct ccagttctat gtatagtaaa atggatttcc cagaaagtca  85680
ctctctatcc ccttgaatag acattagaaa taacatgtac tttaagtggg atttacagag  85740
gaagggggcc tttaattctt taccagtgtg atgtaaaaaa ataactaaca ttaaagttga  85800
ggcctagaaa tagcagcact ggcttaaagt ctgttttcag gtgcaagttt ttctttttat  85860
tcgtgtgtgt gtgtgtgtgt gtgtgtgtgt gtgtgtgtgt gtgtgtttta aatagaagaa  85920
ggaaatgcca atttcagttc ttaaaaatat taatgactgc aacttataaa aatgttacag  85980
actgtattct tccctttgta acagatgaga agattttgaa ctttagtctc tactttttac  86040
tttggtaaga cgatttgaat aaactgcaat atttgcaaaa gattttttga gtatgtggac  86100
atttgacatt ttcagtgtca aatatacatt tcatgtactg tataaacatt ctagaaaaga  86160
gagagaggca gggaggaaac tgctcattaa aaagaacttc accctctctg aaaagggatt  86220
tcctttacag tgctgtgtac taaagtctgt gttgtaaatc agaaagcact gagcacacgt  86280
gttgctgctt tggtagcatc agaagtcagt tttcattagc tttataccat tcactatttc  86340
tgccaagcaa tcttaaatta taaaagaatc ttacttgatt ttgtgattct cctatttgtt  86400
ttctgctcat aaagaaaata ccctaaactg aacaactgca tgctacgttt ttaattttta  86460
agacagctaa tgtgtataag acatttatag ttgtgtataa gtttttgaag tttacaggtg  86520
tttcaatttt gctgctatac tttgttaaca tattttagga atgtttcatt ttagccacaa  86580
ctaggatatt aacattattt tggtggtgat ctccttgtaa tcgtgagatc aaccaaattt  86640
gggaaatttt gatttgtcag atttatgaat tttacagtaa cacaaaagtc tgatttcctg  86700
tatattttta aggcccctat acctttgtca aaataaagtg tcagtgatac atgaaaaaat  86760
cataaactat gttcaggcca aactgatact gactttgtta aaaagctaga tagaaatctg  86820
ttttcttctt ctgttacatc tcctcttctg aagaccactc tgtggattga agatttgaga  86880
tcctaggacc taggctagac agattaggag attttgctgt attttaagtg gcagatgcca  86940
```

```
tggaattcta agcctgttac gaaggaggag aagaagaggc acaatgaccc tgacacagcc  87000
ccttggttga ccacagcaga tacctcactt gagcaagtag atatcagctc agttgcttgc  87060
tgattatctc taacttgtca gtaacttact ttgataacct agatttggga ttctgacagc  87120
atgcagtatg tgcctcataa taatctgctg tttatgaaag acataacatt gtatgtttag  87180
cataatggtt aagagcctgc catctggaat ggtctactta tttgggatcc agatatagta  87240
agctttcact taacatcatc agtaggttct tggaaactgt gaccttaagc aaaacaacat  87300
ctaatgaaac cagttttacc acaggctaat tgatataaag aagagttaag ttcctgtggc  87360
atatttctgg tcacaaaaac atcactaaac ttctaaataa agacccaaaa cacctgtaat  87420
attaaacact gaaataaatg taagctgtat atacatttaa gaataataaa aacaaaaaat  87480
aattatttac ccaatttttg gtgaaccagt gagtgatagt gatcatagtg atggtggatg  87540
aaatcaagga ataaatgcaa agtgaaaatt gtaagaagca cgcctgtcac cagatagctc  87600
agaaataata attagggcag gcttgctcag cattttaaaa ttgcactgtt tattgtcatg  87660
cacttgaatg attatcgcag actttatgaa ttttcatttt ataataattt gtaggccagg  87720
catggtggct catgtctgta atcccagcac tttgggaggc cgaggcaggt ggatcactgg  87780
agatcaggag tttgacacca gcctgaccaa catggggaat ccccgtctct actagaaata  87840
caaaaattag ccaggtgtgg tggtatgcac ctgtaatccc agctatttgg aaggctgagg  87900
caggagaatc gcttgaacct gggaggtgga ggttgcaatg agccgagact gtgccactgc  87960
actccagcct ggtgatagag ctagactctg tctctaatga taatgatgat gatgataata  88020
ataataagta ttcatttatt ttccaatgtg ctcattccag ttcagggtcc agggggccca  88080
cagcttatcc tcatagctca gagcaactga ttgtagacag gacgccaccc cattgtagga  88140
tgcactcaca tgcacactca cactcaaact gggacccttt agacatgcca gttaaccgaa  88200
cgcacacagc tctggaatgc gggaggaaag tgaagtacct ggagaaaaac tacacagaca  88260
tgggaagaac gagctgactc cacacagaca gtggccctgg gctgagctgg gcaggcatca  88320
gtttttttc tttttgtgg gggacggagt ctcactctgt cgcccaggct ggagtgcagt  88380
ggtgcgatct cggctcaccg caacctccgg ctcccatgtt gaagcgattc ttctgcctca  88440
gcctcccaag tagctgggat tacagatgcc caccatcacg cccggctaag ttttgtattt  88500
ttagtagaga tgaggtttca ccatgttggc caggctggtc tcgaactcct aacctcaggt  88560
gatctacccg cctaggcctc ccaaagtgct gggattacag gcgtgagcta ctgcacccag  88620
tcggcatcag tgtttttctc atcaatgtta aaacaatgtt gaacaaaaca tttttcaaag  88680
acctgctgta tggctatttt ctagttgtgt gactttcttt gggaaagtta gctaaccttt  88740
ctgagctgaa atgtcttcat tcataaaatg gggctagtaa taatgcataa ggtttttgta  88800
agaattagaa tcagctaata cttaataaag tacttagacc atactaacta attagtttgt  88860
tgtctttgct attattttga tgtggttgtt gtttggtttc acctgtgtgc taacaggaca  88920
tgctgaaata aaatttaaga attggcttta tgatatagaa aagcaaactt ttgtacaata  88980
tggatatgaa agaccgttgg gaacctattc tttctctctt acctaattca tcttagtctt  89040
tttaaagctt agattttcca aatgagctat agcaaaatat aatgtttaaa aatgttcaaa  89100
ttctaagcag tatgtcatag ttaaataact taaaggttgg tacatctaaa aagccctgta  89160
agaacataat tagtaaaatt ctacaattta gaaaaaatac tagctgacag tgactgattt  89220
ataaaagtaa aataccttt gttagtacta atagcctttt tataaattga tgacaaaaaa  89280
ttgaatgaga tttgcagttc atctttctat gatgttggtt tatttaatct ctataatttg  89340
```

```
ctatatttga aagagcatag aaatggaggt catgataaaa tctaggccca gtgccacaac  89400
taaatccctg taggatctct caaggttttg atttcatctc tgaatggaaa taatgccttc  89460
caagaatatt atgaagatta aaaagttacg tattataaat atacacagag taacaatact  89520
gggaatattg caacttgtaa gaaagaggaa gcatatggca tattctgatg gttagggata  89580
tggactctgt agctgtgatg cctgaaagag aactctgact ccactaaagg ctagttacat  89640
gaaattgtgc agataattta acttctctga gtttgcattt ttctttgtct acataatggg  89700
gataataata gtacctacct catacatagt gttaatttct attagtgatt ctcattaaga  89760
tagtattatt gttcatccct ggttgtttgc catcatgtat ctgagttaga gagtcattga  89820
ttttagaact gaaagagtcc caagaagact atcaggtcga gcaacctacc tcctgttaga  89880
caattagctt tatccatgag ttaccaaagg gggagccgaa gcccagagaa gctgaaagag  89940
ttgttgacgg tcgccccgtg agttggtgat agatatctgg aattccatta gttgcccatt  90000
tcctagttct gggctctgca ttgcactaga atactgtgcc gttctaaata tgaaaaggca  90060
gtatgaccat tgtgcttgtc actttccctt cgctagacgc tatcttaaaa aagtcaggaa  90120
acaacaggtg ctggagagga tgtggagaaa taggaacact tttacactgt tggtgggatt  90180
gtaaactagt tcaaccatta tggaaaacag tatggcgatt cctcaaggat ctagaactag  90240
atgtaccata tgacccagcc atcccattac tgggtatata cccaaaggat tataaatcat  90300
gctgctataa agacacatgc acacgtatgt ttattgcggc actattcaca atagcaaaga  90360
cttggaatca acccaaatgt ccaccagtga cagactggat taagaaaatg tggcacatat  90420
acaccatgga atactatgca gccataaaaa aggatgagtt tgtgtccttt gtagggacat  90480
ggatgcagct ggaaaccgtc attcttagca aactatcaca agaacagaaa accaaacacc  90540
gcatgttctc actcataggt gggaactgaa caatgagatc acttgggctc gggaagggga  90600
acatcacaca ctggggccta tcatggggag gggggaggga ttgcattggg agttatacct  90660
gatgtaaatg acgagttgat aggtgctgac gagttgatgg gtgcagcaca gcaacatggc  90720
acaagtatac atatgtaaca aacctgcacg ttatgcacat gtaccctaga acttaaagta  90780
taataataaa aaataataaa aaaaagaaag aaatttaacc tgtgactttc agatcactta  90840
gaaccttggt tgaacagtgt tttctagtgt tctttagtat atctttttgt catcttttgt  90900
tgtctttggg ttcccccaaa agagctatac tctgtgtgcc aggaaacttc acacgtggct  90960
gtcttctctt cctcgacttc cctctctact tacctttcca gctcatagtg aatcagaaga  91020
cttctctgac acctttctct gtctaaaggt ccttccatat tctcgtatgg cagcatgaat  91080
cacagtgtat tttaactggc cttttctttg tatgtctcct acaatgagct gttgaagctt  91140
catgaaaaca caatctgttt tactctgggc agttataatt ccaattacaa agcacatttc  91200
ctggctcctg gctaggaact cgatcatttt ttgatgcatc cttgctcagg actttctgat  91260
tcggtcttaa aacattttgg ggcatctcgt tctcctggtt tctggaaaca tattctcata  91320
ctgctatgaa ggtttttttct gacatttcca acttctctta aattgattca gcaaatgttt  91380
ttccataata aatatcgttg atatgtcatc aatatggaga gcaacaacag aatgcagtga  91440
ggaaactcct cccctggagg tctgagaatc tagattccgg ttctcacaga gccaccacct  91500
tggtgaccat ggacagtaga cctgctgagt ctcagtttcc ttatccctaa agtggggata  91560
ttaatagaac ctgttctcag agatgttacc aagattaaaa taaccaagat aattcctgta  91620
gattatttgg catagtgcct gccacatact aagcgagagt tagcatccat caatttagta  91680
```

```
tgatcataaa aaatgaacag actaaaggaa gtaaccagaa agaaagaaat tctgttaatt  91740
cttaaaatgt aatctttttt tttttttttt tttttttttt actgtggctg tcctagattc  91800
ttattaaaag ctgagagact gagagacttg tcattttgaa catgacatca gtggaacagc  91860
ttatgattca ataattgcat catcctggac aagcaccagt agaagcaagt caggacatgt  91920
gataaaagac attgattttg cccctcctcc ctctttgtat tttctttact ataaaattat  91980
tgatgttaag cccatagcac taatatttca gttcaattca taataaaatt tgaggacatt  92040
tgaatatatt atctgttata aattataatt ttatatttgg ccatggagta tttgaagtgg  92100
gtcttttctt tcacaaaaat tctatttcaa taactaaaaa atagtcttag gagaagtatt  92160
atttaaggac aggtttatat taaataatgt catttcactt tcaacttcct ggtggttaaa  92220
aaaaatatgc taatactaaa ggatatgata cacatgttct gttagaacag ttttggcaat  92280
tagaagactt ctcttcttgt gtttgaaagg gatgttactc gggttagtta tgagccatgt  92340
atccagatgt cctgaaagga ccagtggtgg atgtatttct atttttgtct tttttttttt  92400
ctttctggca ttctagttgc tgagtgactt ttgttttcag ctcttctcac aatcaccatt  92460
gttctaataa ctttgcttaa atagaacatc tccttttgct ataagccatg gggcctttac  92520
cattaatttt ttaaagtact gaaatgagaa cctcataaat taaagaacac tcctgattct  92580
gagttaacag atcctactaa gccttttgca gatggaaatt tcctttaaat tggtttgttt  92640
tcctttaaca ttccattatc ctactgttca ttctttggag ctgtgatttg tttcatatat  92700
ttcaggcttc tcactaaatc aagtcatata agttattatt tggatcattt tgaaactaca  92760
acagcttatc aaacctctga aagaagagtt ttgtgtttgc ccacagaccg aagaactgat  92820
tcagttttac tggctgagct accttcatta ttcatattta attcctggta ctgagggtgg  92880
gaggagagag aggaacagaa aagatgtaac tattgggtac taggcttaat atatgggtga  92940
taaaataata tgtacaacaa gcccccatga cacgtgttta cctgtttaac aaatcctcac  93000
atgtatcccc aagcctaaaa gtttaaaaat gtatatttgg taaatcattc gatgtgtttt  93060
taaaaatatc atctttcagc cgggtgtggt ggcccacacc tataacccca gcactttggg  93120
aggctgaggc tggcagatca cgaggtcagg agttcaagac caacctggcc aacatggtga  93180
aaccctgtct ctactaaaaa tacaaaaaat agctggggtg tggtggtgtg cacctgtaat  93240
cccagctact caggaggctg aggcaggaga atctcttgaa cccaggaggc ggaggtttca  93300
gtgagccgag attgtgccat tggactccag cctgggtgac agagcaagat tccgtctcaa  93360
aaatatatat ctgtatctat atctatatct atatatctca aatatatata tatatatata  93420
tatatatata tatatatata tatattttag agataattaa cccttcccca gaaggcaggg  93480
ccaaagttaa ggttcttcca ggtcctttgt attccctgta aattttagag tcagcttgtc  93540
aatttctgta cacacacaga aaaaaagcct gctgggatta tgattggtat tgcattgaaa  93600
ttaaatcagt ttgggaagag gagacttact ttggggacag agtctatatt gagtcttcca  93660
atccaggaac attgtatatc tctccattta gtcagatatt gagtttattt caacaatatt  93720
ttcagatctt tagttccttt cagtaatatt ttctcatttt tcctatagag ctcttgcaca  93780
tcttttgtcc cgtatctatt gtgtatatgt gttttgctac agttattaaa ttaatataaa  93840
ttttattttc caattgtttg ttgcaatata tagaactttt tataatattg tgtcctgtga  93900
ccatgctaaa tgaactaatt ctagtcatta tgtcttcaat atccttctct tgaattttca  93960
ttgtcttctc ctctgggact ccgttcatat gtaaggccat ttgatactgt ctctcaggtc  94020
catgaagtaa tttttcttca gtcttttttt ttgtctctgt tcttcggttg aatgaacgcc  94080
```

```
attgataatt tggtatgtaa tggctcactt aaacttcctg ttatttataa gatatttcta  94140
ccctcagttg tctggaatcc tttggtccag agcccctcca atcctcagcc tagaaggaag  94200
gagaaggata gggtgaaagg aatgggagag cgtctagctt cagaacagag atcagaacaa  94260
cagaggagtc atcttggata aggaaacttc cctcaaactt attatttata tcctcagaaa  94320
taagaaaaat aatgcattta tcaaataaaa tgattttgaa aaagggaacc tcagagtata  94380
aaactaaact cttggaaatt aaaaggatga tagcataaat gaaaagctta gttgaaggat  94440
tgaaagataa aagtaagaaa atatcccaaa aataagagca aaaagacagc aatgtaaaat  94500
aggagagaag ataagagaat tagagaacca atttaggagt tctagaaaga gaaaaatgta  94560
gacaacaaaa gggaagaaat catcaaagac tggagtaggg gaggtcatgc tatctgtttc  94620
tttttctatt ttttattttg aattacattt tttttttact gtgaaacaag catatgtacc  94680
taagaatgaa caaaatacat ctgcagtatt gcttaacaac agagataggt tctgagaaat  94740
gcatcattag gtgatgtcat cattgtgcaa acatcataga gtgagcttac acaaatctga  94800
atggtatgtc ctacaataca cctgggctat atggtatagc tgttgctcct aggccacaaa  94860
catagagcat gttactatac tgaacactgt atgcagctct aatacagtgg tgaggattta  94920
tgtatctaaa catagaaaag gtacaataaa aatacagtat aaaagagaag aaaatagtac  94980
acctgtatag gtacttactg tgaatagggc ttccaggatt ggaagttgct gtgagccatt  95040
gagtagtgag taaatgtgaa ggcctagaac atttattata taaagtctac tgtagtgtaa  95100
actctgtaga cttaggctac actaaattta tgaaaaattt tcttcaataa taaattaacc  95160
ttagcctact gtaacttttg tacttcgtaa acttttacct tttttttttt ttaacatttt  95220
gactcctttg tagtaacact tagcttaaaa cacacattgt acagctataa aaaatatttt  95280
atgtccttct tctgtaagct tttttccatt tttaagatgt ttttattttt aaactttgtt  95340
gctaaaaact aatacacaaa cacacccatt agcctaggtc tatacagggt caggatcatc  95400
agtgttcaac cttcacatgt tgtcccactg gaaggccttc gggatgataa caaacacaga  95460
gctgtcgtct cctatgataa caatgccttt ttctgatata cctactgaaa gacctggctg  95520
agactgtttg acagtgctct aaaataatga aaaaaatata atacagtaaa tatataaacc  95580
agcaacagtc atttttttatc attatcaagt attatgtact gtacacagtt gtatttgctg  95640
tattttctat aactggtagc atggtagtag gtttgtttat accagcatca ccacaaacat  95700
aagcattgtg ttgtattaca atgcacagct acagctaagt gataggactt tttcagctcc  95760
attataattt tatgggacca tcactataaa cgctgtccat cattgactga aatttatgtc  95820
gtgcatgacc atacatgcaa tttaatgaat aataattata aagctggcac tgtgtaatat  95880
ccaaccaggg taagaaacag aatattgcct gtaccttgga ggcctccagt atgaccatgt  95940
aagtttacaa atcctatttt gttcctcctc cccagaggta ccactgccct gaaaatgtga  96000
tcattatttt cttgtttttc ttaactacct acataaacat ccttaaacaa tataactcag  96060
tttgtatatt ttgaatccca tattaataga atatcatatg tatatgaatt tatgtgaata  96120
gagtattata tatgtcattt tgcatcttgc ttttttcact caacactgat tcattcatgt  96180
tgtagtatac agctatacat tattcattgc tatgtagaat tatatcctca gagataagaa  96240
gatatatgga tgtttataat aaatcattcc actattacga acatttgagt agtttgtagt  96300
tttggtttac ttaaccaaaa aaatgctgct gccaacattc ttccacattt tactgtatat  96360
gcacattaat ttatttataa gtattaaaat aatttctttt tgaatacatg tctagtgatg  96420
```

```
gagttgctag gtcataggac attcttgtct ttgactttac tggataatgc caaactgtct  96480
tccaaaatga ttatgtcctt aaactcagga tacatcttat tgtcaaatgt tcaatttttg  96540
tcagtctgat ggatgtgtaa tggtatttca ttgtagtttt aatttgcatt tccctgatta  96600
ctaattaagc tgaataactt ttcatgtgtt cattggccat ttgaagttcc tgtactataa  96660
agtatctgtg taagtgtttt gtccattttt ctagttttct gtccttttag ttgaaattca  96720
aatttgccta aatctgttat tctcctagca caagtaactg ggatgctttg ctttagattt  96780
agcctaattc tttatgattt tgtcagcttg atggtgcttt taaggatata tatatgtgtg  96840
tgtgtgcgcg cgcgcatgtg catgtgtgta tatatgtatg tgtgtagttt tttgagacaa  96900
agtctcactc tgtgacgcag gctggagtgc agcggcacaa tcttggctca ctgcagcctc  96960
cacctcctgg attcaagctt ttccctgtct cagccaccca agtagctagg attacaggtg  97020
ttccagcata cccagcgaat ttttgtattt aatagaaaca gggtttcgca atgttgacca  97080
ggctggactc gaactcctca cttcaagcca tctgcctgct ttagcctccc aaagtgctag  97140
aattacaggc gttagcttcc atgcccggcc tggatatctt ttagaaatat tttttatctg  97200
gcactttggt ttttggctgg caggttggca cccacagtct gacctaccat atctataaaa  97260
agaaacctgt aaatggtctt agactttgaa ccagtcttcc tgattttgaa cccctacctt  97320
taccccccag tttttgagcc tttcagaatt tttttcataa taattaggtt gcttcttagc  97380
tttcccgact gctgacttaa cagatctcag gaagccaaca atccttgtcc atctgctttc  97440
tgtcttacaa actgttgctg gtattgtctc ttctctttat tcttagaggt gtatgctttt  97500
aaaaacaaat actgggttcc agagggagct gaaataaaag catgtgttaa atataccatc  97560
tttaaccaga actacatttg actggtcatt ttattttcaa gctcacatac acttcaaaca  97620
gagatatgac taaaggaagt atgtgaacaa cagccagggc tctgaacatc acagattata  97680
tcgtcatact tgaaatattt taaattttga tttaaaatga gagctttata gatatatcct  97740
caatggactg agtgtttaag tatttaacat ccaaaacgtt cttactaatc aagagaagac  97800
aaacacccca acagagaagt aggcaatttt tatcaattgc cagttcacca gatttgtttt  97860
ctgttagaag tgaatatggg gaaatacatg tgctcatgtt ttgcctactt tcctggagcc  97920
agtgagaaga ggctgtttag tgatccatat gataaactct aaagttgtcc attggctttc  97980
cagtcccttc taggaattta acttaaggaa ataatcagac atttgcaaag gtgtatacag  98040
tggtatttat aacagtgaaa aaccaaagaa tgaccaataa tgggagaatg gaagttatag  98100
gcaaatactt tgcaactact aaagaatcat gtaaaatatc tattgacata ggagttttat  98160
caaatgtgaa gtatacagct gaatagtacc tcctcacata taaagcacgg tgcaaagtag  98220
ccatttatat tgttatcccc aaaataaata tatgcaaatt ttttaaagat gaaggctata  98280
tatggaagtg tttgctggtt ttctgtcaaa agaatggtgg ctttatttta taatttaaac  98340
tttttgcggt tttctaaatt gtctaaatag ttaaattttt ataatgtaaa agtgtcttcc  98400
aatttagctt catttgacaa attacctttt cattctatct agctgtgtat ttctaaatga  98460
atttacagca gtaatcttag agcagatgaa tttacaacaa taatcttaga atagactatg  98520
gattagatgt aaaaacatga acttaggaaa aaaatatttt gggctttatg gttacagaaa  98580
gttttcctca gtgtggggat catagctgta ttgagtttat tcagttttcc tttcccacat  98640
gaatgaaaaa tggggccagc ctacagctgg aagtgcctcg gcatgtgcca ctctactgtg  98700
tatgatctga tttcttgatg gctagcaggg agagaagcaa attgcctcct attcaaacca  98760
agaccctctg ccccacaaat agcatcagcc agtcatttaa gctactccct gcagtggcaa  98820
```

```
gaaggtgtga accccttatg ttctctgttg catacccttg tctaattcac tatttcttat  98880
tctttccagg ttttggcttt atgctacatt tcagaaatca taaccttttc tagtattatt  98940
ttattctttt tgacactgtg agaaaatgga tgcttcttat agactattta taccattttg  99000
ctctcttttg ggaggcagag acagggacag agttcctcct caggctaact aggaaaactt  99060
actaactgct tccaatgtaa ttttaaagat ctccctcttt ctattgctcc ctgtactctt  99120
aaatcttttt ttttaatttt aattttaagt tccagggcac atgtgcagga tgtgcaggtt  99180
acgtaggtaa acatgtggcc atggtggctt gctgtaccta tcaacccatc aggtattaag  99240
tctggcttgc attagctatt tttcctaatg tcccaccctg ccacccaaca ggccccagtt  99300
acgctcttaa tccttatagc ttagatgtta tgatccacag tggggttctt acagaaggtt  99360
atggaaaaaa aaaaaaagaa acgctcaaag tgcccgaact ttttaaaaat aatcctggta  99420
cagctaaact catgcactga ctgtccacct aacatgtaac agtctgtgtt gtgatacatt  99480
gttttaacgt tctgaatgct tgtcagcttt cagtattaaa gatgtgaatc atttatcagc  99540
aatgaaacat ttagtctaag gttgtcagct atttatgcta caaattaatg acttgtcctt  99600
aaaatatcaa ttttgtgatt catgttttgg caggtagatg tttagtgttc taattttaaa  99660
ctatgaataa aagttttgcc ataatcattg ttttattggt tccttttctc ccctacccac  99720
tacccaaaaa atcctgcaat tctttttagt taaactttta ggttcaaggg tacatgtgca  99780
ggtttgttat ataagcaaat tttgtatcac aggggtttgg tgtacagatt atttcatcac  99840
ccaggaaata aacatagtac ctgatggata ggttttcagt cttcacccac ttcccaccct  99900
caagtaggcc ccggtgtctg tcattccctt cttcatgtca atgtatactc aatgtttagc  99960
tcctacttat aagtgagaag aacatgtggt atttggtttt ctattcctgt gttagtttgc 100020
ttaggataat ggctgccagc tccatccatg ttgctgcaaa ggacatgatc tcattctttt 100080
tatggctgtg tagaattcca tggtgtatat acaccacatt ttctttatcc agtcttctgt 100140
tgatggtctt ttaggttgat tccatgtctt tgctattgtg agtagtgctg caatgaacat 100200
gcatgtgtct ttatggtaga atcatttata ttcctctggg tacataccta gtgatggaat 100260
tgctgggtca aatggtagtt ctgttttaag ttctctgaga aatcatcaaa ctgctttcca 100320
ctatggctgg attagtttac actcctacca ggtgtgcata cacatttccc tttctctgca 100380
acctcgccag gatctgtaat ttcctgactg tttagtaata gctgttctga ctggtgtgag 100440
atggtatctc attgtggttt tgatttgcat ttctctaatg atcaatgatg ttgaacattt 100500
ttcatatgct tcttggccac atgtgtgtct tcttttgaaa agtgttcatg tccggccggg 100560
cgcggtggct caagcctgta atcccagcac tttgggaggc cgaggcgggc ggatcacgag 100620
gtcaggagat cgagaccatc ctggctgaca cggtgaaacc ccgtctctac taaaaaatac 100680
aaaaaactag ccgggcgagg tggcgggcgc ctgtagtccc agctactggg gaggctgagg 100740
caggagaatt gcgtgacccg ggaggcggag cctgcagtga gctgagatcc ggccactgca 100800
ctccagcctg ggcggcagag caagactctg tctcaaaaaa aaaaaaaaaa aaaaaaaaaa 100860
aaaaagaaaa gtgttcatgt cctttgccca ctttttaatg gagttgtctt ttgcttatta 100920
agttccttat agattctgga tattatactt ttatcagatg catggtttgc aagtattttc 100980
ccccattcta taggttgtct gtttactgtg ttcataattt cttttagtgt gcagaagccc 101040
tttagtttaa ttaggttcca tttgtcaaat tttttgtttg ttgcagttgc ttttggtgtc 101100
tttgtcaaaa tacttgccag ggcctgtgtc cataatagtt tatttcccag gttatcttct 101160
```

```
aaggttttta tatttttagc ttttgtgttt aagtctttaa tgcatcttga cttgattttt 101220
ggatatgatg taagaaaagg tttcactttg aatcttcggc atgttgctag ccaattatcc 101280
cagcaccatt tattgaatag ggagtccttt ccccattgct tgtttttgtt ggctttgtta 101340
aagatcggat ggttttaagt gtgtagtctt atttctgggc tctattctgt tgcattggtc 101400
tatgtgtctg ttttgtacca ataccatgct gttttgatta ctgtaacctt atagtagttc 101460
gaagtcggat aatatggtgc ctccagcttt gttcttttgg tttaggattg ctttggctat 101520
ttgggccttt tttttgattc tgtgtgaatt ttaaaatagt ttttttctaa ttctgtaaag 101580
aatgtcattg gtattttgag agcaatagca ttgaacccgc taattgcttt gggcagtatg 101640
gccattttaa caatattgat tctttctata ccctgcaatg ctttgttgtt gtatttaact 101700
ttttggttgt gaagtttttt tcagggatga ttttgttgaa agtaacaact ctaaaaatta 101760
tgttagtaat taaaatttta agtaaagact tttattttca gagattccat ttctcttaga 101820
ctttggagct gttaacagga taatccaatc tgtagtggta ctcagcagtt tctgtttcct 101880
gcatgcagaa ctgcttatat gaaaacacac ttttaaaaat gctttcttat ggctgacatt 101940
cacattctta ttctttttga ttcttttcaa aaagggattc agtttgttaa aaatattttt 102000
tgcaatactt ttatgaagat acaaactctg acagagcttt taaaacaagt ttgagagaat 102060
agtattaatt ttatttgtaa atctgaagat tattttagaa aaaaggaaaa tatttactat 102120
tattttcatt ataaatgctt atcaatttta aagcttccac attgcacatc tcccactgca 102180
acagtagcta ccatttattc tttctcaaaa agtgctgtgt gcccttgaaa tttttacatt 102240
ttgaagaata tccctaaaat tttaaaaatt agaagaaaca cattactttt ctaatgagtg 102300
ttataaaatg aaccacagta acctatactc acttagactg tgaaaaacaa ccaaaaccaa 102360
aatttatttt ctattgctaa attttcaaaa gtgaaaatat atgatagttt acatggcaca 102420
tcactgttat tgtgaattga taaatgtata tgtagacaaa tatgtgtaaa tcagagtaca 102480
tacacattac atacagtgcc acaatacatt tttagtatgt tttgactgat atttaattat 102540
ataatttacc aaaaggatct caccagaatg tggaatagta ctgaatttta gaacaattca 102600
cacgtttaaa aaaaaaaaaa atgtagtcag ccccttttatc tgtatctggg gaatgcaggg 102660
taaaggaata gtaaatgagt attggtataa aaaaaaaaaa aaggtgttac tttcttacct 102720
gtgatacctg ttactttggg tatcatttga cctttatttc tgtgaaacaa aggagttcta 102780
acatcctcta attattataa tattgttcta atttaatcta tcttaacctg tgacacagtt 102840
tgaaaaccaa gcttttacta ttggcatgtg caaaaaaata aagcagcaag tagacttgga 102900
atcttgaatg caaatttaga ttttgcctct taataaatgt ataatacagt gtcctgggac 102960
cagttctctt aatttctgag tcctagtttc tgcatctgtc aaatgggatt agagatacct 103020
actttcagga tgtgatatgg tttgactgtg tccccaccga aatcttatct tgaattgtaa 103080
tccccacatg ttgagggagg gacctggtgt gaggtgtttg gatcatggag gagatttcct 103140
ccatgctgtt ctcatgatag tgagggagat ctcaaaagat ctgatggttt aaatatggca 103200
gtttgccctg tgctttctct ctctcctgcc accatgtaag actttccttg cttcctcttt 103260
gccttctgcc atgattgtat gtttcttgag gcctccccag cattgtagaa ctatgagtaa 103320
attaaacctc ccttataaat tacccagtct cagatactct ttatagcagt gtaaaaactg 103380
actaatacag agaattggta ctggcagaat tgggtactgc tataaagata acctgaaaat 103440
gtgaagcgac tttggaactg ggtaacggtc agtggttgga acagtttgga gggctcagaa 103500
gaaaactgga agatacagga aaatttggaa cttcctagag acttgtgaat acttttgacc 103560
```

aaaatgctaa tagtgatgtg gacggtgaag tccaggctga agtggactca gatagagatg 103620
aggaacttac tgggaactgg accaaatgtt atttttgcta tgctttagca aaaagactgg 103680
cagccttttg ctgctgccct agagaagtga agaactttga acttgagaga gatgatttag 103740
ggtatcgagc agaagaaatt tctaagcagc aaagcatctt agtggtgacc tggctgattc 103800
tgaaagcatt cattcatatg cattcacaaa gatatagttt gaaattggaa cttaggttta 103860
gaagtgaagc agagcataaa ggtctggaaa atttgcagcc tgactatgta gtagaaaaga 103920
aaaccccatt ttctgtggag gaattcaaac cagatgcaga aatgtgaata agtaacaagg 103980
agctgaatgt taataaccaa gacaatggag aaaatgtctc cagggcatgg cagagatctt 104040
cgggggcagc ccctcccatc acaggcctga gacctagaag ggaaaaatgg tttcctggtc 104100
agggtctcac tgctctgtac agctttacga catgggccct gcatccctgc cactccagct 104160
ccaactgtgg ctaaaagggg ccaagttata gcttgcacca ttgcttcaga ggatgcaagt 104220
ctgatgcttt ggcagcttct atgtggtgtt gggcctgcag gtgcgcagaa gacaagagct 104280
gaggtttggg aacttgtgcc tgtatttcag agaatgtata gaaacgcctg catgtccagg 104340
tagaagactg ctgcagaggc aaagccctca tggagaacct ctgctagggc agtgtgaaag 104400
ggaaatgtgg ggttggatcc cccatacaga gtccccacct agtggagctg tgagaagagg 104460
gccaatgtcc tccaggctcc agaaaggatt cactgagagg ttgcagtatg cacctggaaa 104520
agccacagaa tgccagcctg tgaaagccac aggggcaccc ttctgagcca caggggtgga 104580
gctgcccaag ggtatgaaag cccacccctt actgcagtgt gccctgaata tgagacatgg 104640
agtcaaagga gatttgggag cttttagagt taagggctgc ccagctgggt ttcagatttg 104700
catggcgcct gtggcccttg gtttggccaa tttctcccat ttggaacagg aatatttacc 104760
caatgcctgt tccctcattg tatcttggaa gtaactaact tgcttttgat tttataggct 104820
cataagtgga agggacttgc cttgtctcag atgagacttt ggtcttggac ttttgagtta 104880
atgcagtaat gagttaagac taggggactg ttgtgaaggc ataattggtt ttaaaatgtg 104940
aaaagacatg ggatttgaga tgggtcaggt gcaaaatgat atgggttggc tctgtcccca 105000
cccaaatcta atctttaatt gtaacgccca tgttttgggg gagggacctg gtgggaggca 105060
attggatcat gggaggaggt ttttccatgc tgttcttgtg atagggagtt ctcaggagag 105120
ctgatggttt aaatgtggca gtttcccctg tgctctctct ctcctgccgc catgtaagac 105180
gtgccttgtt tcccctgccc cttccaccat gatcgtacat ttcctaaggc ttccccagcc 105240
atgcagaact gtgagtcaat taaacctcct ttctgaataa attacccaat ctcaggtagt 105300
atctttatag cagtgtcaga atggactaat acaggatagt aatgaagatt acagaatatg 105360
tagatcaaga agtgctaagt aaatagcagc tattattatg tagtcaaatt gaatgtatac 105420
attgtggtac ttcagtgtcc tttaaattga gtaactagaa atttgttggc tttctcaatc 105480
tgctcacatc agatgacatg ttattttatg cctatacttt tttctggtta atagatataa 105540
atctattcac tcaacttcta tttacaaaac tggtagtgtg gcaagacgtc tcctttctag 105600
ttaaggctgt ataatattaa gttcatttta cttaaattaa ctatggtttg ggaaatgctt 105660
ttcatatcat catgtatgcc caacttgata ctttagtggg acagtatatt tcagaaaaaa 105720
caaatgtatc ccccaaaatt ctagggttga atacattagt caaacatata acagtgtact 105780
tcagagttcc tctaagggca aaactcatgg tatgaaatac aaaacactca tatttatact 105840
tttgtatttt tgaaatgcag tcttcatgtt aatttagcat tttaatgacc agcatgacat 105900
tatcttaata atttggaatg ccattatgtt catttaagac ttaatatagt aagtatctga 105960
agaaaaaaat ggaagttact gaatgctttt gtatctctta attataattt gtgctccact 106020
gtgatatgaa gaagaggcaa aaacagaaat taactttgat gtttaacctt accttaagac 106080
tgttaagtgg cccacataat cttaaaaaac tctgtcaggc ttaatggatg ttactctgca 106140
ggtccctgcc aagcagcagt cataaggtta tgaggcacat ggattttgga attaggaaga 106200
gctgaattca gattcaggtg ttgccttata atgtgacttt gggcaaataa aaggcccaat 106260
ttttgtattc ttacctgtaa aatggactca gtaaaaaata tttgagataa tttatttact 106320
gtacctagcc atgcagcttg acacacagaa ttacaagtca gtagtttcca gtatgattat 106380
tgtgaaaggg atattttgtt tcacctactg aaaacttttt cagtcttaaa atttttatct 106440
aattggctgt attggagatg tctgctatat aacttttata taatcttaaa aactatttct 106500
ttcctccttg atcttctggg gataagctta ccaatatttt cattatttac taaatatagc 106560
agcccccacc ccttatttat ggaggatagg ttccaaaacc cccagtgtat gcttgaaacc 106620
acccaaattc tatatgtata atgtttttcc tatacataca tacctatggt taaagtttaa 106680
tttattagga acagtaaaag agtaaccgta actaataata gaataaaaca attaaacaat 106740
atgccagcat cactaatctt gtgctttagg gccattatta agtaaaataa gggttgcttg 106800
aacacaatca ctgtgatacc gtggcagtcc aactggtaac agagatagtg atgtggtttg 106860
gctgtgtcct caccaaaatc tcaacttgaa ttgtatctcc cagaattcct atgtgttgtg 106920
ggacagaccc agggggaggt aattgaatca tgggatctgg tctttccctt gctattctca 106980
tgatagttaa caagtctcac atgatctgat gggtttatca ggggtttccc cttttgcctc 107040
ttcctcattt ttctcttgcc accaccatgt atcctgccat gattcctgcc atggcctcct 107100
gccatgattc tggggcttcc ccagccatgt ggaactctaa gtccaattaa acttcttttt 107160
gttcccagtt ttgggtatgt catcacaagc atgaaaatgg actaatacag taaactggta 107220
ccagtagagt gggtgttgct gaaaagatac ccaaaaatgt ggaagcaact ttggaactgg 107280
gtaacaggca gagtttggaa cggtttggaa gactcagaag aagacggcaa aatgtgggaa 107340
agttaggagc ctcttagaaa catgttgaat ggctttgacc aaaatgctga tagtgatatg 107400
aacaataagg tccaggctga ggtggtctca gatgtatatt aggaacttgt tgggaactgg 107460
agcaaaggtt actattgtta tgttttagca aaaagagtgg tggcattttg cccctgccct 107520
agagatttgt ggaactttga acttgagaga gatgatttag ggtatctgat ggaagaaatt 107580
tctaagcagc aaagcactta aaaggtgact tgggtgctgt taaaagcatt ctgttttaaa 107640
agggaaacag cataaaactt cagaaaattt gcagcctgac aatgcggttg aaaagagaaa 107700
cccatatttt gagaagaaat taaagctggc tgcaaatatt tgcataagta gcacggagcc 107760
tcatgcgaat ccctaagacc atggggaaaa tgtctccatg gccatgtcag acaccttcaa 107820
agtagccctt cccatcacag gcccagaggc ccaggaggaa aaagtggttt catgggccag 107880
gtccaggatc ctcatgctgt gtgcaggcta gggactttgt gccctgtatc ccagctgctc 107940
cagctgtggc tgaaaggggc caaagtagag ctcaggctgt ggcttcagag ggtggaagcc 108000
ccaagccttg gcagcttcca catggtgttg agcctgtggg tgcacagaag tcaagaactg 108060
tggtttggga atgtccgcct agattttaga agatgtatgg aaacacctgg atacccaggc 108120
agaagtttta ctgcagggca gggctgtcat ggagaacctc tgctagggca gtgcagaagg 108180
gaaatgtggg attggagccc tcacacagag tccctactgg ggcactgccc agtggagctg 108240
tgggaagaga gctgtcatcc accagacccc agaatggtag atccaccgat agcttgcact 108300

```
gtgtacctgg aaaatccgca gacactcaac gccaccctgt gaaagtagct gggaggtagg 108360
ctgtaccctg caaagtcaca ggggcagaac tgcccaagac catgggaatt catcttttgt 108420
atcagcgtcc tggatgtgag acctgaggtc aaaggagatc attctggagc tttaaaattt 108480
ggttatctca ctggatttca ctttcatggg ccctgtaacc ccctttgttt tggccaattt 108540
ctcccatttg gaacagctgt atttaacctc tgacactgca tggcacacct cccccccccc 108600
acccccgcc cttgtatcta ggaagtcact agcttgcttt tgattttata ggctcatagg 108660
cagaagggac ttacttgcct tgtctcagat gagactttgg actgtggact tttgggttaa 108720
tactgaaata agctaagact ttgggggact gttgggaaag catgattggt tttgaaatgt 108780
gaggactgag atttggaggg gcccaggggc agaatgatac agtttgggct gtgttctcac 108840
ccaaatctca aacttgaact gtatgtccca gaattcccat gtgttgtggg agggacctgg 108900
tggggagggg gtgtggtaat caaatcatgg gggctggtct ttcctgtgct attctcatga 108960
tagtgaataa gactaacaag atctcatggg tttatcaggg gtttccactt ttgcctcttc 109020
ctcatttttc tcttgccacc accatgtaag aagtaccttt cacctcctgc catgattctg 109080
aggcctcccc agccgtgtgg aactgtaagt ccaattaaac ctctttttct tcccagtatt 109140
gggtatgtct ttatcagcag tgtgaaaaca actaatacag atgactagta agggactaac 109200
cgccagggag cgtctccagt ggatatgctg ggcaaaggga tgattcacgt tccagggcat 109260
aagatctcat tactcagaat tgcacagaat ttaaaactta tgaattgttt acttctggaa 109320
ttttccattt aatgttttca aactgttgtt gattgcaggt acctgaaact ctcaaaagtg 109380
aaaccacaga taagtgggga gtcctgtatg taaaattatt cctttaaatt gtttcagtgg 109440
atttgtaggg acctgagtgt gaagtgagag cagcagcatc aaaacctgag ggaaatttag 109500
atagcaaaag aaactcatct agtatactgg cgtgacagag gaaccaagaa gttctcatgt 109560
taatgtgaga atctaagaat taaagaatta agcctttgcc tttgagggaa ggaaagggta 109620
gtgtggcttt aaatcaggtt gagattgttt ctgagggttc tttttccttc ctttatattg 109680
atatgaatag agacacaact gttctgcatt tccatttgtt tttataaatg tctttgtagg 109740
acttaggaac tgctaattat ggaatataag atatacatta gtttgaggaa catctgaaaa 109800
ttaggtcaaa tgacacagac tgtcacacaa ttttaagaca aatgttttta cctatttgac 109860
ctagtctggc aatccctatt tgggcagaaa tcttcatttg caggtcatga ttggaagcag 109920
ggacagaaaa aaattgccac cttttttgta ttatgttacc aagacatcaa acctacaaag 109980
ttcaaagcat tatttctcaa gttgaaggcc tggatagacc tcagcttctc agttctgaca 110040
ctttatcata gtggagaagg aagaagattg cttaagaaca ctgatgttgg tgtcagaaag 110100
acctgggttt gaaccctgac tttactagtt acttaggtca ctttaggcaa ctcacgtttt 110160
ctaaatcttg tttcctcatc tataaatgct gaaaatagta cccacctcat aggtctgtgg 110220
agaggattaa atgggataat ctatacaaag aaagagcttg cataatagtg cctagtaata 110280
gtgagattat acctgtattc tgattataat ctcataaatt tagttgtctc agagttcttt 110340
tgcaaaacag ataaagatat aaagtatgag taagcaaaat aagtgaacat acactgaaat 110400
tttacaagat gctggtgata tggagagacc caagacatgg gcccctaaaa gaaattattg 110460
atagaaacag gatacatata cgtcaaaagg taacatagga tcatctgtgc aaagtgctat 110520
atggcagtgt tttaggaatt ctagaagctg tcatggatta gaaataccat ggtggacact 110580
tcagacaagg aaaacagatc ttagcaaaag ctactcctat catagggcct tgataaatat 110640
```

ttgtgggatc caggatccct gtagtgataa agaaactaca tggattatgt aggggagtga 110700
gaagacatat gactggaaaa ataaagaacc aaattgtgga ccatattgag cttgtactat 110760
acacagtgga ggagcccttc agattttaa tcatgttgag aaaagagtgt tagcagtgtg 110820
tgggggatag aatggaaaga gaagccagtg ctagaaggac tacttagtat caaccattgc 110880
agtggttaaa gcaagaggtg agggaaggca tgcattagaa tggcggcggt cagagtggat 110940
gggaaggaaa aggtcctgac atagtgttac acggagtaat aaataggatg tggaagatgg 111000
gttagaattg gcaaatctct gcatgtaagt ctggattact aaacatagtg agagcaattc 111060
aaatctctct ttaagaatcg aataaaatat ttagaaataa gttactgttg tacttgaggt 111120
gaacacaaat ggcatttcaa agatgctcga gataccttgt tggaaacagg cgacaacttc 111180
accattgtct ccaacatgtt cttgccttct ttgaagatgt catgttcata attctgaatg 111240
tctgaaccat ctattatcct tgtatgttct tatgtgtgag gaaccataag gtgggaacaa 111300
aatccagtct taattctaaa aataaccatg caatgaaaaa gttttcagtc tttgttctta 111360
ccatacttgt tcttggtatt ctgtttacca ttcaatgtac tattatggct tctccttaaa 111420
actcacatcc cctaatgcaa gcctgagcaa acaggactga gaacacaccg cctgagaagg 111480
gagtgcttgg ggtctcaaga cttactctgt ttttctccat ctttgacact tggtttgaag 111540
aaccaaaaag gatacagctg ttaggaagca agttacccaa acacagtgac caaacagtgg 111600
attaattctt ccaatgagaa agaaatacat tatttctatg aaacagatta gactttaagt 111660
agcttagata acatgattat attctctcta caaataaata cacaggacct aagaaaccct 111720
ttatagatcc aagtgtttc ctctccactt ttccatcccc aaacctgcct tgcaagacat 111780
ggccagctta tttggagtta attaaatcaa gaccttcgtt ttacagacaa ggaaaccaag 111840
cccagagaca ttgagtacta ggccactgct gtcttacagg tctgaaaaat cctttactga 111900
aaattctctt aatctattaa tgtataggtt ttgttgctgt aaccctctcc ccaagaggag 111960
tgaatataaa tgatgcagag tttggatggc taccttaata tgaacctaaa gttgaaacca 112020
atacaaacct ctctcaataa atgcaaagca aagagaataa tcagtctttc tttggcttgt 112080
taaataagat aaaacgtgtt ctgctaaaac catttaacag aaatattgtg aaaggtttcc 112140
cctaaagcat ttttctattt gatttgaaaa ctattccata gcttattatc caacaaatca 112200
gtaatccttt agctaatgca gagataaatg ggcagtcaga aaacataatc acctggtgta 112260
tgcagctgag tatttacgtt tttcctactg aacaaagata agaaaaatgc aggtgacttt 112320
aatgtgtaaa aactaccttt tagtgctagc gctagaggga aaaagaaatt actggctcaa 112380
gccaatcctg tacttgataa ctaagctgta tagtccatag cttggcttca gccctgtttt 112440
gaatctcttt ttggactttt cttgagtgga ctgtttaggg ctgcttcagt agtgcagttg 112500
ttgcattttt aagcatagtc tagaaggttt taaaatgttt ctggtccttt tttttttttt 112560
tttttccttt tccactttat gttgcttaaa gctttatggc caggttttct catcctcagc 112620
attactgaca tttgaagctg gatacttctt tgtggtgggg gctgtcctgt gccttgtagg 112680
atggttacag catccctcgc ctcgtctccc ttagatgcca atagcatttc ccccaccgtg 112740
ataaccaaaa gtgttttcag acattgccaa gtgtctccta gagagcaaaa ttactctctg 112800
ttgagaactg cagtgttatg gtatttgcac aaaaactgac aagccaatgg gaatataccc 112860
attctattgg tagttgtaaa aaattaatcc agttatagca gctgtatttc tggaaatttt 112920
ttccatatta acacttgctt tctgaggtgg tatctttttt tttcctccca gtgcattaca 112980
ctgaaaaatc gccgattaat tcacttaaat tgaagactaa gccaatcatg tcatttgggt 113040
aatagttgac caactctgcc cctttctctg tcagggaaag cctctaattt agtaagcaat 113100
actgtatcct tttgtcaagt acattaccac tcctattagc agtagagcaa ttgagacaga 113160
gcaaggttaa aaggtcacca agctattaca tggtagagtt aagttatgaa ttgtagcctg 113220
tctggtttag agtcttcact ttactagtct ccataacagc aattcttcca gtgtggtcca 113280
tggggccctg ggagtctccc ctgaaagggc agactatttt cacagtaaca cacactttat 113340
ttgccatttc attatgtcaa catttgcact gatagtacaa aagcaaagat gagtaaaact 113400
gttggcatct tagtatacag tagttaactg tattcactgc catgcactta aaatgtttga 113460
agaagcaaaa aaattattaa ttacattaaa tttcaaccct taaatacatg tggtctttct 113520
catgtcactg tgacaatatg agaagatgca taatccactt acatcacata tagcatttga 113580
tagttgtctc aaaaaaaagt gtgtataaga ttaaacagtg aattaacccc cttttttca 113640
tggaatacca tgagagataa actctggttt tcagccttgg gtatttggtg atgttttccc 113700
aaaatgactg aagtaaacgt agcactttaa ggaaaacaac ttaaagtatt tgttgccaat 113760
tgataatata ggtttcaagc aaaaattagc atttttgaag acttatatct gacactgtga 113820
gcttgacaaa tgtgactctt ttctattatg aactatgtca acatttgaaa gatctgtata 113880
actcagtgaa ccagtatttt ccaaatgact aatgcatgat aatagaaaat catgcatggg 113940
taaaagatac attcaaagtg caagatagac taacagattt cagtgtaaca atcaaaagtt 114000
cattgataac agttttggat tccacattgc aatactaaaa tctttaaaaa gctaaattgt 114060
caaatgttgg tgtagtatca acaaaaggaa atctataatt acctgaactt aagtttctgg 114120
aggaccatta accttctgca agctcacagg gaagactgta gatcctttcc ctgagatcct 114180
ccagaaagga agaagaaaag ataatcctta ggggtagggt agaaacctat tgtgtgatga 114240
tcacaagtat gtaacaatgc tttatataac tctaatatat ataatccaca caaacccccct 114300
aaaatggcac taataaggga atagactcaa agaagttaag tcagctagcc actgtcacag 114360
ctattagagc actggagcta ggatttgaac ccagatttgt ctgtatgtaa agctgattct 114420
cttcgtaata gtactgagac acaagaggca gctacaaaat actctgatac tccttcctag 114480
accagagttt caaggtttgt tatcatttgt agcatgatac tggatcctca cagtgcctgc 114540
ctttcattca ggtgccagga aacatctgcc tgaatgaatg ggtgtaattt acctgcacat 114600
tttacatgct tctcaaggtg tgtgattaac tcataatcca tccatgactt tcacccgtaa 114660
tcctccttgt ggcaattgct ttgcttgcga gaaaattaag tagacatatc tagctttatg 114720
catggttttc tctctctgaa ctctaacatt aaagctcagc ttcaggaatt attcagtttc 114780
tactacattt gccattctga ttgggaacca ccagcattca ggtactcacc tggaacaagg 114840
cattttgttc caagggttct tcacttaaaa gcaagcaccc tagcaatagt tcataatgga 114900
actttttaac attctcagaa tgtttggcat agctgtgaac acacattgag caatcaataa 114960
ctattacaga taatgatgcc cttaagacca ggacatttag ctttaccatt caaagggggt 115020
gaaatatgca ctcttactat agtgtacttt tggttccttc tgccatgtat ccttatcctt 115080
aataaaagat gtcaatttca tatagttttc tcttgagttc tgactgtttt attgtaccct 115140
agccctttta acaatatcaa acttgcaact gaataccatt tagcattcat ccattttttc 115200
cagtggtgtt caatataggc catcttagtc ctcctatttg tatgacaaaa attgattttt 115260
ttcaccgata tctgtggtac atctggcagc tttccatgta ctcagttctt atctgatgta 115320
gcccagaatg actgcctgaa gggatgccaa aagcctgatt aagattccag atttttagct 115380

```
actgtattat caatccattt gttcatttca gttttacttt cccttgtcat ctgtagctta 115440
cagttgagtg gcctaaacat gttttgcata tattccaata tttaagaatt tgggaaatac 115500
ggtcctagga tttagagtta ataccacctt ccacttatat aatacttact cacaaaatct 115560
tcagtgtttc tgaaaaagaa aaaggaacat gaacatgtat tgaagcagga acttgtagta 115620
gattttctat gtgttatctt attgtcacaa cacacacaca ggtgatatcc ttcccagttt 115680
actgatgagg aaacacaggg gtcaaactgg tagataccta tccaaggtaa cagaagctgt 115740
gaagtggtac agctgggatc taaaacatgt caacttcacc atagataggt catacctgcc 115800
acggcctgta tgaccacatc caggggtgat gacatcattt tcacagggtt gttgagagct 115860
aaaactacaa agtactacaa actattattt aaaatataaa tacatactat atatgcatat 115920
gtgtgtatat ataattcctt ggggaaacat ttcagaatac cgtcctaacc tttaaacaat 115980
gcactcattt tctgtaaact aatatacaga caactggttg gttcctaaaa atagctgtca 116040
ggtgacagag attggctgag caagaatagg agtatcttca gaatagaagc cagagaggtt 116100
tttgcttccc caacacattg ttgcaccatt ccctgttcca ggaccttcct acttctctgt 116160
aaaactctgg cccaaagcag ctcctctaca ttagtcacaa gtttccatta atcagggtag 116220
cctgtgctgg acctacagca gaagtcattt caggttattc tcttctgtta caggctttca 116280
acatgtagtc agtccactca cccaaatcta gcagggaatc aatgccttgt aatacggaag 116340
catctagaaa ttcttcttaa cagtgttcag agaacaatgt gaaaccctgg ggccttttcc 116400
cagaattcgg gtggtgggaa tgctgtcctg gtgactaagg ctgttaggta agcagacagt 116460
tggcaagatt caggaagctt catttgagga cagaatttag ggggagcatt tgaatttact 116520
ggcttaatta cttaagggaa catttataaa agaaattgtc attctacagt tattaccttt 116580
taacttttat tcctaaagag aacaatagca ccaaaaatatg ttacttggta aatgtaattc 116640
ataaccagac tgataactat aaaaaatttt tgttactttg ctctgtgaat tagtttaaat 116700
atatttgtaa ttgaaattta ctactgttat tggctgaaat aaaagaaaga taataaagga 116760
taacagagac aactaacacc caatttaagt ttatttctaa gtgccatctc ttttagagaa 116820
aaggcaaatt aagaaaagtt tagagagagg tactagtatg tttatgaact tgtatagatg 116880
ataagcaaaa cagactttag tatgtagaat tccagaatca acaggttgcc agcatccatg 116940
tttttgaaga tttgcttaag aacacaacca aaaatggaat aggcagtctc taattataag 117000
cagaaggcta caaaatcatt ttagctgcat aatacagttc tagttctaaa gtcaacacgt 117060
aagaggaaaa ttccttagga agatacaaca ttgaaaacca ttgtatcatg taatatgaaa 117120
tgcaataatt aatttttcct ccagtaataa aaagatcact gtttcgttgg tttataaaaa 117180
tacatcttta tcagcaaatg tggcaaaatg ttaagaattg gtgaatattg gtaaaaagta 117240
tatatctatt gtacaattct ttcaactttt ctttgagatt gaaaattttt aaaacaacaa 117300
attatctttt aaacacctag taatcactag accggcactc tttgtggtga gaaaatgaaa 117360
aatgttagag actagactag taaaagaagc agattcacat ttctatcttt ttcttcaggc 117420
caaagagtca tagagtggag tgggcagaat ggaactcact tttgaaagcc tagtgctttg 117480
tccagtctta ctacaagcca gacaggaagg ttatagaaaa tgtttctgga tcagtcttgt 117540
ctgagtcata tgaaattgtg gtttcagcca agatgatatt aggaattgag agacatggga 117600
caaaactttt aagattgtaa aaacattttg attctaatgg gaaacatggg tagaattgta 117660
acgacacttg attgaatttt aaaagatgcc tgtataagat cttaaattag gaaaaaaatt 117720
atgtcctaag caattaggca taggaggcat ctttttagga tgatggaaat atcctctctc 117780
```

```
ctgattgtga tagtagttat gtgactattt aacgaaagcc ataaattata gatttagaaa 117840
acagtcaatg ttattgtgta tgacacctta ataaaggtga ttataaaaat aaacaaatcc 117900
taagcatcta aaaaaaaaaa aaaaaaaaaa cgaagtgaac cagaaccaca ccattctatt 117960
ttggagacac ttcaaaagaa atgacctcat tcttaatttt gtttaaagaa gaatataaca 118020
tgatttgaat atatttagat aggatatttt agtgcctgct agcacttgaa gccatagttc 118080
agtgtgcgca ttctgactat gaagtgagaa gctaagagaa ctgtattttg atatttcttt 118140
gacagttaaa tcataacact gttcttcccc ttctttagcc ccagcatgag accagatgta 118200
agctctcctc catccagctc ctcaacagca acaacaggac cacctccgaa actctgcctg 118260
gtgtgctctg atgaagcatc aggatgtcat tatggagtct taacttgtgg aagctgtaaa 118320
gtttcttca aaagagcagt ggaaggtagt gtgtgttttg aagagtttta tttttcctct 118380
acttggtttt catttctcag ggtggatttt gaaatttcca ttatatgcaa agcccatgaa 118440
ggctaaatat cagttaagag ggcagaggag ggtggcttct aggtcctcta atgtgcagta 118500
aattatttaa aacaacaaca caaaaagatc tagaatgaaa tagaaaagta taagttgatg 118560
cctgggagtt tggtcaggga gcataaggta acactataag aaagtactat catacgaaat 118620
gatggtgtta agtttgggca taacataatg ttcattgcgt tagaaatatg ggctttaact 118680
tccataagct aatagatttc aaagtcaaca cctatactgg cctggcaaaa atgtgagaca 118740
cagaactgca acaggaaaaa aaaagacatt catttcattt cttattcatt ttttttctat 118800
taagccaggg cactgtgcta agtggtataa ataccaataa gacctgatcc ttaccctctg 118860
ggaagtcaca ctccactgaa gtgaaagatg agttaacagt gacaaggtgc agagattata 118920
attcggagga gggagagaga aactcggcct gaggaggtca ggaaaggtat tttagagaaa 118980
gtgatttcac tatataaatg ttgtattaat ataaatctta ctttgttatg gattcagact 119040
gctgacaggg caacagcatt atcttcctaa aggagaaatt cattccacag caaacctatt 119100
agaagagagt ctaaaatttc ctaatattac cagtgactcc tcttggaaaa aaaatagtca 119160
tataatttag ttatttctaa agtttgaaag cagtgtggcc taaaggtgtg attatattaa 119220
tttttaaaga aacatattta ttattcattc attgtatgag gattattatt tgtctcatgt 119280
tgtgtttgca tatccatgag agttagatga gtcattttct tttgttttac tttttaatac 119340
attagcaaat tataaaatta ctcatattac accacagagg ttacaaggat gccagctttg 119400
gccagtgtag tagtcccacc tattgattag agtcaaaagt aaagcccagc cctgcctagt 119460
gcaatgctcc taataaagtg gatgttattt aacacatacg caaaagacgg aagcatcttc 119520
gtgtcctcac tttactactc gctttcttaa ctgcctaagt atttccatga tataaatgca 119580
gtgataatag taagacagtc cctgacttaa caatttttca acttttatga tggtgggaaa 119640
gtgatatgca ttcagtatgc tccttgactt acagtggggt tgcctccagg taaacccatt 119700
gtgaattgaa aatatcttaa atcgaaaaat gcactattaa cttataatgg gtttatctgg 119760
atgtaacttt gtcttaaaga gcatctgtac tgtatgtaat aaatactgac aaactgattt 119820
ttgaaggtga atttcacaat gaagccttaa atatggctat taaaaatgtt tactttcctc 119880
catttgaatt aaaattgttc tttaaaacag tacaaattca gatgcttata gagaccaact 119940
atgtgtcatt ttggctaaat gtaatacagt tgtggggagg agggcacgtg ttagtattag 120000
agagtgcaca catgccctac ctaaaagcat ccaagtgcaa ttagaacaga aaacaaagct 120060
aaacatacct cccttataga agaccagttc aggccatata ccctctgtgc ttaatccctg 120120
```

```
ctttaaaatt aaattcctat actgttttta ggtaaaattt aattgactat tagctatact 120180
attaaatgtt tgttatttaa gtatttaagt gaagtatgat ggtgagatta catgattaat 120240
aagaaaggtt aaattgtaga gtatgttaag tttttgctct gtttcttcct ttatttggat 120300
tttaatgttc tcaaaaagcc ctttacagct ctaaaattct gcagtccttt gataacctaa 120360
ctcagcaatt cttctgtttt tctatccaga cacaatagaa atatgcctta aagcccagat 120420
acatatttta gaacactttc ttaaacaatt ataaagatgc aacttgtatt atttacatca 120480
tacacttagg actccattct taatacctgc tagaattata ggttatccct caaaattggc 120540
atagtataat atggttatta gcaagttgtt gcactttatt tggagctttg cactaggcag 120600
gggtgggctt tacttttgcc tctaatcaat aggtgggact actacactag ccaaagctgg 120660
catccttgcg gtctctgtgg agtaacgtga gtagtgttat aatttacatc cccataaca 120720
aatgatccaa gagtatgtga tcaatgcagc ataactactc tcttttatta cctgatttca 120780
cacataacat gccatcactt ctgccgtatt ttattggcca catagaccaa tcctggtgaa 120840
ggacgaaaag ggactacaca agaccatgca ttcaaggagg cagagatcac tgggggccat 120900
cttgggaggc tggctaccac acctaccata aatagaaaac cagaattact tgccaaaaat 120960
agattttaac cacacaaata aataccatgt aaacaaaata atgtcacaaa atttcagctg 121020
acttgaagac tcatctttct attagataga aagggaactt accaagtagt agaagacata 121080
ggaactccaa aataagatgt ctcattgtct tatcagaagg gttgtcagga aaatgggctg 121140
ggcactgtgg ctcacaccta ttatcccagc agtttgggag gccaagatgg gaggattgct 121200
tgagacctgg agtttgagac cagccggagc aatataacaa tatcctgtct atacaggaaa 121260
aaaaaaaaaa ttatccaggc atcgtgcctg tagtctcagc tactcaggaa gctaaagcag 121320
gagattcagg ctgcagtgag ctatgacaca ccactgtact ccagcctagg cgacatagca 121380
aggacttgtc taaaaataaa taaacaaata aatgagtcaa ggaatgaatg aatggattga 121440
caggaaatga ctattagctg tacgtggcca tgtgttgtga aatagtgaat actagttaaa 121500
actcctcatt ttatagataa gaaacagata gatagacgtg tccaacttca tgctaataac 121560
cacaaagggc tatttttatc ttatgaaggt acagtgcctc tgatcctata gctcagagtc 121620
ttagctgcac aaaagacata cctggggccg ggcatggtgg ctcacaccta taatcccagc 121680
actttgggag gccgaggcgg gtggatcaca aggtcaggag atcgagacca tcctggctaa 121740
cacagtgaaa ccgtctctac taaaaataca aaaaattagc cgggcgtggt ggcgggcgcc 121800
tgtagtccca gctactcggg aggctgaggc aggagaatgg catgaaccca ggaggtggag 121860
cttgcagtga gccgagatga cgccactgca ctccagtctg ggagacacag tgagactcca 121920
tccccccaaa aagaaaaaaa aaaaaaaaag acatacctgg gatacagaaa tcaatattgg 121980
cataatgtgc acatcctgac atttcagttg gatataaaca aaactttgga atttttcatt 122040
ataagtgggt gatttttttt ctattttttt cttctggtaa ctgtgggaca atgatttaga 122100
gattccttat aaggtataac ttttttgtat tataactgct tcaacaatgg atgtatccat 122160
tgatcctact tttgctttat aggagataga attgggttag tgcttccatt ttgcatccaa 122220
gtaaagaagc tgggaaactt atagagtaca aaaagaaatt gaaacagctg gtacagatat 122280
ttggcattgg agagcagctc tgaacaaagg tgaattatag tccagtcatc aattttgtgg 122340
cctattcttt acaaagaatt gaacctgata cagttaacca tcttccccaa actattatgt 122400
gtttaaaaca caatctgtca gccaggcacg gtggctcatg cttgtaatcc tagcacattg 122460
ggaagctgag gcgggtggat catgaggtca tgagatcgag acaatcctgg ctaacatggt 122520
```

gaaaccttgt ctctactaaa aatacaaaaa gtagccaggc atgatggtac gcacctgtaa 122580
tcccagctac ttcaggaggc tgaggcagga gaatcgcttg aacccgggag gcagaggttg 122640
cagtgagctg agatcatgcc actaaactac tacactccca gcctgggcga cagagcaaga 122700
ctccatctca aaaaaaaaaa aaaaccacaa tctatcaaac tgtttaaaac acagtttgtc 122760
aaaaaagtag ttacccttgt tgggtactgg ctggaattgg gcagaaaggg ggcttgttgg 122820
ggtactgttc tgtttcttga tctgttaacc tgattacata aaggttcttg gtttgtaaaa 122880
atttattaag tggttcactg atgatttgtg tacttttttta aatatgtgaa tactgcagta 122940
aggtttttta ttgcactgtt ttcagtttgt tgaacagaaa aagggagact ctttttgttg 123000
ttgtttgatc tctcgacctc ataatggcaa tgtgggcaag aacacttccc taatcaatac 123060
ctgtgggtgc cttggttaca ttccaccgga aacaaaaaca gatagaggct ctccataaaa 123120
aatatctttg aagacctgtg aaactttaat agtgcctttt attccatata ggacagcaca 123180
attacctatg tgctggaagg aatgattgca tcatcgataa aattcgaaga aaaaactgcc 123240
cagcatgccg ctatcgaaaa tgtcttcagg ctggaatgaa cctggaaggt aatgtaaata 123300
tctgaaagca attgtttgtc tctgtagctt ataaaaattt atcattttac gtttgaagat 123360
acaaggaagc agatgtaata atgtagtcag ttcagtatat atatgcttga ctagcataat 123420
gttactgccc aataaaaatg ggaacttttt ttcatgagtg tgtcatattc tgtttatcca 123480
ctagttctta cacacactga attcagtaca gccagactat atacgaagaa aggaaattat 123540
gtaataatga aacttataca acatgcagca acttgattat tcttactcct tttttcaacc 123600
tcaaaactat tccctaaggt tgggaatgtt tctgtttcat acatatttac atgtccattt 123660
ttctgtttgc cttttaaaag cacacctttt acttggagat ctatgtttta ttacagatct 123720
tcaaaggggg tgtggggaaa aaaatcctca aggaagaact ggatgggttt tgttttggtt 123780
ttcaagtaaa gaagaaacct gggccgggcg cagtggctca cacctgtaat cccagcactt 123840
tgggagacca aggcaggcag atcatgaggt caagagatcg agaccatcct ggctaacatg 123900
gtgaaacctt gtctctacta aaaatacaaa aattagctgg gcatggtggc gtgcacctgt 123960
aatcccagct actcaggagg ctgaggcagg agaattgctt gaacccggga ggcagaggtt 124020
gcagtgagcc gagatcatgt cattgcactc cagcttggcg acagagcaag actctgtccc 124080
agggggagaa aaaaaaaaaa gaaacctgaa actagttata agttcgagtt tcatatccct 124140
gtttatataa caagttgtat aattaacact gatctcagca ttaaaaaatt ttcctctgaa 124200
aaaagtttgg aattctgctg tggttgaaat tgcaagttct gtgaaggtag tgtgatctaa 124260
taacacatat gcttagtatt tattgtgaga ttagcacttt tattcaacaa atacacacca 124320
gcgaggcagt aactagatat aaaatgagta aaatggtgcc tgtattcaag cagtttactg 124380
gctagttagg ttgcagaatc agtcacaaaa tagcatggca caccatagac agcataaggc 124440
cacaggaaca agaggaaggt cacctagttc cttggaagtc aaggaagaag taacattgaa 124500
ttttaaatct accagctgag taggaattag atagatgaaa aataagggca gagacatgat 124560
cagatttgta ttttacaaag actgatctta catggagaga ccaattaaat gaatatggca 124620
gtcctccaga taagagacgg caggcagtac tgagagagaa tggaaaccat gtggttcttt 124680
ttatgattat gatgattatt gttattttag agacagagtc taactcttgt cacccaggct 124740
ggagtgcagt ggcatgaaca tggctcactg cagccttgaa ctcctaagac tcaagccatc 124800
ttcccacccc atagggttac aaatgtacac taccacaccc agctgattat ttttttaatt 124860

```
ttttttttag ttttttgtag agacaaagga gtcttgctat gttgcccagg ctggtgtcta 124920
actcctggcc ttaagtgatc ctcccaatgt ggcctcccaa agtgctggga ttacaggtgt 124980
gagccactgc aactgaccta tgtggttctt ttgataggag agactaattg ttggtgctat 125040
ctagcacaca ctgtgtatgt acatcttggt aaacagaaaa tagatttatg ggtatgacta 125100
tgaagagtct aattccccaa accacacaca caactctatc taggtttgcc caggctattt 125160
aaacttaact gcagagtgtc agcatgttaa acattgattt acataaaatg ataactgccc 125220
actttcttgt aaatgttata aaaactgcag agattaacta aaaaatgcac acagaagttt 125280
gctttcagtt ccccaagggt agtttatttt tgttataaat acagtattcc ccactttctt 125340
agataccaga tctctgtcca gattttacca gtttcatctt gctgctttct aatctcctat 125400
gtatgtaata tactttgacc atttaaatat atattaagac acttgagttt ttagtgccct 125460
ttgggttttt ttctctggtc ccaattttct ctaatattca tttttcatt ttagctattt 125520
tatatttaga aatagatttt gaatgaagct caaaggacaa acccaaataa aattttgttg 125580
tacctctaat atattgtggt tgcttaccca gtaacatttt tagatgcttt tctgaataca 125640
tgtgaagttt aaggtctttg gagctttaag catataatgt ttttctgggc aatttctccc 125700
tatccaaact acaaggaact tctttcatca aaacaaaaaa tacatcaact acaaagtaat 125760
gattttgatg gactaggcta tgaaatttgt ctgtttttc ctccctctta cagtttaata 125820
gcaattgcag tgccctttgc ccttactgca ctagaagacg acccaaggca gtgactgaca 125880
tctgattttt ctattaatta tgccatcact gtcatttcca gttgaatctt ttgttggaca 125940
tcagaaattt ttcttacatg aataaaattt aagcatgcaa tttaggctgc agtttctcaa 126000
aatattgtat taaaaataac caattatatg ctcttataaa ttgtcagtat aacatatcca 126060
gttagtgtag aaattggcat ttgttaaaaa ctactacatg ttagtctttg acacacattc 126120
ttctactttt tggaccctca tattattaaa aacacctttg agtagggcca tgatttactt 126180
tatatccatt tttatactac gtagtagaag aaaattctag cttgttattt catactatga 126240
tatgtactgt gtggcacata tcatatagtt gatccagttc tacttgtaga tgaattgaaa 126300
gaacggctta aaaaagttct tagggtttgt gtgtgtggtt ttactgtaaa agtatcattt 126360
ttgtattaaa ctaaccccag tatacataaa atctgtattt ggcctggcat gtatgtttgc 126420
caggaatctt tggcagaccc taatactcac aatatagatg agccatgtgt ttcacacctt 126480
ttttttttt ttttacaacc ttcagaaata ttctcttgtt catcagagtg cttcccctaa 126540
gccaggaagt ttcgatgata gccccagagt aactttgccc aagtctcttc ataaatgtaa 126600
cttaggactg caagtggtgt atttttatac tcttgcccca taccaagtaa atctcacgat 126660
ttattttaag ggagtggcct tcactgcttc aagtgtctag catttaagaa cggataagat 126720
ttttaatggt gatcctaatt ttttttttaa cttgcttgtt ttctcttgta actaagtgtt 126780
tttattcatt tcattttgag gtatattgta atcaatccaa agtatggctt tgtttttagt 126840
ataaacagtc aaatgaaact tacagtctta gggtattatc agatttatta ccaaatatta 126900
tttaactaat ttttttaagt taataaaccc aatctagtag tttctctctt attttcaact 126960
tatattttag attctggggg tacatgtaca ggtttgttac taagatacat tgtatgatgc 127020
tggtatttgg agtacgattg aacttttcat ccaggaagta agcacagtac ctaacaggtg 127080
ctttttaacg tgtgcctccc ttcctctatc ccctctcttt tatttcccag tgtctgtgcc 127140
catctttatg tctaggtgta ctccatgttt agctcccatt tataaatgag aacccagtat 127200
ttggttttct gcattagttc atgtaggata ctggccgcct gctacatcca tgttgctgca 127260
```

```
aagaacatga tttcattctt tttgtgtcta tatagtattc catggcatat aaacaccaca 127320
ttttctttat ccagtgcact gttgatgggc acctgggttg gttccatgtc tttgctattg 127380
caaaccgtgc tgcagtgaac atatgggtac atgtgtcttt ttgatagaat gaattatttc 127440
tctttgggtg tatgcccagc aataggattg ctaggttgaa tggtagttaa actcttaatt 127500
ctttgaaaaa tctccaaact tctttccaca gtggtgtcat tgtggttttg acttgcagtt 127560
ctctgatgat taacaatcag catttttttca tatgtttgtt ggccacatgt atgtcttttt 127620
ttttttttt ttttttgaga agtgtctgct catgtccttt gcccattttt aatggagttg 127680
tttttgcttg ttaatttaag ttccatataa actctggata ttagggcttt gtcagatgca 127740
tagttagcaa atattttctc ccattctgta gattgtctgt gatagtttct cttgctttgc 127800
agaaactctt tagtttaatt aggtcccatt gtcaattttt gtttttgttg cagttgcttt 127860
tggggattag tcataaattc tttcccaagg ccaatgtcga gaaggttatt tcctaggttt 127920
tcttctagga ttttcatagt ttgaggtctt acatttacat ctttaatcca ccttactaat 127980
ttttgtatgg caataggtag gggtccagtt tcattcttct gcacatggat agccagttat 128040
cccagcacca ttaatgtaat agggagtcgt tttcctatgg cttattttta tcaactttgt 128100
gtagattaga tggctgtagg tttgtgtctt tatttctgga ctctattctg taccattgtg 128160
tgtgtttttt gtactggtac catgctgttt cggttactgt agcctgtagt atagtttgat 128220
ttggggtaat gtgatgttgc cagcttcatt ctttttgctt aggattgctt tggccatttg 128280
gggcattttt tggttccata tgaattttag aatgcttttt gctagttctg taaaaaatga 128340
cattgtagtt tgataggaat agtactgaat ctataaattg ctttgggtag tatgaccatt 128400
ttaactatac tgattctacc agtccatgag catggaatgt tattccattt gtttgtgtca 128460
tctctgattt ctttcagcag tgttttgtag ttctccttgt aaaaatctta aactaactta 128520
gatgcattcc taggtatttt actctttttt gactgttata aatgggattg cattcttgat 128580
ttggctctca gcttgaatat tactggtgta tagaaatgct actgattttt gtacattgat 128640
tttaaatcct gaacctttac caaagttgtt tatcagctca caggagcctt ttggcagagt 128700
cttcagggtt ttctaggtat agaatagtaa gtgaaaagag atcgtttgat tacttctttt 128760
cctatttgga agactttaat ttctttctct tacctgattg ttctgactag gatttccagt 128820
actatgttaa attggaacag tgacattggg catccttgtc ttactgcatt aaggggaatg 128880
cttccagctt ttgcccattt ggtatgatgt tggctgtagg tttgtcatag agggctcttt 128940
cttattttga ggtatgttcc tttgatacct agtttggtga aggtttttat catgcagaga 129000
tgttggattt tatcacaact tcttctgcat ctattgagat gatctttttt ttgtttgttt 129060
atgtggtgaa tcacatttat tgatttgcgt atgttgaaca agccttgcat cccagaaata 129120
aagcctactt gattgtggtg agttaacttt ttgatgtgca gctggattca gtttgctagt 129180
gttttgttga ggatttttat atctgtgttc atcagggaca ttggcctgta gttttgttgt 129240
tgttgttgtt gttgttgtgt ctctaccagg ttttggtatt agaatgatgt ttcccttgta 129300
gaataagtta gggatgaggc cctctttctc gattgctttt ttagaatagt tttagtagga 129360
ttagtaccag ctcttctttg tacatctggt agaatttggc tgtgaatcca tctggtcaag 129420
ggctttttttc agttggtggg ttttttatta ctgattcaat ttcagaactt gttattggtc 129480
tgttcagaat ttcaatttct tcctggttca atctagggag gttgtgtgtt tccatttcca 129540
catatatact tactccaaat aatggcttta tatatacgag gattagctga aacaaaaaat 129600
```

```
gatactttca tagtaaactc caccccggcc ctgacacaca cacataaacc ctgaggtttt 129660
ttaaagcctt tgttccaatt tatccatttc ctctagattt tctactttgt gtgcatagca 129720
gtgcttgtaa tggtgtgaag atcttttttta tttctgtgga atctcttgta atgtcatctt 129780
tgacattatt gtgtttattt gggtcttcac tcttttttc tttgttaatc tagctagtgg 129840
tctatcagtc ttgtttatcc tttcaagtaa ccaactttta taaactaggt tttaagctaa 129900
gtaagatttc tctactttta ttaaggagga agtagcatta ccacaaactc atgaacactt 129960
ctgtggagct cctatattga ctgctaatct tctgtatgct ccagtgggtc aggagtttat 130020
ataaagtaaa gttgcattaa ctaagttgct ttaacatagt gattgcttaa ctaaatgatt 130080
cagttcggtt aactccttcc tgaagatatt ttgaaaaatt aattagtatt atttcttgcc 130140
ccagtcagta cggcacaatt gagttcactt gtactttctg agctgtattc aaaaacatca 130200
gttttctcat ttaggactat atataagtag tgagaaatta attacaaact gagtcataga 130260
aaatgttttt gtttaatcca gcttgttact ctttcttcct tgttctaatg tggagtaatg 130320
tattctaaac catttaaagt tatgactaat tgaggtttta acagtactgt tccagtgtat 130380
tgatttggca catgtgtgtt ctcttttaca ttgtcaacag cacattttat gatttggatc 130440
aagatttcac tgggatactt ctggttgttt aaagagtttc tttacgtatt ggtgtccttc 130500
tttttaaact tttatcactc ctctattaag ttgcgatatc caaatttaaa atattctaaa 130560
aacatgttct cctgcaagtt gaggtaatga tagttgttat atggtaatta ctataatata 130620
tgccaggaac tattctaagc attttacata tttaattctc acagcaaccc tgtgaggtag 130680
ggactaatat tatcctcatt ttacagaagg ggaaatgaag agtcagggag ttaacttgca 130740
cagatatcca gagacaacat ggcaaaacca agacttaaat ccaaatatgc tgatttcagg 130800
tttctgctct ttagtcctgt atcataccat gcctccaaga gagcatggta aactaattag 130860
aatagttcta tcatgattct gtttctgttc tgaaatatta actaaaaatt tttgaatttc 130920
tcagtacccc atttattata gaacacagta agaatggaac cattctaaca ttggacattg 130980
agatattgtt cccaccacca tatctgtcct ccacagacta tatggtgtgt cattttaagg 131040
acagaggatc taaaaatgat ttttaaaggt gatttaaatt tactcttccc tttgcaaaat 131100
ggtttgtatc cctaataatt tgaacaggta cattttaaat tacatttctt gcctttcctt 131160
ggagttctga gtactttccc tctgagagaa caatgtaatt cttatttagt cactaaaaca 131220
aaaataactt caggagtatg aataaatcta ctaaaaagtc tacaggatcc atgttgtagt 131280
ttgattagat ggttccatac caagtcaagg taaaagataa ttaatttata tataatagga 131340
aaatgggtgc tttaggttta tagagtaatc aatataaatc ttccttataa aagggaaatt 131400
tcccacttat aatttatgtg aagtaaagtt tttcatttca tcttcccata tgtttttagt 131460
cccaagcagt atttatgtta gtacctatgt aaaggtgaaa agcgaatttc tctactggta 131520
ctactaatac tatttttagc atgtaatctg ctatcatctt cctatcttga taagtggctt 131580
tgaacaagtg taaatagtgt aattctcttc attgtatata ctaccatgat ttagattaat 131640
cttaaaccac agtttgtaat ccgttattcc aagcttagat ttttttcag tttatagtaa 131700
gagtaatttg ccttacataa ccaatgaaat tgttgcattt agagtgaaag tgagacaaac 131760
aaataattta tagaagaatt tacaaaagtg atttactccg attgttttaa cataccgtta 131820
taatactttg tataaggaat aactatgatg aagtttctgg cctatttgta ggcaaaatta 131880
attgggaata ggttcctctg gatcctttgc tttcagaaaa aaaaaggttt tttcctcctc 131940
ttccatgtca ctttatcata attgctaaat aaaatatttc tcccatctta atagttttag 132000
```

aaagtaaaaa tacttcttga ataaactatg tagcgcagac cttcccatta cagttcattt 132060
ctatgtattt tttaaaatat ccacagctcg aaaaacaaag aaaaaaataa aaggaattca 132120
gcaggccact acaggagtct cacaagaaac ctctgaaaat cctgctaaca aaacaatagt 132180
tcctgcaacg ttaccacaac tcacccctac cctggtgtca ctgttggagg ttattgaacc 132240
tgaagtgtta tatgcaggat atgatagctc tgttccagac tcaacttgga ggatcatgac 132300
cacgctcaac atgttaggag ggcggcaagt gattgcagca gtgaaatggg caaaagcgat 132360
accaggtaag atgcaaaaga taaaagagca actatataaa cctttgtgtt ttcttcagca 132420
aaaacatttt ggcttttata tcatcctgaa cccgtggctt atcttctttc tcttactagt 132480
tctggggact atgaagggga gagtcaggtg aatacaggtg atagggagtt tataataaaa 132540
catttacatt actccctgct tttcaaatca ttatgcacag gatggtaatt tcacatagga 132600
tgatttaata tcagaactcg agttacaaca aagactcact caaaactcct ttgacactga 132660
agttcgggga aagaaaatgt ttttagttaa ttccgtttgt tttccttcat tgtgccactt 132720
ttaaaaatta ggttgtttgt aagattggta aacatcaagt atgttgactc aaaatttgta 132780
ctaaagtaga atgattttaa cccttcacta aatgaaatac tacacattga ttgtaatttt 132840
aaagacaatt ttaaataaaa gtttccctat tggaatttgg tgtggaacag cagaggtnnn 132900
nnnnnnnnnn nnnnnnnnnn nnnnnnnnnn nnnnnnnnnn nnnnnnnnnn nnnnnnnnag 132960
tgtcagctct gactttaaag acagagggaa ttgacaagcc tgtgttcacg caaatagtta 133020
gggacagaac aagaaagtaa cctggcctcc tgtcatcctt gttttagtaa gggggggaaga 133080 ggtgtgaata gcagggcaaa tgttttactt actaatacct caagtcaaga ttcttttctc 133140
ttttttaaaa tcgatacata atagttgtac atatttactg tacatattta tatttagggg 133200
gtacatgtaa taatttgata aaagcacaca acgtgtaagg atcaaatcag agtaactggg 133260
atatgcatca cctcaaacat ttgtttgggg aacattccaa atcttctctt ttagctattt 133320
tgaaatatac agtaaattat tgttaactat agtcatcctg ttgtgctact gaacactaaa 133380
acttatttct attaactatt tttgcaccca tcaacaaatc ccccttcatc cccgtcacac 133440
tggtaatcgc caagccaaga atttcggctt aaattttact atttagttca tgtttactta 133500
agcagacaaa ggtgacaaaa ctggctactt ttttcttttc cacattgaaa gctattagaa 133560
actagcacag agggggctgg gtgtgatggc tcacgcctgt aatcccagac tttgggaggc 133620
ccaggtgggt ggatcacttg aggtcaagag ttcaagacca gcgtggccag catagcaaaa 133680
ccccatccct ctactaaaaa tataaaaatt ggccaggcat ggtggtatgc acctgtattc 133740
ccgactacct gggaggctgg cactgaaaat catttaaacc caggaagcag aggttgcagt 133800
gagccgagat ggcgccattg cactccagcc tgggcgacag agcgagactc tgtctcagaa 133860
aaaagaaaaa aagcacagag ggtttgagtc ttgaagtgtc agatgacaga ggaaaactgt 133920
gtctacctag tatttaattt ccattttctg ttaggggtcc ccttgttttg acagggctaa 133980
ttgatctcat tgctctttgg caattcccac agagatgatg atcttagaat gttgcctcat 134040
acctttattt ctcttaattc aggtttcagg aacttacacc tggatgacca aatgacccta 134100
ctgcaatact cctggatgtt tcttatggca tttgccctgg ggtggagatc atatagacaa 134160
tcaagtgcaa acctgctgtg ttttgctcct gatctgatta ttaatgagta agttgtatgt 134220
gagtcatttt ccctgtattc atagggtatt tttaaccagc tgatgttttc ctgattgact 134280
gctattgtga taattcagga ctgaaacaat cctactaggt atctaggatg taggcaaact 134340

```
ggaaatagag ttatgagtgc ttggggcagg acaagtgtaa tgtagagcaa ttgtacatat 134400
ggcattatta ctgtcccagg acatgtttaa ggatatttac tgagattagt aaagtctgtc 134460
gcaagcaaca aggaatctta ctgtgctatt atttacataa ggctattcca gaaagagaaa 134520
ggagtatgat aaaactcgtg tggattcagt ggggacaatt gtagatgagg atatctaggc 134580
tgatggggtg ggacatatgg acccagacac aagaggtgtc tgtttgcatg gcaggtatct 134640
gtggtttaaa tatgtgaaca agtttgttta actgagagaa gaccaagcct tgaagatttt 134700
ataaatcagc tattctttta tcctctaggc ttattcctgt atctgtgaaa tgtgtcaggt 134760
gtccatttcc ccttacctca ttgcagttgt ttcctcactc gttttctccc tccagtgtga 134820
tgtacatcat taacattaag gatatttaat agcatctctg accaggtaga aagtgagaag 134880
agctaggatg tgacttctgt gctgtgtatc tggtgatgtg aacaccaaga gtctaagagt 134940
ctaacagcaa cagacttgac taacctcaga gatgctgtta aatatcctta atgttcagca 135000
aacatgaacg ttggctaatg tttgcttcct ctagcacagt atgactgcac cacctatctc 135060
cccagcacac agactgtctt tagtatcttc ccactgaccc tccaatccat actctgcatg 135120
atttcaggct tcccacaatc tgacctcact tcctctccca ttgttgtcct tcacacactc 135180
ttcgttccca tccattcttt caagcatact cttagactct tggtgttcac atcaccagat 135240
acacagcaga gaagtcacat tctagctctt ctcactttcc accttatatt actacttttc 135300
atacccctag cttattgcta ttagtacagt ataaacaggg agttcacaca cacatacccc 135360
ggcctaagaa gaataaaaaa tgaaggagat ttgtgtttgt atagaaaaca gaagacacct 135420
tgacttttat tgccaaaaag aggactgttc aaactattga atcacaatgt aacaagatta 135480
ggtagttgga tccaatttta aattaactgg taaatatatt tagtctctgg ggaaactgaa 135540
gacattactc atcagaatcc taccatgctg tttaaaaaat accacgttgg cagtatttat 135600
tttttagtca ctttctaata tgtaatttga aggcatttaa gtggaattaa aagcataaac 135660
agatttatat gaaacaccaa cttatccttc tggtttacaa aacctaattt agggttttta 135720
ctattaaggc attcagattt agctttaagc agtcacagca taatctaatc atgccacata 135780
cattccttat gtaaagtggg atttataaat ttttttcctc aacagattta tattagtttc 135840
attttcatta agggatatgt acttcccatt cttgtgttct catgctgctg catacaagat 135900
gggcagtcct tcaccttttt ttctttcttt tttttttttg agacgagatt cactctgtca 135960
cccaggccca agtgcagtgg tgtgatctgg caacgtccac ctcctgggtt caagcgattc 136020
tctgcctcgg cctcccaaat agctgagatt acaggtgcac tccaccacac tcggctaatt 136080
ttttgcattt ttagtagaga cggggttttg ccatattggc caggctggtc ttgaactcct 136140
gacctcaagt gatcctccca ctttggcatc ccaaagtgct gggattacag gtgtgagccg 136200
ccgcacccag ccctccaccc tttcttagcc cactatgttt ccatactgct ctggtgtctg 136260
tgacaggcag attttgcata tcggaaagta agcattcaag ttctgaccct ctatagagct 136320
gtaaaaccat cactcatggt tgcccttagg tcagaacgtt gtggaaaaaa aatttttgtt 136380
gttgttttta cagtcaacaa gaatgagttt ttacttattc tactatacta caattttatt 136440
gaaattttca gttatatgaa tgtaaccatg cacaagaaac taaaggaaaa aaggtgcctc 136500
ccaaaaaagg agtgttttac ctactattaa ggactgggga ggtgcctctt tggtaagagc 136560
agatttaaaa tttgaagagc ctgtgatcac tttggcagca tgtaattcat gtctgatttg 136620
ttttatataa aagaataagc cacatattta gtagagaaaa atgataacct ttttattgtt 136680
aagtccaaga tgactttctg tcagaaactt aaaaaaaaaa aaatcttgaa gcattttaaa 136740
```

agctgtgaac tgagcccagt ttcaggcttt tagtgtcatt tcagaagtca ggaaacttca 136800
gagatctatt tgaaaatcat aggtgtgtaa tgacttcaga atcataagca agaattggtt 136860
tagtaccttt agtttaaaga atattaaggc atatgcatgt cagaggcaga ttttgagcat 136920
cagaagtcta gaatcaagtt ctaggtctgg ccctctacat aactgtgaac agtgtcacac 136980
atttttgtct ttaggatgga atgttgtgaa aaaacttacc tttaaaaatc aagtgtgtag 137040
gacctaaaat tgtgttgtct aattgaccat attcaagtga taaaccttga tttaaatgag 137100
caactggtaa taagttctat aagaattcta acactttaat taaataataa tgcatggcat 137160
gcatggtaga aaataatgtc tccactgtta cgttagatta ttcattagtc tctttaaaca 137220
gccaagatgc aggaagaagt ttaagggaag ttctccaaaa ttctgatttt atagggaatt 137280
agcaataata ttattgcaat agttgttttt cattataagt tcatagtttt gcaaaacaaa 137340
acagaaatgt actttttgg gggaagtagc attatnnnnn nnnnnnnnnn nnnnnnnnnn 137400
nnnnnnnnnn nnnnnnnnnn nnnnnnnnnn nnnnnnnnnn nnnnnnnnnn actctaccct 137460
gcatgtacga ccaatgtaaa cacatgctgt atgtttcctc tgagttacac aggcttcagg 137520
tatcttatga agaatatctc tgtatgaaaa ccttactgct tctctcttca ggttggtaga 137580
acacctttc actttatgtc aaaagcatga aatatgaaag tctagaaaca aaggttaatt 137640
tgtatacata gtactaataa ttataccaag tctactatta tttcctacta gtcagatgat 137700
ttttatgaat gtaaaatact agaaaggcac agtaagtgat accaagatta gtaagacaaa 137760
taggtatagc agaaacagag aggtatatga gccgcatagg gatctctgtt gataggaatc 137820
tgtgtggacg tttttctcct tccttcctca tgggaagaca tggaaaaaga aagctgacta 137880
cagtgatttt gtgtactata ctgttacttg gttaaagatt ttagttacct aatgagtatt 137940
agcatatata agaaattatg ggagaaaaag acgcatccta gaaaaggtgt gcttaattac 138000
tattgggaat tggttaacat agcattggaa ctggattgtc agacagagat tcactatcta 138060
gaaaatggca acaagagttt ataaaacaaa cttctgtgag attacttttt agctagcaaa 138120
gacaaagatg tcaaagtgat aaactacgat acatccagat gatggaatac tattgagaac 138180
taaaaagaaa tgagctatca agccatgaaa acacatggag gaacgttaaa tgcatactac 138240
taagtgaaaa aaagctaatc tgaaagggct acatactgtg tgattccaac tatataacat 138300
tccataaaag gcaaaacgtg aagacagcaa aaaaaaaaaa aaaaaaaaaa aaaaaaatca 138360
gtggttgcca gggtttagaa gggagggagg gataaatgtg cagagcacag agaattttta 138420
gggcagtgaa aatacttcgt atgctactat aatggtggaa acatgtcatt atacatttgt 138480
ccaaacccga agaatgtcca ccactaagag tgaaccctca actatggact ttgggtggta 138540
atgtgtggga caggaggtat atgaaaaatg tctgtacctt cctcccaatt ttgctgtgaa 138600
cttaaaactg ctctaaaaat gtcttttta aaaaaaagct ctatgaacta gttggtatta 138660
taaaccttag gccatttcca gtaaaagtta cataccaatg tttattaaat actgagttaa 138720
tagctgaata cgtctttcac atacaaatac gtacatttgc agtttttaaa agtcttaatt 138780
ccattagtaa ctgtggtttc atagttgcca aataactgta agctatggat gttgcacaag 138840
actatgactt taaccatttc gtatctattt aaagatttcc aaagcacaca tttgtcttaa 138900
tgctttcaca ctatttttgc tcaacaaaaa gttattttat gttaatggat ataagaagta 138960
ttaataatat ttcagtcaag gcaagagaac ctggtaaaga tcattgctag agacatgttt 139020
aatgttacct gtagcagtac acttgttaaa gaagtgatta agcagttaca taaaattctg 139080

```
atcataactt tgattgatac catgaaggta taattcagtg cctagatact aacaacctta 139140
tttgtttaaa aaaaaaaaaa gtggtttcag ttgcatacat cccagactaa ctgagctgta 139200
tgattttttt cattgtaaat aataagaaaa agtaaattgg cctagtacat atcacaagtt 139260
cttcttttta aaaaataata gaaatataag gatggaaata tataccttaa gatatagact 139320
tctactatga tagactactg gaataggtac tataacctcc caccaaaaat gctagactaa 139380
aacaattaag aactaagtga aggcaggaac ccacagaggt aagtggaact caagccaact 139440
tgctctttga gggcatttgt acaacctggt aaattagttt agtaagttgg agttttttta 139500
agtttataat ctttttaaaa attatttcaa taggattttt ggggaacagg tagtgttagg 139560
ttacatgaat aagttcttta gtggtgattt ctggaatttt ggtgcaccca tcacccgagc 139620
agtatacact gtacccaatg tgtagtcttt catccctcac tcccctcccc aaccccagtc 139680
cccaaagtcc attatatcat tctcatgcct ttgcatcttc atagtttagc tcccacttat 139740
aagtgagaat atgcaatatt tggttttcca tttctgagtt acttcactta taataatggt 139800
ttccagttcc atccaggttg ctgcaaatgc cattattttt ttcctttttg tggctgagta 139860
gtagtccatg gtatgtatat accacatttt ctttatccac tcggtgattg atgggcattt 139920
gggctggttc tgtatattta gtaagtttaa aaacaagaga tggaaatata aatgcagttt 139980
aaaaggcaag tggattggtc tgaaaacaga ttggacacat ttgaagaaac acttgaaatg 140040
tatatctgaa aaaatcagcc agaatacaat tgtttttaat gattgtgtat atgtttgtgt 140100
atataaacca caagggagat ctgtaggtac tgaaaatcac aactggaaaa tggcaacaaa 140160
gctatagaaa ctggaaaaac aatgactttt cttagatccc tcagagaatg gaggtcatag 140220
gacaaaccac cacttcaaaa tttagaacag acaaatacag agaaacagcc aagatcagct 140280
tactggggaa agatgccact gaaggcagga agactaggca attttgatga attgctggag 140340
gctgagcaag gactagtttc agagttaaaa actcccaggg acccagtctt agtgggggtt 140400
tcctgcaatt tcttgggttt accccacaga atttctaact tccagaaact ccacaagatt 140460
cttagggtga agaattccct cctttttctg atagaattag gggaaggta aaaattggaa 140520
atatgtagga gagtgttcac aacaaaggcc tgcactgtaa ggaaaactaa ttcaacagac 140580
cctaatgtga cctgggggga aggcaaactg aggattctgg ccctgtctta gccttcttgt 140640
ctcatttctg aaaatcacag cccagggttt cagacccact aaaaacaact gagatttaat 140700
catatagatt ataaaatact tcacctcccc ctccccaaca ccttaccacc atataaacag 140760
ggctccagga taaaataaca gtggattaca actgagagag ctgcaggaca caagctgttt 140820
aaggagttct taggaaaccc aaagacaacc gaagaaaaag taaataaaaa caaggaaact 140880
agaggaaact gaagcctcta gtacctacaa ctacagcaaa cattaaatac aacctgcctc 140940
ctagccagat tagcatgaaa cctcacacta aaagtcaaat tacttcagtt ttgatatatc 141000
gtgtccagct ttcaacaaaa aaccataagg catgctaaaa tgcaagaaaa aacccacagt 141060
ctgaagagac aaaacaagcg tcagaagcag tcctcagata tgacacaata tttcagttat 141120
cagataggga atttacaata cctatgatta gtaggttaaa ggctccagtg gaaaaagtag 141180
acaacatgca agaagtgatg tatgcagaga gatggaaact ctaaaaataa attgtaagga 141240
atgctgtaag gaaatgcaga atgatgttga tgggctcatc agtagactga gcacagccaa 141300
gcaaagagtc agtgagcttg aagataggtc aaaggaaact cccccaaact caaatgcaat 141360
atgctgaatc gaaaacagtt ataaacatgg tagacattaa tccagctata tcagtaatta 141420
ctgtaaattt gaatgttcta agtacaccaa tcacctattt tttaactagg aggtgaaaat 141480
```

```
aaagtttgcc accagatggt cactaaaaaa ttattagagg gtatacttag gctaaagaaa 141540
aataatcgtg gccaggagtg gtggctctca cctgtaatcc caacactttg ggaggctgag 141600
gcaggcagat cacagggtca agagatcaag accatcctgg ctgacgtggt aaaaccccat 141660
ctcaactaaa aatacaaaaa ttagctgagg atggtagtgt atgcctgtag tcccagctac 141720
tcagtaggct gaggcaggag aatcgcttga acctgggaca tagaggttgc agagagccaa 141780
gatcgcgcca ctgcactcca gcctggtgac agagcgagac tccatctcag aaaaagataa 141840
ataaaagtaa tcccatcttt aagaaggact gaagaataag gaaagtggta aataatgtag 141900
atacatttaa actgacattt actgtgtata taaaataaca gtaacaattt gcttgagggt 141960
taaaaaactt agaactaaag tatgtttaag tttcaaggat gacaactaga aataaggtat 142020
gcagggtatg caaagtacca aaccatcagg ggaagagaat acctaagaaa aacaattcaa 142080
aagaatgaaa gatgtgagag gagggagaaa aatgcataac aagggcatga aaacaggaag 142140
taacagataa ggtacagtag tacagctaaa ttcaaacaca gcagtacttt cattaaatgt 142200
agagatgggg ccaggtgcag tggctcacac ctgtaatccc agcactttgg gaggctgagg 142260
tgggcagatc acttgaggtg aggagttcga gaccagcctg accaacatgg cgaaaccccg 142320
actctactaa aaatataaaa agttagccag gtgtggtggt gcattgttat cccagctact 142380
cgggaggctg aggcaaaaga atcatttgaa cctgggaggc ggaggttgca gtaagccaag 142440
atcgtgccac tgctctccag cctgggtgag agaggaacac tgtctcaaaa ataaaataaa 142500
tgtagagacg gactgaatgc tccaagctaa tctgacagga ttttagaaat aatccaaatt 142560
tatgctattt aaaagagcta tatctgaata aagatactga aaggctgaaa taaaaggatc 142620
aactttgcat agtataacat ggcagacttt ttctgtaaag ggccagatgg taaatgttag 142680
ctttgcacag tctctgtcac agctactaaa ctctgccctt gtggcaggaa catagtcatt 142740
gacaatactc aaatagaaca ggtgtggctg tgttccaata aaactttatt tacaaataca 142800
ggctgcaagt aggttttggc ccataggcca aatttgctgg cccctatact gaccaaaaga 142860
aaactgaagg agctacgtta ttaccaaaca aaatagatgt taaggcaaaa tacttattaa 142920
agcatttgtt caccaggaaa aataattcta aatatatagt ttcaaattac ataatacaaa 142980
aattcataga acaagaatac ttagataaat cttgtaaaaa tagtgagatt ttactatacc 143040
tttctcacaa attaatcaag cagacaaaaa aataaggata tggatgtaca tttcatctct 143100
gttgggtcag tactgaagtg tgagatcatt gggacatatg ttgagtgtgt gtttaaattt 143160
atttttaaaa ctgccaaatt tttccacaat tgttaacatt taccagaaat gtatgagact 143220
taagatatgc tctatatcct cctcagtact tggtactgtc agcctctttc atcataggta 143280
tactgatgat taaagatact aagcatcttt tcacgggctt attggccacc tatatttctt 143340
atttggtata atcttttgcc catttttaa ctgaattatt tatcttctta ttgggtttta 143400
agaattattc aaatattctc aatatagccc tttgttaaat atatgttttg catatgtttt 143460
ctttcagtaa gtggattaca tttacaattt tcttaacaga aaatgtagag atgagcaaaa 143520
gtatgtaatt ctgaagaaag cttcatgtct ttgtgtatta agaaagtttt gcttaatcca 143580
gggttaaaaa gattttctac tatttgtttt cttgtagaaa ttctgtagtt tcagctcaca 143640
tgcttaagta tatgatgcaa ggtaagggac aaggttcatt ttttccccaa aatccgtatc 143700
tggttgcccc agaacttgac tcttttccct attgagttac ttggcaattt tatagaaaat 143760
cagttgtttg tgtatgtgtg ggtctacttt tagactcttg tcttacccaa tgatctgtat 143820
```

gcctatattc atattgataa catcctgtct tgattactat tacattacag taaatcttaa 143880
aatcgggtaa tatgaattct cccaatctgt tgttcttttc caaactcttg ttttggatat 143940
tctagtttcc ttgcatttcc acttttttgt ttggatattc taggatattc tagcttcctt 144000
gcatttccac ttttttgtct tgttttgttt ttttgagatg gcccaggctc ctggcccggg 144060
ctcctgttgc ccaggctgga gtgcagtggc gtgatcttgg ctcattgcag cctccccagt 144120
agctgggatt gcaggcaccc accaccatgc ctggttaatt ttcgtgtttt tagtagagat 144180
ggggtttcgc catgttggcc aggctaaccc tgacctcagg tgatccaccc acctcggcct 144240
cgcaaagtgc tggaattaca ggcatgagcc accacgcctg gtcttccaca tattttttaa 144300
ttagcttgac aatttctacc aaaaaaaaag tcttttgggg ctgggtgtag tggttgctgg 144360
gtgtggtggt tcatgcctgt aatcccacca ctttgagagg ccaaggcagg cagatcgctt 144420
aagcccaaga gtttgagacc agtctgggca aaatggcgaa accctgtcac tacagaaaat 144480
acaaaaaatt agccaggcat ggtagctcgt gcctgtagtc ccagctaccc aggaggctga 144540
ggtgggaggt caaggctgca gtgagccatg atcatgccag tgcactctag cctgggcaac 144600
agagtgagac tctgtctcaa aaacacagtc tgatggaatt tttattagga tagccttgaa 144660
tctatagatc catttgaaaa taattaacat cataaatttc cagtttccag cagggcgcta 144720
tggctcacac ctgtaatccc agcactttgg gatgccgagg tgggcagatc atcaggtcag 144780
gagttcgaga ccagcctgac caacatggtg aaaccctgtc tctactaaaa atacaaaaaa 144840
aatagccagg cgtggtggca caagcctgta gtcccagcta ctcaggaggc tgaggcagga 144900
gaatcgcttg aacctgggag gcagaggttg cagtgagccg agattgtgcc agcctgggca 144960
acagagtgag gttccatctc aaaaaaaaaa aaattccatt gttgagagag aataggaatt 145020
ccagctttgg aggggtgcgg agaccatcaa atcctctttc caaaaaaaaa taactatact 145080
actaagcaga gtatagttcc acaaatattc ttctgtaaag agactcacag tacatatttg 145140
tctttgcagg ccatatagtc cctgttgcaa ttcctcagtt ctacagttgt aacaggaaag 145200
cagctatata caatatgtga atgcttgtgt tctaatacaa atttatttgc aaaatcagga 145260
aaatggcttg aaatggttta agatctagtt ttctgaatag atcatggtat ataatctttt 145320
ccatatatat tttgaatttg gtttgctaat attttgttga tcatttttct atctctcttt 145380
atgaaggatg ttgatctaca gctttctttt cttgtgatat atttttctgg ctttgttacc 145440
agggtagtac tagcctctta aaatgagttg gaagtattct ctgttttctt aaagagttta 145500
tagagtattg atcttattta ttctttaaat atttgatata tgtcaccagt gaagccatct 145560
gggtctggtg ttttctttca gggaaaattt ttaattatta attagatttg cttacttgtt 145620
atatagatct attcagaatt tctatttttc cttgactttg ttttgtaatt tgtgtgtttc 145680
tatgaaatga gccattttgt ctgagttgtc taacttgggc ataaagttgt ttgtaatcta 145740
atcctttaaa ttttgtggga tccatagtgg tgtcccctcc atgatacatt ttgataattt 145800
atgcctgatc atcttttttt cttggtcagt ctacttagaa atttattttg ttagtcttta 145860
caaagaacta atttttagtt tcattgattt tgtccattgt tttttgtttt ttatgtcatt 145920
gattatttct tttttttctg cttgcttttc atttaatttg ttcctctttt tctagtttaa 145980
ggtagaaact tccattatta gttggagacc ttattttctt atatagatgt ttaaagctaa 146040
aaaatttttt atgtattttc attcattttc taatgtcctt catgattttt ttttcattga 146100
cccatgtgta ttgctttaat ttttacatat ttggggattt tctatctctc ttcctattca 146160
tttctaattt aattccattg aggtaggaga tacactgaat gactctaata agttttctga 146220

```
gactttttta ggcagttgct tatggtctat cctgagcgtt ccatgagtgc ttaaaaaaaa 146280
aaacttacac tgtgctcttg ttaagtaggg ttttatgaac atcagttagg tcaagtggat 146340
tgatagagta gttcaggttt tctgtatctt tgctgatttt ctgtctagtt gtgctagatt 146400
cctactactt tgtctacatc cttgctagag cttggtatgg tctttttatt atcgctatcc 146460
tagggagtat gtagttgacc cttgtgactt gccatgcatt taatgactgc ccatgttcat 146520
agcagcatta ttcataatag cagaaaaact tttatcatat gcttttgtgc ctcaagatca 146580
tatatctttc atttttagtc tattaatacg gtataatata ctgttgttta atttttgagt 146640
aattgactag cctttcattc ctgggataaa tcctatttgg ttatgatata atatcctttt 146700
tacatatagc tgaattcagt gtactaaaat tttggtattt ttgcatctaa atccatgagg 146760
gatatattct atagctttgg tgttatgata atatggtatt atttcttcct taaatgtctg 146820
gtaaaactca gcagcgaagc catcttggtt tgcttggagc ctttttgta gaaaggtttt 146880
caagtacaaa ttcatcaaat gtttactgat atttgtttat tcttgagtgg gctttgttgg 146940
tttacatctt tgaaggaatt taactgtttc cttcaaatgt tgaatttatt ggtataaaag 147000
ttattcataa tattcttcta atggttccag catcgctagt attattccct ttcattccgg 147060
acattggtat ttaatatatt cttgcttttt tttttttttt ttaaatcagt ctggctaaaa 147120
gttttcagtt ttaccgatgt tttcatagaa ccagcttggt cttgattttg ttgttgttta 147180
tgcatgttct tagttaggcg tttctactct ttatcctttc catttttctt gtgtttagtt 147240
taccagttta gggtagaagc atatataatt gagacctttc ttttctaata aaagctctta 147300
atgctataaa ttttctaagc actgtcttga ttgcatccca cacattttgc tacgctgtgt 147360
tttcagtact agagatttta aagtttttct tatgatgcct tatttaatcc atagcttact 147420
aaatgtcaaa ttccaaacat ttgggttttt ctacagatat gtttgttact gacttctgtt 147480
taaatctcat ttttgtcaga gagcattcat tgtatgatgt aatcctaagt gtattcagtc 147540
ttgttttatg ttctagatta atgttctgtg tatacttgaa aagaatgcag ttcttgggta 147600
gactgtttca gaaatgtcaa attattgatt ctgagacaaa ggtttttata attgtagatt 147660
gtctgccaaa tatccccttg gaggcaaact ctccccctcc cttttgagaa tcactgatcc 147720
attgtcacct ttttgctggg actaatttag ccttgcttct gagatgtggc ccctaggtct 147780
ctactgaatt ccttgcatat ttaattagat ctttctttcc tctatggcct caagggattt 147840
caccctaagt atgcacgaat ttttactttg tgtacctcct tagtttccag tagtctaacc 147900
cataaattaa agctgcttta gcctccccaa acttcaatct ctttctcctc aatccagcaa 147960
gattgctaga ctctgggttc cctttccctg ctctgcagta tgatgattac tttcaagcaa 148020
aaaggcttag aattaagatt tcttgctcct aggctaggta tggcttacca tctttgtttc 148080
tcttttccta gagatcataa tcatgtattg cttgttttct agttttccag taggagggga 148140
attccaggct gtacttactt cctgcagcca aaagaggatg tcatgttagt gatttcaata 148200
ctaaaacatt aaacaaaaaa tttgagatgg atgaaattat tttatatgca tattgaattg 148260
ggcttcacca tagttatttt tagaattagg actaaccagc aggggagaaa aactataagc 148320
aatcactgtt ttacaatttt gcaataatta gattttctat agcatagtaa tgtgtaaaat 148380
taacccattg ttaacataga atgcccttat cacacctgat tatcactcct gattaagcgg 148440
tcttcatttc atgttaatac tggtatctta gaagtgtcaa gtaatgcttt acggaatcaa 148500
acattttcat acatagtcat tagtctaatt ctaatgatcc agtgaaaaag agcaggaaag 148560
```

atgctcaagg aggttatact gaagtccaca tggcaagtaa gaaataagtc accacgccca 148620
gccaagaggt cttaacacct gaaatcccag cactttggga ggccgaggca ggtggaattg 148680
cttgaacctg ggagatagga ggtggaagtt acagtgagcc gagatcacac cactgcactc 148740
cagcctaagc cacacagcga gactctgtct tgggcaaaac aaaaaaaaaa aaaaaaaaca 148800
aattaagact tctcaaagct cctaaatcca cagcttttcc tttataccag catcttctaa 148860
aaatgtcagc agcagtgaag tttccgtttg ggaaataatg cattccctct ctctggagag 148920
tgtatgggag tatctccaag aagtactgaa agagtgtatg ggagtatctc caagaagtac 148980
tgaaattcag aagtctgcct aatatgtatt aaacattaag cttttctcaa actttgacca 149040
ccaaatcctt tttctccctc taaccatagt taacacagaa tcagtgttcc caagagcaca 149100
ctgtgaaaaa tgtagcactc tacaaaagtc ctaatctcca caggattcag tgaaaccatg 149160
attaaccctc tcttccttgt ccttattagt accatttttt gaagagtaat gtaatgtacc 149220
ccccaaaatt tttttttttt tttttgagac agagtctcgc tgtgtcgccc agcctggagt 149280
gcagtggccg gatctcagtt cactgcaagc tccgcctcct gggtttacgc cattctcctg 149340
cctcagcctc ccaagtagct aggactacag gcacccgcca cctcgcccgg ctagtttttt 149400
tttttttagt agagatgggg tttcaccgtg ttagccagga tggtctcgat ctcctgacct 149460
cgtgatccac ccgtctcggc ctcccaaagt gctgggatta caggcttgag ccacttcgcc 149520
cggccccaaa atttttatta ccagtttcac taacaagaat ccatgtacct aaggaaggac 149580
agatatctgc tccctattaa gacataccta ttagctacat taaaaaaaaa aaaatgtatt 149640
gcatggcgat tttaaagtta taattaactg gtgatatcac agatattcta agatgtaatt 149700
gctggaataa acactgttgt tgaagccttc tatttatctc aataccagaa ttaaactaaa 149760
gtgcagaatg gcagacaaag ttaactaaaa atcactgtat tatttcatct ggtcttccaa 149820
atagctttgt gagctaggga ggaaggtatc atcatcagtt ccattttata gatgagaaat 149880
caagtgattt actcaaggtt aagtcctcta attctttgtt atcctgcatt ttctcttggc 149940
tgtagtttaa taatcctgag aaaatgctta tattttaggg tgcattaaga gtacacagac 150000
agtgttaagt gcccgtcttg catgtatgaa aagttacagc aagaaatttg gctggaaacg 150060
gtggctcaca cctataatcc tagcactttg ggaggcttag gcaggaggac tgcttgagcc 150120
caggagttta agaccagcct gggcaacata gggagatcct gtctctacaa aaaaatttag 150180
ccagacctgg tggcttgtgc ctacagtcct agctactcag gaggctgagg tgggaggatc 150240
acttgagcaa atgaggtcaa ggctccagtg agctatgatt atgccactgc actccagcct 150300
ggttgacaca gtgagaccct gggtgacaca gtgagaccct atctcaaaaa aaaaaaaaga 150360
aaagaaaaag aaaatccttt aattgacttc atcttaacct tttagttcct aaagacggtc 150420
tgaagagcca agagctattt gatgaaatta gaatgaccta catcaaagag ctaggaaaag 150480
ccattgtcaa gagggaagga aactccagcc agaactggca gcggttttat caactgacaa 150540
aactcttgga ttctatgcat gaagtaagtg tcgaacataa aaccaaatat aagaattttc 150600
tgggacaaag tatattttga ttagtgcata taattatata ccaacagcac ccccactcca 150660
tccccagttt gtggatgttg gtgatagctt cagttcaact tatgaacttc agttttgtag 150720
acatttttcc taagaccaat tatgaaatat cctttcatct tataaaatca cgatgttatt 150780
atagaattga ataacacttt ttaaaaagta tgattaatcc attaaattag aataatgtac 150840
cctttatata ggtaccacag cggttcatga aataattcca tataattcta catacaatca 150900
aagaaacttg tacagaagtg cttatttttc acctggggaa tttcagtgag attggtatat 150960
tctaggccag ataatttttt caaaatagag gacaacaaac atgagctgtt cccactcacc 151020
aattttgaag cctaatcatt actatatttt ctcttgcagg tggttgaaaa tcttcttaac 151080
tattgcttcc aaacattttt ggataagacc atgagtattg aattcccaga gatgttagct 151140
gaaatcatca ccaatcagat accaaaatat tcaaatggaa atatcaaaaa acttctgttt 151200
catcaaaagt gactgcctta ataagaatgg ttgccttaaa gaaagtcgaa ttaatagctt 151260
ttattgtata aactctcagt ttgtcctgta gaggttttgt tgttttattt tttattgttt 151320
tcgtctgttg ttttgtttta aatacgcact acatgtggtt tatagagggc caagacttgg 151380
caacagaagc aattgagtca tcacttttca gtgatgggag agtagacggt gaaatttcat 151440
taagttagta tatcccagaa attagaaacc ttaatatgtg gacgtaatct ccatagtcaa 151500
agaaggatgg cacctaaacc accagtgccc aaagtctgtg tgatgaactt tctgctcata 151560
ctttttcaca gttggctgga tgaaattttc tagactttct gttggtgtat ccccccctgt 151620
atagttaaga tagcattttt gatttatgca tggaaacctg aaaaaagttt acaagtgtat 151680
atcagaaaag ggaagttgtg ccttttatag ctattactgt ctggttttaa caatttcctt 151740
tatatttagt gaactacgct tgctcatttt ttcttacata atttttttatt caagttattg 151800 tacagctgtt taagatgggc agctagttcg tagctttccc aaataaactc taaacattaa 151860
tcttctgtgt gaaaatgggt tggtgcttct aacctgatgg cacttagcta tcagaagacc 151920
acaaaattga ctcaaatctc cagtattctt gtcaaaaaaa agctcacatt ttgtatatat 151980
ctgcttcagt ggagaattat ataggttgtg caaattcacc atcctaactg gtatgagcac 152040
ctagtccagg gacctgctgg gtaaactgtg gatgatggtt gcaaaagact gatttaaaaa 152100
tcactaccaa gaggccctgt ctgtacctaa tgccctattt ttgcaaaggc tatatggcaa 152160
gaaagctggt aaactatttg tctttcagga ccttttgaag tagtttgtat aacttcttaa 152220
aagttgtgat tccagacaac cagctgtaac acagctgaga gaattttaat cagagcaagt 152280
aattcctctc actaaacttt acccaaaaac taaatctcta atatggcaaa aatggctaga 152340
cacccatttt cacattccca tctgtcacca attggttaat ctttcctgat ggtacaggaa 152400
agctcagcta ctgatttttg tgatttagaa ctgtatgtca gacatccatg tttgtaaaac 152460
tacacatccc taatgtgtgc catagagttt aacacaagtc ctgtgaattt cttcactgtt 152520
gaaaattatt ttaaacaaaa tagaagctgt agtagccctt tctgtgtgca ccttaccaac 152580
tttctgtaaa ctcaaaactt aacatattta ctaagccaca agaaatttga tttctattca 152640
aggtggccaa attatttgtg taatagaaaa ctgaaaatct aatattaaaa atatggaact 152700
tctaatatat ttttatattt agttatagtt tcagatatat atcatattgg tattcactaa 152760
tctgggaagg gaagggctac tgcagcttta catgcaattt attaaaatga ttgtaaaata 152820
gcttgtatag tgtaaaataa gaatgatttt tagatgagat tgttttatca tgacatgtta 152880
tatatttttt gtaggggtca aagaaatgct gatggataac ctatatgatt tatagtttgt 152940
acatgcattc atacaggcag cgttggtctc agaacccaaa caatttgctc taggggaaga 153000
gggagatgga gactggtcct gtgtgcagtg aaggttgctg aggctctgac ccaatgagat 153060
tacagaggaa gttaccctct gcctcccatt ctgaccaccc ttctcattcc aacagtgagt 153120
ctgtcagtgc aggtttagtt tactcaatct ccccttgcac taaagtatgt aaacaggaga 153180
caggaaagtg gtgcttacat acttaaaggc accatctaat agtgggttac tttcacatac 153240
aggcctcccc cagcagttga atgacaacag aagtttggca atagtttgca tagaggtacc 153300

```
agcaatatgt aaatagtgca gaatctcata ggttgccaat aatacactaa ttcctttcta 153360
tcctacaaca agagtttatt tccaaataaa atgaggacat gtttttgttt tctttgaatg 153420
ctttttgaat gttatttgtt attttcagta ttttggagaa attatttaat aaaaaacaat 153480
catttgcttt ttgaatgctc tctaaaaggg aatgtaatat tttaagatgg tttgtaaccc 153540
agctggataa atttttggtg cctaagaaaa ctgcttgaat atttttatca atgacagtgt 153600
taagtttcaa aaagagcttc tacaatgtag attatcattc atttatagaa cgttatgtgg 153660
ttaaaaccag aaagcacatc tcacacatta atctgatttt cgtcccaaca atcttggcgc 153720
tcaaaaaata gaactcaatg aaaaaaagat tatgtgtact ttgctgtcaa taataagtca 153780
actgatattc atcaacaact ataggaggct tttcattaaa tgggaaaaga agctgtgccc 153840
ttttagaata catgggggaa aagaaagtca tcttaattat gtttaactag ggacttaagt 153900
gctatagggt ggtgctgttt gaaagcagct ttatttccta tgtatgtgtt atctggttat 153960
cccaacccaa actattgaag tttgtagtaa cttcagtgag agttggttac tcacaacaaa 154020
tcctgaaaag tatttttaat tactggtgta aaaaagtgac ctcctcagtg tttgtaggca 154080
ttctgtggga tactatacag gcagaactga ggcacttgga acacttttgg ggtttatata 154140
cccaaatgcc taaaactgtg ggaggaaacc ctggccatcc cataaggaaa actagcatga 154200
tttgtgtcta tgaagtgctg gataattagc atgggatgag ctctgggcat gcccacgaag 154260
gaaagccacg ctcccttgag aattcagagg ctagggagca attccagttt cacctaagtc 154320
tcataatttc agttcccttt taaaaaccct aaaaactaca ccaccatgga atgcaaaata 154380
ttgttataca acacattgat ctgtcaaact tccagaacca tggcagcctt cagtgagatt 154440
tcgatcttgg ctggtcactc cctgactgta gctgtaggtg aatgtgtttt tttatgtgcc 154500
tggttttagt gtcagaaggg aaataaaagt gtaaggagga cactttaagc cctttgggtg 154560
gagtttcata atatcccaga ctattttcaa gcaacctggt ccacccagga ttagtgacca 154620
ggttttcagg aaaggatttg cttctctcta gaaaatgtct gaaaggattc tattttctga 154680
tgaaaggctg tatgaaaata ccctcctcaa ataacttgct taactacata tagattcaag 154740
tgtgtcaata ttctattttg tatattaaat gctatataat ggggacaaat ctatattata 154800
ctgtgtatgg cattattaag aagctttttc attatttttt atcacagtaa ttttaaaatg 154860
tgtaaaaatt aaaaccagtg actcctgttt aaaaataaaa gttgtagttt tttattcatg 154920
ctgaataata atctgtagtt aaaaaaaaaa aatgtctttt tacctacgca gtgaaatgtc 154980
agactgtaaa accttgtgtg gaaatgttta actttttattt tttcatttaa atttgctgtt 155040
ctggtattac caaaccacac atttgtaccg aattggcagt aaatgttagt tagccattta 155100
cagcaatgcc aaatatggag aaacatcata ataaaaaaaa actgcttttt cattatgtga 155160
ctccaacatg cttttgtaga acttgtacag ttccgattgt ccaatctgat ttttgttcta 155220
ctaaaagtag agctaccccc gcttcaggaa ccctaagata atatggtggg catttaaatg 155280
tcggtgtggc aatgttcaca tgctaatatg gcataaattc aaaataagct tagccctggt 155340
gccaaagacc tgaagattat cccatccatg cctcaaatgg ttgtgtgcca attactgcaa 155400
agggtactaa gggaaggaga aactcctgag gctgcctcaa atgtatgtct ttatcacaaa 155460
agatatttta tttaagcaaa cattatctag tcaaaattct tagcttattt tgaaatcaac 155520
tcttcaagaa aaaggaataa acatttaata taaatatcat ggcaatattg cacatagaat 155580
agaaaggtgg ggcagtgtag tggcaagtca gctattctat acaattcatt cagtattttc 155640
caaaacattt gatattgagg ccatatccag gaactggatg acctaacaaa cttcttggag 155700
```

```
tacttttttt tttcacaaga gagctccatc actaagaaaa aaagaattgt gatttaaaag 155760

ccaaatttgc cttatccatc attatgtgca ccaagtattt gctacctgcc tactatataa 155820

tattgaagat acaacatgaa taagaaaaat actattgcta ccctcagtca cttagagtat 155880

gtgattggaa aagtgtgtaa cacacctttc ccagtgtctt caggtataat gcagagatac 155940

agatatggca tcaatatgta tacacattat ggctctacca ttcactttta gtagtaacct 156000

tacatttctg tagaacacct tcacacacat ttttaataag cctcaccgaa tgaataaatg 156060

acatgaaaat aacgaggcag attattctcg tttccatttt ataagtaaac tctataagaa 156120

agtaaacagg ctcagaattt aaggaactga ttcatagccc ctagctccca tgttattgaa 156180

gtttgaatgg aaagccttta atgaggccat tcatctatca gatgtcaaag agcatgtctc 156240

tggcctatga gcctctcagg gaactggtta tgtttttctg ttttaaatta atgctttact 156300

gagcacttac tatgtgccag gcacaatgat cattcaacat atctcatttt atcttagtac 156360

ccctctaaag tactactgca aagcagtgat attatatcct cattatattt atatcaggaa 156420

actggcttaa agaattgagt cacttgccta gagtcaccaa gctccagaat ccatagtttt 156480

aaccacttga gaaattatta atatgagcta actagggcga gtgagcccaa gttgatcatt 156540

atgtgtctcg tcttctgaca tgtcctcgtt taatcccttt tgctaccata tcaattttga 156600

cttagaaatt taacaatgat acattagtcc ctgcttatct atggaggata tgttccaaga 156660

ctcccaatgg atgcctgaaa cagatagtac tgaactgtat attttttcct atattacata 156720

cctatgataa agttaattta caaactagat gcagcaagag attaacaata actcaattac 156780

aacaatatac tgtaataaaa gctatgtgaa tgtgatctct cgaaaaatcg tactacactg 156840

agggtaaatg aaaccacaga aagtgaaact gcagataagg aggggactat tgtatttcct 156900

tctcttaaaa acatgtgtct tgtaccctag ggtggttgat ggtggacaat agtagttgcc 156960

cacagattac agaatgccct ctggtttgtc taatacacaa c                     157001
```

<210> SEQ ID NO 3

<400> SEQUENCE: 3

000

<210> SEQ ID NO 4
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 4

```
gtcaaaggtg ctttggtctg                                               20
```

<210> SEQ ID NO 5
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 5

```
tccacagatc tctagggcag                                               20
```

<210> SEQ ID NO 6
<211> LENGTH: 20

<212> TYPE: DNA
<213> ORGANISM: Artificial sequence
<220> FEATURE:
<223> OTHER INFORMATION: Synthetic oligonucleotide

<400> SEQUENCE: 6
ggtagaaata tagttgttcc 20

<210> SEQ ID NO 7
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 7
ttcatgtgtc tgcatcatgt 20

<210> SEQ ID NO 8
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 8
atttggctat tgtgggattc 20

<210> SEQ ID NO 9
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 9
ggcatccagc gagcaccaaa 20

<210> SEQ ID NO 10
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 10
agccatggtg atcaggaggc 20

<210> SEQ ID NO 11
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 11
ggtctggatt acagcataaa 20

<210> SEQ ID NO 12
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 12
tactggtgct tgtccaggat 20

<210> SEQ ID NO 13
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 13
tctgcgcacc tgcaggccca 20

<210> SEQ ID NO 14
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 14
acttcttaca tggtggtggc 20

<210> SEQ ID NO 15
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 15
gcaactatga aaccacagtt 20

<210> SEQ ID NO 16
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 16
ggtatatatt tccatcctta 20

<210> SEQ ID NO 17
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 17
cgacctattg aggtttgcaa 20

<210> SEQ ID NO 18
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 18
gcagacattt tattaccaat 20

<210> SEQ ID NO 19
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 19
gtacatctgt cctccagagg 20

<210> SEQ ID NO 20
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 20
tattcatgtc atagtggtac 20

<210> SEQ ID NO 21
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 21
gctgtattca tgtcatagtg 20

<210> SEQ ID NO 22
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 22
gcgcacctgc aggcccaaca 20

<210> SEQ ID NO 23
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 23
ccctcaggtt ttgatgctgc 20

<210> SEQ ID NO 24
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 24
ccacagatct ctagggcagg 20

<210> SEQ ID NO 25
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 25
gtggtagaaa tatagttgtt 20

<210> SEQ ID NO 26
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 26
gtgtctgcat catgtctctc 20

<210> SEQ ID NO 27
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 27
tgtgtctgca tcatgtctct 20

<210> SEQ ID NO 28
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 28
tcatgtgtct gcatcatgtc 20

<210> SEQ ID NO 29
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 29
tatttcatgt gtctgcatca 20

<210> SEQ ID NO 30
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 30
ggctattgtg ggattctcct 20

<210> SEQ ID NO 31
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 31
tggctattgt gggattctcc 20

<210> SEQ ID NO 32
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 32
ttggctattg tgggattctc 20

<210> SEQ ID NO 33
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 33
gcatccagcg agcaccaaag 20

<210> SEQ ID NO 34
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 34
gggcatccag cgagcaccaa 20

<210> SEQ ID NO 35
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 35
cagccatggt gatcaggagg 20

<210> SEQ ID NO 36
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 36
gcagccatgg tgatcaggag 20

<210> SEQ ID NO 37
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 37
tgcagccatg gtgatcagga 20

<210> SEQ ID NO 38
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 38
ctgcagccat ggtgatcagg 20

<210> SEQ ID NO 39

<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 39
gtctggatta cagcataaac 20

<210> SEQ ID NO 40
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 40
ttggtctgga ttacagcata 20

<210> SEQ ID NO 41
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 41
cttggtctgg attacagcat 20

<210> SEQ ID NO 42
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 42
ccttggtctg gattacagca 20

<210> SEQ ID NO 43
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 43
gtgcttgtcc aggatgatgc 20

<210> SEQ ID NO 44
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 44
ctactggtgc ttgtccagga 20

<210> SEQ ID NO 45
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 45
tgcgcacctg caggcccaac 20

<210> SEQ ID NO 46
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 46
cttcttacat ggtggtggca 20

<210> SEQ ID NO 47
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 47
tacttcttac atggtggtgg 20

<210> SEQ ID NO 48
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 48
gtacttctta catggtggtg 20

<210> SEQ ID NO 49
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 49
ggtacttctt acatggtggt 20

<210> SEQ ID NO 50
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 50
aggtacttct tacatggtgg 20

<210> SEQ ID NO 51
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 51
caggttttga tgctgctgct 20

<210> SEQ ID NO 52
<211> LENGTH: 20
<212> TYPE: DNA

```
<213> ORGANISM: Artificial sequence
<220> FEATURE:
<223> OTHER INFORMATION: Synthetic oligonucleotide

<400> SEQUENCE: 52

ctcaggtttt gatgctgctg                                    20


<210> SEQ ID NO 53
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 53

cctcaggttt tgatgctgct                                    20


<210> SEQ ID NO 54
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 54

ggcaactatg aaaccacagt                                    20


<210> SEQ ID NO 55
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 55

tggcaactat gaaaccacag                                    20


<210> SEQ ID NO 56
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 56

aggtatatat ttccatcctt                                    20


<210> SEQ ID NO 57
<211> LENGTH: 27
<212> TYPE: DNA
<213> ORGANISM: Artificial sequence
<220> FEATURE:
<223> OTHER INFORMATION: Synthetic oligonucleotide

<400> SEQUENCE: 57

gcgtttgctc ttcttcttgc gtttttt                            27


<210> SEQ ID NO 58
<211> LENGTH: 27
<212> TYPE: DNA
<213> ORGANISM: Artificial sequence
<220> FEATURE:
<223> OTHER INFORMATION: Primer

<400> SEQUENCE: 58

ggagatcata tagacaatca agtgcaa                            27
```

<210> SEQ ID NO 59
<211> LENGTH: 26
<212> TYPE: DNA
<213> ORGANISM: Artificial sequence
<220> FEATURE:
<223> OTHER INFORMATION: Primer

<400> SEQUENCE: 59
gggtagagtc attctctgct cattaa 26

<210> SEQ ID NO 60
<211> LENGTH: 23
<212> TYPE: DNA
<213> ORGANISM: Artificial sequence
<220> FEATURE:
<223> OTHER INFORMATION: Probe

<400> SEQUENCE: 60
ctgtgttttg ctcctgatct gat 23

<210> SEQ ID NO 61
<211> LENGTH: 18
<212> TYPE: DNA
<213> ORGANISM: Artificial sequence
<220> FEATURE:
<223> OTHER INFORMATION: Primer

<400> SEQUENCE: 61
ttaggagggc ggcaagtg 18

<210> SEQ ID NO 62
<211> LENGTH: 25
<212> TYPE: DNA
<213> ORGANISM: Artificial sequence
<220> FEATURE:
<223> OTHER INFORMATION: Primer

<400> SEQUENCE: 62
aggtgtaagt tcctgaaacc tggta 25

<210> SEQ ID NO 63
<211> LENGTH: 24
<212> TYPE: DNA
<213> ORGANISM: Artificial sequence
<220> FEATURE:
<223> OTHER INFORMATION: Probe

<400> SEQUENCE: 63
tgcagcagtg aaatgggcaa aggc 24

<210> SEQ ID NO 64
<211> LENGTH: 27
<212> TYPE: DNA
<213> ORGANISM: Artificial sequence
<220> FEATURE:
<223> OTHER INFORMATION: Primer

<400> SEQUENCE: 64
ggagatcata tagacaatca agtgcaa 27

<210> SEQ ID NO 65
<211> LENGTH: 26
<212> TYPE: DNA
<213> ORGANISM: Artificial sequence
<220> FEATURE:

-continued

```
<223> OTHER INFORMATION: Primer

<400> SEQUENCE: 65

gggtagagtc attctctgct cattaa                                   26


<210> SEQ ID NO 66
<211> LENGTH: 23
<212> TYPE: DNA
<213> ORGANISM: Artificial sequence
<220> FEATURE:
<223> OTHER INFORMATION: Probe

<400> SEQUENCE: 66

ctgtgttttg ctcctgatct gat                                      23


<210> SEQ ID NO 67
<211> LENGTH: 18
<212> TYPE: DNA
<213> ORGANISM: Artificial sequence
<220> FEATURE:
<223> OTHER INFORMATION: Primer

<400> SEQUENCE: 67

gcgcagcagc cagatctc                                            18


<210> SEQ ID NO 68
<211> LENGTH: 24
<212> TYPE: DNA
<213> ORGANISM: Artificial sequence
<220> FEATURE:
<223> OTHER INFORMATION: Primer

<400> SEQUENCE: 68

tctcccatat acagtcccat tgag                                     24


<210> SEQ ID NO 69
<211> LENGTH: 15
<212> TYPE: DNA
<213> ORGANISM: Artificial sequence
<220> FEATURE:
<223> OTHER INFORMATION: Probe

<400> SEQUENCE: 69

ccaaagcagt ttcac                                               15
```

ANTISENSE MODULATION OF GCCR EXPRESSION

RELATED APPLICATIONS

This application is a continuation of U.S. patent application Ser. No. 13/660,885, filed Oct. 25, 2012, which is a non-provisional filing claiming priority to U.S. Provisional Application No. 61/551,378, filed Oct. 25, 2011, each of which is herein incorporated in its entirety.

SEQUENCE LISTING

The present application is being filed along with a Sequence Listing in electronic format. The Sequence Listing is provided as a file entitled BIOL0159USC1SEQ_ST25.txt created Oct. 24, 2014, which is 420 Kb in size. The information in the electronic format of the sequence listing is incorporated herein by reference in its entirety.

FIELD

Provided herein are methods, compounds, and compositions for reducing expression of GCCR mRNA and protein in an animal. Such methods, compounds, and compositions are useful, for example, to treat, prevent, delay or ameliorate diseases associated with metabolic disorders, particularly disorders associated with diabetes.

BACKGROUND

Diabetes is a chronic metabolic disorder characterized by impaired insulin secretion and/or action. In type 2 diabetes (T2DM), insulin resistance leads to an inability of insulin to control the activity of gluconeogenic enzymes, and many subjects also exhibit inappropriate levels of circulating glucagon (GC) in the fasting and postprandial state. Glucagon is secreted from the α-cells of the pancreatic islets and regulates glucose homeostasis through modulation of hepatic glucose production (Quesada et al., J. Endocrinol. 2008. 199: 5-19).

Glucagon exerts its action on target tissues via the activation of glucocorticoid receptor (GCCR). The glucocorticoid receptor is a 62 kDa protein that is a member of the class B G-protein coupled family of receptors (Brubaker et al., Recept. Channels. 2002. 8: 179-88). GCCR activation leads to signal transduction by G proteins ($G_s\alpha$ and $G_q$), whereby $G_s\alpha$ activates adenylate cyclase, which causes cAMP production, resulting in an increase in levels of protein kinase A. GCCR signaling in the liver results in increased hepatic glucose production by induction of glycogenolysis and gluconeogenesis along with inhibition of glycogenesis (Jiang and Zhang. Am. J. Physiol. Endocrinol. Metab. 2003. 284: E671-E678). GCCR is also expressed in extrahepatic tissues, which includes heart, intestinal smooth muscle, kidney, brain, and adipose tissue (Hansen et al., Peptides. 1995. 16: 1163-1166).

Development of GCCR inhibitors have been hampered by the unfavorable side effects associated with systemic GCCR inhibition, including activation of the hypothalamic-pituitary adrenal (HPA) axis. Inhibition of GCCR activity in the brain can lead to an increase in circulating adrenocorticotropic hormone due to feedback regulation and a consequent increase in secretion of adrenal steroids (Philibert et al., Front. Horm. Res. 1991. 19: 1-17). This, in turn, can produce a myriad of negative chronic steroid-related side-effects. Other studies have demonstrated that specific inactivation of GCCR resulted in hypoglycemia upon prolonged fasting (Opherk et al., Mol. Endocronol. 2004. 18: 1346-1353).

It has previously been demonstrated in pre-clinical models that administration of GCCR antisense oligonucleotides results in tissue-specific accumulation and reduced GCCR expression in liver and adipose tissue (PCT Pub. No. WO2005/071080; PCT Pub. No. WO2007/035759) without affecting GCCR mRNA levels in the CNS or adrenal glands. Thus, antisense inhibition of GCCR mRNA expression has be shown to improve hyperglycemia and hyperlipidemia without activating the HPA axis. The present invention provides compositions and methods for modulating GCCR expression. Antisense compounds for modulating expression of GCCR are disclosed in the aforementioned published patent applications. However, there remains a need for additional improved compounds. The compounds and treatment methods described herein provide significant advantages over the treatments options currently available for GCCR related disorders.

All documents, or portions of documents, cited in this application, including, but not limited to, patents, patent applications, articles, books, and treatises, are hereby expressly incorporated-by-reference for the portions of the document discussed herein, as well as in their entirety.

SUMMARY

Provided herein are methods, compounds, and compositions for modulating expression of GCCR and treating, preventing, delaying or ameliorating diseases associated with metabolic disorders, particularly disorders associated with diabetes and/or a symptom thereof.

DETAILED DESCRIPTION

It is to be understood that both the foregoing general description and the following detailed description are exemplary and explanatory only and are not restrictive described herein, as claimed. Herein, the use of the singular includes the plural unless specifically stated otherwise. As used herein, the use of "or" means "and/or" unless stated otherwise. Furthermore, the use of the term "including" as well as other forms, such as "includes" and "included", is not limiting. Also, terms such as "element" or "component" encompass both elements and components comprising one unit and elements and components that comprise more than one subunit, unless specifically stated otherwise.

The section headings used herein are for organizational purposes only and are not to be construed as limiting the subject matter described. All documents, or portions of documents, cited in this application, including, but not limited to, patents, patent applications, articles, books, and treatises, are hereby expressly incorporated-by-reference for the portions of the document discussed herein, as well as in their entirety.

DEFINITIONS

Unless specific definitions are provided, the nomenclature utilized in connection with, and the procedures and techniques of analytical chemistry, synthetic organic chemistry, and medicinal and pharmaceutical chemistry described herein are those well known and commonly used in the art. Standard techniques can be used for chemical synthesis, and chemical analysis. Where permitted, all documents, or portions of documents, cited in this application, including, but not limited to, all patents, applications, published applications and other journal publications, GENBANK Accession Numbers and associated sequence information obtainable through databases such as National Center for Biotechnology Information (NCBI) and other data referred to throughout in the disclosure herein are incorporated by reference for the portions of the document discussed herein, as well as in their entirety.

Unless otherwise indicated, the following terms have the following meanings:

"2'-O-methoxyethyl" (also 2'-MOE and 2'-O$(CH_2)_2$—$OCH_3$) refers to an O-methoxy-ethyl modification of the 2' position of a furosyl ring. A 2'-O-methoxyethyl modified sugar is a modified sugar.

"2'-O-methoxyethyl nucleotide" means a nucleotide comprising a 2'-O-methoxyethyl modified sugar moiety.

"3' target site" refers to the nucleotide of a target nucleic acid which is complementary to the 3'-most nucleotide of a particular antisense compound.

"5' target site" refers to the nucleotide of a target nucleic acid which is complementary to the 5'-most nucleotide of a particular antisense compound.

"5-methylcytosine" means a cytosine modified with a methyl group attached to the 5' position. A 5-methylcytosine is a modified nucleobase.

"About" means within ±10% of a value. For example, if it is stated, "a marker may be increased by about 50%", it is implied that the marker may be increased between 45%-55%.

"Active pharmaceutical agent" means the substance or substances in a pharmaceutical composition that provide a therapeutic benefit when administered to an individual. For example, in certain embodiments an antisense oligonucleotide targeted to GCCR is an active pharmaceutical agent.

"Active target region" or "target region" means a region to which one or more active antisense compounds is targeted. "Active antisense compounds" means antisense compounds that reduce target nucleic acid levels or protein levels.

"Adiposity" or "Obesity" refers to the state of being obese or an excessively high amount of body fat or adipose tissue in relation to lean body mass. The amount of body fat includes concern for both the distribution of fat throughout the body and the size and mass of the adipose tissue deposits. Body fat distribution can be estimated by skin-fold measures, waist-to-hip circumference ratios, or techniques such as ultrasound, computed tomography, or magnetic resonance imaging. According to the Center for Disease Control and Prevention, individuals with a body mass index (BMI) of 30 or more are considered obese. The term "Obesity" as used herein includes conditions where there is an increase in body fat beyond the physical requirement as a result of excess accumulation of adipose tissue in the body. The term "obesity" includes, but is not limited to, the following conditions: adult-onset obesity; alimentary obesity; endogenous or inflammatory obesity; endocrine obesity; familial obesity; hyperinsulinar obesity; hyperplastic-hypertrophic obesity; hypogonadal obesity; hypothyroid obesity; lifelong obesity; morbid obesity and exogenous obesity.

"Administered concomitantly" refers to the co-administration of two agents in any manner in which the pharmacological effects of both are manifest in the patient at the same time. Concomitant administration does not require that both agents be administered in a single pharmaceutical composition, in the same dosage form, or by the same route of administration. The effects of both agents need not manifest themselves at the same time. The effects need only be overlapping for a period of time and need not be coextensive.

"Administering" means providing an agent to an animal, and includes, but is not limited to, administering by a medical professional and self-administering.

"Agent" means an active substance that can provide a therapeutic benefit when administered to an animal. "First Agent" means a therapeutic compound provided herein. For example, a first agent can be an antisense oligonucleotide targeting GCCR. "Second agent" means a second therapeutic compound described herein (e.g. a second antisense oligonucleotide targeting GCCR) and/or a non-GCCR therapeutic compound.

"Amelioration" refers to a lessening of at least one indicator, sign, or symptom of an associated disease, disorder, or condition. The severity of indicators can be determined by subjective or objective measures, which are known to those skilled in the art.

"Animal" refers to a human or non-human animal, including, but not limited to, mice, rats, rabbits, dogs, cats, pigs, and non-human primates, including, but not limited to, monkeys and chimpanzees.

"Antisense activity" means any detectable or measurable activity attributable to the hybridization of an antisense compound to its target nucleic acid. In certain embodiments, antisense activity is a decrease in the amount or expression of a target nucleic acid or protein encoded by such target nucleic acid.

"Antisense compound" means an oligomeric compound that is capable of undergoing hybridization to a target nucleic acid through hydrogen bonding.

"Antisense inhibition" means reduction of target nucleic acid levels or target protein levels in the presence of an antisense compound complementary to a target nucleic acid compared to target nucleic acid levels or target protein levels in the absence of the antisense compound.

"Antisense oligonucleotide" means a single-stranded oligonucleotide having a nucleobase sequence that permits hybridization to a corresponding region or segment of a target nucleic acid.

"Bicyclic sugar" means a furosyl ring modified by the bridging of two non-geminal ring atoms. A bicyclic sugar is a modified sugar.

"Bicyclic nucleic acid" or "BNA" refers to a nucleoside or nucleotide wherein the furanose portion of the nucleoside or nucleotide includes a bridge connecting two carbon atoms on the furanose ring, thereby forming a bicyclic ring system.

"Cap structure" or "terminal cap moiety" means chemical modifications, which have been incorporated at either terminus of an antisense compound.

"Chemically distinct region" refers to a region of an antisense compound that is in some way chemically different than another region of the same antisense compound. For example, a region having 2'-O-methoxyethyl nucleotides is chemically distinct from a region having nucleotides without 2'-O-methoxyethyl modifications.

"Chimeric antisense compound" means an antisense compound that has at least two chemically distinct regions.

"Co-administration" means administration of two or more agents to an individual. The two or more agents can be in a single pharmaceutical composition, or can be in separate pharmaceutical compositions. Each of the two or more agents can be administered through the same or different routes of administration. Co-administration encompasses parallel or sequential administration.

"Cholesterol" is a sterol molecule found in the cell membranes of all animal tissues. Cholesterol must be transported in an animal's blood plasma by lipoproteins including very low density lipoprotein (VLDL), intermediate density lipoprotein (IDL), low density lipoprotein (LDL), and high density lipoprotein (HDL). "Plasma cholesterol" refers to the sum of all lipoproteins (VDL, IDL, LDL, HDL) esterified and/or non-esterified cholesterol present in the plasma or serum.

"Complementarity" means the capacity for pairing between nucleobases of a first nucleic acid and a second nucleic acid.

"Contiguous nucleobases" means nucleobases immediately adjacent to each other.

"Deoxyribonucleotide" means a nucleotide having a hydrogen at the 2' position of the sugar portion of the nucleotide. Deoxyribonucleotides may be modified with any of a variety of substituents.

"Diabetes mellitus" or "diabetes" is a syndrome characterized by disordered metabolism and abnormally high blood sugar (hyperglycemia) resulting from insufficient levels of insulin or reduced insulin sensitivity. The characteristic symptoms are excessive urine production (polyuria) due to high blood glucose levels, excessive thirst and increased fluid intake (polydipsia) attempting to compensate for increased urination, blurred vision due to high blood glucose effects on the eye's optics, unexplained weight loss, and lethargy.

"Diabetic dyslipidemia" or "type 2 diabetes with dyslipidemia" means a condition characterized by Type 2 diabetes and, typically, elevated lipids such as cholesterol and triglycerides as well as lipoproteins such as low-density lipoprotein (LDL) and elevated small, dense LDL particles. Such condition may also be characterized by reduced HDL-C.

"Diluent" means an ingredient in a composition that lacks pharmacological activity, but is pharmaceutically necessary or desirable. For example, the diluent in an injected composition can be a liquid, e.g. saline solution.

"Dyslipidemia" refers to a disorder of lipid and/or lipoprotein metabolism, including lipid and/or lipoprotein overproduction or deficiency. Dyslipidemias may be manifested by elevation of lipids such as cholesterol and triglycerides as well as lipoproteins such as low-density lipoprotein (LDL) cholesterol.

"Dosage unit" means a form in which a pharmaceutical agent is provided, e.g. pill, tablet, or other dosage unit known in the art. In certain embodiments, a dosage unit is a vial containing lyophilized antisense oligonucleotide. In certain embodiments, a dosage unit is a vial containing reconstituted antisense oligonucleotide.

"Dose" means a specified quantity of a pharmaceutical agent provided in a single administration, or in a specified time period. In certain embodiments, a dose can be administered in one, two, or more boluses, tablets, or injections. For example, in certain embodiments where subcutaneous administration is desired, the desired dose requires a volume not easily accommodated by a single injection, therefore, two or more injections can be used to achieve the desired dose. In certain embodiments, the pharmaceutical agent is administered by infusion over an extended period of time or continuously. Doses can be stated as the amount of pharmaceutical agent per hour, day, week, or month.

"Effective amount" or "therapeutically effective amount" means the amount of active pharmaceutical agent sufficient to effectuate a desired physiological outcome in an individual in need of the agent. The effective amount can vary among individuals depending on the health and physical condition of the individual to be treated, the taxonomic group of the individuals to be treated, the formulation of the composition, assessment of the individual's medical condition, and other relevant factors.

"Fully complementary" or "100% complementary" means each nucleobase of a nucleobase sequence of a first nucleic acid has a complementary nucleobase in a second nucleobase sequence of a second nucleic acid. In certain embodiments, a first nucleic acid is an antisense compound and a target nucleic acid is a second nucleic acid.

"Gapmer" means a chimeric antisense compound in which an internal region having a plurality of nucleosides that support RNase H cleavage is positioned between external regions having one or more nucleosides, wherein the nucleosides comprising the internal region are chemically distinct from the nucleoside or nucleosides comprising the external regions. The internal region can be referred to as a "gap segment" and the external regions can be referred to as "wing segments."

"Gap-widened" means a chimeric antisense compound having a gap segment of 12 or more contiguous 2'-deoxyribonucleosides positioned between and immediately adjacent to 5' and 3' wing segments having from one to six nucleosides.

"Glucocorticoid receptor" or "GCCR" means any nucleic acid or protein of GCCR.

"GCCR expression" means the level of mRNA transcribed from the gene encoding GCCR or the level of protein translated from the mRNA. GCCR expression can be determined by art known methods such as a Northern or Western blot.

"GCCR nucleic acid" means any nucleic acid encoding GCCR. For example, in certain embodiments, a GCCR nucleic acid includes a DNA sequence encoding GCCR, a RNA sequence transcribed from DNA encoding GCCR (including genomic DNA comprising introns and exons), and a mRNA sequence encoding GCCR. "GCCR mRNA" means a mRNA encoding a GCCR protein.

"Glucose" is a monosaccharide used by cells as a source of energy and inflammatory intermediate. "Plasma glucose" refers to glucose present in the plasma.

"Hybridization" means the annealing of complementary nucleic acid molecules. In certain embodiments, complementary nucleic acid molecules include an antisense compound and a target nucleic acid.

"Hyperlipidemia" or "hyperlipemia" is a condition characterized by elevated serum lipids or circulating (plasma) lipids. This condition manifests an abnormally high concentration of fats. The lipid fractions in the circulating blood are cholesterol, low density lipoproteins, very low density lipoproteins and triglycerides.

"Hypertriglyceridemia" means a condition characterized by elevated triglyceride levels.

"Identifying" or "selecting an animal with metabolic" means identifying or selecting a subject having been diagnosed with a metabolic disease, or a metabolic disorder; or, identifying or selecting a subject having any symptom of a metabolic disease, including, but not limited to, metabolic syndrome, hyperglycemia, hypertriglyceridemia, hypertension increased insulin resistance, decreased insulin sensitivity, above normal body weight, and/or above normal body fat or any combination thereof. Such identification may be accomplished by any method, including but not limited to, standard clinical tests or assessments, such as measuring serum or circulating (plasma) blood-glucose, measuring serum or circulating (plasma) triglycerides, measuring blood-pressure, measuring body fat, measuring body weight, and the like.

"Immediately adjacent" means there are no intervening elements between the immediately adjacent elements.

"Individual" or "subject" or "animal" means a human or non-human animal selected for treatment or therapy.

"Inhibiting the expression or activity" refers to a reduction or blockade of the expression or activity of a RNA or protein and does not necessarily indicate a total elimination of expression or activity.

"Insulin resistance" is defined as the condition in which normal amounts of insulin are inadequate to produce a normal insulin response from fat, muscle and liver cells. Insulin resistance in fat cells results in hydrolysis of stored triglycerides, which elevates free fatty acids in the blood plasma. Insulin resistance in muscle reduces glucose uptake whereas insulin resistance in liver reduces glucose storage, with both effects serving to elevate blood glucose. High plasma levels of insulin and glucose due to insulin resistance often leads to metabolic syndrome and type 2 diabetes.

"Insulin sensitivity" is a measure of how effectively an individual processes glucose. An individual having high insulin sensitivity effectively processes glucose whereas an individual with low insulin sensitivity does not effectively process glucose.

"Internucleoside linkage" refers to the chemical bond between nucleosides.

"Intravenous administration" means administration into a vein.

"Linked nucleosides" means adjacent nucleosides which are bonded together.

"Lipid-lowering therapy" or "lipid lowering agent" means a therapeutic regimen provided to a subject to reduce one or more lipids in a subject. In certain embodiments, a lipid-lowering therapy is provided to reduce one or more of ApoB, total cholesterol, LDL-C, VLDL-C, IDL-C, non-HDL-C, triglycerides, small dense LDL particles, and Lp(a) in a subject. Examples of lipid-lowering therapy include statins, fibrates, and MTP inhibitors.

"Major risk factors" refers to factors that contribute to a high risk for a particular disease or condition. In certain embodiments, major risk factors for coronary heart disease include, without limitation, cigarette smoking, hypertension, low HDL-C, family history of coronary heart disease, age, and other factors disclosed herein.

"Metabolic disease" or "metabolic disorder" refers to a condition characterized by an alteration or disturbance in metabolic function. "Metabolic" and "metabolism" are terms well known in the art and generally include the whole range of biochemical processes that occur within a living organism. Metabolic diseases or disorders include, but are not limited to, obesity, diabetes, hyperglycemia, prediabetes, non-alcoholic fatty liver disease (NAFLD), metabolic syndrome, insulin resistance, diabetic dyslipidemia, or hypertriglyceridemia or a combination thereof.

"Metabolic syndrome" means a condition characterized by a clustering of lipid and non-lipid cardiovascular risk factors of metabolic origin. In certain embodiments, metabolic syndrome is identified by the presence of any 3 of the following factors: waist circumference of greater than 102 cm in men or greater than 88 cm in women; serum triglyceride of at least 150 mg/dL; HDL-C less than 40 mg/dL in men or less than 50 mg/dL in women; blood pressure of at least 130/85 mmHg; and fasting glucose of at least 110 mg/dL. These determinants can be readily measured in clinical practice (JAMA, 2001, 285: 2486-2497).

"Mismatch" or "non-complementary nucleobase" refers to the case when a nucleobase of a first nucleic acid is not capable of pairing with the corresponding nucleobase of a second or target nucleic acid.

"Mixed dyslipidemia" means a condition characterized by elevated cholesterol and elevated triglycerides.

"Modified internucleoside linkage" refers to a substitution or any change from a naturally occurring internucleoside bond (i.e. a phosphodiester internucleoside bond).

"Modified nucleobase" refers to any nucleobase other than adenine, cytosine, guanine, thymidine, or uracil. An "unmodified nucleobase" means the purine bases adenine (A) and guanine (G), and the pyrimidine bases thymine (T), cytosine (C), and uracil (U).

"Modified nucleoside" means a nucleoside having, independently, a modified sugar moiety or modified nucleobase.

"Modified nucleotide" means a nucleotide having, independently, a modified sugar moiety, modified internucleoside linkage, or modified nucleobase. A "modified nucleoside" means a nucleoside having, independently, a modified sugar moiety or modified nucleobase.

"Modified oligonucleotide" means an oligonucleotide comprising at least one modified nucleotide.

"Modified sugar" refers to a substitution or change from a natural sugar.

"Motif" means the pattern of chemically distinct regions in an antisense compound.

"Naturally occurring internucleoside linkage" means a 3' to 5' phosphodiester linkage.

"Natural sugar moiety" means a sugar found in DNA (2'-H) or RNA (2'-OH).

"Non-alcoholic fatty liver disease" or "NAFLD" means a condition characterized by fatty inflammation of the liver that is not due to excessive alcohol use (for example, alcohol consumption of over 20 g/day). In certain embodiments, NAFLD is related to insulin resistance and the metabolic syndrome. NAFLD encompasses a disease spectrum ranging from simple triglyceride accumulation in hepatocytes (hepatic steatosis) to hepatic steatosis with inflammation (steatohepatitis), fibrosis, and cirrhosis.

"Nonalcoholic steatohepatitis" (NASH) occurs from progression of NAFLD beyond deposition of triglycerides. A "second hit" capable of inducing necrosis, inflammation, and fibrosis is required for development of NASH. Candidates for the second-hit can be grouped into broad categories: factors causing an increase in oxidative stress and factors promoting expression of proinflammatory cytokines "Nucleic acid" refers to molecules composed of monomeric nucleotides. A nucleic acid includes ribonucleic acids (RNA), deoxyribonucleic acids (DNA), single-stranded nucleic acids, double-stranded nucleic acids, small interfering ribonucleic acids (siRNA), and microRNAs (miRNA). A nucleic acid can also comprise a combination of these elements in a single molecule.

"Nucleobase" means a heterocyclic moiety capable of pairing with a base of another nucleic acid.

"Nucleobase sequence" means the order of contiguous nucleobases independent of any sugar, linkage, or nucleobase modification.

"Nucleoside" means a nucleobase linked to a sugar.

"Nucleoside mimetic" includes those structures used to replace the sugar or the sugar and the base and not necessarily the linkage at one or more positions of an oligomeric compound such as for example nucleoside mimetics having morpholino, cyclohexenyl, cyclohexyl, tetrahydropyranyl, bicyclo or tricyclo sugar mimetics e.g. non furanose sugar units.

"Nucleotide" means a nucleoside having a phosphate group covalently linked to the sugar portion of the nucleoside.

"Nucleotide mimetic" includes those structures used to replace the nucleoside and the linkage at one or more positions of an oligomeric compound such as for example peptide nucleic acids or morpholinos (morpholinos linked by —N(H)—C(═O)—O— or other non-phosphodiester linkage).

"Oligomeric compound" or "oligomer" refers to a polymeric structure comprising two or more sub-structures and capable of hybridizing to a region of a nucleic acid molecule. In certain embodiments, oligomeric compounds are oligonucleosides. In certain embodiments, oligomeric compounds are oligonucleotides. In certain embodiments, oligomeric compounds are antisense compounds. In certain embodiments, oligomeric compounds are antisense oligonucleotides. In certain embodiments, oligomeric compounds are chimeric oligonucleotides.

"Oligonucleotide" means a polymer of linked nucleosides each of which can be modified or unmodified, independent one from another.

"Parenteral administration" means administration through injection or infusion. Parenteral administration includes subcutaneous administration, intravenous administration, intramuscular administration, intraarterial administration, intraperitoneal administration, or intracranial administration, e.g. intrathecal or intracerebroventricular administration. Administration can be continuous, or chronic, or short or intermittent.

"Peptide" means a molecule formed by linking at least two amino acids by amide bonds. Peptide refers to polypeptides and proteins.

"Pharmaceutical agent" means a substance that provides a therapeutic benefit when administered to an individual. For example, in certain embodiments, an antisense oligonucleotide targeted to GCCR is pharmaceutical agent.

"Pharmaceutical composition" means a mixture of substances suitable for administering to an individual. For example, a pharmaceutical composition can comprise one or more active agents and a sterile aqueous solution.

"Pharmaceutically acceptable carrier" means a medium or diluent that does not interfere with the structure of the oligonucleotide. Certain, of such carries enable pharmaceutical compositions to be formulated as, for example, tablets, pills, dragees, capsules, liquids, gels, syrups, slurries, suspension and lozenges for the oral ingestion by a subject. For example, a pharmaceutically acceptable carrier can be a sterile aqueous solution.

"Pharmaceutically acceptable derivative" encompasses pharmaceutically acceptable salts, conjugates, prodrugs or isomers of the compounds described herein.

"Pharmaceutically acceptable salts" means physiologically and pharmaceutically acceptable salts of antisense compounds, i.e., salts that retain the desired biological activity of the parent oligonucleotide and do not impart undesired toxicological effects thereto.

"Phosphorothioate linkage" means a linkage between nucleosides where the phosphodiester bond is modified by replacing one of the non-bridging oxygen atoms with a sulfur atom. A phosphorothioate linkage is a modified internucleoside linkage.

"Portion" means a defined number of contiguous (i.e. linked) nucleobases of a nucleic acid. In certain embodiments, a portion is a defined number of contiguous nucleobases of a target nucleic acid. In certain embodiments, a portion is a defined number of contiguous nucleobases of an antisense compound.

"Prevent" refers to delaying or forestalling the onset or development of a disease, disorder, or condition for a period of time from minutes to indefinitely. Prevent also means reducing risk of developing a disease, disorder, or condition.

"Prodrug" means a therapeutic agent that is prepared in an inactive form that is converted to an active form within the body or cells thereof by the action of endogenous enzymes or other chemicals or conditions.

"Side effects" means physiological responses attributable to a treatment other than the desired effects. In certain embodiments, side effects include injection site reactions, liver function test abnormalities, renal function abnormalities, liver toxicity, renal toxicity, central nervous system abnormalities, myopathies, and malaise. For example, increased aminotransferase levels in serum can indicate liver toxicity or liver function abnormality. For example, increased bilirubin can indicate liver toxicity or liver function abnormality.

"Single-stranded oligonucleotide" means an oligonucleotide which is not hybridized to a complementary strand.

"Specifically hybridizable" refers to an antisense compound having a sufficient degree of complementarity between an antisense oligonucleotide and a target nucleic acid to induce a desired effect, while exhibiting minimal or no effects on non-target nucleic acids under conditions in which specific binding is desired, i.e. under physiological conditions in the case of in vivo assays and therapeutic treatments.

"Statin" means an agent that inhibits the activity of HMG-CoA reductase.

"Subcutaneous administration" means administration just below the skin.

"Targeting" or "targeted" means the process of design and selection of an antisense compound that will specifically hybridize to a target nucleic acid and induce a desired effect.

"Target nucleic acid," "target RNA," and "target RNA transcript" all refer to a nucleic acid capable of being targeted by antisense compounds.

"Target segment" means the sequence of nucleotides of a target nucleic acid to which an antisense compound is targeted. "5' target site" refers to the 5'-most nucleotide of a target segment. "3' target site" refers to the 3'-most nucleotide of a target segment.

"Therapeutically effective amount" means an amount of an agent that provides a therapeutic benefit to an individual.

"Therapeutic lifestyle change" means dietary and lifestyle changes intended to lower fat/adipose tissue mass and/or cholesterol. Such change can reduce the risk of developing heart disease, and may includes recommendations for dietary intake of total daily calories, total fat, saturated fat, polyunsaturated fat, monounsaturated fat, carbohydrate, protein, cholesterol, insoluble fiber, as well as recommendations for physical activity.

"Triglyceride" or "TG" means a lipid or neutral fat consisting of glycerol combined with three fatty acid molecules.

"Type 2 diabetes," (also known as "type 2 diabetes mellitus" or "diabetes mellitus, type 2", and formerly called "diabetes mellitus type 2", "non-insulin-dependent diabetes (NIDDM)", "obesity related diabetes", or "adult-onset diabetes") is a metabolic disorder that is primarily characterized by insulin resistance, relative insulin deficiency, and hyperglycemia.

"Treat" refers to administering a pharmaceutical composition to an animal to effect an alteration or improvement of a disease, disorder, or condition.

"Unmodified nucleotide" means a nucleotide composed of naturally occurring nucleobases, sugar moieties, and internucleoside linkages. In certain embodiments, an unmodified nucleotide is an RNA nucleotide (i.e. β-D-ribonucleosides) or a DNA nucleotide (i.e. β-D-deoxyribonucleoside).

Certain Embodiments

Certain embodiments provide methods, compounds, and compositions for inhibiting GCCR expression.

Certain embodiments provide antisense compounds targeted to a GCCR nucleic acid. In certain embodiments, the GCCR nucleic acid sequence is a human sequence. In certain embodiments, the GCCR nucleic acid is the complement of GENBANK Accession No. NT_029289.10 truncated from nucleotides 3818000 to 3980000 (incorporated herein as SEQ ID NO: 1). In certain embodiments, the GCCR nucleic acid is a rhesus monkey sequence. In certain embodiment, the GCCR nucleic acid sequence is the complement of GENBANK Accession No. NW_001120987.1 truncated from nucleotides 1334000 to 1491000 (incorporated herein as SEQ ID NO: 2).

In certain embodiments, the compounds or compositions provided herein comprise a modified oligonucleotide consisting of 12 to 30 nucleosides having a nucleobase sequence complementary to an equal length portion of SEQ ID NO: 1 or 2 or both.

In certain embodiments, the compounds or compositions provided herein consist of 12 to 30 linked nucleosides and have a nucleobase sequence comprising at least 8, 9, 10, 11, 12, 13, 14, 15, 16, 17, 18, 19, or 20 contiguous nucleobases of any of SEQ ID NOs: 4-56.

In certain embodiments, the compounds or compositions provided herein consist of 12 to 30 linked nucleosides and have a nucleobase sequence comprising at least 8, 9, 10, 11, 12, 13, 14, 15, 16, 17, 18, 19, or 20 contiguous nucleobases of any of SEQ ID NOs: 6, 7, 10, 11, 33, 35, 36, 39, 42, and 43.

In certain embodiments, the compound or composition provided herein is or comprises ISIS NOs: 420470, 420476, 426130, 426183, 426261, 426262, 426115, 426168, 426246, 426172, 426325, and 426267.

In certain embodiments, the compounds or compositions provided herein consist of 12 to 30 linked nucleosides and have a nucleobase sequence comprising at least 8, 9, 10, 11, 12, 13, 14, 15, 16, 17, 18, 19, or 20 contiguous nucleobases of SEQ ID NO: 36.

In certain embodiments, the compound or composition is or comprises ISIS NO: 426115.

In certain embodiments, the compounds or compositions provided herein comprise a modified oligonucleotide consisting of 15 to 30 nucleosides having a nucleobase sequence complementary to an equal length portion of SEQ ID NO: 1 or 2 or both.

In certain embodiments, the compounds or compositions provided herein consist of 15 to 30 linked nucleosides and have a nucleobase sequence comprising at least 8, 9, 10, 11, 12, 13, 14, 15, 16, 17, 18, 19, or 20 contiguous nucleobases of any of SEQ ID NOs: 4-56.

In certain embodiments, the compounds or compositions provided herein consist of 15 to 30 linked nucleosides and have a nucleobase sequence comprising at least 8, 9, 10, 11, 12, 13, 14, 15, 16, 17, 18, 19, or 20 contiguous nucleobases of any of SEQ ID NOs: 6, 7, 10, 11, 33, 35, 36, 39, 42, and 43.

In certain embodiments, the compound or composition provided herein is or comprises ISIS NOs: 420470, 420476, 426130, 426183, 426261, 426262, 426115, 426168, 426246, 426172, 426325, and 426267.

In certain embodiments, the compounds or compositions provided herein consist of 15 to 30 linked nucleosides and have a nucleobase sequence comprising at least 8, 9, 10, 11, 12, 13, 14, 15, 16, 17, 18, 19, or 20 contiguous nucleobases of SEQ ID NO: 36.

In certain embodiments, the compound or composition provided herein is or comprise ISIS NO: 426115.

In certain embodiments, the compounds or compositions provided herein comprise a modified oligonucleotide consisting of 16 to 21 nucleosides having a nucleobase sequence complementary to an equal length portion of SEQ ID NO: 1 or 2 or both In certain embodiments, the compounds or compositions provided herein comprise a modified oligonucleotide consisting of 16 to 21 linked nucleosides and have a nucleobase sequence comprising at least 8, 9, 10, 11, 12, 13, 14, 15, 16, 17, 18, 19, or 20 contiguous nucleobases of any of SEQ ID NOs: 4-56.

In certain embodiments, the compounds or compositions provided herein comprise a modified oligonucleotide consisting of 16 to 21 linked nucleosides and have a nucleobase sequence comprising at least 8, 9, 10, 11, 12, 13, 14, 15, 16, 17, 18, 19, or 20 contiguous nucleobases of any of SEQ ID NOs: 6, 7, 10, 11, 33, 35, 36, 39, 42, and 43.

In certain embodiments, the compounds or compositions provided herein comprise a modified oligonucleotide consisting of 16 to 21 linked nucleosides and have a nucleobase sequence comprising at least 8, 9, 10, 11, 12, 13, 14, 15, 16, 17, 18, 19, or 20 contiguous nucleobases of SEQ ID NO: 36.

In certain embodiments, the compounds or compositions provided herein comprise a modified oligonucleotide consisting of 17 to 35 nucleosides having a nucleobase sequence complementary to an equal length portion of any of SEQ ID NOs: 1 and 2.

In certain embodiments, the compounds or compositions provided herein comprise a modified oligonucleotide consisting of 17 to 35 linked nucleosides and have a nucleobase sequence comprising at least 8, 9, 10, 11, 12, 13, 14, 15, 16, 17, 18, 19, or 20 contiguous nucleobases of SEQ ID NOs: 4-56.

In certain embodiments, the compounds or compositions provided herein comprise a modified oligonucleotide consisting of 17 to 35 linked nucleosides and have a nucleobase sequence comprising at least 8, 9, 10, 11, 12, 13, 14, 15, 16, 17, 18, 19, or 20 contiguous nucleobases of SEQ ID NOs: 6, 7, 10, 11, 33, 35, 36, 39, 42, and 43.

In certain embodiments, the compounds or compositions provided herein can consist of 17 to 35 linked nucleosides and have a nucleobase sequence comprising at least 8, 9, 10, 11, 12, 13, 14, 15, 16, 17, 18, 19, or 20 contiguous nucleobases of SEQ ID NO: 36.

In certain embodiments, the compounds or compositions provided herein comprise a modified oligonucleotide consisting of 17 to 30 nucleosides having a nucleobase sequence complementary to an equal length portion of SEQ ID NO: 1 or 2 or both.

In certain embodiments, the compounds or compositions provided herein comprise a modified oligonucleotide consisting of 17 to 30 linked nucleosides and have a nucleobase sequence comprising at least 8, 9, 10, 11, 12, 13, 14, 15, 16, 17, 18, 19, or 20 contiguous nucleobases of SEQ ID NOs: 4-56.

In certain embodiments, the compounds or compositions provided herein comprise a modified oligonucleotide consisting of 17 to 30 linked nucleosides and have a nucleobase sequence comprising at least 8, 9, 10, 11, 12, 13, 14, 15, 16, 17, 18, 19, or 20 contiguous nucleobases of SEQ ID NOs: 6, 7, 10, 11, 33, 35, 36, 39, 42, and 43.

In certain embodiments, the compounds or compositions provided herein comprise a modified oligonucleotide consisting of 17 to 30 linked nucleosides and have a nucleobase sequence comprising at least 8, 9, 10, 11, 12, 13, 14, 15, 16, 17, 18, 19, or 20 contiguous nucleobases of SEQ ID NO: 36.

In certain embodiments, the compounds or compositions provided herein comprise a modified oligonucleotide consisting of 17 to 25 nucleosides having a nucleobase sequence complementary to an equal length portion of SEQ ID NO: 1 or 2 or both.

In certain embodiments, the compounds or compositions provided herein comprise a modified oligonucleotide consisting of 17 to 25 linked nucleosides and have a nucleobase sequence comprising at least 8, 9, 10, 11, 12, 13, 14, 15, 16, 17, 18, 19, or 20 contiguous nucleobases of SEQ ID NOs: 4-56.

In certain embodiments, the compounds or compositions provided herein comprise a modified oligonucleotide consisting of 17 to 25 linked nucleosides and have a nucleobase sequence comprising at least 8, 9, 10, 11, 12, 13, 14, 15, 16, 17, 18, 19, or 20 contiguous nucleobases of SEQ ID NOs: 6, 7, 10, 11, 33, 35, 36, 39, 42, and 43.

In certain embodiments, the compounds or compositions provided herein comprise a modified oligonucleotide consisting of 17 to 25 linked nucleosides and have a nucleobase sequence comprising at least 8, 9, 10, 11, 12, 13, 14, 15, 16, 17, 18, 19, or 20 contiguous nucleobases of SEQ ID NO: 36.

In certain embodiments, the compounds or compositions described herein comprise a modified oligonucleotide consisting of 17 to 24 nucleosides having a nucleobase sequence complementary to an equal length portion of SEQ ID NO: 1 or 2 or both.

In certain embodiments, the compounds or compositions provided herein comprise a modified oligonucleotide consisting of 17 to 24 linked nucleosides and have a nucleobase sequence comprising at least 8, 9, 10, 11, 12, 13, 14, 15, 16, 17, 18, 19, or 20 contiguous nucleobases of SEQ ID NOs: 4-56.

In certain embodiments, the compounds or compositions provided herein comprise a modified oligonucleotide consisting of 17 to 24 linked nucleosides and have a nucleobase sequence comprising at least 8, 9, 10, 11, 12, 13, 14, 15, 16, 17, 18, 19, or 20 contiguous nucleobases of SEQ ID NOs: 6, 7, 10, 11, 33, 35, 36, 39, 42, and 43.

In certain embodiments, the compounds or compositions provided herein comprise a modified oligonucleotide consisting of 17 to 24 linked nucleosides and have a nucleobase sequence comprising at least 8, 9, 10, 11, 12, 13, 14, 15, 16, 17, 18, 19, or 20 contiguous nucleobases of SEQ ID NO: 36.

In certain embodiments, the compounds or compositions provided herein comprise a modified oligonucleotide consisting of 17 to 23 nucleosides having a nucleobase sequence complementary to an equal length portion of SEQ ID NO: 1 or 2 or both.

In certain embodiments, the compounds or compositions provided herein comprise a modified oligonucleotide consisting of 17 to 23 linked nucleosides and have a nucleobase sequence comprising at least 8, 9, 10, 11, 12, 13, 14, 15, 16, 17, 18, 19, or 20 contiguous nucleobases of SEQ ID NOs: 4-56.

In certain embodiments, the compounds or compositions provided herein comprise a modified oligonucleotide consisting of 17 to 23 linked nucleosides and have a nucleobase sequence comprising at least 8, 9, 10, 11, 12, 13, 14, 15, 16, 17, 18, 19, or 20 contiguous nucleobases of SEQ ID NOs: 6, 7, 10, 11, 33, 35, 36, 39, 42, and 43.

In certain embodiments, the compounds or compositions provided herein comprise a modified oligonucleotide consisting of 17 to 23 linked nucleosides and have a nucleobase sequence comprising at least 8, 9, 10, 11, 12, 13, 14, 15, 16, 17, 18, 19, or 20 contiguous nucleobases of SEQ ID NO: 36.

In certain embodiments, the compounds or compositions provided herein comprise a modified oligonucleotide consisting of 17 to 22 nucleosides having a nucleobase sequence complementary to an equal length portion of SEQ ID NO: 1 or 2 or both.

In certain embodiments, the compounds or compositions provided herein comprise a modified oligonucleotide consisting of 17 to 22 linked nucleosides and have a nucleobase sequence comprising at least 8, 9, 10, 11, 12, 13, 14, 15, 16, 17, 18, 19, or 20 contiguous nucleobases of SEQ ID NOs: 4-56.

In certain embodiments, the compounds or compositions provided herein comprise a modified oligonucleotide consisting of 17 to 22 linked nucleosides and have a nucleobase sequence comprising at least 8, 9, 10, 11, 12, 13, 14, 15, 16, 17, 18, 19, or 20 contiguous nucleobases of SEQ ID NOs: 6, 7, 10, 11, 33, 35, 36, 39, 42, and 43.

In certain embodiments, the compounds or compositions provided herein comprise a modified oligonucleotide consisting of 17 to 22 linked nucleosides and have a nucleobase sequence comprising at least 8, 9, 10, 11, 12, 13, 14, 15, 16, 17, 18, 19, or 20 contiguous nucleobases of SEQ ID NO: 36.

In certain embodiments, the compounds or compositions provided herein comprise a modified oligonucleotide consisting of 17 to 21 nucleosides having a nucleobase sequence complementary to an equal length portion of SEQ ID NO: 1 or 2 or both.

In certain embodiments, the compounds or compositions provided herein comprise a modified oligonucleotide consisting of 17 to 21 linked nucleosides and have a nucleobase sequence comprising at least 8, 9, 10, 11, 12, 13, 14, 15, 16, 17, 18, 19, or 20 contiguous nucleobases of SEQ ID NOs: 4-56.

In certain embodiments, the compounds or compositions provided herein comprise a modified oligonucleotide consisting of 17 to 21 linked nucleosides and have a nucleobase sequence comprising at least 8, 9, 10, 11, 12, 13, 14, 15, 16, 17, 18, 19, or 20 contiguous nucleobases of SEQ ID NOs: 6, 7, 10, 11, 33, 35, 36, 39, 42, and 43.

In certain embodiments, the compounds or compositions provided herein comprise a modified oligonucleotide consisting of 17 to 21 linked nucleosides and have a nucleobase sequence comprising at least 8, 9, 10, 11, 12, 13, 14, 15, 16, 17, 18, 19, or 20 contiguous nucleobases of SEQ ID NO: 36.

In certain embodiments, the compounds or compositions provided herein comprise a modified oligonucleotide consisting of 20 nucleosides having a nucleobase sequence complementary to an equal length portion of SEQ ID NO: 1 or 2 or both.

In certain embodiments, the compounds or compositions provided herein comprise a modified oligonucleotide consisting of 20 linked nucleosides and have a nucleobase sequence comprising at least 8, 9, 10, 11, 12, 13, 14, 15, 16, 17, 18, 19, or 20 contiguous nucleobases of SEQ ID NOs: 4-56.

In certain embodiments, the compounds or compositions provided herein comprise a modified oligonucleotide consisting of 20 linked nucleosides and have a nucleobase sequence comprising at least 8, 9, 10, 11, 12, 13, 14, 15, 16, 17, 18, 19, or 20 contiguous nucleobases of SEQ ID NOs: 6, 7, 10, 11, 33, 35, 36, 39, 42, and 43.

In certain embodiments, the compounds or compositions provided herein comprise a modified oligonucleotide consisting of 20 linked nucleosides and have a nucleobase sequence comprising at least 8, 9, 10, 11, 12, 13, 14, 15, 16, 17, 18, 19, or 20 contiguous nucleobases of SEQ ID NO: 36.

In certain embodiments, the compounds or compositions provided herein comprise a modified oligonucleotide consisting of 20 nucleosides having a nucleobase sequence complementary to an equal length portion of SEQ ID NO: 1 or 2 or both.

In certain embodiments, the compounds or compositions provided herein comprise a modified oligonucleotide consisting of 20 linked nucleosides and have a nucleobase sequence comprising at least 8, 9, 10, 11, 12, 13, 14, 15, 16, 17, 18, 19, or 20 contiguous nucleobases of SEQ ID NOs: 4-56.

In certain embodiments, the compounds or compositions provided herein comprise a modified oligonucleotide consisting of 20 linked nucleosides and have a nucleobase sequence comprising at least 8, 9, 10, 11, 12, 13, 14, 15, 16, 17, 18, 19, or 20 contiguous nucleobases of SEQ ID NOs: 6, 7, 10, 11, 33, 35, 36, 39, 42, and 43.

In certain embodiments, the compounds or compositions provided herein comprise a modified oligonucleotide consisting of 20 linked nucleosides and have a nucleobase sequence comprising at least 8, 9, 10, 11, 12, 13, 14, 15, 16, 17, 18, 19, or 20 contiguous nucleobases of SEQ ID NO: 36.

In certain embodiments, the compounds or compositions provided herein comprise a salt of the modified oligonucleotide.

In certain embodiments, the compounds or compositions provided herein further comprise a pharmaceutically acceptable carrier or diluent.

In certain embodiments, the nucleobase sequence of the modified oligonucleotide is at least 70%, 75%, 80%, 85%, 90%, 95%, 96%, 97%, 98%, 99% or 100% complementary to any one of SEQ ID NOs: 1 and 2 as measured over the entirety of the modified oligonucleotide.

In certain embodiments, the nucleobase sequence of the modified oligonucleotide has at least 70%, 75%, 80%, 85%, 90%, 95%, 96%, 97%, 98%, 99% or 100% identity to any one of SEQ ID NOs: 4-56 as measured over the entirety of the modified oligonucleotide.

In certain embodiments, the nucleobase sequence of the modified oligonucleotide has at least 70%, 75%, 80%, 85%, 90%, 95%, 96%, 97%, 98%, 99% or 100% identity to any one of SEQ ID NOs: 6, 7, 10, 11, 33, 35, 36, 39, 42, and 43 as measured over the entirety of the modified oligonucleotide.

In certain embodiments, the nucleobase sequence of the modified oligonucleotide has at least 70%, 75%, 80%, 85%, 90%, 95%, 96%, 97%, 98%, 99% or 100% identity to SEQ ID NO: 36 as measured over the entirety of the modified oligonucleotide.

In certain embodiments, antisense compounds or modified oligonucleotides target a region of a GCCR nucleic acid. In certain embodiments, such compounds or oligonucleotides targeted to a region of a GCCR nucleic acid have a contiguous nucleobase portion that is complementary to an equal length nucleobase portion of the region. For example, the portion can be at least an 8, 9, 10, 11, 12, 13, 14, 15, 16, 17, 18, 19 or 20 contiguous nucleobases. Such portion is complementary to an equal length portion of a region recited herein. In certain embodiments, such compounds or oligonucleotide target the following nucleotide regions of SEQ ID NO: 1: 33116-33135, 33296-33315, 33673-33692, 33716-33755, 33716-33751, 33716-33735, 33732-33755, 33732-33755, 33736-33755, 37217-37236, 51878-51898, 51878-51897, 51879-51898, 57825-57846, 57825-57844, 57827-57846, 59951-59978, 59951-59975, 59951-59974, 59951-59971, 59951-59970, 59952-59978, 59952-59975, 59952-59974, 59952-59971, 59955-59978, 59955-59975, 59955-59974, 59956-59978, 59956-59975, 59959-59978, 60935-60958, 60935-60956, 60935-60955, 60935-60954, 60936-60958, 60936-60956, 60936-60955, 60937-60958, 60937-60956, 60939-60958, 63677-63698, 63677-63697, 63677-63696, 63678-63698, 63678-63697, 63679-63698, 65938-65961, 65938-65960, 65938-65959, 65938-65958, 65938-65957, 65939-65961, 65939-65960, 65939-65959, 65939-65958, 65940-65961, 65940-65960, 65940-65959, 65941-65961, 65941-65960, 65942-65961, 76224-76248, 76224-76247, 76224-76246, 76224-76244, 76224-76243, 76225-76248, 76225-76247, 76225-76246, 76225-76244, 76227-76248, 76227-76247, 76227-76246, 76228-76248, 76228-76247, 76229-76248, 95513-95538, 95513-95537, 95513-95532, 95518-95538, 95518-95537, 95519-95538, 104247-104266, 109346-109368, 109346-109366, 109346-109365, 109347-109368, 109347-109366, 109349-109368, 109473-109492, 112218-112242, 112218-112241, 112218-122240, 112218-112239, 112218-112238, 112218-112237, 112219-112242, 112219-112241, 112219-112240, 112219-112239, 112219-112238, 112220-112242, 112220-112241, 112220-112240, 112220-112239, 112221-112242, 112221-112241, 112221-112240, 112222-112242, 112222-112241, 112223-112242, 114154-114178, 114154-114177, 114154-114176, 114154-114175, 114154-114174, 114154-114173, 114155-114178, 114155-114177, 114155-114176, 114155-114175, 114155-114174, 114156-114178, 114156-114177, 114156-114176, 114156-114175, 114157-114178, 114157-114177, 114157-114176, 114158-114178, 114158-114177, 114159-114178, 114587-114610, 114587-114609, 114587-114608, 114587-114606, 114589-114610, 114589-114609, 114589-114608, 114590-114610, 114590-114609, 114591-114610, 139287-139306, 143259-143280, 143259-143279, 143259-143278, 143260-143280, 143260-143279, 143261-143280, 143737-143757, 143737-143756, and 143738-143757.

In certain embodiments, antisense compounds or modified oligonucleotides target a region of a GCCR nucleic acid. In certain embodiments, such compounds or oligonucleotides targeted to a region of a GCCR nucleic acid have a contiguous nucleobase portion that is complementary to an equal length nucleobase portion of the region. For example, the portion can be at least an 8, 9, 10, 11, 12, 13, 14, 15, 16, 17, 18, 19 or 20 contiguous nucleobases portion complementary to an equal length portion of a region recited herein. In certain embodiments, such compounds or oligonucleotide target the following nucleotide regions of SEQ ID NO: 1: 57825-57844, 59956-59975, 63677-63696, 65938-65959, 65938-65958, 65938-65957, 65939-65959, 65939-65958, 65940-65959, 76224-76243, 76225-76244, 76229-76248, and 95513-95532.

In certain embodiments, antisense compounds or modified oligonucleotides target a region of a GCCR nucleic acid. In certain embodiments, such compounds or oligonucleotides targeted to a region of a GCCR nucleic acid have a contiguous nucleobase portion that is complementary to an equal length nucleobase portion of the region. For example, the portion can be at least an 8, 9, 10, 11, 12, 13, 14, 15, 16, 17, 18, 19 or 20 contiguous nucleobases portion complementary to an equal length portion of a region recited herein. In certain embodiments, such compounds or oligonucleotide target the following nucleotide region of SEQ ID NO: 1: 65940-65959.

In certain embodiments, the following antisense compounds target a region of SEQ ID NO: 1, a nucleic acid encoding human GCCR and demonstrate at least 55% inhibition of GCCR expression: ISIS NOs: 361137, 361141, 361151, 361155, 361156, 377131, 414641, 414648, 414681, 420450, 420470, 420476, 420479, 420488, 420493, 420522, 420599, 420634, 420644, 420764, 426110, 426115, 426116, 426117, 426128, 426136, 426142, 426143, 426161, 426172, 426177, 426183, 426187, 426189, 426246, 426255, 426261, 426262, 426263, 426264, 426325, and 426345.

In certain embodiments, the following antisense compounds target a region of SEQ ID NO: 1, a nucleic acid encoding human GCCR and demonstrate at least 60% inhibition of GCCR expression: ISIS NOs: 361137, 361141, 361151, 361155, 361156, 377131, 414641, 414648, 414681, 420450, 420470, 420476, 420479, 420488, 420493, 420522, 420599, 420634, 420644, 420764, 426110, 426115, 426116, 426117, 426128, 426143, 426177, 426183, 426187, 426246, 426255, 426261, and 426262.

In certain embodiments, the following antisense compounds target a region of SEQ ID NO: 1, a nucleic acid encoding human GCCR and demonstrate at least 65% inhibition of GCCR expression: ISIS NOs: 361137, 361141, 361151, 361155, 361156, 377131, 414641, 414648, 414681, 420450, 420470, 420476, 420479, 420488, 420493, 420522, 420599, 420634, 420644, 420764, 426110, 426115, 426117, 426128, 426143, 426177, 426183, 426187, 426246, 426255, and 426261.

In certain embodiments, the following antisense compounds target a region of SEQ ID NO: 1, a nucleic acid encoding human GCCR and demonstrate at least 70% inhibition of GCCR expression: ISIS NOs: 361137, 361155, 361156, 377131, 414641, 414648, 414681, 420450, 420470, 420476, 420479, 420488, 420493, 420522, 420599, 420634, 420644, 420764, 426115, 426117, 426128, 426183, and 426261.

In certain embodiments, the following antisense compounds target a region of SEQ ID NO: 1, a nucleic acid encoding human GCCR and demonstrate at least 75% inhibition of GCCR expression: ISIS NOs: 361137, 361155, 377131, 414641, 414681, 420450, 420470, 420476, 420488, 420493, 420522, 420599, 420634, 420644, and 420764.

In certain embodiments, the following antisense compounds target a region of SEQ ID NO: 1, a nucleic acid encoding human GCCR and demonstrate at least 80% inhibition of GCCR expression: ISIS NOs: 377131, 414641, 414681, 420450, 420476, and 420634.

In certain embodiments, the following antisense compounds target a region of SEQ ID NO: 1, a nucleic acid encoding human GCCR and demonstrate at least 85% inhibition of GCCR expression: ISIS NOs: 414681, 420450, 420476, and 420634.

In certain embodiments, the following antisense compounds target a region of SEQ ID NO: 1, a nucleic acid encoding human GCCR and demonstrate an $IC_{50}$ value of less than 3 μM using electroporation for transfection: ISIS NOs: 377131, 414641, 414681, 420450, 420470, 420476, 420493, 420522, 420599, 420644, 426110, 426115, 426116, 426117, 426119, 426124, 426128, 426130, 426131, 426136, 426137, 426142, 426143, 426144, 426150, 426157, 426161, 426168, 426171, 426172, 426177, 426183, 426185, 426187, 426189, 426199, 426203, 426229, 426246, 426255, 426261, 426262, 426263, 426264, 426267, 426281, 426301, 426302, 426306, 426323, 426324, 426325, 426343, 426345, 426346, 426347, 426401, 426403, 426404, and 426405.

In certain embodiments, the following antisense compounds target a region of SEQ ID NO: 1, a nucleic acid encoding human GCCR and demonstrate an $IC_{50}$ value of less than 2 μM using electroporation for transfection: ISIS NOs: 377131, 414641, 414681, 420450, 420470, 420476, 420493, 420522, 420599, 420644, 426110, 426115, 426116, 426117, 426119, 426128, 426130, 426136, 426137, 426142, 426143, 426144, 426150, 426157, 426168, 426171, 426172, 426183, 426185, 426189, 426203, 426246, 426261, 426262, 426263, 426264, 426267, 426281, 426301, 426324, 426325, 426345, and 426347.

In certain embodiments, the following antisense compounds target a region of SEQ ID NO: 1, a nucleic acid encoding human GCCR and demonstrate an $IC_{50}$ value of less than 1 μM using electroporation for transfection: ISIS NOs: 426115, 426128, 426172, 426261, and 426325.

In certain embodiments, the following antisense compounds target a region of SEQ ID NO: 1, a nucleic acid encoding human GCCR and demonstrate an $IC_{50}$ value of less than 50 nM using lipofectin as a transfection agent: ISIS NOs: 377131, 414641, 414648, 414681, 420450, 420470, 420488, 420493, 420522, 420599, 420644, 426110, 426115, 426116, 426117, 426119, 426124, 426128, 426130, 426131, 426136, 426137, 426142, 426143, 426144, 426150, 426157, 426161, 426168, 426171, 426172, 426177, 426183, 426185, 426187, 426189, 426199, 426203, 426216, 426229, 426246, 426255, 426261, 426262, 426263, 426264, 426267, 426276, 426281, 426293, 426301, 426302, 426306, 426323, 426324, 426325, 426331, 426334, 426336, 426337, 426343, 426344, 426345, 426347, 426390, 426401, 426402, 426403, 426404, and 426405.

In certain embodiments, the following antisense compounds target a region of SEQ ID NO: 1, a nucleic acid encoding human GCCR and demonstrate an $IC_{50}$ value of less than 40 nM using lipofectin as a transfection agent: ISIS NOs: 377131, 414641, 414681, 420450, 420493, 420522, 420599, 420644, 426110, 426115, 426116, 426117, 426119, 426124, 426128, 426130, 426131, 426142, 426143, 426157, 426168, 426171, 426172, 426177, 426183, 426185, 426187, 426189, 426199, 426203, 426216, 426246, 426255, 426261, 426262, 426263, 426264, 426267, 426276, 426281, 426293, 426301, 426302, 426306, 426324, 426331, 426336, 426337, 426343, 426344, 426345, 426347, 426401, 426402, 426403, 426404, and 426405.

In certain embodiments, the following antisense compounds target a region of SEQ ID NO: 1, a nucleic acid encoding human GCCR and demonstrate an $IC_{50}$ value of less than 30 nM using lipofectin as a transfection agent: ISIS NOs: 414641, 420493, 420599, 426110, 426115, 426116, 426117, 426130, 426131, 426168, 426171, 426172, 426177, 426183, 426185, 426187, 426189, 426246, 426255, 426261, 426262, 426263, 426264, 426324, 426344, 426345, and 426402.

In certain embodiments, the following antisense compounds target a region of SEQ ID NO: 1, a nucleic acid encoding human GCCR and demonstrate an $IC_{50}$ value of less than 20 nM using lipofectin as a transfection agent: ISIS NOs: 414641, 426110, 426115, 426116, 426117, 426172, 426177, 426183, 426187, 426255, 426262, and 426263.

Certain embodiments provide compounds comprising a modified oligonucleotide consisting of 20 linked nucleosides wherein the linked nucleosides comprise at least an 8 contiguous nucleobase portion that is complementary to an equal length nucleobase portion within the region selected from nucleotides 57825-57844, 59956-59975, 63677-63696, 65938-65959, 65938-65958, 65938-65957, 65939-65959, 65939-65958, 65940-65959, 76224-76243, 76225-76244, 76229-76248, and 95513-95532 of SEQ ID NO: 1. In certain embodiments, the modified oligonucleotide has at least a 9, at least a 10, at least an 11, at least a 12, at least a 13, at least a 14, at least a 15, at least a 16, at least a 17, at an 18, or at least a 19 contiguous nucleobase portion of which is complementary to an equal length portion within the region selected from nucleotides 57825-57844, 59956-59975, 63677-63696, 65938-65959, 65938-65958, 65938-65957, 65939-65959, 65939-65958, 65940-65959, 76224-76243, 76225-76244, 76229-76248, and 95513-95532 of SEQ ID NO: 1. In certain embodiments, the modified oligonucleotide is 90%, 95%, 99%, or 100% complementary to a nucleic acid encoding human GCCR e.g. SEQ ID NO: 1

Certain embodiments provide compounds comprising a modified oligonucleotide consisting of at least 20 linked nucleosides 60% complementary within the region selected from nucleotides 57825-57844, 59956-59975, 63677-63696, 65938-65959, 65938-65958, 65938-65957, 65939-65959, 65939-65958, 65940-65959, 76224-76243, 76225-76244, 76229-76248, and 95513-95532 of SEQ ID NO: 1.

Certain embodiments provide compounds comprising a modified oligonucleotide consisting of at least 20 linked nucleosides 70% complementary within the region selected from nucleotides 57825-57844, 59956-59975, 63677-63696, 65938-65959, 65938-65958, 65938-65957, 65939-65959, 65939-65958, 65940-65959, 76224-76243, 76225-76244, 76229-76248, and 95513-95532 of SEQ ID NO: 1.

Certain embodiments provide compounds comprising a modified oligonucleotide consisting of at least 20 linked nucleosides 80% complementary within the region selected from 57825-57844, 59956-59975, 63677-63696, 65938-65959, 65938-65958, 65938-65957, 65939-65959, 65939-65958, 65940-65959, 76224-76243, 76225-76244, 76229-76248, and 95513-95532 of SEQ ID NO: 1.

Certain embodiments provide compounds comprising a modified oligonucleotide consisting of at least 20 linked nucleosides 90% complementary within the region selected from nucleotides 57825-57844, 59956-59975, 63677-63696, 65938-65959, 65938-65958, 65938-65957, 65939-65959, 65939-65958, 65940-65959, 76224-76243, 76225-76244, 76229-76248, and 95513-95532 of SEQ ID NO: 1.

Certain embodiments provide compounds comprising a modified oligonucleotide consisting of at least 20 linked nucleosides 95% complementary within the region selected from nucleotides 57825-57844, 59956-59975, 63677-63696, 65938-65959, 65938-65958, 65938-65957, 65939-65959, 65939-65958, 65940-65959, 76224-76243, 76225-76244, 76229-76248, and 95513-95532 of SEQ ID NO: 1.

Certain embodiments provide compounds comprising a modified oligonucleotide consisting of at least 20 linked nucleosides 99% complementary within the region selected from nucleotides 57825-57844, 59956-59975, 63677-63696, 65938-65959, 65938-65958, 65938-65957, 65939-65959, 65939-65958, 65940-65959, 76224-76243, 76225-76244, 76229-76248, and 95513-95532 of SEQ ID NO: 1.

Certain embodiments provide compounds comprising a modified oligonucleotide consisting of at least 20 linked nucleosides 100% complementary within the region selected from nucleotides 57825-57844, 59956-59975, 63677-63696, 65938-65959, 65938-65958, 65938-65957, 65939-65959, 65939-65958, 65940-65959, 76224-76243, 76225-76244, 76229-76248, and 95513-95532 of SEQ ID NO: 1.

Certain embodiments provide compounds comprising a modified oligonucleotide consisting of 20 linked nucleosides 60% complementary within nucleotides 65940-65959 of SEQ ID NO: 1.

Certain embodiments provide compounds comprising a modified oligonucleotide consisting of 20 linked nucleosides 70% complementary within nucleotides 65940-65959 of SEQ ID NO: 1.

Certain embodiments provide compounds comprising a modified oligonucleotide consisting of 20 linked nucleosides 80% complementary within nucleotides 65940-65959 of SEQ ID NO: 1.

Certain embodiments provide compounds comprising a modified oligonucleotide consisting of 20 linked nucleosides 90% complementary within nucleotides 65940-65959 of SEQ ID NO: 1.

Certain embodiments provide compounds comprising a modified oligonucleotide consisting of 20 linked nucleosides 95% complementary within nucleotides 65940-65959 of SEQ ID NO: 1

Certain embodiments provide compounds comprising a modified oligonucleotide consisting of 20 linked nucleosides 99% complementary within nucleotides 65940-65959 of SEQ ID NO: 1.

Certain embodiments provide compounds comprising a modified oligonucleotide consisting of 20 linked nucleosides 100% complementary within nucleotides 65940-65959 of SEQ ID NO: 1.

In certain embodiments, such compounds or oligonucleotides targeted to a region of a GCCR nucleic acid have a contiguous nucleobase portion that is complementary to an equal length nucleobase portion of the region 65940-65959 of SEQ ID NO: 1

In certain embodiments, the following nucleotide regions of SEQ ID NO: 1, when targeted by antisense compounds or oligonucleotides, displays at least 65% inhibition: 57825-57844, 59956-59975, 63677-63696, 65938-65959, 65938-65958, 65938-65957, 65939-65959, 65939-65958, 65940-65959, 76224-76243, 76225-76244, 76229-76248, and 95513-95532.

In certain embodiments, the following antisense compounds target a region of SEQ ID NO: 1, a nucleic acid encoding human GCCR and demonstrate at least 55% inhibition of GCCR expression: ISIS NOs: 4, 5, 6, 7, 8, 9, 10, 11, 12, 13, 14, 15, 16, 17, 18, 19, 20, 21, 22, 23, 24, 30, 31, 35, 36, 37, 38, 42, 43, 45, 48, 54, and 56.

In certain embodiments, the following antisense compounds target a region of SEQ ID NO: 1, a nucleic acid encoding human GCCR and demonstrate at least 60% inhibition of GCCR expression: ISIS NOs: 4, 5, 6, 7, 8, 9, 10, 11, 12, 13, 14, 15, 16, 17, 18, 19, 20, 21, 22, 23, 24, 31, 35, 36, 37, 38, and 45.

In certain embodiments, the following antisense compounds target a region of SEQ ID NO: 1, a nucleic acid encoding human GCCR and demonstrate at least 65% inhibition of GCCR expression: ISIS NOs: 4, 5, 6, 7, 8, 9, 10, 11, 12, 13, 14, 15, 16, 17, 18, 19, 20, 21, 22, 23, 24, 31, 36, 38, and 45.

In certain embodiments, the following antisense compounds target a region of SEQ ID NO: 1, a nucleic acid encoding human GCCR and demonstrate at least 70% inhibition of GCCR expression: ISIS NOs: 4, 5, 6, 7, 8, 9, 10, 11, 12, 13, 14, 15, 16, 17, 20, 21, 22, 23, 24, 36, and 38.

In certain embodiments, the following antisense compounds target a region of SEQ ID NO: 1, a nucleic acid encoding human GCCR and demonstrate at least 75% inhibition of GCCR expression: ISIS NOs: 4, 5, 6, 7, 9, 10, 11, 12, 13, 14, 15, 16, 17, 20, and 22.

In certain embodiments, the following antisense compounds target a region of SEQ ID NO: 1, a nucleic acid encoding human GCCR and demonstrate at least 80% inhibition of GCCR expression: ISIS NOs: 4, 5, 7, 13, 16, and 22.

In certain embodiments, the following antisense compounds target a region of SEQ ID NO: 1, a nucleic acid encoding human GCCR and demonstrate at least 85% inhibition of a GCCR expression: ISIS NOs: 5, 7, 13, and 16.

In certain embodiments, the compounds provided herein have a greater therapeutic potential than ISIS NOs: 361137, 361141, 361151, 361156, 377131, 361143, and 361155 (Disclosed in PCT Pub No. WO 2007/035759 incorporated herein by reference). In certain embodiments, the compounds provided herein have better in vitro inhibition over ISIS NOs: 361137, 361141, 361151, 361156, 377131, 361143, and 361155. In certain embodiments, the compounds provided herein have better in vivo inhibition over ISIS NOs: 361137, 361141, 361151, 361156, 377131, 361143, and 361155. In certain embodiments, the compounds provided herein have a better tolerability profile than ISIS NOs: 361137, 361141, 361151, 361156, 377131, 361143, and 361155.

In certain embodiments, the compound provided herein consists of a single-stranded modified oligonucleotide.

In certain embodiments, the modified oligonucleotide consists of 8, 9, 10, 11, 12, 13, 14, 15, 16, 17, 18, 19, 20, 21, 22, 23, 24, 25, 26, 27, 28, 29, 30, 31, 32, 33, 34 or 35 linked nucleosides. In certain embodiments, the modified oligonucleotide consists of 21 linked nucleosides. In certain embodiments, the modified oligonucleotide consists of 20 linked nucleosides. In certain embodiments, the modified oligonucleotide consists of 19 linked nucleosides. In certain embodiments, the modified oligonucleotide consists of 18 linked nucleosides. In certain embodiments, the modified oligonucleotide consists of 20 linked nucleosides. In certain embodiments, the modified oligonucleotide consists of 16 linked nucleosides.

In certain embodiments, at least one internucleoside linkage of the modified oligonucleotide is a modified internucleoside linkage. In certain embodiments, each internucleoside linkage is a phosphorothioate internucleoside linkage.

In certain embodiments, at least one nucleoside of said modified oligonucleotide comprises a modified nucleobase. In certain embodiments, the modified nucleobase is a 5-methylcytosine.

In certain embodiments, the modified oligonucleotide comprises: a) a gap segment consisting of linked deoxynucleosides; b) a 5' wing segment consisting of linked nucleosides; and c) a 3' wing segment consisting of linked nucleosides. The gap segment is positioned between the 5' wing segment and the 3' wing segment and each nucleoside of each wing segment comprises a modified sugar.

In certain embodiments, the modified oligonucleotide consists of 20 linked nucleosides, the gap segment consisting of ten linked deoxynucleosides, the 5' wing segment consisting of five linked nucleosides, the 3' wing segment consisting of five linked nucleosides, each nucleoside of each wing segment comprises a 2'-O-methoxyethyl modified sugar, each internucleoside linkage is a phosphorothioate linkage and each cytosine is a 5-methylcytosine.

In certain embodiments, the modified oligonucleotide consists of 20 linked nucleosides, the gap segment consisting of fourteen linked deoxynucleosides, the 5' wing segment consisting of three linked nucleosides, the 3' wing segment consisting of three linked nucleosides, each nucleoside of each wing segment comprises a 2'-O-methoxyethyl modified sugar, each internucleoside linkage is a phosphorothioate linkage and each cytosine is a 5-methylcytosine.

In certain embodiments, the modified oligonucleotide consists of 20 linked nucleosides, the gap segment consisting of thirteen linked deoxynucleosides, the 5' wing segment consisting of two linked nucleosides, the 3' wing segment consisting of five linked nucleosides, each nucleoside of each wing segment comprises a 2'-O-methoxyethyl modified sugar, each internucleoside linkage is a phosphorothioate linkage and each cytosine is a 5-methylcytosine.

In certain embodiments, the compounds or compositions provided herein comprise a modified oligonucleotide consisting of 20 linked nucleosides having a nucleobase sequence comprising at least 8 contiguous nucleobases complementary to an equal length portion of any of SEQ ID NOs: 1 and 2, wherein the modified oligonucleotide comprises: a) a gap segment consisting of ten linked deoxynucleosides; b) a 5' wing segment consisting of five linked nucleosides; and c) a 3' wing segment consisting of five linked nucleosides. The gap segment is positioned between the 5' wing segment and the 3' wing segment, each nucleoside of each wing segment comprises a 2'-O-methoxyethyl modified sugar, each internucleoside linkage is a phosphorothioate linkage and each cytosine residue is a 5-methylcytosine.

In certain embodiments, the compounds or compositions provided herein comprise a modified oligonucleotide consisting of 20 linked nucleosides having a nucleobase sequence comprising at least 8 contiguous nucleobases complementary to an equal length portion of any of SEQ ID NO: 1, wherein the modified oligonucleotide comprises: a) a gap segment consisting of ten linked deoxynucleosides; b) a 5' wing segment consisting of five linked nucleosides; and c) a 3' wing segment consisting of five linked nucleosides. The gap segment is positioned between the 5' wing segment and the 3' wing segment, each nucleoside of each wing segment comprises a 2'-O-methoxyethyl modified sugar, each internucleoside linkage is a phosphorothioate linkage and each cytosine residue is a 5-methylcytosine.

In certain embodiments, the compounds or compositions provided herein comprise a modified oligonucleotide consisting of 20 linked nucleosides having a nucleobase sequence comprising at least 19 contiguous nucleobases of SEQ ID NOs: 6, 7, 10, 11, 33, 35, 36, 39, 42, and 43, wherein the modified oligonucleotide comprises: a) a gap segment consisting of ten linked deoxynucleosides; b) a 5' wing segment consisting of five linked nucleosides; and c) a 3' wing segment consisting of five linked nucleosides. The gap segment is positioned between the 5' wing segment and the 3' wing segment, each nucleoside of each wing segment comprises a 2'-O-methoxyethyl modified sugar, each internucleoside linkage is a phosphorothioate linkage and each cytosine residue is a 5-methylcytosine.

In certain embodiments, the compounds or compositions provided herein comprise a modified oligonucleotide consisting of 20 linked nucleosides having a nucleobase sequence comprising at least 19 contiguous nucleobases of SEQ ID NO: 36 wherein the modified oligonucleotide comprises: a) a gap segment consisting of ten linked deoxynucleosides; b) a 5' wing segment consisting of five linked nucleosides; and c) a 3' wing segment consisting of five linked nucleosides. The gap segment is positioned between the 5' wing segment and the 3' wing segment, each nucleoside of each wing segment comprises a 2'-O-methoxyethyl modified sugar, each internucleoside linkage is a phosphorothioate linkage and each cytosine residue is a 5-methylcytosine.

In certain embodiments, the compounds or compositions provided herein comprise a modified oligonucleotide consisting of 20 linked nucleosides having a nucleobase sequence comprising at least 19 contiguous nucleobases of SEQ ID NO: 36, wherein the modified oligonucleotide comprises: a) a gap segment consisting of ten linked deoxynucleosides; b) a 5' wing segment consisting of four linked nucleosides; and c) a 3' wing segment consisting of four linked nucleosides. The gap segment is positioned between the 5' wing segment and the 3' wing segment, each nucleoside of each wing segment comprises a 2'-O-methoxyethyl modified sugar, each internucleoside linkage is a phosphorothioate linkage and each cytosine residue is a 5-methylcytosine.

In certain embodiments, the compounds or compositions provided herein comprise a modified oligonucleotide consisting of 20 linked nucleosides having a nucleobase sequence comprising at least 8 contiguous nucleobases complementary to an equal length portion of any of SEQ ID NOs: 1 and 2, wherein the modified oligonucleotide comprises: a) a gap segment consisting of fourteen linked deoxynucleosides; b) a 5' wing segment consisting of three linked nucleosides; and c) a 3' wing segment consisting of three linked nucleosides. The gap segment is positioned between the 5' wing segment and the 3' wing segment, each nucleoside of each wing segment comprises a 2'-O-methoxyethyl modified sugar, each internucleoside linkage is a phosphorothioate linkage and each cytosine residue is a 5-methylcytosine.

In certain embodiments, the compounds or compositions provided herein comprise a modified oligonucleotide consisting of 20 linked nucleosides having a nucleobase sequence comprising at least 8 contiguous nucleobases complementary to an equal length portion of any of SEQ ID NO: 1, wherein the modified oligonucleotide comprises: a) a gap segment consisting of thirteen linked deoxynucleosides; b) a 5' wing segment consisting of two linked nucleosides; and c) a 3' wing segment consisting of five linked nucleosides. The gap segment is positioned between the 5' wing segment and the 3' wing segment, each nucleoside of each wing segment comprises a 2'-O-methoxyethyl modified sugar, each internucleoside linkage is a phosphorothioate linkage and each cytosine residue is a 5-methylcytosine.

In certain embodiments, the compounds or compositions provided herein comprise a modified oligonucleotide consisting of 20 linked nucleosides having a nucleobase sequence comprising at least 19 contiguous nucleobases of SEQ ID NOs: 6, 7, 10, 11, 33, 35, 36, 39, 42, and 43, wherein the modified oligonucleotide comprises: a) a gap segment consisting of ten linked deoxynucleosides; b) a 5' wing segment consisting of five linked nucleosides; and c) a 3' wing segment consisting of five linked nucleosides. The gap segment is positioned between the 5' wing segment and the 3' wing segment, each nucleoside of each wing segment comprises a 2'-O-methoxyethyl modified sugar, each internucleoside linkage is a phosphorothioate linkage and each cytosine residue is a 5-methylcytosine.

In certain embodiments, the compounds or compositions provided herein comprise a modified oligonucleotide consisting of 20 linked nucleosides having a nucleobase sequence comprising at least 19 contiguous nucleobases of SEQ ID NO: 36, wherein the modified oligonucleotide comprises: a) a gap segment consisting of ten linked deoxynucleosides; b) a 5' wing segment consisting of five linked nucleosides; and c) a 3' wing segment consisting of five linked nucleosides. The gap segment is positioned between the 5' wing segment and the 3' wing segment, each nucleoside of each wing segment comprises a 2'-O-methoxyethyl modified sugar, each internucleoside linkage is a phosphorothioate linkage and each cytosine residue is a 5-methylcytosine.

In certain embodiments, the compounds or compositions provided herein comprise a modified oligonucleotide consisting of 20 linked nucleosides having a nucleobase sequence of SEQ ID NO: 36 wherein the modified oligonucleotide comprises: a) a gap segment consisting of ten linked deoxynucleosides; b) a 5' wing segment consisting of five linked nucleosides; and c) a 3' wing segment consisting of six linked nucleosides. The gap segment is positioned between the 5' wing segment and the 3' wing segment, each nucleoside of each wing segment comprises a 2'-O-methoxyethyl modified sugar, each internucleoside linkage is a phosphorothioate linkage and each cytosine residue is a 5-methylcytosine.

Certain embodiments provide methods, compounds, and compositions for inhibiting GCCR expression.

Certain embodiments provide a method of reducing GCCR expression in an animal comprising administering to the animal a compound as described herein. In certain embodiments, the compound comprises a modified oligonucleotide 12 to 30 linked nucleosides in length targeted to GCCR. In certain embodiments, the compound comprises a modified oligonucleotide 15 to 30 linked nucleosides in length targeted to GCCR. In certain embodiments, the compound comprises a modified oligonucleotide 18 to 21 linked nucleosides in length targeted to GCCR. In certain embodiments, the compound comprises a modified oligonucleotide 17 to 35 linked nucleosides in length targeted to GCCR. In certain embodiments, the compound comprises a modified oligonucleotide 17 to 25 linked nucleosides in length targeted to GCCR. In certain embodiments, the compound comprises a modified oligonucleotide 17 to 24 linked nucleosides in length targeted to GCCR. In certain embodiments, the compound comprises a modified oligonucleotide 17 to 23 linked nucleosides in length targeted to GCCR. In certain embodiments, the compound comprises a modified oligonucleotide 17 to 22 linked nucleosides in length targeted to GCCR. In certain embodiments, the compound comprises a modified oligonucleotide 17 to 21 linked nucleosides in length targeted to GCCR. In certain embodiments, the compound comprises a modified oligonucleotide 20 linked nucleosides in length targeted to GCCR. In certain embodiments, the compound comprises a modified oligonucleotide 20 linked nucleosides in length targeted to GCCR.

Certain embodiments provide a method of preventing, ameliorating or treating a metabolic disease in an animal comprising administering to the animal a compound as described herein. In certain embodiments, the compound comprises a modified oligonucleotide 12 to 30 linked nucleosides in length targeted to GCCR. In certain embodiments, the compound comprises a modified oligonucleotide 20 linked nucleosides in length targeted to GCCR. Examples of metabolic diseases or disorders include, but are not limited to diabetes, hyperglycemia, prediabetes, obesity, non-alcoholic fatty liver disease (NAFLD), metabolic syndrome, insulin resistance, diabetic dyslipidemia, or hypertriglyceridemia or a combination thereof.

Certain embodiments provide a method of preventing, ameliorating or treating obesity in an animal comprising administering to the animal a compound as described herein. In certain embodiments, the compound comprises a modified oligonucleotide 12 to 30 linked nucleosides in length targeted to GCCR. In certain embodiments, the compound comprises a modified oligonucleotide 20 linked nucleosides in length targeted to GCCR. In certain embodiments, the compound comprises a modified oligonucleotide 20 linked nucleosides in length targeted to GCCR. In certain embodiments, the compound or composition comprises the compound of ISIS NOs: 420470, 420476, 426130, 426183, 426261, 426262, 426115, 426168, 426246, 426172, 426325, and 426267. In certain embodiments, the compound or composition comprises the compound of ISIS NO: 426115.

Certain embodiments provide a method of reducing body weight in an animal comprising administering to the animal a compound as described herein. In certain embodiments, the compound comprises a modified oligonucleotide 12 to 30 linked nucleosides in length targeted to GCCR. In certain embodiments, the compound comprises a modified oligonucleotide 20 linked nucleosides in length targeted to GCCR. In certain embodiments, reduction of body weight in an animal prevents, ameliorates or treats a metabolic disease. In certain embodiments, reduction of body weight in an animal prevents, ameliorates or treats diabetes. In certain embodiments, reduction of body weight in an animal prevents, ameliorates or treats obesity. In certain embodiments, reduction of body weight in an animal prevents, ameliorates or treats metabolic syndrome. In certain embodiments, reduction of body weight in an animal prevents, ameliorates or treats insulin resistance. In certain embodiments, reduction of body weight in an animal prevents, ameliorates or treats hyperglycemia. In certain embodiments, reduction of body weight in an animal prevents, ameliorates or treats NAFLD. In certain embodiments, reduction of body weight in an animal prevents, ameliorates or treats diabetic dyslipidemia. In certain embodiments, the glucose levels are reduced by at least 5%, 10%, 20%, 30%, 35%, 40%, 45%, 50%, 55%, 60%, 65%, 70%, 75%, 80%, 85%, 90%, 95% or 100%.

Certain embodiments provide a method of reducing glucose levels in an animal comprising administering to the animal a compound as described herein. In certain embodiments, the compound comprises a modified oligonucleotide 12 to 30 linked nucleosides in length targeted to GCCR. In certain embodiments, the compound comprises a modified oligonucleotide 20 linked nucleosides in length targeted to GCCR. In certain embodiments, reduction of glucose levels in an animal prevents, ameliorates or treats a metabolic disease. In certain embodiments, reduction of glucose levels in an animal prevents, ameliorates or treats diabetes. In certain embodiments, reduction of glucose levels in an animal prevents, ameliorates or treats obesity. In certain embodiments, reduction of glucose levels in an animal prevents, ameliorates or treats metabolic syndrome. In certain embodiments, reduction of glucose levels in an animal prevents, ameliorates or treats insulin resistance. In certain embodiments, reduction of glucose levels in an animal prevents, ameliorates or treats hyperglycemia. In certain embodiments, reduction of glucose levels in an animal prevents, ameliorates or treats NAFLD. In certain embodiments, reduction of glucose levels in an animal prevents, ameliorates or treats diabetic dyslipidemia. In certain embodiments, the glucose level is reduced by at least 5%, 10%, 20%, 30%, 35%, 40%, 45%, 50%, 55%, 60%, 65%, 70%, 75%, 80%, 85%, 90%, 95% or 100%.

In certain embodiments, GCCR has the human sequence as set forth in any of the GENBANK Accession Numbers: the complement of GENBANK Accession No. NT_029289.10 truncated from nucleotides 3818000 to 3980000 (incorporated herein as SEQ ID NO: 1). In certain embodiments, GCCR has the rhesus monkey sequence as set forth in the complement of GENBANK Accession No. NW_001120987.1 truncated from nucleotides 1334000 to 1491000 (incorporated herein as SEQ ID NO: 2).

In certain embodiments, the compounds or compositions provided herein comprise a salt thereof, and a pharmaceutically acceptable carrier or diluent. In certain embodiments, the composition comprises a modified oligonucleotide consisting of 17 to 35 linked nucleosides and having a nucleobase sequence comprising at least 20 contiguous nucleobases of a nucleobase sequence recited in SEQ ID NOs: 6, 7, 10, 11, 33, 35, 36, 39, 42, and 43 or a salt thereof and a pharmaceutically acceptable carrier or diluent. In certain embodiments, the composition comprises a modified oligonucleotide consisting of 20 to 25 linked nucleosides and having a nucleobase sequence comprising at least 20 contiguous nucleobases of a nucleobase sequence recited in SEQ ID NOs: 6, 7, 10, 11, 33, 35, 36, 39, 42, and 43 or a salt thereof and a pharmaceutically acceptable carrier or diluent. In certain embodiments, the composition comprises a modified oligonucleotide consisting of 20 linked nucleosides and having a nucleobase sequence comprising at least 20 contiguous nucleobases of a nucleobase sequence recited in SEQ ID NOs: 6, 7, 10, 11, 33, 35, 36, 39, 42, and 43 or a salt thereof and a pharmaceutically acceptable carrier or diluent.

In certain embodiments, the compounds or compositions provided herein comprise a salt thereof, and a pharmaceutically acceptable carrier or diluent. In certain embodiments, the composition comprises a modified oligonucleotide consisting of 17 to 35 linked nucleosides and having a nucleobase sequence comprising at least 20 contiguous nucleobases of a nucleobase sequence recited in SEQ ID NO: 36 or a salt thereof and a pharmaceutically acceptable carrier or diluent. In certain embodiments, the composition comprises a modified oligonucleotide consisting of 17 to 25 linked nucleosides and having a nucleobase sequence comprising at least 20 contiguous nucleobases of a nucleobase sequence recited in SEQ ID NO: 36 or a salt thereof and a pharmaceutically acceptable carrier or diluent. In certain embodiments, the composition comprises a modified oligonucleotide consisting of 20 linked nucleosides and having a nucleobase sequence comprising at least 20 contiguous nucleobases of a nucleobase sequence recited in SEQ ID NO: 36 or a salt thereof and a pharmaceutically acceptable carrier or diluent.

Certain embodiments provide a method for treating an animal with a GCCR related disease or condition comprising: a) identifying said animal with the GCCR related disease or condition, and b) administering to said animal a therapeutically effective amount of a compound comprising a modified oligonucleotide consisting of 12 to 30 linked nucleosides and having a nucleobase sequence at least 90% complementary to any of SEQ ID NOs: 1 and 2 as measured over the entirety of said modified oligonucleotide. In certain embodiments, the therapeutically effective amount of the compound administered to the animal treats or reduces the GCCR related disease or condition, or a symptom thereof, in the animal. In certain embodiments, the GCCR related disease or condition is obesity. In certain embodiments, the GCCR related disease or condition is diabetes.

Certain embodiments provide a method for treating an animal with a GCCR related disease or condition comprising: a) identifying said animal with the GCCR related disease or condition, and b) administering to said animal a therapeutically effective amount of a compound comprising a modified oligonucleotide consisting of 20 linked nucleosides and having a nucleobase sequence at least 100% complementary to any of SEQ ID NOs: 1 and 2 as measured over the entirety of said modified oligonucleotide. In certain embodiments, the therapeutically effective amount of the compound administered to the animal treats or reduces the GCCR related disease or condition, or a symptom thereof, in the animal. In certain embodiments, the GCCR related disease or condition is obesity. In certain embodiments, the GCCR related disease or condition is diabetes.

Certain embodiments provide methods of treating, preventing, or ameliorating a metabolic disease. In certain embodiments the metabolic disease is obesity, diabetes, hyperglycemia, prediabetes, non-alcoholic fatty liver disease (NAFLD), metabolic syndrome, insulin resistance, diabetic dyslipidemia, or hypertriglyceridemia or a combination thereof.

Certain embodiments provide methods comprising administering to an animal a compound as described herein to an animal. In certain embodiments, the method comprises administering to an animal a modified oligonucleotide consisting of 17 to 35 linked nucleosides and having a nucleobase sequence comprising at least 20 contiguous nucleobases of a nucleobase sequence recited in SEQ ID NOs: 6, 7, 10, 11, 33, 35, 36, 39, 42, and 43.

Certain embodiments provide methods comprising administering to an animal a compound as described herein to an animal. In certain embodiments, the method comprises administering to an animal a modified oligonucleotide consisting of 17 to 35 linked nucleosides and having a nucleobase sequence comprising at least 20 contiguous nucleobases of a nucleobase sequence recited in SEQ ID NO: 6, 7, 10, 11, 33, 35, 36, 39, 42, and 43.

Certain embodiments provide methods comprising administering to an animal a compound as described herein to an animal. In certain embodiments, the method comprises administering to an animal a modified oligonucleotide consisting of 17 to 35 linked nucleosides and having a nucleobase sequence comprising at least 20 contiguous nucleobases of a nucleobase sequence selected from among the nucleobase sequences recited in SEQ ID NO: 36.

In certain embodiments, the animal is a human.

In certain embodiments, the administering prevents, treats, ameliorates, or slows progression of a metabolic disease as described herein.

In certain embodiments, the administering prevents, treats, ameliorates, or slows progression of obesity as described herein.

In certain embodiments, the administering prevents, treats, ameliorates, or slows progression of diabetes as described herein.

In certain embodiments, the compound is co-administered with a second agent.

In certain embodiments, the compound and the second agent are administered concomitantly.

In certain embodiments, the administering is parenteral administration.

Certain embodiments further provide a method to reduce GCCR mRNA or protein expression in an animal comprising administering to the animal a compound or composition as described herein to reduce GCCR mRNA or protein expression in the animal. In certain embodiments, the animal is a human. In certain embodiments, reducing GCCR mRNA or protein expression prevents, treats, ameliorates, or slows progression of metabolic disease. In certain embodiments, the metabolic disease or condition is diabetes. In certain embodiments, the metabolic disease or condition is obesity.

Certain embodiments provide a method for treating a human with a metabolic disease comprising identifying the human with the disease and administering to the human a therapeutically effective amount of a compound or composition as described herein. In certain embodiments, the treatment reduces a symptom selected from the group consisting of metabolic syndrome, hyperglycemia, hypertriglyceridemia, hypertension, increased glucose levels, increased insulin resistance, decreased insulin sensitivity, above normal body weight, and/or above normal body fat or any combination thereof.

Certain embodiments provide a method for treating a human with obesity comprising identifying the human with the disease and administering to the human a therapeutically effective amount of a compound or composition as described herein. In certain embodiments, the treatment reduces a symptom selected from the group consisting of metabolic syndrome, hyperglycemia, hypertriglyceridemia, hypertension, increased glucose levels, increased insulin resistance, decreased insulin sensitivity, above normal body weight, and/or above normal body fat or any combination thereof.

Certain embodiments provide a method for treating a human with diabetes comprising identifying the human with the disease and administering to the human a therapeutically effective amount of a compound or composition as described herein. In certain embodiments, the treatment reduces a symptom selected from the group consisting of metabolic syndrome, hyperglycemia, hypertriglyceridemia, hypertension, increased glucose levels, increased insulin resistance, decreased insulin sensitivity, above normal body weight, and/or above normal body fat or any combination thereof.

Further provided is a method for reducing or preventing metabolic disease comprising administering to a human a therapeutically effective amount compound or composition as described herein, thereby reducing or preventing metabolic disease.

Further provided is a method for reducing or preventing obesity comprising administering to a human a therapeutically effective amount compound or composition as described herein, thereby reducing or preventing diabetes.

Further provided is a method for reducing or preventing diabetes comprising administering to a human a therapeutically effective amount compound or composition as described herein, thereby reducing or preventing diabetes.

Further provided is a method for ameliorating a symptom of metabolic disease, comprising administering to a human in need thereof a compound comprising a modified oligonucleotide consisting of 17 to 35 linked nucleosides, wherein said modified oligonucleotide specifically hybridizes to SEQ ID NO: 1 or 2, thereby ameliorating a symptom of metabolic disease in the human.

Further provided is a method for ameliorating a symptom of diabetes, comprising administering to a human in need thereof a compound comprising a modified oligonucleotide consisting of 17 to 35 linked nucleosides, wherein said modified oligonucleotide specifically hybridizes to SEQ ID NO: 1 or 2, thereby ameliorating a symptom of diabetes in the human.

Further provided is a method for ameliorating a symptom of metabolic disease, comprising administering to a human in need thereof a compound comprising a modified oligonucleotide consisting of 12 to 30 linked nucleosides, wherein said modified oligonucleotide specifically hybridizes to SEQ ID NO: 1 or 2, thereby ameliorating a symptom of metabolic disease in the human.

Further provided is a method for ameliorating a symptom of diabetes, comprising administering to a human in need thereof a compound comprising a modified oligonucleotide consisting of 12 to 30 linked nucleosides, wherein said modified oligonucleotide specifically hybridizes to SEQ ID NO: 1 or 2, thereby ameliorating a symptom of diabetes in the human.

Further provided is a method for ameliorating a symptom of metabolic disease, comprising administering to a human in need thereof a compound comprising a modified oligonucleotide consisting of 20 linked nucleosides, wherein said modified oligonucleotide specifically hybridizes to SEQ ID NO: 1 or 2, thereby ameliorating a symptom of metabolic disease in the human.

Further provided is a method for ameliorating a symptom of diabetes, comprising administering to a human in need thereof a compound comprising a modified oligonucleotide consisting of 20 linked nucleosides, wherein said modified oligonucleotide specifically hybridizes to SEQ ID NO: 1 or 2, thereby ameliorating a symptom of diabetes in the human.

Further provided is a method for reducing the rate of progression of a symptom associated with metabolic disease, comprising administering to a human in need thereof a compound comprising a modified oligonucleotide consisting of 20 to 35 linked nucleosides, wherein said modified oligonucleotide specifically hybridizes to SEQ ID NO: 1 or 2, thereby reducing the rate of progression a symptom of metabolic disease in the human.

Further provided is a method for reducing the rate of progression of a symptom associated with diabetes, comprising administering to a human in need thereof a compound comprising a modified oligonucleotide consisting of 17 to 35 linked nucleosides, wherein said modified oligonucleotide specifically hybridizes to SEQ ID NO: 1 or 2, thereby reducing the rate of progression a symptom of diabetes in the human.

Further provided is a method for reducing the rate of progression of a symptom associated with metabolic disease, comprising administering to a human in need thereof a compound comprising a modified oligonucleotide consisting of 12 to 30 linked nucleosides, wherein said modified oligonucleotide specifically hybridizes to SEQ ID NO: 1 or 2, thereby reducing the rate of progression a symptom of metabolic disease in the human.

Further provided is a method for reducing the rate of progression of a symptom associated with diabetes, comprising administering to a human in need thereof a compound comprising a modified oligonucleotide consisting of 12 to 30 linked nucleosides, wherein said modified oligonucleotide specifically hybridizes to SEQ ID NO: 1 or 2, thereby reducing the rate of progression a symptom of diabetes in the human.

Further provided is a method for reducing the rate of progression of a symptom associated with metabolic disease, comprising administering to a human in need thereof a compound comprising a modified oligonucleotide consisting of 20 linked nucleosides, wherein said modified oligonucleotide specifically hybridizes to SEQ ID NO: 1 or 2, thereby reducing the rate of progression a symptom of metabolic disease in the human.

Further provided is a method for reducing the rate of progression of a symptom associated with diabetes, comprising administering to a human in need thereof a compound comprising a modified oligonucleotide consisting of 20 linked nucleosides, wherein said modified oligonucleotide specifically hybridizes to SEQ ID NO: 1 or 2, thereby reducing the rate of progression a symptom of diabetes in the human.

Also provided are methods and compounds for the preparation of a medicament for the treatment, prevention, or amelioration of metabolic disease.

Also provided are methods and compounds for the preparation of a medicament for the treatment, prevention, or amelioration of obesity.

Also provided are methods and compounds for the preparation of a medicament for the treatment, prevention, or amelioration of diabetes.

Also provided are methods and compounds for the preparation of a medicament for the treatment, prevention, or amelioration of metabolic syndrome.

Certain embodiments provide the use of a compound as described herein in the manufacture of a medicament for treating, ameliorating, or preventing metabolic disease.

Certain embodiments provide the use of a compound as described herein in the manufacture of a medicament for treating, ameliorating, or preventing obesity.

Certain embodiments provide the use of a compound as described herein in the manufacture of a medicament for treating, ameliorating, or preventing diabetes.

Certain embodiments provide the use of a compound as described herein in the manufacture of a medicament for treating, ameliorating, or preventing metabolic syndrome.

Certain embodiments provide a compound as described herein for use in treating, preventing, or ameliorating metabolic disease as described herein by combination therapy with an additional agent or therapy as described herein. Agents or therapies can be co-administered or administered concomitantly.

Certain embodiments provide a compound as described herein for use in treating, preventing, or ameliorating diabetes as described herein by combination therapy with an additional agent or therapy as described herein. Agents or therapies can be co-administered or administered concomitantly.

Certain embodiments provide the use of a compound as described herein in the manufacture of a medicament for treating, preventing, or ameliorating metabolic disease as described herein by combination therapy with an additional agent or therapy as described herein. Agents or therapies can be co-administered or administered concomitantly.

Certain embodiments provide the use of a compound as described herein in the manufacture of a medicament for treating, preventing, or ameliorating obesity as described herein by combination therapy with an additional agent or therapy as described herein. Agents or therapies can be co-administered or administered concomitantly.

Certain embodiments provide the use of a compound as described herein in the manufacture of a medicament for treating, preventing, or ameliorating diabetes as described herein by combination therapy with an additional agent or therapy as described herein. Agents or therapies can be co-administered or administered concomitantly.

Certain embodiments provide the use of a compound as described herein in the manufacture of a medicament for treating, preventing, or ameliorating diabetes as described herein by combination therapy with an additional agent or therapy as described herein. Agents or therapies can be co-administered or administered concomitantly.

Certain embodiments provide the use of a compound as described herein in the manufacture of a medicament for treating, preventing, or ameliorating metabolic disease as described herein in a patient who is subsequently administered an additional agent or therapy as described herein.

Certain embodiments provide the use of a compound as described herein in the manufacture of a medicament for treating, preventing, or ameliorating obesity as described herein in a patient who is subsequently administered an additional agent or therapy as described herein.

Certain embodiments provide the use of a compound as described herein in the manufacture of a medicament for treating, preventing, or ameliorating diabetes as described herein in a patient who is subsequently administered an additional agent or therapy as described herein.

Certain embodiments provide the use of a compound as described herein in the manufacture of a medicament for treating, preventing, or ameliorating metabolic syndrome as described herein in a patient who is subsequently administered an additional agent or therapy as described herein.

Certain embodiments provide a kit for treating, preventing, or ameliorating metabolic disease as described herein wherein the kit comprises:

(i) a compound as described herein; and alternatively (ii) an additional agent or therapy as described herein.

Certain embodiments provide a kit for treating, preventing, or ameliorating obesity as described herein wherein the kit comprises:

(i) a compound as described herein; and alternatively (ii) an additional agent or therapy as described herein.

Certain embodiments provide a kit for treating, preventing, or ameliorating diabetes as described herein wherein the kit comprises:

(i) a compound as described herein; and alternatively (ii) an additional agent or therapy as described herein.

Certain embodiments provide a kit for treating, preventing, or ameliorating metabolic syndrome as described herein wherein the kit comprises:

(i) a compound as described herein; and alternatively (ii) an additional agent or therapy as described herein.

A kit as described herein may further include instructions for using the kit to treat, prevent, or ameliorate metabolic disease as described herein by combination therapy as described herein. In certain embodiments, the metabolic disease is obesity. In certain embodiments, the metabolic disease is diabetes.

Antisense Compounds

Oligomeric compounds include, but are not limited to, oligonucleotides, oligonucleosides, oligonucleotide analogs, oligonucleotide mimetics, antisense compounds, antisense oligonucleotides, and siRNAs. An oligomeric compound may be "antisense" to a target nucleic acid, meaning that is capable of undergoing hybridization to a target nucleic acid through hydrogen bonding.

In certain embodiments, an antisense compound has a nucleobase sequence that, when written in the 5' to 3' direction, comprises the reverse complement of the target segment of a target nucleic acid to which it is targeted. In certain such embodiments, an antisense oligonucleotide has a nucleobase sequence that, when written in the 5' to 3' direction, comprises the reverse complement of the target segment of a target nucleic acid to which it is targeted.

In certain embodiments, an antisense compound targeted to a GCCR nucleic acid is 10 to 30 nucleotides in length. In other words, antisense compounds are from 10 to 30 linked nucleobases. In other embodiments, the antisense compound comprises a modified oligonucleotide consisting of 8 to 80, 10 to 50, 15 to 30, 18 to 21, 20 to 80, 20 to 35, 20 to 30, 20 to 29, 20 to 28, 20 to 27, 20 to 26, 20 to 25, 20 to 24, 20 to 23, 20 to 22, 20 to 21 or 20 linked nucleobases. In certain such embodiments, the antisense compound comprises a modified oligonucleotide consisting of 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 linked nucleobases in length, or a range defined by any two of the above values.

In certain embodiments, the antisense compound comprises a shortened or truncated modified oligonucleotide. The shortened or truncated modified oligonucleotide can have a single nucleoside deleted from the 5' end (5' truncation), or alternatively from the 3' end (3' truncation). A shortened or truncated oligonucleotide may have two nucleosides deleted from the 5' end, or alternatively may have two subunits deleted from the 3' end. Alternatively, the deleted nucleosides may be dispersed throughout the modified oligonucleotide, for example, in an antisense compound having one nucleoside deleted from the 5' end and one nucleoside deleted from the 3' end.

When a single additional nucleoside is present in a lengthened oligonucleotide, the additional nucleoside may be located at the 5' or 3' end of the oligonucleotide. When two or more additional nucleosides are present, the added nucleosides may be adjacent to each other, for example, in an oligonucleotide having two nucleosides added to the 5' end (5' addition), or alternatively to the 3' end (3' addition), of the oligonucleotide. Alternatively, the added nucleoside may be dispersed throughout the antisense compound, for example, in an oligonucleotide having one nucleoside added to the 5' end and one subunit added to the 3' end.

It is possible to increase or decrease the length of an antisense compound, such as an antisense oligonucleotide, and/or introduce mismatch bases without eliminating activity. For example, in Woolf et al. (Proc. Natl. Acad. Sci. USA 89:7305-7309, 1992), a series of antisense oligonucleotides 13-25 nucleobases in length were tested for their ability to induce cleavage of a target RNA in an oocyte injection model. Antisense oligonucleotides 25 nucleobases in length with 8 or 11 mismatch bases near the ends of the antisense oligonucleotides were able to direct specific cleavage of the target mRNA, albeit to a lesser extent than the antisense oligonucleotides that contained no mismatches. Similarly, target specific cleavage was achieved using 13 nucleobase antisense oligonucleotides, including those with 1 or 3 mismatches.

Gautschi et al (J. Natl. Cancer Inst. 93:463-471, March 2001) demonstrated the ability of an oligonucleotide having 100% complementarity to the bcl-2 mRNA and having 3 mismatches to the bcl-xL mRNA to reduce the expression of both bcl-2 and bcl-xL in vitro and in vivo. Furthermore, this oligonucleotide demonstrated potent anti-tumor activity in vivo.

Maher and Dolnick (Nuc. Acid. Res. 16:3341-3358, 1988) tested a series of tandem 14 nucleobase antisense oligonucleotides, and a 28 and 42 nucleobase antisense oligonucleotides comprised of the sequence of two or three of the tandem antisense oligonucleotides, respectively, for their ability to arrest translation of human DHFR in a rabbit reticulocyte assay. Each of the three 14 nucleobase antisense oligonucleotides alone was able to inhibit translation, albeit at a more modest level than the 28 or 42 nucleobase antisense oligonucleotides.

Antisense Compound Motifs

In certain embodiments, antisense compounds targeted to a GCCR nucleic acid have chemically modified subunits arranged in patterns, or motifs, to confer to the antisense compounds properties such as enhanced inhibitory activity, increased binding affinity for a target nucleic acid, or resistance to degradation by in vivo nucleases.

Chimeric antisense compounds typically contain at least one region modified so as to confer increased resistance to nuclease degradation, increased cellular uptake, increased binding affinity for the target nucleic acid, and/or increased inhibitory activity. A second region of a chimeric antisense compound may optionally serve as a substrate for the cellular endonuclease RNase H, which cleaves the RNA strand of an RNA:DNA duplex.

Antisense compounds having a gapmer motif are considered chimeric antisense compounds. In a gapmer an internal region having a plurality of nucleotides that supports RNaseH cleavage is positioned between external regions having a plurality of nucleotides that are chemically distinct from the nucleosides of the internal region. In the case of an antisense oligonucleotide having a gapmer motif, the gap segment generally serves as the substrate for endonuclease cleavage, while the wing segments comprise modified nucleosides. In certain embodiments, the regions of a gapmer are differentiated by the types of sugar moieties comprising each distinct region. The types of sugar moieties that are used to differentiate the regions of a gapmer may in some embodiments include β-D-ribonucleosides, β-D-deoxyribonucleosides, 2'-modified nucleosides (such 2'-modified nucleosides may include 2'-MOE and 2'-O—$CH_3$, among others), and bicyclic sugar modified nucleosides (such bicyclic sugar modified nucleosides may include those having a constrained ethyl). In certain embodiments, wings may include several modified sugar moieties, including, for example 2'-MOE and constrained ethyl. In certain embodiments, wings may include several modified and unmodified sugar moieties. In certain embodiments, wings may include various combinations of 2'-MOE nucleosides, constrained ethyl nucleosides, and 2'-deoxynucleosides.

Each distinct region may comprise uniform sugar moieties, variant, or alternating sugar moieties. The wing-gap-wing motif is frequently described as "X-Y-Z", where "X" represents the length of the 5'-wing, "Y" represents the length of the gap, and "Z" represents the length of the 3'-wing. "X" and "Z" may comprise uniform, variant, or alternating sugar moieties. In certain embodiments, "X" and "Y" may include one or more 2'-deoxynucleosides. "Y" may comprise 2'-deoxynucleosides. As used herein, a gapmer described as "X-Y-Z" has a configuration such that the gap is positioned immediately adjacent to each of the 5'-wing and the 3' wing. Thus, no intervening nucleotides exist between the 5'-wing and gap, or the gap and the 3'-wing. Any of the antisense compounds described herein can have a gapmer motif. In certain embodiments, "X" and "Z" are the same, in other embodiments they are different. In certain embodiments, "Y" is between 8 and 15 nucleosides. X, Y, or Z can be any of 1, 2, 3, 4, 5, 6, 7, 8, 9, 10, 11, 12, 13, 14, 15, 16, 17, 18, 19, 20, 25, 30 or more nucleosides.

In certain embodiments, antisense compounds targeted to a GCCR nucleic acid possess a 3-14-3 gapmer motif.

In certain embodiments, antisense compounds targeted to a GCCR nucleic acid possess a 5-10-5 gapmer motif.

In certain embodiments, antisense compounds targeted to a GCCR nucleic acid possess a 5-10-6 gapmer motif.

In certain embodiments, antisense compounds targeted to a GCCR nucleic acid possess a 3-10-3 gapmer motif.

In certain embodiments, antisense compounds targeted to a GCCR nucleic acid possess a 4-12-4 gapmer motif.

In certain embodiments, antisense compounds targeted to a GCCR nucleic acid possess a 2-13-5 gapmer motif.

Target Nucleic Acids, Target Regions and Nucleotide Sequences

In certain embodiments, GCCR has the human sequence as set forth in any of the GENBANK Accession Numbers: the complement of GENBANK Accession No. NT_029289.10 truncated from nucleotides 3818000 to 3980000 (incorporated herein as SEQ ID NO: 1). In certain embodiments, GCCR has the rhesus monkey sequence as set forth in the complement of GENBANK Accession No. NW_001120987.1 truncated from nucleotides 1334000 to 1491000 (incorporated herein as SEQ ID NO: 2)

It is understood that the sequence set forth in each SEQ ID NO in the Examples contained herein is independent of any modification to a sugar moiety, an internucleoside linkage, or a nucleobase. As such, antisense compounds defined by a SEQ ID NO may comprise, independently, one or more modifications to a sugar moiety, an internucleoside linkage, or a nucleobase. Antisense compounds described by Isis Number (Isis No) indicate a combination of nucleobase sequence and motif.

In certain embodiments, a target region is a structurally defined region of the target nucleic acid. For example, a target region may encompass a 3' UTR, a 5' UTR, an exon, an intron, an exon/intron junction, a coding region, a translation initiation region, translation termination region, or other defined nucleic acid region. The structurally defined regions for GCCR can be obtained by accession number from sequence databases such as NCBI and such information is incorporated herein by reference. In certain embodiments, a target region may encompass the sequence from a 5' target site of one target segment within the target region to a 3' target site of another target segment within the same target region.

Targeting includes determination of at least one target segment to which an antisense compound hybridizes, such that a desired effect occurs. In certain embodiments, the desired effect is a reduction in mRNA target nucleic acid levels. In certain embodiments, the desired effect is reduction of levels of protein encoded by the target nucleic acid or a phenotypic change associated with the target nucleic acid.

A target region may contain one or more target segments. Multiple target segments within a target region may be overlapping. Alternatively, they may be non-overlapping. In certain embodiments, target segments within a target region are separated by no more than about 300 nucleotides. In certain embodiments, target segments within a target region are separated by a number of nucleotides that is, is about, is no more than, is no more than about, 250, 200, 150, 100, 90, 80, 70, 60, 50, 40, 30, 20, or 10 nucleotides on the target nucleic acid, or is a range defined by any two of the preceding values. In certain embodiments, target segments within a target region are separated by no more than, or no more than about, 5 nucleotides on the target nucleic acid. In certain embodiments, target segments are contiguous. Contemplated are target regions defined by a range having a starting nucleic acid that is any of the 5' target sites or 3' target sites listed herein.

Suitable target segments may be found within a 5' UTR, a coding region, a 3' UTR, an intron, an exon, or an exon/intron junction. Target segments containing a start codon or a stop codon are also suitable target segments. A suitable target segment may specifically exclude a certain structurally defined region such as the start codon or stop codon.

The determination of suitable target segments may include a comparison of the sequence of a target nucleic acid to other sequences throughout the genome. For example, the BLAST algorithm may be used to identify regions of similarity amongst different nucleic acids. This comparison can prevent the selection of antisense compound sequences that may hybridize in a non-specific manner to sequences other than a selected target nucleic acid (i.e., non-target or off-target sequences).

There may be variation in activity (e.g., as defined by percent reduction of target nucleic acid levels) of the antisense compounds within an active target region. In certain embodiments, reductions in GCCR mRNA levels are indicative of inhibition of GCCR expression. Reductions in levels of a GCCR protein are also indicative of inhibition of target mRNA expression. Further, phenotypic changes are indicative of inhibition of GCCR expression. In certain embodiments, reduced glucose levels, reduced lipid levels, and reduced body weight can be indicative of inhibition of GCCR expression. In certain embodiments, amelioration of symptoms associated with metabolic disease can be indicative of inhibition of GCCR expression. In certain embodiments, amelioration of symptoms associated with diabetes can be indicative of inhibition of GCCR expression. In certain embodiments, reduction of insulin resistance is indicative of inhibition of GCCR expression. In certain embodiments, reduction of diabetes biomarkers can be indicative of inhibition of GCCR expression.

Hybridization

In some embodiments, hybridization occurs between an antisense compound disclosed herein and a GCCR nucleic acid. The most common mechanism of hybridization involves hydrogen bonding (e.g., Watson-Crick, Hoogsteen or reversed Hoogsteen hydrogen bonding) between complementary nucleobases of the nucleic acid molecules.

Hybridization can occur under varying conditions. Stringent conditions are sequence-dependent and are determined by the nature and composition of the nucleic acid molecules to be hybridized.

Methods of determining whether a sequence is specifically hybridizable to a target nucleic acid are well known in the art. In certain embodiments, the antisense compounds provided herein are specifically hybridizable with a GCCR nucleic acid.

Complementarity

An antisense compound and a target nucleic acid are complementary to each other when a sufficient number of nucleobases of the antisense compound can hydrogen bond with the corresponding nucleobases of the target nucleic acid, such that a desired effect will occur (e.g., antisense inhibition of a target nucleic acid, such as a GCCR nucleic acid).

An antisense compound may hybridize over one or more segments of a GCCR nucleic acid such that intervening or adjacent segments are not involved in the hybridization event (e.g., a loop structure, mismatch or hairpin structure).

In certain embodiments, the antisense compounds provided herein, or a specified portion thereof, are, or are at least, 70%, 80%, 85%, 86%, 87%, 88%, 89%, 90%, 91%, 92%, 93%, 94%, 95%, 96%, 97%, 98%, 99%, or 100% complementary to a GCCR nucleic acid, a target region, target segment, or specified portion thereof. Percent complementarity of an antisense compound with a target nucleic acid can be determined using routine methods.

For example, an antisense compound in which 18 of 20 nucleobases of the antisense compound are complementary to a target region, and would therefore specifically hybridize, would represent 90 percent complementarity. In this example, the remaining non-complementary nucleobases may be clustered or interspersed with complementary nucleobases and need not be contiguous to each other or to complementary nucleobases. As such, an antisense compound which is 18 nucleobases in length having 4 (four) non-complementary nucleobases which are flanked by two regions of complete complementarity with the target nucleic acid would have 77.8% overall complementarity with the target nucleic acid and would thus fall within the scope of the present invention. Percent complementarity of an antisense compound with a region of a target nucleic acid can be determined routinely using BLAST programs (basic local alignment search tools) and PowerBLAST programs known in the art (Altschul et al., J. Mol. Biol., 1990, 215, 403 410; Zhang and Madden, Genome Res., 1997, 7, 649 656). Percent homology, sequence identity or complementarity, can be determined by, for example, the Gap program (Wisconsin Sequence Analysis Package, Version 8 for Unix, Genetics Computer Group, University Research Park, Madison, Wis.), using default settings, which uses the algorithm of Smith and Waterman (Adv. Appl. Math., 1981, 2, 482 489).

In certain embodiments, the antisense compounds provided herein, or specified portions thereof, are fully complementary (i.e. 100% complementary) to a target nucleic acid, or specified portion thereof. For example, antisense compound may be fully complementary to a GCCR nucleic acid, or a target region, or a target segment or target sequence thereof. As used herein, "fully complementary" means each nucleobase of an antisense compound is capable of precise base pairing with the corresponding nucleobases of a target nucleic acid. For example, a 20 nucleobase antisense compound is fully complementary to a target sequence that is 400 nucleobases long, so long as there is a corresponding 20 nucleobase portion of the target nucleic acid that is fully complementary to the antisense compound. Fully complementary can also be used in reference to a specified portion of the first and/or the second nucleic acid. For example, a 20 nucleobase portion of a 30 nucleobase antisense compound can be "fully complementary" to a target sequence that is 400 nucleobases long. The 20 nucleobase portion of the 30 nucleobase oligonucleotide is fully complementary to the target sequence if the target sequence has a corresponding 20 nucleobase portion wherein each nucleobase is complementary to the 20 nucleobase portion of the antisense compound. At the same time, the entire 30 nucleobase antisense compound may or may not be fully complementary to the target sequence, depending on whether the remaining 10 nucleobases of the antisense compound are also complementary to the target sequence.

The location of a non-complementary nucleobase may be at the 5' end or 3' end of the antisense compound. Alternatively, the non-complementary nucleobase or nucleobases may be at an internal position of the antisense compound. When two or more non-complementary nucleobases are present, they may be contiguous (i.e. linked) or non-contiguous. In one embodiment, a non-complementary nucleobase is located in the wing segment of a gapmer antisense oligonucleotide.

In certain embodiments, antisense compounds that are, or are up to 12, 13, 14, 15, 16, 17, 18, 19, or 20 nucleobases in length comprise no more than 4, no more than 3, no more than 2, or no more than 1 non-complementary nucleobase(s) relative to a target nucleic acid, such as a GCCR nucleic acid, or specified portion thereof.

In certain embodiments, antisense compounds that are, or are up to 12, 13, 14, 15, 16, 17, 18, 19, 20, 21, 22, 23, 24, 25, 26, 27, 28, 29, or 30 nucleobases in length comprise no more than 6, no more than 5, no more than 4, no more than 3, no more than 2, or no more than 1 non-complementary nucleobase(s) relative to a target nucleic acid, such as a GCCR nucleic acid, or specified portion thereof.

The antisense compounds provided herein also include those which are complementary to a portion of a target nucleic acid. As used herein, "portion" refers to a defined number of contiguous (i.e. linked) nucleobases within a region or segment of a target nucleic acid. A "portion" can also refer to a defined number of contiguous nucleobases of an antisense compound. In certain embodiments, the antisense compounds, are complementary to at least an 8 nucleobase portion of a target segment. In certain embodiments, the antisense compounds are complementary to at least a 12 nucleobase portion of a target segment. In certain embodiments, the antisense compounds are complementary to at least a 13 nucleobase portion of a target segment. In certain embodiments, the antisense compounds are complementary to at least a 14 nucleobase portion of a target segment. In certain embodiments, the antisense compounds are complementary to at least a 15 nucleobase portion of a target segment. In certain embodiments, the antisense compounds are complementary to at least a 16 nucleobase portion of a target segment. In certain embodiments, the antisense compounds are complementary to at least a 17 nucleobase portion of a target segment. In certain embodiments, the antisense compounds are complementary to at least a 18 nucleobase portion of a target segment. In certain embodiments, the antisense compounds are complementary to at least a 19 nucleobase portion of a target segment. In certain embodiments, the antisense compounds are complementary to at least a 20 nucleobase portion of a target segment. Also contemplated are antisense compounds that are complementary to at least a 9, 10, 11, 12, 13, 14, 15, 16, 17, 18, 19, 20, or more nucleobase portion of a target segment, or a range defined by any two of these values.

Identity

The antisense compounds provided herein may also have a defined percent identity to a particular nucleotide sequence, SEQ ID NO, or compound represented by a specific Isis number, or portion thereof. As used herein, an antisense compound is identical to the sequence disclosed herein if it has the same nucleobase pairing ability. For example, a RNA which contains uracil in place of thymidine in a disclosed DNA sequence would be considered identical to the DNA sequence since both uracil and thymidine pair with adenine. Shortened and lengthened versions of the antisense compounds described herein as well as compounds having non-identical bases relative to the antisense compounds provided herein also are contemplated. The non-identical bases may be adjacent to each other or dispersed throughout the antisense compound. Percent identity of an antisense compound is calculated according to the number of bases that have identical base pairing relative to the sequence to which it is being compared.

In certain embodiments, the antisense compounds, or portions thereof, are at least 70%, 75%, 80%, 85%, 90%, 91%, 92%, 93%, 94%, 95%, 96%, 97%, 98%, 99% or 100% identical to one or more of the antisense compounds or SEQ ID NOs, or a portion thereof, disclosed herein.

Modifications

A nucleoside is a base-sugar combination. The nucleobase (also known as base) portion of the nucleoside is normally a heterocyclic base moiety. Nucleotides are nucleosides that further include a phosphate group covalently linked to the sugar portion of the nucleoside. For those nucleosides that include a pentofuranosyl sugar, the phosphate group can be linked to the 2',3' or 5' hydroxyl moiety of the sugar. Oligonucleotides are formed through the covalent linkage of adjacent nucleosides to one another, to form a linear polymeric oligonucleotide. Within the oligonucleotide structure, the phosphate groups are commonly referred to as forming the internucleoside linkages of the oligonucleotide.

Modifications to antisense compounds encompass substitutions or changes to internucleoside linkages, sugar moieties, or nucleobases. Modified antisense compounds are often preferred over native forms because of desirable properties such as, for example, enhanced cellular uptake, enhanced affinity for nucleic acid target, increased stability in the presence of nucleases, or increased inhibitory activity.

Chemically modified nucleosides may also be employed to increase the binding affinity of a shortened or truncated antisense oligonucleotide for its target nucleic acid. Consequently, comparable results can often be obtained with shorter antisense compounds that have such chemically modified nucleosides.

Modified Internucleoside Linkages

The naturally occurring internucleoside linkage of RNA and DNA is a 3' to 5' phosphodiester linkage. Antisense compounds having one or more modified, i.e. non-naturally occurring, internucleoside linkages are often selected over antisense compounds having naturally occurring internucleoside linkages because of desirable properties such as, for example, enhanced cellular uptake, enhanced affinity for target nucleic acids, and increased stability in the presence of nucleases.

Oligonucleotides having modified internucleoside linkages include internucleoside linkages that retain a phosphorus atom as well as internucleoside linkages that do not have a phosphorus atom. Representative phosphorus containing internucleoside linkages include, but are not limited to, phosphodiesters, phosphotriesters, methylphosphonates, phosphoramidate, and phosphorothioates. Methods of preparation of phosphorous-containing and non-phosphorous-containing linkages are well known.

In certain embodiments, antisense compounds targeted to a GCCR nucleic acid comprise one or more modified internucleoside linkages. In certain embodiments, the modified internucleoside linkages are phosphorothioate linkages. In certain embodiments, each internucleoside linkage of an antisense compound is a phosphorothioate internucleoside linkage.

Modified Sugar Moieties

Antisense compounds provided herein can optionally contain one or more nucleosides wherein the sugar group has been modified. Such sugar modified nucleosides may impart enhanced nuclease stability, increased binding affinity, or some other beneficial biological property to the antisense compounds. In certain embodiments, nucleosides comprise a chemically modified ribofuranose ring moiety. Examples of chemically modified ribofuranose rings include, without limitation, addition of substituent groups (including 5' and 2' substituent groups); bridging of non-geminal ring atoms to form bicyclic nucleic acids (BNA); replacement of the ribosyl ring oxygen atom with S, N(R), or C(R1)(R)2 (R═H, $C_1$-$C_{12}$ alkyl or a protecting group); and combinations thereof. Examples of chemically modified sugars include, 2'-F-5'-methyl substituted nucleoside (see, PCT International Application WO 2008/101157, published on Aug. 21, 2008 for other disclosed 5',2'-bis substituted nucleosides), replacement of the ribosyl ring oxygen atom with S with further substitution at the 2'-position (see, published U.S. Patent Application US2005/0130923, published on Jun. 16, 2005), or, alternatively, 5'-substitution of a BNA (see, PCT International Application WO 2007/134181, published on Nov. 22, 2007, wherein LNA is substituted with, for example, a 5'-methyl or a 5'-vinyl group).

Examples of nucleosides having modified sugar moieties include, without limitation, nucleosides comprising 5'-vinyl, 5'-methyl (R or S), 4'-S, 2'-F, 2'-$OCH_3$, and 2'-$O(CH_2)2OCH_3$ substituent groups. The substituent at the 2' position can also be selected from allyl, amino, azido, thio, O-allyl, O—$C_1$-$C_{10}$ alkyl, $OCF_3$, $O(CH_2)2SCH_3$, $O(CH_2)2$-O—N(Rm)(Rn), and O—$CH_2$—C(═O)—N(Rm)(Rn), where each Rm and Rn is, independently, H or substituted or unsubstituted $C_1$-$C_{10}$ alkyl.

As used herein, "bicyclic nucleosides" refer to modified nucleosides comprising a bicyclic sugar moiety. Examples of bicyclic nucleosides include, without limitation, nucleosides comprising a bridge between the 4' and the 2' ribosyl ring atoms. In certain embodiments, antisense compounds provided herein include one or more bicyclic nucleosides wherein the bridge comprises a 4' to 2' bicyclic nucleoside. Examples of such 4' to 2' bicyclic nucleosides, include, but are not limited to, one of the formulae: 4'-($CH_2$)—O-2' (LNA); 4'-($CH_2$)—S-2; 4'-$(CH_2)_2$—O-2' (ENA); 4'-CH($CH_3$)—O-2' and 4'-CH($CH_2OCH_3$)—O-2', and analogs thereof (see, U.S. Pat. No. 7,399,845, issued on Jul. 15, 2008); 4'-C($CH_3$)($CH_3$)—O-2', and analogs thereof (see, published PCT International Application WO2009/006478, published Jan. 8, 2009); 4'-$CH_2$—N($OCH_3$)-2', and analogs thereof (see, published PCT International Application WO2008/150729, published Dec. 11, 2008); 4'-$CH_2$—O—N($CH_3$)-2' (see, published U.S. Patent Application US2004/0171570, published Sep. 2, 2004); 4'-$CH_2$—N(R)—O-2', wherein R is H, $C_1$-$C_{12}$ alkyl, or a protecting group (see, U.S. Pat. No. 7,427,672, issued on Sep. 23, 2008); 4'-$CH_2$—C(H)($CH_3$)-2' (see, Chattopadhyaya, et al., *J. Org. Chem.,* 2009, 74, 118-134); and 4'-$CH_2$—C(═$CH_2$)-2', and analogs thereof (see, published PCT International Application WO 2008/154401, published on Dec. 8, 2008). Also see, for example: Singh et al., *Chem. Commun.,* 1998, 4, 455-456; Koshkin et al., *Tetrahedron,* 1998, 54, 3607-3630; Wahlestedt et al., *Proc. Natl. Acad. Sci. U.S.A.,* 2000, 97, 5633-5638; Kumar et al., *Bioorg. Med. Chem. Lett.,* 1998, 8, 2219-2222; Singh et al., *J. Org. Chem.,* 1998, 63, 10035-10039; Srivastava et al., *J. Am. Chem. Soc.,* 129 (26) 8362-8379 (Jul. 4, 2007); Elayadi et al., *Curr. Opinion Invens. Drugs,* 2001, 2, 558-561; Braasch et al., *Chem. Biol.,* 2001, 8, 1-7; Orum et al., *Curr. Opinion Mol. Ther.,* 2001, 3, 239-243; U.S. Pat. Nos. 6,670,461, 7,053,207, 6,268,490, 6,770,748, 6,794,499, 7,034,133, 6,525,191, 7,399,845; published PCT International applications WO 2004/106356, WO 94/14226, WO 2005/021570, and WO 2007/134181; U.S. Patent Publication Nos. US2004/0171570, US2007/0287831, and US2008/0039618; and U.S. patent Ser. Nos. 12/129,154, 60/989,574, 61/026,995, 61/026,998, 61/056,564, 61/086,231, 61/097,787, and 61/099,844; and PCT International Application Nos. PCT/US2008/064591, PCT/US2008/066154, and PCT/US2008/068922. Each of the foregoing bicyclic nucleosides can be prepared having one or more stereochemical sugar configurations including for example α-L-ribofuranose and β-D-ribofuranose (see PCT international application PCT/DK98/00393, published on Mar. 25, 1999 as WO 99/14226).

In certain embodiments, bicyclic sugar moieties of BNA nucleosides include, but are not limited to, compounds having at least one bridge between the 4' and the 2' position of the pentofuranosyl sugar moiety wherein such bridges independently comprises 1 or from 2 to 4 linked groups independently selected from —$[C(R_a)(R_b)]_n$—, —$C(R_a)$═$C(R_b)$—, —$C(R_a)$═N—, —C(═$NR_a$)—, —C(═O)—, —C(═S)—, —O—, —$Si(R_a)_2$—, —$S(═O)_x$—, and —$N(R_a)$—;

wherein:

x is 0, 1, or 2;

n is 1, 2, 3, or 4;

each $R_a$ and $R_b$ is, independently, H, a protecting group, hydroxyl, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_5$-$C_{20}$ aryl, substituted $C_5$-$C_{20}$ aryl, heterocycle radical, substituted heterocycle radical, heteroaryl, substituted heteroaryl, $C_5$-$C_7$ alicyclic radical, substituted $C_5$-$C_7$ alicyclic radical, halogen, $OJ_1$, $NJ_1J_2$, $SJ_1$, $N_3$, $COOJ_1$, acyl (C(═O)—H), substituted acyl, CN, sulfonyl ($S(═O)_2$-$J_1$), or sulfoxyl (S(═O)-$J_1$); and each $J_1$ and $J_2$ is, independently, H, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_5$-$C_{20}$ aryl, substituted $C_5$-$C_{20}$ aryl, acyl (C(═O)—H), substituted acyl, a heterocycle radical, a substituted heterocycle radical, $C_1$-$C_{12}$ aminoalkyl, substituted $C_1$-$C_{12}$ aminoalkyl, or a protecting group.

In certain embodiments, the bridge of a bicyclic sugar moiety is, —$[C(R_a)(R_b)]_n$—, —$[C(R_a)(R_b)]_n$—O—, —$C(R_aR_b)$—N(R)—O— or, —$C(R_aR_b)$—O—N(R)—. In certain embodiments, the bridge is 4'-$CH_2$-2', 4'-$(CH_2)_2$-2', 4'-$(CH_2)_3$-2', 4'-$CH_2$—O-2', 4'-$(CH_2)_2$—O-2', 4'-$CH_2$—O—N(R)-2', and 4'-$CH_2$—N(R)—O-2'-, wherein each R is, independently, H, a protecting group, or $C_1$-$C_{12}$ alkyl.

In certain embodiments, bicyclic nucleosides are further defined by isomeric configuration. For example, a nucleoside comprising a 4'-2' methylene-oxy bridge, may be in the α-L configuration or in the β-D configuration. Previously, α-L-methyleneoxy (4'-$CH_2$—O-2') BNA's have been incorporated into antisense oligonucleotides that showed antisense activity (Frieden et al., *Nucleic Acids Research,* 2003, 21, 6365-6372).

In certain embodiments, bicyclic nucleosides include, but are not limited to, (A) α-L-Methyleneoxy (4'-$CH_2$—O-2') BNA, (B) β-D-Methyleneoxy (4'-$CH_2$—O-2') BNA, (C) Ethyleneoxy (4'-$(CH_2)_2$—O-2') BNA, (D) Aminooxy (4'-$CH_2$—O—N(R)-2') BNA, (E) Oxyamino (4'-$CH_2$—N(R)—O-2') BNA, (F) Methyl(methyleneoxy) (4'-CH($CH_3$)—O-2') BNA, (G) methylene-thio (4'-$CH_2$—S-2') BNA, (H) methylene-amino (4'-CH2-N(R)-2') BNA, (I) methyl carbocyclic (4'-$CH_2$—CH($CH_3$)-2') BNA, and (J) propylene carbocyclic (4'-$(CH_2)_3$-2') BNA as depicted below.

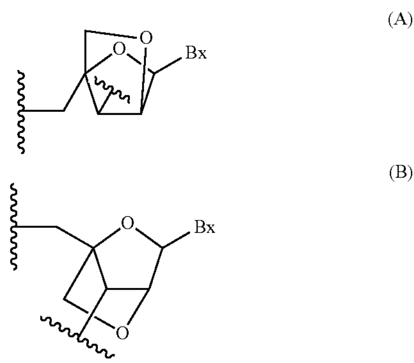

-continued (C)

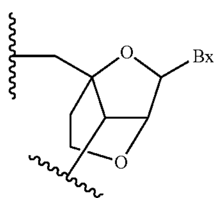

(D)

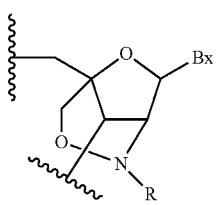

(E)

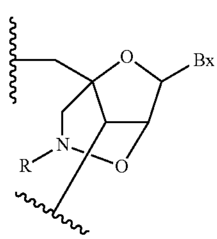

(F)

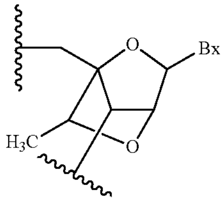

(G)

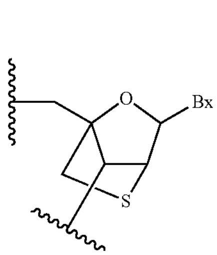

(H)

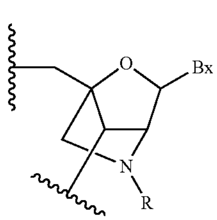

(I)

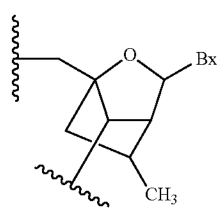

-continued (J)

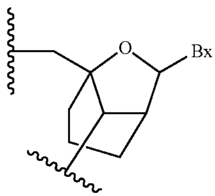

wherein Bx is the base moiety and R is, independently, H, a protecting group or $C_1$-$C_{12}$ alkyl.

In certain embodiments, bicyclic nucleoside having Formula I:

I

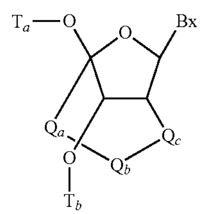

wherein:

Bx is a heterocyclic base moiety;

-$Q_a$-$Q_b$-$Q_c$- is —$CH_2$—N($R_c$)—$CH_2$—, —C(=O)—N($R_c$)—$CH_2$—, —$CH_2$—O—N($R_c$)—, —$CH_2$—N($R_c$)—O—, or —N($R_c$)—O—$CH_2$;

$R_c$ is $C_1$-$C_{12}$ alkyl or an amino protecting group; and $T_a$ and $T_b$ are each, independently, H, a hydroxyl protecting group, a conjugate group, a reactive phosphorus group, a phosphorus moiety, or a covalent attachment to a support medium.

In certain embodiments, bicyclic nucleoside having Formula II:

II

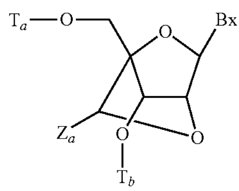

wherein:

Bx is a heterocyclic base moiety;

$T_a$ and $T_b$ are each, independently, H, a hydroxyl protecting group, a conjugate group, a reactive phosphorus group, a phosphorus moiety, or a covalent attachment to a support medium;

$Z_a$ is $C_1$-$C_6$ alkyl, $C_2$-$C_6$ alkenyl, $C_2$-$C_6$ alkynyl, substituted $C_1$-$C_6$ alkyl, substituted $C_2$-$C_6$ alkenyl, substituted $C_2$-$C_6$ alkynyl, acyl, substituted acyl, substituted amide, thiol, or substituted thio.

In one embodiment, each of the substituted groups is, independently, mono or poly substituted with substituent groups independently selected from halogen, oxo, hydroxyl, $OJ_c$, $NJ_cJ_d$, $SJ_c$, $N_3$, $OC(=X)J_c$, and $NJ_eC(=X)NJ_cJ_d$, wherein each $J_c$, $J_d$, and $J_e$ is, independently, H, $C_1$-$C_6$ alkyl, or substituted $C_1$-$C_6$ alkyl and X is O or $NJ_c$.

In certain embodiments, bicyclic nucleoside having Formula III:

III

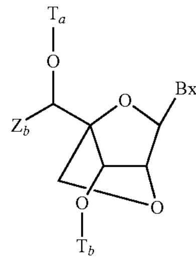

wherein:

Bx is a heterocyclic base moiety;

$T_a$ and $T_b$ are each, independently, H, a hydroxyl protecting group, a conjugate group, a reactive phosphorus group, a phosphorus moiety, or a covalent attachment to a support medium;

$Z_b$ is $C_1$-$C_6$ alkyl, $C_2$-$C_6$ alkenyl, $C_2$-$C_6$ alkynyl, substituted $C_1$-$C_6$ alkyl, substituted $C_2$-$C_6$ alkenyl, substituted $C_2$-$C_6$ alkynyl, or substituted acyl (C(═O)—).

In certain embodiments, bicyclic nucleoside having Formula IV:

IV

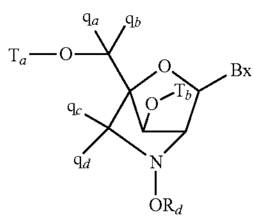

wherein:

Bx is a heterocyclic base moiety;

$T_a$ and $T_b$ are each, independently H, a hydroxyl protecting group, a conjugate group, a reactive phosphorus group, a phosphorus moiety, or a covalent attachment to a support medium;

$R_d$ is $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, or substituted $C_2$-$C_6$ alkynyl;

each $q_a$, $q_b$, $q_c$ and $q_d$ is, independently, H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, or substituted $C_2$-$C_6$ alkynyl, $C_1$-$C_6$ alkoxyl, substituted $C_2$-$C_6$ alkoxyl, acyl, substituted acyl, $C_1$-$C_6$ aminoalkyl, or substituted $C_1$-$C_6$ aminoalkyl;

In certain embodiments, bicyclic nucleoside having Formula V:

V

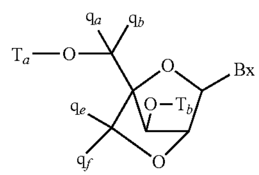

wherein:

Bx is a heterocyclic base moiety;

$T_a$ and $T_b$ are each, independently, H, a hydroxyl protecting group, a conjugate group, a reactive phosphorus group, a phosphorus moiety, or a covalent attachment to a support medium;

$q_a$, $q_b$, $q_e$ and $q_f$ are each, independently, hydrogen, halogen, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_1$-$C_{12}$ alkoxy, substituted $C_1$-$C_{12}$ alkoxy, $OJ_j$, $SJ_j$, $SOJ_j$, $SO_2J_j$, $NJ_jJ_k$, $N_3$, CN, C(═O)$OJ_j$, C(═O)$NJ_jJ_k$, C(═O)$J_j$, —O—C(═O)$NJ_jJ_k$, N(H)C(═NH)$NJ_jJ_k$, N(H)C(═O)$NJ_jJ_k$ or N(H)C(═S)$NJ_jJ_k$;

or $q_e$ and $q_f$ together are ═C($q_g$)($q_h$);

$q_g$ and $q_h$ are each, independently, H, halogen, $C_1$-$C_{12}$ alkyl, or substituted $C_1$-$C_{12}$ alkyl.

The synthesis and preparation of the methyleneoxy (4'-$CH_2$—O-2') BNA monomers adenine, cytosine, guanine, 5-methyl-cytosine, thymine, and uracil, along with their oligomerization, and nucleic acid recognition properties have been described (see, e.g., Koshkin et al., *Tetrahedron,* 1998, 54, 3607-3630). BNAs and preparation thereof are also described in WO 98/39352 and WO 99/14226.

Analogs of methyleneoxy (4'-$CH_2$—O-2') BNA, methyleneoxy (4'-$CH_2$—O-2') BNA, and 2'-thio-BNAs, have also been prepared (see, e.g., Kumar et al., *Bioorg. Med. Chem. Lett.,* 1998, 8, 2219-2222). Preparation of locked nucleoside analogs comprising oligodeoxyribonucleotide duplexes as substrates for nucleic acid polymerases has also been described (see, e.g., Wengel et al., WO 99/14226). Furthermore, synthesis of 2'-amino-BNA, a novel comformationally restricted high-affinity oligonucleotide analog, has been described in the art (see, e.g., Singh et al., *J. Org. Chem.,* 1998, 63, 10035-10039). In addition, 2'-amino- and 2'-methylamino-BNA's have been prepared and the thermal stability of their duplexes with complementary RNA and DNA strands has been previously reported.

In certain embodiments, bicyclic nucleoside having Formula VI:

VI

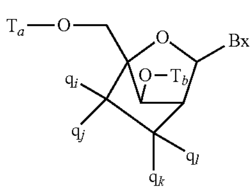

wherein:

Bx is a heterocyclic base moiety;

$T_a$ and $T_b$ are each, independently, H, a hydroxyl protecting group, a conjugate group, a reactive phosphorus group, a phosphorus moiety, or a covalent attachment to a support medium;

each $q_i$, $q_k$, $q_k$ and $q_l$ is, independently, H, halogen, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_1$-$C_{12}$ alkoxyl, substituted $C_1$-$C_{12}$ alkoxyl, $OJ_j$, $SJ_j$, $SOJ_j$, $SO_2J_j$, $NJ_jJ_k$, $N_3$, CN, C(═O)$OJ_j$, C(═O)$J_j$, O—C(═O)$NJ_jJ_k$, N(H)C(═NH)$NJ_jJ_k$, N(H)C(═O)$NJ_jJ_k$, or N(H)C(═S)$NJ_jJ_k$; and $q_i$ and $q_j$ or $q_l$ and $q_k$ together are ═C($q_g$)($q_h$), wherein $q_g$ and $q_h$ are each, independently, H, halogen, $C_1$-$C_{12}$ alkyl, or substituted $C_1$-$C_{12}$ alkyl.

One carbocyclic bicyclic nucleoside having a 4'-$(CH_2)_3$-2' bridge and the alkenyl analog, bridge 4'-CH═CH—$CH_2$-2', have been described (see, e.g., Freier et al., *Nucleic Acids Research,* 1997, 25(22), 4429-4443 and Albaek et al., *J. Org. Chem.,* 2006, 71, 7731-7740). The synthesis and preparation of carbocyclic bicyclic nucleosides along with their oligomerization and biochemical studies have also been described (see, e.g., Srivastava et al., *J. Am. Chem. Soc.* 2007, 129(26), 8362-8379).

As used herein, "4'-2' bicyclic nucleoside" or "4' to 2' bicyclic nucleoside" refers to a bicyclic nucleoside comprising a furanose ring comprising a bridge connecting the 2' carbon atom and the 4' carbon atom.

As used herein, "monocylic nucleosides" refer to nucleosides comprising modified sugar moieties that are not bicyclic sugar moieties. In certain embodiments, the sugar moiety, or sugar moiety analogue, of a nucleoside may be modified or substituted at any position.

As used herein, "2'-modified sugar" means a furanosyl sugar modified at the 2' position. In certain embodiments, such modifications include substituents selected from: a halide, including, but not limited to substituted and unsubstituted alkoxy, substituted and unsubstituted thioalkyl, substituted and unsubstituted amino alkyl, substituted and unsubstituted alkyl, substituted and unsubstituted allyl, and substituted and unsubstituted alkynyl. In certain embodiments, 2' modifications are selected from substituents including, but not limited to: $O[(CH_2)_nO]_mCH_3$, $O(CH_2)NH_2$, $O(CH_2)_nCH_3$, $O(CH_2)_nONH_2$, $OCH_2C(=O)N(H)CH_3$, and $O(CH_2)_nON[(CH_2)_nCH_3]_2$, where n and m are from 1 to about 10. Other 2'-substituent groups can also be selected from: $C_1$-$C_{12}$ alkyl; substituted alkyl; alkenyl; alkynyl; alkaryl; aralkyl; O-alkaryl or O-aralkyl; SH; $SCH_3$; OCN; Cl; Br; CN; $CF_3$; $OCF_3$; $SOCH_3$; $SO_2CH_3$; $ONO_2$; $NO_2$; $N_3$; $NH_2$; heterocycloalkyl; heterocycloalkaryl; aminoalkylamino; polyalkylamino; substituted silyl; an RNA cleaving group; a reporter group; an intercalator; a group for improving pharmacokinetic properties; and a group for improving the pharmacodynamic properties of an antisense compound, and other substituents having similar properties. In certain embodiments, modified nucleosides comprise a 2'-MOE side chain (see, e.g., Baker et al., J. Biol. Chem., 1997, 272, 11944-12000). Such 2'-MOE substitution have been described as having improved binding affinity compared to unmodified nucleosides and to other modified nucleosides, such as 2'-O-methyl, O-propyl, and O-aminopropyl. Oligonucleotides having the 2'-MOE substituent also have been shown to be antisense inhibitors of gene expression with promising features for in vivo use (see, e.g., Martin, P., *Helv. Chim. Acta,* 1995, 78, 486-504; Altmann et al., *Chimia,* 1996, 50, 168-176; Altmann et al., *Biochem. Soc. Trans.,* 1996, 24, 630-637; and Altmann et al., *Nucleosides Nucleotides,* 1997, 16, 917-926).

As used herein, a "modified tetrahydropyran nucleoside" or "modified THP nucleoside" means a nucleoside having a six-membered tetrahydropyran "sugar" substituted in for the pentofuranosyl residue in normal nucleosides (a sugar surrogate). Modified THP nucleosides include, but are not limited to, what is referred to in the art as hexitol nucleic acid (HNA), anitol nucleic acid (ANA), manitol nucleic acid (MNA) (see Leumann, C J. *Bioorg. & Med. Chem.* (2002) 10:841-854), fluoro HNA (F-HNA), or those compounds having Formula X:

Formula X

X

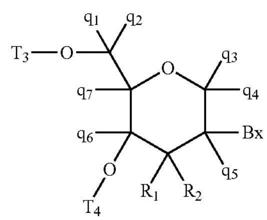

wherein independently for each of said at least one tetrahydropyran nucleoside analog of Formula X:

Bx is a heterocyclic base moiety;

$T_3$ and $T_4$ are each, independently, an internucleoside linking group linking the tetrahydropyran nucleoside analog to the antisense compound or one of $T_3$ and $T_4$ is an internucleoside linking group linking the tetrahydropyran nucleoside analog to the antisense compound and the other of $T_3$ and $T_4$ is H, a hydroxyl protecting group, a linked conjugate group, or a 5' or 3'-terminal group;

$q_1$, $q_2$, $q_3$, $q_4$, $q_5$, $q_6$ and $q_7$ are each, independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, or substituted $C_2$-$C_6$ alkynyl; and one of $R_1$ and $R_2$ is hydrogen and the other is selected from halogen, substituted or unsubstituted alkoxy, $NJ_1J_2$, $SJ_1$, $N_3$, $OC(=X)J_1$, $OC(=X)NJ_1J_2$, $NJ_3C(=X)NJ_1J_2$, and CN, wherein X is O, S, or $NJ_1$, and each $J_1$, $J_2$, and $J_3$ is, independently, H or $C_1$-$C_6$ alkyl.

In certain embodiments, the modified THP nucleosides of Formula X are provided wherein $q_m$, $q_n$, $q_p$, $q_r$, $q_s$, $q_t$, and $q_u$ are each H. In certain embodiments, at least one of $q_m$, $q_n$, $q_p$, $q_r$, $q_s$, $q_t$, and $q_u$ is other than H. In certain embodiments, at least one of $q_m$, $q_n$, $q_p$, $q_r$, $q_s$, $q_t$ is methyl. In certain embodiments, THP nucleosides of Formula X are provided wherein one of $R_1$ and $R_2$ is F. In certain embodiments, $R_1$ is fluoro and $R_2$ is H, $R_1$ is methoxy and $R_2$ is H, and $R_1$ is methoxyethoxy and $R_2$ is H.

As used herein, "2'-modified" or "2'-substituted" refers to a nucleoside comprising a sugar comprising a substituent at the 2' position other than H or OH. 2'-modified nucleosides, include, but are not limited to, bicyclic nucleosides wherein the bridge connecting two carbon atoms of the sugar ring connects the 2' carbon and another carbon of the sugar ring and nucleosides with non-bridging 2' substituents, such as allyl, amino, azido, thio, O-allyl, O—$C_1$-$C_{10}$ alkyl, —$OCF_3$, O—$(CH_2)_2$—O—$CH_3$, 2'-$O(CH_2)_2SCH_3$, O—$(CH_2)_2$—O—$N(R_m)(R_n)$, or O—$CH_2$—C(=P)—$N(R_m)(R_n)$, where each $R_m$ and $R_n$ is, independently, H or substituted or unsubstituted $C_1$-$C_{10}$ alkyl. 2'-modified nucleosides may further comprise other modifications, for example, at other positions of the sugar and/or at the nucleobase.

As used herein, "2'-F" refers to a sugar comprising a fluoro group at the 2' position.

As used herein, "2'-OMe" or "2'-$OCH_3$" or "2'-O-methyl" each refers to a sugar comprising an —$OCH_3$ group at the 2' position of the sugar ring.

As used herein, "oligonucleotide" refers to a compound comprising a plurality of linked nucleosides. In certain embodiments, one or more of the plurality of nucleosides is modified. In certain embodiments, an oligonucleotide comprises one or more ribonucleosides (RNA) and/or deoxyribonucleosides (DNA).

Many other bicyclo and tricyclo sugar surrogate ring systems are also known in the art that can be used to modify nucleosides for incorporation into antisense compounds (see, e.g., review article: Leumann, J. C., *Bioorganic & Medicinal Chemistry,* 2002, 10, 841-854). Such ring systems can undergo various additional substitutions to enhance activity.

Methods for the preparations of modified sugars are well known to those skilled in the art.

In nucleotides having modified sugar moieties, the nucleobase moieties (natural, modified, or a combination thereof) are maintained for hybridization with an appropriate nucleic acid target.

In certain embodiments, antisense compounds comprise one or more nucleotides having modified sugar moieties. In certain embodiments, the modified sugar moiety is 2'-MOE. In certain embodiments, the 2'-MOE modified nucleotides are arranged in a gapmer motif. In certain embodiments, the modified sugar moiety is a cEt. In certain embodiments, the cEt modified nucleotides are arranged throughout the wings of a gapmer motif.

Modified Nucleobases

Nucleobase (or base) modifications or substitutions are structurally distinguishable from, yet functionally interchangeable with, naturally occurring or synthetic unmodified nucleobases. Both natural and modified nucleobases are capable of participating in hydrogen bonding. Such nucleobase modifications may impart nuclease stability, binding affinity or some other beneficial biological property to antisense compounds. Modified nucleobases include synthetic and natural nucleobases such as, for example, 5-methylcytosine (5-me-C). Certain nucleobase substitutions, including 5-methylcytosine substitutions, are particularly useful for increasing the binding affinity of an antisense compound for a target nucleic acid. For example, 5-methylcytosine substitutions have been shown to increase nucleic acid duplex stability by 0.6-1.2° C. (Sanghvi, Y. S., Crooke, S. T. and Lebleu, B., eds., *Antisense Research and Applications*, CRC Press, Boca Raton, 1993, pp. 276-278).

Additional unmodified nucleobases include 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl ($-C{\equiv}C-CH_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine.

Heterocyclic base moieties may also include those in which the purine or pyrimidine base is replaced with other heterocycles, for example 7-deaza-adenine, 7-deazaguanosine, 2-aminopyridine and 2-pyridone. Nucleobases that are particularly useful for increasing the binding affinity of antisense compounds include 5-substituted pyrimidines, 6-azapyrimidines and N-2, N-6 and O-6 substituted purines, including 2 aminopropyladenine, 5-propynyluracil and 5-propynylcytosine.

In certain embodiments, antisense compounds targeted to a GCCR nucleic acid comprise one or more modified nucleobases. In certain embodiments, gap-widened antisense oligonucleotides targeted to a GCCR nucleic acid comprise one or more modified nucleobases. In certain embodiments, the modified nucleobase is 5-methylcytosine. In certain embodiments, each cytosine is a 5-methylcytosine.

Compositions and Methods for Formulating Pharmaceutical Compositions

Antisense oligonucleotides may be admixed with pharmaceutically acceptable active or inert substance for the preparation of pharmaceutical compositions or formulations. Compositions and methods for the formulation of pharmaceutical compositions are dependent upon a number of criteria, including, but not limited to, route of administration, extent of disease, or dose to be administered.

Antisense compound targeted to a GCCR nucleic acid can be utilized in pharmaceutical compositions by combining the antisense compound with a suitable pharmaceutically acceptable diluent or carrier. A pharmaceutically acceptable diluent includes phosphate-buffered saline (PBS). PBS is a diluent suitable for use in compositions to be delivered parenterally. Accordingly, in one embodiment employed in the methods described herein, is a pharmaceutical composition comprising an antisense compound targeted to a GCCR nucleic acid and a pharmaceutically acceptable diluent. In certain embodiments, the pharmaceutically acceptable diluent is PBS. In certain embodiments, the antisense compound is an antisense oligonucleotide.

Pharmaceutical compositions comprising antisense compounds encompass any pharmaceutically acceptable salts, esters, or salts of such esters, or any other oligonucleotide which, upon administration to an animal, including a human, is capable of providing (directly or indirectly) the biologically active metabolite or residue thereof. Accordingly, for example, the disclosure is also drawn to pharmaceutically acceptable salts of antisense compounds, prodrugs, pharmaceutically acceptable salts of such prodrugs, and other bioequivalents. Suitable pharmaceutically acceptable salts include, but are not limited to, sodium and potassium salts.

Pharmaceutically acceptable salts of the compounds described herein may be prepared by methods well-known in the art. For a review of pharmaceutically acceptable salts, see Stahl and Wermuth, Handbook of Pharmaceutical Salts: Properties, Selection and Use (Wiley-VCH, Weinheim, Germany, 2002). Sodium salts of antisense oligonucleotides are useful and are well accepted for therapeutic administration to humans. Accordingly, in one embodiment the compounds described herein are in the form of a sodium salt.

A prodrug can include the incorporation of additional nucleosides at one or both ends of an antisense compound which are cleaved by endogenous nucleases within the body, to form the active antisense compound.

Conjugated Antisense Compounds

Antisense compounds may be covalently linked to one or more moieties or conjugates which enhance the activity, cellular distribution or cellular uptake of the resulting antisense oligonucleotides. Typical conjugate groups include cholesterol moieties and lipid moieties. Additional conjugate groups include carbohydrates, phospholipids, biotin, phenazine, folate, phenanthridine, anthraquinone, acridine, fluoresceins, rhodamines, coumarins, and dyes.

Antisense compounds can also be modified to have one or more stabilizing groups that are generally attached to one or both termini of antisense compounds to enhance properties such as, for example, nuclease stability. Included in stabilizing groups are cap structures. These terminal modifications protect the antisense compound having terminal nucleic acid from exonuclease degradation, and can help in delivery and/or localization within a cell. The cap can be present at the 5'-terminus (5'-cap), or at the 3'-terminus (3'-cap), or can be present on both termini. Cap structures are well known in the art and include, for example, inverted deoxy abasic caps. Further 3' and 5'-stabilizing groups that can be used to cap one or both ends of an antisense compound to impart nuclease stability include those disclosed in WO 03/004602 published on Jan. 16, 2003.

Cell Culture and Antisense Compound Treatment

The effects of antisense compounds on the level, activity or expression of GCCR nucleic acids can be tested in vitro in a variety of cell types. Cell types used for such analyses are available from commercial vendors (e.g. American Type Culture Collection, Manassus, Va.; Zen-Bio, Inc., Research Triangle Park, N.C.; Clonetics Corporation, Walkersville, Md.) and cells are cultured according to the vendor's instructions using commercially available reagents (e.g. Invitrogen Life Technologies, Carlsbad, Calif.). Illustrative cell types include, but are not limited to, HepG2 cells and primary hepatocytes.

In Vitro Testing of Antisense Oligonucleotides

Described herein are methods for treatment of cells with antisense oligonucleotides, which can be modified appropriately for treatment with other antisense compounds.

In general, cells are treated with antisense oligonucleotides when the cells reach approximately 60-80% confluence in culture.

One reagent commonly used to introduce antisense oligonucleotides into cultured cells includes the cationic lipid transfection reagent LIPOFECTIN® (Invitrogen, Carlsbad, Calif.). Antisense oligonucleotides are mixed with LIPOFECTIN® in OPTI-MEM® 1 (Invitrogen, Carlsbad, Calif.) to achieve the desired final concentration of antisense oligonucleotide and a LIPOFECTIN® concentration that typically ranges 2 to 12 ug/mL per 100 nM antisense oligonucleotide.

Another reagent used to introduce antisense oligonucleotides into cultured cells includes LIPOFECTAMINE 2000® (Invitrogen, Carlsbad, Calif.). Antisense oligonucleotide is mixed with LIPOFECTAMINE 2000® in OPTI-MEM® 1 reduced serum medium (Invitrogen, Carlsbad, Calif.) to achieve the desired concentration of antisense oligonucleotide and a LIPOFECTAMINE® concentration that typically ranges 2 to 12 ug/mL per 100 nM antisense oligonucleotide.

Another reagent used to introduce antisense oligonucleotides into cultured cells includes Cytofectin® (Invitrogen, Carlsbad, Calif.). Antisense oligonucleotide is mixed with Cytofectin® in OPTI-MEM® 1 reduced serum medium (Invitrogen, Carlsbad, Calif.) to achieve the desired concentration of antisense oligonucleotide and a Cytofectin® concentration that typically ranges 2 to 12 ug/mL per 100 nM antisense oligonucleotide.

Another technique used to introduce antisense oligonucleotides into cultured cells includes electroporation.

Cells are treated with antisense oligonucleotides by routine methods. Cells are typically harvested 16-24 hours after antisense oligonucleotide treatment, at which time RNA or protein levels of target nucleic acids are measured by methods known in the art and described herein. In general, when treatments are performed in multiple replicates, the data are presented as the average of the replicate treatments.

The concentration of antisense oligonucleotide used varies from cell line to cell line. Methods to determine the optimal antisense oligonucleotide concentration for a particular cell line are well known in the art. Antisense oligonucleotides are typically used at concentrations ranging from 1 nM to 300 nM when transfected with LIPOFECTAMINE2000®, Lipofectin or Cytofectin. Antisense oligonucleotides are used at higher concentrations ranging from 625 to 20,000 nM when transfected using electroporation.

RNA Isolation

RNA analysis can be performed on total cellular RNA or poly(A)+ mRNA. Methods of RNA isolation are well known in the art. RNA is prepared using methods well known in the art, for example, using the TRIZOL® Reagent (Invitrogen, Carlsbad, Calif.) according to the manufacturer's recommended protocols.

Analysis of Inhibition of Target Levels or Expression

Inhibition of levels or expression of a GCCR nucleic acid can be assayed in a variety of ways known in the art. For example, target nucleic acid levels can be quantitated by, e.g., Northern blot analysis, competitive polymerase chain reaction (PCR), or quantitative real-time PCR. RNA analysis can be performed on total cellular RNA or poly(A)+ mRNA. Methods of RNA isolation are well known in the art. Northern blot analysis is also routine in the art. Quantitative real-time PCR can be conveniently accomplished using the commercially available ABI PRISM® 7600, 7700, or 7900 Sequence Detection System, available from PE-Applied Biosystems, Foster City, Calif. and used according to manufacturer's instructions.

Quantitative Real-Time PCR Analysis of Target RNA Levels

Quantitation of target RNA levels may be accomplished by quantitative real-time PCR using the ABI PRISM® 7600, 7700, or 7900 Sequence Detection System (PE-Applied Biosystems, Foster City, Calif.) according to manufacturer's instructions. Methods of quantitative real-time PCR are well known in the art.

Prior to real-time PCR, the isolated RNA is subjected to a reverse transcriptase (RT) reaction, which produces complementary DNA (cDNA) that is then used as the substrate for the real-time PCR amplification. The RT and real-time PCR reactions are performed sequentially in the same sample well. RT and real-time PCR reagents are obtained from Invitrogen (Carlsbad, Calif.). RT, real-time-PCR reactions are carried out by methods well known to those skilled in the art.

Gene (or RNA) target quantities obtained by real time PCR are normalized using either the expression level of a gene whose expression is constant, such as cyclophilin A, or by quantifying total RNA using RIBOGREEN® (Invitrogen, Inc. Carlsbad, Calif.). Cyclophilin A expression is quantified by real time PCR, by being run simultaneously with the target, multiplexing, or separately. Total RNA is quantified using RIBOGREEN® RNA quantification reagent (Invitrogen, Inc. Eugene, Oreg.). Methods of RNA quantification by RIBOGREEN® are taught in Jones, L. J., et al, (Analytical Biochemistry, 1998, 265, 368-374). A CYTOFLUOR® 4000 instrument (PE Applied Biosystems) is used to measure RIBOGREEN® fluorescence.

Probes and primers are designed to hybridize to a GCCR nucleic acid. Methods for designing real-time PCR probes and primers are well known in the art, and may include the use of software such as PRIMER EXPRESS® Software (Applied Biosystems, Foster City, Calif.).

Analysis of Protein Levels

Antisense inhibition of GCCR nucleic acids can be assessed by measuring GCCR protein levels. Protein levels of GCCR can be evaluated or quantitated in a variety of ways well known in the art, such as immunoprecipitation, Western blot analysis (immunoblotting), enzyme-linked immunosorbent assay (ELISA), quantitative protein assays, protein activity assays (for example, caspase activity assays), immunohistochemistry, immunocytochemistry or fluorescence-activated cell sorting (FACS). Antibodies directed to a target can be identified and obtained from a variety of sources, such as the MSRS catalog of antibodies (Aerie Corporation, Birmingham, Mich.), or can be prepared via conventional monoclonal or polyclonal antibody generation methods well known in the art. Antibodies useful for the detection of human and rat GCCR are commercially available.

In Vivo Testing of Antisense Compounds

Antisense compounds, for example, antisense oligonucleotides, are tested in animals to assess their ability to inhibit expression of GCCR and produce phenotypic changes. Testing may be performed in normal animals, or in experimental disease models. For administration to animals, antisense oligonucleotides are formulated in a pharmaceutically acceptable diluent, such as phosphate-buffered saline. Administration includes parenteral routes of administration. Following a period of treatment with antisense oligonucleotides, RNA is isolated from tissue and changes in GCCR nucleic acid expression are measured. Changes in GCCR protein levels are also measured.

Certain Indications

In certain embodiments, provided herein are methods of treating an individual comprising administering one or more pharmaceutical compositions as described herein. In certain embodiments, the individual has metabolic related disease.

As shown in the examples below, compounds targeted to GCCR, as described herein, have been shown to reduce the severity of physiological symptoms of metabolic related diseases, including metabolic syndrome, diabetes mellitus, insulin resistance, diabetic dyslipidemia, hypertriglyceridemia, obesity and weight gain e.g., the animals continued to experience symptoms, but the symptoms were less severe compared to untreated animals. In certain experiments, the compounds reduced blood glucose levels. In other experiments, the compounds reduce the symptoms of diabetes. In other experiments, the compounds inhibit weight gain. In other experiments, the compounds inhibit hypertriglyceridemia. In certain embodiments, the compounds restore function therefore demonstrating reversal of disease by treatment with a compound as described herein. In certain embodiments, animals treated for a longer period of time experience less severe symptoms than those administered the compounds for a shorter period of time.

Diabetes mellitus is characterized by numerous physical and physiological signs and/or symptoms. Any symptom known to one of skill in the art to be associated with Type 2 diabetes can be ameliorated or otherwise modulated as set forth above in the methods described above. In certain embodiments, the sign or symptom is a physical symptom such as increased glucose levels, increased weight gain, frequent urination, unusual thirst, extreme hunger, extreme fatigue, blurred vision, frequent infections, tingling or numbness at the extremities, dry and itchy skin, weight loss, slow-healing sores, and swollen gums. In certain embodiments, the sign or symptom is a physiological symptom such as increased insulin resistance, increased glucose levels, increased fat mass, decreased metabolic rate, decreased glucose clearance, decreased glucose tolerance, decreased insulin sensitivity, decreased hepatic insulin sensitivity, increased adipose tissue size and weight, increased body fat, and increased body weight.

In certain embodiments, the physical sign or symptom is increased glucose levels. In certain embodiments, the sign or symptom is weight gain. In certain embodiments, the sign or symptom is frequent urination. In certain embodiments, the sign or symptom is unusual thirst. In certain embodiments, the sign or symptom is extreme hunger. In certain embodiments, the sign or symptom is extreme fatigue. In certain embodiments, the sign or symptom is blurred vision. In certain embodiments, the sign or symptom is frequent infections. In certain embodiments, the sign or symptom is tingling or numbness at the extremities. In certain embodiments, the sign or symptom is dry and itchy skin. In certain embodiments, the sign or symptom is weight loss. In certain embodiments, the sign or symptom is slow-healing sores. In certain embodiments, the sign or symptom is swollen gums. In certain embodiments, the sign or symptom is increased insulin resistance. In certain embodiments, the sign or symptom is increased glucose levels. In certain embodiments, the sign or symptom is increased fat mass. In certain embodiments, the sign or symptom is decreased metabolic rate. In certain embodiments, the sign or symptom is decreased glucose clearance. In certain embodiments, the sign or symptom is decreased glucose tolerance. In certain embodiments, the sign or symptom is decreased insulin sensitivity. In certain embodiments, the sign or symptom is decreased hepatic insulin sensitivity. In certain embodiments, the sign or symptom is increased adipose tissue size and weight.

In certain embodiments, the sign or symptom is increased body fat. In certain embodiments, the sign or symptom is increased body weight.

In certain embodiments, provided are methods of treating an individual comprising administering one or more pharmaceutical compositions as described herein. In certain embodiments, the individual has metabolic related disease.

In certain embodiments, administration of an antisense compound targeted to a GCCR nucleic acid results in reduction of GCCR expression by at least about 15, 20, 25, 30, 35, 40, 45, 50, 55, 60, 65, 70, 75, 80, 85, 90, 95 or 99%, or a range defined by any two of these values.

In certain embodiments, pharmaceutical compositions comprising an antisense compound targeted to GCCR are used for the preparation of a medicament for treating a patient suffering or susceptible to metabolic related disease.

In certain embodiments, the methods described herein include administering a compound comprising a modified oligonucleotide having a contiguous nucleobases portion as described herein of a sequence recited in SEQ ID NO: 36. In certain embodiments, the compound is ISIS 426115.

Certain Combination Therapies

In certain embodiments, one or more pharmaceutical compositions described herein are co-administered with one or more other pharmaceutical agents. In certain embodiments, such one or more other pharmaceutical agents are designed to treat the same disease, disorder, or condition as the one or more pharmaceutical compositions described herein. In certain embodiments, such one or more other pharmaceutical agents are designed to treat a different disease, disorder, or condition as the one or more pharmaceutical compositions described herein. In certain embodiments, such one or more other pharmaceutical agents are designed to treat an undesired side effect of one or more pharmaceutical compositions as described herein. In certain embodiments, one or more pharmaceutical compositions are co-administered with another pharmaceutical agent to treat an undesired effect of that other pharmaceutical agent. In certain embodiments, one or more pharmaceutical compositions are co-administered with another pharmaceutical agent to produce a combinational effect. In certain embodiments, one or more pharmaceutical compositions are co-administered with another pharmaceutical agent to produce a synergistic effect.

In certain embodiments, a first agent and one or more second agents are administered at the same time. In certain embodiments, the first agent and one or more second agents are administered at different times. In certain embodiments, the first agent and one or more second agents are prepared together in a single pharmaceutical formulation. In certain embodiments, the first agent and one or more second agents are prepared separately.

In certain embodiments, the second compound is administered prior to administration of a pharmaceutical composition described herein. In certain embodiments, the second compound is administered following administration of a pharmaceutical composition described herein. In certain embodiments, the second compound is administered at the same time as a pharmaceutical composition described herein. In certain embodiments, the dose of a co-administered second compound is the same as the dose that would be administered if the second compound was administered alone. In certain embodiments, the dose of a co-administered second compound is lower than the dose that would be administered if the second compound was administered alone. In certain embodiments, the dose of a co-administered second compound is greater than the dose that would be administered if the second compound was administered alone.

In certain embodiments, the co-administration of a second compound enhances the effect of a first compound, such that co-administration of the compounds results in an effect that is greater than the effect of administering the first compound alone. In certain embodiments, the co-administration results in effects that are additive of the effects of the compounds when administered alone. In certain embodiments, the co-administration results in effects that are supra-additive of the effects of the compounds when administered alone. In certain embodiments, the first compound is an antisense compound. In certain embodiments, the second compound is an antisense compound.

In certain embodiments, second agents include, but are not limited to, a glucose-lowering agent. The glucose lowering agent can include, but is not limited to, a therapeutic lifestyle change, PPAR agonist, a dipeptidyl peptidase (IV) inhibitor, a GLP-1 analog, insulin or an insulin analog, an insulin secretagogue, a SGLT2 inhibitor, a human amylin analog, a biguanide, an alpha-glucosidase inhibitor, or a combination thereof. The glucose-lowering agent can include, but is not limited to metformin, sulfonylurea, rosiglitazone, meglitinide, thiazolidinedione, alpha-glucosidase inhibitor or a combination thereof. The sulfonylurea can be acetohexamide, chlorpropamide, tolbutamide, tolazamide, glimepiride, a glipizide, a glyburide, or a gliclazide. The meglitinide can be nateglinide or repaglinide. The thiazolidinedione can be pioglitazone or rosiglitazone. The alpha-glucosidase can be acarbose or miglitol.

In some embodiments, the glucose-lowering therapeutic is a GLP-1 analog. In some embodiments, the GLP-1 analog is exendin-4 or liraglutide.

In other embodiments, the glucose-lowering therapeutic is a sulfonylurea. In some embodiments, the sulfonylurea is acetohexamide, chlorpropamide, tolbutamide, tolazamide, glimepiride, a glipizide, a glyburide, or a gliclazide.

In some embodiments, the glucose-lowering drug is a biguanide. In some embodiments, the biguanide is metformin, and in some embodiments, blood glucose levels are decreased without increased lactic acidosis as compared to the lactic acidosis observed after treatment with metformin alone.

In some embodiments, the glucose-lowering drug is a meglitinide. In some embodiments, the meglitinide is nateglinide or repaglinide.

In some embodiments, the glucose-lowering drug is a thiazolidinedione. In some embodiments, the thiazolidinedione is pioglitazone, rosiglitazone, or troglitazone. In some embodiments, blood glucose levels are decreased without greater weight gain than observed with rosiglitazone treatment alone.

In some embodiments, the glucose-lowering drug is an alpha-glucosidase inhibitor. In some embodiments, the alpha-glucosidase inhibitor is acarbose or miglitol.

In a certain embodiment, a co-administered glucose-lowering agent is ISIS 113715.

In a certain embodiment, glucose-lowering therapy is therapeutic lifestyle change.

In certain embodiments, second agents include, but are not limited to, lipid-lowering agents. The lipid-lowering agent can include, but is not limited to atorvastatin, simvastatin, rosuvastatin, and ezetimibe. In certain such embodiments, the lipid-lowering agent is administered prior to administration of a pharmaceutical composition described herein. In certain such embodiments, the lipid-lowering agent is administered following administration of a pharmaceutical composition described herein. In certain such embodiments the lipid-lowering agent is administered at the same time as a pharmaceutical composition described herein. In certain such embodiments the dose of a co-administered lipid-lowering agent is the same as the dose that would be administered if the lipid-lowering agent was administered alone. In certain such embodiments the dose of a co-administered lipid-lowering agent is lower than the dose that would be administered if the lipid-lowering agent was administered alone. In certain such embodiments the dose of a co-administered lipid-lowering agent is greater than the dose that would be administered if the lipid-lowering agent was administered alone.

In certain embodiments, a co-administered lipid-lowering agent is a HMG-CoA reductase inhibitor. In certain such embodiments the HMG-CoA reductase inhibitor is a statin. In certain such embodiments the statin is selected from atorvastatin, simvastatin, pravastatin, fluvastatin, and rosuvastatin.

In certain embodiments, a co-administered lipid-lowering agent is a cholesterol absorption inhibitor. In certain such embodiments, cholesterol absorption inhibitor is ezetimibe.

In certain embodiments, a co-administered lipid-lowering agent is a co-formulated HMG-CoA reductase inhibitor and cholesterol absorption inhibitor. In certain such embodiments the co-formulated lipid-lowering agent is ezetimibe/simvastatin.

In certain embodiments, a co-administered lipid-lowering agent is a microsomal triglyceride transfer protein inhibitor (MTP inhibitor).

In certain embodiments, a co-administered lipid-lowering agent is an oligonucleotide targeted to ApoB.

In certain embodiments, second agents include, but are not limited to an anti-obesity drug or agent. Such anti-obesity agents include but are not limited to Orlistat or Rimonabant, and may be administered as described above as adipose or body weight lowering agents. In certain embodiments, the antisense compound may be co-administered with appetite suppressants. Such appetite suppressants include but are not limited to diethylpropion tenuate, mazindol, orlistat, phendimetrazine, and phentermine, and may be administered as described herein. In certain embodiment, the anti-obesity agents are CNS based or GLP-1 based such as, but not limited to, liraglutide.

Formulations

The compounds provided herein may also be admixed, conjugated or otherwise associated with other molecules, molecule structures or mixtures of compounds, as for example, liposomes, receptor-targeted molecules, or other formulations, for assisting in uptake, distribution and/or absorption. Representative United States patents that teach the preparation of such uptake, distribution and/or absorption-assisting formulations include, but are not limited to, U.S. Pat. Nos. 5,108,921; 5,354,844; 5,416,016; 5,459,127; 5,521,291; 5,543,158; 5,547,932; 5,583,020; 5,591,721;

4,426,330; 4,534,899; 5,013,556; 5,108,921; 5,213,804; 5,227,170; 5,264,221; 5,356,633; 5,395,619; 5,416,016; 5,417,978; 5,462,854; 5,469,854; 5,512,295; 5,527,528; 5,534,259; 5,543,152; 5,556,948; 5,580,575; and 5,595,756, each of which is herein incorporated by reference.

The antisense compounds provided herein can be included in a pharmaceutical composition or formulation. The pharmaceutical composition can include any pharmaceutically acceptable salts, esters, or salts of such esters, or any other compound which, upon administration to an animal, including a human, is capable of providing (directly or indirectly) the biologically active metabolite or residue thereof.

The term "pharmaceutically acceptable salts" refers to physiologically and pharmaceutically acceptable salts of the compounds provided herein: i.e., salts that retain the desired biological activity of the parent compound and do not impart undesired toxicological effects thereto. The term "pharmaceutically acceptable salt" includes a salt prepared from pharmaceutically acceptable non-toxic acids or bases, including inorganic or organic acids and bases. For oligonucleotides, preferred examples of pharmaceutically acceptable salts and their uses are further described in U.S. Pat. No. 6,287,860, which is incorporated herein in its entirety. Sodium salts have been shown to be suitable forms of oligonucleotide drugs.

The term "pharmaceutically acceptable derivative" encompasses, but is not limited to, pharmaceutically acceptable salts, solvates, hydrates, esters, prodrugs, polymorphs, isomers, isotopically labeled variants of the compounds described herein.

The pharmaceutical compositions described herein may be administered in a number of ways depending upon whether local or systemic treatment is desired and upon the area to be treated. Administration may be parenteral. Parenteral administration includes but is not limited to subcutaneous, intravenous or intramuscular injection or infusion.

Parenteral administration, is preferred to target GCCR expression in the liver and plasma. Oligonucleotides with at least one 2'-O-methoxyethyl modification are believed to be particularly useful for parenteral administration.

The pharmaceutical formulations described herein, which may conveniently be presented in unit dosage form, may be prepared according to conventional techniques well known in the pharmaceutical industry. Such techniques include the step of bringing into association the active ingredients with the pharmaceutical carrier(s) or excipient(s). In general, the formulations are prepared by uniformly and intimately bringing into association the active ingredients with liquid carriers or finely divided solid carriers or both.

The compositions described herein may also be formulated as suspensions in aqueous, non-aqueous or mixed media. The suspension may also contain stabilizers.

Pharmaceutical compositions described herein include, but are not limited to, solutions, emulsions, and liposome-containing formulations. The pharmaceutical compositions and formulations described herein may comprise one or more penetration enhancers, carriers, excipients or other active or inactive ingredients.

Formulations include liposomal formulations. As used in the present invention, the term "liposome" means a vesicle composed of amphiphilic lipids arranged in a spherical bilayer or bilayers. Liposomes are unilamellar or multilamellar vesicles which have a membrane formed from a lipophilic material and an aqueous interior that contains the composition to be delivered. Cationic liposomes are positively charged liposomes which are believed to interact with negatively charged DNA molecules to form a stable complex. Liposomes that are pH-sensitive or negatively-charged are believed to entrap DNA rather than complex with it. Both cationic and noncationic liposomes have been used to deliver DNA to cells.

Liposomes also include "sterically stabilized" liposomes, a term which, as used herein, refers to liposomes comprising one or more specialized lipids that, when incorporated into liposomes, result in enhanced circulation lifetimes relative to liposomes lacking such specialized lipids. Liposomes and their uses are further described in U.S. Pat. No. 6,287,860, which is incorporated herein in its entirety.

In another embodiment, formulations include saline formulations. In certain embodiments, a formulation consists of the compounds described herein and saline. In certain embodiments, a formulation consists essentially of the compounds described herein and saline. In certain embodiments, the saline is pharmaceutically acceptable grade saline. In certain embodiments, the saline is buffered saline. In certain embodiments, the saline is phosphate buffered saline (PBS).

In certain embodiments, a formulation excludes liposomes. In certain embodiments, the formulation excludes sterically stabilized liposomes. In certain embodiments, a formulation excludes phospholipids. In certain embodiments, the formulation consists essentially of the compounds described herein and saline and excludes liposomes.

The pharmaceutical formulations and compositions may also include surfactants. Surfactants and their uses are further described in U.S. Pat. No. 6,287,860, which is incorporated herein in its entirety.

In one embodiment, the present invention employs various penetration enhancers to affect the efficient delivery of nucleic acids, particularly oligonucleotides. Penetration enhancers and their uses are further described in U.S. Pat. No. 6,287,860, which is incorporated herein in its entirety.

Compositions and formulations for parenteral administration, including intravenous, subcutaneous and intramuscular injection or infusion may include sterile aqueous solutions which may also contain buffers, diluents and other suitable additives such as, but not limited to, penetration enhancers, carrier compounds and other pharmaceutically acceptable carriers or excipients.

In another related embodiment, compositions provided herein may contain one or more antisense compounds, particularly oligonucleotides, targeted to a first nucleic acid and one or more additional antisense compounds targeted to a second nucleic acid target. Alternatively, compositions provided herein may contain two or more antisense compounds targeted to different regions of the same nucleic acid target. Numerous examples of antisense compounds are known in the art. Two or more combined compounds may be used together or sequentially.

Dosing

Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. Optimum dosages may vary depending on the relative potency of individual oligonucleotides, and can generally be estimated based on $EC_{50}$s found to be effective in in vitro and in vivo animal models. In general, dosage is from 0.01 μg to 100 g per kg of body weight, and may be given once or more daily, weekly, monthly or yearly, or at desired intervals. Following successful treatment, it may be desirable to have the patient undergo maintenance therapy to prevent the recurrence of the disease state, wherein the oligonucleotide is administered in maintenance doses, ranging from 0.01 μg to 100 g per kg of body weight, once or more daily.

While the present invention has been described with specificity in accordance with certain of its preferred embodiments, the following examples serve only to illustrate the invention and are not intended to limit the same. Each of the references, GenBank accession numbers, and the like recited in the present application is incorporated herein by reference in its entirety.

Certain Compounds

About seven hundred and sixty newly designed and previously disclosed antisense compounds of various lengths, motifs and backbone composition were tested for their effect on human GCCR mRNA in vitro in several cell types (Examples 1 and 2). The new compounds were compared with previously designed compounds, including ISIS 377131, ISIS 361137, ISIS 361141, ISIS 361151, ISIS 361155, and ISIS 361156 which have previously been determined to be some of the most potent antisense compounds in vitro (see e.g., PCT Pub. No. WO 2007/035759). Of the about seven hundred and sixty newly designed and previously designed antisense compounds, only those compounds which were selected for further study based on in vitro activity are presented.

Fifteen of these compounds were selected and additional new compounds were designed based on these compounds. The 317 new compounds were designed by creating compounds shifted slightly upstream and downstream (i.e. microwalk) of the original compounds. The new and original compounds were tested using electroporation for transfection and separately using lipofectin as the transfection reagent (Example 3). Of the 332 compounds tested, only those compounds which were selected for further study based on in vitro activity are presented. The 72 compounds selected for dose response assay were tested by individually using electroporation and lipofectin as the transfection reagents (Example 4). In the dose response assays described in Examples 4 and 5, several exemplary compounds were found to be more potent than the benchmark compound, ISIS 377131. Twenty nine compounds were selected for a dose response assay with electroporation as the transfection reagent (Example 5), from which twelve oligonucleotides were selected for in vivo rodent tolerability studies.

Twelve compounds, ISIS 420470 (SEQ ID NO: 6), ISIS 420476 (SEQ ID NO: 7), ISIS 426115 (SEQ ID NO: 36), ISIS 426130 (SEQ ID NO: 33), ISIS 426168 (SEQ ID NO: 39), ISIS 426172 (SEQ ID NO: 42), ISIS 426183 (SEQ ID NO: 10), ISIS 426246 (SEQ ID NO: 11), ISIS 426261 (SEQ ID NO: 10), ISIS 426262 (SEQ ID NO: 35), ISIS 426267 (SEQ ID NO: 43), and ISIS 426325 (SEQ ID NO: 42), were tested for tolerability in a CD1 mouse model, as well as a Sprague-Dawley rat model. The compound ISIS 377131 (SEQ ID NO: 4) was carried forward as a benchmark. The compounds are complementary to the regions 57825-57844, 59956-59975, 63677-63696, 65938-65957, 65939-65958, 65940-65959, 76224-76243, 76229-76248, 76255-76274, and 95513-95532 of SEQ ID NO: 1.

Liver function markers, such as alanine transaminase, aspartate transaminase and bilirubin, and kidney function markers, such as BUN and creatinine, as well as markers of inflammation were measured (Examples 6 and 7). The 13 compounds were also assayed for long-term effects on tolerability in a CD/1GS rat model for 12 weeks (Example 8). Liver function markers, such as alanine transaminase and aspartate transaminase, and kidney function markers, such as urine protein to creatinine were measured.

Final evaluation of these rodent tolerability studies (Examples 6-8) led to the selection of all twelve of the compounds for additional studies.

Due to having advantageous properties including in vitro potency and in vivo tolerability, in certain embodiments the compounds provided herein have a nucleobase sequence containing a portion of at least an 8, at least a 9, at least a 10, at least an 11, at least a 12, at least a 14, at least a 15, at least a 16, at least a 17, at least a 18, at least a 19 or at least a 20 contiguous nucleobases of one of SEQ ID NOs: 6, 7, 36, 33, 39, 42, 10, 11, 35 and 43. In certain embodiments, the compounds have a nucleobase sequence containing a portion of at least an 8, at least a 9, at least a 10, at least an 11, at least a 12, at least a 14, at least a 15, at least a 16, at least a 17, at least a 18, at least a 19 or at least a 20 contiguous nucleobases complementary to an equal length portion of one of the regions 57825-57844, 59956-59975, 63677-63696, 65938-65957, 65939-65958, 65940-65959, 76224-76243, 76225-76244, 76229-76248, and 95513-95532 of SEQ ID NO: 1. In certain embodiments, the compounds targeting the listed regions or having a nucleobase portion of a sequence recited in the listed SEQ ID NOs can be of various length, as further described herein, and can have one of various motifs, as further described herein. In certain embodiments, a compound has the specific length and motif, as indicated by the ISIS NOs: 420470, 426476, 426115, 426130, 426168, 426172, 426183, 426246, 426261, 426262, 426267, and 426325.

These twelve compounds were tested for activity, pharmacokinetic profile and tolerability in cynomolgus monkeys (Example 9). Treatment with some of the compounds caused reduction of GCCR mRNA expression in liver tissue. Specifically, treatment with ISIS 420476, ISIS 426115, and ISIS 426325 caused significant reduction of GCCR mRNA expression in liver tissue, compared to the PBS control.

Tolerability studies in cynomolgus monkeys (Example 9) were also performed, with measurements of body and organ weights; measurements of ALT, AST, alkaline phosphatase, and bilirubin levels to assess liver function; measurements of BUN and creatinine levels to assess renal function; measurements of CRP and immune cell counts to assess inflammation status; and measurement of oligonucleotide concentrations in the liver and kidney to assess pharmacokinetics of the compounds. Treatment with ISIS 426115 was well tolerated, as indicated by baseline values of all the parameters listed above.

Viscosity of ISIS 420476, ISIS 426115 and ISIS 426325 was also measured (Example 10) and found to be optimal in all three cases.

Accordingly, provided herein are antisense compounds with any one or more of the improved characteristics. In a certain embodiments, the compounds as described herein are efficacious by virtue of having at least one of an in vitro $IC_{50}$ in a human cell of less than 3 μM, less than 2.5 μM, less than 2 μM, less than 1.5 μM, less than 1 μM, when delivered to a HepG2 cell line using electroporation, as described in Examples 4 and 5. In certain embodiments, the compounds as described herein are efficacious by virtue of having at least one of an in vitro $IC_{50}$ in a human cell of less than 50 nM, less than 45 nM less than 40 nM, less than 35 nM less than 30 nM, less than 25 nM less than 20 nM, when delivered to a HepG2 cell line using lipofectin reagent, as described in Example 4. In certain embodiments, the compounds as described herein are highly tolerable, as demonstrated by having at least one of an increase of ALT or AST value of no more than 50 fold, no more than 40 fold, no more than 30 fold, no more than 20 fold, no more than 10 fold, no more than 5 fold, no more than, no more than 4 fold, no more than 3 fold, or no more than 2 fold over saline treated animals; or an increase in liver, spleen or kidney weight of no more than 30%, no more than 20%, no more than 15%, no more than 12%, no more than 10%, 5 no more than % or no more than 2%.

EXAMPLES

Non-Limiting Disclosure and Incorporation by Reference

While certain compounds, compositions and methods described herein have been described with specificity in accordance with certain embodiments, the following examples serve only to illustrate the compounds described herein and are not intended to limit the same. Each of the references recited in the present application is incorporated herein by reference in its entirety.

Example 1

Antisense Inhibition of Human Glucocorticoid Receptor (GCCR) in HepG2 Cells

Antisense oligonucleotides were designed to target a human GCCR nucleic acid and were tested for their effects on GCCR mRNA in vitro. ISIS 377131, previously described in PCT Pub No. WO2005/071080, was also included in the assay. Cultured HepG2 cells at a density of 10,000 cells per well were transfected using lipofectin reagent with 120 nM antisense oligonucleotide. After a treatment period of approximately 24 hours, RNA was isolated from the cells and GCCR mRNA levels were measured by quantitative real-time PCR using human primer probe set RTS1408 (forward sequence GGAGATCATATA-GACAATCAAGTGCAA, designated herein as SEQ ID NO: 58; reverse sequence GGGTAGAGTCATTCTCTGCT-CATTAA, designated herein as SEQ ID NO: 29; probe sequence CTGTGTTTTGCTCCTGATCTGAT, designated herein as SEQ ID NO: 60). GCCR mRNA levels were adjusted according to total RNA content, as measured by RIBOGREEN®. Results are presented as percent inhibition of GCCR, relative to untreated control cells. Of the 460 oligonucleotides tested, only those selected for further studies are presented.

The newly designed chimeric antisense oligonucleotides in Table 1 were designed as 5-10-5 MOE gapmers. The gapmers are 20 nucleosides in length, wherein the central gap segment comprises of ten 2'-deoxynucleosides and is flanked on both sides (in the 5' and 3' directions) by wings comprising five nucleosides each. Each nucleoside in the 5' wing segment and each nucleoside in the 3' wing segment has a 2'-MOE modification. The internucleoside linkages throughout each gapmer are phosphorothioate (P═S) linkages. All cytosine residues throughout each gapmer are 5-methylcytosines. "Human Target start site" indicates the 5'-most nucleoside to which the gapmer is targeted in the human gene sequence. The gapmers were targeted to intronic sequences or intron-exon junctions of the human GCCR genomic sequence, designated herein as SEQ ID NO: 1 (the complement of GENBANK Accession No. NT_029289.10 truncated from nucleotides 3818000 to 3980000). The data indicates that antisense oligonucleotides targeted to the intronic regions of SEQ ID NO: 1 significantly reduce GCCR mRNA levels.

TABLE 1

Inhibition of human GCCR mRNA levels by chimeric antisense oligonucleotides having 5-10-5 MOE wings and deoxy gap targeted to SEQ ID NO: 1

| ISIS NO | Human Start Site | Region | Sequence | % inhi-bition | SEQ ID NO |
|---|---|---|---|---|---|
| 377131 | 37217 | exon 2 | GTCAAAGGTG CTTTGGTCTG | 81 | 4 |
| 420450 | 51879 | intron 2 | TCCACAGATC TCTAGGGCAG | 87 | 5 |
| 420470 | 57825 | intron 2 | GGTAGAAATA TAGTTGTTCC | 77 | 6 |
| 420476 | 59956 | intron 2 | TTCATGTGTC TGCATCATGT | 86 | 7 |
| 420479 | 60939 | intron 2 | ATTTGGCTAT TGTGGGATTC | 71 | 8 |
| 420488 | 63678 | intron 2 | GGCATCCAGC GAGCACCAAA | 79 | 9 |
| 420493 | 65938 | intron 2 | AGCCATGGTG ATCAGGAGGC | 78 | 10 |
| 420522 | 76225 | intron 2 | GGTCTGGATT ACAGCATAAA | 78 | 11 |
| 420599 | 95518 | intron 2 | TACTGGTGCT TGTCCAGGAT | 79 | 12 |
| 420634 | 109349 | intron 2 | TCTGCGCACC TGCAGGCCCA | 91 | 13 |
| 420644 | 112219 114155 | intron 2 | ACTTCTTACA TGGTGGTGGC | 76 | 14 |
| 420764 | 143259 | intron 7 | GCAACTATGA AACCACAGTT | 76 | 15 |
| 414681 | 143737 | intron 7 | GGTATATATT TCCATCCTTA | 83 | 16 |

Example 2

Antisense Inhibition of Human GCCR in HepG2 Cells

Additional antisense oligonucleotides were designed targeting a GCCR nucleic acid and were tested for their effects on GCCR mRNA in vitro. ISIS 361137, ISIS 361141, ISIS 361151, ISIS 361156, ISIS 377131, ISIS 361143, and ISIS 361155, previously described in PCT Pub No. WO2005/071080, were also included in the assay. Cultured HepG2 cells at a density of 10,000 cells per well were transfected using lipofectin reagent with 120 nM antisense oligonucleotide. After a treatment period of approximately 24 hours, RNA was isolated from the cells and GCCR mRNA levels were measured by quantitative real-time PCR using human primer probe set RTS1408. GCCR mRNA levels were adjusted according to total RNA content, as measured by RIBOGREEN®. Results are presented as percent inhibition of GCCR, relative to untreated control cells. Of the 298 new oligonucleotides tested, only those selected for further studies are presented.

The newly designed chimeric antisense oligonucleotides in Table 2 were designed as 5-10-5 MOE gapmers. The gapmers are 20 nucleosides in length, wherein the central gap segment comprises of ten 2'-deoxynucleosides and is flanked on both sides (in the 5' and 3' directions) by wings comprising five nucleosides each. Each nucleoside in the 5' wing segment and each nucleoside in the 3' wing segment has a 2'-MOE modification. The internucleoside linkages throughout each gapmer are phosphorothioate (P═S) linkages. All cytosine residues throughout each gapmer are 5-methylcytosines. “Human Target start site” indicates the 5'-most nucleoside to which the gapmer is targeted in the human gene sequence. The gapmers were targeted to exonic sequences, intronic sequences or intron-exon junctions of SEQ ID NO: 1.

TABLE 2

Inhibition of human GCCR mRNA levels by chimeric antisense oligonucleotides having 5-10-5 MOE wings and deoxy gap targeted to SEQ ID NO: 1

| ISIS NO | Human Start Site | Region | Sequence | % inhibition | SEQ ID NO |
|---|---|---|---|---|---|
| 361137 | 33116 | exon 2 | CGACCTATTG AGGTTTGCAA | 77 | 17 |
| 361141 | 33673 | exon 2 | GCAGACATTT TATTACCAAT | 65 | 18 |
| 361151 | 33716 | exon 2 | GTACATCTGT CCTCCAGAGG | 66 | 19 |
| 361155 | 33732 | exon 2 | TATTCATGTC ATAGTGGTAC | 75 | 20 |
| 361156 | 33736 | exon 2 | GCTGTATTCA TGTCATAGTG | 73 | 21 |
| 377131 | 33296 | exon 2 | GTCAAAGGTG CTTTGGTCTG | 82 | 4 |
| 414641 | 104247 | intron 2 | GCGCACCTGC AGGCCCAACA | 80 | 22 |
| 414648 | 109473 | intron 2 | CCCTCAGGTT TTGATGCTGC | 74 | 23 |
| 414681 | 139287 | intron 7 | GGTATATATT TCCATCCTTA | 87 | 16 |

Example 3

Antisense Inhibition of Human GCCR in HepG2 Cells by Oligonucleotides Designed by Microwalk Additional gapmers were designed based on the gapmers presented in Tables 1 and 2. These gapmers were designed by creating gapmers shifted slightly upstream and downstream (i.e. “microwalk”) of the original gapmers from Tables 1 and 2. Gapmers were also created with various motifs, e.g. 5-10-5 MOE, 3-14-3 MOE, and 2-13-5 MOE motifs. These gapmers were tested in vitro. Cultured HepG2 cells at a density of 20,000 cells per well were transfected using electroporation with 2,000 nM antisense oligonucleotide. After a treatment period of approximately 24 hours, RNA was isolated from the cells and GCCR mRNA levels were measured by quantitative real-time PCR. The human primer probe set RTS1408 was used to measure GCCR mRNA levels. GCCR mRNA levels were adjusted according to total RNA content, as measured by RIBOGREEN®. Results are presented as percent inhibition of GCCR, relative to untreated control cells. The results are presented in Table 3.

The gapmers were also tested for their activity using lipofectin as the transfection reagent. Cultured HepG2 cells at a density of 10,000 cells per well were transfected using lipofectin with 50 nM antisense oligonucleotide. After a treatment period of approximately 24 hours, RNA was isolated from the cells and GCCR mRNA levels were measured by quantitative real-time PCR. The human primer probe set RTS1408 was used to measure GCCR mRNA levels. GCCR mRNA levels were adjusted according to total RNA content, as measured by RIBOGREEN®. Results are presented as percent inhibition of GCCR, relative to untreated control cells. The results are also presented in Table 3.

The chimeric antisense oligonucleotides in Table 3 were designed as 5-10-5 MOE, 3-14-3 MOE, or 2-13-5 MOE gapmers. The gapmers designated with an asterisk (*) in Table 3 are the original gapmers from which gapmers, ISIS 426106-426405, were designed via microwalk. ISIS 377131 was included in this assay and the activity of the newly designed gapmers was compared to the activity of ISIS 377131. The 5-10-5 gapmers are 20 nucleosides in length, wherein the central gap segment is comprised of ten 2'-deoxynucleosides and is flanked on both sides (in the 5' and 3' directions) by wings comprising five nucleosides each. The 3-14-3 gapmers are 20 nucleosides in length, wherein the central gap segment is comprised of fourteen 2'-deoxynucleosides and is flanked on both sides (in the 5' and 3' directions) by wings comprising three nucleosides each. The 2-13-5 gapmers are 20 nucleosides in length, wherein the central gap segment is comprised of thirteen 2'-deoxynucleosides and is flanked on the 5' and the 3' directions with wings comprising two and five nucleosides respectively. For each of the motifs (5-10-5, 3-14-3, and 2-113-5), each nucleoside in the 5' wing segment and each nucleoside in the 3' wing segment has a 2'-MOE modification. The internucleoside linkages throughout each gapmer are phosphorothioate (P═S) linkages. All cytosine residues throughout each gapmer are 5-methylcytosines. “Target start site” indicates the 5'-most nucleoside to which the gapmer is targeted. Each gapmer listed in Table 3 is targeted to SEQ ID NO: 1 (the complement of GENBANK Accession No. NT_029289.10 truncated from nucleotides 3818000 to 3980000). Only those gapmers which were selected for further studies are presented.

TABLE 3

Inhibition of human GCCR mRNA levels by chimeric antisense oligonucleotides

| ISIS No | Start Site | Sequence | Motif | % inhibition using electroporation | % inhibition using lipofectin | SEQ ID NO |
|---|---|---|---|---|---|---|
| 377131 | 37217 | GTCAAAGGTG CTTTGGTCTG | 4-12-4 | 67 | 37 | 4 |
| 426128 | 51878 | CCACAGATCT CTAGGGCAGG | 5-10-5 | 73 | 45 | 24 |
| 426199 | 51878 | CCACAGATCT CTAGGGCAGG | 3-14-3 | 54 | 28 | 24 |

TABLE 3-continued

Inhibition of human GCCR mRNA levels by chimeric antisense oligonucleotides

| ISIS No | Start Site | Sequence | Motif | % inhibition using electroporation | % inhibition using lipofectin | SEQ ID NO |
|---|---|---|---|---|---|---|
| 426276 | 51878 | CCACAGATCTCTAGGGCAGG | 2-13-5 | 47 | 47 | 24 |
| 420450* | 51879 | TCCACAGATCTCTAGGGCAG | 5-10-5 | 73 | 21 | 5 |
| 420470* | 57825 | GGTAGAAATATAGTTGTTCC | 5-10-5 | 54 | 26 | 6 |
| 426331 | 57827 | GTGGTAGAAATATAGTTGTT | 5-10-5 | 33 | 29 | 25 |
| 426150 | 59951 | GTGTCTGCATCATGTCTCTC | 5-10-5 | 50 | 20 | 26 |
| 426301 | 59951 | GTGTCTGCATCATGTCTCTC | 2-13-5 | 50 | 22 | 26 |
| 426302 | 59952 | TGTGTCTGCATCATGTCTCT | 2-13-5 | 17 | 48 | 27 |
| 426229 | 59955 | TCATGTGTCTGCATCATGTC | 3-14-3 | 23 | 34 | 28 |
| 420476* | 59956 | TTCATGTGTCTGCATCATGT | 5-10-5 | 53 | 59 | 7 |
| 426306 | 59956 | TTCATGTGTCTGCATCATGT | 2-13-5 | 24 | 46 | 7 |
| 426157 | 59959 | TATTTCATGTGTCTGCATCA | 5-10-5 | 45 | 20 | 29 |
| 426142 | 60935 | GGCTATTGTGGGATTCTCCT | 5-10-5 | 59 | 52 | 30 |
| 426216 | 60935 | GGCTATTGTGGGATTCTCCT | 3-14-3 | 50 | 46 | 30 |
| 426143 | 60936 | TGGCTATTGTGGGATTCTCC | 5-10-5 | 60 | 50 | 31 |
| 426293 | 60936 | TGGCTATTGTGGGATTCTCC | 2-13-5 | 51 | 7 | 31 |
| 426144 | 60937 | TTGGCTATTGTGGGATTCTC | 5-10-5 | 48 | 25 | 32 |
| 420479* | 60939 | ATTTGGCTATTGTGGGATTC | 5-10-5 | 30 | 26 | 8 |
| 426130 | 63677 | GCATCCAGCGAGCACCAAAG | 5-10-5 | 49 | 46 | 33 |
| 420488* | 63678 | GGCATCCAGCGAGCACCAAA | 5-10-5 | 55 | 50 | 9 |
| 426203 | 63678 | GGCATCCAGCGAGCACCAAA | 3-14-3 | 31 | 38 | 9 |
| 426131 | 63679 | GGGCATCCAGCGAGCACCAA | 5-10-5 | 52 | 32 | 34 |
| 426281 | 63679 | GGGCATCCAGCGAGCACCAA | 2-13-5 | 38 | 53 | 34 |
| 420493* | 65938 | AGCCATGGTGATCAGGAGGC | 5-10-5 | 53 | 49 | 10 |
| 426183 | 65938 | AGCCATGGTGATCAGGAGGC | 3-14-3 | 68 | 70 | 10 |
| 426261 | 65938 | AGCCATGGTGATCAGGAGGC | 2-13-5 | 72 | 65 | 10 |
| 426262 | 65939 | CAGCCATGGTGATCAGGAGG | 2-13-5 | 34 | 61 | 35 |
| 426115 | 65940 | GCAGCCATGGTGATCAGGAG | 5-10-5 | 56 | 71 | 36 |
| 426185 | 65940 | GCAGCCATGGTGATCAGGAG | 3-14-3 | 41 | 51 | 36 |
| 426263 | 65940 | GCAGCCATGGTGATCAGGAG | 2-13-5 | 46 | 57 | 36 |
| 426116 | 65941 | TGCAGCCATGGTGATCAGGA | 5-10-5 | 45 | 61 | 37 |
| 426264 | 65941 | TGCAGCCATGGTGATCAGGA | 2-13-5 | 42 | 58 | 37 |
| 426117 | 65942 | CTGCAGCCATGGTGATCAGG | 5-10-5 | 58 | 70 | 38 |
| 426187 | 65942 | CTGCAGCCATGGTGATCAGG | 3-14-3 | 42 | 69 | 38 |
| 426168 | 76224 | GTCTGGATTACAGCATAAAC | 5-10-5 | 43 | 31 | 39 |
| 420522* | 76225 | GGTCTGGATTACAGCATAAA | 5-10-5 | 44 | 33 | 11 |
| 426246 | 76225 | GGTCTGGATTACAGCATAAA | 3-14-3 | 60 | 39 | 11 |
| 426323 | 76227 | TTGGTCTGGATTACAGCATA | 2-13-5 | 32 | 50 | 40 |
| 426171 | 76228 | CTTGGTCTGGATTACAGCAT | 5-10-5 | 53 | 47 | 41 |
| 426324 | 76228 | CTTGGTCTGGATTACAGCAT | 2-13-5 | 51 | 33 | 41 |
| 426172 | 76229 | CCTTGGTCTGGATTACAGCA | 5-10-5 | 53 | 56 | 42 |
| 426325 | 76229 | CCTTGGTCTGGATTACAGCA | 2-13-5 | 43 | 57 | 42 |
| 426119 | 95513 | GTGCTTGTCCAGGATGATGC | 5-10-5 | 44 | 45 | 43 |
| 426189 | 95513 | GTGCTTGTCCAGGATGATGC | 3-14-3 | 44 | 59 | 43 |
| 426267 | 95513 | GTGCTTGTCCAGGATGATGC | 2-13-5 | 41 | 45 | 43 |
| 420599* | 95518 | TACTGGTGCTTGTCCAGGAT | 5-10-5 | 63 | 51 | 12 |
| 426124 | 95519 | CTACTGGTGCTTGTCCAGGA | 5-10-5 | 41 | 54 | 44 |
| 414641* | 109346 | GCGCACCTGCAGGCCCAACA | 5-10-5 | 43 | 76 | 22 |

TABLE 3-continued

Inhibition of human GCCR mRNA levels by chimeric antisense oligonucleotides

| ISIS No | Start Site | Sequence | Motif | % inhibition using electroporation | % inhibition using lipofectin | SEQ ID NO |
|---|---|---|---|---|---|---|
| 426177 | 109346 | GCGCACCTGC AGGCCCAACA | 3-14-3 | 29 | 68 | 22 |
| 426255 | 109346 | GCGCACCTGC AGGCCCAACA | 2-13-5 | 13 | 68 | 22 |
| 426110 | 109347 | TGCGCACCTG CAGGCCCAAC | 5-10-5 | 45 | 69 | 45 |
| 420634* | 109349 | TCTGCGCACC TGCAGGCCCA | 5-10-5 | 37 | 62 | 13 |
| 426343 | 112218 114154 | CTTCTTACAT GGTGGTGGCA | 5-10-5 | 42 | 21 | 46 |
| 420644* | 112219 114155 | ACTTCTTACA TGGTGGTGGC | 5-10-5 | 44 | 40 | 14 |
| 426401 | 112219 114155 | ACTTCTTACA TGGTGGTGGC | 2-13-5 | 31 | 50 | 14 |
| 426344 | 112220 114156 | TACTTCTTAC ATGGTGGTGG | 5-10-5 | 32 | 44 | 47 |
| 426402 | 112220 114156 | TACTTCTTAC ATGGTGGTGG | 2-13-5 | 33 | 40 | 47 |
| 426345 | 112221 114157 | GTACTTCTTA CATGGTGGTG | 5-10-5 | 49 | 55 | 48 |
| 426403 | 112221 114157 | GTACTTCTTA CATGGTGGTG | 2-13-5 | 31 | 37 | 48 |
| 426346 | 112222 114158 | GGTACTTCTT ACATGGTGGT | 5-10-5 | 38 | 37 | 49 |
| 426404 | 112222 114158 | GGTACTTCTT ACATGGTGGT | 2-13-5 | 40 | 34 | 49 |
| 426347 | 112223 114159 | AGGTACTTCT TACATGGTGG | 5-10-5 | 42 | 41 | 50 |
| 426405 | 112223 114159 | AGGTACTTCT TACATGGTGG | 2-13-5 | 30 | 31 | 50 |
| 426334 | 114587 | CAGGTTTTGA TGCTGCTGCT | 5-10-5 | 15 | 37 | 51 |
| 426390 | 114587 | CAGGTTTTGA TGCTGCTGCT | 2-13-5 | 15 | 42 | 51 |
| 426336 | 114589 | CTCAGGTTTT GATGCTGCTG | 5-10-5 | 15 | 36 | 52 |
| 426337 | 114590 | CCTCAGGTTT TGATGCTGCT | 5-10-5 | 20 | 44 | 53 |
| 414648* | 114591 | CCCTCAGGTT TTGATGCTGC | 5-10-5 | 23 | 37 | 23 |
| 420764* | 143259 | GCAACTATGA AACCACAGTT | 5-10-5 | 41 | 14 | 15 |
| 426136 | 143260 | GGCAACTATG AAACCACAGT | 5-10-5 | 56 | 33 | 54 |
| 426137 | 143261 | TGGCAACTAT GAAACCACAG | 5-10-5 | 47 | 28 | 55 |
| 414681* | 143737 | GGTATATATT TCCATCCTTA | 5-10-5 | 36 | 57 | 16 |
| 426161 | 143738 | AGGTATATAT TTCCATCCTT | 5-10-5 | 13 | 55 | 56 |

Example 4

Dose-Dependent Antisense Inhibition of Human GCCR in HepG2 Cells

Gapmers from Example 3 exhibiting significant in vitro inhibition of human GCCR were tested under various conditions in HepG2 cells. Cells were plated at a density of 20,000 cells per well and transfected using electroporation with 0.8 μM, 1.5 μM, 3.0 μM, or 6.0 μM concentrations of antisense oligonucleotide, as specified in Table 4. After a treatment period of approximately 16 hours, RNA was isolated from the cells and GCCR mRNA levels were measured by quantitative real-time PCR. Human GCCR primer probe set RTS1408 was used to measure mRNA levels. GCCR mRNA levels were adjusted according to total RNA content, as measured by RIBOGREEN®. Results are presented as percent inhibition of GCCR, relative to untreated control cells.

The gapmers were also tested at various doses in HepG2 cells using the transfection reagent, lipofectin. Cells were plated at a density of 10,000 cells per well and transfected using lipofectin reagent with 17.5 nM, 35 nM, 70 nM or 140 nM concentrations of antisense oligonucleotide, as specified in Table 5.

After a treatment period of approximately 16 hours, RNA was isolated from the cells and GCCR mRNA levels were measured by quantitative real-time PCR. Human GCCR primer probe set RTS1408 was used to measure mRNA levels. GCCR mRNA levels were adjusted according to total RNA content, as measured by RIBOGREEN®. Results are presented as percent inhibition of GCCR, relative to untreated control cells.

The half maximal inhibitory concentration ($IC_{50}$) of each oligonucleotide is also presented in Tables 4 and 5, and was calculated by plotting the concentrations of oligonucleotides used versus the percent inhibition of GCCR mRNA expression achieved at each concentration, and noting the concentration of oligonucleotide at which 50% inhibition of GCCR mRNA expression was achieved compared to the control. As illustrated in Tables 4 and 5, GCCR mRNA levels were significantly reduced in a dose-dependent manner in antisense oligonucleotide treated cells. Certain exemplary compounds demonstrated greater potency than the benchmark, ISIS 377131.

TABLE 4

Dose-dependent antisense inhibition of human GCCR expression in HepG2 cells using electroporation

| ISIS No | 0.8 μM | 1.5 μM | 3.0 μM | 6.0 μM | $IC_{50}$ (μM) |
|---|---|---|---|---|---|
| 377131 | 28 | 43 | 66 | 83 | 2.0 |
| 414641 | 30 | 50 | 77 | 93 | 1.4 |
| 414648 | 8 | 32 | 50 | 61 | 3.4 |
| 414681 | 28 | 43 | 61 | 84 | 1.8 |
| 420450 | 36 | 57 | 68 | 90 | 1.3 |
| 420470 | 34 | 58 | 70 | 89 | 1.3 |
| 420476 | 36 | 51 | 81 | 93 | 1.3 |
| 420488 | 12 | 28 | 54 | 58 | 3.5 |
| 420493 | 32 | 42 | 66 | 82 | 1.7 |
| 420522 | 32 | 52 | 73 | 90 | 1.4 |
| 420599 | 28 | 52 | 73 | 80 | 1.5 |
| 420644 | 30 | 48 | 58 | 72 | 1.9 |
| 426110 | 20 | 40 | 57 | 78 | 2.2 |
| 426115 | 35 | 51 | 76 | 82 | 1.3 |
| 426116 | 32 | 48 | 74 | 80 | 1.5 |
| 426117 | 20 | 41 | 72 | 88 | 1.8 |
| 426119 | 33 | 52 | 72 | 80 | 1.4 |
| 426124 | 18 | 30 | 64 | 78 | 2.3 |
| 426128 | 40 | 51 | 82 | 91 | 1.2 |
| 426130 | 5 | 32 | 47 | 74 | 3.0 |
| 426131 | 26 | 23 | 41 | 60 | 4.3 |
| 426136 | 19 | 42 | 71 | 81 | 1.9 |
| 426137 | 5 | 25 | 48 | 73 | 3.1 |
| 426142 | 28 | 36 | 69 | 85 | 1.8 |
| 426143 | 14 | 38 | 59 | 80 | 2.3 |
| 426144 | 8 | 29 | 50 | 69 | 3.1 |
| 426150 | 26 | 42 | 69 | 81 | 1.8 |
| 426157 | 23 | 48 | 71 | 88 | 1.7 |
| 426161 | 17 | 34 | 52 | 68 | 2.8 |
| 426168 | 36 | 56 | 75 | 94 | 1.2 |
| 426171 | 34 | 49 | 78 | 90 | 1.4 |
| 426172 | 46 | 63 | 83 | 92 | 0.8 |
| 426177 | 19 | 35 | 55 | 83 | 2.3 |
| 426183 | 36 | 71 | 77 | 93 | 1.0 |
| 426185 | 36 | 43 | 65 | 78 | 1.6 |
| 426187 | 22 | 42 | 57 | 81 | 2.1 |
| 426189 | 31 | 45 | 68 | 84 | 1.6 |
| 426199 | 13 | 37 | 40 | 76 | 2.9 |
| 426203 | 0 | 6 | 16 | 33 | 1.8 |
| 426216 | 3 | 28 | 32 | 60 | 4.5 |
| 426229 | 5 | 23 | 55 | 83 | 2.6 |
| 426246 | 38 | 59 | 86 | 94 | 1.1 |
| 426255 | 19 | 29 | 62 | 77 | 2.4 |
| 426261 | 62 | 76 | 92 | 97 | <0.8 |
| 426262 | 23 | 26 | 57 | 71 | 2.7 |
| 426263 | 25 | 40 | 70 | 90 | 1.7 |
| 426264 | 18 | 46 | 67 | 88 | 1.8 |
| 426267 | 45 | 54 | 78 | 90 | 1.0 |
| 426276 | 0 | 14 | 33 | 68 | 4.1 |
| 426281 | 0 | 8 | 15 | 44 | 1.0 |
| 426293 | 5 | 11 | 48 | 55 | 4.5 |
| 426301 | 26 | 47 | 76 | 92 | 1.6 |
| 426302 | 18 | 36 | 64 | 75 | 2.3 |
| 426306 | 12 | 17 | 60 | 85 | 2.5 |
| 426323 | 16 | 28 | 58 | 76 | 2.5 |
| 426324 | 27 | 54 | 81 | 94 | 1.4 |
| 426325 | 75 | 61 | 86 | 97 | <0.8 |
| 426331 | 13 | 33 | 45 | 72 | 3.0 |
| 426334 | 1 | 16 | 41 | 63 | 4.1 |
| 426336 | 5 | 31 | 38 | 63 | 3.9 |
| 426337 | 16 | 29 | 35 | 64 | 4.1 |
| 426343 | 19 | 34 | 45 | 74 | 2.8 |
| 426344 | 11 | 26 | 42 | 70 | 3.4 |
| 426345 | 23 | 42 | 74 | 83 | 1.8 |
| 426346 | 23 | 41 | 60 | 82 | 2.0 |
| 426347 | 29 | 43 | 65 | 83 | 1.8 |
| 426390 | 13 | 19 | 30 | 60 | 5.2 |
| 426401 | 21 | 39 | 60 | 76 | 2.2 |
| 426402 | 14 | 16 | 37 | 67 | 4.0 |
| 426403 | 24 | 33 | 52 | 77 | 2.4 |
| 426404 | 27 | 39 | 54 | 86 | 2.0 |
| 426405 | 19 | 31 | 51 | 73 | 2.7 |

TABLE 5

Dose-dependent antisense inhibition of human GCCR expression in HepG2 cells using lipofectin reagent

| ISIS No | 17.5 nM | 35.0 nM | 70.0 nM | 140.0 nM | $IC_{50}$ (nM) |
|---|---|---|---|---|---|
| 377131 | 27 | 55 | 78 | 87 | 33.0 |
| 414641 | 54 | 74 | 89 | 96 | <17.5 |
| 414648 | 28 | 41 | 66 | 83 | 42.0 |
| 414681 | 30 | 48 | 68 | 85 | 37.0 |
| 420450 | 27 | 47 | 74 | 77 | 39.1 |
| 420470 | 22 | 45 | 59 | 75 | 49.4 |
| 420476 | 38 | 58 | 74 | 88 | 27.3 |
| 420488 | 28 | 48 | 72 | 71 | 40.3 |
| 420493 | 41 | 62 | 75 | 85 | 23.2 |
| 420522 | 32 | 57 | 72 | 78 | 31.8 |
| 420599 | 37 | 55 | 73 | 82 | 28.9 |
| 420644 | 32 | 53 | 75 | 84 | 32.0 |
| 426110 | 55 | 69 | 89 | 95 | <17.5 |
| 426115 | 45 | 62 | 76 | 69 | 17.8 |
| 426116 | 47 | 67 | 81 | 92 | 18.1 |
| 426117 | 49 | 68 | 83 | 92 | 16.7 |
| 426119 | 36 | 53 | 68 | 70 | 33.4 |
| 426124 | 22 | 53 | 73 | 89 | 37.0 |
| 426128 | 34 | 48 | 73 | 83 | 33.7 |
| 426130 | 32 | 55 | 81 | 93 | 29.7 |
| 426131 | 41 | 52 | 71 | 79 | 28.4 |
| 426136 | 12 | 41 | 63 | 80 | 50.8 |
| 426137 | 14 | 41 | 62 | 87 | 47.8 |
| 426142 | 32 | 51 | 74 | 81 | 33.6 |
| 426143 | 34 | 54 | 76 | 82 | 30.7 |
| 426144 | 21 | 48 | 71 | 86 | 40.2 |
| 426150 | 27 | 49 | 66 | 76 | 40.8 |
| 426157 | 31 | 55 | 68 | 79 | 34.6 |
| 426161 | 23 | 43 | 70 | 86 | 41.6 |
| 426168 | 37 | 56 | 75 | 86 | 27.9 |
| 426171 | 42 | 56 | 73 | 83 | 25.3 |
| 426172 | 52 | 67 | 83 | 90 | <17.5 |
| 426177 | 42 | 72 | 88 | 97 | 19.1 |
| 426183 | 54 | 70 | 86 | 92 | <17.5 |
| 426185 | 36 | 61 | 82 | 87 | 25.9 |
| 426187 | 50 | 64 | 83 | 95 | 17.9 |
| 426189 | 40 | 62 | 79 | 86 | 23.5 |
| 426199 | 33 | 58 | 74 | 84 | 30.4 |
| 426203 | 29 | 46 | 74 | 90 | 36.0 |
| 426216 | 26 | 51 | 67 | 80 | 39.6 |
| 426229 | 23 | 44 | 70 | 90 | 40.2 |
| 426246 | 41 | 54 | 74 | 84 | 26.6 |
| 426255 | 43 | 69 | 88 | 96 | 19.8 |
| 426261 | 43 | 67 | 86 | 96 | 20.3 |
| 426262 | 44 | 65 | 82 | 90 | 19.7 |
| 426263 | 45 | 65 | 80 | 87 | 19.0 |
| 426264 | 36 | 57 | 83 | 95 | 27.0 |
| 426267 | 22 | 51 | 73 | 85 | 38.2 |
| 426276 | 28 | 56 | 77 | 92 | 32.4 |
| 426281 | 25 | 48 | 72 | 89 | 37.4 |
| 426293 | 30 | 46 | 72 | 79 | 37.5 |
| 426301 | 29 | 60 | 70 | 85 | 32.2 |
| 426302 | 22 | 48 | 72 | 89 | 39.2 |
| 426306 | 37 | 45 | 76 | 91 | 31.8 |
| 426323 | 19 | 44 | 71 | 88 | 41.9 |
| 426324 | 34 | 57 | 76 | 84 | 29.1 |
| 426325 | 2 | 48 | 70 | 89 | 46.9 |
| 426331 | 29 | 54 | 67 | 78 | 36.8 |
| 426334 | 20 | 39 | 65 | 81 | 47.3 |
| 426336 | 30 | 47 | 67 | 84 | 37.9 |
| 426337 | 31 | 55 | 71 | 89 | 32.7 |
| 426343 | 33 | 52 | 70 | 76 | 34.3 |
| 426344 | 38 | 53 | 72 | 85 | 29.5 |
| 426345 | 43 | 59 | 78 | 83 | 22.7 |
| 426346 | 34 | 56 | 62 | 35 | >140.0 |
| 426347 | 36 | 53 | 71 | 79 | 31.3 |
| 426390 | 24 | 38 | 62 | 84 | 46.6 |
| 426401 | 35 | 49 | 69 | 82 | 34.0 |
| 426402 | 39 | 52 | 71 | 83 | 29.7 |
| 426403 | 29 | 54 | 72 | 86 | 33.9 |
| 426404 | 36 | 56 | 70 | 78 | 30.1 |
| 426405 | 33 | 53 | 73 | 86 | 32.1 |

Example 5

Dose-Dependent Antisense Inhibition of Human GCCR in HepG2 Cells

Gapmers selected from Example 4 were tested at various doses in HepG2 cells. Cells were plated at a density of 20,000 cells per well and transfected using electroporation with 0.5 μM, 1.0 μM, 2.0 μM, 4.0 μM or 8.0 μM concentrations of antisense oligonucleotide, as specified in Table 6. After a treatment period of approximately 16 hours, RNA was isolated from the cells and GCCR mRNA levels were measured by quantitative real-time PCR. Human GCCR primer probe set RTS1408 was used to measure mRNA levels. GCCR mRNA levels were adjusted according to total RNA content, as measured by RIBOGREEN®. Results are presented as percent inhibition of GCCR, relative to untreated control cells. As illustrated in Table 6, GCCR mRNA levels were reduced in a dose-dependent manner in antisense oligonucleotide treated cells. Certain exemplary compounds demonstrated greater potency than the benchmark ISIS 377131.

TABLE 6

Dose-dependent antisense inhibition of human GCCR expression in HepG2 cells using electroporation

| ISIS No | 0.5 μM | 1.0 μM | 2.0 μM | 4.0 μM | 8.0 μM | $IC_{50}$ (μM) |
|---|---|---|---|---|---|---|
| 377131 | 19 | 42 | 65 | 83 | 90 | 1.4 |
| 414641 | 23 | 48 | 67 | 88 | 95 | 1.2 |
| 420450 | 29 | 49 | 65 | 81 | 94 | 1.1 |
| 420470 | 15 | 25 | 47 | 72 | 91 | 2.0 |
| 420476 | 14 | 36 | 67 | 86 | 94 | 1.5 |
| 420644 | 22 | 33 | 51 | 69 | 87 | 1.8 |
| 426110 | 13 | 33 | 52 | 77 | 93 | 1.8 |
| 426115 | 32 | 53 | 70 | 84 | 90 | 0.9 |
| 426116 | 27 | 44 | 71 | 87 | 90 | 1.1 |
| 426119 | 30 | 41 | 66 | 78 | 84 | 1.2 |
| 426128 | 37 | 54 | 77 | 82 | 94 | 0.8 |
| 426130 | 21 | 38 | 55 | 80 | 92 | 1.5 |
| 426131 | 1 | 33 | 39 | 74 | 86 | 2.2 |
| 426142 | 33 | 45 | 72 | 89 | 93 | 1.0 |
| 426143 | 29 | 44 | 69 | 85 | 93 | 1.1 |
| 426168 | 15 | 47 | 59 | 77 | 91 | 1.5 |
| 426171 | 15 | 23 | 45 | 72 | 88 | 2.1 |
| 426172 | 31 | 48 | 68 | 81 | 91 | 1.1 |
| 426183 | 23 | 51 | 79 | 91 | 97 | 1.0 |
| 426246 | 0 | 5 | 0 | 5 | 0 | >8.0 |
| 426261 | 36 | 60 | 81 | 88 | 95 | 0.7 |
| 426262 | 15 | 26 | 55 | 76 | 92 | 1.8 |
| 426267 | 18 | 44 | 57 | 80 | 90 | 1.5 |
| 426325 | 25 | 46 | 74 | 89 | 97 | 1.1 |
| 426344 | 11 | 3 | 37 | 60 | 78 | 3.1 |
| 426345 | 7 | 20 | 43 | 65 | 82 | 2.5 |
| 426347 | 16 | 26 | 41 | 72 | 85 | 2.1 |
| 426402 | 3 | 9 | 35 | 54 | 80 | 3.2 |
| 426404 | 15 | 26 | 40 | 70 | 89 | 2.1 |

Example 6

Tolerability of Antisense Oligonucleotides Targeting Human GCCR in CD1 Mice

CD10 mice (Charles River, Mass.) are a multipurpose model of mice frequently utilized for safety and efficacy testing. The mice were treated with ISIS antisense oligonucleotides selected from the study described in Example 5, and evaluated for changes in the levels of various markers.

Treatment

Eight-week old male CD1 mice were maintained at a 12-hour light/dark cycle and fed Purina mouse chow 5001 ad libitum. The mice were acclimated for at least 7 days in the research facility before initiation of the experiment. Groups of four CD1 mice each were injected subcutaneously twice a week for 4 weeks with 50 mg/kg of ISIS 377131, ISIS 420470, ISIS 420476, ISIS 426115, ISIS 426130, ISIS 426168, ISIS 426172, ISIS 426183, ISIS 426246, ISIS 426261, ISIS 426262, ISIS 426267, or ISIS 426325. Blood samples were collected via tail snip prior to dosing and at weeks 2, 3, and 4 after dosing. Three days after the last dose at each time point, mice were euthanized and organs and plasma were harvested for further analysis. Mice treated with ISIS 426267 died before the end of the study. Therefore, samples from mice treated with ISIS 426267 was not included in any assay Plasma Chemistry To evaluate the effect of ISIS oligonucleotides on liver and kidney function, plasma levels of transaminases, cholesterol, glucose, and triglycerides were measured using an automated clinical chemistry analyzer (Hitachi Olympus AU400e, Melville, N.Y.). Plasma levels of ALT (alanine transaminase) and AST (aspartate transaminase) were measured and the results are presented in Tables 7 and 8 expressed in IU/L. Plasma levels of cholesterol, glucose and triglycerides were also measured using the same clinical chemistry analyzer and the results are also presented in Tables 9, 10, and 11.

TABLE 7

ALT levels (IU/L) of CD1 mice at week 4

| | Week 0 | Week 2 | Week 3 | Week 4 |
|---|---|---|---|---|
| PBS | 25 | 23 | 31 | 25 |
| ISIS 377131 | 24 | 41 | 32 | 50 |
| ISIS 420470 | 31 | 53 | 62 | 97 |
| ISIS 420476 | 24 | 46 | 56 | 83 |
| ISIS 426115 | 23 | 29 | 39 | 47 |
| ISIS 426130 | 21 | 29 | 41 | 37 |
| ISIS 426168 | 22 | 31 | 64 | 65 |
| ISIS 426172 | 24 | 32 | 35 | 39 |
| ISIS 426183 | 22 | 29 | 43 | 50 |
| ISIS 426261 | 23 | 39 | 77 | 93 |
| ISIS 426262 | 28 | 34 | 43 | 81 |
| ISIS 426246 | 25 | 291 | 535 | 1061 |
| ISIS 426325 | 26 | 32 | 52 | 145 |

TABLE 8

AST levels (IU/L) of CD1 mice at week 4

| | Week 0 | Week 2 | Week 3 | Week 4 |
|---|---|---|---|---|
| PBS | 46 | 40 | 45 | 38 |
| ISIS 377131 | 42 | 43 | 38 | 62 |
| ISIS 420470 | 38 | 64 | 62 | 152 |
| ISIS 420476 | 41 | 47 | 77 | 112 |
| ISIS 426115 | 42 | 34 | 43 | 66 |
| ISIS 426130 | 41 | 33 | 42 | 43 |
| ISIS 426168 | 50 | 37 | 63 | 81 |
| ISIS 426172 | 45 | 41 | 44 | 48 |
| ISIS 426183 | 55 | 35 | 46 | 62 |
| ISIS 426261 | 52 | 47 | 64 | 75 |
| ISIS 426262 | 45 | 43 | 47 | 88 |
| ISIS 426246 | 43 | 236 | 245 | 525 |
| ISIS 426325 | 45 | 48 | 53 | 88 |

TABLE 9

| Cholesterol levels (mg/dL) of CD1 mice at week 4 | | | | |
|---|---|---|---|---|
| | Week 0 | Week 2 | Week 3 | Week 4 |
| PBS | 152 | 166 | 176 | 161 |
| ISIS 377131 | 141 | 162 | 149 | 175 |
| ISIS 420470 | 159 | 181 | 193 | 201 |
| ISIS 420476 | 132 | 161 | 165 | 179 |
| ISIS 426115 | 115 | 131 | 143 | 140 |
| ISIS 426130 | 120 | 148 | 160 | 157 |
| ISIS 426168 | 123 | 138 | 161 | 159 |
| ISIS 426172 | 134 | 163 | 161 | 161 |
| ISIS 426183 | 135 | 166 | 154 | 164 |
| ISIS 426261 | 128 | 146 | 158 | 172 |
| ISIS 426262 | 149 | 208 | 197 | 248 |
| ISIS 426246 | 156 | 283 | 225 | 183 |
| ISIS 426325 | 128 | 140 | 117 | 81 |

TABLE 10

| Glucose levels (mg/dL) of CD1 mice at week 4 | | | | |
|---|---|---|---|---|
| | Week 0 | Week 2 | Week 3 | Week 4 |
| PBS | 205 | 196 | 223 | 185 |
| ISIS 377131 | 188 | 211 | 203 | 175 |
| ISIS 420470 | 200 | 194 | 206 | 186 |
| ISIS 420476 | 192 | 222 | 216 | 175 |
| ISIS 426115 | 184 | 180 | 185 | 167 |
| ISIS 426130 | 166 | 225 | 205 | 218 |
| ISIS 426168 | 170 | 209 | 190 | 181 |
| ISIS 426172 | 200 | 220 | 232 | 190 |
| ISIS 426183 | 176 | 229 | 217 | 203 |
| ISIS 426261 | 174 | 212 | 219 | 192 |
| ISIS 426262 | 203 | 232 | 200 | 197 |
| ISIS 426246 | 209 | 220 | 202 | 142 |
| ISIS 426325 | 172 | 204 | 204 | 154 |

TABLE 11

| Triglyceride levels (mg/dL) of CD1 mice at week 4 | | | |
|---|---|---|---|
| | Week 2 | Week 3 | Week 4 |
| PBS | 165 | 212 | 143 |
| ISIS 377131 | 187 | 137 | 158 |
| ISIS 420470 | 170 | 138 | 104 |
| ISIS 420476 | 172 | 130 | 109 |
| ISIS 426115 | 176 | 142 | 127 |
| ISIS 426130 | 125 | 133 | 173 |
| ISIS 426168 | 167 | 123 | 124 |
| ISIS 426172 | 175 | 166 | 177 |
| ISIS 426183 | 162 | 92 | 108 |
| ISIS 426261 | 139 | 70 | 91 |
| ISIS 426262 | 126 | 88 | 98 |
| ISIS 426246 | 67 | 58 | 63 |
| ISIS 426325 | 136 | 132 | 102 |

Example 7

Tolerability of Antisense Oligonucleotides Targeting Human GCCR in Sprague-Dawley Rats Sprague-Dawley rats were treated with ISIS antisense oligonucleotides from the study described in Example 6 and evaluated for changes in the levels of various markers.

Treatment

Eight week-old male rats were maintained on a 12-hour light/dark cycle and fed Purina normal rat chow ad libitum. Animals were acclimated at least 7 days in the research facility before the initiation of the experiment. Groups of four Sprague-Dawley rats each were injected subcutaneously twice a week with 50 mg/kg of ISIS 377131, ISIS 420470, ISIS 420476, ISIS 426115, ISIS 426130, ISIS 426168, ISIS 426172, ISIS 426183, ISIS 426246, ISIS 426261, ISIS 426262, ISIS 426267, or ISIS 426325. Blood samples were collected via tail snip prior to dosing and at weeks 2, 3, and 4 after dosing. Three days after the last dose at each time point, rats were euthanized and organs and plasma were harvested for further analysis.

Plasma Chemistry

To evaluate the effect of ISIS oligonucleotides on liver and kidney function, plasma levels of transaminases, cholesterol, glucose, and triglycerides were measured using an automated clinical chemistry analyzer (Hitachi Olympus AU400e, Melville, N.Y.). Plasma levels of ALT (alanine transaminase) and AST (aspartate transaminase) were measured and the results are presented in Tables 12 and 13, expressed in IU/L. Plasma levels of cholesterol, glucose and triglycerides were also measured using the same clinical chemistry analyzer and the results are also presented in Tables 14-16, expressed in mg/dL. 'n/a' indicates that the plasma chemistry marker for that particular time point had not been measured.

TABLE 12

| ALT levels (IU/L) of Sprague-Dawley rats | | | | |
|---|---|---|---|---|
| | Week 0 | Week 2 | Week 3 | Week 4 |
| PBS | 47 | 49 | 52 | 71 |
| ISIS 377131 | 46 | 59 | 51 | 103 |
| ISIS 420470 | 55 | 59 | 64 | 105 |
| ISIS 420476 | 47 | 59 | 41 | 63 |
| ISIS 426115 | 53 | 79 | 151 | 198 |
| ISIS 426130 | 50 | 56 | 50 | 74 |
| ISIS 426168 | 44 | 54 | 53 | 106 |
| ISIS 426172 | 46 | 60 | 46 | 123 |
| ISIS 426183 | 54 | 61 | 140 | 288 |
| ISIS 426261 | 46 | 63 | 116 | 132 |
| ISIS 426262 | 41 | 66 | 56 | 78 |
| ISIS 426246 | 58 | 56 | 74 | 362 |
| ISIS 426267 | 50 | 487 | 242 | 227 |
| ISIS 426325 | 51 | 63 | 71 | 108 |

TABLE 13

| AST levels (IU/L) of Sprague-Dawley rats | | | | |
|---|---|---|---|---|
| | Week 0 | Week 2 | Week 3 | Week 4 |
| PBS | 73 | 87 | 83 | 85 |
| ISIS 377131 | 71 | 76 | 72 | 127 |
| ISIS 420470 | 95 | 83 | 109 | 141 |
| ISIS 420476 | 72 | 80 | 78 | 104 |
| ISIS 426115 | 82 | 92 | 226 | 192 |
| ISIS 426130 | 74 | 75 | 75 | 86 |
| ISIS 426168 | 72 | 78 | 112 | 155 |
| ISIS 426172 | 76 | 77 | 87 | 188 |
| ISIS 426183 | 75 | 90 | 207 | 361 |
| ISIS 426261 | 72 | 87 | 144 | 140 |
| ISIS 426262 | 72 | 94 | 97 | 119 |
| ISIS 426246 | 92 | 82 | 108 | 269 |
| ISIS 426267 | 86 | 400 | 264 | 206 |
| ISIS 426325 | 83 | 75 | 90 | 126 |

TABLE 14

| Cholesterol levels (mg/dL) of Sprague-Dawley rats | | | | |
|---|---|---|---|---|
| | Week 0 | Week 2 | Week 3 | Week 4 |
| PBS | 93 | 72 | 71 | 65 |
| ISIS 377131 | 111 | 41 | 36 | 40 |
| ISIS 420470 | 103 | 37 | 42 | 42 |
| ISIS 420476 | 85 | 59 | 59 | 59 |
| ISIS 426115 | 116 | 81 | 95 | 110 |
| ISIS 426130 | 89 | 59 | 49 | 54 |
| ISIS 426168 | 68 | 43 | 46 | 72 |
| ISIS 426172 | 81 | 49 | 53 | 118 |
| ISIS 426183 | 87 | 89 | 111 | 245 |
| ISIS 426261 | 84 | 67 | 54 | 70 |
| ISIS 426262 | 80 | 60 | 49 | 60 |
| ISIS 426246 | 78 | 59 | 62 | 91 |
| ISIS 426267 | 89 | 58 | 70 | 72 |
| ISIS 426325 | 83 | 44 | 49 | 71 |

TABLE 15

| Glucose levels (mg/dL) of Sprague-Dawley rats | | | | |
|---|---|---|---|---|
| | Week 0 | Week 2 | Week 3 | Week 4 |
| PBS | 184 | 172 | 159 | 157 |
| ISIS 377131 | 191 | 175 | 146 | 138 |
| ISIS 420470 | 191 | 134 | 162 | 161 |
| ISIS 420476 | 185 | 151 | 159 | 188 |
| ISIS 426115 | 191 | 151 | 124 | 142 |
| ISIS 426130 | 191 | 161 | 161 | 154 |
| ISIS 426168 | 189 | 158 | 142 | 233 |
| ISIS 426172 | 189 | 150 | 143 | 288 |
| ISIS 426183 | 183 | 154 | 146 | 268 |
| ISIS 426261 | 176 | 150 | 134 | 142 |
| ISIS 426262 | 163 | 169 | 143 | 141 |
| ISIS 426246 | 200 | 152 | 148 | 156 |
| ISIS 426267 | 193 | 121 | 137 | 142 |
| ISIS 426325 | 174 | 146 | 154 | 147 |

TABLE 16

| Triglyceride levels (mg/dL) of Sprague-Dawley rats | | | | |
|---|---|---|---|---|
| | Week 0 | Week 2 | Week 3 | Week 4 |
| PBS | 73 | 66 | 124 | 96 |
| ISIS 377131 | 81 | 32 | 33 | 32 |
| ISIS 420470 | 71 | 42 | 35 | 31 |
| ISIS 420476 | 79 | 41 | 59 | 43 |
| ISIS 426115 | 48 | 43 | 35 | 26 |
| ISIS 426130 | 84 | 37 | 52 | 40 |
| ISIS 426168 | 62 | 44 | 56 | 37 |
| ISIS 426172 | 65 | 46 | 51 | n/a |
| ISIS 426183 | 74 | 26 | 44 | n/a |
| ISIS 426261 | 71 | 55 | 37 | 40 |
| ISIS 426262 | 91 | 36 | 34 | 27 |
| ISIS 426246 | 136 | 56 | 43 | 36 |
| ISIS 426267 | 120 | 42 | 34 | 29 |
| ISIS 426325 | 75 | 82 | 86 | 67 |

Example 8

Long-Term Tolerability of Antisense Oligonucleotides Targeting Human GCCR in CD/1GS Rats CD/1GS rats were treated for 12 weeks with ISIS antisense oligonucleotides selected from the studies described in Examples 6 and 7, and evaluated for changes in the levels of various markers.

Treatment

Eight week-old male rats were placed in metabolic cages, maintained on a 12-hour light/dark cycle and fed Purina normal rat chow ad libitum. Animals were acclimated at least 7 days in the research facility before the initiation of the experiment. Groups of four rats each were injected subcutaneously twice a week for 12 weeks with 30 mg/kg of ISIS 377131, ISIS 420470, ISIS 420476, ISIS 426115, ISIS 426130, ISIS 426168, ISIS 426172, ISIS 426183, ISIS 426246, ISIS 426261, ISIS 426262, ISIS 426267, or ISIS 426325. Blood samples were collected via tail snip prior to dosing and at weeks 2, 4, 6, 8, 10 and 12 after dosing. Three days after the last dose at each time point, rats were euthanized and organs and plasma were harvested for further analysis. Rats treated with ISIS 426267 died before the end of the study. Therefore, ISIS 426267 was not included in any further studies.

Liver Function

To evaluate the effect of ISIS oligonucleotides on liver function, plasma levels of transaminases, cholesterol, glucose, and triglycerides were measured using an automated clinical chemistry analyzer (Hitachi Olympus AU400e, Melville, N.Y.). The plasma levels of ALT and AST taken at week 12 are presented in Table 17, expressed as fold increase over the values of the PBS control. None of the antisense oligonucleotides caused any changes in any plasma chemistry markers outside the expected range for antisense oligonucleotides.

TABLE 17

| Fold-increase in plasma chemistry markers of Sprague-Dawley rats compared to the PBS control | | |
|---|---|---|
| | ALT | AST |
| ISIS 377131 | 1.0 | 1.5 |
| ISIS 420470 | 0.7 | 0.6 |
| ISIS 420476 | 1.7 | 2.6 |
| ISIS 426115 | 4.2 | 2.5 |
| ISIS 426130 | 1.1 | 1.4 |
| ISIS 426168 | 1.6 | 1.7 |
| ISIS 426172 | 1.8 | 2.1 |
| ISIS 426183 | 1.3 | 0.8 |
| ISIS 426261 | 1.2 | 0.9 |
| ISIS 426262 | 2.0 | 1.4 |
| ISIS 426246 | 1.1 | 0.8 |
| ISIS 426325 | 3.8 | 3.4 |

Renal Function

To evaluate the effect of ISIS oligonucleotides on renal function, urine concentrations of total urine protein and creatinine were measured using an automated clinical chemistry analyzer (Hitachi Olympus AU400e, Melville, N.Y.). The results are presented in Table 18 as a ratio, as well as the fold increase in the ratio taken at week 12. Those antisense oligonucleotides that did not cause any changes in any renal metabolic marker outside the expected range for antisense oligonucleotides were selected for further study.

TABLE 18

| Effect of antisense oligonucleotide treatment on renal metabolic markers of Sprague-Dawley rats | |
|---|---|
| | Fold Increase |
| PBS | 1 |
| ISIS 377131 | 7 |
| ISIS 420470 | 63 |

TABLE 18-continued

| Effect of antisense oligonucleotide treatment on renal metabolic markers of Sprague-Dawley rats | |
|---|---|
| | Fold Increase |
| ISIS 420476 | 6 |
| ISIS 426115 | 12 |
| ISIS 426130 | 5 |
| ISIS 426168 | 16 |
| ISIS 426172 | 7 |
| ISIS 426183 | 61 |
| ISIS 426261 | 60 |
| ISIS 426262 | 54 |
| ISIS 426246 | 68 |
| ISIS 426325 | 11 |

The results of both the mouse and rat studies indicated that ISIS 426115 was the most well tolerated antisense oligonucleotide targeting GCCR.

Example 9

Tolerability of ISIS Antisense Oligonucleotides Targeting Human GCCR in Cynomolgus Monkeys Cynomolgus monkeys were treated with ISIS antisense oligonucleotides from studies described in Examples 6, 7, and 8. Antisense oligonucleotide activity and tolerability was evaluated.

The human oligonucleotides selected are fully cross-reactive with rhesus monkey gene sequences. The greater the complementarity between the human oligonucleotide and the rhesus monkey sequence, the more likely the human oligonucleotide can cross-react with the rhesus monkey sequence. The human oligonucleotides were compared to the rhesus monkey genomic sequence (SEQ ID NO: 2; the complement of GENBANK Accession No. NW_001120987.1 truncated from nucleotides 1334000 to 1491000), based on similarity to human exons, and the results are displayed in Table 19. "Rhesus start site" indicates the 5'-most nucleotide to which the gapmer is targeted in the rhesus monkey gene sequence.

TABLE 19

Complementarity of antisense oligonucleotides targeting human GCCR to SEQ ID NO: 2

| ISIS No | Motif | Rhesus Start Site | Sequence | SEQ ID NO |
|---|---|---|---|---|
| 420470 | 5-10-5 | 53479 | GGTAGAAATATAGTTGTTCC | 6 |
| 420476 | 5-10-5 | 55628 | TTCATGTGTCTGCATCATGT | 7 |
| 426130 | 5-10-5 | 59602 | GCATCCAGCGAGCACCAAAG | 33 |
| 426183 | 3-14-3 | 61848 | AGCCATGGTGATCAGGAGGC | 10 |
| 426261 | 2-13-5 | 61848 | AGCCATGGTGATCAGGAGGC | 10 |
| 426262 | 2-13-5 | 61849 | CAGCCATGGTGATCAGGAGG | 35 |
| 426115 | 5-10-5 | 61850 | GCAGCCATGGTGATCAGGAG | 36 |
| 426168 | 5-10-5 | 72083 | GTCTGGATTACAGCATAAAC | 39 |
| 426246 | 3-14-3 | 72084 | GGTCTGGATTACAGCATAAA | 11 |
| 426172 | 5-10-5 | 72088 | CCTTGGTCTGGATTACAGCA | 42 |
| 426325 | 2-13-5 | 72088 | CCTTGGTCTGGATTACAGCA | 42 |
| 426267 | 2-13-5 | 91877 | GTGCTTGTCCAGGATGATGC | 43 |

Treatment

The study was conducted at WuXi PharmaTech testing facility, People's Republic of China. Male 2-5 year-old cynomolgous monkeys were tested twice for tuberculosis before being used for the study and were quarantined for at least 14 days prior to the initiation of dosing. Twenty four groups of five randomly assigned male cynomolgus monkeys each were injected subcutaneously thrice per week for the first week, and subsequently once a week for the next 11 weeks, with either 8 mg/kg or 20 mg/kg of ISIS 420470, ISIS 420476, ISIS 426115, ISIS 426130, ISIS 426168, ISIS 426172, ISIS 426183, ISIS 426246, ISIS 426261, ISIS 426262, ISIS 426267, or ISIS 426325. A control group of 16 cynomolgus monkeys was injected with PBS subcutaneously thrice per week for the first week, and subsequently once a week for the next 11 weeks.

During the study period, the monkeys were observed daily for signs of illness or distress. Any animal showing adverse effects to the treatment was removed and referred to the veterinarian and Study Director. Clinical observations and mortality checks were performed pre-dose and at least once a day during the dosing regimen. Body weights were measured once a week. Blood samples were collected 5 days before the treatment as well as on various days of the study period and analyzed. The animals were fasted for at least 13 hours (overnight) prior to blood collection. Blood was collected by venipuncture from a peripheral vein from restrained, conscious animals. Terminal sacrifices of all groups were conducted on day 86, which was 48 hours after the last dose.

Inhibition Studies

RNA Analysis

At the end of the study, RNA was extracted from liver tissue for real-time PCR analysis of GCCR using primer probe set mkGCCR_1 (forward sequence TTAGGAGGGCGGCAAGTG, designated herein as SEQ ID NO: 61; reverse sequence AGGTGTAAGTTCCTGAAACCTGGTA, designated herein as SEQ ID NO: 62; probe sequence TGCAGCAGTGAAATGGGCAAAGGC; designated herein as SEQ ID NO: 63). The data was also analyzed using prime probe set mkGCCR_5 (forward sequence GGAGATCATATAGACAATCAAGTGCAA, designated herein as SEQ ID NO: 64; reverse sequence GGGTAGAGTCATTCTCTGCTCATTAA, designated herein as SEQ ID NO: 65; probe sequence CTGTGTTTTGCTCCTGATCTGAT; designated herein as SEQ ID NO: 66). Results are presented as percent inhibition of GCCR, relative to PBS control, normalized to the house-keeping gene, cyclophilin. As shown in Table 20, treatment with ISIS 426325, ISIS 420476, and ISIS 426115 significantly reduced GCCR mRNA levels.

TABLE 20

| Inhibition of GCCR mRNA in the cynomolgus monkey liver relative to the PBS control | | | | |
|---|---|---|---|---|
| | 8 mg/kg dose | | 20 mg/kg dose | |
| ISIS No | primer probe set mkGCCR_1 | primer probe set mkGCCR_5 | primer probe set mkGCCR_1 | primer probe set mkGCCR_5 |
| 420470 | 34 | 0 | 51 | 57 |
| 420476 | 53 | 67 | 76 | 87 |
| 426115 | 52 | 66 | 6 | 49 |
| 426130 | 27 | 38 | 34 | 48 |
| 426168 | 31 | 53 | 42 | 54 |
| 426172 | 28 | 37 | 41 | 51 |
| 426183 | 43 | 55 | 49 | 59 |
| 426246 | 31 | 61 | 50 | 68 |
| 426261 | 41 | 55 | 36 | 73 |
| 426262 | 41 | 8 | 49 | 59 |
| 426267 | 45 | 64 | 43 | 64 |
| 426325 | 68 | 72 | 73 | 79 |

Protein Analysis

Approximately 1 mL of blood was collected from all available animals at week 11 and placed in tubes containing the potassium salt of EDTA. The tubes were centrifuged (3000 rpm for 10 min at room temperature) to obtain plasma. GCCR protein levels were measured in the plasma by western analysis using Santa Cruz sc-1003 rabbit polyclonal antibody. The results are presented in Table 21, expressed as percentage inhibition compared to the PBS control levels. The results indicate that ISIS 426325, ISIS 420476, and ISIS 426115 significantly reduced GCCR protein levels.

TABLE 21

| GCCR protein level reduction in the cynomolgus monkey plasma relative to control levels | | |
|---|---|---|
| | Dose (mg/kg) | % reduction |
| ISIS 426325 | 8 | 70 |
| | 20 | 61 |
| ISIS 420476 | 8 | 63 |
| | 20 | 62 |
| ISIS 426115 | 8 | 57 |
| | 20 | 52 |
| ISIS 426261 | 8 | 21 |
| | 20 | 28 |
| ISIS 426183 | 8 | 0 |
| | 20 | 0 |

Tolerability Studies

Body and Organ Weight Measurements

To evaluate the effect of ISIS oligonucleotides on the overall health of the animals, body and organ weights were measured at week 12. The data is presented in Table 22. Treatment with ISIS 420476 caused increase in spleen weight. Treatment with the remaining ISIS oligonucleotides caused no significant change outside the expected range for antisense oligonucleotides.

TABLE 22

| Final body and organ weight in the cynomolgus monkey at week 12 | | | | | |
|---|---|---|---|---|---|
| | Dose (mg/kg) | Body weight | Kidney | Spleen | Liver |
| PBS | — | 2744 | 5 | 3 | 52 |
| ISIS 426325 | 8 | 3000 | 6 | 6 | 63 |
| | 20 | 2882 | 7 | 6 | 72 |
| ISIS 426172 | 8 | 2786 | 6 | 4 | 63 |
| | 20 | 2750 | 6 | 5 | 63 |
| ISIS 426183 | 8 | 3026 | 6 | 4 | 58 |
| | 20 | 2822 | 6 | 5 | 58 |
| ISIS 426168 | 8 | 2724 | 6 | 4 | 60 |
| | 20 | 2868 | 7 | 5 | 72 |
| ISIS 420476 | 8 | 2980 | 7 | 4 | 71 |
| | 20 | 2798 | 7 | 9 | 77 |
| ISIS 426267 | 8 | 2788 | 7 | 6 | 73 |
| | 20 | 2826 | 6 | 5 | 78 |
| ISIS 426261 | 8 | 2590 | 6 | 4 | 57 |
| | 20 | 2596 | 5 | 6 | 59 |
| ISIS 426246 | 8 | 2612 | 6 | 4 | 57 |
| | 20 | 2470 | 6 | 6 | 67 |
| ISIS 426115 | 8 | 2572 | 5 | 5 | 56 |
| | 20 | 2642 | 6 | 7 | 62 |
| ISIS 426262 | 8 | 2952 | 6 | 6 | 60 |
| | 20 | 2980 | 6 | 6 | 67 |
| ISIS 420470 | 8 | 2588 | 8 | 9 | 70 |
| | 20 | 2782 | 7 | 6 | 80 |
| ISIS 426130 | 8 | 2958 | 6 | 3 | 62 |
| | 20 | 2870 | 6 | 4 | 61 |

Liver Function

To evaluate the effect of ISIS oligonucleotides on hepatic function, blood samples were collected from all the study groups on week 11. Approximately 3 mL of blood was collected from fasted animals and placed in tubes for serum separation. Serum was obtained by stabilization of the tubes at room temperature for 30-80 min followed by centrifugation (2,000 g×15 minutes at room temperature). Levels of transaminases were measured using a Hitachi-917/911 chemistry analyzer. Plasma levels of ALT and AST were measured and the results are presented in Table 23, expressed in IU/L. Alkaline phosphatase (ALP), which is synthesized in increased amounts by damaged liver cells and is also a marker of liver disease, was similarly measured. The data is also presented in Table 23. Bilirubin is also a liver metabolic marker and was similarly measured. and the data is also presented in Table 23, expressed in mg/dL. None of the ISIS oligonucleotides caused any change in these liver function markers outside the expected range for antisense oligonucleotides.

TABLE 23

| Levels of liver function markers in cynomolgus monkey plasma | | | | | |
|---|---|---|---|---|---|
| | Dose (mg/kg) | ALT (IU/L) | AST (IU/L) | ALP (IU/L) | Bilirubin (mg/dL) |
| PBS | — | 52 | 71 | 1310 | 4 |
| ISIS 426325 | 8 | 51 | 62 | 1408 | 4 |
| | 20 | 38 | 46 | 1464 | 5 |
| ISIS 426172 | 8 | 55 | 61 | 1643 | 4 |
| | 20 | 56 | 55 | 1442 | 4 |
| ISIS 426183 | 8 | 47 | 57 | 1633 | 3 |
| | 20 | 65 | 61 | 1603 | 6 |
| ISIS 426168 | 8 | 37 | 41 | 1907 | 2 |
| | 20 | 55 | 46 | 1990 | 2 |
| ISIS 420476 | 8 | 65 | 41 | 2088 | 2 |
| | 20 | 53 | 46 | 1698 | 2 |
| ISIS 426267 | 8 | 42 | 40 | 1738 | 2 |
| | 20 | 68 | 47 | 1982 | 1 |
| ISIS 426261 | 8 | 59 | 93 | 1193 | 4 |
| | 20 | 41 | 47 | 1158 | 4 |
| ISIS 426246 | 8 | 57 | 64 | 1108 | 3 |
| | 20 | 35 | 60 | 1376 | 3 |

TABLE 23-continued

Levels of liver function markers in cynomolgus monkey plasma

| | Dose (mg/kg) | ALT (IU/L) | AST (IU/L) | ALP (IU/L) | Bilirubin (mg/dL) |
|---|---|---|---|---|---|
| ISIS 426115 | 8 | 42 | 61 | 1369 | 3 |
| | 20 | 87 | 68 | 1418 | 3 |
| ISIS 426262 | 8 | 41 | 45 | 1973 | 3 |
| | 20 | 49 | 48 | 1637 | 3 |
| ISIS 420470 | 8 | 51 | 57 | 2137 | 2 |
| | 20 | 65 | 59 | 2568 | 2 |
| ISIS 426130 | 8 | 33 | 42 | 1884 | 2 |
| | 20 | 44 | 54 | 2279 | 3 |

Kidney Function

To evaluate the effect of ISIS oligonucleotides on renal function, blood samples were collected from all the study groups on week 11. Approximately 3 mL of blood was collected from fasted animals and placed in tubes for serum separation. Serum was obtained by stabilization of the tubes at room temperature for 30-80 min followed by centrifugation (2,000 g×15 minutes at room temperature). Concentrations of BUN and creatinine were measured at week 11 using a Hitachi-917/911 chemistry analyzer. Results are presented in Table 24, expressed in mg/dL. None of the ISIS oligonucleotides caused any change in these renal function markers outside the expected range for antisense oligonucleotides.

TABLE 24

Plasma BUN and creatinine levels (mg/dL) in cynomolgus monkeys

| | Dose (mg/kg) | BUN | Creatinine |
|---|---|---|---|
| PBS | — | 7 | 56 |
| ISIS 426325 | 8 | 8 | 58 |
| | 20 | 7 | 57 |
| ISIS 426172 | 8 | 8 | 54 |
| | 20 | 7 | 53 |
| ISIS 426183 | 8 | 6 | 62 |
| | 20 | 8 | 66 |
| ISIS 426168 | 8 | 7 | 46 |
| | 20 | 6 | 46 |
| ISIS 420476 | 8 | 7 | 51 |
| | 20 | 8 | 55 |
| ISIS 426267 | 8 | 7 | 43 |
| | 20 | 6 | 50 |
| ISIS 426261 | 8 | 7 | 56 |
| | 20 | 7 | 54 |
| ISIS 426246 | 8 | 7 | 53 |
| | 20 | 6 | 54 |
| ISIS 426115 | 8 | 8 | 57 |
| | 20 | 7 | 52 |
| ISIS 426262 | 8 | 7 | 54 |
| | 20 | 6 | 58 |
| ISIS 420470 | 8 | 7 | 61 |
| | 20 | 6 | 61 |
| ISIS 426130 | 8 | 7 | 56 |
| | 20 | 6 | 57 |

Markers of Inflammation

To evaluate any inflammatory effect of ISIS oligonucleotides in cynomolgus monkeys, blood samples were taken at week 11. C-reactive protein (CRP), which is synthesized in the liver and which serves as a marker of inflammation, was also similarly measured on week 11 using a Hitachi-917/911 chemistry analyzer. The results are presented in Table 25. Treatment with ISIS 426172 and ISIS 420470 caused increase in CRP levels. Treatment with the remaining ISIS oligonucleotides did not cause any change outside the expected range for antisense oligonucleotides.

Approximately 1.3 mL blood was collected in a tube treated with EDTA and used for the measurement of hematology parameter. Samples were analyzed for red blood cell (RBC) count, white blood cells (WBC) count, individual white blood cell percentages, such as that of monocytes, neutrophils, lymphocytes, as well as for platelet count and hematocrit (%), using an ADVIA120 hematology analyzer (Bayer, USA). The data is presented in Table 26. Treatment with ISIS 426168 and ISIS 420476 caused increase in lymphocyte counts. Treatment with ISSI 426325, ISIS 426172, ISIS 426262, and ISIS 420470 caused increase in neutrophil counts. Treatment with the remaining ISIS oligonucleotides did not cause any significant pro-inflammatory response beyond that expected for antisense oligonucleotides.

TABLE 25

CRP levels in cynomolgus monkeys

| | Dose (mg/kg) | CRP (mg/L) |
|---|---|---|
| PBS | — | 4 |
| ISIS 426325 | 8 | 6 |
| | 20 | 5 |
| ISIS 426172 | 8 | 17 |
| | 20 | 11 |
| ISIS 426183 | 8 | 5 |
| | 20 | 3 |
| ISIS 426168 | 8 | 3 |
| | 20 | 3 |
| ISIS 420476 | 8 | 4 |
| | 20 | 6 |
| ISIS 426267 | 8 | 4 |
| | 20 | 4 |
| ISIS 426261 | 8 | 4 |
| | 20 | 3 |
| ISIS 426246 | 8 | 6 |
| | 20 | 3 |
| ISIS 426115 | 8 | 4 |
| | 20 | 3 |
| ISIS 426262 | 8 | 4 |
| | 20 | 6 |
| ISIS 420470 | 8 | 20 |
| | 20 | 12 |
| ISIS 426130 | 8 | 3 |
| | 20 | 4 |

TABLE 26

Blood cells counts in cynomolgus monkeys

| | Dose (mg/kg) | WBC ($\times 10^3/\mu L$) | RBC ($\times 10^6/\mu L$) | Platelet ($\times 1000/\mu L$) | Hematocrit (%) | Lymphocytes (%) | Neutrophil (%) | Monocytes (%) |
|---|---|---|---|---|---|---|---|---|
| PBS | — | 13 | 6 | 500 | 47 | 56 | 39 | 2 |
| ISIS | 8 | 11 | 6 | 471 | 43 | 52 | 44 | 2 |
| 426325 | 20 | 13 | 6 | 454 | 45 | 45 | 52 | 2 |
| ISIS | 8 | 12 | 6 | 496 | 48 | 44 | 51 | 2 |

TABLE 26-continued

Blood cells counts in cynomolgus monkeys

| | Dose (mg/kg) | WBC ($\times 10^3/\mu L$) | RBC ($\times 10^6/\mu L$) | Platelet ($\times 1000/\mu L$) | Hematocrit (%) | Lymphocytes (%) | Neutrophil (%) | Monocytes (%) |
|---|---|---|---|---|---|---|---|---|
| 426172 | 20 | 14 | 6 | 437 | 45 | 42 | 54 | 2 |
| ISIS | 8 | 15 | 6 | 494 | 42 | 44 | 52 | 2 |
| 426183 | 20 | 12 | 6 | 466 | 45 | 61 | 34 | 2 |
| ISIS | 8 | 15 | 6 | 334 | 43 | 76 | 18 | 3 |
| 426168 | 20 | 18 | 6 | 401 | 44 | 73 | 22 | 3 |
| ISIS | 8 | 15 | 6 | 484 | 44 | 71 | 22 | 4 |
| 420476 | 20 | 15 | 6 | 455 | 42 | 70 | 24 | 3 |
| ISIS | 8 | 16 | 5 | 377 | 41 | 52 | 43 | 2 |
| 426267 | 20 | 14 | 5 | 488 | 41 | 42 | 52 | 3 |
| ISIS | 8 | 13 | 6 | 414 | 43 | 48 | 48 | 2 |
| 426261 | 20 | 12 | 5 | 414 | 40 | 47 | 48 | 3 |
| ISIS | 8 | 10 | 6 | 403 | 44 | 47 | 49 | 3 |
| 426246 | 20 | 17 | 6 | 421 | 45 | 43 | 54 | 2 |
| ISIS | 8 | 12 | 6 | 408 | 42 | 49 | 45 | 3 |
| 426115 | 20 | 15 | 6 | 457 | 44 | 47 | 50 | 2 |
| ISIS | 8 | 13 | 5 | 443 | 41 | 46 | 50 | 3 |
| 426262 | 20 | 15 | 6 | 402 | 44 | 46 | 50 | 2 |
| ISIS | 8 | 14 | 6 | 461 | 43 | 39 | 56 | 3 |
| 420470 | 20 | 12 | 5 | 445 | 43 | 45 | 50 | 2 |
| ISIS | 8 | 15 | 6 | 466 | 44 | 41 | 54 | 3 |
| 426130 | 20 | 16 | 6 | 425 | 42 | 48 | 45 | 2 |

Pharmacokinetic Studies

Measurement of Oligonucleotide Concentration

The concentration of the full-length oligonucleotide, as well as the total oligonucleotide concentration (including the degraded form), was measured at week 12. The method used is a modification of previously published methods (Leeds et al., 1996; Geary et al., 1999) which consist of a phenol-chloroform (liquid-liquid) extraction followed by a solid phase extraction. An internal standard (ISIS 355868, a 27-mer 2'-O-methoxyethyl modified phosphorothioate oligonucleotide, GCGTTTGCTCTTCTTCTTGCGTTTTTT, designated herein as SEQ ID NO: 57) was added prior to extraction. Tissue sample concentrations were calculated using calibration curves, with a lower limit of quantitation (LLOQ) of approximately 1.14 μg/g. The ratio of the concentrations in the kidney versus the liver was calculated. The results are presented in Tables 27 and 28, expressed as μg/g tissue.

TABLE 27

Full-length oligonucleotide concentration (μg/g) in the liver of cynomolgus monkey

| ISIS No | Dose (mg/kg) | Kidney | Liver | Kidney/Liver Ratio |
|---|---|---|---|---|
| 426325 | 8 | 685 | 390 | 1.8 |
| | 20 | 1558 | 654 | 2.4 |
| 426172 | 8 | 643 | 483 | 1.3 |
| | 20 | 1159 | 1042 | 1.1 |
| 426183 | 8 | 655 | 537 | 1.2 |
| | 20 | 1245 | 820 | 1.5 |
| 426168 | 8 | 751 | 388 | 1.9 |
| | 20 | 1906 | 765 | 2.5 |
| 420476 | 8 | 939 | 463 | 2.0 |
| | 20 | 1318 | 689 | 1.9 |
| 426267 | 8 | 709 | 401 | 1.8 |
| | 20 | 1507 | 893 | 1.7 |
| 426261 | 8 | 453 | 382 | 1.2 |
| | 20 | 930 | 720 | 1.3 |
| 426246 | 8 | 595 | 248 | 2.4 |
| | 20 | 1479 | 425 | 3.5 |
| 426115 | 8 | 1035 | 511 | 2.0 |
| | 20 | 1403 | 1067 | 1.3 |

TABLE 27-continued

Full-length oligonucleotide concentration (μg/g) in the liver of cynomolgus monkey

| ISIS No | Dose (mg/kg) | Kidney | Liver | Kidney/Liver Ratio |
|---|---|---|---|---|
| 426262 | 8 | 558 | 410 | 1.4 |
| | 20 | 1506 | 921 | 1.6 |
| 420470 | 8 | 811 | 275 | 2.9 |
| | 20 | 2938 | 609 | 4.8 |
| 426130 | 8 | 718 | 425 | 1.7 |
| | 20 | 1715 | 769 | 2.2 |

TABLE 28

Total oligonucleotide concentration (μg/g) in the liver of cynomolgus monkey

| ISIS No | Dose (mg/kg) | Kidney | Liver | Kidney/Liver Ratio |
|---|---|---|---|---|
| 426325 | 8 | 870 | 523 | 1.7 |
| | 20 | 2139 | 875 | 2.4 |
| 426172 | 8 | 922 | 688 | 1.3 |
| | 20 | 1681 | 1313 | 1.3 |
| 426183 | 8 | 905 | 809 | 1.1 |
| | 20 | 1791 | 1232 | 1.5 |
| 426168 | 8 | 909 | 507 | 1.8 |
| | 20 | 2477 | 951 | 2.6 |
| 420476 | 8 | 1367 | 636 | 2.1 |
| | 20 | 2057 | 948 | 2.2 |
| 426267 | 8 | 858 | 505 | 1.7 |
| | 20 | 1816 | 1103 | 1.6 |
| 426261 | 8 | 607 | 580 | 1.0 |
| | 20 | 1770 | 1098 | 1.6 |
| 426246 | 8 | 898 | 404 | 2.2 |
| | 20 | 2897 | 653 | 4.4 |
| 426115 | 8 | 1478 | 773 | 1.9 |
| | 20 | 2102 | 1542 | 1.4 |
| 426262 | 8 | 815 | 786 | 1.0 |
| | 20 | 2340 | 1438 | 1.6 |
| 420470 | 8 | 1051 | 401 | 2.6 |
| | 20 | 4012 | 815 | 4.9 |
| 426130 | 8 | 987 | 677 | 1.5 |
| | 20 | 2496 | 1144 | 2.2 |

Example 10

Measurement of Viscosity of ISIS Antisense Oligonucleotides Targeting Human GCCR The viscosity of three of the antisense oligonucleotides tested in the monkey study described in Example 9 was measured with the aim of screening out antisense oligonucleotides which have a viscosity more than 40 cP. Oligonucleotides having a viscosity greater than 40 cP would be too viscous to be administered to any subject.

ISIS oligonucleotides (32-35 mg) were weighed into a glass vial, 120 μL of water was added and the antisense oligonucleotide was dissolved into solution by heating the vial at 50° C. Part of (75 μL) the pre-heated sample was pipetted to a micro-viscometer (Cambridge). The temperature of the micro-viscometer was set to 25° C. and the viscosity of the sample was measured. Another part (20 μL) of the pre-heated sample was pipetted into 10 mL of water for UV reading at 260 nM at 85° C. (Cary UV instrument). The results are presented in Table 29 and indicate that all the antisense oligonucleotides solutions are optimal in their viscosity under the criterion stated above.

TABLE 29

Viscosity and concentration of ISIS antisense oligonucleotides targeting human GCCR

| ISIS No. | Viscosity (cP) | Concentration (mg/mL) |
|---|---|---|
| 420476 | 4.18 | 179 |
| 426115 | 17.6 | 178 |
| 426325 | 4.17 | 164 |

Example 11

Dose Response Confirmation of Antisense Oligonucleotides Targeting Human GCCR in Rhesus Monkey LLC-MK2 Cells Select gapmers from the monkey study described in Example 9 were tested at various doses in LLC-MK2 cells. The ISIS oligonucleotides tested are cross-reactive with rhesus monkey GCCR gene (SEQ ID NO: 2; the complement of GENBANK Accession No. NW_001120987.1 truncated from nucleotides 1334000 to 1491000).

Cells were plated at a density of 25,000 cells per well and transfected using electroporation with 0.09 μM, 0.19 nM, 0.38 μM, 0.75 μM 1.50 μM, 3.00 μM, 6.00 μM or 12.00 μM concentrations of antisense oligonucleotide, as specified in Table 32. After a treatment period of approximately 16 hours, RNA was isolated from the cells and GCCR mRNA levels were measured by quantitative real-time PCR. Human GCCR primer probe set RTS1408 was used to measure mRNA levels. GCCR mRNA levels were adjusted according to total RNA content, as measured by RIBOGREEN®. Results are presented as percent inhibition of GCCR, relative to untreated control cells. As illustrated in Table 30, GCCR mRNA levels were reduced in a dose-dependent manner in LLC-MK2 cells treated with the ISIS oligonucleotides tested.

TABLE 30

Dose-dependent antisense inhibition of human GCCR in LLC-MK2 using electroporation

| ISIS No | 0.09 μM | 0.19 μM | 0.38 μM | 0.75 μM | 1.50 μM | 3.00 μM | 6.00 μM | 12.00 μM | $IC_{50}$ (μM) |
|---|---|---|---|---|---|---|---|---|---|
| 377131 | 10 | 21 | 31 | 63 | 82 | 94 | 98 | 97 | 0.6 |
| 420476 | 0 | 2 | 4 | 30 | 45 | 71 | 93 | 97 | 1.7 |
| 426115 | 3 | 6 | 20 | 46 | 67 | 87 | 94 | 95 | 0.9 |
| 426261 | 6 | 24 | 31 | 52 | 77 | 94 | 97 | 97 | 0.6 |
| 426325 | 3 | 12 | 22 | 28 | 51 | 77 | 95 | 99 | 1.2 |

Example 12

Effect of ISIS 426115 Targeting Human/Rhesus GCCR in Cynomolgus Monkeys

Since ISIS 426115 was demonstrated by the study above to be both a highly potent and tolerable antisense oligonucleotide, it was selected for a second cynomolgus monkey study.

Treatment

Prior to the study, the monkeys were kept in quarantine for a 5-week period, during which the animals were observed daily for general health. The monkeys were 2-3 years old and weighed between 2 and 5 kg. One group of five randomly assigned male cynomolgus monkeys was injected subcutaneously with ISIS 426115 using a stainless steel dosing needle and syringe of appropriate size into the intracapsular region and outer thigh of the monkeys. The monkeys were dosed four times a week for the first week (days 1, 3, 5, and 7) as loading doses, and subsequently once a week for weeks 2-13, with 40 mg/kg of ISIS 426115. A control group of 8 cynomolgus monkeys was injected with PBS subcutaneously thrice four times a week for the first week (days 1, 3, 5, and 7), and subsequently once a week for weeks 2-13.

During the study period, the monkeys were observed twice daily for signs of illness or distress. Any animal experiencing more than momentary or slight pain or distress due to the treatment, injury or illness was treated by the veterinary staff with approved analgesics or agents to relieve the pain after consultation with the Study Director. Any animal in poor health or in a possible moribund condition was identified for further monitoring and possible euthanasia. Scheduled euthanasia of the animals was conducted on day 93 by exsanguination after ketamine/xylazine-induced anesthesia and administration of sodium pentobarbital. The protocols described in the Example were approved by the Institutional Animal Care and Use Committee (IACUC).

Tolerability Studies

Liver Function

To evaluate the effect of ISIS oligonucleotides on hepatic function, blood samples were collected from all groups. The blood samples were collected via femoral venipuncture on day 95, 48 hrs post-dosing. The monkeys were fasted overnight prior to blood collection. Blood was collected in tubes containing $K_2$-EDTA anticoagulant, which were centrifuged to obtain plasma. Levels of various liver function markers were measured using a Toshiba 200FR NEO chemistry analyzer (Toshiba Co., Japan). Plasma levels of ALT and AST were measured and the results are presented in Table 31, expressed in IU/L. Bilirubin, a liver function marker, was similarly measured and is presented in Table 31, expressed in mg/dL. Treatment with ISIS 426115 was well tolerated in terms of the liver function in monkeys.

TABLE 31

| Levels of liver metabolic markers in cynomolgus monkey plasma | | |
|---|---|---|
| | PBS | ISIS 426115 |
| ALT (IU/L) | 42 | 46 |
| AST (IU/L) | 42 | 46 |
| Bilirubin (mg/dL) | 0.18 | 0.26 |

Kidney Function

To evaluate the effect of ISIS 426115 on kidney function, blood samples were collected from all groups. The blood samples were collected via femoral venipuncture on day 95, 48 hrs post-dosing. The monkeys were fasted overnight prior to blood collection. Blood was collected in tubes containing $K_2$-EDTA anticoagulant, which were centrifuged to obtain plasma. Concentrations of BUN and creatinine were measured using a Toshiba 200FR NEO chemistry analyzer (Toshiba Co., Japan). Results are presented in Table 32, expressed in mg/dL.

The plasma data indicate that treatment with ISIS 426115 was well tolerated in terms of the kidney function in monkeys.

TABLE 32

| Effect Plasma BUN and creatinine levels (mg/dL) in cynomolgus monkeys | | |
|---|---|---|
| | PBS | ISIS 426115 |
| BUN | 17 | 19 |
| Creatinine | 0.60 | 0.58 |

This study taken into account with the study described in Example 9 further corroborates that ISIS 426115 is a well-tolerated antisense oligonucleotide targeting GCCR.

What is claimed is:

1. A compound comprising a modified antisense oligonucleotide consisting of 12 to 30 linked nucleosides having a nucleobase sequence comprising a portion of at least 8 contiguous nucleobases complementary to an equal length portion of nucleobases 51878-51898, 60935-60958, 104247-104266, 109346-109492, 112218-112242, 114154-114610, 139287-139306, 143259-143757 of SEQ ID NO: 1, wherein the nucleobase sequence of the modified antisense oligonucleotide is at least 90% complementary to SEQ ID NO: 1 and wherein the modified antisense oligonucleotide inhibits GCCR expression.

2. The compound of claim 1, wherein the modified antisense oligonucleotide is single-stranded.

3. The compound of claim 1, wherein said modified antisense oligonucleotide is at least 95% complementary to SEQ ID NO: 1.

4. The compound of claim 1, wherein said modified antisense oligonucleotide is at least 98% complementary to SEQ ID NO: 1.

5. The compound of claim 1, wherein said modified antisense oligonucleotide is 100% complementary to SEQ ID NO: 1.

6. The compound of claim 1, wherein at least one internucleoside linkage is a modified internucleoside linkage.

7. The compound of claim 6, wherein each internucleoside linkage is a phosphorothioate internucleoside linkage.

8. The compound of claim 1, wherein at least one nucleoside of the modified antisense oligonucleotide comprises a modified sugar.

9. The compound of claim 8, wherein the at least one modified sugar is a bicyclic sugar.

10. The compound of claim 9, wherein each of the at least one bicyclic sugar comprises a 4'-($CH_2$)—O-2', 4'-$(CH_2)_2$—O-2', or 4'-CH($CH_3$)—O-2' group.

11. The compound of claim 9, wherein each of the at least one bicyclic sugar comprises a 4'-CH($CH_3$)—O-2' bridge.

12. The compound of claim 8, wherein at least one modified sugar comprises a 2'-O-methoxyethyl group.

13. The compound of claim 1, wherein at least one nucleoside comprises a modified nucleobase.

14. The compound of claim 13, wherein the modified nucleobase is a 5-methylcytosine.

15. The compound of claim of claim 1, wherein the modified antisense oligonucleotide comprises:

a gap segment consisting of linked deoxynucleosides;

a 5' wing segment consisting of linked nucleosides; and a 3' wing segment consisting of linked nucleosides;

wherein the gap segment is positioned between the 5' wing segment and the 3' wing segment and wherein each nucleoside of each wing segment comprises a modified sugar.

16. A composition comprising the compound of claim 1 or salt thereof and at least one of a pharmaceutically acceptable carrier or diluent.

17. A method of preventing, treating, ameliorating or delaying the onset of a disease or condition associated with GCCR in an animal comprising administering to the animal a therapeutically or prophylactically effective amount of compound of claim 1 or the composition of claim 16 wherein administering the compound or composition prevents, treats, ameliorates or delays the onset of the disease or condition.

18. The method of claim 17, wherein the animal is human.

19. The method of claim 17, wherein the disease or condition is diabetes.

20. The method of claim 17, wherein the disease or condition is Type 2 diabetes.

21. The method of claim 17, comprising co-administering the compound or composition and a second agent.

22. The method of claim 21, wherein the second agent is a glucose lowering agent.

23. The method of claim 22, wherein the compound or composition and the second agent are administered concomitantly.

24. The compound of claim 1, wherein the modified oligonucleotide comprises a portion of at least 8 contiguous nucleobases of the sequence of SEQ ID Nos: 5, 8, 13, 14, 15, 16, 22, 23, 24, 30, 31, 32, 45, 46, 47, 48, 49, 50, 51, 52, 53, 54, 55, or 56.

* * * * *